US010457731B2

(12) United States Patent
Jarjour et al.

(10) Patent No.: US 10,457,731 B2
(45) Date of Patent: Oct. 29, 2019

(54) MULTIPARTITE SIGNALING PROTEINS AND USES THEREOF

(71) Applicant: bluebird bio, Inc., Cambridge, MA (US)

(72) Inventors: Jordan Jarjour, Seattle, WA (US); Alexander Astrakhan, Seattle, WA (US); Michael Certo, Medford, MA (US)

(73) Assignee: bluebird bio, Inc., Cambridge, MA (US)

( * ) Notice: Subject to any disclaimer, the term of this patent is extended or adjusted under 35 U.S.C. 154(b) by 0 days.

(21) Appl. No.: 16/219,640

(22) Filed: Dec. 13, 2018

(65) Prior Publication Data
US 2019/0112372 A1 Apr. 18, 2019

Related U.S. Application Data

(63) Continuation of application No. 14/908,734, filed as application No. PCT/US2014/047852 on Jul. 23, 2014, now Pat. No. 10,196,444.

(60) Provisional application No. 61/934,092, filed on Jan. 31, 2014, provisional application No. 61/859,697, filed on Jul. 29, 2013.

(51) Int. Cl.
| | |
|---|---|
| *A61K 48/00* | (2006.01) |
| *C07H 21/04* | (2006.01) |
| *C07K 14/00* | (2006.01) |
| *C07K 16/28* | (2006.01) |
| *A61K 35/17* | (2015.01) |
| *A61K 39/00* | (2006.01) |
| *A61K 45/06* | (2006.01) |
| *C07K 14/705* | (2006.01) |
| *C07K 16/40* | (2006.01) |
| *C12N 9/12* | (2006.01) |
| *C12N 9/90* | (2006.01) |
| *C07K 14/725* | (2006.01) |
| *C07K 14/73* | (2006.01) |
| *C07K 14/735* | (2006.01) |
| *C12N 9/06* | (2006.01) |
| *C12N 9/16* | (2006.01) |
| *C12N 15/85* | (2006.01) |

(52) U.S. Cl.
CPC .......... *C07K 16/2803* (2013.01); *A61K 35/17* (2013.01); *A61K 39/0005* (2013.01); *A61K 45/06* (2013.01); *C07K 14/7051* (2013.01); *C07K 14/7056* (2013.01); *C07K 14/70503* (2013.01); *C07K 14/70514* (2013.01); *C07K 14/70517* (2013.01); *C07K 14/70521* (2013.01); *C07K 14/70535* (2013.01); *C07K 14/70578* (2013.01); *C07K 14/70596* (2013.01); *C07K 16/2896* (2013.01); *C07K 16/40* (2013.01); *C12N 9/003* (2013.01); *C12N 9/12* (2013.01); *C12N 9/16* (2013.01); *C12N 9/90* (2013.01); *C12N 15/85* (2013.01); *C12Y 207/11001* (2013.01); *C12Y 502/01008* (2013.01); *C07H 21/04* (2013.01); *C07K 2317/622* (2013.01); *C07K 2319/03* (2013.01); *C07K 2319/70* (2013.01); *C12N 2510/00* (2013.01)

(58) Field of Classification Search
CPC .... C12N 2510/00; C12N 15/85; C07H 21/04; C07K 14/70535; C07K 14/70503; C07K 14/70514; C07K 14/70517; C07K 14/70521; C07K 14/70578; C07K 2319/03; C07K 2319/70
USPC ...................... 424/93.21; 530/350; 536/23.4
See application file for complete search history.

(56) References Cited

U.S. PATENT DOCUMENTS

| | | | |
|---|---|---|---|
| 5,871,753 | A | 2/1999 | Crabtree et al. |
| 5,910,573 | A | 6/1999 | Pluckthun et al. |
| 6,291,158 | B1 | 9/2001 | Winter et al. |
| 6,291,161 | B1 | 9/2001 | Lerner et al. |
| 6,423,498 | B1 | 7/2002 | Markland et al. |
| 6,649,595 | B2 | 11/2003 | Clackson et al. |
| 6,972,193 | B1 | 12/2005 | Crabtree et al. |
| 10,196,444 | B2 | 2/2019 | Jarjour et al. |
| 2007/0065431 | A1 | 3/2007 | Coia et al. |
| 2013/0287752 | A1 | 10/2013 | Davila et al. |
| 2015/0266973 | A1 | 9/2015 | Jarjour et al. |
| 2016/0311901 | A1 | 10/2016 | Jarjour et al. |

FOREIGN PATENT DOCUMENTS

| | | |
|---|---|---|
| JP | 2002-503667 A | 2/2002 |
| JP | 2002-508971 A | 3/2002 |
| WO | WO 1999/036553 A2 | 7/1999 |
| WO | WO 1999/041258 A1 | 8/1999 |
| WO | WO 2006/072620 A1 | 7/2006 |
| WO | WO 2006/095164 A1 | 9/2006 |

(Continued)

OTHER PUBLICATIONS

Abate-Daga and Davila, "CAR models: next-generation CAR modifications for enhanced T-cell function." Oncolytics (2016); 3 (16014): 1-7.

(Continued)

*Primary Examiner* — Shin Lin Chen
(74) *Attorney, Agent, or Firm* — Cooley LLP

(57) ABSTRACT

Nucleic acids that encode chemically-inducible fusion proteins, vectors that contain nucleic acids that encode chemically-inducible fusion proteins, chemically-inducible fusion proteins, chemically-inducible fusion protein complexes, and non-natural cells that are modified to express chemically-inducible fusion proteins to spatially and temporally control immune cell signal initiation and downstream responses for treating disease.

27 Claims, 27 Drawing Sheets

Specification includes a Sequence Listing.

(56) References Cited

FOREIGN PATENT DOCUMENTS

| WO | WO 2007/098934 A1 | 9/2007 |
|---|---|---|
| WO | WO 2012/082841 A2 | 6/2012 |
| WO | WO 2014/127261 A1 | 8/2014 |
| WO | WO 2015/017214 A1 | 2/2015 |

OTHER PUBLICATIONS

Alder, M. et al., "Antibody responses of variable lymphocyte receptors in the lamprey", Nat Immunol. (2008); 9(3):319-327.
Banaszynski, L.A., et al., "Characterization of the FKBP Rapamycin FRB Ternary Complex." Journal of the American Chemical Society (2005); 127.13: 4715-4721.
Baral, et al., "Experimental therapy of African trypanosomiasis with a nanobody-conjugated human trypanolytic factor", Nat Med. (2006); 12(5): 580-584.
Barthelemy, PA. et al., "Comprehensive analysis of the factors contributing to the stability and solubility of autonomous human VH domains", J Biol Chem. (2008); 283(6):3639-3654.
Bayle, J.H., et al., "Rapamycin analogs with differential binding specificity permit orthogonal control of protein activity." Chemistry & Biology (2006); 13.1: 99-107.
Beavil, A. et al., "Alpha-helical coiled-coil stalks in the low-affinity receptor for IgE (Fc epsilon RII/CD23) and related C-type lectins", Proc Natl Acad Sci U S A. (1992); 89(2):753-757.
Belshaw, P.J., et al., "Controlling protein association and subcellular localization with a synthetic ligand that induces heterodimerization of proteins." Proc. Natl. Acad. Sci. USA (1996); 93: 4604-4607.
Beste, G. et al., "Small antibody-like proteins with prescribed ligand specificities derived from the lipocalin fold", Proc Natl Acad Sci U S A. (1999); 96(5):1898-903.
Binz, HK, et al., "Designing repeat proteins: well-expressed, soluble and stable proteins from combinatorial libraries of consensus ankyrin repeat proteins", J. Mol. Biol. (2003); 332(2): 489-503.
Brentjens, R. et al.,"Safety and persistence of adoptively transferred autologous CD19-targeted T cells in patients with relapsed or chemotherapy refractory B-cell leukemias", Blood (2011); 118(18): 4817-4828.
Brentjens, R. et al.,"CD19-Targeted T Cells Rapidly Induce Molecular Remissions in Adults with Chemotherapy-Refractory Acute Lymphoblastic Leukemia." Science Translational Medicine (2013); 5(177): 177ra38.
Brown, E. et al., "A mammalian protein targeted by G1-arresting rapamycin-receptor complex", Nature (1994); 369(6483): 756-758.
Capon, D. et al., "Designing CD4 immunoadhesins for AIDS therapy", Nature (1989); 337(6207): 525-531.
Carpenito, C. et. al., "Control of large, established tumor xenografts with genetically retargeted human T cells containing CD28 and CD137 domains", Proc Natl Acad Sci USA (2009); 106(9):3360-3365.
Challita, P. et al., "Multiple modifications in cis elements of the long terminal repeat of retroviral vectors lead to increased expression and decreased DNA methylation in embryonic carcinoma cells", J Virol. (1995) 69(2): 748-755.
Cortez-Retamozo, V. et al., "Efficient cancer therapy with a nanobody-based conjugate", Cancer Res. (2004); 64(8):2853-2857.
Craik, D. et al., "Plant cyclotides: A unique family of cyclic and knotted proteins that defines the cyclic cystine knot structural motif", J. Mol. Biol. (1999); 294(5): 1327-1336.
Curran, K.J., et al., "Chimeric antigen receptors for T cell immunotherapy: current understanding and future directions." Journal of Gene Medicine (2012); 14(6): 405-415.
Donnelly, M. et al., "The 'cleavage' activities of foot-and-mouth disease virus 2A site-directed mutants and naturally occurring '2A-like' sequences", J Gen Virol. (2001); 82 (Pt 5):1027-1041.
Dotti, et al., "Design and development of therapies using chimeric antigen receptor-expressing T cells." Immunol Rev. (2014); 257 (1): 107-126, 35 pages. First published: Dec. 13, 2013.

Duong, C. et al., "Enhancing the specificity of T-cell cultures for adoptive immunotherapy of cancer", Immunotherapy (2011); 3(1): 33-48.
Extended European Search Report for European Application No. 14832043.5 dated Feb. 10, 2017, 11 pages.
Fegan, Adrian, et al. "Chemically controlled protein assembly: techniques and applications." Chemical Reviews (2010); 110.6: 3315-3336.
Ghahroudi, et al., "Selection and identification of single domain antibody fragments from camel heavy-chain antibodies", FEBS Lett. (1997); 414(3):521-526.
Grünberg, Raik, et al., "Building blocks for protein interaction devices." Nucleic Acids Research (2010); 38.8: 2645-2662.
Grupp, S.A. et al., "Chimeric antigen receptor-modified T cells for acute lymphoid leukemia", N Engl J Med. (2013); 368(16): 1509-1518.
Hackel, B. et al., "Picomolar affinity fibronectin domains engineered utilizing loop length diversity, recursive mutagenesis, and loop shuffling", J Mol Biol. (2008); 381(5):1238-1252.
Hamers-Casterman, C. et al., "Naturally occurring antibodies devoid of light chains", Nature (1993); 363(6428):446-448.
Herrin, B. et al., "Structure and specificity of lamprey monoclonal antibodies", Proc Natl Acad Sci U S A. (2008); 105(6):2040-2045.
Hu, S. et al., "Minibody: A novel engineered anti-carcinoembryonic antigen antibody fragment (single-chain Fv-CH3) which exhibits rapid, high-level targeting of xenografts" Cancer Res. (1996); 56(13):3055-3061.
Huang, C. et al.,"Scorpion-toxin mimics of CD4 in complex with human immunodeficiency virus gp120 crystal structures, molecular mimicry, and neutralization breadth", Structure (2005); 13(5):755-768.
Hoet, R. et al., "Generation of high-affinity human antibodies by combining donor-derived and synthetic complementarity-determining-region diversity", Nat Biotechnol. (2005); 23(3):344-348.
Hsu, C. et al., "Primary human T lymphocytes engineered with a codon-optimized IL-15 gene resist cytokine withdrawal-induced apoptosis and persist long-term in the absence of exogenous cytokine", J Immunol. (2005); 175(11):7226-34.
International Application No. PCT/US2014/047852, International Search Report and Written Opinion dated Nov. 21, 2014, 11 pages.
International Application No. PCT/US2014/047852, International Preliminary Report on Patentability dated Feb. 2, 2016, 8 pages.
Irion, S. et al., "Identification and targeting of the ROSA26 locus in human embryonic stem cells", Nat Biotechnol. (2007); 25(12):1477-1482.
Janeway, C. et al., "The Immune System in Health and Disease",Immunobiology (1999); 4th edition, Current Biology Publications p. 148, 149, and 172.
Jespers, L. et al., "Aggregation-resistant domain antibodies selected on phage by heat denaturation", Nat Biotechnol. (2004); 22(9):1161-1165.
June, C. et al., "T-cell therapy at the threshold", Nat Biotechnol. (2012); 30(7): 611-614.
Kalos, et al., "T Cells with Chimeric Antigen Receptors Have Potent Antitumor Effects and Can Establish Memory in Patients with Advanced Leukemia", Sci Transl Med. Aug. 10, 2011; 3(95): 95ra73. doi:10.1126/scitranslmed.3002842.
Kalos, M. et al., "T cells with chimeric antigen receptors have potent antitumor effects and can establish memory in patients with advanced leukemia", Sci Transl Med. (2011); 3(95):95ra73.
Kay, J.E. "Structure-function relationships in the FK506-binding protein (FKBP) family of peptidylprolyl cis-trans isomerases", Biochem J. (1996); 314 (Pt 2):361-385.
Kochenderfer, J. et al., "Treating B-cell cancer with T cells expressing anti-CD19 chimeric antigen receptors", Nat Rev Clin Oncol. (2013); 10(5):267-276.
Kochenderfer, J. et al., "B-cell depletion and remissions of malignancy along with cytokine-associated toxicity in a clinical trial of anti-CD19 chimeric-antigen-receptor-transduced T cells", Blood (2012); 119(12):2709-2720.

(56) References Cited

OTHER PUBLICATIONS

Kowolik, C. et al., "CD28 costimulation provided through a CD19-specific chimeric antigen receptor enhances in vivo persistence and antitumor efficacy of adoptively transferred T cells", Cancer Res. (2006); 66(22): 10995-11004.
Lee, S. et al., "Design of a binding scaffold based on variable lymphocyte receptors of jawless vertebrates by module engineering", Proc Natl Acad Sci U S A. (2012); 109(9):3299-3304.
Leung, Wai-Hang et al., "Small molecule-regulated antigen recognition system for inducible T cell targeting of cancer cells." Bluebird Bio, Cambridge, MA, United States. Molecular Therapy, (Apr. 2016) vol. 24, Supp. Suppl. 1, pp. S110, Abstract No. 277, 2 pages.
Main, E. et al., "Design of stable alpha-helical arrays from an idealized TPR motif", Structure (2003); 11(5):497-508.
Manzke, O. et al., "CD3X anti-nitrophenyl bispecific diabodies: universal immunotherapeutic tools for retargeting T cells to tumors", Int J Cancer. (1999); 82(5):700-708.
Martin, L. et al., "Rational design of a CD4 mimic that inhibits HIV-1 entry and exposes cryptic neutralization epitopes", Nat. Biotechnol. (2003); 21(1): 71-76.
Milone, M. et al., "Chimeric receptors containing CD137 signal transduction domains diate enhanced survival of T cells and increased antileukemic efficacy in vivo", Mol Ther. (2009); 17(8):1453-64.
Nguyen, V. et al., "Heavy-chain antibodies in Camelidae; a case of evolutionary innovation", Immunogenetics (2002); 54(1): 39-47.
Nguyen, V. et al., "The specific variable domain of camel heavy-chain antibodies is encoded in the germline", J. Mol. Biol. (1998); 275(3): 413-418.
Nord, K. et al., "A combinatorial library of an alpha-helical bacterial receptor domain", Protein Eng. (1995); 8(6): 601-608.
Nord, K. et al., "Binding proteins selected from combinatorial libraries of an alpha-helical bacterial receptor domain", Nat. Biotechnol. (1997); 15(8): 772-777.
Nord, K. et al., "Recombinant human factor VIII-specific affinity ligands selected from phage-displayed combinatorial libraries of protein A", Eur J Biochem. (2001); 268(15):4269-4277.
Parker, M. "Antibody mimics based on human fibronectin type three domain engineered for thermostability and high-affinity binding to vascular endothelial growth factor receptor two", Protein Eng Des Sel. (2005); 18(9):435-444.
Pule, M.A. et al., "A chimeric T cell antigen receptor that augments cytokine release and supports clonal expansion of primary human T cells", Mol Ther. (2005); 12(5):933-941. Epub Jun. 23, 2005.
Quintarelli, C. "Co-expression of cytokine and suicide genes to enhance the activity and safety of tumor-specific cytotoxic T lymphocytes", Blood (2007); 110(8):2793-2802.
Restifo, N.P. et al., "Adoptive immunotherapy for cancer: harnessing the T cell response", Nat Rev Immunol. (2012); 12(4)269-281.
Richards, J. et al., "Engineered fibronectin type III domain with a RGDWXE sequence binds with enhanced affinity and specificity to human avb3 integrin", J. Mol. Biol. (2003); 326(5): 1475-1488.
Roux, K. et al., "Structural analysis of the nurse shark (new) antigen receptor (NAR): molecular convergence of NAR and unusual mammalian immunoglobulins", Proc Natl Acad Sci U S A. (1998); 95(20):11804-11809.
Ryan, M. et al., "Virus-encoded proteinases of the picornavirus super-group", J Gen Virol. (1997); 78 (Pt 4): 699-723.
Sato, A. et al, "Genes encoding putative natural killer cell C-type lectin receptors in teleostean fishes", Proc Natl Acad Sci U S A. (2003); 100(13):7779-7784.
Schonfeld, D. et al., "An engineered lipocalin specific for CTLA-4 reveals a combining site with structural and conformational features similar to antibodies", Proc Natl Acad Sci U S A. (2009); 106(20):8198-8203.
Skerra, A. "Alternative binding proteins: anticalins—harnessing the structural plasticity of the lipocalin ligand pocket to engineer novel binding activities", FEBS J. (2008); 275(11):2677-2683.
Schlessinger, J., "Cell Signaling by Receptor Tyrosine Kinases." Cell (2000); 103: 211-225.
Spencer, David M., et al. "Controlling signal transduction with synthetic ligands." Science (1993); 262: 1019-1024.
Standaert, R. et al., "Molecular cloning and overexpression of the human FK506-binding protein FKBP", Nature (1990); 346(6285): 671-674.
Stephan, M. et al., "T cell-encoded CD80 and 4-1BBL induce auto- and transcostimulation, resulting in potent tumor rejection", Nat Med. (2007); 13(12): 1440-1449.
Stumpp, M. et al., "Designing repeat proteins: modular leucine-rich repeat protein libraries based on the mammalian ribonuclease inhibitor family", J. Mol. Biol. (2003); 332(2): 471-487.
Tal, et al., "An NCR1-based chimeric receptor endows T-cells with multiple anti-tumor specificities." Oncotarget (2014); 5 (21): 10949-10958.
Till, B. et al., "CD20-specific adoptive immunotherapy for lymphoma using a chimeric antigen receptor with both CD28 and 4-1BB domains: pilot clinical trial results". Blood (2012); 119(17):3940-3950.
U.S. Appl. No. 14/608,098, Office Action dated Jun. 28, 2016, 25 pages.
Varadamsetty, G, et al., "Designed Armadillo repeat proteins: library generation, characterization and selection of peptide binders with high specificity", J. Mol. Biol. (2012); 424(1-2): 68-87.
Vincke, C. et al., "General strategy to humanize a camelid single-domain antibody and identification of a universal humanized nanobody scaffold", J Biol Chem. (2009); 284(5):3273-3284.
Vita, C. et al., "Scorpion toxins as natural scaffolds for protein engineering", Proc Natl Acad Sci U S A. (1995); 92(14):6404-6408.
Weisel, J. et al., "A model for fibrinogen: domains and sequence", Science (1985); 230(4732): 1388-1391.
White, I. et al., "Comparison of the glycosyl-phosphatidylinositol cleavage/attachment site between mammalian cells and parasitic protozoa", J Cell Sci. (2000); 113 (Pt 4):721-727.
Wilkie, S. et al., "Dual targeting of ErbB2 and MUC1 in breast cancer using chimeric antigen receptors engineered to provide complementary signaling", J. Clin. Immunol. (2012); 32(5): 1059-1070.
Zelensky and Gready. "The C-type lectin-like domain superfamily", FEBS J. (2005); 272(24):6179-6217.

MULTIPARTITE SIGNALING PROTEINS AND USES THEREOF

CROSS REFERENCE TO RELATED APPLICATIONS

This application claims the benefit under 35 U.S.C. § 119(e) of U.S. Provisional Application No. 61/934,092, filed Jan. 31, 2014, and U.S. Provisional Application No. 61/859,697, filed Jul. 29, 2013, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_036_02WO_ST25.txt. The text file is 433 KB, was created on Jul. 23, 2014, and is being submitted electronically via EFS-Web.

BACKGROUND

Technical Field

The present disclosure relates to compositions and methods for using multi-component proteins in immunotherapy and, more particularly, using chemically induced multimerization to generate chimeric antigen receptor proteins for modulating spatial and temporal control of cellular signal initiation and downstream responses during adoptive immunotherapy.

Description of the Related Art

Cellular therapy is emerging as a powerful paradigm for delivering complex signals for biological action. In contrast to small molecule and biologic drug compositions, cells have the potential to execute unique therapeutic tasks owing to their myriad sensory and response programs and increasingly defined mechanisms of genetic control. To achieve such therapeutic value, cells need to be outfitted with machinery for sensing and integrating chemical and/or biological information associated with local physiological environments.

The most clinically advanced example of engineered sensory-response machinery is chimeric antigen receptors (CARs) in genetically engineered T cells for use in adoptive cellular immunotherapy (see June et al., *Nat. Biotechnol.* 30:611, 2012; Restifo et al., *Nat. Rev. Immunol.* 12:269, 2012). Antigen binding stimulates the signaling domains on the intracellular segment of the CAR, thereby transducing signals that unleash inflammatory and cytotoxicity mechanisms. CAR-based adoptive cellular immunotherapy has been used to treat cancer patients with tumors refractory to conventional standard-of-care treatments (see Grupp et al., *N. Engl. J. Med.* 368:1509, 2013; Kalos et al., *Sci. Transl. Med.* 3:95ra73, 2011).

In addition to targeting and initiating T cell activation, an effective adoptive cellular immunotherapy would preferably also modulate T cell expansion and persistence, as well as the strength and quality of T cell signaling. But, current CAR-mediated T cell responses do not realize the full potential of T cell activation and proliferation. Improvement of CAR function has been achieved by including costimulatory signaling domains into the CAR structure (see, e.g., Kowolik et al., *Cancer Res.* 66:10995, 2006; Milone et al., *Mol. Ther.* 17:1453, 2009; Pule et al., *Mol. Ther.* 12:933, 2005; Carpenito et al., *Proc. Nat'l Acad. Sci. U.S.A.* 106: 3360, 2009), but the clinical results have been mixed (see, e.g., Brentjens et al., *Blood* 118:4817; 2011; Till et al., *Blood* 119:3940, 2012; Kochenderfer and Rosenberg, *Nat. Rev. Clin. Oncol.* 10:267, 2013). Others have included, in addition to a CAR, co-expression of costimulatory ligands (see, e.g., Stephan et al., *Nat. Med.* 13:1440, 2007), costimulatory receptors (see, e.g., Duong et al., *Immunother.* 3:33, 2011; Wilkie et al., *J. Clin. Immunol.* 32:1059, 2012), and cytokines (see, e.g., Hsu et al., *J. Immunol.* 175:7226, 2005; Quintarelli et al., *Blood* 110:2793, 2007).

A concern with the use of CARs is toxicity, which arises in two forms: one is the targeted destruction of normal tissue and the second is cytokine-release associated adverse events (e.g., cytokine storm). For example, collateral damage observed with CD19-targeted CARs is B-cell aplasia (Kalos et al., 2011; Kochenderfer et al., *Blood* 119:2709, 2012). Such off-target effects could be very dangerous, particularly if the target antigen is found on other tissues, such as the heart or lung. The cytokine storms associated with large numbers of activated T cells can be life threatening (Kalos et al., 2011; Kochenderfer et al., 2012). Unlike conventional drug treatments where reducing drug dosage can control toxicity, the proliferation of T cells cannot be controlled with current CAR technologies and, therefore, immunopathology will result once a threshold level of T cells is reached.

In view of the limitations associated with CAR-mediated T cell responses, there is a need in the art for alternative compositions and methods useful for immunotherapy in which modulation of immune cell signal initiation and expansion is controllable. The present disclosure meets such needs, and further provides other related advantages.

SUMMARY OF THE INVENTION

The present disclosure describes non-natural cell compositions having signal transduction systems that are controlled—both in their activation and deactivation—by pharmacological agents. Numerous pharmacologically controlled, multipartite signal transduction systems are contemplated herein.

In various embodiments, a non-natural cell is provided, comprising: a first nucleic acid molecule encoding a first fusion protein comprising a first multimerization domain, a hydrophobic domain, and an actuator domain, wherein the first multimerization domain localizes extracellularly when the first fusion protein is expressed; and a second nucleic acid molecule encoding a second fusion protein comprising a binding domain and a second multimerization domain, wherein the second fusion protein localizes extracellularly when expressed; wherein a first bridging factor promotes the formation of a polypeptide complex on the non natural cell surface with the bridging factor associated with and disposed between the multimerization domains of the first and second fusion proteins.

In a particular embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a further embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a certain embodiment, the first multimerization domain comprises a first FKBP polypeptide or variant thereof, and the second multimerization domain comprises a first FRB polypeptide or variant thereof.

In a particular embodiment, the first multimerization domain comprises a first FRB polypeptide or variant thereof, and the second multimerization domain comprises a first FKBP polypeptide or variant thereof.

In one embodiment, the bridging factor is sirolimus, everolimus, novolimus, pimecrolimus, ridaforolimus, tacrolimus, temsirolimus, umirolimus, or zotarolimus.

In an additional embodiment, the first nucleic acid molecule encodes a first fusion protein further comprising a third multimerization domain.

In a further embodiment, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In a particular embodiment, a second bridging factor promotes the association of at least two first fusion proteins with the bridging factor associated with and disposed between the third multimerization domains of the first fusion proteins.

In a particular embodiment, the protein complex is a homocomplex comprising at least two first fusion proteins.

In a further embodiment, the first fusion protein has at least one multimerization domain of FKBP, DHFR or GyrB.

In a certain embodiment, the binding domain of the polypeptide complex specifically binds to a target located on a target cell surface.

In an additional embodiment, the protein complex is a heterocomplex comprising one or more first fusion proteins and one or more second fusion proteins.

In an additional embodiment, the binding domain of the protein heterocomplex specifically binds to a target located on a target cell surface.

In a particular embodiment, the hydrophobic domain is a transmembrane domain.

In another particular embodiment, the transmembrane domain is a CD4, CD8 or CD28 transmembrane domain.

In one embodiment, the actuator domain comprises a lymphocyte receptor signaling domain.

In a certain embodiment, the actuator domain comprises one or a plurality of immunoreceptor tyrosine-based activation motifs (ITAMs).

In a certain embodiment, the actuator domain comprises CD3ε, CD3δ, CD3ζ, pTα, TCRα, TCRβ, FcRα, FcRβ, FcRγ, NKG2D, CD22, CD79A, or CD79B, or any combination thereof.

In a particular embodiment, the first nucleic acid molecule encodes the first fusion protein further comprising a different actuator domain, a costimulatory domain, an adhesion factor, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In a particular embodiment, the actuator domain comprises a cytoplasmic portion that associates with a cytoplasmic signaling protein.

In one embodiment, the cytoplasmic signaling protein is a lymphocyte receptor or signaling domain thereof, a protein comprising a plurality of immunoreceptor tyrosine-based activation motifs (ITAMs), a costimulatory domain, an adhesion factor, or any combination thereof.

In an additional embodiment, the lymphocyte receptor or signaling domain thereof is CD3ε, CD3δ, CD3ζ, pTα, TCRα, TCRβ, FcRα, FcRβ, FcRγ, NKG2D, CD22, CD79A, or CD79B, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In a particular embodiment, a non-natural cell overexpresses a costimulatory factor, an immunomodulatoy factor, an agonist for a costimulatory factor, an agonist for an immunomodulatoy factor, or any combination thereof.

In one embodiment, the second nucleic acid molecule further encodes a secretion signal such that the second fusion protein is secreted from the non natural cell when expressed, and optionally further encodes an anchor domain.

In a certain embodiment, the binding domain of the second fusion protein is a single chain antibody variable region, a receptor ectodomain, or a ligand.

In an additional embodiment, the single chain antibody variable region is a domain antibody, sFv, scFv, F(ab')2, or Fab.

In a particular embodiment, the binding domain of the second fusion protein is amino terminal to the multimerization domain.

In one embodiment, the binding domain of the second fusion protein is carboxy terminal to the multimerization domain.

In a further embodiment, the second nucleic acid molecule encoding the second fusion protein further comprises a sequence encoding a linker disposed between the binding domain and the second multimerization domain.

In a particular embodiment, the cell further comprises a third nucleic acid molecule encoding a third fusion protein comprising a binding domain and a second multimerization domain, wherein the third fusion protein localizes extracellularly when expressed.

In a related particular embodiment, the fusion proteins comprising a binding domain have one, two, three, or four binding domains.

In an additional embodiment, the one, two, three, or four binding domains are specific for one target or up to four different targets.

In a certain embodiment, the binding domain is specific for a target that is an antigen associated with a cancer, an inflammatory disease, an autoimmune disease, or a graft versus host disease.

In a particular embodiment, the cancer is a solid malignancy or a hematologic malignancy.

In an additional embodiment, the hematologic malignancy associated antigen target is CD19, CD20, CD22, CD33, or CD37.

In one embodiment, the binding domain specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R☐, IL13R-α2, KDR, κ light chain, λ light chain, LeY, L1CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a certain embodiment, the first bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In one embodiment, the second bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a further embodiment, the encoded first fusion protein comprises a first multimerization domain of FRB T2098L, a transmembrane domain, a costimulatory domain of 4-1BB, and actuator domain of CD3ζ; wherein the second encoded fusion protein comprises a binding domain of an scFv specific for CD19 and a second multimerization domain of FKBP12; and wherein the first bridging factor that promotes the formation of a polypeptide complex on the non natural cell surface is rapalog AP21967.

In a particular embodiment, the first fusion protein has an amino acid sequence as set forth in SEQ ID NO.:15 and the second fusion protein has an amino acid sequence as set forth in SEQ ID NO.:1.

In various embodiments, a method for treating a hyperproliferative, inflammatory, autoimmune, or graft-versus-host disease is provided, comprising: administering a recombinant cell comprising a first and a second nucleic acid molecule, wherein the first nucleic acid molecule encodes a first fusion protein comprising a first multimerization domain, a hydrophobic domain, and an actuator domain, wherein the first multimerization domain localizes extracellularly when the first fusion protein is expressed, and the second nucleic acid molecule encodes a second fusion protein comprising a binding domain and a second multimerization domain, wherein the second fusion protein localizes extracellularly when expressed; and administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative, inflammatory, autoimmune, or graft-versus-host disease cell to promote an immunomodulatory response and thereby treats the hyperproliferative, inflammatory, autoimmune, or graft-versus-host disease.

In various embodiments, a method for treating a hyperproliferative, inflammatory, autoimmune, or graft-versus-host disease, comprising: administering a non-natural cell comprising a first nucleic acid molecule encoding a first fusion protein comprising a first multimerization domain, a hydrophobic domain, and an actuator domain, wherein the first multimerization domain localizes extracellularly when the first fusion protein is expressed; administering a second fusion protein comprising a binding domain and a second multimerization domain; and administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative, inflammatory, autoimmune, or graft-versus-host disease cell to promote an immunomodulatory response and thereby treats the hyperproliferative, inflammatory, autoimmune, or graft-versus-host disease.

In a further embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a particular embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a particular embodiment, the first multimerization domain comprises a first FKBP polypeptide or variant thereof, and the second multimerization domain comprises a first FRB polypeptide or variant thereof.

In one embodiment, the first multimerization domain comprises a first FRB polypeptide or variant thereof, and the second multimerization domain comprises a first FKBP polypeptide or variant thereof.

In a certain embodiment, the bridging factor is sirolimus, everolimus, novolimus, pimecrolimus, ridaforolimus, tacrolimus, temsirolimus, umirolimus, or zotarolimus.

In another certain embodiment, the first nucleic acid molecule encodes a first fusion protein further comprising a third multimerization domain.

In a particular embodiment, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In one embodiment, a second bridging factor promotes the association of at least two first fusion proteins with the bridging factor associated with and disposed between the third multimerization domains of the first fusion proteins.

In an additional embodiment, the protein complex is a homocomplex comprising at least two first fusion proteins.

In an additional embodiment, the first fusion protein has at least one multimerization domain of FKBP, DHFR or GyrB.

In a particular embodiment, the binding domain of the polypeptide complex specifically binds to a target located on a target hyperproliferative disease cell surface.

In a further embodiment, the protein complex is a heterocomplex comprising one or more first fusion proteins and one or more second fusion proteins.

In a further embodiment, the binding domain of the protein heterocomplex specifically binds to a target located on a target hyperproliferative disease cell surface.

In one further embodiment, the hydrophobic domain is a transmembrane domain.

In a particular embodiment, the transmembrane domain is a CD4, CD8 or CD28 transmembrane domain.

In another particular embodiment, the actuator domain comprises a lymphocyte receptor signaling domain.

In yet another particular embodiment, the actuator domain comprises a plurality of immunoreceptor tyrosine-based activation motifs (ITAMs).

In still yet another particular embodiment, the actuator domain comprises CD3ε, CD3δ, CD3ζ, pTα, TCRα, TCRβ, FcRα, FcRβ, FcRγ, NKG2D, CD22, CD79A, or CD79B, or any combination thereof.

In a certain embodiment, the first nucleic acid molecule encodes the first fusion protein further comprising a different actuator domain, a costimulatory domain, an adhesion factor, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In an additional embodiment, the actuator domain comprises a cytoplasmic portion that associates with a cytoplasmic signaling protein.

In one particular embodiment, the cytoplasmic signaling protein is a lymphocyte receptor or signaling domain thereof, a protein comprising one or a plurality of immunoreceptor tyrosine-based activation motifs (ITAMs), a costimulatory domain, an adhesion factor, or any combination thereof.

In a particular embodiment, the lymphocyte receptor or signaling domain thereof is CD3ε, CD3δ, CD3ζ, pTα, TCRα, TCRβ, FcRα, FcRβ, FcRγ, NKG2D, CD22, CD79A, or CD79B, or any combination thereof.

In one embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In another embodiment, the cytoplasmic signaling protein is combination of CD3ζ and 4-1BB or a combination of CD3ζ and OX40.

In yet another embodiment, the non-natural cell is further overexpressing a costimulatory factor, an immunomodulatoy factor, an agonist for a costimulatory factor, an agonist for an immunomodulatoy factor, or any combination thereof.

In a certain embodiment, the binding domain of the second fusion protein is a single chain antibody variable region, a receptor ectodomain, or a ligand.

In one certain embodiment, the single chain antibody variable region is a domain antibody, sFv, scFv, F(ab')2, or Fab.

In a particular embodiment, the binding domain of the second fusion protein is amino terminal to the multimerization domain.

In an additional embodiment, the binding domain of the second fusion protein is carboxy terminal to the multimerization domain.

In a particular embodiment, the second fusion protein further comprises a linker disposed between the binding domain and the second multimerization domain.

In an additional embodiment, the cell further comprises a third nucleic acid molecule encoding a third fusion protein comprising a binding domain and a second multimerization domain, wherein the third fusion protein localizes extracellularly when expressed.

In a certain embodiment, the fusion proteins comprising a binding domain have one, two, three, or four binding domains.

In one embodiment, the one, two, three, or four binding domains are specific for one target or up to four different targets.

In a particular embodiment, the binding domain is specific for a target that is an antigen associated with a cancer.

In a further embodiment, the cancer is a solid malignancy or a hematologic malignancy.

In a further embodiment, the hematologic malignancy associated antigen target is CD19, CD20, CD22, CD33, or CD37.

In one embodiment, the binding domain specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R□, IL13R-α2, KDR, κ light chain, λ light chain, LeY, L1 CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a particular embodiment, the first bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a particular embodiment, the second bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In an additional embodiment, the first fusion protein comprises a first multimerization domain of FRB T2098L, a transmembrane domain, a costimulatory domain of 4-1BB, and actuator domain of CD3ζ; wherein the second fusion protein comprises a binding domain of an scFv specific for CD19 and a second multimerization domain of FKBP12; and wherein the first bridging factor that promotes the formation of a polypeptide complex on the non natural cell surface is rapalog AP21967.

In one embodiment, the first fusion protein has an amino acid sequence as set forth in SEQ ID NO.:15 and the second fusion protein has an amino acid sequence as set forth in SEQ ID NO.:1.

In a particular embodiment, the method further comprises administering an agent that antagonizes or blocks an inhibitor of T-cell activation.

In a further embodiment, the agent antagonizes or blocks a T-cell ligand.

In a particular embodiment, the agent antagonizes or blocks a T-cell receptor.

In an additional embodiment, the agent that antagonizes or blocks an inhibitor of T-cell activation is an anti-PD1 antibody or antigen binding fragment thereof, anti-PD-L1 antibody or antigen binding fragment thereof, or an anti CTLA4 antibody or antigen binding fragment thereof or an engineered homing endonuclease that targets PD-1.

In a particular embodiment, the method further comprises administering a cytokine agonist.

In various embodiments, a fusion polypeptide heterocomplex is provided, comprising: a first fusion protein comprising a first multimerization domain, a hydrophobic domain, and an actuator domain; a second fusion protein comprising an extracellular binding domain and second multimerization domain; and a bridging factor; wherein the first fusion protein, second fusion protein, and bridging factor associate to form a polypeptide heterocomplex with the bridging factor associated with and disposed between the multimerization domains of the first and second fusion proteins.

In one embodiment, the binding domain is a single chain antibody variable region, a receptor ectodomain, or a ligand.

In a further embodiment, the single chain antibody variable region is a domain antibody, sFv, scFv, F(ab')2, or Fab.

In one embodiment, the binding domain is amino terminal to the multimerization domain.

In a particular embodiment, the binding domain is carboxy terminal to the multimerization domain.

In a particular embodiment, the first multimerization domain comprises a first FKBP polypeptide or variant thereof, and the second multimerization domain comprises a first FRB polypeptide or variant thereof.

In a certain embodiment, the first multimerization domain comprises a first FRB polypeptide or variant thereof, and the second multimerization domain comprises a first FKBP polypeptide or variant thereof.

In an additional embodiment, the hydrophobic domain is a transmembrane domain.

In a certain embodiment, the actuator domain comprises a lymphocyte receptor chain.

In one embodiment, the bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In an additional embodiment, the second fusion protein further comprises an anchor domain.

In a particular embodiment, the anchor domain is a transmembrane domain.

In a further embodiment, the second fusion protein further comprises a sub-threshold signaling domain.

In a particular embodiment, the anchor domain is a GPI signal sequence.

In one embodiment, the GPI signal sequence has been altered and the second fusion protein further comprises a GPI molecule.

In a further embodiment, the binding domain is specific for a target that is an antigen associated with a cancer, an inflammatory disease, an autoimmune disease, or a graft versus host disease.

In an additional embodiment, the cancer is a hematologic malignancy having an antigen target of CD19, CD20, CD22, CD33, or CD37.

In various embodiments, a nucleic acid molecule is provided that encodes any one or more of the fusion proteins contemplated herein.

In a further embodiment, the nucleic acid molecule is disposed between 5' and 3' polynucleotide sequences homologous to a genomic locus.

In various embodiments, an expression vector is provided, containing a nucleic acid contemplated herein.

In a particular embodiment, the first and second fusion proteins are encoded as a polycistronic message or as a single protein separated by a 2A peptide.

In a particular embodiment, the polycistronic message comprises an internal ribosome entry site (IRES) between the nucleotide sequences that encode the fusion proteins.

In various embodiments, a non-natural cell is provided, comprising: a first nucleic acid molecule encoding a first fusion protein comprising a binding domain that binds a receptor on a T cell and a first multimerization domain, wherein the first fusion protein is secreted from the cell; and a second nucleic acid molecule encoding a second fusion protein comprising a binding domain that binds a target located on a target cell surface and a second multimerization domain, wherein the second fusion protein is secreted from the cell; wherein a bridging factor promotes the formation of a polypeptide complex with the bridging factor associated with and disposed between the multimerization domains of the first and second fusion proteins.

In a certain embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a particular embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a further embodiment, the first multimerization domain comprises a first FKBP polypeptide or variant thereof, and the second multimerization domain comprises a first FRB polypeptide or variant thereof.

In a particular embodiment, the first multimerization domain comprises a first FRB polypeptide or variant thereof, and the second multimerization domain comprises a first FKBP polypeptide or variant thereof.

In one embodiment, the bridging factor is sirolimus, everolimus, novolimus, pimecrolimus, ridaforolimus, tacrolimus, temsirolimus, umirolimus, or zotarolimus.

In a particular embodiment, a non-natural cell further overexpresses a costimulatory factor, an immunomodulatoy factor, an agonist for a costimulatory factor, an agonist for an immunomodulatoy factor, or any combination thereof.

In a certain embodiment, the binding domain of the first fusion protein and the binding domain of the second fusion protein are each independently selected from the group consisting of: a single chain antibody variable region, a receptor ectodomain, or a ligand.

In a further embodiment, the single chain antibody variable region is a domain antibody, sFv, scFv, F(ab')2, or Fab.

In an additional embodiment, the binding domain of the first fusion protein is amino terminal to the first multimerization domain.

In one embodiment, the binding domain of the first fusion protein is carboxy terminal to the first multimerization domain.

In an additional embodiment, the binding domain of the second fusion protein is amino terminal to the second multimerization domain.

In a particular embodiment, the binding domain of the second fusion protein is carboxy terminal to the second multimerization domain.

In one embodiment, the first nucleic acid molecule encoding the first fusion protein further comprises a sequence encoding a linker disposed between the binding domain and the first multimerization domain.

In a particular embodiment, the second nucleic acid molecule encoding the second fusion protein further comprises a sequence encoding a linker disposed between the binding domain and the second multimerization domain.

In a particular embodiment, the binding domain of the second nucleic acid molecule is specific for a target that is an antigen associated with a cancer, an inflammatory disease, an autoimmune disease, or a graft versus host disease.

In a certain embodiment, the cancer is a solid malignancy or a hematologic malignancy.

In a certain embodiment, the hematologic malignancy associated antigen target is CD19, CD20, CD22, CD33, or CD37.

In one embodiment, the binding domain of the second nucleic acid molecule specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R☐, IL13R-α2, KDR, κ light chain, λ light chain, LeY, L1 CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In an additional embodiment, the bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a particular embodiment, the first nucleic acid encodes a first fusion protein comprising a binding domain of an scFv specific for CD3 and a first multimerization domain of FRB T2098L; wherein the second nucleic acid encodes a second fusion protein comprising a binding domain of an scFv specific for CD19 and a second multimerization domain of FKBP12; and wherein the bridging factor that promotes the formation of a polypeptide complex is rapalog AP21967.

In a further embodiment, the first nucleic acid encodes a first fusion protein comprising a binding domain of an scFv specific for CD3 and a first multimerization domain of FRB T2098L; wherein the second nucleic acid encodes a second fusion protein comprising a binding domain of an scFv specific for BCMA and a second multimerization domain of FKBP12; and wherein the bridging factor that promotes the formation of a polypeptide complex is rapalog AP21967.

In various embodiments, a method for treating a hyperproliferative, inflammatory, autoimmune, or graft-versus-host disease, is provided comprising: administering a non-natural cell contemplated herein and administering a bridging factor, wherein the bridging factor promotes the formation of a polypeptide complex with the bridging factor associated with and disposed between the multimerization domains of the first and second fusion proteins; wherein the binding domain of the second fusion polypeptide specifically binds a cell surface target on a hyperproliferative disease cell to promote an immunomodulatory response and thereby treats the hyperproliferative disease.

In various embodiments, a method for treating a hyperproliferative, inflammatory, autoimmune, or graft-versus-host disease, is provided comprising: administering a first fusion protein comprising a binding domain that binds a receptor on a T cell and a first multimerization domain; and a second fusion protein comprising a binding domain that binds a cell surface target on a hyperproliferative, inflammatory, autoimmune, or graft-versus-host disease cell and a second multimerization domain; and administering a bridging factor that promotes the formation of a polypeptide complex with the bridging factor associated with and disposed between the multimerization domains of the first and second fusion proteins; thereby treating the hyperproliferative, inflammatory, autoimmune, or graft-versus-host disease.

In various embodiments, a fusion polypeptide heterocomplex is provided, comprising: a first fusion protein comprising a binding domain that binds a receptor on a T cell and a first multimerization domain; a second fusion protein comprising a binding domain that binds a cell surface target on a target cell; and a bridging factor; wherein the first fusion protein, second fusion protein, and bridging factor associate to form a polypeptide heterocomplex with the bridging factor associated with and disposed between the multimerization domains of the first and second fusion proteins.

In a particular embodiment, the first and second multimerization domains are the same or different.

In a further embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a certain embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In an additional embodiment, the first multimerization domain comprises a first FKBP polypeptide or variant thereof, and the second multimerization domain comprises a first FRB polypeptide or variant thereof.

In a certain embodiment, the first multimerization domain comprises a first FRB polypeptide or variant thereof, and the second multimerization domain comprises a first FKBP polypeptide or variant thereof.

In a particular embodiment, the bridging factor is sirolimus, everolimus, novolimus, pimecrolimus, ridaforolimus, tacrolimus, temsirolimus, umirolimus, or zotarolimus.

In one embodiment, the binding domain of the first fusion protein and the binding domain of the second fusion protein are each independently selected from the group consisting of: a single chain antibody variable region, a receptor ectodomain, or a ligand.

In a further embodiment, the single chain antibody variable region is a domain antibody, sFv, scFv, F(ab')2, or Fab.

In an additional embodiment, the binding domain of the second fusion polypeptide specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R☐, IL13R-α2, KDR, κ light chain, λ light chain, LeY, L1 CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a certain embodiment, the first fusion protein comprises a binding domain of an scFv specific for CD3 and a first multimerization domain of FRB T2098L; the second fusion protein comprises a binding domain of an scFv specific for CD19 and a second multimerization domain of FKBP12; and the bridging factor is rapalog AP21967.

In a particular embodiment, the first fusion protein comprises a binding domain of an scFv specific for CD3 and a first multimerization domain of FRB T2098L; the second fusion protein comprises a binding domain of an scFv specific for BCMA and a second multimerization domain of FKBP12; and the bridging factor is rapalog AP21967.

In various embodiments, a nucleic acid molecule encoding any one or more of the fusion proteins contemplated herein is provided.

In a particular embodiment, the nucleic acid molecule is disposed between 5' and 3' polynucleotide sequences homologous to a genomic locus.

In various embodiments, an expression vector containing a nucleic acid contemplated herein is provided.

In one embodiment, the expression vector comprises the first and second fusion proteins encoded as a polycistronic message or as a single protein separated by a 2A peptide.

In another embodiment, the polycistronic message comprises an internal ribosome entry site (IRES) between the nucleotide sequences that encode the fusion proteins.

BRIEF DESCRIPTION THE DRAWINGS

Figure 5:
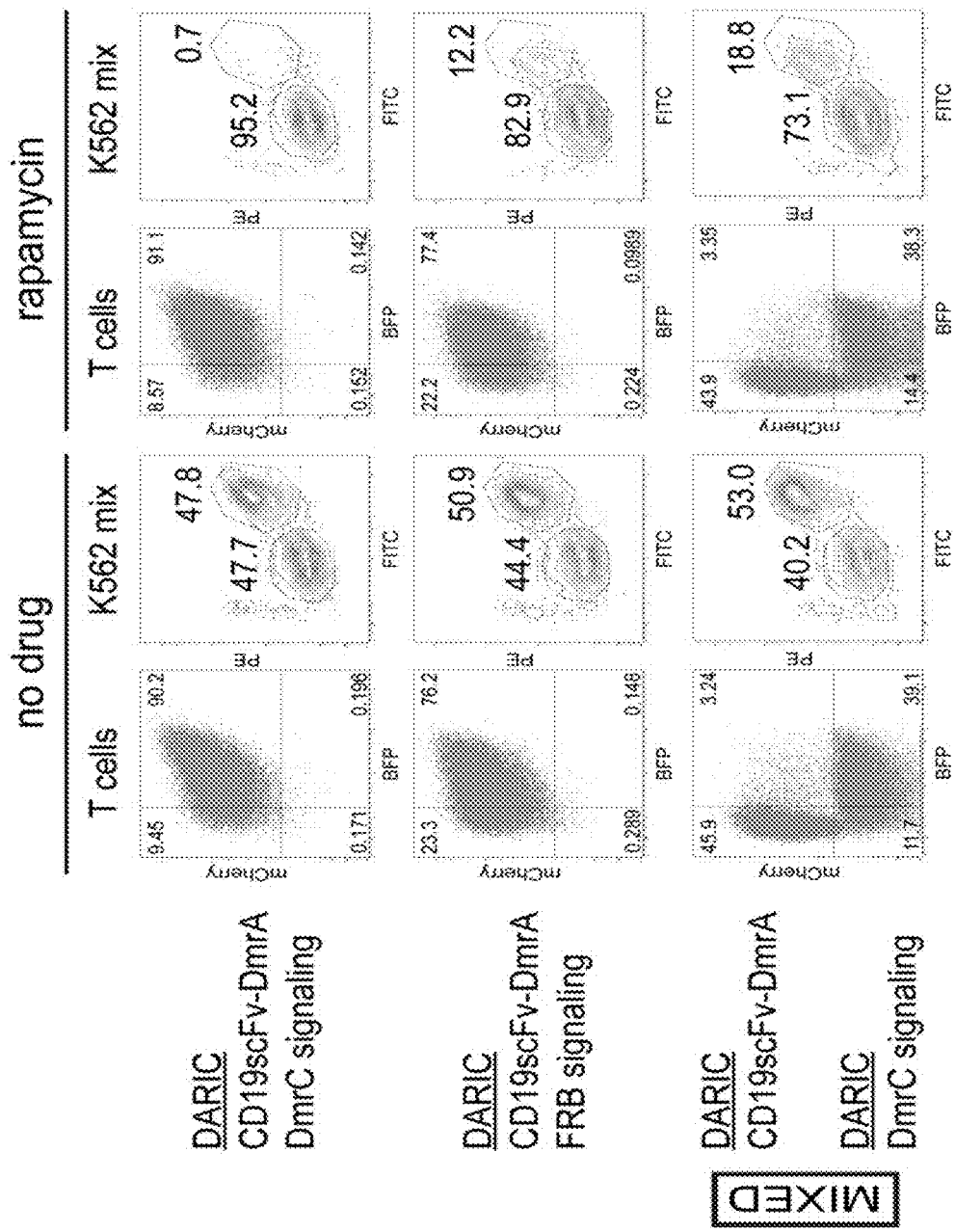
Figure 5:
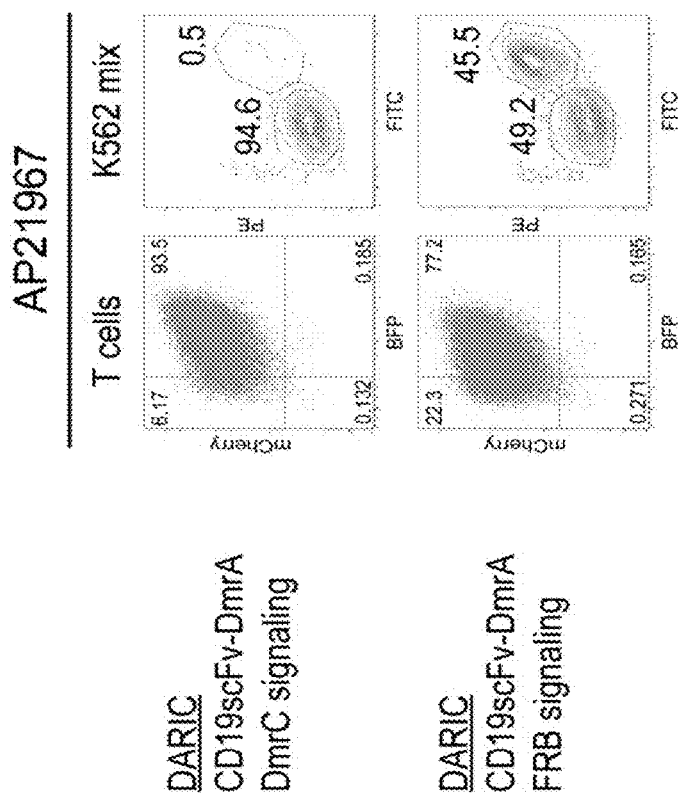

FIG. 5 shows that use of independent multimerization domains having different specificities for bridging components allows for directed cytotoxic activity of human T cells expressing a multipartite signaling complex of this disclosure. In addition, this figure shows that human T cells expressing a multipartite signaling complex of this disclosure can be cytotoxic even when the DARIC binding and signaling components are individually expressed in separate cells.

Figure 6:
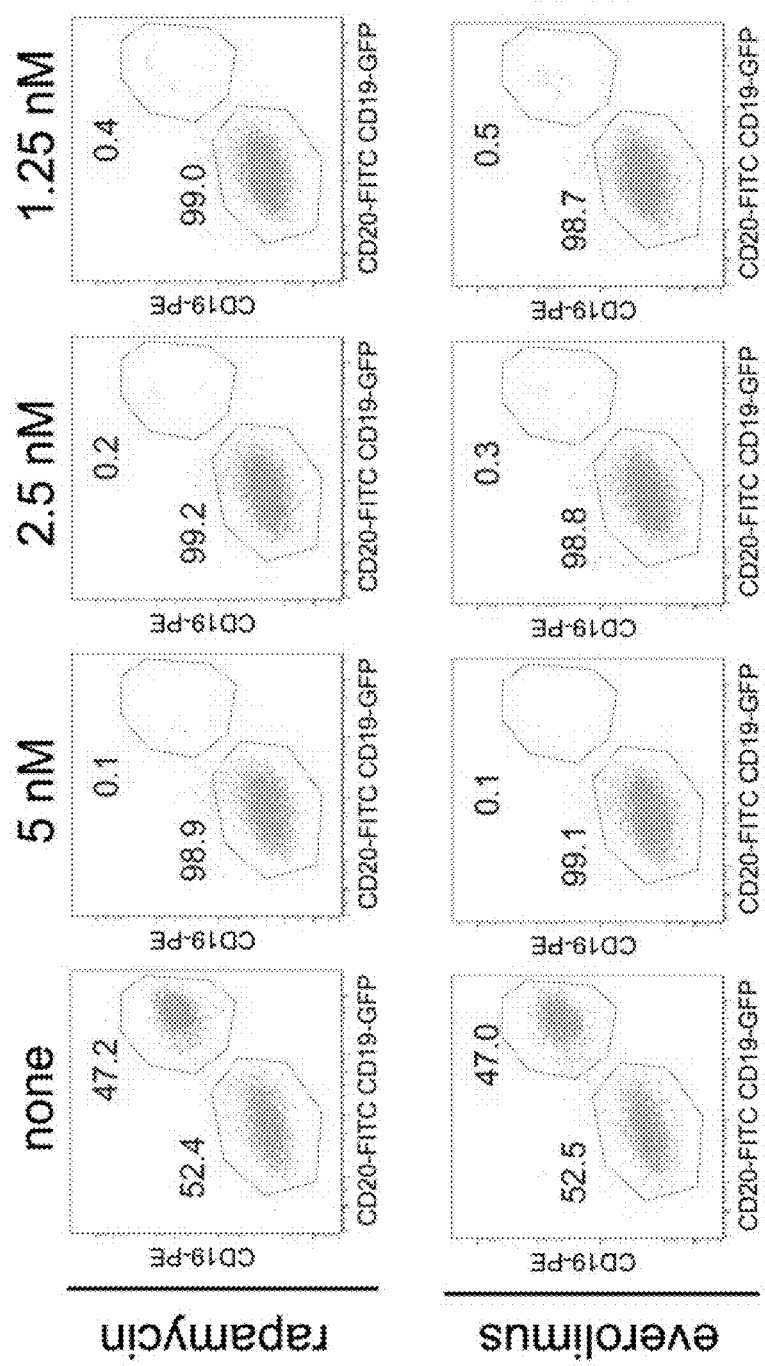
Figure 6:
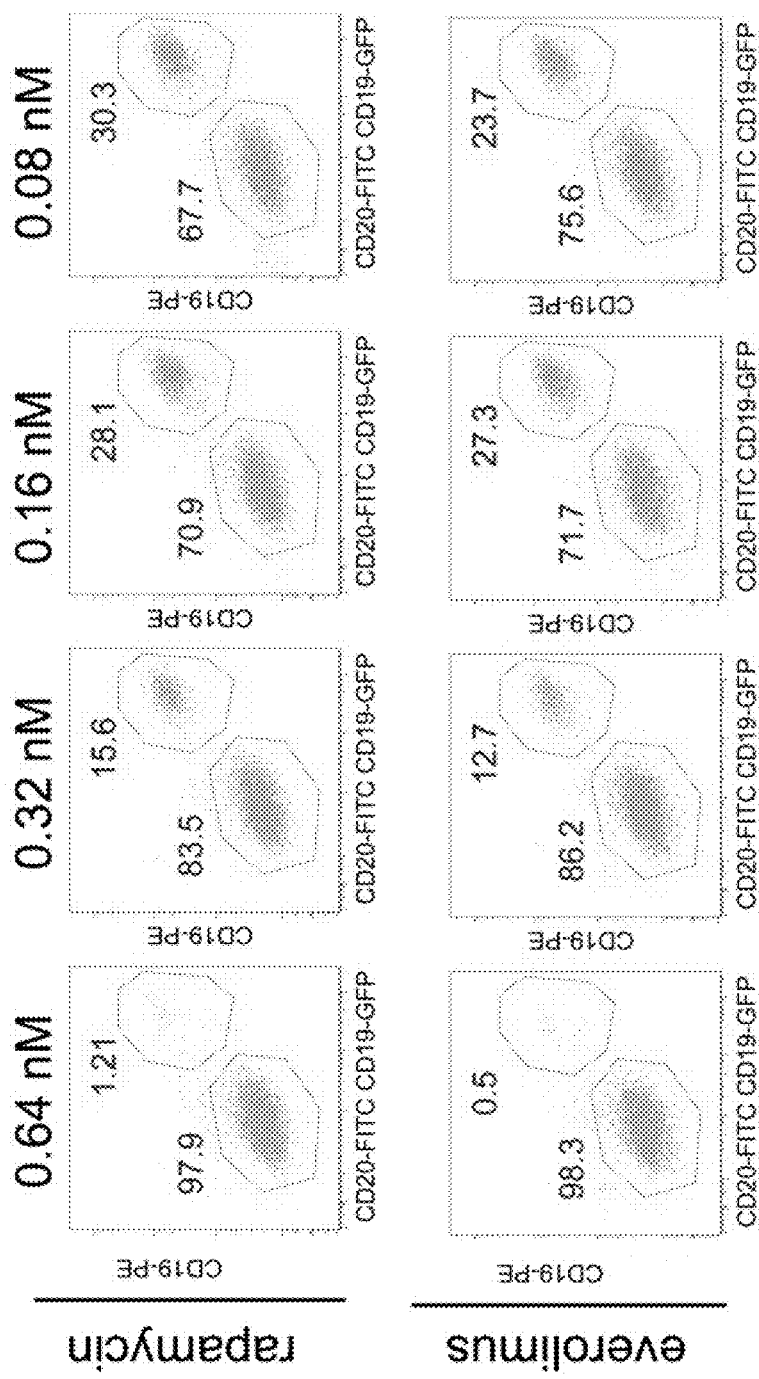

FIG. 6 shows that bridging factors can function in the DARIC system at clinically relevant concentrations.

Figure 7:
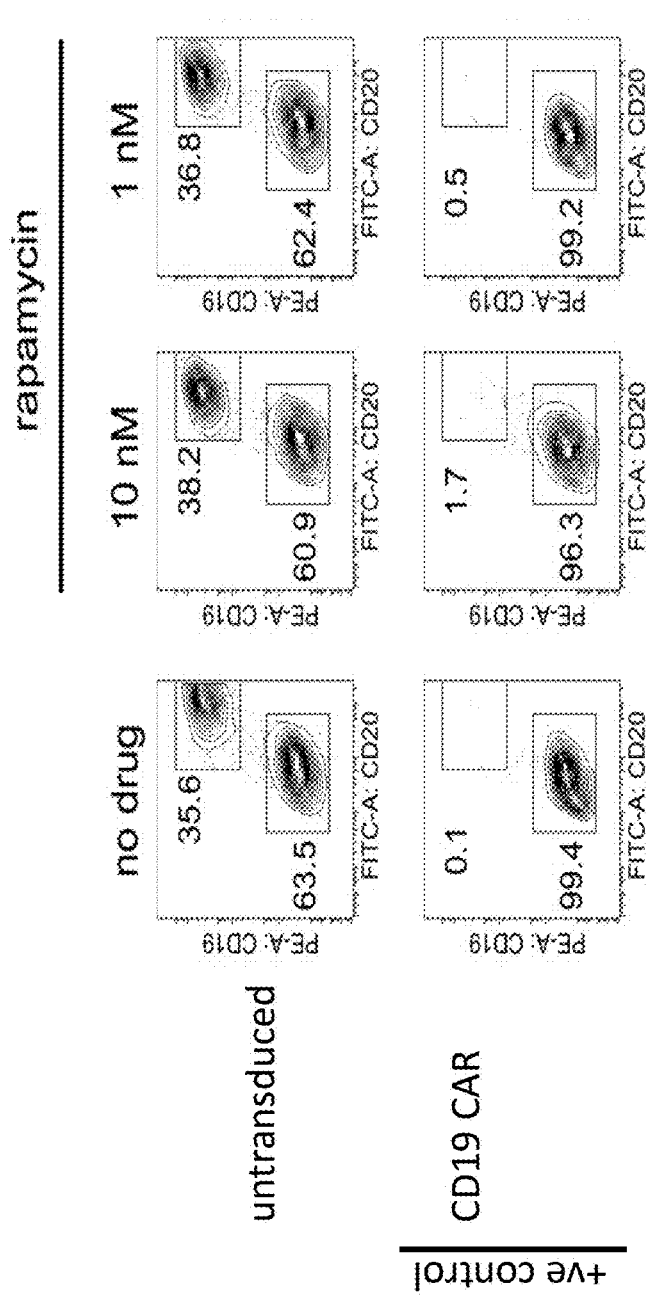
Figure 7:
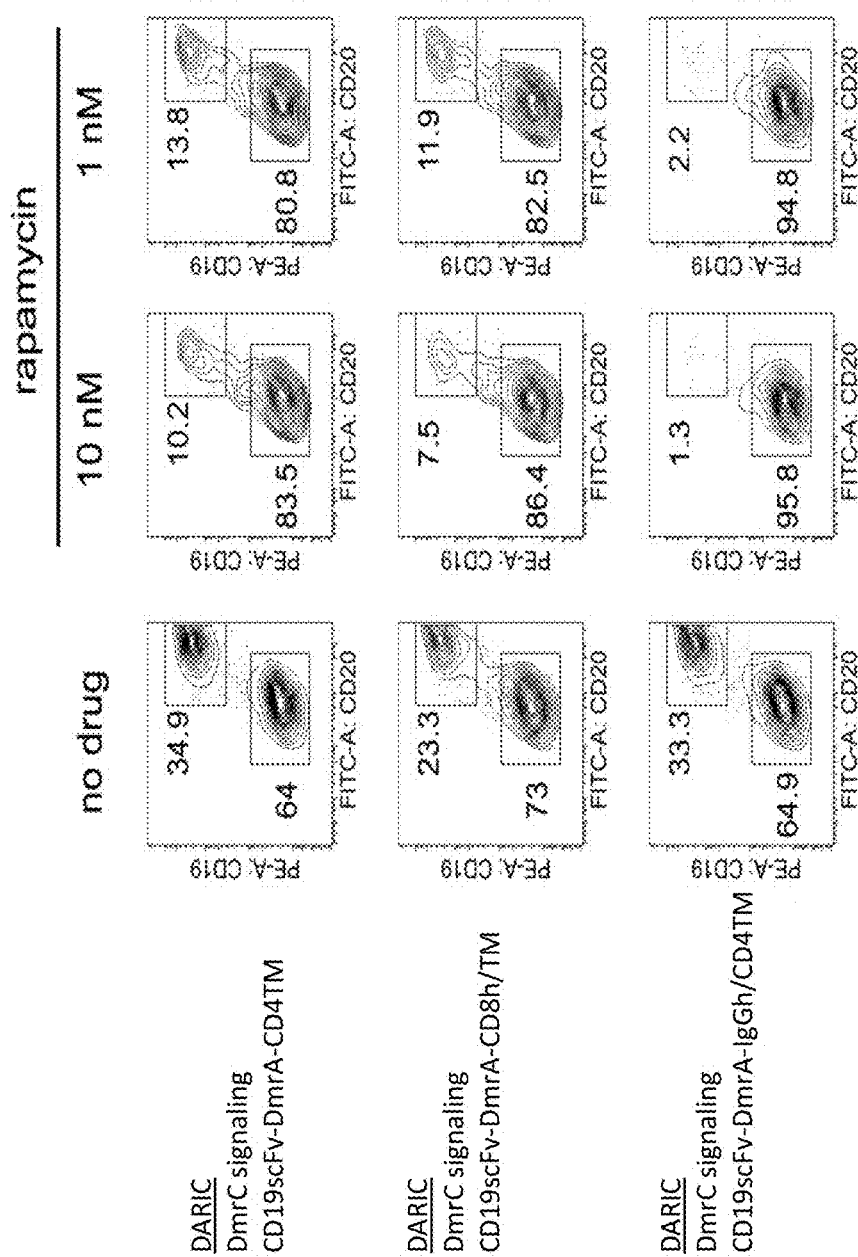

FIG. 7 shows that a DARIC binding component can be released from a cell or tethered to the cell surface and still functionally associate with a DARIC signaling component to form a multipartite signaling complex of this disclosure.

Figure 8:
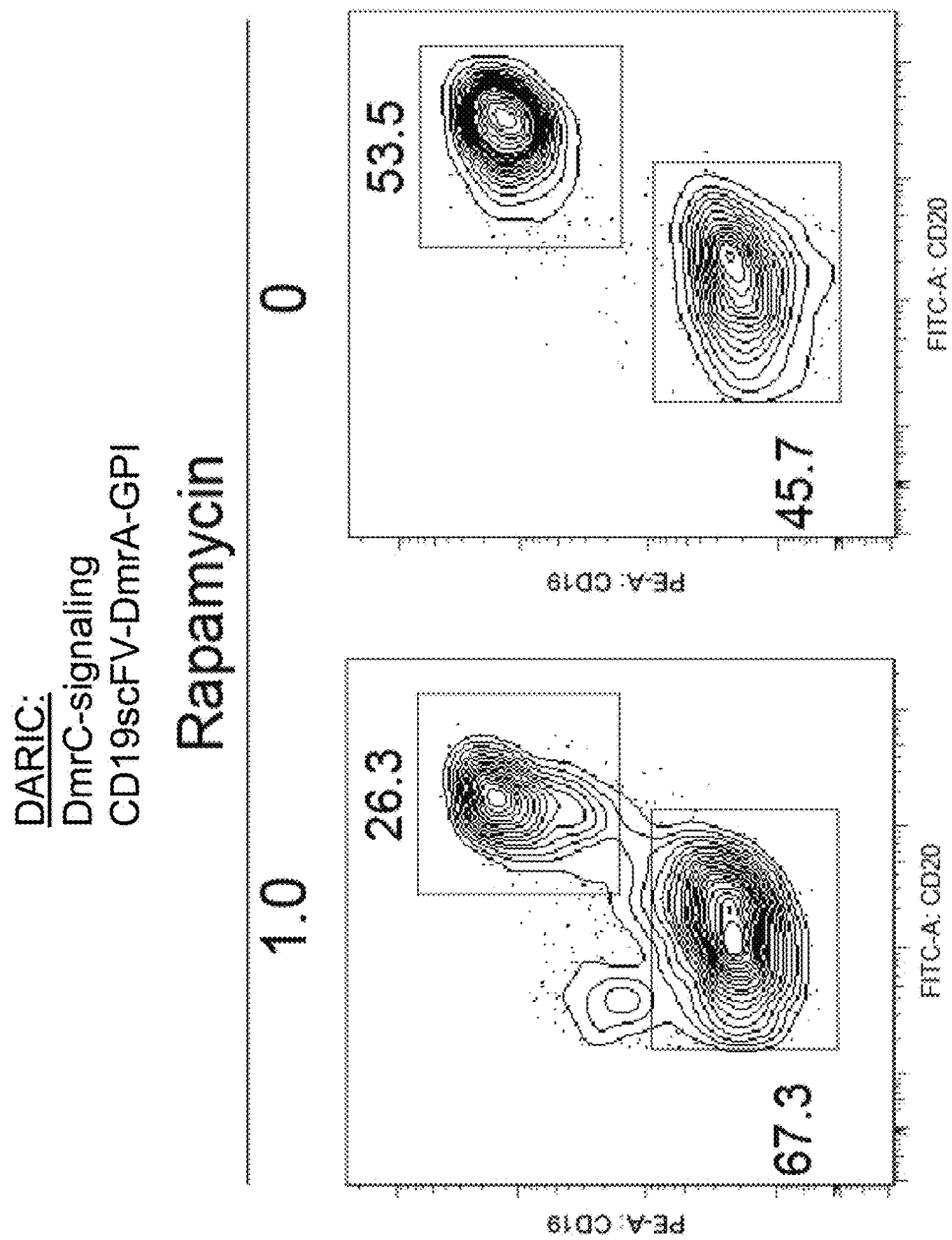

FIG. 8 shows that a DARIC binding component may be tethered to the cell surface via GPI-anchor and still functionally associate with a DARIC signaling component in the presence of a bridging factor to form a multipartite signaling complex of this disclosure.

Figure 9:
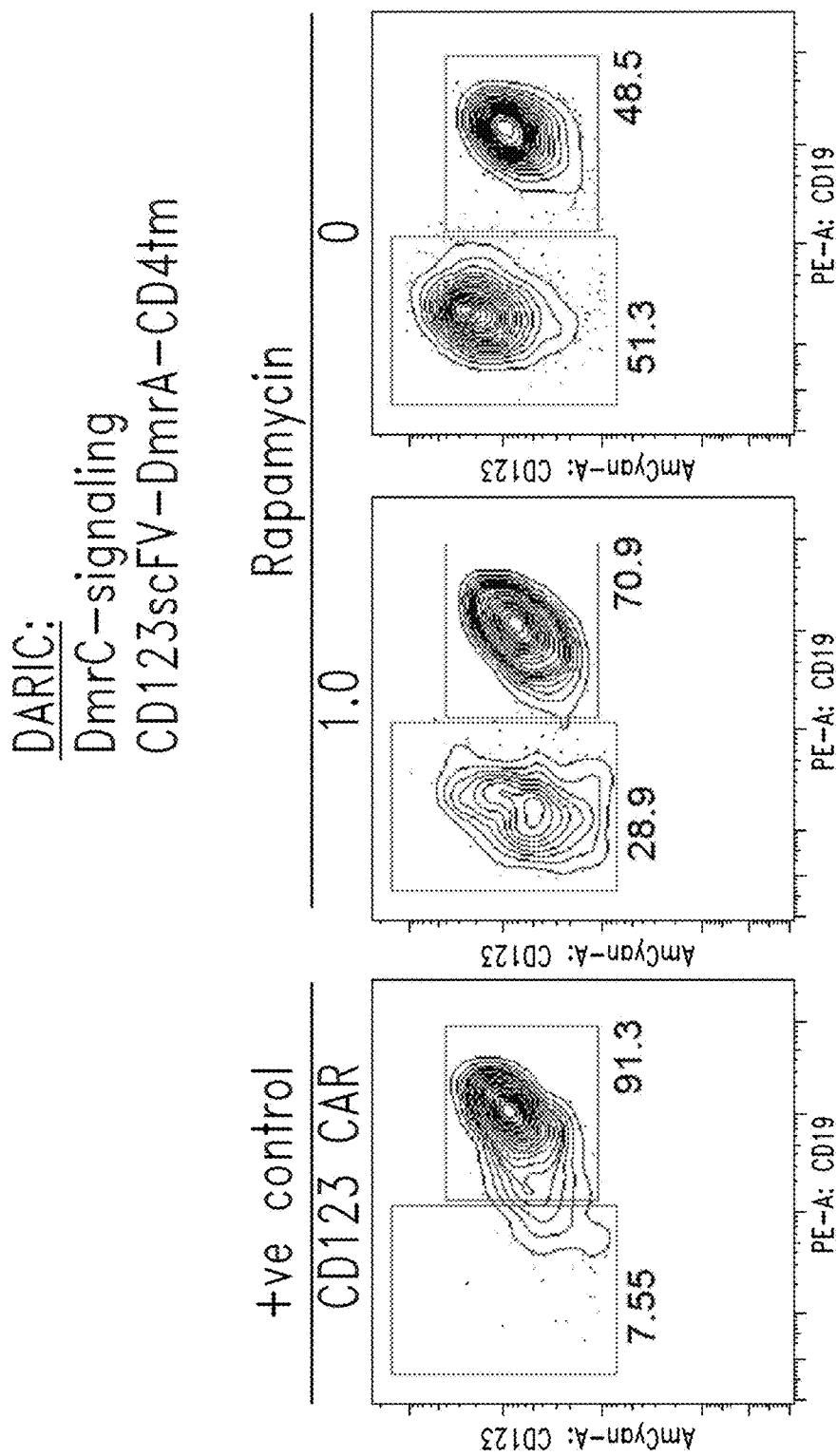

FIG. 9 shows a DARIC system targeting an additional model antigen, CD123, that may be used either to eradicate a myeloid cancer, or in a conditioning regimen to ablate myeloid cells prior to a bone marrow transplant.

Figure 10:
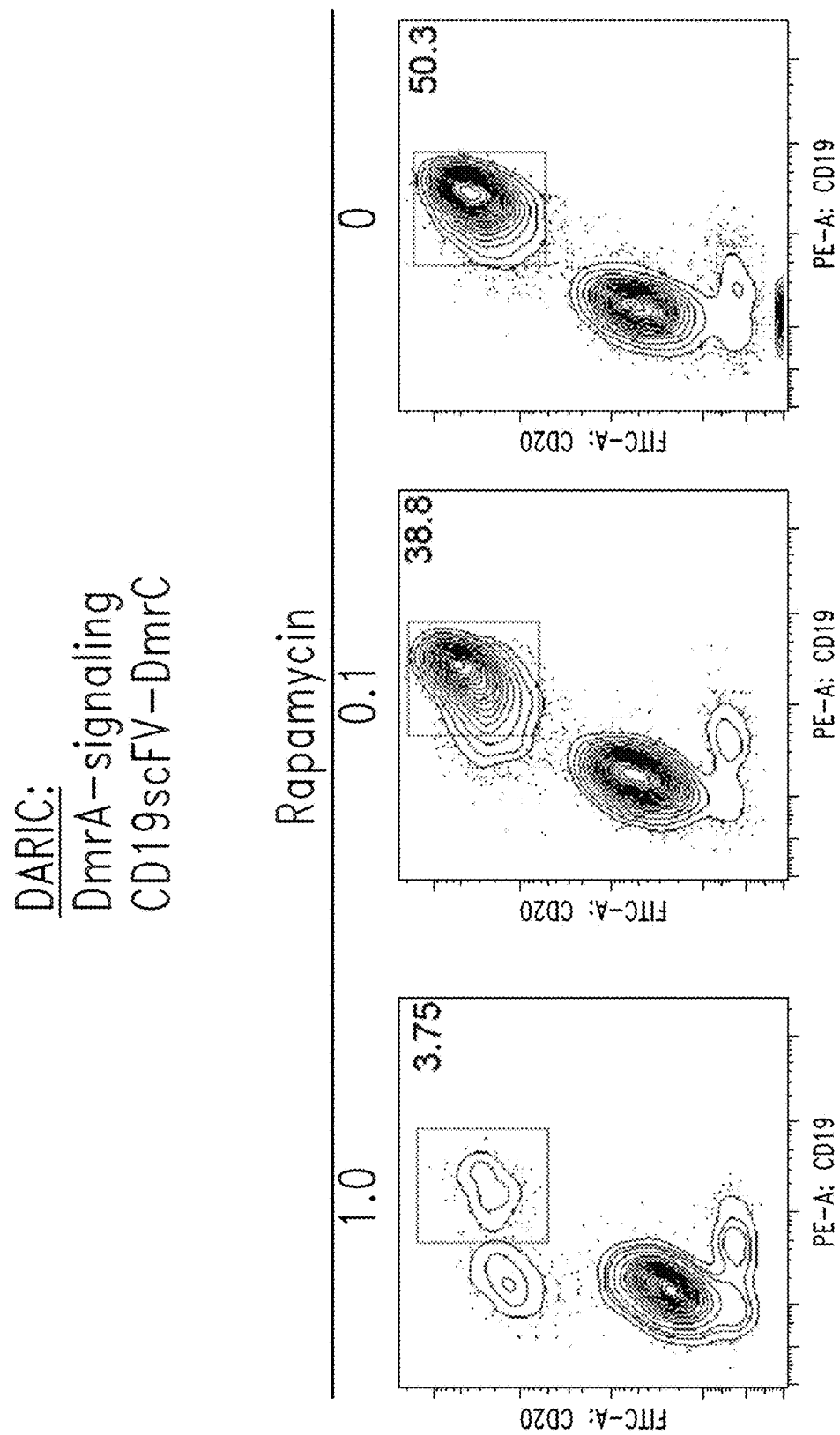

FIG. 10 shows that the FRB and FKBP12 multimerization domains may be appended to the DARIC binding component or signaling component and still form a functional multipartite signaling complex in the presence of a bridging factor.

Figure 11:
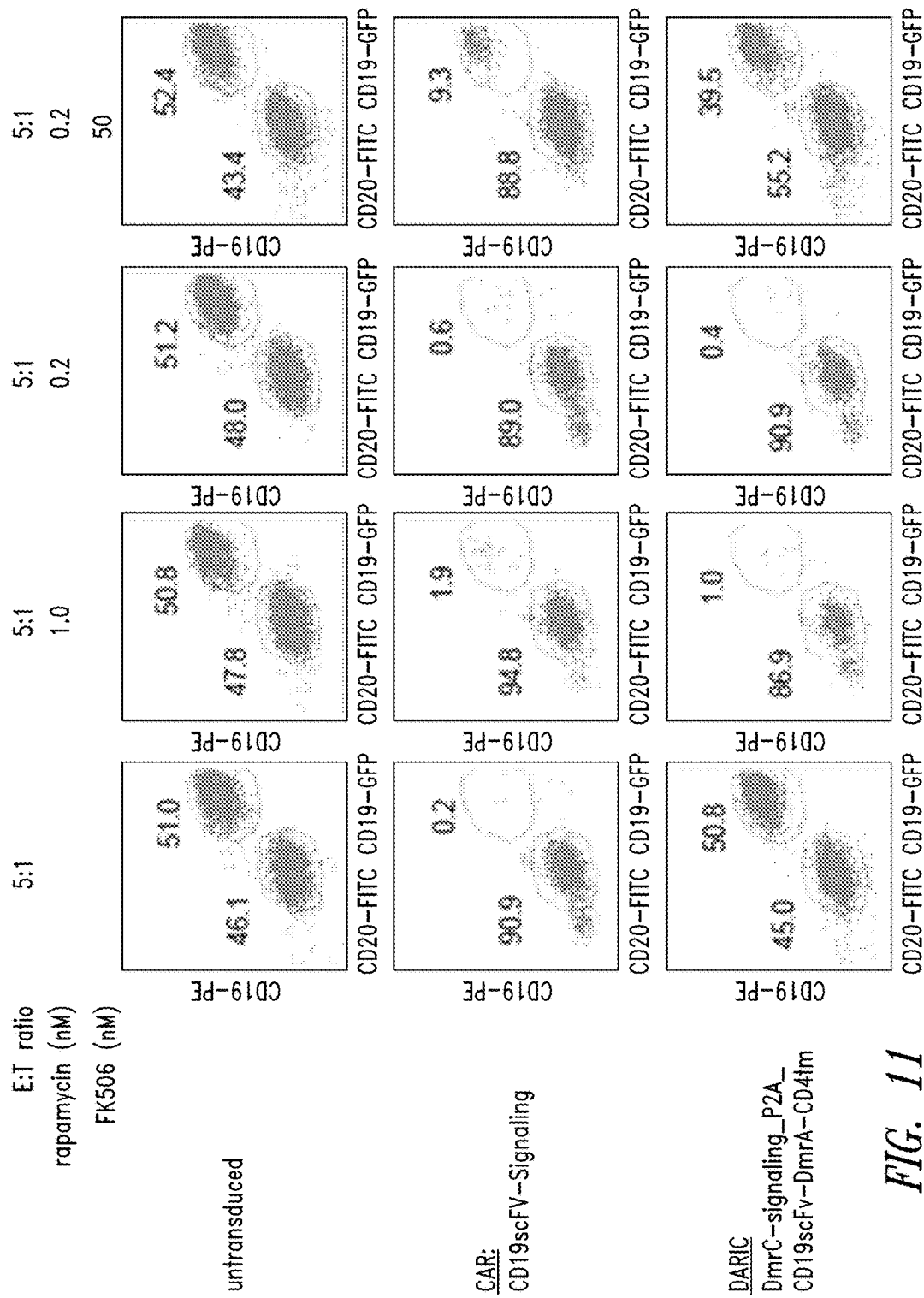

FIG. 11 shows that the coupling of the DARIC binding and signaling components can be deactivated by the addition of an anti-bridging factor, a monovalent drug that binds only to one of the multimerization domains and thereby blocks the activation of the cell.

DETAILED DESCRIPTION

In one embodiment, multi-component fusion proteins for use in modulating a biological response to immunotherapy, such as adoptive immunotherapy, are provided. By way of background, signal transduction by cell surface receptors converts extracellular information into intracellular responses and requires machinery for both ligand recognition and transmembrane signal transduction. Cell surface receptors recognize ligands through the use of an extracellular binding domain and, upon ligand binding, transduce signals across the plasma membrane via membrane spanning domains connected with intracellular signaling domains. These occur either as single-chain units, where binding and signaling are linked directly, or through multi-chain contacts whereby cell surface binding of ligand allows intracellular interactions of signaling domains with other proteins to mediate cell signal transduction.

An advantage of the compositions and methods contemplated herein is to provide both spatial and temporal control over such signal transduction binding and signaling activities. In one embodiment, this disclosure provides a binding component and a signaling component that are each expressed as separate fusion proteins, but contain an extracellular multimerization mechanism (bridging factor) for recoupling of the two functional components on a cell surface—referred to herein as DARIC binding and signaling components—which provides temporal control. Since the binding component is either secreted, expressed on the surface, or delivered in a recombinant form, it is then present in the extracellular environment without being basally coupled to any cell signal transduction machinery. The transmembrane signaling fusion protein to be expressed by the cell of interest comprises one or more intracellular signaling (actuator) domains fused via a transmembrane domain to an extracellular multimerization domain, such as a FRB or FKBP12 protein (whichever is not present on the binding component). Only upon the application of the FRB/FKBP12 coupling drug (e.g., rapamycin or a rapalog thereof) do the binding and signaling components form a complex that is capable of initiating signal transduction.

Figure 1A:
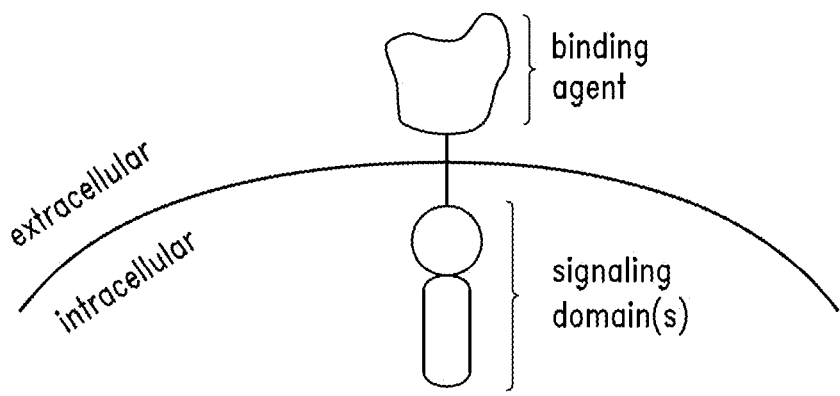
FIGS. 1A-1M show schematics of various types of multipartite signaling complexes of this disclosure.
Figure 1A:
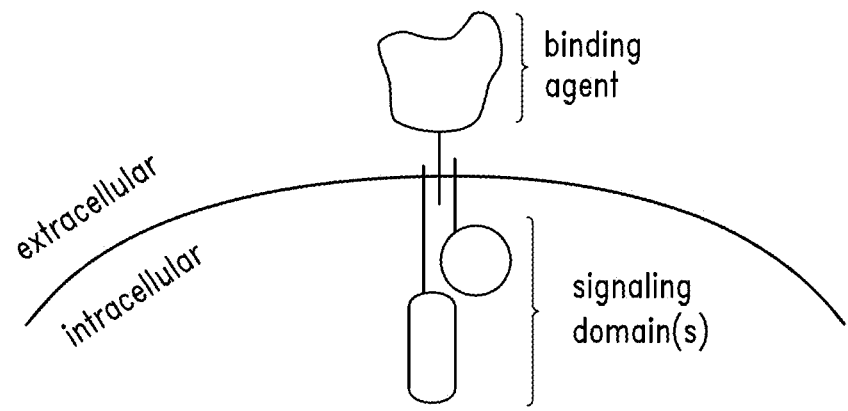
Figure 1B:
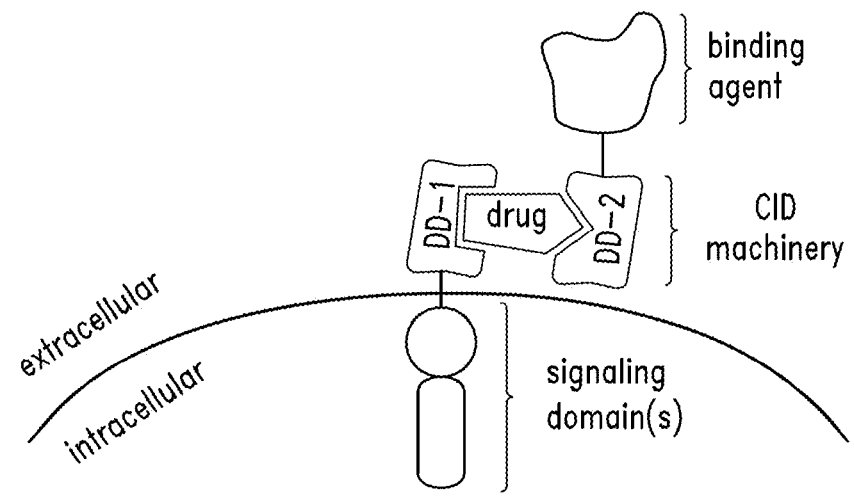
Figure 1B:
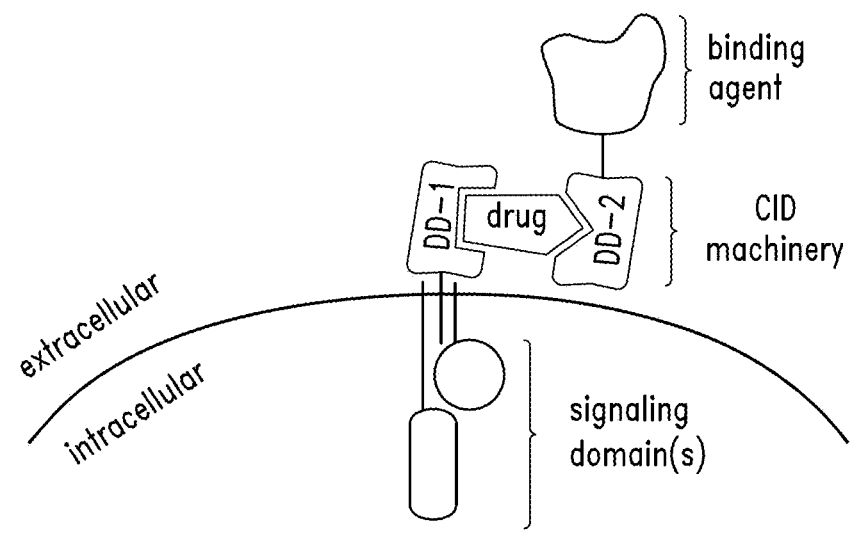
Figure 1C:
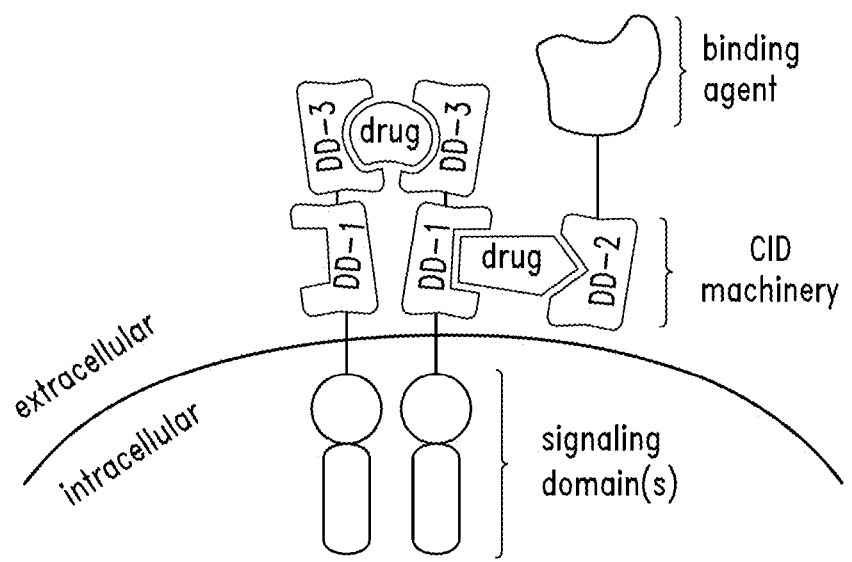
Figure 1D:
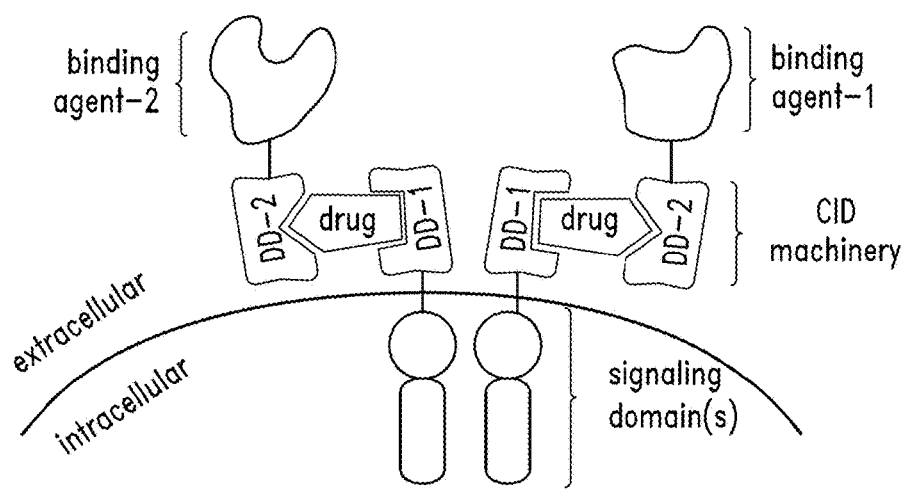
Figure 1E:
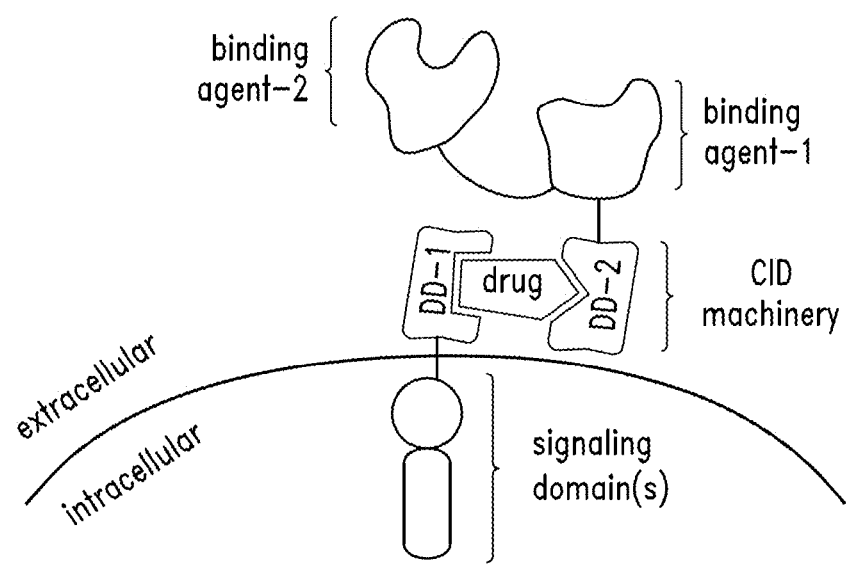
Figure 1F:
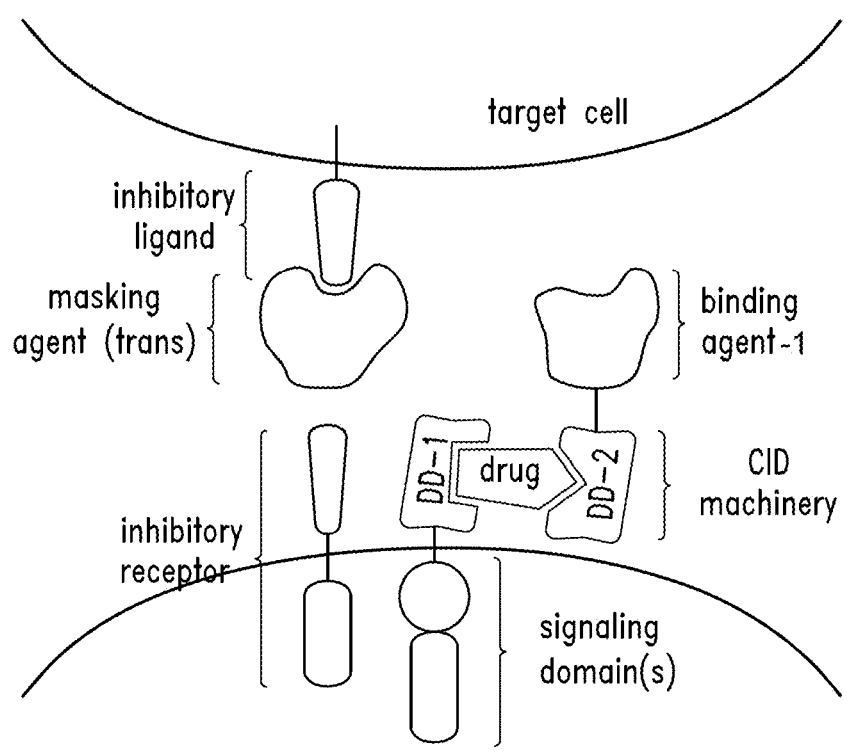
Figure 1G:
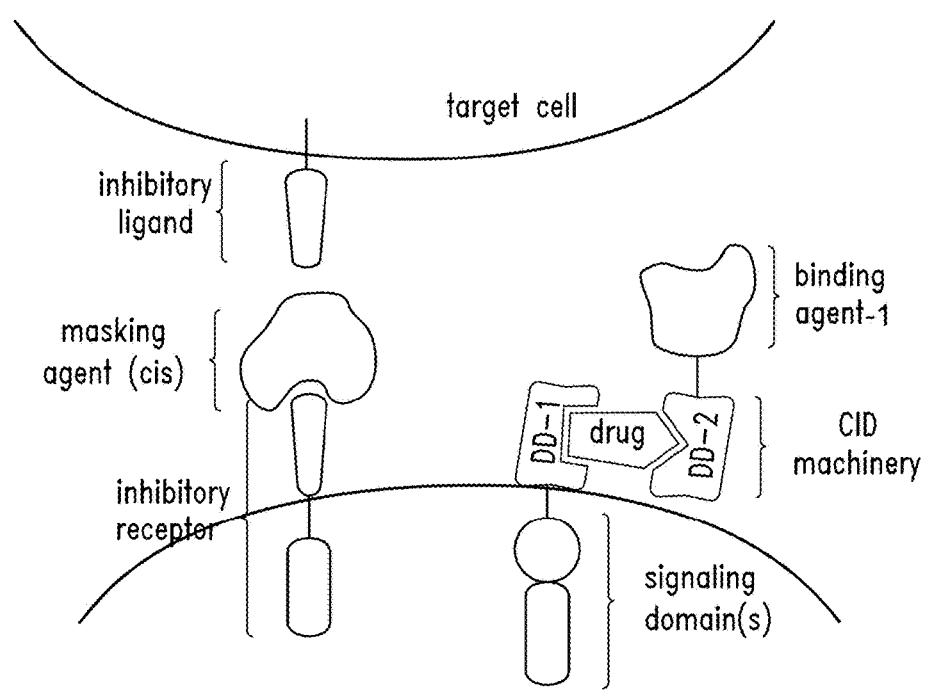
Figure 1H:
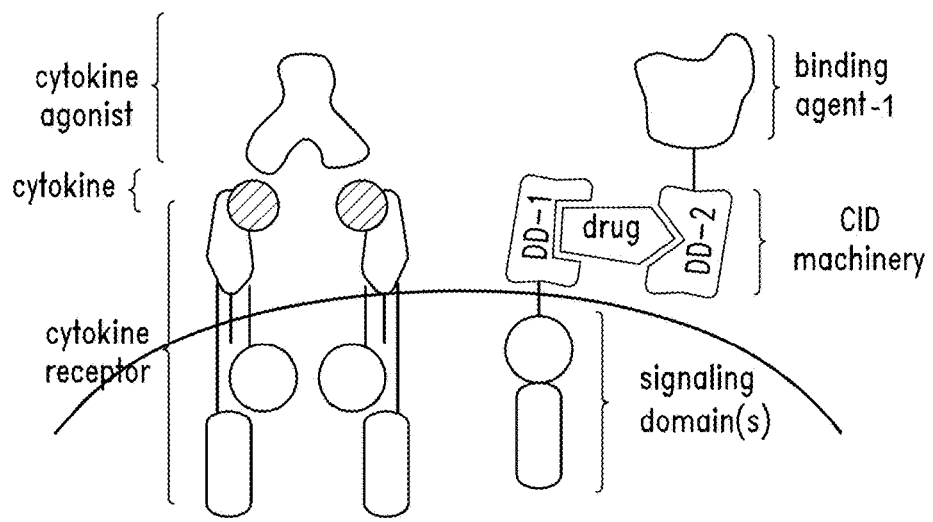
Figure 1I:
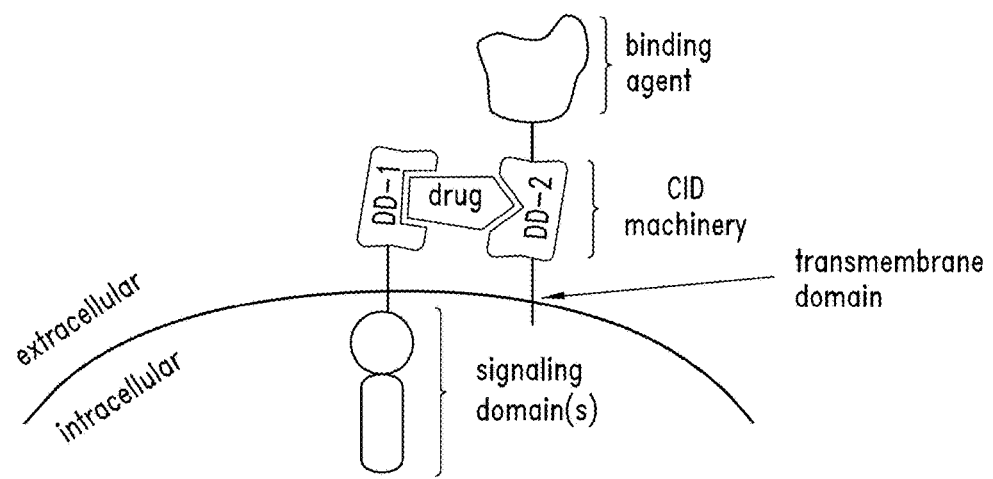
Figure 1J:
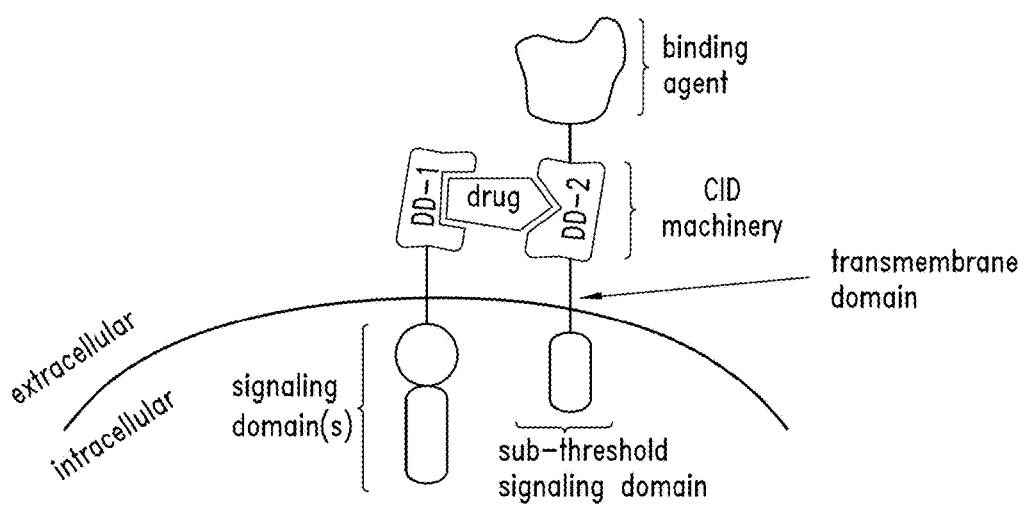
Figure 1K:
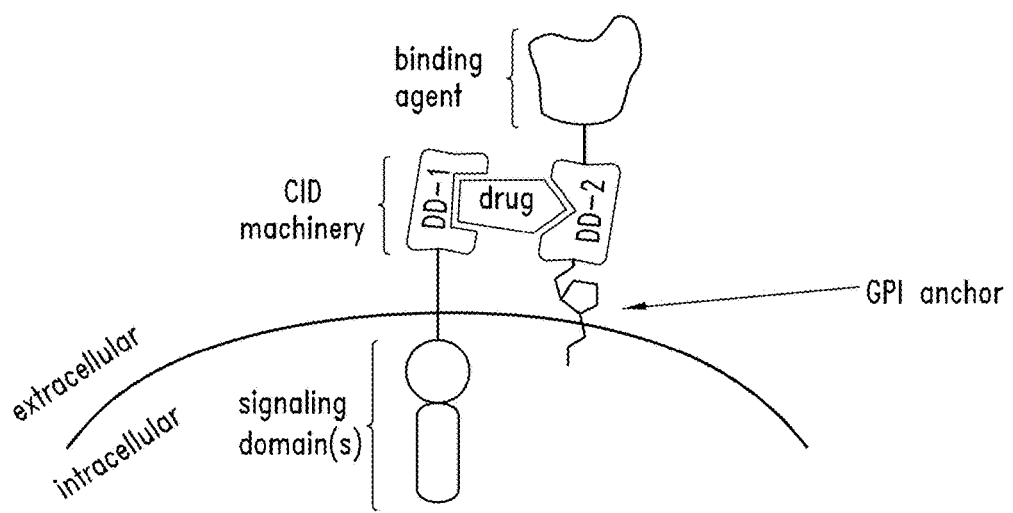
Figure 1L:
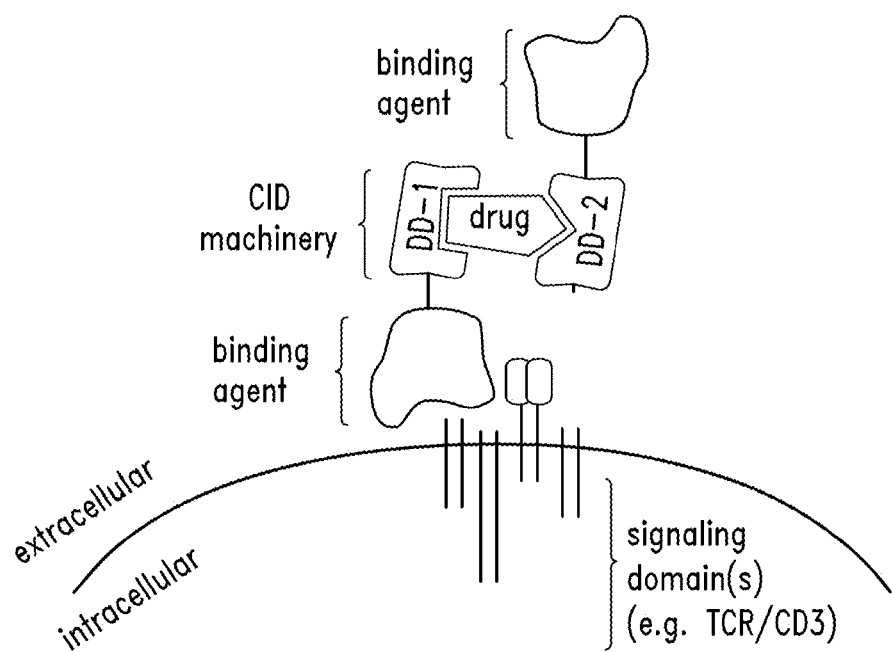
Figure 1M:
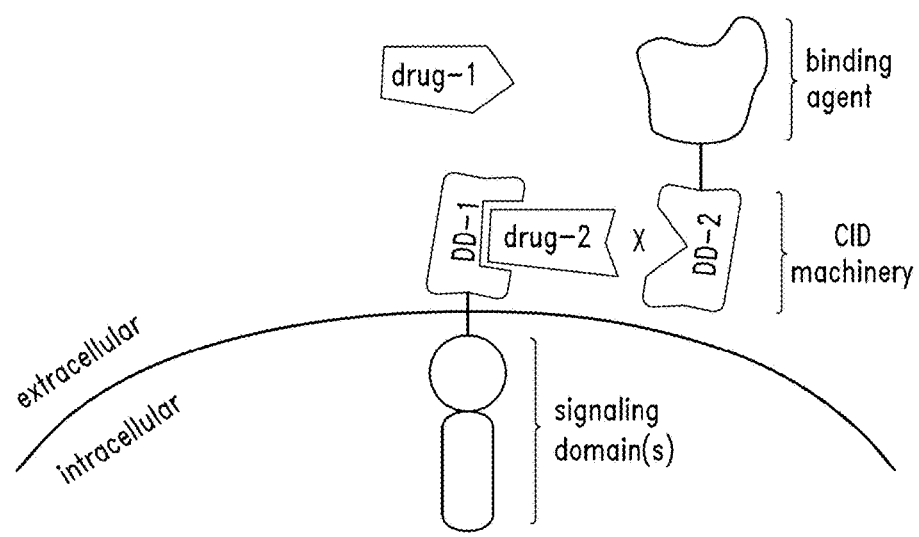
Figure 2:
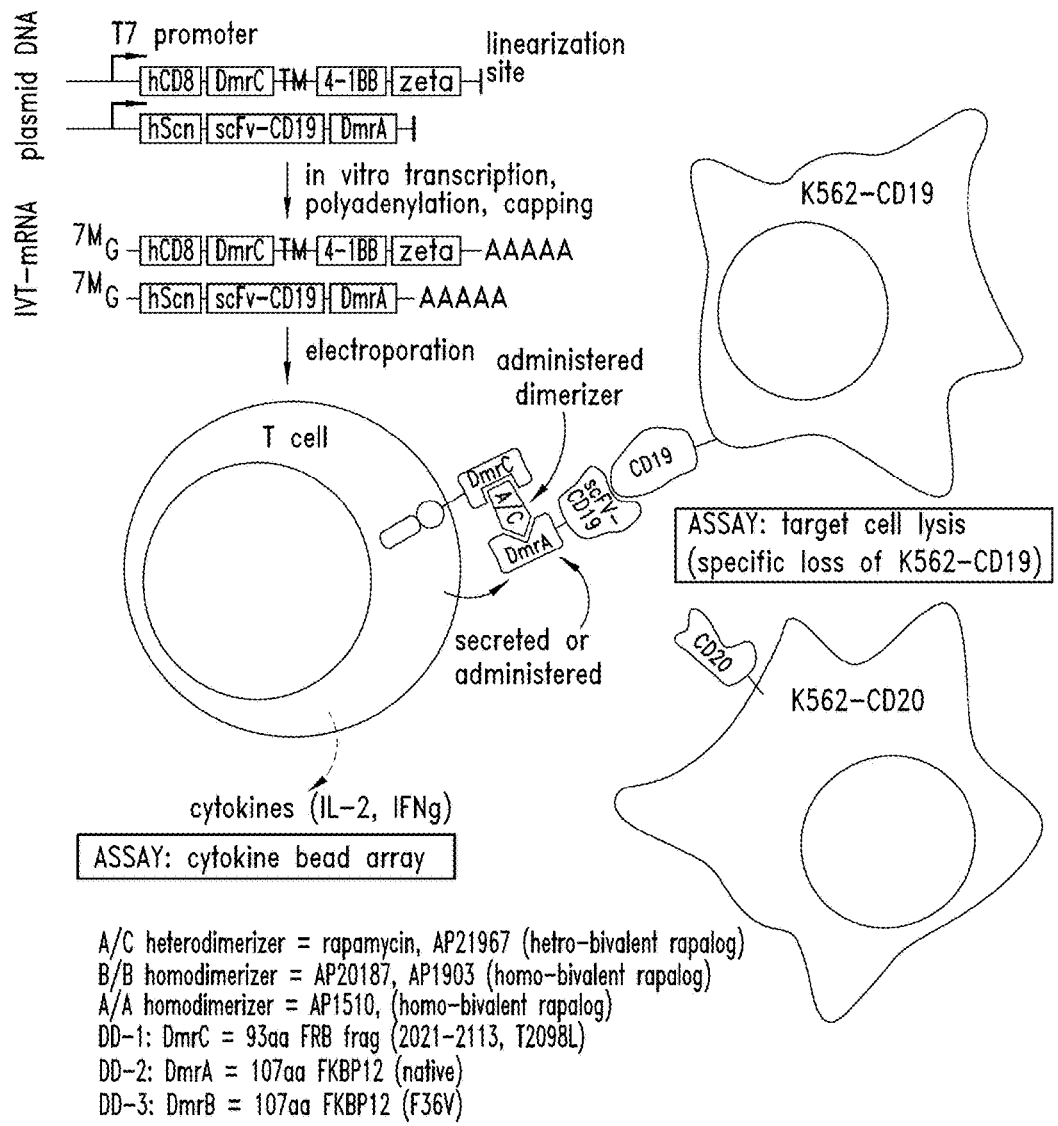
FIG. 2 shows a schematic of an assay to detect specific cell killing and cytokine secretion with a particular multipartite signaling complex of this disclosure.

In a particular embodiment, a deconstructed drug regulated bispecific T cell engager (BiTE) expressed as separate fusion proteins is provided. See FIG. 1L. The BiTE comprises a DARIC signaling component comprising a binding agent that binds a T cell receptor and a first multimerization domain; and a DARIC binding component comprising a binding agent that binds an antigen on a target cell and a second multimerization domain, such as a FRB or FKBP12 protein (whichever is not present on the binding component). Only upon the application of the FRB/FKBP12 coupling drug (e.g., rapamycin or a rapalog thereof) do the BiTE components form a complex that is capable of initiating signal transduction.

But, the temporal control achieved through the multimerization mechanism described herein only primes the machinery for signaling. The chemically induced multimerization reconstitutes a signaling-potentiated receptor, but it does not activate downstream signaling because there is no aggregation of intracellular signaling components. Spatial control is, therefore, achieved on the basis of the presence or absence of a target recognized by the binding domain on the binding component. Since the binding component fusion protein is secreted to the outside of the cell (or applied extraneously), it accumulates only where target is present, such that cells will only become activated when both target (e.g., cell surface antigen) and the bridging factor are present.

In certain embodiments, a recombinant cell comprising a first nucleic acid molecule encoding a first fusion protein comprising a first multimerization domain, a hydrophobic domain, and an actuator domain, wherein the first multimerization domain localizes extracellularly when the first fusion protein is expressed is administered to a subject having a hyperproliferative disease (e.g., cancer), an inflammatory disease, an autoimmune disease, or a graft-versus-host disease. Such a fusion protein can be referred to as a DARIC signaling component, which may be expressed as one or more transmembrane protein(s). A DARIC signaling component may contain more than one multimerization domain, including a multimerization domain that promotes homodimerization in the presence of homo-bivalent bridging factor. In such an embodiment (see FIG. 1c), the administration of a bridging factor will promote some level of basal signaling in the absence of binding to an extracellular target—for example, as a way to drive cell proliferation in vitro or in vivo prior to activation with a DARIC binding component (which in this context functions like a drug). For T cells, it is known that lower level activation promotes proliferation, whereas the higher order multimerization (as would occur by high density of antigen on a target cell and heterodimerization of the DARIC components with a bridging component) would lead to activation of a cytotoxicity response.

In further embodiments, a subject receiving a recombinant (non-natural) cell (e.g., T cell) expressing a DARIC signaling component may be further administered, simultaneously or sequentially, a fusion protein comprising a binding domain and a multimerization domain—a DARIC binding component—and a bridging factor (e.g., rapamycin or rapalog thereof) to promote the formation of a polypeptide complex on the non-natural cell surface with the bridging factor associated with and disposed between the multimerization domains of the first and second fusion proteins (DARIC signaling and binding components, respectively). In certain embodiments, a nucleic acid molecule further encodes a fusion protein comprising a secretion signal, a binding domain and a multimerization domain, wherein the fusion protein (DARIC binding component) is secreted from the non-natural cell when expressed. In some embodiments, a nucleic acid molecule further encodes a fusion protein comprising a secretion signal, a binding domain and a multimerization domain, wherein the expressed fusion protein (DARIC binding component) is secreted and tethered or anchored to the cell surface of the non-natural cell (see FIG. 1I-K). The DARIC binding component will specifically bind to a target cell (e.g., cancer, autoimmune) either before or after associating with the DARIC signaling component through the bridging factor, wherein the tripartite association of the two DARIC components and bridging factor will trigger a cellular response that treats the hyperproliferative, inflammatory, autoimmune, or graft-versus-host disease. For example, the presence at least one DARIC binding component and a cell surface target would lead to increasing signals proportional to the density of target due to multimerization.

In a further embodiment, the DARIC signaling component may be created by leveraging existing activating receptors on the cell (e.g., T cell) surface using a drug regulated bi-specific engager (BiTE). In this instance, both DARIC components are secreted: a binding component that binds to a target cell, and a signaling component that binds to a receptor (e.g., the TCR/CD3 complex) on a T cell. In one embodiment, a non-natural cell secretes both components. In another embodiment, one or more non-natural cells secretes one or more of the components.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" means (1)±1%, ±2%, ±3%, ±4%, ±5%, ±10%, ±15%, or ±20% of the indicated range, value or structure; (2) a value includes the inherent variation of error for the method being employed to determine the value; or (3) a value includes the variation that exists among replicate experiments, unless otherwise indicated. It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

As used herein, a protein or polypeptide "consists essentially of" several domains (e.g., a binding domain, a linker or spacer, a hydrophobic domain, a multimerization domain, an actuator domain) when the portions outside of the several domains (e.g., amino acids at the amino- or carboxy-terminus or between two domains), in combination, contribute to at most 20% (e.g., at most 15%, 10%, 8%, 6%, 5%, 4%, 3%, 2% or 1%) of the length of the protein or polypeptide and do not substantially affect (i.e., do not alter the activity by more than 50%, such as no more than 40%, 30%, 25%, 20%, 15%, 10%, 5%, 4%, 3%, 2%, 1%) the activities of one or more of the various domains (e.g., the target binding affinity of the binding domain, the capability of the multimerization domain to facilitate complex formation, and the capability of the actuator domain to transmit functional signals to a cell). In certain embodiments, a protein (e.g., a single chain polypeptide) consists essentially of a binding domain that specifically binds a target, a linker, and a multimerization domain, wherein the protein may comprise junction amino acids at the amino- and/or carboxy-terminus of the protein or between two different domains (e.g., between the binding domain and the multimerization domain, between the multimerization domain and the linker).

A "fusion protein" or "chimeric protein," as used herein, refers to a protein that includes polypeptide components derived from one or more parental proteins or polypeptides and does not naturally occur in a host cell. A fusion protein will contain two or more naturally-occurring amino acid sequences that are linked together in a way that does not occur naturally. For example, a fusion protein may have two or more portions from the same protein linked in a way not normally found in a cell, or a fusion protein may have portions from two, three, four, five or more different proteins linked in a way not normally found in a cell. A fusion protein can be encoded by a nucleic acid molecule wherein a nucleotide sequence encoding one protein or portion thereof is appended in frame with, and optionally separated by nucleotides that encode a linker, spacer or junction amino acids, a nucleic acid molecule that encodes one or more different proteins or a portion thereof. In certain embodiments, a nucleic acid molecule encoding a fusion protein is introduced into a host cell and expressed.

As used herein, the term "host" refers to a cell (e.g., T cell) or microorganism that may be genetically modified with an exogenous nucleic acid molecule to produce a polypeptide of interest (e.g., DARIC binding or signaling components). In certain embodiments, a host cell may optionally already possess or be modified to include other genetic modifications that confer desired properties related or unrelated to fusion protein biosynthesis (e.g., deleted, altered or truncated TCR; increased costimulatory factor expression). In certain embodiments, a host cell is a human T cell or a human T cell with TCRα, TCRβ, or both knocked out with a site-specific nuclease (e.g., a LAGLIDADG homing endonuclease. LHE).

As used herein, "recombinant" or "non-natural" refers to an organism, microorganism, cell, nucleic acid molecule, or vector that has at least one engineered genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a non-natural cell or is progeny of a non-natural cell having one or more such modifications. Genetic alterations include, for example, modifications introducing expressible nucleic acid molecules encoding proteins, or other nucleic acid molecule additions, deletions, substitutions or other functional alteration of a cell's genetic material. For example, recombinant cells may express genes or other nucleic acid molecules that are not found in identical or homologous form within a native (wild-type) cell (e.g., a fusion or chimeric protein), or may provide an altered expression pattern of endogenous genes, such as being over-expressed, under-expressed, minimally expressed, or not expressed at all.

Recombinant methods for expression of exogenous or heterologous nucleic acids in cells are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Exemplary exogenous proteins or enzymes to be expressed include scFv, CD3ζ, FKBP, FRB, cytokines, or any combination thereof. Genetic modifications to nucleic acid molecules encoding fusion proteins can confer a biochemical or metabolic capability to a recombinant or non-natural cell that is altered from its naturally occurring state.

As used herein, the term "endogenous" or "native" refers to a gene, protein, compound or activity that is normally present in a host cell. The term "homologous" or "homolog" refers to a molecule or activity from an exogenous (non-native) source that is the same or similar molecule or activity as that found in or derived from a host cell, species or strain.

As used herein, "heterologous" nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a gene or a nucleic acid molecule in a way that is different than the gene or a nucleic acid molecule that is normally expressed in nature or culture. In certain embodiments, a heterologous nucleic acid molecule may be homologous to a native host cell gene, but may have an altered expression level or have a different sequence or both. In other embodiments, heterologous or exogenous nucleic acid molecules may not be endogenous to a host cell or host genome (e.g., fusion protein), but instead may have been introduced into a host cell by transformation (e.g., transfection, electroporation), wherein the added molecule may integrate into the host genome or can exist as extra-chromosomal genetic material either transiently (e.g., mRNA) or stably for more than one generation (e.g., episomal viral vector, plasmid or other self-replicating vector).

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. When two or more exogenous nucleic acid molecules are introduced into a host cell, it is understood that the two more exogenous nucleic acid molecules can be introduced as a single nucleic acid molecule (e.g., on a single vector), on separate vectors, as single or multiple mRNA molecules, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

For example, a cell can be modified to express two or more heterologous or exogenous nucleic acid molecules, which may be the same or different, that encode one or more fusion proteins, as disclosed herein. In certain embodiments, a host cell will contain a first nucleic acid molecule encoding a first fusion protein and a separate second nucleic acid molecule encoding a second fusion protein, or a host cell will contain a single polycistronic nucleic acid molecule that encodes a first fusion protein and second fusion protein, or single nucleic acid molecule that encodes a first fusion protein, a self-cleaving amino acid sequence and a second fusion protein.

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S), for example, ENLY- FQG and ENLYFQS, wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

A "polypeptide complex" or "protein complex," as used herein, refers to a dimer, trimer, or higher order multimer formed by at least two different single chain polypeptides, comprising at least one chain having a binding domain specific for a target and one chain having an actuator domain. This term does not include an antibody formed from four single chain polypeptides (i.e., two light chains and two heavy chains). A "dimer" refers to a biological entity that contains two subunits associated with each other, and a "polypeptide complex" refers to a biological entity that includes at least two proteins subunits and a bridging factor associated with each other, via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis).

A "single chain polypeptide" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). In certain embodiments, a single chain polypeptide may have or form one or more intrachain disulfide bonds. In certain other embodiments, two or more single chain polypeptides (e.g., fusion proteins) may associate via an interchain disulfide bond to provide a potentially active complex, provided the complex is made up of at least one non-natural protein, such as fusion or chimeric proteins and is not a natural antibody.

A "multimerization domain," as used herein, refers to a polypeptide molecule that preferentially interacts or associates with another different polypeptide molecule directly or via a bridging molecule, wherein the interaction of the different multimerization domains substantially contribute to or efficiently promote multimerization (i.e., the formation of a dimer, trimer, or multipartite complex, which may be a homodimer, heterodimer, homotrimer, heterotrimer, homomultimer, heteromultimer). Representative multimerization domains of the present disclosure include an FKBP, FRB, calcineurin, cyclophilin, bacterial DHFR, PYL1, ABI1, GIB1, GAI, or variants thereof, as provided herein.

In certain embodiments, a polypeptide complex comprises (i) a first fusion protein having a first multimerization domain and (ii) second fusion protein having a second multimerization domain that is not the same as the first multimerization domain, wherein the first and second multimerization domains substantially contribute to or efficiently promote formation of the polypeptide complex in the presence of a bridging factor. The interaction(s) between the first and second multimerization domains substantially contributes to or efficiently promotes the multimerization of the first and second fusion proteins if there is a statistically significant reduction in the association between the first and second fusion proteins in the absence of the first multimerization domain, the second multimerization domain, or the bridging factor. In certain embodiments, when the first and second fusion proteins are co-expressed, at least about 60%, for instance, at least about 60% to about 70%, at least about 70% to about 80%, at least about 80% to about 90%, 91%, 92%, 93%, 94%, 95%, 96%, 97%, 98%, 99%, or 100%, and at least about 90% to about 92%, 93%, 94%, 95%, 96%, 97%, 98%, or 99% of the first and second single chain polypeptides form multimers with each other in the presence of a bridging factor.

As used herein, "hydrophobic domain" refers to an amino acid sequence having a three-dimensional structure that is thermodynamically stable in a cell membrane. The structure of a hydrophobic domain may comprise an alpha helix, a beta barrel, a beta sheet, a beta helix, or any combination thereof. In certain embodiments, a hydrophobic domain is a transmembrane domain, such as one derived from an integral membrane protein (e.g., receptor, cluster of differentiation (CD) molecule, enzyme, transporter, cell adhesion molecule, or the like).

As used herein, "anchor domain" refers to an amino acid sequence or other molecule that promotes tethering, anchoring or association of a fusion protein of this disclosure with a cell surface. Exemplary anchor domains include an amino acid sequence with a structure that is stable in a cell membrane or an amino acid sequence that promotes the addition of a glycolipid (also known as glycosyl phosphatidylinositols or GPIs), or the like. By way of background, a GPI molecule is post-translationally attached to a protein target by a transamidation reaction, which results in the cleavage of a carboxy-terminal GPI signal sequence (see, e.g., White et al., *J. Cell Sci.* 113:721, 2000) and the simultaneous transfer of the already synthesized GPI anchor molecule to the newly formed carboxy-terminal amino acid (see www.ncbi.nlm.nih.gov/books/NBK20711 for exemplary GPI anchors, which GPI anchors are incorporated by reference in their entirety. In certain embodiments, an anchor domain is a hydrophobic domain (e.g., transmembrane domain) or a GPI signal sequence. In some embodiments, a nucleic acid molecule encoding a fusion protein of this disclosure with an anchor domain results in a fusion protein further comprising a GPI molecule.

An "actuator domain," as used herein, directly or indirectly, promotes a biological or physiological response in a cell when receiving the appropriate signal. In certain embodiments, the actuator domain is part of a protein or protein complex that receives a signal when bound or it binds to a target molecule and the binding triggers a signal from the actuator domain. The actuator domain may directly promote a cellular response when it contains signaling domains or motifs, such as an immunoreceptor tyrosine-based activation motif (ITAM). In other embodiments, an actuator domain will indirectly promote a cellular response by associating with one or more other proteins that directly promote a cellular response. Exemplary actuator domains include CD2, CD3ε, CD3δ, CD3ζ, pTα, TCRα, TCRβ, FcRα, FcRβ, FcRγ, NKG2D, CD79A, CD79B, CD22, CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In particular embodiments, a "transmembrane domain" refers to a portion of the signaling component that fuses an extracellular multimerization domain and one or more intracellular signaling domains and anchors the signaling component to the plasma membrane of the T cell. In certain embodiments, a "transmembrane domain" refers to a portion of the binding component that is fused to an extracellular multimerization domain and anchors the binding component to the plasma membrane of the T cell. The transmembrane domain may be derived either from a natural, synthetic, semi-synthetic, or recombinant source. Illustrative transmembrane domains may be derived from (i.e., comprise at least the transmembrane region(s) of) the alpha, beta or zeta chain of the T-cell receptor, CD3ε, CD3ζ, CD4, CD5, CD8a, CD9, CD 16, CD22, CD27, CD28, CD33, CD37, CD45, CD64, CD80, CD86, CD 134, CD137, CD152, CD 154, and PD1. In various embodiments, a transmembrane domain of a binding component and/or signaling component is fused to a short oligo- or polypeptide linker, preferably between 1, 2, 3, 4, 5, 6, 7, 8, 9, or 10 amino acids in length and that optionally links the transmembrane domain and the intracellular signaling domain of the signaling component.

A "binding domain" (also referred to as a "binding region," "binding agent," or "binding moiety"), as used herein, refers to a protein, polypeptide, oligopeptide, or peptide that possesses the ability to specifically recognize and bind to a target (e.g., CD19, CD20). A binding domain includes any naturally occurring, synthetic, semi-synthetic, or recombinantly produced binding partner for a biological molecule or another target of interest. Exemplary binding domains include single chain antibody variable regions (e.g., domain antibodies, sFv, scFv, Fab), receptor ectodomains (e.g., c-Met), or ligands (e.g., cytokines, chemokines, or cell surface associated ligands). In particular embodiments, a binding domain comprises an antibody or antigen binding fragment thereof, including but not limited to a Camel Ig (a camelid antibody (VHH)), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody). A variety of assays are known for identifying binding domains of the present disclosure that specifically bind a particular target, including Western blot, ELISA, and Biacore analysis.

A binding domain and a fusion protein thereof "specifically binds" a target if it binds the target with an affinity or $K_a$ (i.e., an equilibrium association constant of a particular binding interaction with units of 1/M) equal to or greater than $10^5$ M$^{-1}$, while not significantly binding other components present in a test sample. Binding domains (or fusion proteins thereof) may be classified as "high affinity" binding domains (or fusion proteins thereof) and "low affinity" binding domains (or fusion proteins thereof). "High affinity" binding domains refer to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$. "Low affinity" binding domains refer to those binding domains with a $K_a$ of up to $10^7$ M$^{-1}$, up to $10^6$ M$^{-1}$, up to $10^5$ M$^{-1}$. Alternatively, affinity may be defined as an equilibrium dissociation constant ($K_d$) of a particular binding interaction with units of M (e.g., $10^{-5}$ M to $10^{-13}$ M). Affinities of binding domain polypeptides and fusion proteins according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"T cell receptor" (TCR) is a molecule found on the surface of T cells that, along with CD3, is generally responsible for recognizing antigens bound to major histocompatibility complex (MHC) molecules. It consists of a disulfide-linked heterodimer of the highly variable α and β chains in most T cells. In other T cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see, Abbas and Lichtman, *Cellular and Molecular Immunology* (5th Ed.), Editor: Saunders, Philadelphia, 2003; Janeway et al., *Immunobiology: The Immune System in Health and Disease,* 4th Ed., Current Biology Publications, p 148, 149, and 172, 1999). TCR as used in the present disclosure may be from one or various animal species, including human, mouse, rat, or other mammals.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure may be from one or various animal species, including human, mouse, rat, or other mammals.

"TCR complex," as used herein, refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "VL" and "VH" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light heavy chain. The term "CH" refers to an "immunoglobulin heavy chain constant region" or a "heavy chain constant region,"

which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

As used herein, "an Fc region constant domain portion" or "Fc region portion" refers to the heavy chain constant region segment of the Fc fragment (the "fragment crystallizable" region or Fc region) from an antibody, which can include one or more constant domains, such as CH2, CH3, CH4, or any combination thereof. In certain embodiments, an Fc region portion includes the CH2 and CH3 domains of an IgG, IgA, or IgD antibody and any combination thereof, or the CH3 and CH4 domains of an IgM or IgE antibody and any combination thereof. In one embodiment, the CH2CH3 or the CH3CH4 structures are from the same antibody isotype, such as IgG, IgA, IgD, IgE, or IgM. By way of background, the Fc region is responsible for the effector functions of an immunoglobulin, such as ADCC (antibody-dependent cell-mediated cytotoxicity), ADCP (antibody-dependent cellular phagocytosis), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., Nature, 337:525 (1989)).

A "linker" or "spacer" refers to an amino acid sequence that connects two proteins, polypeptides, peptides, domains, regions, or motifs and may provide a spacer function compatible with interaction of the two sub-binding (e.g., multi-merization) domains so that the resulting polypeptide retains a specific binding affinity to a target molecule or retains signaling activity (e.g., actuator domain activity). In certain embodiments, a linker is comprised of about two to about 35 amino acids, for instance, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1 or IgG4.

"Junction amino acids" or "junction amino acid residues" refer to one or more (e.g., about 2-10) amino acid residues between two adjacent motifs, regions or domains of a polypeptide, such as between a binding domain and an adjacent multimerization domain or between a hydrophobic region and an adjacent multimerization domain or between a peptide linker or spacer that links two motifs, regions or domains and an adjacent actuator domain. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a sequence identity to a wild type motif, region, domain, peptide, polypeptide, or protein (e.g., a wild type human FKBP12, FRP, ITAM, CD3ζ, TCR) of at least 75% (e.g., 80%, 82%, 84%, 86%, 88%, 90%, 91%, 92%, 93%, 94%, 95%, 96%, 97%, 98%, 99%, or 99.5%). For example, an "altered FKBP" refers to a FKBP with a sequence identity to a wild type FKBP (e.g., a human FKBP) of at least 75% (e.g., 80%, 82%, 84%, 86%, 88%, 90%, 91%, 92%, 93%, 94%, 95%, 96%, 97%, 98%, 99%, or 99.5%). Similarly, an "altered CD3ζ" refers to a CD3ζ with a sequence identity to a wild type CD3ζ (e.g., a human CD3ζ) of at least 75% (e.g., 80%, 82%, 84%, 86%, 88%, 90%, 91%, 92%, 93%, 94%, 95%, 96%, 97%, 98%, 99%, or 99.5%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, morpholino, or the like. The term "nucleic acid molecule" also includes "peptide nucleic acids" (PNAs), which comprise naturally occurring or modified nucleic acid bases attached to a polyamide backbone. Nucleic acid molecules can be either single stranded or double stranded.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In other embodiments, a mutation is a substitution of one or more nucleotides or residues.

The term "construct" refers to any polynucleotide that contains a recombinant nucleic acid. A construct may be present in a vector (e.g., a bacterial vector, a viral vector) or may be integrated into a genome. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) and/or expression of nucleic acids to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpes-virus (e.g., Herpes Simplex virus types 1 and 2, Epstein-Barr virus, cytomegalovirus), and poxvirus (e.g., vaccinia, fowl-pox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

"Lentiviral vector," as used herein, means HIV-based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

"Integrative lentiviral vectors (or LV)," as used herein, means such vectors as examples of those that are able to integrate into the genome of a target cell.

By "non-integrative lentiviral vectors" (or NILV) is meant efficient gene delivery vectors that do not integrate into the genome of a target cell through the action of the viral integrase. In one embodiment, a NILV refers to a lentivirus having an integrase protein mutated to specifically decrease its integrase activity. Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values are generated by the NCBI BLAST2.0 software as defined by Altschul et al. (1997) "Gapped BLAST and PSI-BLAST: a new generation of protein database search programs," Nucleic Acids Res. 25:3389-3402, with the parameters set to default values.

In certain embodiments, an altered immunoglobulin domain only contains conservative amino acid substitutions of a wild type immunoglobulin domain. In certain other embodiments, an altered immunoglobulin domain only contains non-conservative amino acid substitutions of a wild type immunoglobulin domain. In yet other embodiments, an altered immunoglobulin domain contains both conservative and non-conservative amino acid substitutions.

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. New York, N.Y. (1975), pp. 71-77; Lewin, Genes IV, Oxford University Press, N.Y. and Cell Press, Cambridge, Mass. (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation. Generally, a "derivative" differs from an "analogue" in that a parent polypeptide may be the starting material to generate a "derivative," whereas the parent polypeptide may not necessarily be used as the starting material to generate an "analogue." A derivative may have different chemical, biological or physical properties of the parent polypeptide. For example, a derivative may be more hydrophilic or it may have altered reactivity (e.g., a CDR having an amino acid change that alters its affinity for a target, or FKBP having an amino acid change that alters its affinity for rapamycin or a rapalog thereof) as compared to the parent polypeptide.

A "receptor" is a protein present in the plasma membrane or in the cytoplasm of a cell to which a signal molecule (i.e., a ligand, such as a hormone, neurotransmitter, toxin, cytokine) may bind or attach. The binding of the single molecule to the receptor may result in a conformational change of the receptor, which can initiate a cellular response. However, some ligands merely block receptors without inducing any response (e.g., antagonists). Some receptor proteins are peripheral membrane proteins, many hormone and neurotransmitter receptors are transmembrane proteins that are embedded in the phospholipid bilayer of cell membranes, and another major class of receptors are intracellular proteins such as those for steroid and intracrine peptide hormone receptors.

As used herein, the term "isolated" refers to a substance that has been removed from the source in which it naturally occurs. A substance need not be purified in order to be isolated. For example, a protein produced in a host cell is considered isolated when it is removed or released from the cell. A protein contained within a crude cell lysate fraction is considered "isolated" for purposes of the present disclosure. Further, an "isolated nucleic acid molecule" refers to a polynucleotide molecule in the form of a separate fragment or as a component of a larger nucleic acid construct, which has been separated from its source cell, including the chromosome it normally resides in, at least once. For example, a DNA molecule that encodes a recombinant polypeptide, peptide, or variant thereof, which has been separated from the genomic DNA of a cell, is an isolated nucleic acid molecule. Another example of an isolated nucleic acid molecule is a bacteriophage promoter (e.g., T5 or T7), or nucleic acid expression control sequence, which can be cloned into a vector capable of replication in a suitable host cell. Still another example of an isolated nucleic acid molecule is a chemically synthesized or PCR synthesized nucleic acid molecule.

As used herein, the term "purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods.

"Treatment," "treating" or "ameliorating" refers to either a therapeutic treatment or prophylactic/preventative treatment. A treatment is therapeutic if at least one symptom of disease in an individual receiving treatment improves or a treatment may delay worsening of a progressive disease in an individual, or prevent onset of additional associated diseases.

A "therapeutically effective amount (or dose)" or "effective amount (or dose)" of a specific binding molecule or compound refers to that amount of the compound sufficient to result in amelioration of one or more symptoms of the disease being treated in a statistically significant manner. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously.

The term "pharmaceutically acceptable" refers to molecular entities and compositions that do not produce allergic or other serious adverse reactions when administered using routes well known in the art.

A "subject in need" refers to a subject at risk of, or suffering from, a disease, disorder or condition that is amenable to treatment or amelioration with a non-natural cell, polypeptide complex or a composition thereof provided herein. In certain embodiments, a subject is a human.

Additional definitions are provided throughout the present disclosure.

In certain aspects, the instant disclosure is directed to a non-natural cell, comprising (a) a first nucleic acid molecule encoding a first fusion protein comprising a first multimerization domain, a hydrophobic domain, and an actuator domain, wherein the first multimerization domain localizes extracellularly when the first fusion protein is expressed; and (b) a second nucleic acid molecule encoding a second fusion protein comprising a binding domain and a second multimerization domain, wherein the second fusion protein localizes extracellularly, either secreted from the cell or anchored to the cell surface, when expressed; wherein a first bridging factor promotes the formation of a polypeptide complex on the non-natural cell surface with the bridging factor associated with and disposed between the multimerization domains of the first and second fusion proteins. In certain embodiments, the second fusion protein (e.g., DARIC binding component) further comprises an anchor domain (e.g., transmembrane domain, GPI signal sequence), wherein the extracellularly localized second fusion protein is tethered or anchored to the surface of the non-natural cell. In certain embodiments, a fusion protein is anchored to the surface of a non-natural cell by a transmembrane domain, such as a transmembrane domain from CD4, CD8, CD28 or the like. In some embodiments, a fusion protein is anchored to the surface of a non-natural cell by a GPI molecule.

In a further embodiment, a first fusion protein, rather than comprising its own hydrophobic and actuator domains, instead comprises a binding domain that binds to a transmembrane protein expressed on the surface of a T cell that comprises a hydrophobic and actuator domain (e.g., TCR/CD3 or the like).

In further aspects, the instant disclosure is directed to a first non-natural cell comprising a heterologous nucleic acid molecule encoding a first fusion protein comprising a first multimerization domain, a hydrophobic domain, and an actuator domain, wherein the first multimerization domain localizes extracellularly when the first fusion protein is expressed; and a second non-natural cell comprising a heterologous a second nucleic acid molecule encoding a second fusion protein comprising a binding domain and a second multimerization domain, wherein the second fusion protein is released extracellularly when expressed; wherein a first bridging factor promotes the formation of a polypeptide complex on the first non-natural cell surface with the bridging factor associated with and disposed between the multimerization domains of the first and second fusion proteins.

In certain embodiments, the first and second multimerization domains are the same or different. Exemplary bridging factors that associate with multimerization domains and are useful with the fusion proteins of this disclosure include rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Exemplary rapamycin analogs (rapalogs) include those disclosed in U.S. Pat. No. 6,649,595, which rapalog structures are incorporated herein by reference. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. Alternatively, "substantially reduced immunosuppressive effect" refers to a rapalog having an $EC_{50}$ value in such an in vitro assay that is at least 10 to 250 times larger than the $EC_{50}$ value observed for rapamycin in the same assay. Other exemplary rapalogs include everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a *Candida* FRAP homolog. Information concerning the nucleotide sequences, cloning, and other aspects of these proteins is already known in the art. For example, a protein sequence accession number for a human mTOR is GenBank Accession No. L34075.1 (Brown et al., *Nature* 369:756, 1994).

FRB domains for use in the fusion proteins of this disclosure generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. A FRB domain for use in fusion proteins of this disclosure will be capable of binding to a complex of an FKBP protein bound to rapamycin or a rapalog thereof of this disclosure. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. For the purpose of this disclosure, FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain". Information concerning the nucleotide sequences, cloning, and other aspects of various FKBP species is known in the art (see, e.g., Staendart et al., *Nature* 346:671, 1990 (human FKBP12); Kay, *Biochem. J.* 314:361, 1996). Homologous FKBP proteins in other mammalian species, in yeast, and in other organisms are also known in the art and may be used in the fusion proteins disclosed herein. The size of FKBP domains for use in this invention varies, depending on which FKBP protein is employed. An FKBP domain of a fusion protein of this disclosure will be capable of binding to rapamycin or a rapalog thereof and participating in a tripartite complex with an FRB-containing protein (as may be determined by any means, direct or indirect, for detecting such binding).

The peptide sequence of an FKBP domain of an FKBP fusion protein of this invention comprises (a) a naturally occurring FKBP peptide sequence, preferably derived from the human FKBP12 protein (GenBank Accession No. AAA58476.1) or a peptide sequence derived therefrom, from another human FKBP, from a murine or other mammalian FKBP, or from some other animal, yeast or fungal FKBP; (b) a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other multimerization domain pairs include FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of at least two first fusion proteins with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the fusion proteins of the instant disclosure and at the same time inhibit or block an unwanted or pathological inflammatory response in a clinical setting.

In certain embodiments, a first fusion protein (e.g., DARIC signaling component) has a first multimerization domain comprising a first FKBP polypeptide or variant thereof, and a second fusion protein (e.g., DARIC binding component) has a second multimerization domain comprising a first FRB polypeptide or variant thereof. In other embodiments, a first fusion protein (e.g., DARIC signaling component) has a first multimerization domain comprising a first FRB polypeptide or variant thereof, and a second fusion protein (e.g., DARIC binding component) has a second multimerization domain comprising a first FKBP polypeptide or variant thereof. In any of these embodiments, the second fusion protein further comprises an anchor domain (e.g., transmembrane domain, GPI signal sequence) and optionally a sub-threshold signaling domain. In some embodiments, a second fusion protein contains a GPI molecule, wherein the GPI signal sequence has been removed or altered to attach the GPI molecule.

In certain embodiments, a first nucleic acid molecule encoding a first fusion protein comprising a first multimerization domain, a third multimerization domain, a hydrophobic domain, and an actuator domain, wherein the first and third multimerization domains localize extracellularly when the first fusion protein is expressed in a cell. In certain embodiments, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In still further embodiments, a second bridging factor promotes the association of at least two first fusion proteins with the bridging factor associated with and disposed between the third multimerization domains of the first fusion proteins. In certain embodiments, a protein complex that is formed is a homocomplex comprising at least two first fusion proteins, wherein the multimerization domains may be DHFR (with the bridging molecule being methotrexate) or GyrB (with the bridging molecule being coumermycin) or FKBP (with the bridging molecule being AP1903 or AP20187). In certain other embodiments, a protein complex is a heterocomplex comprising one or more first fusion proteins and one or more second fusion proteins.

In certain embodiments, a hydrophobic domain is a transmembrane domain, such as a transmembrane domain from CD4, CD8, CD28, or the like. In some embodiments, a fusion protein (e.g., DARIC binding component) comprises an anchor domain, such as a transmembrane domain or GPI signal sequence. In further embodiments, a fusion protein (e.g., DARIC binding component) contains a GPI molecule, wherein the GPI signal sequence has been removed or altered to attach the GPI molecule.

In further embodiments, the actuator domain comprises a lymphocyte receptor signaling domain or comprises an amino acid sequences having one or a plurality of immunoreceptor tyrosine-based activation motifs (ITAMs). In still further embodiments, an actuator domain comprises a cytoplasmic portion that associates with a cytoplasmic signaling protein, wherein the cytoplasmic signaling protein is a lymphocyte receptor or signaling domain thereof, a protein comprising a plurality of immunoreceptor tyrosine-based activation motifs (ITAMs), a costimulatory domain, an adhesion factor, or any combination thereof. Exemplary actuator domains include, but are not limited to, CD2, CD3ε, CD3δ, CD3ζ, pTα, TCRα, TCRβ, FcRα, FcRβ, FcRγ, NKG2D, CD22, CD79A, and CD79B, CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof. In yet further embodiments, a first nucleic acid molecule encodes the first fusion protein further comprising one or more different actuator domains, costimulatory domains, adhesion factors, or any combination thereof. As used herein, the term, "costimulatory signaling domain," or "costimulatory domain", refers to an intracellular signaling domain of a costimulatory factor. Exemplary costimulatory domains include, but are not limited to intracellular signaling domains from CD2, CD27, CD28, CD30, CD40, LAT, Zap70, ICOS, DAP10, 4-1BB, CARD11, HVEM, LAG3, SLAMF1, Lck, Fyn, Slp76, TRIM, and OX40.

In certain embodiments, a non-natural cell further overexpresses a costimulatory factor, an immunomodulatory factor, an agonist for a costimulatory factor, an agonist for an immunomodulatoy factor, or any combination thereof. In a related embodiment, cofactor IL-12 is overexpressed or supplied to the cell.

Fusion protein binding domains useful in the instant invention include those known in the art or as described herein, or those generated by a variety of methods known in the art (see, e.g., U.S. Pat. Nos. 6,291,161 and 6,291,158). For example, fusion protein binding domains may be identified by screening a Fab phage library for Fab fragments that specifically bind to a target of interest (see Hoet et al., Nat. Biotechnol. 23:344, 2005). Additionally, traditional strategies for hybridoma development, such as using a target antigen as an immunogen in convenient systems (e.g., mice, HuMAb Mouse®, TC Mouse™, KM-Mouse®, llamas, sheep, chicken, rats, hamsters, rabbits, etc.), can be used to develop anti-target antibodies having target-specific binding domains of interest.

Sources of further binding domains include target-specific antibody variable domains from various species (which can be formatted as antibodies, sFvs, scFvs, Fabs, or soluble VH domain or domain antibodies), including human, rodent, avian, and ovine. Additional sources of binding domains include variable domains of antibodies from other species, such as camelid (from camels, dromedaries, or llamas (Ghahroudi et al., FEBS Letters 414:521, 1997; Vincke et al., J. Biol. Chem. 284:3273, 2009; and Hamers-Casterman et al., Nature 363:446, 1993; and Nguyen et al., J. Mol. Biol. 275:413, 1998), nurse sharks (Roux et al., Proc. Nat'l. Acad. Sci. (USA) 95:11804, 1998), spotted ratfish (Nguyen et al., Immunogenetics 54:39, 2002), or lamprey (Herrin et al., Proc. Nat'l. Acad. Sci. (USA) 105:2040, 2008 and Alder et al., Nature Immunol. 9:319, 2008). These antibodies can apparently form antigen-binding regions using only heavy chain variable region, i.e., these functional antibodies are homodimers of heavy chains only (referred to as "heavy chain antibodies") (Jespers et al., Nat. Biotechnol. 22:1161, 2004; Cortez-Retamozo et al., Cancer Res. 64:2853, 2004; Baral et al., Nature Med. 12:580, 2006, and Barthelemy et al., J. Biol. Chem. 283:3639, 2008).

Other alternative sources of target-specific binding domains includes sequences that encode random peptide libraries or sequences that encode an engineered diversity of amino acids in loop regions of alternative non-antibody scaffolds, such as fibrinogen domains (see, e.g., Weisel et al. (1985) Science 230:1388), Kunitz domains (see, e.g., U.S. Pat. No. 6,423,498), ankyrin repeat proteins (also known as DARPins; Binz et al., J. Mol. Biol. 332:489, 2003 and Binz et al., Nat. Biotechnol. 22:575, 2004), fibronectin binding domains (also known as adnectins or monobodies; Richards et al., J. Mol. Biol. 326:1475, 2003; Parker et al., Protein Eng. Des. Sel. 18:435, 2005 and Hackel et al., J. Mol. Biol. 381:1238, 2008), cysteine-knot miniproteins (Vita et al., Proc. Nat'l. Acad. Sci. (USA) 92:6404, 1995; Martin et al., Nat. Biotechnol. 21:71, 2002 and Huang et al., Structure 13:755, 2005), tetratricopeptide repeat domains (Main et al., Structure 11:497, 2003 and Cortajarena et al., ACS Chem. Biol. 3:161, 2008), leucine-rich repeat domains (Stumpp et al., J. Mol. Biol. 332:471, 2003), anticalins (Skerra, FEBS J. 275:2677, 2008), lipocalin domains (see, e.g., PCT Publication No. WO 2006/095164, Beste et al., Proc. Nat'l. Acad. Sci. (USA) 96:1898, 1999 and Schonfeld et al., Proc. Nat'l. Acad. Sci. (USA) 106:8198, 2009), armadillo repeat proteins (ArmRPs; Varadamsetty et al., J. Mol. Biol. 424:68, 2012), diabodies (Manzke et al., Int. J. Cancer 82:700, 1999), repebodies (Lee et al., Proc. Nat'l. Acad. Sci. U.S.A. 109: 3299, 2012), minibodies (Hu et al., Cancer Res. 56:3055, 1996), cyclotides (Craik et al., J. Mol. Biol. 294:1327, 1999), V-like domains (see, e.g., US Patent Application Publication No. 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb$^2$ or Fcab™ (see, e.g., PCT Publication Nos. WO 2007/098934; WO 2006/072620), or the like (Nord et al., Protein Eng. 8:601, 1995; Nord et al., Nat. Biotechnol. 15:772, 1997; Nord et al., Eur. J. Biochem. 268:4269, 2001; and Binz et al. (2005) Nat. Biotechnol. 23:1257, 2005).

In certain embodiments, the binding domain of the second fusion protein is a single chain antibody variable region, a receptor ectodomain, or a ligand. In further embodiments, the single chain antibody variable region is a domain antibody, sFv, scFv, F(ab')$_2$, or Fab. In still further embodiments, the binding domain of the second fusion protein is amino or carboxy terminal to the multimerization domain.

In certain further aspects, a non-natural cell comprises a nucleic acid molecule that encodes a fusion comprising a binding domain and multimerization domain, and optionally an anchor domain (e.g., transmembrane domain, GPI signal sequence) or an anchor domain with a sub-threshold signaling domain, wherein the binding domain specifically binds to a target located on a target cell surface. In further embodiments, a binding domain is specific for a target that is an antigen associated with a cancer (e.g., solid malignancy, hematologic malignancy), an inflammatory disease, an autoimmune disease, or a graft versus host disease. Exemplary target antigens include, but are not limited to, α-folate receptor, α$_v$β$_6$ integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11Rα, IL13R-α2, KDR, κ light chain, λ light chain, LeY, L1CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In certain embodiments, such a binding fusion protein (DARIC binding component) forms a tripartite complex with DARIC signaling component and a bridging factor to form a polypeptide complex. Exemplary bridging factors for such a complex include rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In other embodiments, the instant disclosure is directed to a non-natural cell comprising (a) a heterologous first nucleic acid molecule encoding a first fusion protein comprising a first multimerization domain, a hydrophobic domain, and an actuator domain, wherein the first multimerization domain localizes extracellularly when the first fusion protein is expressed; and (b) a second nucleic acid molecule encoding a second fusion protein comprising a binding domain, a second multimerization domain and an anchor domain (e.g., transmembrane domain, GPI molecule), wherein the second fusion protein localizes to the cell surface when expressed; wherein a first bridging factor promotes the formation of a polypeptide complex on the non-natural cell surface with the bridging factor associated with and disposed between the multimerization domains of the first and second fusion proteins. In certain embodiments, the second fusion protein further comprises an intracellularly localized sub-threshold signaling domain.

As used herein, a "sub-threshold signaling domain" is not capable of inducing or activating a sufficiently robust signal transduction cascade in the presence of one or more other sub-threshold signaling domains, but can induce or activate a signal transduction cascade or adjust a signal qualitatively in the presence of an actuator domain. For example, a second fusion protein tethered to a cell surface that associates with another second fusion protein tethered to a cell surface will not induce or will minimally activate signal transduction. Exemplary sub-threshold signaling domains include costimulatory domains, such as CD28, CD2, CD4, CD5, CD8, CD9, CD27, CD44, CD46, CD81, CD137, LFA-1, ICAM-1, VLA-4, OX40, 4-1BB, LIGHT, SLAM, ICOS, CTLA-4, PD-1, or the like.

In particular embodiments, an encoded first fusion protein comprises a first multimerization domain of FRB T2098L, a transmembrane domain, a costimulatory domain of 4-1BB, and actuator domain of CD3ζ; wherein the second encoded fusion protein comprises a binding domain of an scFv specific for CD19 and a second multimerization domain of FKBP12, and optionally an anchor domain (e.g., transmembrane domain, GPI signal sequence) or an anchor domain with a sub-threshold signaling domain; and wherein the first bridging factor that promotes the formation of a polypeptide complex on the non-natural cell surface is rapalog AP21967. An exemplary first fusion protein has an amino acid sequence as set forth in SEQ ID NO.:15 and an exemplary second fusion protein has an amino acid sequence as set forth in SEQ ID NO.:1 or 56.

In certain embodiments, a DARIC binding component may have multiple binding domains. For example, a non-natural cell further comprises a third nucleic acid molecule encoding a third fusion protein comprising a binding domain and a second multimerization domain, optionally an anchor domain (e.g., transmembrane domain, GPI signal sequence) or an anchor domain with a sub-threshold signaling domain, wherein the third fusion protein localizes extracellularly when expressed. In related embodiments, the fusion proteins comprise a binding domain have one, two, three, or four binding domains, wherein the one, two, three, or four binding domains are specific for one target or up to four different targets.

In any of the aforementioned embodiments, a second nucleic acid molecule encoding a second (binding) fusion protein may further comprise a sequence encoding a linker, spacer or junction amino acids disposed between the binding domain and the second multimerization domain. In certain embodiments, a second nucleic acid molecule encoding a second fusion protein (e.g., DARIC binding component) further comprises an anchor domain (e.g., transmembrane domain, GPI signal sequence) and optionally a sub-threshold signaling domain. In further embodiments, a second fusion protein (e.g., DARIC binding component) contains a GPI molecule, wherein the GPI signal sequence has been removed or altered to attach the GPI molecule.

Exemplary diseases or disorders associated with excess receptor-mediated signal transduction include cancer (e.g., solid malignancy and hematologic malignancy), autoimmune or inflammatory diseases or conditions, sepsis resulting from bacterial infection, and viral infection.

In one aspect, the present disclosure provides a method for directing T cell activation, comprising administering to a subject in need thereof an effective amount of a DARIC binding component or a pharmaceutical composition thereof that specifically binds a target, such as a cell surface target that is a tumor-specific antigen or other antigen of choice at a site or cell where T cell activation is desired.

Pharmaceutically acceptable carriers for therapeutic use are also well known in the pharmaceutical art, and are described, for example, in the *Physicians Desk Reference*, 62nd edition. Oradell, N.J.: Medical Economics Co., 2008; Goodman & Gilman's *The Pharmacological Basis of Therapeutics*, Eleventh Edition. McGraw-Hill, 2005; *Remington: The Science and Practice of Pharmacy*, 20th Edition. Baltimore, Md.: Lippincott Williams & Wilkins, 2000; and *The Merck Index*, Fourteenth Edition. Whitehouse Station, N.J.: Merck Research Laboratories, 2006; each of which is hereby incorporated by reference in relevant parts. Exemplary pharmaceutically acceptable carriers include sterile saline and phosphate buffered saline at physiological pH. Preservatives, stabilizers, dyes and the like may be provided in the pharmaceutical composition. In addition, antioxidants and suspending agents may also be used.

Pharmaceutical compositions may also contain diluents such as buffers, antioxidants such as ascorbic acid, low molecular weight (less than about 10 residues) polypeptides, proteins, amino acids, carbohydrates (e.g., glucose, sucrose, dextrins), chelating agents (e.g., EDTA), glutathione and other stabilizers and excipients. Neutral buffered saline or saline mixed with nonspecific serum albumin are exemplary diluents.

In another aspect, the present disclosure provides a method for inhibiting growth, metastasis or metastatic growth of a malignancy (e.g., a solid malignancy or a hematologic malignancy), comprising administering to a subject in need thereof an effective amount of a cell encoding a polypeptide complex provided herein or a composition thereof.

A wide variety of cancers, including solid malignancy and hematologic malignancy, are amenable to the compositions and methods disclosed herein. Types of cancer that may be treated include adenocarcinoma of the breast, prostate, pancreas, colon and rectum; all forms of bronchogenic carcinoma of the lung (including squamous cell carcinoma, adenocarcinoma, small cell lung cancer and non-small cell lung cancer); myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; non-Hodgkin's lymphoma; plasmacytoma; reticuloendotheliosis; melanoma; renal cell carcinoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; and glioblastoma multiforme. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Additional exemplary cancers that are also amenable to the compositions and methods disclosed herein are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

In certain embodiments, cells encoding polypeptide complexes useful for inhibiting growth of a solid malignancy or metastasis or metastatic growth of a solid malignancy or a hematologic malignancy include those that specifically bind to a tumor or cancer antigen and a second target antigen on the cancer cell.

In another aspect, the present disclosure provides a method for treating an autoimmune or inflammatory disease, disorder or condition, comprising administering to a subject in need thereof an effective amount of a cell encoding a polypeptide complex provided herein or a composition thereof.

Exemplary autoimmune or inflammatory diseases, disorders or conditions that may be treated by the fusion proteins and compositions and unit dose forms thereof include inflammatory bowel disease (e.g., Crohn's disease or ulcerative colitis), diabetes mellitus (e.g., type I diabetes), dermatomyositis, polymyositis, pernicious anaemia, primary biliary cirrhosis, acute disseminated encephalomyelitis (ADEM), Addison's disease, ankylosing spondylitis, antiphospholipid antibody syndrome (APS), autoimmune hepatitis, Goodpasture's syndrome, Graves' disease, Guillain-Barré syndrome (GBS), Hashimoto's disease, idiopathic thrombocytopenic purpura, systemic lupus erythematosus, lupus nephritis, neuropsychiatric lupus, multiple sclerosis (MS), myasthenia gravis, pemphigus vulgaris, asthma, psoriatic arthritis, rheumatoid arthritis, Sjögren's syndrome, temporal arteritis (also known as "giant cell arteritis"), autoimmune hemolytic anemia, Bullous pemphigoid, vasculitis, coeliac disease, chronic obstructive pulmonary disease, endometriosis, Hidradenitis suppurativa, interstitial cystitis, morphea, scleroderma, narcolepsy, neuromyotonia, vitiligo, and autoimmune inner ear disease.

In certain embodiments, a method for treating a hyperproliferative, inflammatory, autoimmune, or graft-versus-host disease, comprises (a) administering a recombinant cell comprising a first and a second nucleic acid molecule, wherein the first nucleic acid molecule encodes a first fusion protein comprising a first multimerization domain, a hydrophobic domain, and an actuator domain, wherein the first multimerization domain localizes extracellularly when the first fusion protein is expressed, and the second nucleic acid molecule encodes a second fusion protein comprising a binding domain and a second multimerization domain, wherein the second fusion protein localizes extracellularly when expressed; and (c) administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative disease cell to promote an immunomodulatory response and thereby treats the hyperproliferative disease.

In particular embodiments, a method for treating a hyperproliferative, inflammatory, autoimmune, or graft-versus-host disease, comprises (a) administering one or more recombinant cells comprising a first nucleic acid molecule and a second nucleic acid molecule, wherein the first nucleic acid molecule encodes a first fusion protein comprising a binding agent that binds a receptor expressed on a T cell and first multimerization domain, and the second nucleic acid molecule encodes a second fusion protein comprising a binding agent that binds a cell surface target on a hyperproliferative disease cell and a second multimerization domain, and (c) administering a bridging factor, wherein the bridging factor promotes the formation of a polypeptide complex, e.g., a BiTE, with the bridging factor associated with and disposed between the multimerization domains of the first and second fusion proteins; wherein the binding agent of the first fusion protein binds a receptor on a T cell and the binding agent of the second fusion protein binds a cell surface target on a hyperproliferative disease cell to promote an immunomodulatory response and thereby treats the hyperproliferative disease.

In other embodiments, a method for treating a hyperproliferative, inflammatory, autoimmune, or graft-versus-host disease, comprises (a) administering a non-natural cell comprising a first nucleic acid molecule encoding a first fusion protein comprising a first multimerization domain, a hydrophobic domain, and an actuator domain, wherein the first multimerization domain localizes extracellularly when the first fusion protein is expressed; (b) administering a second fusion protein comprising a binding domain and a second multimerization domain, optionally comprising an anchor domain (e.g., transmembrane domain, GPI signal sequence) or an anchor domain with a sub-threshold signaling domain; and (c) administering a bridging factor, wherein the bridging factor promotes the formation of a polypeptide heterocomplex on the recombinant cell surface with the bridging factor associated with and disposed between the multimerization domains of the first and second fusion proteins; wherein the binding domain of the polypeptide heterocomplex specifically binds a cell surface target on a hyperproliferative disease cell to promote an immunomodulatory response and thereby treats the hyperproliferative disease.

Any of the aforementioned non-natural cells, fusion proteins, bridging factors and other accessory molecules may be used in the methods of treatment of this disclosure. In certain embodiments, a method further comprises administering an agent that antagonizes or blocks an inhibitor of T cell activation, such as an agent that antagonizes or blocks a T cell ligand or a T cell receptor. In certain embodiments, an agent that antagonizes or blocks an inhibitor of T cell activation is an anti-PD1 antibody, anti-PD-L1 antibody, or an anti-CTLA4 antibody or antigen binding fragment thereof, or an engineered homing endonuclease that targets PD-1. In further embodiments, the method further comprises administering a cytokine agonist.

The cells, fusion proteins, bridging factors, other accessory molecules or compositions thereof of the present disclosure may be administered orally, topically, transdermally, parenterally, by inhalation spray, vaginally, rectally, or by intracranial injection, or any combination thereof. In certain embodiments, fusion proteins, bridging factors, or compositions thereof are administered parenterally. The term "parenteral," as used herein, includes subcutaneous injections, intravenous, intramuscular, intracisternal injection, or infusion techniques. Administration by intravascular, intravenous, intraarterial, intradermal, intramuscular, intramammary, intraperitoneal, intrathecal, retrobulbar, intrapulmonary injection and/or surgical implantation at a particular site is contemplated as well. In certain embodiments, fusion proteins, bridging factors, or compositions thereof are administered by injection, such as intravenously.

Also contemplated is the administration of recombinant cells with a bridging factor, recombinant cells with a fusion protein and a bridging factor, or compositions thereof in combination with a second agent. A second agent may be one accepted in the art as a standard treatment for a particular disease state or disorder, such as in cancer, inflammation, autoimmunity, and infection. Exemplary second agents contemplated include recombinant cells with a bridging factor, recombinant cells with a fusion protein and a bridging factor, or compositions thereof that bind to targets different from those that the primary protein complex binds, polyclonal antibodies, monoclonal antibodies, immunoglobulin-derived fusion proteins, chemotherapeutics, ionizing radiation, steroids, NSAIDs, anti-infective agents, or other active and ancillary agents, or any combination thereof.

Second agents useful in combination with recombinant cells with a bridging factor, recombinant cells with a fusion protein and a bridging factor, or compositions thereof provided herein may be steroids, NSAIDs, mTOR inhibitors (e.g., rapamycin (sirolimus), temsirolimus, deforolimus, everolimus, zotarolimus, curcumin, farnesylthiosalicylic acid), calcineurin inhibitors (e.g., cyclosporine, tacrolimus), anti-metabolites (e.g., mycophenolic acid, mycophenolate mofetil), polyclonal antibodies (e.g., anti-thymocyte globulin), monoclonal antibodies (e.g., daclizumab, basiliximab), and CTLA4-Ig fusion proteins (e.g., abatacept or belatacept).

Second agents useful for inhibiting growth of a solid malignancy, inhibiting metastasis or metastatic growth of a solid malignancy, or treating or ameliorating a hematologic malignancy include chemotherapeutic agents, ionizing radiation, and other anti-cancer drugs. Examples of chemotherapeutic agents contemplated as further therapeutic agents include alkylating agents, such as nitrogen mustards (e.g., mechlorethamine, cyclophosphamide, ifosfamide, melphalan, and chlorambucil); bifunctional chemotherapeutics (e.g., bendamustine); nitrosoureas (e.g., carmustine (BCNU), lomustine (CCNU), and semustine (methyl-CCNU)); ethyleneimines and methyl-melamines (e.g., triethylenemelamine (TEM), triethylene thiophosphoramide (thiotepa), and hexamethylmelamine (HMM, altretamine)); alkyl sulfonates (e.g., buslfan); and triazines (e.g., dacabazine (DTIC)); antimetabolites, such as folic acid analogues (e.g., methotrexate, trimetrexate, and pemetrexed (multi-targeted antifolate)); pyrimidine analogues (such as 5-fluorouracil (5-FU), fluorodeoxyuridine, gemcitabine, cytosine arabinoside (AraC, cytarabine), 5-azacytidine, and 2,2'-difluorodeoxycytidine); and purine analogues (e.g., 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA)); Type I topoisomerase inhibitors such as camptothecin (CPT), topotecan, and irinotecan; natural products, such as epipodophylotoxins (e.g., etoposide and teniposide); and vinca alkaloids (e.g., vinblastine, vincristine, and vinorelbine); anti-tumor antibiotics such as actinomycin D, doxorubicin, and bleomycin; radiosensitizers such as 5-bromodeozyuridine, 5-iododeoxyuridine, and bromodeoxycytidine; platinum coordination complexes such as cisplatin, carboplatin, and oxaliplatin; substituted ureas, such as hydroxyurea; and methylhydrazine derivatives such as N-methylhydrazine (MIH) and procarbazine.

Further therapeutic agents contemplated by this disclosure for treatment of autoimmune diseases are referred to as immunosuppressive agents, which act to suppress or mask the immune system of the individual being treated. Immunosuppressive agents include, for example, non-steroidal anti-inflammatory drugs (NSAIDs), analgesics, glucocorticoids, disease-modifying antirheumatic drugs (DMARDs) for the treatment of arthritis, or biologic response modifiers. Compositions in the DMARD description are also useful in the treatment of many other autoimmune diseases aside from rheumatoid arthritis.

Exemplary NSAIDs include ibuprofen, naproxen, naproxen sodium, Cox-2 inhibitors (such as Vioxx or Celebrex), and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g. etanercept (Enbrel), adalimumab (Humira) and infliximab (Remicade)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In still further aspects, the instant disclosure provides a fusion polypeptide heterocomplex, comprising (a) a first fusion protein comprising a first multimerization domain, a hydrophobic domain, and an actuator domain; (b) a second fusion protein comprising an extracellular binding domain and second multimerization domain; and (c) a bridging factor; wherein the first fusion protein, second fusion protein, and bridging factor associate to form a polypeptide heterocomplex with the bridging factor associated with and disposed between the multimerization domains of the first and second fusion proteins. Any of the aforementioned fusion protein components and bridging factors and may be used in these embodiments.

In other aspects, the instant disclosure provides a nucleic acid molecule encoding any one or more of the aforementioned fusion proteins. Such nucleic acid molecules may be incorporated into an expression vector (e.g., lentiviral vector), wherein the first and second fusion proteins are encoded as a polycistronic message or as a single protein separated by a 2A peptide. In certain embodiments, the polycistronic message comprises an internal ribosome entry site (IRES) between the nucleotide sequences that encode the fusion proteins.

Illustrative examples of DARIC binding and signaling components are provided in SEQ ID NOs: 1-75 and below in Table 1.

TABLE 1

Exemplary DARIC Binding and Signaling Components

| SEQ ID NO. | Construct | Sequence |
|---|---|---|
| 1 | scFvCD19-FKBP protein | MGSDIQMTQTTSSLSASLGDRVTISCRASQDISKYLNWYQQKPDG TVKLLIYHTSRLHSGVPSRFSGSGSGTDYSLTISNLEQEDIATYFCQ QGNTLPYTFGGGTKLEITGSTSGSGKPGSGEGSTKGEVKLQESGP GLVAPSQSLSVTCTVSGVSLPDYGVSWIRQPPRKGLEWLGVIWGS ETTYYNSALKSRLTIIKDNSKSQVFLKMNSLQTDDTAIYYCAKHY YYGGSYAMDYWGQGTSVTVSSASGGGGSGVQVETISPGDGRTFP KRGQTCVVHYTGMLEDGKKFDSSRDRNKPFKFMLGKQEVIRGW EEGVAQMSVGQRAKLTISPDYAYGATGHPGIIPPHATLVFDVELL KLEG |
| 2 | SS-scFvCD19-FKBP mRNA | AUGCCCCUGGGCCUGCUGUGGCUGGGCCUGGCCCUGCUGGGC GCCCUGCACGCCCAGGCCGGAUCCGAUAUCCAGAUGACCCAG ACCACCAGCAGCCUGAGCGCCAGCCUGGGCGAUAGAGUGACC AUCAGCUGCAGAGCCAGCCAGGACAUCAGCAAGUACCUGAA CUGGUAUCAGCAGAAACCCGACGGCACCGUGAAGCUGCUGA UCUACCACACCAGCAGACUGCACAGCGGCGUGCCCAGCAGAU UUUCUGGCAGCGGCUCCGGCACCGACUACAGCCUGACCAUCU CCAACCUGGAACAGGAAGAUAUCGCUACCUACUUCUGUCAG CAAGGCAACACCCUGCCCUACACCUUCGGCGGAGGCACCAAG CUGGAAAUCACCGGCAGCACAAGCGGCAGCGGCAAGCCUGG AUCUGGCGAGGGAAGCACCAAGGGCGAAGUGAAACUGCAGG AAAGCGGCCCUGGACUGGUGGCCCCAAGCCAGUCUCUGAGCG UGACCUGUACCGUGUCCGGCGUGUCCCUGCCUGACUAUGGCG UGUCCUGGAUCAGACAGCCCCCCAGAAAGGGCCUGGAAUGG CUGGGAGUGAUCUGGGGCAGCGAGACAACCUACUACAACAG CGCCCUGAAGUCCCGGCUGACCAUCAUCAAGGACAACUCCAA GAGCCAGGUGUUCCUGAAGAUGAACAGCCUGCAGACCGACG ACACCGCCAUCUACUACUGCGCCAAGCACUACUACUACGGCG GCAGCUACGCCAUGGACUACUGGGGCCAGGGCACAAGCGUG ACCGUGUCCAGCGCUAGCGGCGGAGGUGGGAGCGGAGUGCA GGUGGAAACCAUCUCCCCAGGAGACGGGCGCACCUUCCCCAA |

TABLE 1-continued

Exemplary DARIC Binding and Signaling Components

| SEQ ID NO. | Construct | Sequence |
|---|---|---|
| | | GCGCGGCCAGACCUGCGUGGUGCACUACACCGGGAUGCUUG<br>AAGAUGGAAAGAAAUUUGAUUCCUCCCGGGACAGAAACAAG<br>CCCUUUAAGUUUAUGCUAGGCAAGCAGGAGGUGAUCCGAGG<br>CUGGGAAGAAGGGGUUGCCCAGAUGAGUGUGGGUCAGAGAG<br>CCAAACUGACUAUAUCUCCAGAUUAUGCCUAUGGUGCCACU<br>GGGCACCCAGGCAUCAUCCCACCACAUGCCACUCUCGUCUUC<br>GAUGUGGAGCUUCUAAAACUGGAAGGCUGA |
| 3 | SS-scFvCD19-FKBP DNA | ATGCCCCTGGGCCTGCTGTGGCTGGGCCTGGCCCTGCTGGGCG<br>CCCTGCACGCCCAGGCCGGATCCGATATCCAGATGACCCAGAC<br>CACCAGCAGCCTGAGCGCCAGCCTGGGCGATAGAGTGACCAT<br>CAGCTGCAGAGCCAGCCAGGACATCAGCAAGTACCTGAACTG<br>GTATCAGCAGAAACCCGACGGCACCGTGAAGCTGCTGATCTAC<br>CACACCAGCAGACTGCACAGCGGCGTGCCCAGCAGATTTTCTG<br>GCAGCGGCTCCGGCACCGACTACAGCCTGACCATCTCCAACCT<br>GGAACAGGAAGATATCGCTACCTACTTCTGTCAGCAAGGCAAC<br>ACCCTGCCCTACACCTTCGGCGGAGGCACCAAGCTGGAAATCA<br>CCGGCAGCACAAGCGGCAGCGGCAAGCCTGGATCTGGCGAGG<br>GAAGCACCAAGGGCGAAGTGAAACTGCAGGAAAGCGGCCCTG<br>GACTGGTGGCCCCAAGCCAGTCTCTGAGCGTGACCTGTACCGT<br>GTCCGGCGTGTCCCTGCCTGACTATGGCGTGTCCTGGATCAGA<br>CAGCCCCCCAGAAAGGGCCTGGAATGGCTGGGAGTGATCTGG<br>GGCAGCGAGACAACCTACTACAACAGCGCCCTGAAGTCCCGG<br>CTGACCATCATCAAGGACAACTCCAAGAGCCAGGTGTTCCTGA<br>AGATGAACAGCCTGCAGACCGACGACACCGCCATCTACTACTG<br>CGCCAAGCACTACTACTACGGCGGCAGCTACGCCATGGACTAC<br>TGGGGCCAGGGCACAAGCGTGACCGTGTCCAGCGCTAGCGGC<br>GGAGGTGGGAGCGGAGTGCAGGTGGAAACCATCTCCCCAGGA<br>GACGGGCGCACCTTCCCCAAGCGCGGCCAGACCTGCGTGGTGC<br>ACTACACCGGGATGCTTGAAGATGGAAAGAAATTTGATTCCTC<br>CCGGGACAGAAACAAGCCCTTTAAGTTTATGCTAGGCAAGCA<br>GGAGGTGATCCGAGGCTGGGAAGAAGGGGTTGCCCAGATGAG<br>TGTGGGTCAGAGAGCCAAACTGACTATATCTCCAGATTATGCC<br>TATGGTGCCACTGGGCACCCAGGCATCATCCCACCACATGCCA<br>CTCTCGTCTTCGATGTGGAGCTTCTAAAACTGGAAGGCTGA |
| 4 | scFvCD19-FKBP (F36V) protein | MGSDIQMTQTTSSLSASLGDRVTISCRASQDISKYLNWYQQKPDG<br>TVKLLIYHTSRLHSGVPSRFSGSGSGTDYSLTISNLEQEDIATYFCQ<br>QGNTLPYTFGGGTKLEITGSTSGSGKPGSGEGSTKGEVKLQESGP<br>GLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHY<br>YYGGSYAMDYWGQGTSVTVSSASGGGGSGVQVETISPGDGRTFP<br>KRGQTCVVHYTGMLEDGKKVDSSRDRNKPFKFMLGKQEVIRGW<br>EEGVAQMSVGQRAKLTISPDYAYGATGHPGIIPPHATLVFDVELL<br>KLEG |
| 5 | SS-scFvCD19-FKBP (F36V) mRNA | AUGCCCCUGGGCCUGCUGUGGCUGGGCCUGGCCCUGCUGGGC<br>GCCCUGCACGCCCAGGCCGGAUCCGAUAUCCAGAUGACCCAG<br>ACCACCAGCAGCCUGAGCGCCAGCCUGGGCGAUAGAGUGACC<br>AUCAGCUGCAGAGCCAGCCAGGACAUCAGCAAGUACCUGAA<br>CUGGUAUCAGCAGAAACCCGACGGCACCGUGAAGCUGCUGA<br>UCUACCACACCAGCAGACUGCACAGCGGCGUGCCCAGCAGAU<br>UUUCUGGCAGCGGCUCCGGCACCGACUACAGCCUGACCAUCU<br>CCAACCUGGAACAGGAAGAUAUCGCUACCUACUUCUGUCAG<br>CAAGGCAACACCCUGCCCUACACCUUCGGCGGAGGCACCAAG<br>CUGGAAAUCACCGGCAGCACAAGCGGCAGCGGCAAGCCUGG<br>AUCUGGCGAGGGAAGCACCAAGGGCGAAGUGAAACUGCAGG<br>AAAGCGGCCCUGGACUGGUGGCCCCAAGCCAGUCUCUGAGCG<br>UGACCUGUACCGUGUCCGGCGUGUCCCUGCCUGACUAUGGCG<br>UGUCCUGGAUCAGACAGCCCCCCAGAAAGGGCCUGGAAUGG<br>CUGGGAGUGAUCUGGGGCAGCGAGACAACCUACUACAACAG<br>CGCCCUGAAGUCCCGGCUGACCAUCAUCAAGGACAACUCCAA<br>GAGCCAGGUGUUCCUGAAGAUGAACAGCCUGCAGACCGACG<br>ACACCGCCAUCUACUACUGCGCCAAGCACUACUACUACGGCG<br>GCAGCUACGCCAUGGACUACUGGGGCCAGGGCACAAGCGUG<br>ACCGUGUCCAGCGCUAGCGGCGGAGGUGGGAGCGGAGUGCA<br>GGUGGAAACCAUCUCCCCAGGAGACGGGCGCACCUUCCCCAA<br>GCGCGGCCAGACCUGCGUGGUGCACUACACCGGGAUGCUUG<br>AAGAUGGAAAGAAAUUUGAUUCCUCCCGGGACAGAAACAAG<br>CCCUUUAAGUUUAUGCUAGGCAAGCAGGAGGUGAUCCGAGG<br>CUGGGAAGAAGGGGUUGCCCAGAUGAGUGUGGGUCAGAGAG<br>CCAAACUGACUAUAUCUCCAGAUUAUGCCUAUGGUGCCACU<br>GGGCACCCAGGCAUCAUCCCACCACAUGCCACUCUCGUCUUC<br>GAUGUGGAGCUUCUAAAACUGGAAGGCUGA |

TABLE 1-continued

Exemplary DARIC Binding and Signaling Components

| SEQ ID NO. | Construct | Sequence |
|---|---|---|
| 6 | SS-scFvCD19-FKBP (F36V) DNA | ATGCCCCTGGGCCTGCTGTGGCTGGGCCTGGCCCTGCTGGGCG<br>CCCTGCACGCCCAGGCCGGATCCGATATCCAGATGACCCAGAC<br>CACCAGCAGCCTGAGCGCCAGCCTGGGCGATAGAGTGACCAT<br>CAGCTGCAGAGCCAGCCAGGACATCAGCAAGTACCTGAACTG<br>GTATCAGCAGAAACCCGACGGCACCGTGAAGCTGCTGATCTAC<br>CACACCAGCAGACTGCACAGCGGCGTGCCCAGCAGATTTTCTG<br>GCAGCGGCTCCGGCACCGACTACAGCCTGACCATCTCCAACCT<br>GGAACAGGAAGATATCGCTACCTACTTCTGTCAGCAAGGCAAC<br>ACCCTGCCCTACACCTTCGGCGGAGGCACCAAGCTGGAAATCA<br>CCGGCAGCACAAGCGGCAGCGGCAAGCCTGGATCTGGCGAGG<br>GAAGCACCAAGGGCGAAGTGAAACTGCAGGAAAGCGGCCCTG<br>GACTGGTGGCCCCAAGCCAGTCTCTGAGCGTGACCTGTACCGT<br>GTCCGGCGTGTCCCTGCCTGACTATGGCGTGTCCTGGATCAGA<br>CAGCCCCCAGAAAGGGCCTGGAATGGCTGGGAGTGATCTGG<br>GGCAGCGAGACAACCTACTACAACAGCGCCCTGAAGTCCCGG<br>CTGACCATCATCAAGGACAACTCCAAGAGCCAGGTGTTCCTGA<br>AGATGAACAGCCTGCAGACCGACGACACCGCCATCTACTACTG<br>CGCCAAGCACTACTACTACGGCGGCAGCTACGCCATGGACTAC<br>TGGGGCCAGGGCACAAGCGTGACCGTGTCCAGCGCTAGCGGC<br>GGAGGTGGGAGCGGAGTGCAGGTGGAAACCATCTCCCCAGGA<br>GACGGGCGCACCTTCCCCAAGCGCGGCCAGACCTGCGTGGTGC<br>ACTACACCGGGATGCTTGAAGATGGAAAGAAAGTTGATTCCTC<br>CCGGGACAGAAACAAGCCCTTTAAGTTTATGCTAGGCAAGCA<br>GGAGGTGATCCGAGGCTGGGAAGAAGGGGTTGCCCAGATGAG<br>TGTGGGTCAGAGAGCCAAACTGACTATATCTCCAGATTATGCC<br>TATGGTGCCACTGGGCACCCAGGCATCATCCCACCACATGCCA<br>CTCTCGTCTTCGATGTGGAGCTTCTAAAACTGGAAGGCTGA |
| 7 | scFvCD19-FRB (T2098L) protein | MGSDIQMTQTTSSLSASLGDRVTISCRASQDISKYLNWYQQKPDG<br>TVKLLIYHTSRLHSGVPSRFSGSGSGTDYSLTISNLEQEDIATYFCQ<br>QGNTLPYTFGGGTKLEITGSTSGSGKPGSGEGSTKGEVKLQESGP<br>GLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHY<br>YYGGSYAMDYWGQGTSVTVSSASGGGGSILWHEMWHEGLEEA<br>SRLYFGERNVKGMFEVLEPLHAMMERGPQTLKETSFNQAYGRDL<br>MEAQEWCRKYMKSGNVKDLLQAWDLYYHVFRRISKG |
| 8 | SS-scFvCD19-FRB (T2098L) mRNA | AUGCCCCUGGGCCUGCUGUGGCUGGGCCUGGCCCUGCUGGGC<br>GCCCUGCACGCCCAGGCCGGAUCCGAUAUCCAGAUGACCCAG<br>ACCACCAGCAGCCUGAGCGCCAGCCUGGGCGAUAGAGUGACC<br>AUCAGCUGCAGAGCCAGCCAGGACAUCAGCAAGUACCUGAA<br>CUGGUAUCAGCAGAAACCCGACGGCACCGUGAAGCUGCUGA<br>UCUACCACACCAGCAGACUGCACAGCGGCGUGCCCAGCAGAU<br>UUUCUGGCAGCGGCUCCGGCACCGACUACAGCCUGACCAUCU<br>CCAACCUGGAACAGGAAGAUAUCGCUACCUACUUCUGUCAG<br>CAAGGCAACACCCUGCCCUACACCUUCGGCGGAGGCACCAAG<br>CUGGAAAUCACCGGCAGCACAAGCGGCAGCGGCAAGCCUGG<br>AUCUGGCGAGGGAAGCACCAAGGGCGAAGUGAAACUGCAGG<br>AAAGCGGCCCUGGACUGGUGGCCCCAAGCCAGUCUCUGAGCG<br>UGACCUGUACCGUGUCCGGCGUGUCCCUGCCUGACUAUGGCG<br>UGUCCUGGAUCAGACAGCCCCCCAGAAAGGGCCUGGAAUGG<br>CUGGGAGUGAUCUGGGGCAGCGAGACAACCUACUACAACAG<br>CGCCCUGAAGUCCCGGCUGACCAUCAUCAAGGACAACUCCAA<br>GAGCCAGGUGUUCCUGAAGAUGAACAGCCUGCAGACCGACG<br>ACACCGCCAUCUACUACUGCGCCAAGCACUACUACUACGGCG<br>GCAGCUACGCCAUGGACUACUGGGGCCAGGGCACAAGCGUG<br>ACCGUGUCCAGCGCUAGCGGCGGAGGUGGGAGCAUCCUCUG<br>GCAUGAGAUGUGGCAUGAAGGCCUGGAAGAGGCAUCUCGUU<br>UGUACUUUGGGGAAAGGAACGUGAAAGGCAUGUUUGAGGUG<br>CUGGAGCCCUUGCAUGCUAUGAUGGAACGGGGCCCCCAGAC<br>UCUGAAGGAAACAUCCUUUAAUCAGGCCUAUGGUCGAGAUU<br>UAAUGGAGGCCCAAGAGUGGUGCAGGAAGUACAUGAAAUCA<br>GGGAAUGUCAAGGACCUCCUCCAAGCCUGGGACCUCUAUUA<br>UCAUGUGUUCCGACGAAUCUCAAAGGGCUGA |
| 9 | SS-scFvCD19-FRB (T2098L) DNA | ATGCCCCTGGGCCTGCTGTGGCTGGGCCTGGCCCTGCTGGGCG<br>CCCTGCACGCCCAGGCCGGATCCGATATCCAGATGACCCAGAC<br>CACCAGCAGCCTGAGCGCCAGCCTGGGCGATAGAGTGACCAT<br>CAGCTGCAGAGCCAGCCAGGACATCAGCAAGTACCTGAACTG<br>GTATCAGCAGAAACCCGACGGCACCGTGAAGCTGCTGATCTAC<br>CACACCAGCAGACTGCACAGCGGCGTGCCCAGCAGATTTTCTG<br>GCAGCGGCTCCGGCACCGACTACAGCCTGACCATCTCCAACCT<br>GGAACAGGAAGATATCGCTACCTACTTCTGTCAGCAAGGCAAC |

TABLE 1-continued

Exemplary DARIC Binding and Signaling Components

| SEQ ID NO. | Construct | Sequence |
|---|---|---|
| | | ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCCCCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCATCCTCTGGCATGAGATGTGGCATGAAGGC CTGGAAGAGGCATCTCGTTTGTACTTTGGGGAAAGGAACGTGA AAGGCATGTTTGAGGTGCTGGAGCCCTTGCATGCTATGATGGA ACGGGGCCCCAGACTCTGAAGGAAACATCCTTTAATCAGGCC TATGGTCGAGATTTAATGGAGGCCCAAGAGTGGTGCAGGAAG TACATGAAATCAGGGAATGTCAAGGACCTCCTCCAAGCCTGGG ACCTCTATTATCATGTGTTCCGACGAATCTCAAAGGGCTGA |
| 13 | scFvCD19-TM-41BB-CD3z-BFP mRNA | AUGGCUCUGCCUGUGACAGCUCUGCUGCUGCCUCUGGCCCUG CUGCUCCAUGCCGCCAGACCCGGAUCCGAUAUCCAGAUGACC CAGACCACCAGCAGCCUGAGCGCCAGCCUGGGCGAUAGAGUG ACCAUCAGCUGCAGAGCCAGCCAGGACAUCAGCAAGUACCUG AACUGGUAUCAGCAGAAACCCGACGGCACCGUGAAGCUGCU GAUCUACCACACCAGCAGACUGCACAGCGGCGUGCCCAGCAG AUUUUCUGGCAGCGGCUCCGGCACCGACUACAGCCUGACCAU CUCCAACCUGGAACAGGAAGAUAUCGCUACCUACUUCUGUC AGCAAGGCAACACCCUGCCCUACACCUUCGGCGGAGGCACCA AGCUGGAAAUCACCGGCAGCACAAGCGGCAGCGGCAAGCCU GGAUCUGGCGAGGGAAGCACCAAGGGCGAAGUGAAACUGCA GGAAAGCGGCCCUGGACUGGUGGCCCCAAGCCAGUCUCUGA GCGUGACCUGUACCGUGUCCGGCGUGUCCCUGCCUGACUAUG GCGUGUCCUGGAUCAGACAGCCACCCAGAAAGGGCCUGGAA UGGCUGGGAGUGAUCUGGGGCAGCGAGACAACCUACUACAA CAGCGCCCUGAAGUCCCGGCUGACCAUCAUCAAGGACAACUC CAAGAGCCAGGUGUUCCUGAAGAUGAACAGCCUGCAGACCG ACGACACCGCCAUCUACUACUGCGCCAAGCACUACUACUACG GCGGCAGCUACGCCAUGGACUACUGGGGCCAGGGCACAAGC GUGACCGUGUCCAGCGCUAGCGCCAAGCCUACCACCACCCCU GCCCCUAGACCUCCAACACCCGCCCCAACAAUCGCCAGCCAG CCUCUGUCUCUGAGGCCCGAGGCUUGUAGACCAGCUGCUGGC GGAGCCGUGCACACCAGAGGACUGGAUUUCGCCUGCGACAU CUACAUCUGGGCCCCUCUGGCCGGCACAUGUGGCGUGCUGCU GCUGAGCCUCGUGAUCACCAUGCAUAAACGGGGCAGAAAGA AACUCCUGUAUAUAUUCAAACAACCAUUUAUGAGACCAGUA CAAACUACUCAAGAGGAAGAUGGCUGUAGCUGCCGAUUUCC AGAAGAAGAAGAAGGAGGAUGUGAACUGCGGGUGAAGUUCA GCAGAAGCGCCGACGCCCCUGCCUACCAGCAGGGCCAGAAUC AGCUGUACAACGAGCUGAACCUGGGCAGAAGGGAAGAGUAC GACGUCCUGGAUAAGCGGAGAGGCCGGGACCCUGAGAUGGG CGGCAAGCCUCGGCGGAAGAACCCCCAGGAAGGCCUGUAUA ACGAACUGCAGAAAGACAAGAUGGCCGAGGCCUACAGCGAG AUCGGCAUGAAGGGCGAGCGGAGGCGGGGCAAGGGCCACGA CGGCCUGUAUCAGGGCCUGUCCACCGCCACCAAGGAUACCUA CGACGCCCUGCACAUGCAGGCCCUGCCCCCAAGGGGCGGCCG CUCCGGUGAGGGCAGAGGAAGUCUUCUAACAUGCGGUGACG UGGAGGAGAAUCCGGGCCCCUCUAGAAGCGAGCUGAUUAAG GAGAACAUGCACAUGAAGCUGUACAUGGAGGGCACCGUGGA CAACCAUCACUUCAAGUGCACAUCCGAGGGCGAAGGCAAGCC CUACGAGGGCACCCAGACCAUGAGAAUCAAGGUGGUCGAGG GCGGCCCUCUCCCCUUCGCCUUCGACAUCCUGGCUACUAGCU UCCUCUACGGCAGCAAGACCUUCAUCAACCACACCCAGGGCA UCCCCGACUUCUUCAAGCAGUCCUUCCCUGAGGGCUUCACAU GGGAGAGAGUCACCACAUACGAAGACGGGGGCGUGCUGACC GCUACCCAGGACACCAGCCUCCAGGACGGCUGCCUCAUCUAC AACGUCAAGAUCAGAGGGGUGAACUUCACAUCCAACGGCCC UGUGAUGCAGAAGAAAACACUCGGCUGGGAGGCCUUCACCG AGACGCUGUACCCCGCUGACGGCGGCCUGGAAGGCAGAAAC GACAUGGCCCUGAAGCUCGUGGGCGGGAGCCAUCUGAUCGC AAACAUCAAGACCACAUAUAGAUCCAAGAAACCCGCUAAGA ACCUCAAGAUGCCUGGCGUCUACUAUGUGGACUACAGACUG GAAAGAAUCAAGGAGGCCAACAACGAGACCUACGUCGAGCA GCACGAGGUGGCAGUGGCCAGAUACUGCGACCUCCCUAGCA AACUGGGGCACAAGCUUAAUUGA |

TABLE 1-continued

Exemplary DARIC Binding and Signaling Components

| SEQ ID NO. | Construct | Sequence |
|---|---|---|
| 15 | FRB (T2098L)-TM-41BB-CD3z protein | MGSILWHEMWHEGLEEASRLYFGERNVKGMFEVLEPLHAMMER GPQTLKETSFNQAYGRDLMEAQEWCRKYMKSGNVKDLLQAWD LYYHVFRRISKASAKPTTTPAPRPPTPAPTIASQPLSLRPEACRPAA GGAVHTRGLDFACDIYIWAPLAGTCGVLLLSLVITMHKRGRKKL LYIFKQPFMRPVQTTQEEDGCSCRFPEEEEGGCELRVKFSRSADAP AYQQGQNQLYNELNLGRREEYDVLDKRRGRDPEMGGKPRRKNP QEGLYNELQKDKMAEAYSEIGMKGERRRGKGHDGLYQGLSTAT KDTYDALHMQALPPRG |
| 16 | SS-FRB (T2098L)-TM-41BB-CD3z mRNA | AUGGCUCUGCCUGUGACAGCUCUGCUGCUGCCUCUGGCCCUG CUGCUCCAUGCCGCCAGACCCGGAUCCAUCCUCUGGCAUGAG AUGUGGCAUGAAGGCCUGGAAGAGGCAUCUCGUUUGUACUU UGGGGAAAGGAACGUGAAAGGCAUGUUUGAGGUGCUGGAGC CCUUGCAUGCUAUGAUGGAACGGGGCCCCCAGACUCUGAAG GAAACAUCCUUUAAUCAGGCCUAUGGUCGAGAUUUAAUGGA GGCCCAAGAGUGGUGCAGGAAGUACAUGAAAUCAGGGAAUG UCAAGGACCUCCUCCAAGCCUGGGACCUCUAUUAUCAUGUG UUCCGACGAAUCUCAAAGGCUAGCGCCAAGCCUACCACCACC CCUGCCCCUAGACCUCCAACACCCGCCCCAACAAUCGCCAGC CAGCCUCUGUCUCUGAGGCCCGAGGCUUGUAGACCAGCUGCU GGCGGAGCCGUGCACACCAGAGGACUGGAUUUCGCCUGCGA CAUCUACAUCUGGGCCCCUCUGGCCGGCACAUGUGGCGUGCU GCUGCUGAGCCUCGUGAUCACCAUGCAUAAACGGGGCAGAA AGAAACUCCUGUAUAUAUUCAAACAACCAUUUAUGAGACCA GUACAAACUACUCAAGAGGAAGAUGGCUGUAGCUGCCGAUU UCCAGAAGAAGAAGGAGGAUGUGAACUGCGGGUGAAGU UCAGCAGAAGCGCCGACGCCCCUGCCUACCAGCAGGGCCAGA AUCAGCUGUACAACGAGCUGAACCUGGGCAGAAGGGAAGAG UACGACGUCCUGGAUAAGCGGAGAGGCCGGGACCCUGAGAU GGGCGGCAAGCCUCGGCGGAAGAACCCCCAGGAAGGCCUGU AUAACGAACUGCAGAAAGACAAGAUGGCCGAGGCCUACAGC GAGAUCGGCAUGAAGGGCGAGCGGAGGCGGGGCAAGGGCCA CGACGGCCUGUAUCAGGGCCUGUCCACCGCCACCAAGGAUAC CUACGACGCCCUGCACAUGCAGGCCCUGCCCCCAAGGGGC |
| 17 | SS-FRB (T2098L)-TM-41BB-CD3z DNA | ATGGCTCTGCCTGTGACAGCTCTGCTGCTGCCTCTGGCCCTGCT GCTCCATGCCGCCAGACCCGGATCCATCCTCTGGCATGAGATG TGGCATGAAGGCCTGGAAGAGGCATCTCGTTTGTACTTTGGGG AAAGGAACGTGAAAGGCATGTTTGAGGTGCTGGAGCCCTTGC ATGCTATGATGGAACGGGGCCCCCAGACTCTGAAGGAAACAT CCTTTAATCAGGCCTATGGTCGAGATTTAATGGAGGCCCAAGA GTGGTGCAGGAAGTACATGAAATCAGGGAATGTCAAGGACCT CCTCCAAGCCTGGGACCTCTATTATCATGTGTTCCGACGAATCT CAAAGGCTAGCGCAAGCCTACCACCACCCCTGCCCCTAGACC TCCAACACCCGCCCCAACAATCGCCAGCCAGCCTCTGTCTCTG AGGCCCGAGGCTTGTAGACCAGCTGCTGGCGGAGCCGTGCAC ACCAGAGGACTGGATTTCGCCTGCGACATCTACATCTGGGCCC CTCTGGCCGGCACATGTGGCGTGCTGCTGCTGAGCCTCGTGAT CACCATGCATAAACGGGGCAGAAAGAAACTCCTGTATATATTC AAACAACCATTTATGAGACCAGTACAAACTACTCAAGAGGAA GATGGCTGTAGCTGCCGATTTCCAGAAGAAGAAGAAGGAGGA TGTGAACTGCGGGTGAAGTTCAGCAGAAGCGCCGACGCCCCT GCCTACCAGCAGGGCCAGAATCAGCTGTACAACGAGCTGAAC CTGGGCAGAAGGGAAGAGTACGACGTCCTGGATAAGCGGAGA GGCCGGGACCCTGAGATGGGCGGCAAGCCTCGGCGGAAGAAC CCCCAGGAAGGCCTGTATAACGAACTGCAGAAAGACAAGATG GCCGAGGCCTACAGCGAGATCGGCATGAAGGGCGAGCGGAGG CGGGGCAAGGGCCACGACGGCCTGTATCAGGGCCTGTCCACC GCCACCAAGGATACCTACGACGCCCTGCACATGCAGGCCCTGC CCCCAAGGGGC |
| 18 | SS-FRB (T2098L)-spacer-TM-41BB-CD3z DNA | ATGGCTCTGCCTGTGACAGCTCTGCTGCTGCCTCTGGCCCTGCT GCTCCATGCCGCCAGACCCGGATCCATCCTCTGGCATGAGATG TGGCATGAAGGCCTGGAAGAGGCATCTCGTTTGTACTTTGGGG AAAGGAACGTGAAAGGCATGTTTGAGGTGCTGGAGCCCTTGC ATGCTATGATGGAACGGGGCCCCCAGACTCTGAAGGAAACAT CCTTTAATCAGGCCTATGGTCGAGATTTAATGGAGGCCCAAGA GTGGTGCAGGAAGTACATGAAATCAGGGAATGTCAAGGACCT CCTCCAAGCCTGGGACCTCTATTATCATGTGTTCCGACGAATCT CAAAGGCTAGCGAGAGCAAGTACGGACCGCCCTGCCCACCTT GCCCTGCCCCCGAGTTCCTGGGCGGACCCAGCGTGTTCCTGTT CCCACCCAAGCCCAAGGACACCCTGATGATCAGCCGGACCCCC GAGGTGACCTGCGTGGTGGTGGACGTGAGCCAGGAAGATCCC |

TABLE 1-continued

Exemplary DARIC Binding and Signaling Components

| SEQ ID NO. | Construct | Sequence |
|---|---|---|
| | | GAGGTCCAGTTCAATTGGTACGTGGACGGCGTGGAAGTGCAC<br>AACGCCAAGACCAAGCCCAGAGAGGAACAGTTCAACAGCACC<br>TACCCGGGTGGTGTCTGTGCTGACCGTGCTGCACCAGGACTGGC<br>TGAACGGCAAAGAATACAAGTGCAAGGTGTCCAACAAGGGCC<br>TGCCCAGCAGCATCGAAAAGACCATCAGCAAGGCCAAGGGCC<br>AGCCTCGCGAGCCCCAGGTGTACACCCTGCCTCCCTCCCAGGA<br>AGAGATGACCAAGAACCAGGTGTCCCTGACCTGCCTGGTGAA<br>GGGCTTCTACCCCAGCGACATCGCCGTGGAGTGGGAGAGCAA<br>CGGCCAGCCTGAGAACAACTACAAGACCACCCCTCCCGTGCTG<br>GACAGCGACGGCAGCTTCTTCCTGTACAGCCGGCTGACCGTGG<br>ACAAGAGCCGGTGGCAGGAAGGCAACGTCTTTAGCTGCAGCG<br>TGATGCACGAGGCCCTGCACAACCACTACACCCAGAAGAGCC<br>TGAGCCTGTCCCTGGGCAAGATGCATAAACGGGGCAGAAAGA<br>AACTCCTGTATATATTCAAACAACCATTTATGAGACCAGTACA<br>AACTACTCAAGAGGAAGATGGCTGTAGCTGCCGATTTCCAGAA<br>GAAGAAGAAGGAGGATGTGAACTGCGGGTGAAGTTCAGCAGA<br>AGCGCCGACGCCCCTGCCTACCAGCAGGGCCAGAATCAGCTGT<br>ACAACGAGCTGAACCTGGGCAGAAGGGAAGAGTACGACGTCC<br>TGGATAAGCGGAGAGGCCGGGACCCTGAGATGGGCGGCAAGC<br>CTCGGCGGAAGAACCCCCAGGAAGGCCTGTATAACGAACTGC<br>AGAAAGACAAGATGGCCGAGGCCTACAGCGAGATCGGCATGA<br>AGGGCGAGCGGAGGCGGGGCAAGGGCCACGACGGCCTGTATC<br>AGGGCCTGTCCACCGCCACCAAGGATACCTACGACGCCCTGCA<br>CATGCAGGCCCTGCCCCCAAGGGGC |
| 19 | FKBP (F36V)-TM-<br>41BB-CD3z protein | MGSGVQVETISPGDGRTFPKRGQTCVVHYTGMLEDGKKVDSSRD<br>RNKPFKFMLGKQEVIRGWEEGVAQMSVGQRAKLTISPDYAYGA<br>TGHPGIIPPHATLVFDVELLKLEASAKPTTTPAPRPPTPAPTIASQPL<br>SLRPEACRPAAGGAVHTRGLDFACDIYIWAPLAGTCGVLLLSLVI<br>TMHKRGRKKLLYIFKQPFMRPVQTTQEEDGCSCRFPEEEEGGCEL<br>RVKFSRSADAPAYQQGQNQLYNELNLGRREEYDVLDKRRGRDP<br>EMGGKPRRKNPQEGLYNELQKDKMAEAYSEIGMKGERRRGKGH<br>DGLYQGLSTATKDTYDALHMQALPPRG |
| 20 | SS-FKBP (F36V)-TM-<br>41BB-CD3z mRNA | AUGGCUCUGCCUGUGACAGCUCUGCUGCUGCCUCUGGCCCUG<br>CUGCUCCAUGCCGCCAGACCCGGAUCCGGAGUGCAGGUGGAA<br>ACCAUCUCCCCAGGAGACGGGCGCACCUUCCCCAAGCGCGGC<br>CAGACCUGCGUGGUGCACUACACCGGGAUGCUUGAAGAUGG<br>AAAGAAAGUUGAUUCCUCCCGGGACAGAAACAAGCCCUUUA<br>AGUUUAUGCUAGGCAAGCAGGAGGUGAUCCGAGGCUGGGAA<br>GAAGGGGUUGCCCAGAUGAGUGUGGGUCAGAGAGCCAAACU<br>GACUAUAUCUCCAGAUUAUGCCUAUGGUGCCACUGGGCACC<br>CAGGCAUCAUCCCACCACAUGCCACUCUCGUCUUCGAUGUGG<br>AGCUUCUAAAACUGGAAGCUAGCGCCAAGCCUACCACCACCC<br>CUGCCCCUAGACCUCCAACACCCGCCCCAACAAUCGCCAGCC<br>AGCCUCUGUCUCUGAGGCCCGAGGCUUGUAGACCAGCUGCU<br>GGCGGAGCCGUGCACACCAGAGGACUGGAUUUCGCCUGCGA<br>CAUCUACAUCUGGGCCCCUCUGGCCGGCACAUGUGGCGUGCU<br>GCUGCUGAGCCUCGUGAUCACCAUGCAUAAACGGGGCAGAA<br>AGAAACUCCUGUAUAUAUUCAAACAACCAUUUAUGAGACCA<br>GUACAAACUACUCAAGAGGAAGAUGGCUGUAGCUGCCGAUU<br>UCCAGAAGAAGAAGAAGGAGGAUGUGAACUGCGGGUGAAGU<br>UCAGCAGAAGCGCCGACGCCCCUGCCUACCAGCAGGGCCAGA<br>AUCAGCUGUACAACGAGCUGAACCUGGGCAGAAGGGAAGAG<br>UACGACGUCCUGGAUAAGCGGAGAGGCCGGGACCCUGAGAU<br>GGGCGGCAAGCCUCGGCGGAAGAACCCCCAGGAAGGCCUGU<br>AUAACGAACUGCAGAAAGACAAGAUGGCCGAGGCCUACAGC<br>GAGAUCGGCAUGAAGGGCGAGCGGAGGCGGGGCAAGGGCCA<br>CGACGGCCUGUAUCAGGGCCUGUCCACCGCCACCAAGGAUAC<br>CUACGACGCCCUGCACAUGCAGGCCCUGCCCCCAAGGGGC |
| 21 | SS-FKBP (F36V)-TM-<br>41BB-CD3z DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAAGTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGCTAGCGCCAAGCCTACCACCACCCCTGCCCCTAGACC<br>TCCAACACCCGCCCCAACAATCGCCAGCCAGCCTCTGTCTCTG<br>AGGCCCGAGGCTTGTAGACCAGCTGCTGGCGGAGCCGTGCAC<br>ACCAGAGGACTGGATTTCGCCTGCGACATCTACATCTGGGCCC |

| SEQ ID NO. | Construct | Sequence |
|---|---|---|
| | | CTCTGGCCGGCACATGTGGCGTGCTGCTGCTGAGCCTCGTGAT<br>CACCATGCATAAACGGGGCAGAAAGAAACTCCTGTATATATTC<br>AAACAACCATTTATGAGACCAGTACAAACTACTCAAGAGGAA<br>GATGGCTGTAGCTGCCGATTTCCAGAAGAAGAAGAAGGAGGA<br>TGTGAACTGCGGGTGAAGTTCAGCAGAAGCGCCGACGCCCCT<br>GCCTACCAGCAGGGCCAGAATCAGCTGTACAACGAGCTGAAC<br>CTGGGCAGAAGGGAAGAGTACGACGTCCTGGATAAGCGGAGA<br>GGCCGGGACCCTGAGATGGGCGGCAAGCCTCGGCGGAAGAAC<br>CCCCAGGAAGGCCTGTATAACGAACTGCAGAAAGACAAGATG<br>GCCGAGGCCTACAGCGAGATCGGCATGAAGGGCGAGCGGAGG<br>CGGGGCAAGGGCCACGACGGCCTGTATCAGGGCCTGTCCACC<br>GCCACCAAGGATACCTACGACGCCCTGCACATGCAGGCCCTGC<br>CCCCAAGGGGC |
| 22 | SS-FKBP (F36V)-<br>spacer-TM-41BB-CD3z<br>DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAAGTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGCTAGCGAGAGCAAGTACGGACCGCCCTGCCCACCTT<br>GCCCTGCCCCCGAGTTCCTGGGCGGACCCAGCGTGTTCCTGTT<br>CCCACCCAAGCCCAAGGACACCCTGATGATCAGCCGGACCCCC<br>GAGGTGACCTGCGTGGTGGTGGACGTGAGCCAGGAAGATCCC<br>GAGGTCCAGTTCAATTGGTACGTGGACGGCGTGGAAGTGCAC<br>AACGCCAAGACCAAGCCCAGAGAGGAACAGTTCAACAGCACC<br>TACCGGGTGGTGTCTGTGCTGACCGTGCTGCACCAGGACTGGC<br>TGAACGGCAAAGAATACAAGTGCAAGGTGTCCAACAAGGGCC<br>TGCCCAGCAGCATCGAAAAGACCATCAGCAAGGCCAAGGGCC<br>AGCCTCGCGAGCCCCAGGTGTACACCCTGCCTCCCTCCCAGGA<br>AGAGATGACCAAGAACCAGGTGTCCCTGACCTGCCTGGTGAA<br>GGGCTTCTACCCCAGCGACATCGCCGTGGAGTGGGAGAGCAA<br>CGGCCAGCCTGAGAACAACTACAAGACCACCCCTCCCGTGCTG<br>GACAGCGACGGCAGCTTCTTCCTGTACAGCCGGCTGACCGTGG<br>ACAAGAGCCGGTGGCAGGAAGGCAACGTCTTTAGCTGCAGCG<br>TGATGCACGAGGCCCTGCACAACCACTACACCCAGAAGAGCC<br>TGAGCCTGTCCCTGGGCAAGATGCATAAACGGGGCAGAAAGA<br>AACTCCTGTATATATTCAAACAACCATTTATGAGACCAGTACA<br>AACTACTCAAGAGGAAGATGGCTGTAGCTGCCGATTTCCAGAA<br>GAAGAAGAAGGAGGATGTGAACTGCGGGTGAAGTTCAGCAGA<br>AGCGCCGACGCCCCTGCCTACCAGCAGGGCCAGAATCAGCTGT<br>ACAACGAGCTGAACCTGGGCAGAAGGGAAGAGTACGACGTCC<br>TGGATAAGCGGAGAGGCCGGGACCCTGAGATGGGCGGCAAGC<br>CTCGGCGGAAGAACCCCCAGGAAGGCCTGTATAACGAACTGC<br>AGAAAGACAAGATGGCCGAGGCCTACAGCGAGATCGGCATGA<br>AGGGCGAGCGGAGGCGGGGCAAGGGCCACGACGGCCTGTATC<br>AGGGCCTGTCCACCGCCACCAAGGATACCTACGACGCCCTGCA<br>CATGCAGGCCCTGCCCCCAAGGGGC |
| 23 | FKBP-TM-41BB-CD3z<br>protein | MGSGVQVETISPGDGRTFPKRGQTCVVHYTGMLEDGKKFDSSRD<br>RNKPFKFMLGKQEVIRGWEEGVAQMSVGQRAKLTISPDYAYGA<br>TGHPGIIPPHATLVFDVELLKLEASAKPTTTPAPRPPTPAPTIASQPL<br>SLRPEACRPAAGGAVHTRGLDFACDIYIWAPLAGTCGVLLLSLVI<br>TMHKRGRKKLLYIFKQPFMRPVQTTQEEDGCSCRFPEEEEGGCEL<br>RVKFSRSADAPAYQQGQNQLYNELNLGRREEYDVLDKRRGRDP<br>EMGGKPRRKNPQEGLYNELQKDKMAEAYSEIGMKGERRRGKGH<br>DGLYQGLSTATKDTYDALHMQALPPRG |
| 24 | FKBP-TM-41BB-CD3z<br>mRNA | AUGGCUCUGCCUGUGACAGCUCUGCUGCUGCCUCUGGCCCUG<br>CUGCUCCAUGCCGCCAGACCCGGAUCCGGAGUGCAGGUGGAA<br>ACCAUCUCCCCAGGAGACGGGCGCACCUUCCCCAAGCGCGGC<br>CAGACCUGCGUGGUGCACUACACCGGGAUGCUUGAAGAUGG<br>AAAGAAAGUUGAUUCCUCCCGGGACAGAAACAAGCCCUUUA<br>AGUUUAUGCUAGGCAAGCAGGAGGUGAUCCGAGGCUGGGAA<br>GAAGGGGUUGCCCAGAUGAGUGUGGGUCAGAGAGCCAAACU<br>GACUAUAUCUCCAGAUUAUGCCUAUGGUGCCACUGGGCACC<br>CAGGCAUCAUCCCACCACAUGCCACUCUCGUCUUCGAUGUGG<br>AGCUUCUAAAACUGGAAGCUAGCGCCAAGCCUACCACCACCC<br>CUGCCCCUAGACCUCCAACACCCGCCCCAACAAUCGCCAGCC<br>AGCCUCUGUCUCUGAGGCCCGAGGCUUGUAGACCAGCUGCU<br>GGCGGAGCCGUGCACACCAGAGGACUGGAUUUCGCCUGCGA |

TABLE 1-continued

Exemplary DARIC Binding and Signaling Components

| SEQ ID NO. | Construct | Sequence |
|---|---|---|
| | | CAUCUACAUCUGGGCCCCUCUGGCCGGCACAUGUGGCGUGCU
GCUGCUGAGCCUCGUGAUCACCAUGCAUAAACGGGGCAGAA
AGAAACUCCUGUAUAUAUUCAAACAACCAUUUAUGAGACCA
GUACAAACUACUCAAGAGGAAGAUGGCUGUAGCUGCCGAUU
UCCAGAAGAAGAAGAAGGAGGAUGUGAACUGCGGGUGAAGU
UCAGCAGAAGCGCCGACGCCCCUGCCUACCAGCAGGGCCAGA
AUCAGCUGUACAACGAGCUGAACCUGGGCAGAAGGGAAGAG
UACGACGUCCUGGAUAAGCGGAGAGGCCGGGACCCUGAGAU
GGGCGGCAAGCCUCGGCGGAAGAACCCCCAGGAAGGCCUGU
AUAACGAACUGCAGAAAGACAAGAUGGCCGAGGCCUACAGC
GAGAUCGGCAUGAAGGGCGAGCGGAGGCGGGGCAAGGGCCA
CGACGGCCUGUAUCAGGGCCUGUCCACCGCCACCAAGGAUAC
CUACGACGCCCUGCACAUGCAGGCCCUGCCCCCAAGGGGC |
| 25 | FKBP-TM-41BB-CD3z DNA | ATGGCTCTGCCTGTGACAGCTCTGCTGCTGCCTCTGGCCCTGCT
GCTCCATGCCGCCAGACCCGGATCCGGAGTGCAGGTGGAAAC
CATCTCCCCAGGAGACGGGCGCACCTTCCCCAAGCGCGGCCAG
ACCTGCGTGGTGCACTACACCGGGATGCTTGAAGATGGAAAG
AAATTTGATTCCTCCCGGGACAGAAACAAGCCCTTTAAGTTTA
TGCTAGGCAAGCAGGAGGTGATCCGAGGCTGGGAAGAAGGGG
TTGCCCAGATGAGTGTGGGTCAGAGAGCCAAACTGACTATATC
TCCAGATTATGCCTATGGTGCCACTGGGCACCCAGGCATCATC
CCACCACATGCCACTCTCGTCTTCGATGTGGAGCTTCTAAAAC
TGGAAGCTAGCGCCAAGCCTACCACCACCCCTGCCCCTAGACC
TCCAACACCCGCCCCAACAATCGCCAGCCAGCCTCTGTCTCTG
AGGCCCGAGGCTTGTAGACCAGCTGCTGGCGGAGCCGTGCAC
ACCAGAGGACTGGATTTCGCCTGCGACATCTACATCTGGGCCC
CTCTGGCCGGCACATGTGGCGTGCTGCTGCTGAGCCTCGTGAT
CACCATGCATAAACGGGGCAGAAAGAAACTCCTGTATATATTC
AAACAACCATTTATGAGACCAGTACAAACTACTCAAGAGGAA
GATGGCTGTAGCTGCCGATTTCCAGAAGAAGAAGAAGGAGGA
TGTGAACTGCGGGTGAAGTTCAGCAGAAGCGCCGACGCCCCT
GCCTACCAGCAGGGCCAGAATCAGCTGTACAACGAGCTGAAC
CTGGGCAGAAGGGAAGAGTACGACGTCCTGGATAAGCGGAGA
GGCCGGGACCCTGAGATGGGCGGCAAGCCTCGGCGGAAGAAC
CCCCAGGAAGGCCTGTATAACGAACTGCAGAAAGACAAGATG
GCCGAGGCCTACAGCGAGATCGGCATGAAGGGCGAGCGGAGG
CGGGGCAAGGGCCACGACGGCCTGTATCAGGGCCTGTCCACC
GCCACCAAGGATACCTACGACGCCCTGCACATGCAGGCCCTGC
CCCCAAGGGGC |
| 26 | FKBP-spacer-TM-41BB-CD3z DNA | ATGGCTCTGCCTGTGACAGCTCTGCTGCTGCCTCTGGCCCTGCT
GCTCCATGCCGCCAGACCCGGATCCGGAGTGCAGGTGGAAAC
CATCTCCCCAGGAGACGGGCGCACCTTCCCCAAGCGCGGCCAG
ACCTGCGTGGTGCACTACACCGGGATGCTTGAAGATGGAAAG
AAATTTGATTCCTCCCGGGACAGAAACAAGCCCTTTAAGTTTA
TGCTAGGCAAGCAGGAGGTGATCCGAGGCTGGGAAGAAGGGG
TTGCCCAGATGAGTGTGGGTCAGAGAGCCAAACTGACTATATC
TCCAGATTATGCCTATGGTGCCACTGGGCACCCAGGCATCATC
CCACCACATGCCACTCTCGTCTTCGATGTGGAGCTTCTAAAAC
TGGAAGCTAGCGAGAGCAAGTACGGACCGCCCTGCCCACCTT
GCCCTGCCCCCGAGTTCCTGGGCGGACCCAGCGTGTTCCTGTT
CCCACCCAAGCCCAAGGACACCCTGATGATCAGCCGGACCCCC
GAGGTGACCTGCGTGGTGGTGGACGTGAGCCAGGAAGATCCC
GAGGTCCAGTTCAATTGGTACGTGGACGGCGTGGAAGTGCAC
AACGCCAAGACCAAGCCCAGAGAGGAACAGTTCAACAGCACC
TACCGGGTGGTGTCTGTGCTGACCGTGCTGCACCAGGACTGGC
TGAACGGCAAAGAATACAAGTGCAAGGTGTCCAACAAGGGCC
TGCCCAGCAGCATCGAAAAGACCATCAGCAAGGCCAAGGGCC
AGCCTCGCGAGCCCCAGGTGTACACCCTGCCTCCCTCCCAGGA
AGAGATGACCAAGAACCAGGTGTCCCTGACCTGCCTGGTGAA
GGGCTTCTACCCCAGCGACATCGCCGTGGAGTGGGAGAGCAA
CGGCCAGCCTGAGAACAACTACAAGACCACCCCTCCCGTGCTG
GACAGCGACGGCAGCTTCTTCCTGTACAGCCGGCTGACCGTGG
ACAAGAGCCGGTGGCAGGAAGGCAACGTCTTTAGCTGCAGCG
TGATGCACGAGGCCCTGCACAACCACTACACCCAGAAGAGCC
TGAGCCTGTCCCTGGGCAAGATGCATAAACGGGGCAGAAAGA
AACTCCTGTATATATTCAAACAACCATTTATGAGACCAGTACA
AACTACTCAAGAGGAAGATGGCTGTAGCTGCCGATTTCCAGAA
GAAGAAGAAGGAGGATGTGAACTGCGGGTGAAGTTCAGCAGA
AGCGCCGACGCCCCTGCCTACCAGCAGGGCCAGAATCAGCTGT
ACAACGAGCTGAACCTGGGCAGAAGGGAAGAGTACGACGTCC
TGGATAAGCGGAGAGGCCGGGACCCTGAGATGGGCGGCAAGC
CTCGGCGGAAGAACCCCCAGGAAGGCCTGTATAACGAACTGC |

TABLE 1-continued

Exemplary DARIC Binding and Signaling Components

| SEQ ID NO. | Construct | Sequence |
|---|---|---|
| | | AGAAAGACAAGATGGCCGAGGCCTACAGCGAGATCGGCATGA<br>AGGGCGAGCGGAGGCGGGGCAAGGGCCACGACGGCCTGTATC<br>AGGGCCTGTCCACCGCCACCAAGGATACCTACGACGCCCTGCA<br>CATGCAGGCCCTGCCCCCAAGGGGC |
| 37 | SS-2xDmrB-DmrC-TM-41BB-CD3z protein | MALPVTALLLPLALLLHAARPGSGGVQVETISPGDGRTFPKRGQT<br>CVVHYTGMLEDGKKVDSSRDRNKPFKFMLGKQEVIRGWEEGVA<br>QMSVGQRAKLTISPDYAYGATGHPGIIPPHATLVFDVEFLKLESGT<br>SGTSGVQVETISPGDGRTFPKRGQTCVVHYTGMLEDGKKVDSSR<br>DRNKPFKFMLGKQEVIRGWEEGV |
| 38 | SS-2xDmrB-DmrC-TM-41BB-CD3z mRNA | AUGGCUCUGCCUGUGACAGCUCUGCUGCUGCCUCUGGCCCUG<br>CUGCUCCAUGCCGCCAGACCCGGAUCCGGCGGUGUCCAAGUC<br>GAAACUAUAUCGCCUGGCGAUGGCAGAACGUUUCCCAAACG<br>UGGCCAGACCUGUGUCGUACACUAUACCGGCAUGCUAGAGG<br>AUGGGAAAAAGGUUGAUUCCAGUCGCGAUCGGAACAAACCG<br>UUUAAAUUCAUGUUGGGGAAGCAAGAGGUUAUCAGGGGAUG<br>GGAAGAGGGUGUCGCGCAAAUGUCGGUUGGGCAACGUGCGA<br>AACUCACAAUUUCCCCGGAUUACGCAUACGGAGCUACCGGAC<br>ACCCUGGGAUUAUCCCACCGCAUGCGACGCUAGUGUUUGAC<br>GUAGAGUUCUUGAAGCUCGAAUCAGGUACAAGCGGCACUUC<br>UGGCGUACAGGUUGAGACAAUUAGUCCCGGAGACGGACGUA<br>CAUUCCCAAAGAGAGGGCAAACUUGCGUAGUCCAUUACACU<br>GGAAUGUUGGAAGACGGCAAGAAAGUGGACAGUUCAAGAGA<br>CCGCAAUAAGCCUUUCAAGUUUAUGCUCGGAAAACAGGAAG<br>UCAUACGCGGUUGGGAGGAAGGCUGGCUCAGAUGAGCGUC<br>GGACAGAGGGCAAAGUUGACCAUCAGUCCCGACUAUGCGUA<br>UGGCGCGACAGGCCAUCCCGGAAUCAUACCUCCCCACGCAAC<br>CUUGGUAUUCGAUGUCGAACUGCUCAAAUUAGAGGGUAGUA<br>GAUCCAUCCUCUGGCAUGAGAUGUGGCAUGAAGGCCUGGAA<br>GAGGCAUCUCGUUUGUACUUUGGGGAAAGGAACGUGAAAGG<br>CAUGUUUGAGGUGCUGGAGCCCUUGCAUGCUAUGAUGGAAC<br>GGGGCCCCCAGACUCUGAAGGAAACAUCCUUUAAUCAGGCC<br>UAUGGUCGAGAUUUAAUGGAGGCCCAAGAGUGGUGCAGGAA<br>GUACAUGAAAUCAGGGAAUGUCAAGGACCUCCUCCAAGCCU<br>GGGACCUCUAUUAUCAUGUGUUCCGACGAAUCUCAAAGGCU<br>AGCGCCAAGCCUACCACCACCCCUGCCCCUAGACCUCCAACA<br>CCCGCCCCAACAAUCGCCAGCCAGCCUCUGUCUCUGAGGCCC<br>GAGGCUUGUAGACCAGCUGCUGGCGGAGCCGUACACACCAG<br>AGGACUGGAUUUCGCCUGCGACAUCUACAUCUGGGCCCCUCU<br>GGCCGGCACAUGUGGCGUGCUGCUGCUGAGCCUCGUGAUCA<br>CCAUGCAUAAACGGGGCAGAAAGAAACUCCUGUAUAUAUUC<br>AAACAACCAUUUUAUGAGACCAGUACAAACUACUCAAGAGGA<br>AGAUGGCUGUAGCUGCCGAUUUCCAGAAGAAGAAGAAGGAG<br>GAUGUGAACUGCGGGUGAAGUUCAGCAGAAGCGCCGACGCC<br>CCUGCCUACCAGCAGGGCCAGAAUCAGCUGUACAACGAGCUG<br>AACCUGGGCAGAAGGGAAGAGUACGACGUCCUGGAUAAGCG<br>GAGAGGCCGGGACCCUGAGAUGGGCGGCAAGCCUCGGCGGA<br>AGAACCCCAGGAAGGCCCUGUAUAACGAACUGCAGAAAGAC<br>AAGAUGGCCGAGGCCUACAGCGAGAUCGGCAUGAAGGGCGA<br>GCGGAGGCGGGGCAAGGGCCACGACGGCCUGUAUCAGGGCC<br>UGUCCACCGCCACCAAGGAUACCUACGACGCCCUGCACAUGC<br>AGGCCCUGCCCCCAAGGGGC |
| 39 | SS-2xDmrB-DmrC-TM-41BB-CD3z DNA | ATGGCTCTGCCTGTGACAGCTCTGCTGCTGCCTCTGGCCCTGCT<br>GCTCCATGCCGCCAGACCCGGATCCGGCGGTGTCCAAGTCGAA<br>ACTATATCGCCTGGCGATGGCAGAACGTTTCCCAAACGTGGCC<br>AGACCTGTGTCGTACACTATACCGGCATGCTAGAGGATGGGAA<br>AAAGGTTGATTCCAGTCGCGATCGGAACAAACCGTTTAAATTC<br>ATGTTGGGGAAGCAAGAGGTTATCAGGGGATGGGAAGAGGGT<br>GTCGCGCAAATGTCGGTTGGGCAACGTGCGAAACTCACAATTT<br>CCCCGGATTACGCATACGGAGCTACCGGACACCCTGGGATTAT<br>CCCACCGCATGCGACGCTAGTGTTTGACGTAGAGTTCTTGAAG<br>CTCGAATCAGGTACAAGCGGCACTTCTGGCGTACAGGTTGAGA<br>CAATTAGTCCCGGAGACGGACGTACATTCCCAAAGAGAGGGC<br>AAACTTGCGTAGTCCATTACACTGGAATGTTGGAAGACGGCAA<br>GAAAGTGGACAGTTCAAGAGACCGCAATAAGCCTTTCAAGTTT<br>ATGCTCGGAAAACAGGAAGTCATACGCGGTTGGGAGGAAGGC<br>GTGGCTCAGATGAGCGTCGGACAGAGGGCAAAGTTGACCATC<br>AGTCCCGACTATGCGTATGGCGCGACAGGCCATCCCGGAATCA<br>TACCTCCCCACGCAACCTTGGTATTCGATGTCGAACTGCTCAA<br>ATTAGAGGGTAGTAGATCCATCCTCTGGCATGAGATGTGGCAT<br>GAAGGCCTGGAAGAGGCATCTCGTTTGTACTTTGGGGAAAGG<br>AACGTGAAAGGCATGTTTGAGGTGCTGGAGCCCTTGCATGCTA |

TABLE 1-continued

Exemplary DARIC Binding and Signaling Components

| SEQ ID NO. | Construct | Sequence |
|---|---|---|
| | | TGATGGAACGGGGCCCCCAGACTCTGAAGGAAACATCCTTTAA<br>TCAGGCCTATGGTCGAGATTTAATGGAGGCCCAAGAGTGGTGC<br>AGGAAGTACATGAAATCAGGGAATGTCAAGGACCTCCTCCAA<br>GCCTGGGACCTCTATTATCATGTGTTCCGACGAATCTCAAAGG<br>CTAGCGCCAAGCCTACCACCACCCCTGCCCCTAGACCTCCAAC<br>ACCCGCCCCAACAATCGCCAGCCAGCCTCTGTCTCTGAGGCCC<br>GAGGCTTGTAGACCAGCTGCTGGCGGAGCCGTACACACCAGA<br>GGACTGGATTTCGCCTGCGACATCTACATCTGGGCCCCTCTGG<br>CCGGCACATGTGGCGTGCTGCTGCTGAGCCTCGTGATCACCAT<br>GCATAAACGGGGCAGAAAGAAACTCCTGTATATATTCAAACA<br>ACCATTTATGAGACCAGTACAAACTACTCAAGAGGAAGATGG<br>CTGTAGCTGCCGATTTCCAGAAGAAGAAGAAGGAGGATGTGA<br>ACTGCGGGTGAAGTTCAGCAGAAGCGCCGACGCCCCTGCCTAC<br>CAGCAGGGCCAGAATCAGCTGTACAACGAGCTGAACCTGGGC<br>AGAAGGGAAGAGTACGACGTCCTGGATAAGCGGAGAGGCCGG<br>GACCCTGAGATGGGCGGCAAGCCTCGGCGGAAGAACCCCCAG<br>GAAGGCCTGTATAACGAACTGCAGAAAGACAAGATGGCCGAG<br>GCCTACAGCGAGATCGGCATGAAGGGCGAGCGGAGGCGGGGC<br>AAGGGCCACGACGGCCTGTATCAGGGCCTGTCCACCGCCACCA<br>AGGATACCTACGACGCCCTGCACATGCAGGCCCTGCCCCCAAG<br>GGGC |
| 41 | SS-scFvCD19-DmrA-<br>fuP2A-DmrC-TM-<br>41BB-CD3z protein | METDTLLLWVLLLWVPGSTGDYKDEGSDIQMTQTTSSLSASLGD<br>RVTISCRASQDISKYLNWYQQKPDGTVKLLIYHTSRLHSGVPSRFS<br>GSGSGTDYSLTISNLEQEDIATYFCQQGNTLPYTFGGGTKLEITGS<br>TSGSGKPGSGEGSTKGEVKLQESGPGLVAPSQSLSVTCTVSGVSL<br>PDYGVSWIRQPPRKGLEWLGVIWGSE |
| 42 | SS-scFvCD19-DmrA-<br>fuP2A-DmrC-TM-<br>41BB-CD3z DNA | ATGGAGACAGACACACTCCTGCTATGGGTACTGCTGCTCTGGG<br>TTCCAGGTTCCACTGGTGACTACAAGGACGAGGGATCCGATAT<br>CCAGATGACCCAGACCACCAGCCTGAGCGCCAGCCTGGG<br>CGATAGAGTGACCATCAGCTGCAGAGCCAGCCAGGACATCAG<br>CAAGTACCTGAACTGGTATCAGCAGAAACCCGACGGCACCGT<br>GAAGCTGCTGATCTACCACACCAGCAGACTGCACAGCGGCGT<br>GCCCAGCAGATTTTCTGGCAGCGGCTCCGGCACCGACTACAGC<br>CTGACCATCTCCAACCTGGAACAGGAAGATATCGCTACCTACT<br>TCTGTCAGCAAGGCAACACCCTGCCCTACACCTTCGGCGGAGG<br>CACCAAGCTGGAAATCACCGGCAGCACAAGCGGCAGCGGCAA<br>GCCTGGATCTGGCGAGGGAAGCACCAAGGGCGAAGTGAAACT<br>GCAGGAAAGCGGCCCTGGACTGGTGGCCCCAAGCCAGTCTCT<br>GAGCGTGACCTGTACCGTGTCCGGCGTGTCCCTGCCTGACTAT<br>GGCGTGTCCTGGATCAGACAGCCACCCAGAAAGGGCCTGGAA<br>TGGCTGGGAGTGATCTGGGGCAGCGAGACAACCTACTACAAC<br>AGCGCCCTGAAGTCCCGGCTGACCATCATCAAGGACAACTCCA<br>AGAGCCAGGTGTTCCTGAAGATGAACAGCCTGCAGACCGACG<br>ACACCGCCATCTACTACTGCGCCAAGCACTACTACTACGGCGG<br>CAGCTACGCCATGGACTACTGGGGCCAGGGCACAAGCGTGAC<br>CGTGTCCAGCGCTAGCGGCTCAGGAGGAGTGCAGGTTGAAAC<br>CATCTCCCCAGGAGACGGGCGCACCTTCCCGAAGCGCGGACA<br>GACATGCGTGGTGCACTACACCGGGATGCTTGAAGATGGAAA<br>GAAATTCGATTCATCGCGGGACAGAAACAAGCCCTTTAAGTTT<br>ATGCTGGGCAAGCAGGAGGTCATCCGAGGCTGGGAAGAAGGG<br>GTTGCCCAGATGAGTGTCGGCCAGAGAGCCAAACTGACTATAT<br>CACCTGACTACGCCTATGGGCCACTGGGCACCCTGGCATAAT<br>TCCGCCACACGCCACTCTCGTCTTCGATGTGGAGCTTCAAAA<br>CTGGAAGGCGGCCGCGCTCGTTACAAGCGAAGTGTCTCAGGAT<br>CTGGCGCCACGAACTTCTCTCTGTTAAAGCAAGCAGGAGATGT<br>TGAAGAAAACCCCGGGCCTTCAAGATCCATCCTCTGGCATGAG<br>ATGTGGCATGAAGGCCTGGAAGAGGCATCTCGTTTGTACTTTG<br>GGGAAAGGAACGTGAAAGGCATGTTTGAGGTGCTGGAGCCCT<br>TGCATGCTATGATGGAACGGGGCCCCCAGACTCTGAAGGAAA<br>CATCCTTTAATCAGGCCTATGGTCGAGATTTAATGGAGGCCCA<br>AGAGTGGTGCAGGAAGTACATGAAATCAGGGAATGTCAAGGA<br>CCTCCTCCAAGCCTGGGACCTCTATTATCATGTGTTCCGACGA<br>ATCTCAAAGGCTAGCGCCAAGCCTACCACCACCCCTGCCCCTA<br>GACCTCCAACACCCGCCCAACAATCGCCAGCCAGCCTCTGTC<br>TCTGAGGCCCGAGGCTTGTAGACCAGCTGCTGGCGGAGCCGTA<br>CACACCAGAGGACTGGATTTCGCCTGCGACATCTACATCTGGG<br>CCCCTCTGGCCGGCACATGTGGCGTGCTGCTGCTGAGCCTCGT<br>GATCACCATGCATAAACGGGGCAGAAAGAAACTCCTGTATAT<br>ATTCAAACAACCATTTATGAGACCAGTACAAACTACTCAAGAG<br>GAAGATGGCTGTAGCTGCCGATTTCCAGAAGAAGAAGAAGGA<br>GGATGTGAACTGCGGGTGAAGTTCAGCAGAAGCGCCGACGCC<br>CCTGCCTACCAGCAGGGCCAGAATCAGCTGTACAACGAGCTG |

TABLE 1-continued

Exemplary DARIC Binding and Signaling Components

| SEQ ID NO. | Construct | Sequence |
|---|---|---|
| | | AACCTGGGCAGAAGGGAAGAGTACGACGTCCTGGATAAGCGG AGAGGCCGGGACCCTGAGATGGGCGGCAAGCCTCGGCGGAAG AACCCCCAGGAAGGCCTGTATAACGAACTGCAGAAAGACAAG ATGGCCGAGGCCTACAGCGAGATCGGCATGAAGGGCGAGCGG AGGCGGGGCAAGGGCCACGACGGCCTGTATCAGGGCCTGTCC ACCGCCACCAAGGATACCTACGACGCCCTGCACATGCAGGCCC TGCCCCAAGGGGC |
| 44 | SS-scFvCD19-DmrA-fuP2A-FRB-TM-41BB-CD3z protein | METDTLLLWVLLLWVPGSTGDYKDEGSDIQMTQTTSSLSASLGD RVTISCRASQDISKYLNWYQQKPDGTVKLLIYHTSRLHSGVPSRFS GSGSGTDYSLTISNLEQEDIATYFCQQGNTLPYTFGGGTKLEITGS TSGSGKPGSGEGSTKGEVKLQESGPGLVAPSQSLSVTCTVSGVSL PDYGVSWIRQPPRKGLEWLGVIWGSE |
| 45 | SS-scFvCD19-DmrA-fuP2A-FRB-TM-41BB-CD3z DNA | ATGGAGACAGACACACTCCTGCTATGGGTACTGCTGCTCTGGG TTCCAGGTTCCACTGGTGACTACAAGGACGAGGGATCCGATAT CCAGATGACCCAGACCACCAGCAGCCTGAGCGCCAGCCTGGG CGATAGAGTGACCATCAGCTGCAGAGCCAGCCAGGACATCAG CAAGTACCTGAACTGGTATCAGCAGAAACCCGACGGCACCGT GAAGCTGCTGATCTACCACACCAGCAGACTGCACAGCGGCGT GCCCAGCAGATTTTCTGGCAGCGGCTCCGGCACCGACTACAGC CTGACCATCTCCAACCTGGAACAGGAAGATATCGCTACCTACT TCTGTCAGCAAGGCAACACCCTGCCCTACACCTTCGGCGGAGG CACCAAGCTGGAAATCACCGGCAGCACAAGCGGCAGCGGCAA GCCTGGATCTGGCGAGGGAAGCACCAAGGGCGAAGTGAAACT GCAGGAAAGCGGCCCTGGACTGGTGGCCCCAAGCCAGTCTCT GAGCGTGACCTGTACCGTGTCCGGCGTGTCCCTGCCTGACTAT GGCGTGTCCTGGATCAGACAGCCACCCAGAAAGGGCCTGGAA TGGCTGGGAGTGATCTGGGGCAGCGAGAACCTACTACAAC AGCGCCCTGAAGTCCCGGCTGACCATCATCAAGGACAACTCCA AGAGCCAGGTGTTCCTGAAGATGAACAGCCTGCAGACCGACG ACACCGCCATCTACTACTGCGCCAAGCACTACTACTACGGCGG CAGCTACGCCATGGACTACTGGGGCCAGGGCACAAGCGTGAC CGTGTCCAGCGCTAGCGGCTCAGGAGGAGTGCAGGTTGAAAC CATCTCCCCAGGAGACGGGCGCACCTTCCCGAAGCGCGGACA GACATGCGTGGTGCACTACACCGGGATGCTTGAAGATGGAAA GAAATTCGATTCATCGCGGGACAGAAACAAGCCCTTTAAGTTT ATGCTGGGCAAGCAGGAGGTCATCCGAGGCTGGGAAGAAGGG GTTGCCCAGATGAGTGTCGGCCAGAGAGCCAAACTGACTATAT CACCTGACTACGCCTATGGGGCCACTGGGCACCCTGGCATAAT TCCGCCACACGCCACTCTCGTCTTCGATGTGGAGCTTCTAAAA CTGGAAGGCGGCCGCGCTCGTTACAAGCGAAGTGTCTCAGGAT CTGGCGCCACGAACTTCTCTCTGTTAAAGCAAGCAGGAGATGT TGAAGAAAACCCCGGGCCTTCAAGATCCATCCTCTGGCATGAG ATGTGGCATGAAGGCCTGGAAGAGGCATCTCGTTTGTACTTTG GGGAAAGGAACGTGAAAGGCATGTTTGAGGTGCTGGAGCCCT TGCATGCTATGATGGAACGGGGCCCCCAGACTCTGAAGGAAA CATCCTTTAATCAGGCCTATGGTCGAGATTTAATGGAGGCCCA AGAGTGGTGCAGGAAGTACATGAAATCAGGGAATGTCAAGGA CCTCACCCAAGCCTGGGACCTCTATTATCATGTGTTCCGACGA ATCTCAAAGGCTAGCGCCAAGCCTACCACCACCCCTGCCCCTA GACCTCCAACACCCGCCCCAACAATCGCCAGCCAGCCTCTGTC TCTGAGGCCCGAGGCTTGTAGACCAGCTGCTGGCGGAGCCGTA CACACCAGAGGACTGGATTTCGCCTGCGACATCTACATCTGGG CCCCTCTGGCCGGCACATGTGGCGTGCTGCTGCTGAGCCTCGT GATCACCATGCATAAACGGGGCAGAAAGAAACTCCTGTATAT ATTCAAACAACCATTTATGAGACCAGTACAAACTACTCAAGAG GAAGATGGCTGTAGCTGCCGATTTCCAGAAGAAGAAGAAGGA GGATGTGAACTGCGGGTGAAGTTCAGCAGAAGCGCCGACGCC CCTGCCTACCAGCAGGGCCAGAATCAGCTGTACAACGAGCTG AACCTGGGCAGAAGGGAAGAGTACGACGTCCTGGATAAGCGG AGAGGCCGGGACCCTGAGATGGGCGGCAAGCCTCGGCGGAAG AACCCCCAGGAAGGCCTGTATAACGAACTGCAGAAAGACAAG ATGGCCGAGGCCTACAGCGAGATCGGCATGAAGGGCGAGCGG AGGCGGGGCAAGGGCCACGACGGCCTGTATCAGGGCCTGTCC ACCGCCACCAAGGATACCTACGACGCCCTGCACATGCAGGCCC TGCCCCAAGGGGC |
| 47 | SS-scFvCD19-DmrA-fuP2A-2xDmrB-DmrC-TM-41BB-CD3z protein | METDTLLLWVLLLWVPGSTGDYKDEGSDIQMTQTTSSLSASLGD RVTISCRASQDISKYLNWYQQKPDGTVKLLIYHTSRLHSGVPSRFS GSGSGTDYSLTISNLEQEDIATYFCQQGNTLPYTFGGGTKLEITGS TSGSGKPGSGEGSTKGEVKLQESGPGLVAPSQSLSVTCTVSGVSL PDYGVSWIRQPPRKGLEWLGVIWGSE |

TABLE 1-continued

Exemplary DARIC Binding and Signaling Components

| SEQ ID NO. | Construct | Sequence |
|---|---|---|
| 48 | SS-scFvCD19-DmrA-fuP2A-2xDmrB-DmrC-TM-41BB-CD3z DNA | ATGGAGACAGACACACTCCTGCTATGGGTACTGCTGCTCTGGG<br>TTCCAGGTTCCACTGGTGACTACAAGGACGAGGGATCCGATAT<br>CCAGATGACCCAGACCACCAGCAGCCTGAGCGCCAGCCTGGG<br>CGATAGAGTGACCATCAGCTGCAGAGCCAGCCAGGACATCAG<br>CAAGTACCTGAACTGGTATCAGCAGAAACCCGACGGCACCGT<br>GAAGCTGCTGATCTACCACACCAGCAGACTGCACAGCGGCGT<br>GCCCAGCAGATTTTCTGGCAGCGGCTCCGGCACCGACTACAGC<br>CTGACCATCTCCAACCTGGAACAGGAAGATATCGCTACCTACT<br>TCTGTCAGCAAGGCAACACCCTGCCCTACACCTTCGGCGGAGG<br>CACCAAGCTGGAAATCACCGGCAGCACAAGCGGCAGCGGCAA<br>GCCTGGATCTGGCGAGGGAAGCACCAAGGGCGAAGTGAAACT<br>GCAGGAAAGCGGCCCTGGACTGGTGGCCCCAAGCCAGTCTCT<br>GAGCGTGACCTGTACCGTGTCCGGCGTGTCCCTGCCTGACTAT<br>GGCGTGCCTGGATCAGACAGCCACCCAGAAAGGGCCTGGAA<br>TGGCTGGGAGTGATCTGGGGCAGCGAGACAACCTACTACAAC<br>AGCGCCCTGAAGTCCCGGCTGACCATCATCAAGGACAACTCCA<br>AGAGCCAGGTGTTCCTGAAGATGAACAGCCTGCAGACCGACG<br>ACACCGCCATCTACTACTGCGCCAAGCACTACTACTACGGCGG<br>CAGCTACGCCATGGACTACTGGGGCCAGGGCACAAGCGTGAC<br>CGTGTCCAGCGCTAGCGGCTCAGGAGGAGTGCAGGTTGAAAC<br>CATCTCCCCAGGAGACGGGCGCACCTTCCCGAAGCGCGGACA<br>GACATGCGTGGTGCACTACACCGGGATGCTTGAAGATGGAAA<br>GAAATTCGATTCATCGCGGGACAGAAACAAGCCCTTTAAGTTT<br>ATGCTGGGCAAGCAGGAGGTCATCCGAGGCTGGGAAGAAGGG<br>GTTGCCCAGATGAGTGTCGGCCAGAGAGCCAAACTGACTATAT<br>CACCTGACTACGCCTATGGGGCCACTGGGCACCCTGGCATAAT<br>TCCGCCACACGCCACTCTCGTCTTCGATGTGGAGCTTCTAAAA<br>CTGGAAGGCGGCCGCGCTCGTTACAAGCGAAGTGTCTCAGGAT<br>CTGGCGCCACGAACTTCTCTCTGTTAAAGCAAGCAGGAGATGT<br>TGAAGAAAACCCCGGGCCTTCAAGATCCGGCGGTGTCCAAGTC<br>GAAACTATATCGCCTGGCGATGGCAGAACGTTTCCCAAACGTG<br>GCCAGACCTGTGTCGTACACTATACCGGCATGCTAGAGGATGG<br>GAAAAAGGTTGATTCCAGTCGCGATCGGAACAAACCGTTTAA<br>ATTCATGTTGGGGAAGCAAGAGGTTATCAGGGGATGGGAAGA<br>GGGTGTCGCGCAAATGTCGGTTGGGCAACGTGCGAAACTCAC<br>AATTTCCCCGGATTACGCATACGGAGCTACCGGACACCCTGGG<br>ATTATCCCACCGCATGCGACGCTAGTGTTTGACGTAGAGTTCT<br>TGAAGCTCGAATCAGGTACAAGCGGCACTTCTGGCGTACAGGT<br>TGAGACAATTAGTCCCGGAGACGGACGTACATTCCCAAAGAG<br>AGGGCAAACTTGCGTAGTCCATTACACTGGAATGTTGGAAGAC<br>GGCAAGAAAGTGGACAGTTCAAGAGACCGCAATAAGCCTTTC<br>AAGTTTATGCTCGGAAAACAGGAAGTCATACGCGGTTGGGAG<br>GAAGGCGTGGCTCAGATGAGCGTCGGACAGAGGGCAAAGTTG<br>ACCATCAGTCCCGACTATGCGTATGGCGCGACAGGCCATCCCG<br>GAATCATACCTCCCCACGCAACCTTGGTATTCGATGTCGAACT<br>GCTCAAATTAGAGGGTAGTAGATCCATCCTCTGGCATGAGATG<br>TGGCATGAAGGCCTGGAAGAGGCATCTCGTTTGTACTTTGGGG<br>AAAGGAACGTGAAAGGCATGTTTGAGGTGCTGGAGCCCTTGC<br>ATGCTATGATGGAACGGGGCCCCCAGACTCTGAAGGAAACAT<br>CCTTTAATCAGGCCTATGGTCGAGATTTAATGGAGGCCCAAGA<br>GTGGTGCAGGAAGTACATGAAATCAGGGAATGTCAAGGACCT<br>CCTCCAAGCCTGGGACCTCTATTATCATGTGTTCCGACGAATCT<br>CAAAGGCTAGCGCCAAGCCTACCACCACCCCTGCCCCTAGACC<br>TCCAACACCCGCCCCAACAATCGCCAGCCAGCCTCTGTCTCTG<br>AGGCCCGAGGCTTGTAGACCAGCTGCTGGCGGAGCCGTACAC<br>ACCAGAGGACTGGATTTCGCCTGCGACATCTACATCTGGGCCC<br>CTCTGGCCGGCACATGTGGCGTGCTGCTGCTGAGCCTCGTGAT<br>CACCATGCATAAACGGGGCAGAAAGAAACTCCTGTATATATTC<br>AAACAACCATTTATGAGACCAGTACAAACTACTCAAGAGGAA<br>GATGGCTGTAGCTGCCGATTTCCAGAAGAAGAAGAAGGAGGA<br>TGTGAACTGCGGGTGAAGTTCAGCAGAAGCGCCGACGCCCCT<br>GCCTACCAGCAGGGCCAGAATCAGCTGTACAACGAGCTGAAC<br>CTGGGCAGAAGGGAAGAGTACGACGTCCTGGATAAGCGGAGA<br>GGCCGGGACCCTGAGATGGGCGGCAAGCCTCGGCGGAAGAAC<br>CCCCAGGAAGGCCTGTATAACGAACTGCAGAAAGACAAGATG<br>GCCGAGGCCTACAGCGAGATCGGCATGAAGGGCGAGCGGAGG<br>CGGGGCAAGGGCCACGACGGCCTGTATCAGGGCCTGTCCACC<br>GCCACCAAGGATACCTACGACGCCCTGCACATGCAGGCCCTGC<br>CCCCAAGGGGC |

TABLE 1-continued

Exemplary DARIC Binding and Signaling Components

| SEQ ID NO. | Construct | Sequence |
|---|---|---|
| 50 | SS-CD19scFv-DmrA-CD4TM protein | MPLGLLWLGLALLGALHAQAGSDIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYN |
| 51 | SS-CD19scFv-DmrA-CD4TM DNA | ATGCCCCTGGGCCTGCTGTGGCTGGGCCTGGCCCTGCTGGGCGCCCTGCACGCCCAGGCCGGATCCGATATCCAGATGACCCAGACCACCAGCAGCCTGAGCGCCAGCCTGGGCGATAGAGTGACCATCAGCTGCAGAGCCAGCCAGGACATCAGCAAGTACCTGAACTGGTATCAGCAGAAACCCGACGGCACCGTGAAGCTGCTGATCTACCACACCAGCAGACTGCACAGCGGCGTGCCCAGCAGATTTTCTGGCAGCGGCTCCGGCACCGACTACAGCCTGACCATCTCCAACCTGGAACAGGAAGATATCGCTACCTACTTCTGTCAGCAAGGCAACACCCTGCCCTACACCTTCGGCGGAGGCACCAAGCTGGAAATCACCGGCAGCACAAGCGGCAGCGGCAAGCCTGGATCTGGCGAGGGAAGCACCAAGGGCGAAGTGAAACTGCAGGAAAGCGGCCCTGGACTGGTGGCCCCAAGCCAGTCTCTGAGCGTGACCTGTACCGTGTCCGGCGTGTCCCTGCCTGACTATGGCGTGTCCTGGATCAGACAGCCACCCAGAAAGGGCCTGGAATGGCTGGGAGTGATCTGGGGCAGCGAGACAACCTACTACAACAGCGCCCTGAAGTCCCGGCTGACCATCATCAAGGACAACTCCAAGAGCCAGGTGTTCCTGAAGATGAACAGCCTGCAGACCGACGACACCGCCATCTACTACTGCGCCAAGCACTACTACTACGGCGGCAGCTACGCCATGGACTACTGGGGCCAGGGCACAAGCGTGACCGTGTCCAGCGCTAGCGGCGGAGGTGGGAGCGGAGTGCAGGTGGAAACCATCTCCCCAGGAGACGGGCGCACCTTCCCCAAGCGCGGCCAGACCTGCGTGGTGCACTACACCGGGATGCTTGAAGATGGAAAGAAATTTGATTCCTCCCGGGACAGAAACAAGCCCTTTAAGTTTATGCTAGGCAAGCAGGAGGTGATCCGAGGCTGGGAAGAAGGGGTTGCCCAGATGAGTGTGGGTCAGAGAGCCAAACTGACTATATCTCCAGATTATGCCTATGGTGCCACTGGGCACCCAGGCATCATCCCACCACATGCCACTCTCGTCTTCGATGTGGAGCTTCTAAAACTGGAAGGCGGCCGCATGGCCCTGATTGTGCTGGGGGCGTCGCCGGCCTCCTGCTTTTCATTGGGCTAGGCATCTTCTTC |
| 53 | SS-CD19scFv-DmrA-CD8hingeTM protein | MPLGLLWLGLALLGALHAQAGSDIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYN |
| 54 | SS-CD19scFv-DmrA-CD8hingeTM DNA | ATGCCCCTGGGCCTGCTGTGGCTGGGCCTGGCCCTGCTGGGCGCCCTGCACGCCCAGGCCGGATCCGATATCCAGATGACCCAGACCACCAGCAGCCTGAGCGCCAGCCTGGGCGATAGAGTGACCATCAGCTGCAGAGCCAGCCAGGACATCAGCAAGTACCTGAACTGGTATCAGCAGAAACCCGACGGCACCGTGAAGCTGCTGATCTACCACACCAGCAGACTGCACAGCGGCGTGCCCAGCAGATTTTCTGGCAGCGGCTCCGGCACCGACTACAGCCTGACCATCTCCAACCTGGAACAGGAAGATATCGCTACCTACTTCTGTCAGCAAGGCAACACCCTGCCCTACACCTTCGGCGGAGGCACCAAGCTGGAAATCACCGGCAGCACAAGCGGCAGCGGCAAGCCTGGATCTGGCGAGGGAAGCACCAAGGGCGAAGTGAAACTGCAGGAAAGCGGCCCTGGACTGGTGGCCCCAAGCCAGTCTCTGAGCGTGACCTGTACCGTGTCCGGCGTGTCCCTGCCTGACTATGGCGTGTCCTGGATCAGACAGCCACCCAGAAAGGGCCTGGAATGGCTGGGAGTGATCTGGGGCAGCGAGACAACCTACTACAACAGCGCCCTGAAGTCCCGGCTGACCATCATCAAGGACAACTCCAAGAGCCAGGTGTTCCTGAAGATGAACAGCCTGCAGACCGACGACACCGCCATCTACTACTGCGCCAAGCACTACTACTACGGCGGCAGCTACGCCATGGACTACTGGGGCCAGGGCACAAGCGTGACCGTGTCCAGCGCTAGCGGCGGAGGTGGGAGCGGAGTGCAGGTGGAAACCATCTCCCCAGGAGACGGGCGCACCTTCCCCAAGCGCGGCCAGACCTGCGTGGTGCACTACACCGGGATGCTTGAAGATGGAAAGAAATTTGATTCCTCCCGGGACAGAAACAAGCCCTTTAAGTTTATGCTAGGCAAGCAGGAGGTGATCCGAGGCTGGGAAGAAGGGGTTGCCCAGATGAGTGTGGGTCAGAGAGCCAAACTGACTATATCTCCAGATTATGCCTATGGTGCCACTGGGCACCCAGGCATCATCCCACCACATGCCACTCTCGTCTTCGATGTGGAGCTTCTAAAACTGGAAGGCGGCCGCGCCAAGCCTACCACCACCCCTGCCCCTAGACCTCCAACACCCGCCCCAACAATCGCCAGCCAGCCTCTGTCTCTGAGGCCCGAGGCTTGTAGACCAGCTGCTGGCGGAGCCGTGCACACCAGAGGACTGGATTTCGCCTGCGACATCTACATCTGGGCCCCTCTGGCCGGCACATGTGGCGTGCTGCTGCTGAGCCTCGTGATCACC |

TABLE 1-continued

Exemplary DARIC Binding and Signaling Components

| SEQ ID NO. | Construct | Sequence |
|---|---|---|
| 56 | SS-CD19scFv-DmrA-Spacer-CD4TM protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 57 | SS-CD19scFv-DmrA-Spacer-CD4TM DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCACCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCGGAGTGCAGGTGGAAACCATCTCCCCAGGA GACGGGCGCACCTTCCCCAAGCGCGGCCAGACCTGCGTGGTGC ACTACACCGGGATGCTTGAAGATGGAAAGAAATTTGATTCCTC CCGGGACAGAAACAAGCCCTTTAAGTTTATGCTAGGCAAGCA GGAGGTGATCCGAGGCTGGGAAGAAGGGGTTGCCCAGATGAG TGTGGGTCAGAGAGCCAAACTGACTATATCTCCAGATTATGCC TATGGTGCCACTGGGCACCCAGGCATCATCCCACCACATGCCA CTCTCGTCTTCGATGTGGAGCTTCTAAAACTGGAAGGCGGCCG CGAGAGCAAGTACGGACCGCCCTGCCCACCTTGCCCTGCCCCC GAGTTCCTGGGCGGACCCAGCGTGTTCCTGTTCCCACCCAAGC CCAAGGACACCCTGATGATCAGCCGGACCCCCGAGGTGACCT GCGTGGTGGTGGACGTGAGCCAGGAAGATCCCGAGGTCCAGT TCAATTGGTACGTGGACGGCGTGGAAGTGCACAACGCCAAGA CCAAGCCCAGAGAGGAACAGTTCAACAGCACCTACCGGGTGG TGTCTGTGCTGACCGTGCTGCACCAGGACTGGCTGAACGGCAA AGAATACAAGTGCAAGGTGTCCAACAAGGGCCTGCCCAGCAG CATCGAAAAGACCATCAGCAAGGCCAAGGGCCAGCCTCGCGA GCCCCAGGTGTACACCCTGCCTCCCTCCCAGGAAGAGATGACC AAGAACCAGGTGTCCCTGACCTGCCTGGTGAAGGGCTTCTACC CCAGCGACATCGCCGTGGAGTGGGAGAGCAACGGCCAGCCTG AGAACAACTACAAGACCACCCCTCCCGTGCTGGACAGCGACG GCAGCTTCTTCCTGTACAGCCGGCTGACCGTGGACAAGAGCCG GTGGCAGGAAGGCAACGTCTTTAGCTGCAGCGTGATGCACGA GGCCCTGCACAACCACTACACCCAGAAGAGCCTGAGCCTGTCC CTGGGCAAGATGGCCCTGATTGTGCTGGGGGCGTCGCCGGCC TCCTGCTTTTCATTGGGCTAGGCATCTTCTTC |
| 59 | SS-CD19scFv-DmrA-CD52 GPI anchor protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 60 | SS-CD19scFv-DmrA-CD52 GPI anchor DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCACCCAGAAAGGGCCTGGAATGGCTGGGAGTGATCTGG GGCAGCGAGACAACCTACTACAACAGCGCCCTGAAGTCCCGG |

TABLE 1-continued

Exemplary DARIC Binding and Signaling Components

| SEQ ID NO. | Construct | Sequence |
|---|---|---|
| | | CTGACCATCATCAAGGACAACTCCAAGAGCCAGGTGTTCCTGA<br>AGATGAACAGCCTGCAGACCGACGACACCGCCATCTACTACTG<br>CGCCAAGCACTACTACTACGGCGGCAGCTACGCCATGGACTAC<br>TGGGGCCAGGGCACAAGCGTGACCGTGTCCAGCGCTAGCGGC<br>GGAGGTGGGAGCGGAGTGCAGGTGGAAACCATCTCCCCAGGA<br>GACGGGCGCACCTTCCCCAAGCGCGGCCAGACCTGCGTGGTGC<br>ACTACACCGGGATGCTTGAAGATGGAAAGAAATTTGATTCCTC<br>CCGGGACAGAAACAAGCCCTTTAAGTTTATGCTAGGCAAGCA<br>GGAGGTGATCCGAGGCTGGGAAGAAGGGGTTGCCCAGATGAG<br>TGTGGGTCAGAGAGCCAAACTGACTATATCTCCAGATTATGCC<br>TATGGTGCCACTGGGCACCCAGGCATCATCCCACCACATGCCA<br>CTCTCGTCTTCGATGTGGAGCTTCTAAAACTGGAAGGCGGCCG<br>CACCAGCCAAACCAGCAGCCCTCAGCATCCAGCAACATAAG<br>CGGAGGCATTTTCCTTTTCTTCGTGGCCAATGCCATAATCCACC<br>TCTTCTGCTTCAGT |
| 64 | CD8ss-DmrC-CD8TM-<br>41BB-CD3z-P2A-<br>IgKss-CD19scFv-<br>DmrA-CD4TM protein | MALPVTALLLPLALLLHAARPGSILWHEMWHEGLEEASRLYFGE<br>RNVKGMFEVLEPLHAMMERGPQTLKETSFNQAYGRDLMEAQE<br>WCRKYMKSGNVKDLLQAWDLYYHVFRRISKASAGTGSDIYIWA<br>PLAGTCGVLLLSLVITMHKRGRKKLLYIFKQPFMRPVQTTQEEDG<br>CSCRFPEEEEGGCELRVKFSRSADAPAYQQGQNQLYNELNLGRR<br>EEYDVLDKRRGRDPEMGGKPRRKNPQEGLYNELQKDKMAEAYS<br>EIGMKGERRRGKGHDGLYQGLSTATKDTYDALHMQALPPRSGS<br>GATNFSLLKQAGDVEENPGPSMETDTLLLWVLLLWVPGSTGSDI<br>QMTQTTSSLSASLGDRVTISCRASQDISKYLNWYQQKPDGTVKLL<br>IYHTSRLHSGVPSRFSGSGSGTDYSLTISNLEQEDIATYFCQQGNTL<br>PYTFGGGTKLEITGSTSGSGKPGSGEGSTKGEVKLQESGPGLVAPS<br>QSLSVTCTVSGVSLPDYGVSWIRQPPRKGLEWLGVIWGSETTYY<br>NSALKSRLTIIKDNSKSQVFLKMNSLQTDDTAIYYCAKHYYYGGS<br>YAMDYWGQGTSVTVSSASGGGGSGVQVETISPGDGRTFPKRGQT<br>CVVHYTGMLEDGKKFDSSRDRNKPFKFMLGKQEVIRGWEEGVA<br>QMSVGQRAKLTISPDYAYGATGHPGIIPPHATLVFDVELLKLEGG<br>RMALIVLGGVAGLLLFIGLGIFFCVRCRHRRRQ |
| 65 | CD8ss-DmrC-CD8TM-<br>41BB-CD3z-P2A-<br>IgKss-CD19scFv-<br>DmrA-CD4TM DNA | ATGGCTCTGCCCTGTGACAGCTCTGCTGCTGCCTCTGGCCCTGCT<br>GCTCCATGCCGCCAGACCCGGATCCATCCTCTGGCATGAGATG<br>TGGCATGAAGGCCTGGAAGAGGCATCTCGTTTGTACTTTGGGG<br>AAAGGAACGTGAAAGGCATGTTTGAGGTGCTGGAGCCCTTGC<br>ATGCTATGATGGAACGGGGCCCCCAGACTCTGAAGGAAACAT<br>CCTTTAATCAGGCCTATGGTCGAGATTTAATGGAGGCCCAAGA<br>GTGGTGCAGGAAGTACATGAAATCAGGGAATGTCAAGGACCT<br>CCTCCAAGCCTGGGACCTCTATTATCATGTGTTCCGACGAATCT<br>CAAAGGCTAGCGCCGGCACTGGTTCCGACATCTACATCTGGGC<br>CCCTCTGGCCGGCACATGTGGCGTGCTGCTGCTGAGCCTCGTG<br>ATCACCATGCATAAACGGGGCAGAAAGAAACTCCTGTATATAT<br>TCAAACAACCATTTATGAGACCAGTACAAACTACTCAAGAGG<br>AAGATGGCTGTAGCTGCCGATTTCCAGAAGAAGAAGAAGGAG<br>GATGTGAACTGCGGGTGAAGTTCAGCAGAAGCGCCGACGCCC<br>CTGCCTACCAGCAGGGCCAGAATCAGCTGTACAACGAGCTGA<br>ACCTGGGCAGAAGGGAAGAGTACGACGTCCTGGATAAGCGGA<br>GAGGCCGGGACCCTGAGATGGGCGGCAAGCCTCGGCGGAAGA<br>ACCCCCAGGAAGGCCTGTATAACGAACTGCAGAAAGACAAGA<br>TGGCCGAGGCCTACAGCGAGATCGGCATGAAGGGCGAGCGGA<br>GGCGGGGCAAGGGCCACGACGGCCTGTATCAGGGCCTGTCCA<br>CCGCCACCAAGGATACCTACGACGCCCTGCACATGCAGGCCCT<br>GCCCCCAAGGTCAGGATCTGGCGCCACGAACTTCTCTCTGTTA<br>AAGCAAGCAGGAGATGTTGAAGAAAACCCCGGGCCTTCAATG<br>GAGACAGACACACTCCTGCTATGGGTACTGCTGCTCTGGGTTC<br>CAGGTTCCACTGGTTCCGATATCCAGATGACCCAGACCACCAG<br>CAGCCTGAGCGCCAGCCTGGGCGATAGAGTGACCATCAGCTG<br>CAGAGCCAGCCAGGACATCAGCAAGTACCTGAACTGGTATCA<br>GCAGAAACCCGACGGCACCGTGAAGCTGCTGATCTACCACAC<br>CAGCAGACTGCACAGCGGCGTGCCCAGCAGATTTTCTGGCAGC<br>GGCTCCGGCACCGACTACAGCCTGACCATCTCCAACCTGGAAC<br>AGGAAGATATCGCTACCTACTTCTGTCAGCAAGGCAACACCCT<br>GCCCTACACCTTCGGCGGAGGCACCAAGCTGGAAATCACCGG<br>CAGCACAAGCGGCAGCGGCAAGCTGGATCTGGCGAGGGAAG<br>CACCAAGGGCGAAGTGAAACTGCAGGAAAGCGGCCCTGGACT<br>GGTGGCCCCAAGCCAGTCTCTGAGCGTGACCTGTACCGTGTCC<br>GGCGTGTCCCTGCCTGACTATGGCGTGTCCTGGATCAGACAGC<br>CACCCAGAAAGGGCCTGGAATGGCTGGGAGTGATCTGGGGCA<br>GCGAGACAACCTACTACAACAGCGCCCTGAAGTCCCGGCTGA<br>CCATCATCAAGGACAACTCCAAGAGCCAGGTGTTCCTGAAGAT<br>GAACAGCCTGCAGACCGACGACACCGCCATCTACTACTGCGCC |

TABLE 1-continued

Exemplary DARIC Binding and Signaling Components

| SEQ ID NO. | Construct | Sequence |
|---|---|---|
| | | AAGCACTACTACTACGGCGGCAGCTACGCCATGGACTACTGGG<br>GCCAGGGCACAAGCGTGACCGTGTCCAGCGCTAGCGGCGGAG<br>GTGGGAGCGGAGTGCAGGTGGAAACCATCTCCCCAGGAGACG<br>GGCGCACCTTCCCCAAGCGCGGCCAGACCTGCGTGGTGCACTA<br>CACCGGGATGCTTGAAGATGGAAAGAAATTTGATTCCTCCCGG<br>GACAGAAACAAGCCCTTTAAGTTTATGCTAGGCAAGCAGGAG<br>GTGATCCGAGGCTGGGAAGAAGGGGTTGCCCAGATGAGTGTG<br>GGTCAGAGAGCCAAACTGACTATATCTCCAGATTATGCCTATG<br>GTGCCACTGGGCACCCAGGCATCATCCCACCACATGCCACTCT<br>CGTCTTCGATGTGGAGCTTCTAAAACTGGAAGGCGGCCGCATG<br>GCCCTGATTGTGCTGGGGGGCGTCGCCGGCCTCCTGCTTTTCAT<br>TGGGCTAGGCATCTTCTTCTGTGTCAGGTGCCGGCACCGAAGG<br>CGCCAATAA |
| 67 | CD8ss-DmrC-CD8TM-<br>41BB-CD3z-P2A-<br>IgKss-CD19scFv-<br>DmrA-CD4TM codon<br>optimized protein | MALPVTALLLPLALLLHAARPGSILWHEMWHEGLEEASRLYFGE<br>RNVKGMFEVLEPLHAMMERGPQTLKETSFNQAYGRDLMEAQE<br>WCRKYMKSGNVKDLLQAWDLYYHVFRRISKASAGTGSDIYIWA<br>PLAGTCGVLLLSLVITMHKRGRKKLLYIFKQPFMRPVQTTQEEDG<br>CSCRFPEEEEGGCELRVKFSRSADAPAYQQGQNQLYNELNLGRR<br>EEYDVLDKRRGRDPEMGGKPRRKNPQEGLYNELQKDKMAEAYS<br>EIGMKGERRRGKGHDGLYQGLSTATKDTYDALHMQALPPRSGS<br>GATNFSLLKQAGDVEENPGPSMETDTLLLWVLLLWVPGSTGDIQ<br>MTQTTSSLSASLGDRVTISCRASQDISKYLNWYQQKPDGTVKLLI<br>YHTSRLHSGVPSRFSGSGSGTDYSLTISNLEQEDIATYFCQQGNTL<br>PYTFGGGTKLEITGSTSGSGKPGSGEGSTKGEVKLQESGPGLVAPS<br>QSLSVTCTVSGVSLPDYGVSWIRQPPRKGLEWLGVIWGSETTYY<br>NSALKSRLTIIKDNSKSQVFLKMNSLQTDDTAIYYCAKHYYYGGS<br>YAMDYWGQGTSVTVSSPRGGGGSGVQVETISPGDGRTFPKRGQT<br>CVVHYTGMLEDGKKFDSSRDRNKPFKFMLGKQEVIRGWEEGVA<br>QMSVGQRAKLTISPDYAYGATGHPGIIPPHATLVFDVELLKLEGG<br>RMALIVLGGVAGLLLFIGLGIFFCVRCRHRRRQ |
| 68 | CD8ss-DmrC-CD8TM-<br>41BB-CD3z-P2A-<br>IgKss-CD19scFv-<br>DmrA-CD4TM codon<br>optimized DNA | ATGGCCCTCCCTGTGACCGCCCTGCTGCTCCCCCTCGCCCTGTT<br>GCTCCATGCTGCCCGACCTGGATCCATCCTTTGGCACGAGATG<br>TGGCACGAGGGACTCGAAGAAGCGTCCCGGCTGTACTTCGGA<br>GAGCGGAACGTGAAGGGGATGTTCGAAGTGCTGGAACCCCTG<br>CACGCCATGATGGAGCGGGGTCCTCAGACCCTTAAAGAAACA<br>AGCTTCAACCAGGCGTACGGGCGCGACCTGATGGAAGCCCAG<br>GAGTGGTGCCGCAAGTACATGAAGTCCGGAAACGTGAAGGAT<br>CTGCTGCAAGCCTGGGATCTGTACTACCACGTGTTCAGAAGGA<br>TCTCAAAGGCTAGCGCCGGCACTGGTTCGGATATCTACATTTG<br>GGCACCGCTCGCCGGCACTTGTGGAGTGCTGTTGCTGTCCCTC<br>GTGATCACCATGCATAAGAGGGGACGGAAGAAGCTGCTGTAC<br>ATTTTCAAGCAGCCATTCATGCGGCCTGTGCAAACCACCCAGG<br>AGGAGGACGGGTGCAGCTGCCGGTTCCCTGAGGAAGAGGAGG<br>GCGGATGCGAACTGCGCGTGAAGTTCAGCCGGAGCGCAGATG<br>CTCCCGCATACCAACAGGGACAGAACCAGCTGTATAACGAGC<br>TGAACCTGGGCAGAAGGGAAGAGTACGACGTCCTCGACAAGC<br>GGCGGGGACGCGACCCAGAAATGGGAGGAAAGCCCCGCCGGA<br>AGAACCCGCAGGAAGGCCTGTACAACGAGTTGCAGAAAGACA<br>AGATGGCTGAAGCTTACTCGGAGATTGGCATGAAGGGGGAGA<br>GAAGAAGAGGGAAGGGCCACGACGGCCTTTACCAAGGACTGA<br>GCACTGCCACCAAGGACACCTACGATGCGCTGCACATGCAGG<br>CCCTGCCCCCGCGGTCCGGTTCGGGCGCGACTAACTTCAGCCT<br>GCTGAAGCAGGCCGGAGATGTGGAGGAAAACCCTGGACCGTC<br>CATGGAGACTGATACCCTGCTTCTGTGGGTCCTGCTCCTCTGG<br>GTGCCGGGCTCCACCGGTGACATCCAGATGACCCAGACCACCT<br>CATCCCTGAGCGCCTCTCTGGGTGATCGCGTGACTATCTCCTGC<br>CGGGCGTCGCAGGATATCTCCAAGTACCTGAACTGGTACCAGC<br>AAAAACCGGACGGGACCGTGAAACTGCTGATCTACCATACTTC<br>CCGCCTTCATTCCGGAGTGCCCTCCCGGTTTTCCGGCTCGGGTT<br>CAGGGACTGATTATTCGCTGACCATTTCCAACCTGGAGCAGGA<br>GGACATTGCGACCTACTTCTGCCAACAAGGAAACACCCTGCCC<br>TACACTTTCGGTGGTGGAACCAAGCTCGAGATCACCGGATCAA<br>CCTCGGGCAGCGGGAAGCCGGGCAGCGGAGAGGGATCGACGA<br>AAGGAGAAGTCAAGCTGCAGGAATCCGGCCCGGGACTGGTGG<br>CCCCGAGCCAGTCGCTCTCCGTCACTTGCACCGTGTCGGGAGT<br>GTCCTTGCCCGACTACGGAGTGTCATGGATTCGGCAGCCACCT<br>CGCAAGGGCCTGGAATGGCTCGGCGTGATTTGGGGCTCAGAA<br>ACCACATACTACAACAGCGCCCTGAAGTCTCGGCTCACCATCA<br>TCAAGGACAATTCCAAGTCCCAAGTGTTCCTGAAGATGAATAG<br>CTTGCAGACTGACGACACCGCGATCTACTACTGTGCCAAGCAC<br>TACTACTACGGCGGTTCCTACGCCATGGACTACTGGGGACAAG<br>GAACTTCCGTGACTGTCTCCTCCCCTAGGGGGGGTGGTGGTTC |

TABLE 1-continued

Exemplary DARIC Binding and Signaling Components

| SEQ ID NO. | Construct | Sequence |
|---|---|---|
| | | GGGGGTCCAGGTGGAAACCATTTCCCCCGGCGACGGGCGCAC<br>CTTCCCGAAGCGCGGACAGACCTGTGTGGTGCACTATACCGGA<br>ATGCTCGAAGATGGAAAGAAGTTTGACAGCTCCAGGGACCGC<br>AACAAGCCTTTCAAGTTTATGCTTGGAAAGCAGGAAGTCATCC<br>GGGGCTGGGAAGAGGGAGTCGCCCAGATGAGCGTCGGCCAGC<br>GGGCCAAGCTGACGATCTCCCCTGACTATGCCTACGGCGCTAC<br>CGGCCATCCCGGAATCATTCCGCCGCACGCAACCCTCGTGTTC<br>GACGTGGAATTGCTCAAGCTGGAAGGCGGCCGCATGGCGCTG<br>ATAGTGCTCGGCGGAGTGGCCGGACTGCTGCTGTTCATCGGCC<br>TGGGCATCTTCTTCTGCGTGAGATGCCGCCATAGAAGGCGGCA<br>ATGA |
| 70 | SS-DmrC-CD8TM-41BB-CD3z-P2A-SS-CD123scFv-DmrA-CD4TM protein | MRPTWAWWLFLVLLLALWAPARGGSILWHEMWHEGLEEASRL<br>YFGERNVKGMFENLEPLHAMMERGPQTLKETSFNQAYGRDLME<br>AQEWCRKYMKSGNVKDLLQAWDLYYHVFRRISKASAGTGSDIY<br>IWAPLAGTCGVLLLSLVITMHKRGRKKLLYIFKQPFMRPVQTTQE<br>EDGCSCRFPEEEEGGCELRVKFSRSADAPAYQQGQNQLYNELNL<br>GRREEYDVLDKRRGRDPEMGGKPRRKNPQEGLYNELQKDKMAE<br>AYSEIGMKGERRRGKGHDGLYQGLSTATKDTYDALHMQALPPR<br>GGRSGSGATNFSLLKQAGDVEENPGPSLWWRLWWLLLLLLLLW<br>PMVWAPRADYKDIVMTQSHKFMSTSVGDRVNITCKASQNVDSA<br>VAWYQQKPGQSPKALIYSASYRYSGVPDRFTGRGSGTDFTLTISS<br>VQAEDLAVYYCQQYYSTPWTFGGGTKLE1KRGGGGSGGGGSGG<br>GGSGGGGSEVKLVESGGGLVQPGGSLSLSCAASGFTFTDYYMSW<br>VRQPPGKALEWLALIRSKADGYTTEYSASVKGRFTLSRDDSQSIL<br>YLQMNALRPEDSATYYCARDAAYYSYYSPEGAMDYWGQGTSV<br>TVSSSASGGGGSGVQVETISPGDGRTFPKRGQTCVVHYTGMLED<br>GKKFDSSRDRNKPFKFMLGKQEVIRGWEEGVAQMSVGQRAKLTI<br>SPDYAYGATGHPGIIPPHATLVFDVELLKLEGGRMALIVLGGVAG<br>LLLFIGLGIFFCVRCRHRRRQ |
| 71 | SS-DmrC-CD8TM-41BB-CD3z-P2A-SS-CD123scFv-DmrA-CD4TM DNA | ATGCGCCCCACCTGGGCCTGGTGGCTGTTCCTGGTGCTGCTGC<br>TGGCCCTGTGGGCACCCGCTCGCGGCGGATCCATCCTCTGGCA<br>TGAGATGTGGCATGAAGGCCTGGAAGAGGCATCTCGTTTGTAC<br>TTTGGGGAAAGGAACGTGAAAGGCATGTTTGAGGTGCTGGAG<br>CCCTTGCATGCTATGATGGAACGGGGCCCCCAGACTCTGAAGG<br>AAACATCCTTTAATCAGGCCTATGGTCGAGATTTAATGGAGGC<br>CCAAGAGTGGTGCAGGAAGTACATGAAATCAGGGAATGTCAA<br>GGACCTCCTCCAAGCCTGGGACCTCTATTATCATGTGTTCCGA<br>CGAATCTCAAAGGCTAGCGCCGGCACTGGTTCCGACATCTACA<br>TCTGGGCCCCTCTGGCCGGCACATGTGGCGTGCTGCTGCTGAG<br>CCTCGTGATCACCATGCATAAACGGGGCAGAAAGAAACTCCT<br>GTATATATTCAAACAACCATTTATGAGACCAGTACAAACTACT<br>CAAGAGGAAGATGGCTGTAGCTGCCGATTTCCAGAAGAAGAA<br>GAAGGAGGATGTGAACTGCGGGTGAAGTTCAGCAGAAGCGCC<br>GACGCCCCTGCCTACCAGCAGGGCCAGAATCAGCTGTACAAC<br>GAGCTGAACCTGGGCAGAAGGGAAGAGTACGACGTCCTGGAT<br>AAGCGGAGAGGCCGGGACCCTGAGATGGGCGGCAAGCCTCGG<br>CGGAAGAACCCCCAGGAAGGCCTGTATAACGAACTGCAGAAA<br>GACAAGATGGCCGAGGCCTACAGCGAGATCGGCATGAAGGGC<br>GAGCGGAGGCGGGCAAGGGCCACGACGGCCTGTATCAGGGC<br>CTGTCCACCGCCACCAAGGATACCTACGACGCCCTGCACATGC<br>AGGCCCTGCCCCCAAGGGGCGGCCGCTCAGGATCTGGCGCCA<br>CGAACTTCTCTCTGTTAAAGCAAGCAGGAGATGTTGAAGAAAA<br>CCCCGGGCCTTCACTGTGGTGGCGCCTGTGGTGGCTGCTCCTG<br>CTTCTGTTGCTCCTGTGGCCCATGGTGTGGGCCCCTAGGGCGG<br>ACTACAAAGATATTGTGATGACCCAGTCTCACAAATTCATGTC<br>CACATCAGTAGGAGACAGGGTCAACATCACCTGCAAGGCCAG<br>TCAGAATGTGGATAGTGCTGTAGCCTGGTATCAACAGAAACCA<br>GGGCAATCTCCTAAAGCACTGATTTACTCGGCATCCTACCGGT<br>ACAGTGGAGTCCCTGATCGCTTCACAGGCAGGGGATCTGGGAC<br>AGATTTCACTCTCACCATCAGCAGTGTGCAGGCTGAAGACCTG<br>GCAGTTTATTACTGTCAGCAATATTATAGCACTCCGTGGACGT<br>TCGGTGGAGGCACCAAGCTGGAAATCAAACGTGGTGGTGGTG<br>GTTCTGGTGGTGGTGGTTCTGGCGGCGGCGGCTCCGGTGGTGG<br>TGGATCCGAGGTGAAGCTGGTGGAGTCTGGAGGAGGCTTGGT<br>ACAGCCTGGGGGTTCTCTGAGTCTCTCCTGTGCAGCTTCTGGAT<br>TCACCTTCACTGATTACTACATGAGCTGGGTCCGCCAGCCTCC<br>AGGGAAGGCACTTGAGTGGTTGGCTTTGATTAGAAGCAAAGCT<br>GATGGTTACACAACAGAATACAGTGCATCTGTGAAGGGTCGGT<br>TCACCCTCTCCAGAGATGATTCCCAAAGCATCCTCTATCTTCAA<br>ATGAATGCCCTGAGACCTGAAGACAGTGCCACTTATTACTGTG<br>CAAGAGATGCGGCCTACTATAGTTACTATAGTCCCGAGGGGGC<br>TATGGACTACTGGGGTCAAGGAACCTCAGTCACCGTCTCCTCG |

TABLE 1-continued

Exemplary DARIC Binding and Signaling Components

| SEQ ID NO. | Construct | Sequence |
|---|---|---|
| | | AGCGCTAGCGGCGGAGGTGGGAGCGGAGTGCAGGTGGAAACC<br>ATCTCCCCAGGAGACGGGCGCACCTTCCCCAAGCGCGGCCAG<br>ACCTGCGTGGTGCACTACACCGGGATGCTTGAAGATGGAAAG<br>AAATTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGGCGGCCGCATGGCCCTGATTGTGCTGGGGGCGTCGC<br>CGGCCTCCTGCTTTTCATTGGGCTAGGCATCTTCTTCTGTGTCA<br>GGTGCCGGCACCGAAGGCGCCAATAA |

EXAMPLES

Example 1

Construction of DARIC Binding and Signaling Components

The DARIC binding and signaling components were each separately cloned into a plasmid vector containing a T7 promoter, a hScn or hCD8 secretion signal, respectively, and a downstream linearization site. Linearized plasmids were then used as templates for in vitro transcription reactions, followed by 3'-polyadenylation and 5'-capping steps to create mature in vitro transcribed mRNA (IVT-mRNA) to be electroporated into primary human T cells. Human T cells were isolated from PBMCs by negative selection using paramagnetic beads and expanded with anti-CD3/anti-CD28 beads for 48 hours prior to electroporation. Control electroporations using IVT-mRNA encoding fluorescent proteins were performed in parallel to confirm transfection efficiency, or 2A protein-linked fluorescent proteins were incorporated directly into the DARIC component mRNA species.

Exemplary IVT-mRNA encoding binding components (scFv specific for CD19 and multimerization domain FKBP12 ("DmrA"), FKBP12 F36V ("DmrB"), FRB (2021-2113) T2098L ("DmrC")) are provided in SEQ ID NOs.:2, 5, and 8 (scFv specific for CD19 and multimerization domain FKBP12, FKBP12 F36V, or FRB (2021-2113) T2098L, respectively). Exemplary IVT-mRNA encoding signaling components are provided in SEQ ID NOs.:16, 20, and 24 (multimerization domain FRB (2021-2113) T2098L, FKBP12 F36V, or FKBP12, respectively, transmembrane domain, 4-1BB, and CD3ζ).

Multimerization is promoted with a bridging factor, such as rapamycin or rapalogs thereof, or gibberellin or derivatives thereof. Rapamycin and its derivatives (e.g., AP21967, also known as C-16-(S)-7-methylindolerapamycin, $IC_{50}$=10 nM, a chemically modified non-immunosuppressive rapamycin analogue) can induce heterodimerization of FKBP12 and FRB-containing fusion proteins. AP1903 or AP20187 are homo-bivalent drugs based on the FKBP12-interacting component of rapamycin, which can be used in homodimerization scenarios described herein.

Example 2

Cytotoxicity of T Cells Encoding DARIC Components

Recombinant T cells expressing the two DARIC components were incubated with K562 target cells (a human myeloid leukemia cell line), which were modified to express either CD19 or CD20 antigen, to examine target cell lysis. Briefly, T cells were co-incubated with a 50:50 mixture of K562-CD19 and K562-CD20 target cell lines, at 3:1 or 10:1 T cell to target cell ratios. In experimental samples, 500 nM final concentration of the hetero-bivalent rapalog AP21967 was added. The relative percentage of each of the target cell lines was monitored by flow cytometry staining for the CD19 and CD20 antigens to evaluate cell lysis (see FIG. 3).

Figure 3A:
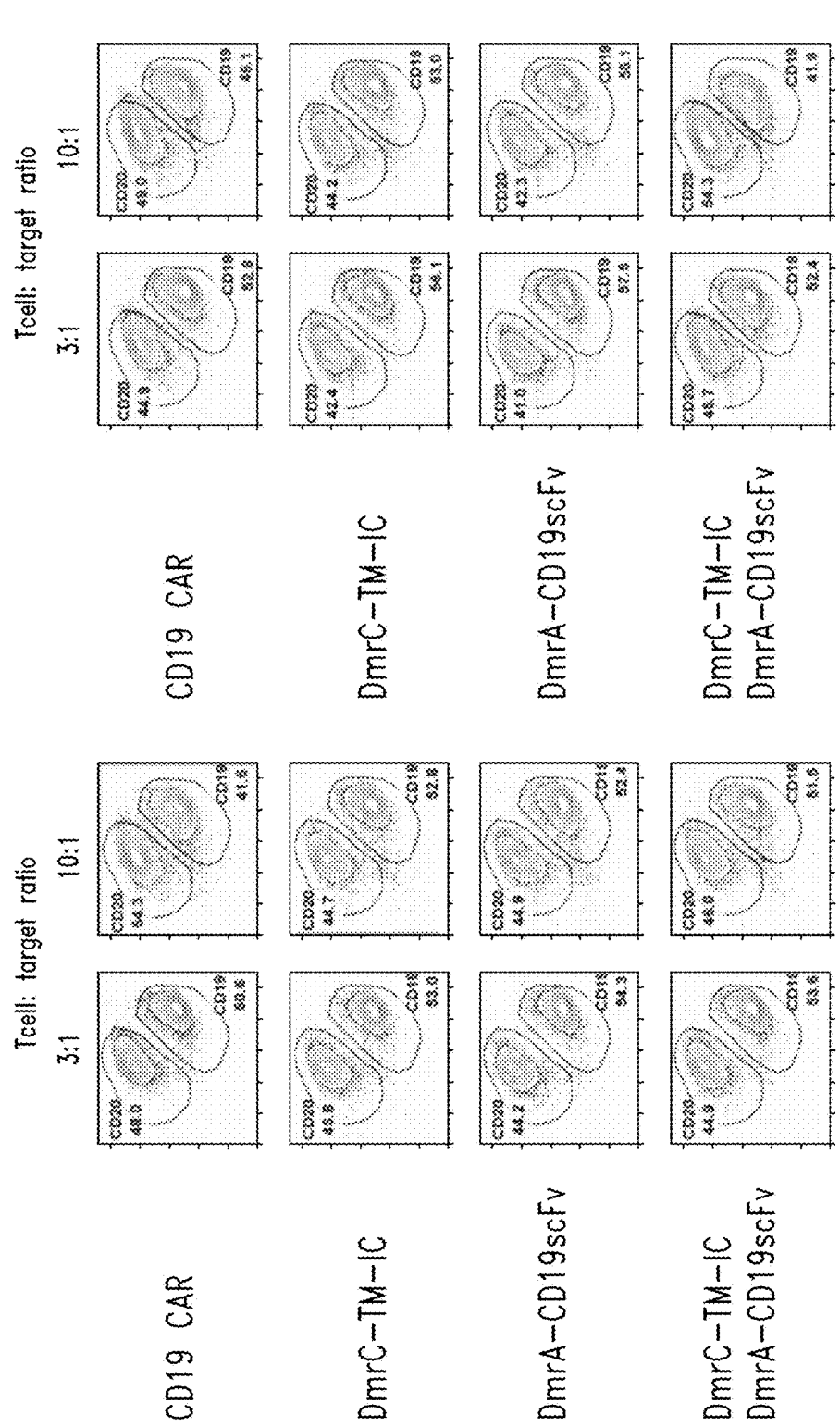
FIGS. 3A and 3B show the cytotoxic properties of human T cells expressing a multipartite signaling complex of this disclosure.

Four samples of primary human T cells were prepared by electroporation with IVT-mRNA encoding (i) an extensively validated single-chain chimeric antigen receptor (CAR) (CD19-CAR, SEQ ID NO.:14, positive control); (ii) the DARIC signaling component only (DSC, SEQ ID NO.:16, negative control); iii) the DARIC binding component only (DBC-CD19, SEQ ID NO.:2, negative control); and (iv) both DARIC binding and signaling components (DSC, SEQ ID NO.:16 plus DBC-CD19, SEQ ID NO.:2). The relative percentages of each of the target cell lines were monitored by flow cytometry staining for the CD19 and CD20 antigens (FIG. 3A).

Figure 3B:
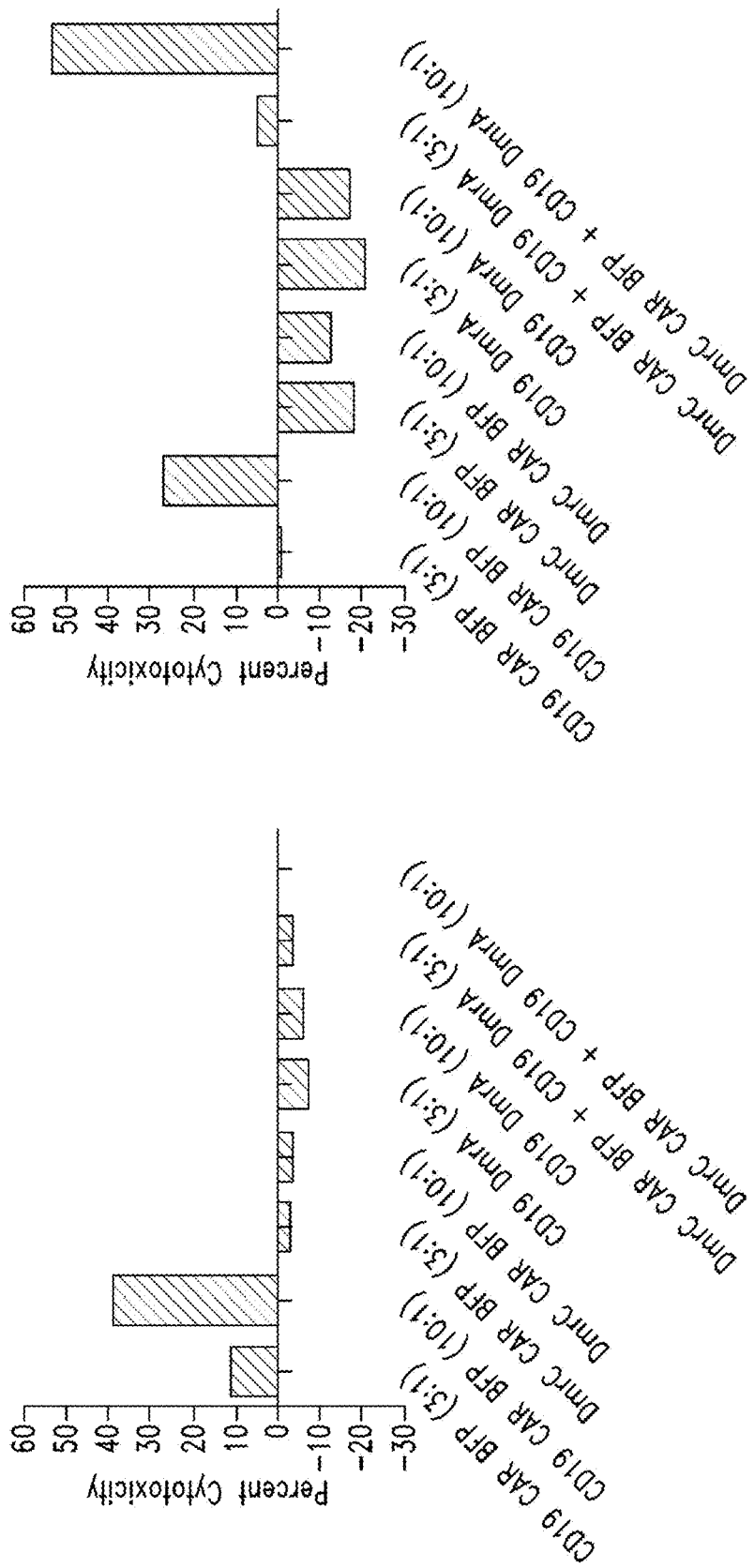

The percent specific cytotoxicity was calculated for each condition as the percentage change relative the input K562-CD19:K562-CD20 ratio. T cells expressing the validated CD19-CAR (SEQ ID NO.:14) showed substantial cytotoxicity and skewing of the ratio of CD19 versus CD20 cells in the live cell gate, particularly at a 10:1 T cell to target cell ratio. The T cells expressing the DARIC binding component alone, DARIC signaling component alone, or both DARIC components but without the addition of the hetero-bivalent rapalog AP21967, showed no significant cytotoxicity. In the presence of AP21967, a substantial specific cytoxicity and loss of the K562-CD19 target cells was observed upon co-incubation with T cells expressing both DARIC components (FIG. 3B).

These results indicate that the DARIC mechanism can reconstitute antigen-specific target cell lysis. Furthermore, the DARIC design enables pharmacological control of antigen-specific T cell cytotoxicity.

Example 3

Cytokine Secretion Profile of T Cells Encoding DARIC Components

Figure 4:
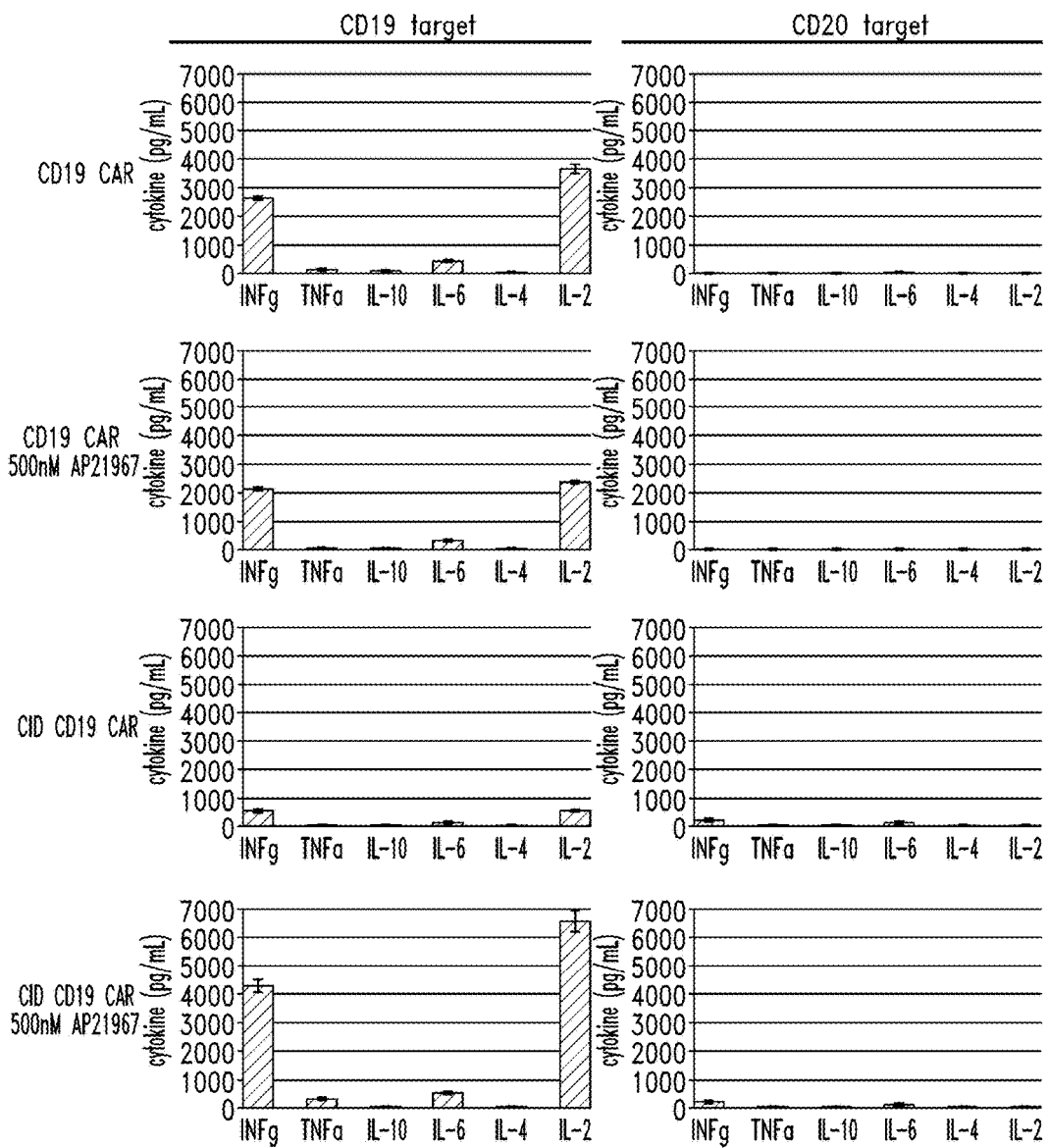
FIG. 4 shows the cytokine secretion profile of human T cells expressing a multipartite signaling complex of this disclosure.

Recombinant T cells expressing the two DARIC components were incubated with K562 target cells (a human myeloid leukemia cell line), which were modified to express either CD19 or CD20 antigen, to examine cytokine expression. Briefly, IVT-mRNA transfected T cells were co-incubated with either the K562-CD19 or K562-CD20 cell lines using T cell to target ratios of 1:1, with or without the addition of 500 nM AP21967. Supernatants were isolated for analysis of cytokine production (see FIG. 4).

Two samples of primary human T cells were isolated, expanded, and then prepared by electroporation with IVT-mRNA encoding either (i) the validated single-chain CAR (CD19-CAR, SEQ ID NO.:13, positive control); or (ii) both DARIC binding and signaling components (DSC, SEQ ID NO.:16 plus DBC-CD19, SEQ ID NO.:2). After extensively washing the expanded and electroporated T cells to remove residual cytokines from the growth media, the T cells were co-incubated with K562 cell lines expressing either the human CD19 antigen (left panels) or the CD20 antigen (right panels) at 1:1 T cell to target cell ratios and in the presence or absence of the AP21967 rapalog. The supernatants were then collected and assayed for analyte concentrations using cytokine capture antibody-labeled beads (Becton Dickenson Cytokine Bead Array, human Th1/Th2 kit). Comparison with recombinant protein standards enabled calculation of absolute concentrations of each of the six cytokines encompassed by the bead array.

Consistent with previous cytotoxicity findings, T cells expressing the positive control CD19-CAR produced substantial amounts of interferon-gamma (IFNγ) and interleukin-2 (IL-2) when co-incubated with CD19 expressing K562 target cells. T cells expressing the DARIC components in the absence of bridging factor AP21967 showed no significant cytokine production, but in the presence of AP21967 produced IFNγ and IL-2 at levels equivalent, or superior, to the single chain CD19-CAR positive control.

Example 4

Lentiviral Delivery of DARIC Components

Primary human T cells were isolated, activated, and then transduced with lentiviral vectors encoding DARIC binding and signaling components (SEQ ID NOS.:44 and 47). The transduced T cells were then co-incubated with about a 50:50 mixture of the K562 target cells expressing either CD19 (K562-CD19) or CD20 (K562-CD20) to evaluate antigen-specific cytotoxicity. The overall ratio of T cells to K562 cells was 5:1 in all samples. In control samples, no bridging factor was added, whereas in experimental samples either rapamycin (10 nM) or AP21967 (100 nM) were applied as the bridging factor for the secreted antigen binding component and the signaling component (see, e.g., FIG. 1B). The DARIC antigen binding component includes a CD19 antigen binding scFv domain and a FKBP12 multimerization domain, which was linked to a mCherry fluorescent protein. Two independent multimerization domains having different specificities for bridging components were tested on the DARIC signaling component: FRB, which is responsive to rapamycin, and the FRB (2021-2113) T2098L variant, which is responsive to both rapamycin and AP21967, each linked to the blue fluorescent protein (BFP).

Flow cytometric analysis of the lentivirus-transduced T cells demonstrated expression of both mCherry and BFP proteins simultaneously, indicating both DARIC components were being expressed within the same cells (see FIG. 5, first column for each treatment). Flow cytometric analysis of the K562 cells demonstrated rapamycin and AP21967-dependent elimination of the CD19 expressing K562 cells in the sample expressing variant FRB (2021-2113) T2098L multimerization domain, whereas no addition of a bridging factor had no effect on cell survival (see FIG. 5, top row of second column for each treatment). But, only rapamycin was able to activate the elimination of the K562-CD19 cells by T cells expressing the FRB dimerization domain, while AP21967 or no addition of a bridging factor had no effect on cell survival (see FIG. 5, second row of second column for each treatment). These data show the specificity of cytotoxic activity that can be achieved with the DARIC multipartite component system.

In addition, two distinct T cell populations were mixed, wherein one population was expressing a DARIC antigen binding component and the other population was expressing a DARIC signaling component. This mixed cell population, when co-cultured with the CD19 and CD20 expressing K562 cells, showed a rapamycin-dependent cytotoxicity response against K562-CD19 cells, while the absence of a bridging factor had no effect on target cell survival (see FIG. 5, bottom row). These data indicate that a DARIC antigen binding component expressed by one T cell population can act in trans with a different population of T cells that express a DARIC signaling component and attack the target cells.

The flexibility of the DARIC system was validated by swapping the multimerization domains such that the DARIC binding component targeting CD19 comprised the FRB based DmrC domain and the DARIC signaling component comprised the FKBP12 based DmrA domain (SEQ ID NOs.:12, 31). Primary human T cells were made to express the 'swapped' DARIC components and then co-incubated with 50:50 mixtures of the K562-CD19 and C562-CD20 target cells either in the absence or presence of the indicated concentrations of rapamycin (FIG. 10). Antigen specific cytotoxicity was observed in the experimental samples containing the bridging factor, but absent from the control sample lacking rapamycin. These data demonstrate that the architecture of the DARIC system is flexible and amenable to a variety of multimerization domain orientations.

Example 5

Titration of Bridging Factors to Sub-Therapeutic Levels

A broad range of bridging factor (rapamycin and everolimus) concentrations were tested to determine whether a DARIC system can function at clinically relevant concentrations. As in the Example 4, primary human T cells were isolated, activated, and then transduced with lentiviral vectors expressing a DARIC binding component (SEQ ID NOS.:1, 4, 7) and a DARIC signaling component (SEQ ID NOS.:15, 19, 23). The DARIC expressing T cells were then co-incubated with 50:50 mixtures of the K562-CD19 and K562-CD20 target cells to evaluate antigen-specific cytotoxicity. The overall ratio of T cells to K562 cells was 5:1 in all samples.

The indicated concentrations of rapamycin and everolimus were added to the co-culture samples and then the cytotoxicity responses were evaluated by flow cytometry (FIG. 6). Cytotoxicity responses were maintained to sub-nanomolar drug concentrations, well below the steady state concentrations of rapamycin and everolimus that are presently achieved when these drugs are administered to patients in the clinic.

Example 6

Use of a Tethered DARIC Binding Component

A series of additional DARIC molecules, in which the antigen binding component was maintained on the T cell surface rather than released into the extracellular space, were tested (see, e.g., FIG. 11). Several protein regions and transmembrane domains were used to anchor the binding domain to the T cell surface (SEQ ID NOS.:50, 53, 56, 59), each altering the spacing or steric parameters governing multimerization of the DARIC binding and signaling components. As in the previous examples, antigen-specific cytotoxicity responses using lentivirus-transduced T cells and 50:50 mixtures of the K562-CD19 and K562-CD20 target cells were used to evaluate the tethered DARIC binding component. The overall ratio of T cells to K562 cells was 5:1 in all samples, with the indicated concentrations of a bridging factor used in experimental samples.

Each design had the property of bridging factor-responsive, antigen-specific cytotoxicity against the K562-CD19 cells. The tethered DARIC binding component containing the CD8 hinge/CD8 transmembrane domain (SEQ ID NO.:53) showed a measurable level of activity in the absence of a bridging factor. The tethered DARIC binding component comprising the IgG4 CH2CH3 spacer with CD4 transmembrane domain (SEQ ID NO.:56) provided the strongest cytotoxic response upon addition of the rapamycin (bridging factor), while the tethered DARIC binding component comprising only the CD4 transmembrane domain (SEQ ID NO.:50) were moderately active (FIG. 7). A DARIC binding components comprising a GPI signal sequence from the CD52 protein (see schematic in FIG. 1K) were also tested. The GPI anchored DARIC produced an antigen specific cytotoxicity response only in the presence of an appropriate bridging factor (FIG. 8). These data demonstrate that a DARIC binding component can be either released or tethered to the cell surface and still function with a DARIC signaling component.

Additional lentiviral constructs comprising tethered DARIC binding components were generated and similarly tested in human T cells, including a modified CD4 transmembrane domain with improved activity over other transmembrane tethered DARIC binding components (SEQ ID NOs.:64-69). Additionally, the DARIC signaling and binding components were integrated into a single open reading frame comprising a 2A peptide situated between the two components (such as that used in FIG. 11), thus validating a simplified DARIC delivery scheme using a single lentiviral vector (SEQ ID NOs.:66, 69, 72).

For any of the DARIC componentry designs, similar results are expected using a variety of lentiviral vector designs, such as those comprising bi-directional promoters (SEQ ID NO.:73) for example, or using alternative transgene delivery vectors (e.g., adenovirus or AAV) and schemes such as including the targeted integration of transgenes via homologous recombination, a process that can be stimulated to high efficiency using gene-specific nucleases.

Example 7

DARIC Targeting of Additional Model Antigens

The DARIC system was extended to an additional model antigen to show the broad applicability of artificial cells expressing drug regulated multipartite receptors ctemplated herein. K562 target cell lines were generated to express the CD123 antigen by sub-cloning this antigen into a lentiviral vector comprising a puromycin selection cassette (SEQ ID NO.:74), lentiviral particles were produced, and K562 cells were infected and selected with puromycin. Primary human T cells were isolated, activated, and then transduced with lentiviral vectors encoding a CD123 targeting DARIC binding component along with the DARIC signaling component (SEQ ID NOs.:70-72). Antigen-specific cytotoxicity responses were evaluated using lentivirus-transduced T cells co-cultured with 50:50 mixtures of the K562-CD19 and K562-CD123 target cells, using a traditional CD123 targeting chimeric antigen receptor (CAR) as a positive control. The overall ratio of T cells to K562 cells was 5:1 in all samples, with the indicated concentrations of a bridging factor used in experimental samples. Cytotoxicity was observed in the positive control sample and in the CD123 DARIC sample containing rapamycin. The results demonstrated that bridging factor dependent cytotoxic activity could be achieved with the DARIC system targeting diverse antigens (FIG. 9).

Example 8

Deactivation of DARIC Using an Anti-Bridging Factor

Deactivation of the DARIC system by the addition of a pharmacological agent that competes for binding to one of the multimerization domains was tested. Primary human T cells expressing either a traditional CD19 targeting CAR or primary human T cells expressing the CD19 targeting DARIC components (SEQ ID NO.:66) were co-incubated with 50:50 mixtures of K562-CD19 and K562-CD20 cells. For the T cells expressing the CD19 targeting CAR (SEQ ID NO.:14), cytotoxicity was observed both in the presence or absence of rapamycin. In contrast, CD19 targeting DARIC T cells, showed efficient antigen-specific cytotoxicity in the presence of sub-nanomolar levels of rapamycin, but showed no cytotoxicity in the absence of the bridging factor (FIG. 11). However, when FK506 was added, a marked reduction in antigen specific cytotoxicity was observed for the DARIC T cells while a minimal reduction was observed for the CAR T cells, indicating that FK506 disrupted the coupling of the DARIC componentry and deactivated the antigen-driven cytotoxicity response.

This example shows that a competitive inhibitor of a bridging factor substantially inhibited DARIC antigen receptors and therefore is suitable for clinical use to limit pathology that can arise as a result of excessive proliferation or activation of administered cells. Without wishing to be bound to any particular theory, this strategy may be particularly effective if the inhibitor has additional immunosuppressive mechanisms of action involving native proteins that contribute in cellular responses, as is true of FK506 inhibiting intracellular cyclophilins that promote T cell proliferative responses.

Example 9

DARIC System Leveraging an Endogenous Signaling Receptor

A DARIC system was designed to provide two secreted DARIC components (SEQ ID NO.:75). The DARIC binding component comprises a binding domain that binds CD19 and the DARIC signaling component comprises a binding domain that binds CD3 and a multimerization domain. This system will be tested using a modified co-culture cytotoxicity experiment. Supernatants from T cells transduced with lentiviral particles encoding the two secreted DARIC components will be transferred to a 50:50 mix of K562-CD19 and K562-CD20 target cells also containing non-transduced T cells. Cytotoxicity will be measured in the presence and absence of bridging factor. Control samples comprising the supernatant that is kept in a decoupled state by not providing the bridging factor are not expected to show any antigen specific cytotoxicity. However, samples in which the supernatant and bridging factor are added are expected to initiate the antigen specific cytotoxicity response. This result will demonstrate that artificial cells can be made to express a soluble DARIC system that can systemically initiate cytotoxicity responses in a drug regulated fashion.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated non-natural cell, comprising:
   (a) a first exogenous polynucleotide encoding a first fusion protein comprising a first multimerization domain, a first transmembrane domain, and an actuator domain, wherein the first multimerization domain localizes extracellularly when the first fusion protein is expressed; and
   (b) a second exogenous polynucleotide encoding a second fusion protein comprising a secretion signal; a binding domain that comprises a single chain antibody, a receptor ectodomain, or a ligand; a second multimerization domain; and a second transmembrane domain, wherein the binding domain and the second multimerization domain localizes extracellularly when expressed;
   wherein a bridging factor promotes the formation of a polypeptide complex on the non-natural cell surface with the bridging factor associated with and disposed between the multimerization domains of the first and second fusion proteins.

2. The isolated non-natural cell of claim 1, wherein the first and second multimerization domains are the same or different.

3. The isolated non-natural cell of claim 1, wherein the multimerization domains of the first and second fusion proteins associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, and trimethoprim (Tmp)-synthetic ligand for FK506 binding protein (FKBP) (SLF) or a derivative thereof.

4. The isolated non-natural cell of claim 1, wherein the first and second multimerization domains are a pair selected from the group consisting of: FKBP and FKBP12-rapamycin binding (FRB), FKBP and calcineurin, FKBP and cyclophilin, FKBP and bacterial dihydrofolate reductase (DHFR), calcineurin and cyclophilin, and PYR1-like 1 (PYL1) and abscisic acid insensitive 1 (ABI1).

5. The isolated non-natural cell of claim 1, wherein the first multimerization domain comprises a first FKBP polypeptide or variant thereof, and the second multimerization domain comprises a first FRB polypeptide or variant thereof.

6. The isolated non-natural cell of claim 1, wherein the first multimerization domain comprises a first FRB polypeptide or variant thereof, and the second multimerization domain comprises a first FKBP polypeptide or variant thereof.

7. The isolated non-natural cell of claim 1, wherein the bridging factor is AP21967, sirolimus, everolimus, novolimus, pimecrolimus, ridaforolimus, tacrolimus, temsirolimus, umirolimus, or zotarolimus.

8. The isolated non-natural cell of claim 1, wherein the first transmembrane domain is a CD4, CD8 or CD28 transmembrane domain.

9. The isolated non-natural cell of claim 1, wherein the first transmembrane domain is a CD8 transmembrane domain.

10. The isolated non-natural cell of claim 1, wherein the second transmembrane domain is a CD4, CD8 or CD28 transmembrane domain.

11. The isolated non-natural cell of claim 1, wherein the second transmembrane domain is a CD4 transmembrane domain.

12. The isolated non-natural cell of claim 1, wherein the actuator domain comprises a lymphocyte receptor signaling domain.

13. The isolated non-natural cell of claim 1, wherein the actuator domain comprises one or a plurality of immunoreceptor tyrosine-based activation motifs (ITAMs).

14. The isolated non-natural cell of claim 1, wherein the actuator domain comprises a lymphocyte receptor signaling domain of a polypeptide selected from the group consisting of: CD3ε, CD3δ, CD3ζ, pre-T cell receptor α (pTα), T cell receptor α (TCRα), T cell receptor β (TCRβ), Fc receptor α (FcRα), Fc receptor β (FcRβ), Fc receptor γ (FcRγ), natural-killer group 2, member D (NKG2D), CD79A, CD79B, and any combination thereof.

15. The isolated non-natural cell of claim 1, wherein the first fusion protein further comprises a different actuator domain, a costimulatory domain, an adhesion factor, or any combination thereof.

16. The isolated non-natural cell of claim 15, wherein the costimulatory domain is from a polypeptide selected from the group consisting of: CD27, CD28, CD30, CD40, linker for activation of T-cells (LAT), zeta-chain-associated protein kinase 70 (Zap70), inducible T-cell costimulator (ICOS), DNAX-activation protein 10 (DAP10), 4-1BB, caspase recruitment domain family member 11 (CARD11), herpesvirus entry mediator (HVEM), lymphocyte activating gene 3 (LAG3), signaling lymphocytic activation molecule family member 1 (SLAMF1), lymphocyte-specific protein tyrosine kinase (Lck), fyn oncogene related to src, fgr, yes (Fyn), SH2 domain-containing leukocyte protein of 76 KDa (Slp76), OX40, and any combination thereof.

17. The isolated non-natural cell of claim 1, wherein the actuator domain comprises a cytoplasmic portion that associates with a cytoplasmic signaling protein.

18. The isolated non-natural cell of claim 17, wherein the cytoplasmic signaling protein is a lymphocyte receptor or signaling domain thereof, a protein comprising a plurality of immunoreceptor tyrosine-based activation motifs (ITAMs), a costimulatory domain, an adhesion factor, or any combination thereof.

19. The isolated non-natural cell of claim 18, wherein the lymphocyte receptor or signaling domain thereof is selected from the group consisting of: CD3ε, CD3δ, CD3ζ, pre-T cell receptor α (pTα), T cell receptor α (TCRα), T cell receptor β (TCRβ), Fc receptor α (FcRα), Fc receptor β (FcRβ), Fc receptor γ (FcRγ), natural-killer group 2, member D (NKG2D), CD22, CD79A, CD79B, and any combination thereof.

20. The isolated non-natural cell of claim 18, wherein the costimulatory domain is selected from the group consisting of: CD27, CD28, CD30, CD40, linker for activation of T-cells (LAT), zeta-chain-associated protein kinase 70 (Zap70), inducible T-cell costimulator (ICOS), DNAX-activation protein 10 (DAP10), 4-1BB, caspase recruitment domain family member 11 (CARD11), herpesvirus entry mediator (HVEM), lymphocyte activating gene 3 (LAG3), signaling lymphocytic activation molecule family member 1 (SLAMF1), lymphocyte-specific protein tyrosine kinase (Lck), fyn oncogene related to src, fgr, yes (Fyn), SH2 domain-containing leukocyte protein of 76 KDa (Slp76), OX40, and any combination thereof.

21. The isolated non-natural cell of claim 1, further comprising a third exogenous polynucleotide encoding a costimulatory factor, an immunomodulatory factor, an agonist for a costimulatory factor, an agonist for an immunomodulatory factor, or any combination thereof.

22. The isolated non-natural cell of claim 1, wherein the binding domain comprises an antibody, single chain variable fragment (scFv) or antigen binding fragment (Fab).

23. The isolated non-natural cell of claim 1, wherein the binding domain is amino terminal to the second multimerization domain.

24. The isolated non-natural cell of claim 1, wherein the second fusion protein further comprises a sequence encoding a linker disposed between the binding domain and the second multimerization domain.

25. The isolated non-natural cell of claim 1, wherein the binding domain specifically binds to a target selected from the group consisting of: α-folate receptor, $α_vβ_6$ integrin, B cell maturation antigen (BCMA), B7 homolog 3 (B7-H3), B7 homolog 6 (B7-H6), Carbonic anhydrase IX (CAIX), CD19, CD20, CD22, CD30, CD33, CD37, CD44, CD44v6, CD44v7/8, CD70, CD123, CD138, CD171, carcinoembryonic antigen (CEA), delta like canonical Notch ligand 4 (DLL4), epithelial glycoprotein 2 (EGP-2), epithelial glycoprotein 40 (EGP-40), chondroitin sulfate proteoglycan 4 (CSPG4), epidermal growth factor receptor (EGFR), EGFR family including ErbB2 (HER2), EGFR variant III (EGFRvIII), epithelial cellular adhesion molecule (EP-CAM), ephrin type-A receptor 2 (EphA2), fibroblast activation protein alpha (FAP), fetal acetylcholine receptor, frizzled class receptor 7 (Fzd7), ganglioside GD2 (GD2), ganglioside GD3 (GD3), Glypican-3 (GPC3), human oncofetal antigen 5T4 (h5T4), interleukin 11 receptor alpha (IL-11Rα), interleukin 13 receptor alpha 2 (IL13R-α2), κ light chain, λ light chain, Lewis Y antigen (LeY), L1 cell adhesion molecule (L1CAM), melanoma antigen gene family member A1 (MAGE-A1), mesothelin, major histocompatibility complex (MHC) presented peptides, mucin 1, cell surface associated (MUC1), mucin 16, cell surface associated (MUC16), neural cell adhesion molecule (NCAM), NKG2D ligands, Notch1, Notch2/3, New York esophageal squamous cell carcinoma 1 (NY-ESO-1), preferentially expressed antigen of melanoma (PRAME), prostate stem cell antigen (PSCA), prostate-specific membrane antigen (PSMA), Survivin, tumor associate glycoprotein 72 (TAG-72), telomerase reverse transcriptase (TERT), vascular endothelial growth factor receptor 2 (VEGFR2), and receptor tyrosine kinase-like orphan receptor 1 (ROR1).

26. The isolated non-natural cell of claim 1, wherein the first fusion protein comprises a FRB T2098L first multimerization domain, a first transmembrane domain, a 4-1BB costimulatory domain, and a CD3t actuator domain; wherein the second fusion protein comprises an anti-CD19 scFv binding domain, an FKBP12 second multimerization domain, and a second transmembrane domain; and wherein the bridging factor that promotes the formation of a polypeptide complex on the non-natural cell surface is rapamycin or rapalog AP21967.

27. The isolated non-natural cell of claim 1, wherein the first fusion protein comprises a FRB T2098L first multimerization domain, a first transmembrane domain, a 4-1BB costimulatory domain, and a CD3ζ actuator domain; wherein the second fusion protein comprises an anti-BCMA scFv binding domain, an FKBP12 second multimerization domain, and a second transmembrane domain; and wherein the bridging factor that promotes the formation of a polypeptide complex on the non-natural cell surface is rapamycin or rapalog AP21967.

\* \* \* \* \*

UNITED STATES PATENT AND TRADEMARK OFFICE
CERTIFICATE OF CORRECTION

PATENT NO. : 10,457,731 B2  
APPLICATION NO. : 16/219640  
DATED : October 29, 2019  
INVENTOR(S) : Jarjour et al.

Page 1 of 1

It is certified that error appears in the above-identified patent and that said Letters Patent is hereby corrected as shown below:

In the Claims

Claim 26 at Column 376, Line 39, that portion reading "costimulatory domain, and a CD3t actuator domain; wherein" should read "costimulatory domain, and a CD3ζ actuator domain; wherein".

Signed and Sealed this  
Seventeenth Day of December, 2019

Andrei Iancu  
*Director of the United States Patent and Trademark Office*

SEQUENCE LISTING

```
<160> NUMBER OF SEQ ID NOS: 75

<210> SEQ ID NO 1
<211> LENGTH: 363
<212> TYPE: PRT
<213> ORGANISM: Artificial Sequence
<220> FEATURE:
<223> OTHER INFORMATION: scFvCD19-DmrA protein

<400> SEQUENCE: 1

Met Gly Ser Asp Ile Gln Met Thr Gln Thr Ser Ser Leu Ser Ala
1               5                   10                  15

Ser Leu Gly Asp Arg Val Thr Ile Ser Cys Arg Ala Ser Gln Asp Ile
            20                  25                  30

Ser Lys Tyr Leu Asn Trp Tyr Gln Gln Lys Pro Asp Gly Thr Val Lys
        35                  40                  45

Leu Leu Ile Tyr His Thr Ser Arg Leu His Ser Gly Val Pro Ser Arg
    50                  55                  60

Phe Ser Gly Ser Gly Ser Gly Thr Asp Tyr Ser Leu Thr Ile Ser Asn
65                  70                  75                  80

Leu Glu Gln Glu Asp Ile Ala Thr Tyr Phe Cys Gln Gln Gly Asn Thr
                85                  90                  95

Leu Pro Tyr Thr Phe Gly Gly Gly Thr Lys Leu Glu Ile Thr Gly Ser
            100                 105                 110

Thr Ser Gly Ser Gly Lys Pro Gly Ser Gly Glu Gly Ser Thr Lys Gly
        115                 120                 125

Glu Val Lys Leu Gln Glu Ser Gly Pro Gly Leu Val Ala Pro Ser Gln
    130                 135                 140

Ser Leu Ser Val Thr Cys Thr Val Ser Gly Val Ser Leu Pro Asp Tyr
145                 150                 155                 160

Gly Val Ser Trp Ile Arg Gln Pro Pro Arg Lys Gly Leu Glu Trp Leu
                165                 170                 175

Gly Val Ile Trp Gly Ser Glu Thr Thr Tyr Tyr Asn Ser Ala Leu Lys
            180                 185                 190

Ser Arg Leu Thr Ile Ile Lys Asp Asn Ser Lys Ser Gln Val Phe Leu
        195                 200                 205

Lys Met Asn Ser Leu Gln Thr Asp Asp Thr Ala Ile Tyr Tyr Cys Ala
    210                 215                 220

Lys His Tyr Tyr Tyr Gly Gly Ser Tyr Ala Met Asp Tyr Trp Gly Gln
225                 230                 235                 240

Gly Thr Ser Val Thr Val Ser Ser Ala Ser Gly Gly Gly Gly Ser Gly
                245                 250                 255

Val Gln Val Glu Thr Ile Ser Pro Gly Asp Gly Arg Thr Phe Pro Lys
```

```
                260                 265                 270
Arg Gly Gln Thr Cys Val Val His Tyr Thr Gly Met Leu Glu Asp Gly
            275                 280                 285

Lys Lys Phe Asp Ser Ser Arg Asp Arg Asn Lys Pro Phe Lys Phe Met
        290                 295                 300

Leu Gly Lys Gln Glu Val Ile Arg Gly Trp Glu Gly Val Ala Gln
305                 310                 315                 320

Met Ser Val Gly Gln Arg Ala Lys Leu Thr Ile Ser Pro Asp Tyr Ala
                325                 330                 335

Tyr Gly Ala Thr Gly His Pro Gly Ile Ile Pro Pro His Ala Thr Leu
            340                 345                 350

Val Phe Asp Val Glu Leu Leu Lys Leu Glu Gly
            355                 360

<210> SEQ ID NO 2
<211> LENGTH: 1149
<212> TYPE: RNA
<213> ORGANISM: Artificial Sequence
<220> FEATURE:
<223> OTHER INFORMATION: SS-scFvCD19-DmrA mRNA

<400> SEQUENCE: 2
augccccugg gccugcugug gcugggccug gcccugcugg gcgcccugca cgcccaggcc        60
ggauccgaua uccagaugac ccagaccacc agcagccuga cgccagccu gggcgauaga       120
gugaccauca gcugcagagc cagccaggac aucagcaagu accugaacug guaucagcag       180
aaacccgacg gcaccgugaa gcugcugauc uaccacacca gcagacugca cagcggcgug       240
cccagcagau uuucuggcag cggcuccggc accgacuaca gccugaccau cuccaaccug       300
gaacaggaag auaucgcuac cuacuucugu cagcaaggca cacccugcc cuacaccuuc       360
ggcggaggca ccaagcugga aaucaccggc agcacaagcg gcagcggcaa gccuggaucu       420
ggcgagggaa gcaccaaggg cgaagugaaa cugcaggaaa gcggcccugg acuggugggc       480
ccaagccagu cucugagcgu gaccuguacc guguccggcg uguccugccc ugacuauggc       540
guguccugga ucagacagcc ccccagaaag ggccuggaau ggcugggagu gaucuggggc       600
agcgagacaa ccuacuacaa cagcgcccug aagucccggc ugaccaucau caaggacaac       660
uccaagagcc aggugaagga ucuguccuug aagagauaga agauccgcaag cacgagaaga       720
cugaccccaa gcaggagacu acuacggcgg cagcuacgcc uggacuacug gggccaggc       780
acaagcguga ccguguccag cgcuagcggc ggaggugggag gcggagugca ggugaaaccc       840
aucucccag gagacgggcg caccuucccc aagcgcggcc agaccugcgu ggugcacuac       900
accgggaugc uugaagaugg aaagaaauuu gauuccuccc gggacagaaa caagcccuuu       960
aaguuauagc uaggcaagca ggaggugauc cgaggcuggg aagaaggggu ugcccagaug      1020
agugugggac agagagccaa acugacauua ucuccagauu augccuaggg ugccagugg      1080
cacccaggca ucauccaccc acaugccacu cucgucuucg auggagcu ucuaaaacug      1140
gaaggcuga                                                              1149

<210> SEQ ID NO 3
<211> LENGTH: 1149
<212> TYPE: DNA
<213> ORGANISM: Artificial Sequence
<220> FEATURE:
<223> OTHER INFORMATION: SS-scFvCD19-DmrA DNA

<400> SEQUENCE: 3
```

```
atgcccctgg gcctgctgtg gctgggcctg gccctgctgg gcgccctgca cgcccaggcc    60
ggatccgata tccagatgac ccagaccacc agcagcctga cgccagcct gggcgataga    120
gtgaccatca gctgcagagc cagccaggac atcagcaagt acctgaactg gtatcagcag   180
aaacccgacg gcaccgtgaa gctgctgatc taccacacca gcagactgca cagcggcgtg   240
cccagcagat tttctggcag cggctccggc accgactaca gcctgaccat ctccaacctg   300
gaacaggaag atatcgctac ctacttctgt cagcaaggca caccctgcc ctacaccttc    360
ggcggaggca ccaagctgga aatcaccggc agcacaagcg gcagcggcaa gcctggatct   420
ggcgagggaa gcaccaaggg cgaagtgaaa ctgcaggaaa gcggccctgg actggtggcc   480
ccaagccagt ctctgagcgt gacctgtacc gtgtccggcg tgtccctgcc tgactatggc   540
gtgtcctgga tcagacagcc ccccagaaag ggcctggaat ggctgggagt gatctggggc   600
agcgagacaa cctactacaa cagcgccctg aagtcccggc tgaccatcat caaggacaac   660
tccaagagcc aggtgttcct gaagatgaac agcctgcaga ccgacgacac cgccatctac   720
tactgcgcca gcactactac tacggcggc agctacgcca tggactactg gggccagggc   780
acaagcgtga ccgtgtccag cgctagcggc ggaggtggga gcggagtgca ggtgaaaacc   840
atctccccag agacgggcg caccttcccc aagcgcggcc agacctgcgt ggtgcactac   900
accgggatgc ttgaagatgg aaagaaattt gattcctccc gggacagaaa caagcccttt   960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggctga                                                           1149
```

<210> SEQ ID NO 4
<211> LENGTH: 363
<212> TYPE: PRT
<213> ORGANISM: Artificial Sequence
<220> FEATURE:
<223> OTHER INFORMATION: scFvCD19-DmrB protein

<400> SEQUENCE: 4

Met Gly Ser Asp Ile Gln Met Thr Gln Thr Thr Ser Ser Leu Ser Ala
1               5                   10                  15

Ser Leu Gly Asp Arg Val Thr Ile Ser Cys Arg Ala Ser Gln Asp Ile
            20                  25                  30

Ser Lys Tyr Leu Asn Trp Tyr Gln Gln Lys Pro Asp Gly Thr Val Lys
        35                  40                  45

Leu Leu Ile Tyr His Thr Ser Arg Leu His Ser Gly Val Pro Ser Arg
    50                  55                  60

Phe Ser Gly Ser Gly Ser Gly Thr Asp Tyr Ser Leu Thr Ile Ser Asn
65                  70                  75                  80

Leu Glu Gln Glu Asp Ile Ala Thr Tyr Phe Cys Gln Gln Gly Asn Thr
                85                  90                  95

Leu Pro Tyr Thr Phe Gly Gly Gly Thr Lys Leu Glu Ile Thr Gly Ser
            100                 105                 110

Thr Ser Gly Ser Gly Lys Pro Gly Ser Gly Glu Gly Ser Thr Lys Gly
        115                 120                 125

Glu Val Lys Leu Gln Glu Ser Gly Pro Gly Leu Val Ala Pro Ser Gln
    130                 135                 140

Ser Leu Ser Val Thr Cys Thr Val Ser Gly Val Ser Leu Pro Asp Tyr

```
                145                 150                 155                 160
Gly Val Ser Trp Ile Arg Gln Pro Pro Arg Lys Gly Leu Glu Trp Leu
                165                 170                 175

Gly Val Ile Trp Gly Ser Glu Thr Thr Tyr Tyr Asn Ser Ala Leu Lys
                180                 185                 190

Ser Arg Leu Thr Ile Ile Lys Asp Asn Ser Lys Ser Gln Val Phe Leu
                195                 200                 205

Lys Met Asn Ser Leu Gln Thr Asp Asp Thr Ala Ile Tyr Tyr Cys Ala
        210                 215                 220

Lys His Tyr Tyr Gly Gly Ser Tyr Ala Met Asp Tyr Trp Gly Gln
225                 230                 235                 240

Gly Thr Ser Val Thr Val Ser Ser Ala Ser Gly Gly Gly Ser Gly
                245                 250                 255

Val Gln Val Glu Thr Ile Ser Pro Gly Asp Gly Arg Thr Phe Pro Lys
                260                 265                 270

Arg Gly Gln Thr Cys Val Val His Tyr Thr Gly Met Leu Glu Asp Gly
                275                 280                 285

Lys Lys Val Asp Ser Ser Arg Asp Arg Asn Lys Pro Phe Lys Phe Met
        290                 295                 300

Leu Gly Lys Gln Glu Val Ile Arg Gly Trp Glu Glu Gly Val Ala Gln
305                 310                 315                 320

Met Ser Val Gly Gln Arg Ala Lys Leu Thr Ile Ser Pro Asp Tyr Ala
                325                 330                 335

Tyr Gly Ala Thr Gly His Pro Gly Ile Ile Pro Pro His Ala Thr Leu
                340                 345                 350

Val Phe Asp Val Glu Leu Leu Lys Leu Glu Gly
                355                 360

<210> SEQ ID NO 5
<211> LENGTH: 1149
<212> TYPE: RNA
<213> ORGANISM: Artificial Sequence
<220> FEATURE:
<223> OTHER INFORMATION: SS-scFvCD19-DmrB mRNA

<400> SEQUENCE: 5
augccccugg gccugcugug gcugggccug gcccugcugg gcgcccugca cgcccaggcc      60
ggauccgaua uccagaugac ccagaccacc agcagccuga cgccagccu gggcgauaga     120
gugaccauca gcugcagagc cagccaggac aucagcaagu accugaacug guaucagcag     180
aaacccgacg gcaccgugaa gcugcugauc uaccacacca gcagacugca cagcggcgug     240
cccagcagau uuucuggcag cggcuccggc accgacuaca gccugaccau cuccaaccug     300
gaacaggaag auaucgcuac cuacuucugu cagcaaggca cacccugcc cuacaccuuc     360
ggcggaggca ccaagcugga aaucaccggc agcacaagcg gcagcggcaa gccuggaucu     420
ggcgagggaa gcaccaaggg cgaagugaaa cugcaggaaa gcggcccugg acugguggcc     480
ccaagccagu cucugagcgu gaccuguacc gugguccggc gucccugcc ugacuauggc     540
guguccugga ucagacagcc ccccagaaag ggccuggaau ggcugggagu gaucuggggc     600
agcgagacaa ccuacuacaa cagcgcccug aaguccggc ugaccaucau caaggacaac     660
uccaagagcc agguguuccu gaagaugaac agccugcaga ccgacgacac cgccaucuac     720
uacugcgcca agcacuacua cuacggcggc agcuacgcca uggacuacug gggccagggc     780
acaagcguga ccguguccag cgcuagcggc ggaggugggca gcggagugca ggaggaaacc     840
```

-continued

| | |
|---|---:|
| aucuccccag gagacgggcg caccuucccc aagcgcggcc agaccugcgu ggugcacuac | 900 |
| accgggaugc uugaagaugg aaagaaaguu gauuccuccc gggacagaaa caagcccuuu | 960 |
| aaguuuaugc uaggcaagca ggaggugauc cgaggcuggg aagaaggggu ugcccagaug | 1020 |
| agugugggue agagagccaa acugacuaua ucuccagauu augccauugg ugccacuggg | 1080 |
| cacccaggca ucaucccacc acaugccacu cucgucuucg auguggagcu cuaaaacug | 1140 |
| gaaggcuga | 1149 |

<210> SEQ ID NO 6
<211> LENGTH: 1149
<212> TYPE: DNA
<213> ORGANISM: Artificial Sequence
<220> FEATURE:
<223> OTHER INFORMATION: SS-scFvCD19-DmrB DNA

<400> SEQUENCE: 6

| | |
|---|---:|
| atgcccctgg gcctgctgtg gctgggcctg gccctgctgg gcgccctgca cgcccaggcc | 60 |
| ggatccgata tccagatgac ccagaccacc agcagcctga cgccagcct gggcgataga | 120 |
| gtgaccatca gctgcagagc cagccaggac atcagcaagt acctgaactg gtatcagcag | 180 |
| aaacccgacg gcaccgtgaa gctgctgatc taccacacca gcagactgca cagcggcgtg | 240 |
| cccagcagat tttctggcag cggctccggc accgactaca gcctgaccat ctccaacctg | 300 |
| gaacaggaag atatcgctac ctacttctgt cagcaaggca cacccctgcc ctacaccttc | 360 |
| ggcggaggca ccaagctgga aatcaccggc agcacaagcg gcagcggcaa gcctggatct | 420 |
| ggcgagggaa gcaccaaggg cgaagtgaaa ctgcaggaaa gcggccctgg actggtggcc | 480 |
| ccaagccagt ctctgagcgt gacctgtacc gtgtccggcg tgtccctgcc tgactatggc | 540 |
| gtgtcctgga tcagacagcc ccccagaaag ggcctggaat ggctgggagt gatctggggc | 600 |
| agcgagacaa cctactacaa cagcgccctg aagtcccggc tgaccatcat caaggacaac | 660 |
| tccaagagcc aggtgttcct gaagatgaac agcctgcaga ccgacgacac cgccatctac | 720 |
| tactgcgcca gcactacta ctacggcggc agctacgcca tggactactg gggccagggc | 780 |
| acaagcgtga ccgtgtccag cgctagcggc ggaggtggga gcggagtgca ggtggaaacc | 840 |
| atctccccag agacgggcg cacccttcccc aagcgcggcc agacctgcgt ggtgcactac | 900 |
| accgggatgc ttgaagatgg aaagaaagtt gattcctccc gggacagaaa caagcccttt | 960 |
| aagtttatgc taggcaagca ggaggtgatc cgaggctggg aagaaggggt tgcccagatg | 1020 |
| agtgtgggtc agagagccaa actgactata tctccagatt atgcctatgg tgccactggg | 1080 |
| cacccaggca tcatcccacc acatgccact ctcgtcttcg atgtggagct ctaaaactg | 1140 |
| gaaggctga | 1149 |

<210> SEQ ID NO 7
<211> LENGTH: 349
<212> TYPE: PRT
<213> ORGANISM: Artificial Sequence
<220> FEATURE:
<223> OTHER INFORMATION: scFvCD19-DmrC protein

<400> SEQUENCE: 7

Met Gly Ser Asp Ile Gln Met Thr Gln Thr Thr Ser Ser Leu Ser Ala
1               5                   10                  15

Ser Leu Gly Asp Arg Val Thr Ile Ser Cys Arg Ala Ser Gln Asp Ile
            20                  25                  30

Ser Lys Tyr Leu Asn Trp Tyr Gln Gln Lys Pro Asp Gly Thr Val Lys

```
                35                  40                  45
Leu Leu Ile Tyr His Thr Ser Arg Leu His Ser Gly Val Pro Ser Arg
 50                  55                  60
Phe Ser Gly Ser Gly Ser Gly Thr Asp Tyr Ser Leu Thr Ile Ser Asn
 65                  70                  75                  80
Leu Glu Gln Glu Asp Ile Ala Thr Tyr Phe Cys Gln Gln Gly Asn Thr
                 85                  90                  95
Leu Pro Tyr Thr Phe Gly Gly Gly Thr Lys Leu Glu Ile Thr Gly Ser
                100                 105                 110
Thr Ser Gly Ser Gly Lys Pro Gly Ser Gly Glu Gly Ser Thr Lys Gly
            115                 120                 125
Glu Val Lys Leu Gln Glu Ser Gly Pro Gly Leu Val Ala Pro Ser Gln
130                 135                 140
Ser Leu Ser Val Thr Cys Thr Val Ser Gly Val Ser Leu Pro Asp Tyr
145                 150                 155                 160
Gly Val Ser Trp Ile Arg Gln Pro Pro Arg Lys Gly Leu Glu Trp Leu
                165                 170                 175
Gly Val Ile Trp Gly Ser Glu Thr Thr Tyr Tyr Asn Ser Ala Leu Lys
                180                 185                 190
Ser Arg Leu Thr Ile Ile Lys Asp Asn Ser Lys Ser Gln Val Phe Leu
            195                 200                 205
Lys Met Asn Ser Leu Gln Thr Asp Asp Thr Ala Ile Tyr Tyr Cys Ala
210                 215                 220
Lys His Tyr Tyr Tyr Gly Gly Ser Tyr Ala Met Asp Tyr Trp Gly Gln
225                 230                 235                 240
Gly Thr Ser Val Thr Val Ser Ser Ala Ser Gly Gly Gly Gly Ser Ile
                245                 250                 255
Leu Trp His Glu Met Trp His Glu Gly Leu Glu Glu Ala Ser Arg Leu
                260                 265                 270
Tyr Phe Gly Glu Arg Asn Val Lys Gly Met Phe Glu Val Leu Glu Pro
            275                 280                 285
Leu His Ala Met Met Glu Arg Gly Pro Gln Thr Leu Lys Glu Thr Ser
290                 295                 300
Phe Asn Gln Ala Tyr Gly Arg Asp Leu Met Glu Ala Gln Glu Trp Cys
305                 310                 315                 320
Arg Lys Tyr Met Lys Ser Gly Asn Val Lys Asp Leu Leu Gln Ala Trp
                325                 330                 335
Asp Leu Tyr Tyr His Val Phe Arg Arg Ile Ser Lys Gly
            340                 345
```

<210> SEQ ID NO 8
<211> LENGTH: 1107
<212> TYPE: RNA
<213> ORGANISM: Artificial Sequence
<220> FEATURE:
<223> OTHER INFORMATION: SS-scFvCD19-DmrC mRNA

<400> SEQUENCE: 8

```
augccccugg gccugcugug gcugggccug gcccugcugg gcgcccugca cgcccaggcc      60
ggauccgaua uccagaugac ccagaccacc agcagccuga gcgccagccu gggcgauaga    120
gugaccauca gcugcagagc cagccaggac aucagcaagu accugaacug guaucagcag    180
aaacccgacg gcaccgugaa gcugcugauc uaccacacca gcagacugca cagcggcgug    240
cccagcagau uuucuggcag cggcuccggc accgacuaca gccugaccau cuccaaccug    300
```

| | |
|---|---:|
| gaacaggaag auaucgcuac cuacuucugu cagcaaggca acacccugcc cuacaccuuc | 360 |
| ggcggaggca ccaagcugga aaucaccggc agcacaagcg gcagcggcaa gccuggaucu | 420 |
| ggcgagggaa gcaccaaggg cgaagugaaa cugcaggaaa gcggcccugg acuguggcc | 480 |
| ccaagccagu cucugagcgu gaccuguacc guguccggcg ugucccugcc ugacuauggc | 540 |
| guguccugga ucagacagcc ccccagaaag gccuggaau ggcugggagu gaucuggggc | 600 |
| agcgagacaa ccuacuacaa cagcgcccug aagucccggc ugaccaucau caaggacaac | 660 |
| uccaagagcc agguguuccu gaagaugaac agccugcaga ccgacgacac cgccaucuac | 720 |
| uacugcgcca agcacuacua cuacggcggc agcuacgcca uggacuacug ggccagggc | 780 |
| acaagcguga ccguguccag cgcuagcggc ggagguggga gcauccucug gcaugagaug | 840 |
| uggcaugaag gccuggaaga ggcaucucgu uuguacuuug gggaaaggaa cgugaaaggc | 900 |
| auguuugagg ugcuggagcc cuugcaugcu augauggaac ggggcccca gacucugaag | 960 |
| gaaacauccu uuaaucaggc cuauggcuga gauuuaaugg aggcccaaga gguggugcagg | 1020 |
| aaguacauga aaucagggaa ugucaaggac cuccuccaag ccugggaccu cuauuaucau | 1080 |
| guguuccgac gaaucucaaa gggcuga | 1107 |

<210> SEQ ID NO 9
<211> LENGTH: 1107
<212> TYPE: DNA
<213> ORGANISM: Artificial Sequence
<220> FEATURE:
<223> OTHER INFORMATION: SS-scFvCD19-DmrC DNA

<400> SEQUENCE: 9

| | |
|---|---:|
| atgccctgg gctgctgtg ctgggcctg ccctgctgg gcgccctgca cgcccaggcc | 60 |
| ggatccgata tccagatgac ccagaccacc agcagcctga cgccagcct gggcgataga | 120 |
| gtgaccatca gctgcagagc cagccaggac atcagcaagt acctgaactg gtatcagcag | 180 |
| aaacccgacg gcaccgtgaa gctgctgatc taccacacca gcagactgca cagcggcgtg | 240 |
| cccagcagat ttctggcag cggctccggc accgactaca gcctgaccat ctccaacctg | 300 |
| gaacaggaag atatcgctac ctacttctgt cagcaaggca cacccctgcc ctacaccttc | 360 |
| ggcggaggca ccaagctgga aatcaccggc agcacaagcg gcagcggcaa gcctggatct | 420 |
| ggcgagggaa gcaccaaggg cgaagtgaaa ctgcaggaaa gcggccctgg actggtggcc | 480 |
| ccaagccagt ctctgagcgt gacctgtacc gtgtccggcg tgtccctgcc tgactatggc | 540 |
| gtgtcctgga tcagacagcc ccccagaaag gcctggaat ggctgggagt gatctggggc | 600 |
| agcgagacaa cctactacaa cagcgccctg aagtcccggc tgaccatcat caaggacaac | 660 |
| tccaagagcc aggtgttcct gaagatgaac agcctgcaga ccgacgacac cgccatctac | 720 |
| tactgcgcca agcactacta ctacggcggc agctacgcca tggactactg ggccagggc | 780 |
| acaagcgtga ccgtgtccag cgctagcggc ggaggtggga gcatcctctg gcatgagatg | 840 |
| tggcatgaag gcctggaaga ggcatctcgt ttgtactttg gggaaaggaa cgtgaaaggc | 900 |
| atgtttgagg tgctggagcc cttgcatgct atgatggaac ggggcccca gactctgaag | 960 |
| gaaacatcct ttaatcaggc ctatggtcga gatttaatgg aggcccaaga gtggtgcagg | 1020 |
| aagtacatga aatcagggaa tgtcaaggac ctcctccaag cctgggacct ctattatcat | 1080 |
| gtgttccgac gaatctcaaa gggctga | 1107 |

<210> SEQ ID NO 10
<211> LENGTH: 7255

```
<212> TYPE: DNA
<213> ORGANISM: Artificial Sequence
<220> FEATURE:
<223> OTHER INFORMATION: pCVL_T7_scFvCD19-DmrA-BFP lentiviral vector

<400> SEQUENCE: 10
aaaaataaac aaatagggt tccgcgcaca tttccccgaa aagtgccacc tgacgtcaat      60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga aagcgaaagg gaaaccagag gagctctctc gacgcaggac tcggcttgct    540
gaagcgcgca cggcaagagg cgaggggcgg cgactggtga gtacgccaaa attttgact     600 agcggaggct agaaggagag gatgggtgc gagagcgtca gtattaagcg ggggagaatt    660
agatcgcgat gggaaaaaat tcggttaagg ccagggggaa agaaaaaata taattaaaa    720 catatagtat gggcaagcag ggagctgaaa cgattcgcag ttaatcctgg cctgttagaa    780
acatcagaag gctgtagaca aatactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaaagag cagtgggaat aggagctttg   1140
ttccttgggt tcttgggagc agcaggaagc actatgggcg cagcgtcaat gacgctgacg   1200
gtacaggcca acaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag atacctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aagggggat tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtcccg    2040 agaagttggg gggaggggtc ggcaattgaa ccggtgccta gagaaggtgg cgcggggtaa   2100
actgggaaag tgatgtcgtg tactggctcc gcctttttcc cgagggtggg ggagaaccgt   2160
```

```
atataagtgc agtagtcgcc gtgaacgttc tttttcgcaa cgggtttgcc gccagaacac    2220
acctgcaggt aatacgactc actatagggt ccactgccgc caccatgccc ctgggcctgc    2280
tgtggctggg cctggccctg ctgggcgccc tgcacgccca ggccggatcc gatatccaga    2340
tgacccagac caccagcagc ctgagcgcca gcctgggcga tagagtgacc atcagctgca    2400
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag gaagatatcg    2580
ctacctactt ctgtcagcaa ggcaacaccc tgccctacac cttcggcgga ggcaccaagc    2640
tggaaatcac cggcagcaca agcggcagcg gcaagcctgg atctggcgag ggaagcacca    2700
agggcgaagt gaaactgcag gaaagcggcc ctggactggt ggccccaagc cagtctctga    2760
gcgtgacctg taccgtgtcc ggcgtgtccc tgcctgacta tggcgtgtcc tggatcagac    2820
agccccccag aaagggcctg aatggctggg gagtgatctg gggcagcgag acaacctact    2880
acaacagcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt gggagcggag tgcaggtgga aaccatctcc ccaggagacg    3120 gcgcacctt ccccaagcgc ggccagacct gcgtggtgca ctacaccggg atgcttgaag    3180
atggaaagaa atttgattcc tcccgggaca gaaacaagcc cttttaagttt atgctaggca    3240 agcaggaggt gatccgaggc tgggaagaag gggttgccca gatgagtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgctccg    3420
gtgagggcag aggaagtctt ctaacatgcg gtgacgtgga ggagaatccg gcccctcta    3480 gaagcgagct gattaaggag aacatgcaca tgaagctgta catggagggc accgtggaca    3540
accatcactt caagtgcaca tccgagggcg aaggcaagcc ctacgagggc acccagacca    3600
tgagaatcaa ggtggtcgag ggcggccctc tccccttcgc cttcgacatc ctggctacta    3660
gcttcctcta cggcagcaag accttcatca accacaccca gggcatcccc gacttcttca    3720
agcagtcctt ccctgagggc ttcacatggg agagagtcac cacatacgaa gacggggggcg    3780 tgctgaccgc tacccaggac accagcctcc aggacggctg cctcatctac aacgtcaaga    3840 tcagagggt gaacttcaca tccaacggcc ctgtgatgca agagaaaaca ctcggctggg    3900
aggccttcac cgagacgctg taccccgctg acggcggcct ggaaggcaga aacgacatgg    3960
ccctgaagct cgtgggcggg agccatctga tcgcaaacat caagaccaca tatagatcca    4020
agaaacccgc taagaacctc aagatgcctg gcgtctacta tgtggactac agactggaaa    4080
gaatcaagga ggccaacaac gagacctacg tcgagcagca cgaggtggca gtggccagat    4140
actgcgacct ccctagcaaa ctgggggcaca agcttaattg agtcgaccga gcatcttacc    4200
gccatttata cccatatttg ttctgttttt cttgatttgg gtatacattt aaatgttaat    4260
agaacaaaat ggtggggcaa tcatttacat ttttagggat atgtaattac tagttcaggt    4320
gtattgccac aagacaaaca tgttaagaaa ctttcccgtt atttacgctc tgttcctgtt    4380
aatcaacctc tggattacaa atttgtgaaa gattgactg atattcttaa ctatgttgct    4440 cctttacgg tgtgtggata tgctgcttta tagcctctgt atctagctat tgcttcccgt    4500
acggctttcg ttttctcctc cttgtataaa tcctggttgc tgtctctttt agaggagttg    4560
```

```
tggcccgttg tccgtcaacg tggcgtggtg tgctctgtgt ttgctgacgc aaccccccact    4620 ggctggggca ttgccaccac ctgtcaactc ctttctggga ctttcgcttt ccccctcccg    4680
atcgccacgg cagaactcat cgccgcctgc cttgcccgct gctggacagg ggctaggttg    4740
ctgggcactg ataattccgt ggtgttgtca tcgaattcgg taccttttta aaagaaaagg    4800
ggggactgga agggctaatt cactcccaac gaagacaaga tatcataact tcgtatagca    4860
tacattatac gaagttataa tttatttgtg aaatttgtga tgctattgct ttatttgtaa    4920
ccatatgttt atttgtgaaa tttgtgatgc tattgcttta tttgtaacca ttgcttttg     4980 cttgtactgg gtctctctgg ttagaccaga tctgagcctg ggagctctct ggctaactag    5040
ggaacccact gcttaagcct caataaagct tgcctcgacc agcctcgact gtgccttcta    5100
gttgccagcc atctgttgtt tgcccctccc ccgtgccttc cttgaccctg gaaggtgcca    5160
ctcccactgt cctttcctaa taaaatgagg aaattgcatc gcattgtctg agtaggtgtc    5220
attctattct gggggggtggg gtggggcagg acagcaaggg ggaggattgg gaagacaata    5280
gcaggcatgc tggggatgcg gtgggctcta tggcctgcag ctgcattaat gaatcggcca    5340
acgcgcgggg agaggcggtt tgcgtattgg gcgctcttcc gcttcctcgc tcactgactc    5400
gctgcgctcg gtcgttcggc tgcggcgagc ggtatcagct cactcaaagg cggtaatacg    5460
gttatccaca gaatcagggg ataacgcagg aaagaacatg tgagcaaaag gccagcaaaa    5520
ggccaggaac cgtaaaaagg ccgcgttgct ggcgtttttc cataggctcc gcccccctga    5580
cgagcatcac aaaaatcgac gctcaagtca gaggtggcga aacccgacag gactataaag    5640
ataccaggcg tttccccctg gaagctccct cgtgcgctct cctgttccga cctgccgct    5700 taccggatac ctgtccgcct ttctcccttc gggaagcgtg gcgctttctc atagctcacg    5760
ctgtaggtat ctcagttcgg tgtaggtcgt tcgctccaag ctgggctgtg tgcacgaacc    5820
ccccgttcag cccgaccgct gcgccttatc cggtaactat cgtcttgagt ccaacccggt    5880
aagacacgac ttatcgccac tggcagcagc cactggtaac aggattagca gagcgaggta    5940
tgtaggcggt gctacagagt tcttgaagtg gtggcctaac tacggctaca ctagaaggac    6000
agtatttggt atctgcgctc tgctgaagcc agttaccttc ggaaaaagag ttggtagctc    6060
ttgatccggc aaacaaacca ccgctggtag cggtggtttt tttgtttgca agcagcagat    6120
tacgcgcaga aaaaaaggat ctcaagaaga tcctttgatc ttttctacgg ggtctgacgc    6180
tcagtggaac gaaaactcac gttaagggat tttggtcatg agattatcaa aaaggatctt    6240
cacctagatc cttttaaatt aaaaatgaag ttttaaatca atctaaagta tatatgagta    6300
aacttggtct gacagttacc aatgcttaat cagtgaggca cctatctcag cgatctgtct    6360
atttcgttca tccatagttg cctgactccc cgtcgtgtag ataactacga tacgggaggg    6420
cttaccatct ggccccagtg ctgcaatgat accgcgagac ccacgctcac cggctccaga    6480
tttatcagca ataaaccagc cagccggaag ggccgagcgc agaagtggtc ctgcaacttt    6540
atccgcctcc atccagtcta ttaattgttg ccgggaagct agagtaagta gttcgccagt    6600
taatagtttg cgcaacgttg ttgccattgc tacaggcatc gtggtgtcac gctcgtcgtt    6660
tggtatggct tcattcagct ccggttccca acgatcaagg cgagttacat gatcccccat    6720
gttgtgcaaa aaagcggtta gctccttcgg tcctccgatc gttgtcagaa gtaagttggc    6780
cgcagtgtta tcactcatgg ttatggcagc actgcataat tctcttactg tcatgccatc    6840
cgtaagatgc ttttctgtga ctggtgagta ctcaaccaag tcattctgag aatagtgtat    6900
```

-continued

| | | |
|---|---|---|
| gcggcgaccg agttgctctt gcccggcgtc aatacgggat aataccgcgc cacatagcag | 6960 | |
| aactttaaaa gtgctcatca ttggaaaacg ttcttcgggg cgaaaactct caaggatctt | 7020 | |
| accgctgttg agatccagtt cgatgtaacc cactcgtgca cccaactgat cttcagcatc | 7080 | |
| ttttactttc accagcgttt ctgggtgagc aaaaacagga aggcaaaatg ccgcaaaaaa | 7140 | |
| gggaataagg gcgacacgga aatgttgaat actcatactc ttcctttttc aatattattg | 7200 | |
| aagcatttat cagggttatt gtctcatgag cggatacata tttgaatgta tttag | 7255 | |

<210> SEQ ID NO 11
<211> LENGTH: 7255
<212> TYPE: DNA
<213> ORGANISM: Artificial Sequence
<220> FEATURE:
<223> OTHER INFORMATION: pCVL_T7_scFvCD19-DmrB-BFP lentiviral vector

<400> SEQUENCE: 11

| | | |
|---|---|---|
| aaaaataaac aaatagggt tccgcgcaca tttccccgaa aagtgccacc tgacgtcaat | 60 | |
| gtagtcttat gcaatactct tgtagtcttg caacatggta acgatgagtt agcaacatgc | 120 | |
| cttacaagga gagaaaaagc accgtgcatg ccgattggtg gaagtaaggt ggtacgatcg | 180 | |
| tgccttatta ggaaggcaac agacgggtct gacatggatt ggacgaacca ctgaattgcc | 240 | |
| gcattgcaga gatattgtat ttaagtgcct agctcgatac ataaacgggt ctctctggtt | 300 | |
| agaccagatc tgagcctggg agctctctgg ctaactaggg aacccactgc ttaagcctca | 360 | |
| ataaagcttg ccttgagtgc ttcaagtagt gtgtgcccgt ctgttgtgtg actctggtaa | 420 | |
| ctagagatcc ctcagaccct tttagtcagt gtggaaaatc tctagcagtg gcgcccgaac | 480 | |
| agggacttga agcgaaagg gaaaccagag gagctctctc gacgcaggac tcggcttgct | 540 | |
| gaagcgcgca cggcaagagg cgaggggcgg cgactggtga gtacgccaaa aattttgact | 600 | |
| agcggaggct agaaggagag agatgggtgc gagagcgtca gtattaagcg ggggagaatt | 660 | |
| agatcgcgat gggaaaaaat tcggttaagg ccagggggga agaaaaaata taaattaaaa | 720 | |
| catatagtat gggcaagcag ggagctagaa cgattcgcag ttaatcctgg cctgttagaa | 780 | |
| acatcagaag gctgtagaca aatactggga cagctacaac catcccttca gacaggatca | 840 | |
| gaagaactta gatcattata taatacagta gcaaccctct attgtgtgca tcaaaggata | 900 | |
| gagataaaag acaccaagga agctttagac aagatagagg aagagcaaaa caaaagtaag | 960 | |
| accaccgcac agcaagcggc cctgatcttc agacctggag gaggagatat gagggacaat | 1020 | |
| tggagaagtg aattatataa atataaagta gtaaaaattg aaccattagg agtagcaccc | 1080 | |
| accaaggcaa agagaagagt ggtgcagaga gaaaaaagag cagtgggaat aggagctttg | 1140 | |
| ttccttgggt tcttgggagc agcaggaagc actatgggcg cagcgtcaat gacgctgacg | 1200 | |
| gtacaggcca gacaattatt gtctggtata gtgcagcagc agaacaattt gctgagggct | 1260 | |
| attgaggcgc aacagcatct gttgcaactc acagtctggg gcatcaagca gctccaggca | 1320 | |
| agaatcctgg ctgtggaaag atacctaaag gatcaacagc tcctggggat ttggggttgc | 1380 | |
| tctggaaaac tcatttgcac cactgctgtg ccttggaatg ctagttggag taatgaatct | 1440 | |
| ctggaacaga tttggaatca cacgacctgg atggagtggg acagagaaat taacaattac | 1500 | |
| acaagcttaa tacactcctt aattgaagaa tcgcaaaacc agcaagaaaa gaatgaacaa | 1560 | |
| gaattattgg aattagataa atgggcaagt ttgtggaatt ggtttaacat aacaaattgg | 1620 | |
| ctgtggtata taaaattatt cataatgata gtaggaggct tggtaggttt aagaatagtt | 1680 | |
| tttgctgtac tttctatagt gaatagagtt aggcagggat attcaccatt atcgtttcag | 1740 | |

```
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aaggggggat tggggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gccttttcc cgagggtggg ggagaaccgt     2160
atataagtgc agtagtcgcc gtgaacgttc tttttcgcaa cgggtttgcc gccagaacac    2220
acctgcaggt aatacgactc actatagggt ccactgccgc caccatgccc ctgggcctgc    2280
tgtggctggg cctggccctg ctgggcgccc tgcacgccca ggccggatcc gatatccaga    2340
tgacccagac caccagcagc ctgagcgcca gcctgggcga tagagtgacc atcagctgca    2400
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag gaagatatcg    2580
ctacctactt ctgtcagcaa ggcaacaccc tgccctacac cttcggcgga ggcaccaagc    2640
tggaaatcac cggcagcaca agcggcagcg gcaagcctgg atctggcgag gaagcacca    2700
agggcgaagt gaaactgcag gaaagcggcc ctggactggt ggccccaagc cagtctctga    2760
gcgtgacctg taccgtgtcc ggcgtgtccc tgcctgacta tggcgtgtcc tggatcagac    2820
agccccccag aaagggcctg aatggctgg gagtgatctg gggcagcgag acaacctact    2880
acaacgcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt gggagcggag tgcaggtgga aaccatctcc ccaggagacg    3120
ggcgcaccct cccccaagcgc ggccagacct cgtggtgca ctacaccggg atgcttgaag    3180
atggaaagaa agttgattcc tcccgggaca gaaacaagcc cttaagtttt atgctaggca    3240
agcaggaggt gatccgaggc tgggaagaag gggttgccca gatgagtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgctccg    3420
gtgagggcag aggaagtctt ctaacatgcg gtgacgtgga ggaatccg ggccctcta     3480
gaagcgagct gattaaggag aacatgcaca tgaagctgta catggagggc accgtggaca    3540
accatcactt caagtgcaca tccgagggcg aaggcaagcc ctacgagggc acccagacca    3600
tgagaatcaa ggtggtcgag ggcggccctc tccccttcgc cttcgacatc ctggctacta    3660
gcttcctcta cggcagcaag accttcatca accacacccca gggcatcccc gacttcttca    3720
agcagtcctt ccctgagggc ttcacatggg agagagtcac cacatacgaa gacggggcg     3780
tgctgaccgc tacccaggac accagcctcc aggacggctg cctcatctac aacgtcaaga    3840
tcagaggggt gaacttcaca tccaacgcc ctgtgatgca gaagaaaaca ctcggctggg      3900
aggccttcac cgagacgctg taccccgctg acggcggcct ggaaggcaga acgacatgg      3960
ccctgaagct cgtgggcggg agccatctga tcgcaaacat caagaccaca tatagatcca    4020
agaaacccgc taagaacctc aagatgcctg gcgtctacta tgtggactac agactggaaa    4080
```

```
gaatcaagga ggccaacaac gagacctacg tcgagcagca cgaggtggca gtggccagat    4140
actgcgacct ccctagcaaa ctggggcaca agcttaattg agtcgaccga gcatcttacc    4200
gccatttata cccatatttg ttctgttttt cttgatttgg gtatacattt aaatgttaat    4260
agaacaaaat ggtggggcaa tcatttacat ttttagggat atgtaattac tagttcaggt    4320
gtattgccac aagacaaaca tgttaagaaa ctttcccgtt atttacgctc tgttcctgtt    4380
aatcaacctc tggattacaa aatttgtgaa agattgactg atattcttaa ctatgttgct    4440
ccttttacgc tgtgtggata tgctgcttta tagcctctgt atctagctat tgcttcccgt    4500
acggctttcg ttttctcctc cttgtataaa tcctggttgc tgtctctttt agaggagttg    4560
tggcccgttg tccgtcaacg tggcgtggtg tgctctgtgt ttgctgacgc aaccccact    4620 ggctggggca ttgccaccac ctgtcaactc ctttctggga ctttcgcttt cccctcccg    4680 atcgccacgg cagaactcat cgccgcctgc cttgcccgct gctggacagg ggctaggttg    4740
ctgggcactg ataattccgt ggtgttgtca tcgaattcgg tacctttta aaagaaaagg    4800 ggggactgga agggctaatt cactcccaac gaagacaaga tatcataact tcgtatagca    4860
tacattatac gaagttataa ttatttgtg aaatttgtga tgctattgct ttatttgtaa    4920
ccatatgttt atttgtgaaa tttgtgatgc tattgctttt tttgtaacca ttgcttttg    4980 cttgtactgg gtctctctgg ttagaccaga tctgagcctg ggagctctct ggctaactag    5040
ggaacccact gcttaagcct caataaagct tgcctcgacc agcctcgact gtgccttcta    5100
gttgccagcc atctgttgtt tgcccctccc ccgtgccttc cttgaccctg gaaggtgcca    5160
ctcccactgt cctttcctaa taaaatgagg aaattgcatc gcattgtctg agtaggtgtc    5220
attctattct ggggggtggg gtggggcagg acagcaaggg ggaggattgg gaagacaata    5280
gcaggcatgc tggggatgcg gtgggctcta tggcctgcag ctgcattaat gaatcggcca    5340
acgcgcgggg agaggcggtt tgcgtattgg gcgctcttcc gcttcctcgc tcactgactc    5400
gctgcgctcg tcgttcggc tgcggcgagc ggtatcagct cactcaaagg cggtaatacg    5460
gttatccaca gaatcagggg ataacgcagg aaagaacatg tgagcaaaag ccagcaaaa    5520 ggccaggaac cgtaaaaagg ccgcgttgct ggcgttttc cataggctcc gcccccctga    5580
cgagcatcac aaaaatcgac gctcaagtca gaggtggcga acccgacag gactataaag    5640 ataccaggcg tttccccctg gaagctccct cgtgcgctct cctgttccga ccctgccgct    5700
taccggatac ctgtccgcct ttctcccttc gggaagcgtg gcgctttctc atagctcacg    5760
ctgtaggtat ctcagttcgg tgtaggtcgt tcgctccaag ctgggctgtg tgcacgaacc    5820
ccccgttcag cccgaccgct gcgccttatc cggtaactat cgtcttgagt ccaacccggt    5880
aagacacgac ttatcgccac tggcagcagc cactggtaac aggattagca gagcgaggta    5940
tgtaggcggt gctacagagt tcttgaagtg gtggcctaac tacggctaca ctagaaggac    6000
agtatttggt atctgcgctc tgctgaagcc agttaccttc ggaaaaagag ttggtagctc    6060
ttgatccggc aaacaaacca ccgctggtag cgtggttttt ttgtttgca agcagcagat    6120 tacgcgcaga aaaaaggat ctcaagaaga tcctttgatc ttttctacgg gtctgacgc    6180 tcagtggaac gaaaactcac gttaagggat tttggtcatg agattatcaa aaaggatctt    6240
cacctagatc cttttaaatt aaaaatgaag ttttaaatca atctaaagta tatatgagta    6300
aacttggtct gacagttacc aatgcttaat cagtgaggca cctatctcag cgatctgtct    6360
atttcgttca tccatagttg cctgactccc cgtcgtgtag ataactacga tacgggaggg    6420
cttaccatct ggccccagtg ctgcaatgat accgcgagac ccacgctcac cggctccaga    6480
```

```
tttatcagca ataaaccagc cagccggaag ggccgagcgc agaagtggtc ctgcaacttt     6540
atccgcctcc atccagtcta ttaattgttg ccgggaagct agagtaagta gttcgccagt     6600
taatagtttg cgcaacgttt ttgccattgc tacaggcatc gtggtgtcac gctcgtcgtt     6660
tggtatggct tcattcagct ccggttccca acgatcaagg cgagttacat gatcccccat     6720
gttgtgcaaa aaagcggtta gctccttcgg tcctccgatc gttgtcagaa gtaagttggc     6780
cgcagtgtta tcactcatgg ttatggcagc actgcataat tctcttactg tcatgccatc     6840
cgtaagatgc ttttctgtga ctggtgagta ctcaaccaag tcattctgag aatagtgtat     6900
gcggcgaccg agttgctctt gcccggcgtc aatacgggga ataccgcgc cacatagcag     6960 aactttaaaa gtgctcatca ttggaaaacg ttcttcgggg cgaaaactct caaggatctt     7020
accgctgttg agatccagtt cgatgtaacc cactcgtgca cccaactgat cttcagcatc     7080
ttttactttc accagcgttt ctgggtgagc aaaaacagga aggcaaaatg ccgcaaaaaa     7140
gggaataagg cgacacgga aatgttgaat actcatactc ttcctttttc aatattattg     7200
aagcatttat cagggttatt gtctcatgag cggatacata tttgaatgta tttag          7255

<210> SEQ ID NO 12
<211> LENGTH: 7213
<212> TYPE: DNA
<213> ORGANISM: Artificial Sequence
<220> FEATURE:
<223> OTHER INFORMATION: pCVL_T7_scFvCD19-DmrC-BFP lentiviral vector

<400> SEQUENCE: 12
aaaaataaac aaatagggt tccgcgcaca tttccccgaa aagtgccacc tgacgtcaat       60
gtagtcttat gcaatactct tgtagtcttg caacatggta acgatgagtt agcaacatgc      120
cttacaagga gagaaaaagc accgtgcatg ccgattggtg gaagtaaggt ggtacgatcg      180
tgccttatta ggaaggcaac agacgggtct gacatggatt ggacgaacca ctgaattgcc      240
gcattgcaga gatattgtat ttaagtgcct agctcgatac ataaacgggt ctctctggtt      300
agaccagatc tgagcctggg agctctctgg ctaactaggg aacccactgc ttaagcctca      360
ataaagcttg ccttgagtgc ttcaagtagt gtgtgcccgt ctgttgtgtg actctggtaa      420
ctagagatcc ctcagaccct tttagtcagt gtggaaaatc tctagcagtg gcgcccgaac      480
agggacttga aagcgaaagg gaaaccagag gagctctctc gacgcaggac tcggcttgct      540
gaagcgcgca cggcaagagg cgaggggcgg cgactggtga gtacgccaaa attttgact       600 agcggaggct agaaggagag agatgggtgc gagagcgtca gtattaagcg ggggagaatt      660
agatcgcgat gggaaaaaat tcggttaagg ccaggggaa agaaaaaata taaattaaaa      720
catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaacctct attgtgtgca tcaaaggata      900
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaaattg aaccattagg agtagcaccc     1080
accaaggcaa agagaagagt ggtgcagaga gaaaaaagag cagtgggaat aggagctttg     1140
ttccttgggt tcttgggagc agcaggaagc actatgggcg cagcgtcaat gacgctgacg     1200
gtacaggcca gacaattatt gtctggtata gtgcagcagc agaacaattt gctgagggct     1260
```

-continued

```
attgaggcgc aacagcatct gttgcaactc acagtctggg gcatcaagca gctccaggca  1320
agaatcctgg ctgtggaaag atacctaaag gatcaacagc tcctggggat ttgggggttgc  1380 tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attccaccatt atcgtttcag  1740 acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aagggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggagggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820 agcccccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcatcc tctggcatga gatgtggcat gaaggcctgg  3120
aagaggcatc tcgtttgtac tttggggaaa ggaacgtgaa aggcatgttt gaggtgctgg  3180
agcccttgca tgctatgatg gaacgggggcc cccagactct gaaggaaaca tcctttaatc  3240
aggcctatgg tcgagattta atggaggccc aagagtggtg caggaagtac atgaaatcag  3300
ggaatgtcaa ggacctcctc caagcctggg acctctatta tcatgtgttc cgacgaatct  3360
caaagggcgg ccgctccggt gagggcagag gaagtcttct aacatgcggt gacgtggagg  3420
agaatccggg ccctctaga agcgagctga ttaaggagaa catgcacatg aagctgtaca  3480
tggagggcac cgtggacaac catcacttca agtgcacatc cgagggcgaa ggcaagccct  3540
acgagggcac ccagaccatg agaatcaagg tggtcgaggg cggccctctc cccttcgcct  3600
tcgacatcct ggctactagc ttcctctacg gcagcaagac cttcatcaac cacacccagg  3660
```

```
gcatcccga cttcttcaag cagtccttcc ctgagggctt cacatgggag agagtcacca    3720
catacgaaga cggggggcgtg ctgaccgcta cccaggacac cagcctccag gacggctgcc  3780
tcatctacaa cgtcaagatc agaggggtga acttcacatc caacggccct gtgatgcaga  3840
agaaaacact cggctgggag gccttcaccg agacgctgta ccccgctgac ggcggcctgg  3900
aaggcagaaa cgacatggcc ctgaagctcg tgggcgggag ccatctgatc gcaaacatca  3960
agaccacata tagatccaag aaacccgcta agaacctcaa gatgcctggc gtctactatg  4020
tggactacag actggaaaga atcaaggagg ccaacaacga gacctacgtc gagcagcacg  4080
aggtggcagt ggccagatac tgcgacctcc ctagcaaact ggggcacaag cttaattgag  4140
tcgaccgagc atcttaccgc catttatacc catatttgtt ctgttttttct tgatttgggt  4200
atacatttaa atgttaatag aacaaaatgg tggggcaatc atttacattt ttagggatat  4260
gtaattacta gttcaggtgt attgccacaa gacaaacatg ttaagaaact ttcccgttat  4320
ttacgctctg ttcctgttaa tcaacctctg gattacaaaa tttgtgaaag attgactgat  4380
attcttaact atgttgctcc ttttacgctg tgtggatatg ctgctttata gcctctgtat  4440
ctagctattg cttcccgtac ggctttcgtt ttctcctcct tgtataaatc ctggttgctg  4500
tctcttttag aggagttgtg gcccgttgtc cgtcaacgtg gcgtggtgtg ctctgtgttt  4560
gctgacgcaa cccccactgg ctggggcatt gccaccacct gtcaactcct ttctgggact  4620
ttcgctttcc cctcccgatc gccacggca gaactcatcg ccgcctgcct tgcccgctgc  4680
tggacagggg ctaggttgct gggcactgat aattccgtgg tgttgtcatc gaattcggta  4740
ccttttaaa agaaaagggg ggactggaag ggctaattca ctcccaacga agacaagata  4800
tcataacttc gtatagcata cattatacga agttataatt tatttgtgaa atttgtgatg  4860
ctattgcttt atttgtaacc atatgtttat ttgtgaaatt tgtgatgcta ttgctttatt  4920
tgtaaccatt gcttttgct tgtactgggt ctctctggtt agaccagatc tgagcctggg  4980
agctctctgg ctaactaggg aacccactgc ttaagcctca ataaagcttg cctcgaccag  5040
cctcgactgt gccttctagt tgccagccat ctgttgtttg ccctccccc gtgccttcct  5100
tgaccctgga aggtgccact cccactgtcc tttcctaata aaatgaggaa attgcatcgc  5160
attgtctgag taggtgtcat tctattctgg ggggtggggt ggggcaggac agcaaggggg  5220
aggattggga agacaaatagc aggcatgctg gggatgcggt gggctctatg gcctgcagct  5280
gcattaatga tcggccaac gcgcgggag aggcggtttg cgtattgggc gctcttccgc    5340
ttcctcgctc actgactcgc tgcgctcggt cgttcggctg cggcgagcgg tatcagctca  5400
ctcaaaggcg gtaatacggt tatccacaga atcaggggat aacgcaggaa agaacatgtg  5460
agcaaaaggc cagcaaaagg ccaggaaccg taaaaaggcc gcgttgctgg cgttttccca  5520
taggctccgc cccctgacg agcatcacaa aaatcgacgc tcaagtcaga ggtggcgaaa   5580
cccgacagga ctataaagat accaggcgtt tccccctgga agctccctcg tgcgctctcc  5640
tgttccgacc ctgccgctta ccggatacct gtccgccttt ctcccttcgg gaagcgtggc  5700
gctttctcat agctcacgct gtaggtatct cagttcggtg taggtcgttc gctccaagct  5760
gggctgtgtg cacgaacccc ccgttcagcc cgaccgctgc gccttatccg gtaactatcg  5820
tcttgagtcc aacccggtaa gacacgactt atcgccactg gcagcagcca ctggtaacag  5880
gattagcaga gcgaggtatg taggcggtgc tacagagttc ttgaagtggt ggcctaacta  5940
cggctacact agaaggacag tatttggtat ctgcgctctg ctgaagccag ttaccttcgg  6000
```

```
aaaaagagtt ggtagctctt gatccggcaa acaaaccacc gctggtagcg gtggttttt    6060 tgtttgcaag cagcagatta cgcgcagaaa aaaggatct  caagaagatc ctttgatctt    6120
ttctacgggg tctgacgctc agtggaacga aaactcacgt taagggattt tggtcatgag    6180
attatcaaaa aggatcttca cctagatcct tttaaattaa aaatgaagtt ttaaatcaat    6240
ctaaagtata tatgagtaaa cttggtctga cagttaccaa tgcttaatca gtgaggcacc    6300
tatctcagcg atctgtctat ttcgttcatc catagttgcc tgactccccg tcgtgtagat    6360
aactacgata cgggagggct taccatctgg ccccagtgct gcaatgatac cgcgagaccc    6420
acgctcaccg gctccagatt tatcagcaat aaaccagcca gccggaaggg ccgagcgcag    6480
aagtggtcct gcaactttat ccgcctccat ccagtctatt aattgttgcc gggaagctag    6540
agtaagtagt tcgccagtta atagtttgcg caacgttgtt gccattgcta caggcatcgt    6600
ggtgtcacgc tcgtcgtttg gtatggcttc attcagctcc ggttcccaac gatcaaggcg    6660
agttacatga tcccccatgt tgtgcaaaaa agcggttagc tccttcggtc ctccgatcgt    6720
tgtcagaagt aagttggccg cagtgttatc actcatggtt atggcagcac tgcataattc    6780
tcttactgtc atgccatccg taagatgctt ttctgtgact ggtgagtact caaccaagtc    6840
attctgagaa tagtgtatgc ggcgaccgag ttgctcttgc ccggcgtcaa tacgggataa    6900
taccgcgcca catagcagaa cttaaaagt  gctcatcatt ggaaaacgtt cttcgggcg     6960 aaaactctca aggatcttac cgctgttgag atccagttcg atgtaaccca ctcgtgcacc    7020
caactgatct tcagcatctt ttactttcac cagcgtttct gggtgagcaa aaacaggaag    7080
gcaaaatgcc gcaaaaaagg gaataagggc gacacggaaa tgttgaatac tcatactctt    7140
cctttttcaa tattattgaa gcatttatca gggttattgt ctcatgagcg gatacatatt    7200
tgaatgtatt tag                                                        7213

<210> SEQ ID NO 13
<211> LENGTH: 2259
<212> TYPE: RNA
<213> ORGANISM: Artificial Sequence
<220> FEATURE:
<223> OTHER INFORMATION: scFvCD19-TM-41BB-CD3z-BFP mRNA

<400> SEQUENCE: 13
auggcucugc cugugacagc ucugcugcug ccucuggccc ugcugcucca ugccgccaga      60
cccggauccg auauccagau gacccagacc accagcagcc ugagcgccag ccugggcgau    120
agagugacca ucagcugcag agccagccag gacaucagca guaccugaa  cugguaucag    180 cagaaacccg acggcaccgu gaagcugcug aucuaccaca ccagcagacu gcacagcggc    240
gugcccagca gauuuucugg cagcggcucc ggcaccgacu acagccugac caucuccaac    300
cuggaacagg aagauaucgc uaccuacuuc ugucagcaag caacacccu  gcccuacacc    360 uucggcggag gcaccaagcu ggaaaucacc ggcagcacaa gcggcagcgg caagccugga    420
ucuggcgagg gaagcaccaa gggcgaagug aaacugcagg aaagcggccc uggacugguu    480
gccccaagcc agucucugag cgugaccugu accgugaccg gcgugucccu gccugacuau    540
ggcguguccu ggaucagaca gccacccaga aagggccugg aauggcuggg agugaucugg    600
ggcagcgaga caaccuacua caacagcgcc cugaagagcc ggcugaccau caucaaggac    660
aacuccaaga gccagguguu ccugaagaug aacagccugc agaccgacga caccgccauc    720
uacuacugcg ccaagcacua cuacuacggc ggcagcuacg ccauggacua cuggggccag    780
ggcacaagcg ugaccgugu  cagcgcuagc gccaagccua ccaccacccc ugcccuaga     840
```

```
ccuccaacac ccgccccaac aaucgccagc cagccucugu cucugaggcc cgaggcuugu    900
agaccagcug cuggcggagc cgugcacacc agaggacugu auuucgccug cgacaucuac    960
aucugggccc cucuggccgg cacaugggc gugcugcugc ugagccucgu gaucaccaug    1020
cauaaacggg gcagaaagaa acuccuguau auauucaaac aaccauuuau gagaccagua    1080
caaacuacuc aagaggaaga uggcuguagc ugccgauuuc agaagaagaa agaaggagga    1140
ugugaacugc gggugaaguu cagcagaagc gccgacgccc cugccuacca gcagggccag    1200
aaucagcugu acaacgagcu gaaccugggc agaagggaag aguacgacgu ccuggauaag    1260
cggagaggcc gggacccuga uggggcggc aagccucggc ggaagaaccc ccaggaaggc    1320
cuguauaacg aacugcagaa agacaagaug gccgaggccu acagcgagau cggcaugaag    1380
ggcgagcgga ggcggggcaa gggccacgac ggccuguauc agggccuguc caccgccacc    1440
aaggauaccu acgacgcccu gcacaugcag gcccugcccc aagggggcgg ccgcuccggu    1500
gagggcagag gaagucuucu aacaugcggu gacguggagg agaauccggg ccccucuaga    1560
agcgagcuga uuaaggagaa cauggacaug aagcuguaca uggagggcac cguggacaac    1620
cauccauuca agugcacauc cgagggcgaa ggcaagcccu acgagggcac ccagaccaug    1680
agaaucaagg uggucgaggg cggcccucuc cccuucgccu ucgacauccu ggcuacuagc    1740
uuccucuacg gcagcaagac cuucaucaac acacccagg gcaucccga cuucuucaag    1800 caguccuucc cugagggcuu cacaugggag agaguacca cauacgaaga cggggggcgug    1860 cugaccgcua cccaggacac cagccuccag gacggcugcc ucaucuacaa cgucaagauc    1920 agaggggguga acuucacauc caacggcccu gugaugcaga gaaaaacacu cggcugggag    1980
gccuucaccg agacgcugua ccccgcugac ggcggccugg aaggcagaaa cgacauggcc    2040
cugaagcucg uggcgggag ccaucugauc gcaaacauca gaccacaua uagauccaag    2100 aaacccgcua agaaccucaa gaugccuggc gucuacuaug uggacuacag acuggaagga    2160
aucaaggagg ccaacaacga gaccuacguc gagcagcacg agguggcagu ggccagauac    2220
ugcgaccucc cuagcaaacu ggggcacaag cuuaauuga    2259
```

<210> SEQ ID NO 14
<211> LENGTH: 7597
<212> TYPE: DNA
<213> ORGANISM: Artificial Sequence
<220> FEATURE:
<223> OTHER INFORMATION: pCVL_T7_scFvCD19-TM-41BB-CD3z-BFP lentiviral
      vector

<400> SEQUENCE: 14

```
aaaaataaac aaatagggt tccgcgcaca tttccccgaa aagtgccacc tgacgtcaat    60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga aagcgaaagg gaaaccagag agctctctc gacgcaggac tcggcttgct    540
gaagcgcgca cggcaagagg cgaggggcgg cgactggtga gtacgccaaa aattttgact    600
```

```
agcggaggct agaaggagag agatgggtgc gagagcgtca gtattaagcg ggggagaatt    660
agatcgcgat gggaaaaaat tcggttaagg ccaggggaa  agaaaaaata taaattaaaa    720
catatagtat gggcaagcag ggagctagaa cgattcgcag ttaatcctgg cctgttagaa    780
acatcagaag gctgtagaca aatactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaaagag cagtgggaat aggagctttg   1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag atacctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag aatagaagaa gaaggtgga   1800 gagagagaca gagacagatc cattcgatta gtgaacggat ctcgacggta tcggttaact   1860
tttaaaagaa aagggggat  tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggaggggtc ggcaattgaa ccggtgccta gagaaggtgg cgcggggtaa   2100
actgggaaag tgatgtcgtg tactggctcc gcctttttcc cgagggtggg ggagaaccgt   2160
atataagtgc agtagtcgcc gtgaacgttc tttttcgcaa cgggtttgcc gccagaacac   2220
acctgcaggt aatacgactc actatagggt ccactgccgc caccatggct ctgcctgtga   2280
cagctctgct gctgcctctg gccctgctgc tccatgccgc cagacccgga tccgatatcc   2340
agatgaccca gaccaccagc agcctgagcg ccagcctggg cgatagagtg accatcagct   2400
gcagagccag ccaggacatc agcaagtacc tgaactggta tcagcagaaa cccgacggca   2460
ccgtgaagct gctgatctac cacaccagca gactgcacag cggcgtgccc agcagatttt   2520
ctggcagcgc ctccggcacc gactacgcc  tgaccatctc caacctggaa caggaagata   2580
tcgctaccta cttctgtcag caaggcaaca ccctgcccta ccttcggc  ggaggcacca   2640 agctggaaat caccggcagc acaagcggca gcggcaagcc tggatctggc gagggaagca   2700
ccaagggcga agtgaaactg caggaaagcg gccctggact ggtggcccca agccagtctc   2760
tgagcgtgac ctgtaccgtg tccggcgtgt ccctgcctga ctatggcgtg tcctggatca   2820
gacagccacc cagaaagggc ctggaatggc tgggagtgat ctgggcagc  gagacaacct   2880 actacaacag cgccctgaag tcccggctga ccatcatcaa ggacaactcc aagagccagg   2940
```

```
tgttcctgaa gatgaacagc ctgcagaccg acgacaccgc catctactac tgcgccaagc    3000
actactacta cggcggcagc tacgccatgg actactgggg ccagggcaca agcgtgaccg    3060
tgtccagcgc tagcgccaag cctaccacca cccctgcccc tagacctcca cacccgccc     3120 caacaatcgc cagccagcct ctgtctctga ggcccgaggc ttgtagacca gctgctggcg    3180
gagccgtgca caccagagga ctggatttcg cctgcgacat ctacatctgg gcccctctgg    3240
ccggcacatg tggcgtgctg ctgctgagcc tcgtgatcac catgcataaa cggggcagaa    3300
agaaactcct gtatatattc aaacaaccat ttatgagacc agtacaaact actcaagagg    3360
aagatggctg tagctgccga tttccagaag aagaagaagg aggatgtgaa ctgcgggtga    3420
agttcagcag aagcgccgac gcccctgcct accagcaggg ccagaatcag ctgtacaacg    3480
agctgaacct gggcagaagg gaagagtacg acgtcctgga taagcggaga ggccgggacc    3540
ctgagatggg cggcaagcct cggcggaaga accccccagga aggcctgtat aacgaactgc    3600
agaaagacaa gatggccgag gcctacagcg agatcggcat gaagggcgag cggaggcggg    3660
gcaagggcca cgacggcctg tatcagggcc tgtccaccgc caccaaggat acctacgacg    3720
ccctgcacat gcaggccctg ccccaaggg gcggccgctc cggtgagggc agaggaagtc    3780
ttctaacatg cggtgacgtg gaggagaatc cgggcccctc tagaagcgag ctgattaagg    3840
agaacatgca catgaagctg tacatggagg caccgtgga caaccatcac ttcaagtgca    3900
catccgaggg cgaaggcaag ccctacgagg gcacccagac catgagaatc aaggtggtcg    3960
agggcggccc tctcccctc gccttcgaca tcctggctac tagcttcctc tacggcagca    4020
agaccttcat caaccacacc cagggcatcc ccgacttctt caagcagtcc ttccctgagg    4080
gcttcacatg ggagagagtc accacatacg aagacggggg cgtgctgacc gctacccagg    4140
acaccagcct ccaggacggc tgcctcatct acaacgtcaa gatcagaggg gtgaacttca    4200
catccaacgg ccctgtgatg cagaagaaaa cactcggctg ggaggccttc accgagacgc    4260
tgtaccccgc tgacggcggc ctggaaggca gaaacgacat ggcccctgaag ctcgtgggcg    4320 ggagccatct gatcgcaaac atcaagacca catatagatc caagaaaccc gctaagaacc    4380
tcaagatgcc tggcgtctac tatgtggact acagactgga aagaatcaag gaggccaaca    4440
acgagaccta cgtcgagcag cacgaggtgg cagtggccag atactgcgac ctccctagca    4500
aactggggca caagcttaat tgagtcgacc gagcatctta ccgccattta tacccatatt    4560
tgttctgttt ttcttgattt gggtatacat ttaaatgtta atagaacaaa atggtggggc    4620
aatcatttac attttagg atatgtaatt actagttcag gtgtattgcc acaagacaaa    4680
catgttaaga aactttcccg ttatttacgc tctgttcctg ttaatcaacc tctggattac    4740
aaaatttgtg aaagattgac tgatattctt aactatgttg ctccttttac gctgtgtgga    4800
tatgctgctt tatagcctct gtatctagct attgcttccc gtacggcttt cgttttctcc    4860
tccttgtata aatcctggtt gctgtctctt ttagaggagt tgtggcccgt tgtccgtcaa    4920
cgtggcgtgg tgtgctctgt gtttgctgac gcaaccccca ctggctgggg cattgccacc    4980
acctgtcaac tcctttctgg actttcgct ttccccctcc cgatcgccac ggcagaactc    5040
atcgccgcct gccttgcccg ctgctggaca ggggctaggt tgctgggcac tgataattcc    5100
gtggtgttgt catcgaattc ggtaccttt taaagaaaa ggggggactg aagggctaa     5160 ttcactccca acgaagacaa gatatcataa cttcgtatag catacattat acgaagttat    5220
aatttatttg tgaaatttgt gatgctattg ctttatttgt aaccatatgt ttatttgtga    5280
aatttgtgat gctattgctt tatttgtaac cattgctttt tgcttgtact gggtctctct    5340
```

```
ggttagacca gatctgagcc tgggagctct ctggctaact agggaaccca ctgcttaagc   5400
ctcaataaag cttgcctcga ccagcctcga ctgtgccttc tagttgccag ccatctgttg   5460
tttgcccctc ccccgtgcct tccttgaccc tggaaggtgc cactcccact gtcctttcct   5520
aataaaatga ggaaattgca tcgcattgtc tgagtaggtg tcattctatt ctgggggtg    5580 gggtggggca ggacagcaag ggggaggatt gggaagacaa tagcaggcat gctggggatg   5640
cggtgggctc tatggcctgc agctgcatta atgaatcggc caacgcgcgg ggagaggcgg   5700
tttgcgtatt gggcgctctt ccgcttcctc gctcactgac tcgctgcgct cggtcgttcg   5760
gctgcggcga gcggtatcag ctcactcaaa ggcggtaata cggttatcca cagaatcagg   5820
ggataacgca ggaaagaaca tgtgagcaaa aggccagcaa aaggccagga accgtaaaaa   5880
ggccgcgttg ctggcgtttt tccataggct ccgcccccct gacgagcatc acaaaaatcg   5940
acgctcaagt cagaggtggc gaaacccgac aggactataa agataccagg cgtttccccc   6000
tggaagctcc ctcgtgcgct ctcctgttcc gaccctgccg cttaccggat acctgtccgc   6060
ctttctccct tcgggaagcg tggcgctttc tcatagctca cgctgtaggt atctcagttc   6120
ggtgtaggtc gttcgctcca agctgggctg tgtgcacgaa ccccccgttc agcccgaccg   6180
ctgcgcctta tccggtaact atcgtcttga gtccaaccccg gtaagacacg acttatcgcc   6240
actggcagca gccactggta acaggattag cagagcgagg tatgtaggcg gtgctacaga   6300
gttcttgaag tggtggccta actacggcta cactagaagg acagtatttg gtatctgcgc   6360
tctgctgaag ccagttacct tcggaaaaag agttggtagc tcttgatccg gcaaacaaac   6420
caccgctggt agcggtggtt tttttgtttg caagcagcag attacgcgca gaaaaaaagg   6480
atctcaagaa gatcctttga tcttttctac ggggtctgac gctcagtgga acgaaaactc   6540
acgttaaggg attttggtca tgagattatc aaaaaggatc ttcacctaga tccttttaaa   6600
ttaaaaatga gtttttaaat caatctaaag tatatatgag taaacttggt ctgacagtta   6660
ccaatgctta atcagtgagg cacctatctc agcgatctgt ctatttcgtt catccatagt   6720
tgcctgactc cccgtcgtgt agataactac gatacgggag ggcttaccat ctggccccag   6780
tgctgcaatg ataccgcgag acccacgctc accggctcca gatttatcag caataaacca   6840
gccagccgga agggccgagc gcagaagtgg tcctgcaact ttatccgcct ccatccagtc   6900
tattaattgt tgccgggaag ctagagtaag tagttcgcca gttaatagtt tgcgcaacgt   6960
tgttgccatt gctacaggca tcgtggtgtc acgctcgtcg tttggtatgg cttcattcag   7020
ctccggttcc caacgatcaa ggcgagttac atgatccccc atgttgtgca aaaaagcggt   7080
tagctccttc ggtcctccga tcgttgtcag aagtaagttg gccgcagtgt tatcactcat   7140
ggttatggca gcactgcata attctcttac tgtcatgcca tccgtaagat gcttttctgt   7200
gactggtgag tactcaacca agtcattctg agaatagtgt atgcggcgac cgagttgctc   7260
ttgcccggcg tcaatacggg ataataccgc gccacatagc agaactttaa aagtgctcat   7320
cattggaaaa cgttcttcgg ggcgaaaact ctcaaggatc ttaccgctgt tgagatccag   7380
ttcgatgtaa cccactcgtg cacccaactg atcttcagca tcttttactt tcaccagcgt   7440
ttctgggtga gcaaaaacag gaaggcaaaa tgccgcaaaa aagggaataa gggcgacacg   7500
gaaatgttga atactcatac tcttcctttt tcaatattat tgaagcattt atcagggtta   7560
ttgtctcatg agcggataca tatttgaatg tatttag                           7597
```

<210> SEQ ID NO 15

<211> LENGTH: 324
<212> TYPE: PRT
<213> ORGANISM: Artificial Sequence
<220> FEATURE:
<223> OTHER INFORMATION: DmrC-TM-41BB-CD3z protein

<400> SEQUENCE: 15

```
Met Gly Ser Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
    50                  55                  60

Gln Glu Trp Cys Arg Lys Tyr Met Lys Ser Gly Asn Val Lys Asp Leu
65                  70                  75                  80

Leu Gln Ala Trp Asp Leu Tyr Tyr His Val Phe Arg Arg Ile Ser Lys
                85                  90                  95

Ala Ser Ala Lys Pro Thr Thr Thr Pro Ala Pro Arg Pro Pro Thr Pro
            100                 105                 110

Ala Pro Thr Ile Ala Ser Gln Pro Leu Ser Leu Arg Pro Glu Ala Cys
        115                 120                 125

Arg Pro Ala Ala Gly Gly Ala Val His Thr Arg Gly Leu Asp Phe Ala
    130                 135                 140

Cys Asp Ile Tyr Ile Trp Ala Pro Leu Ala Gly Thr Cys Gly Val Leu
145                 150                 155                 160

Leu Leu Ser Leu Val Ile Thr Met His Lys Arg Gly Arg Lys Lys Leu
                165                 170                 175

Leu Tyr Ile Phe Lys Gln Pro Phe Met Arg Pro Val Gln Thr Thr Gln
            180                 185                 190

Glu Glu Asp Gly Cys Ser Cys Arg Phe Pro Glu Glu Glu Glu Gly Gly
        195                 200                 205

Cys Glu Leu Arg Val Lys Phe Ser Arg Ser Ala Asp Ala Pro Ala Tyr
    210                 215                 220

Gln Gln Gly Gln Asn Gln Leu Tyr Asn Glu Leu Asn Leu Gly Arg Arg
225                 230                 235                 240

Glu Glu Tyr Asp Val Leu Asp Lys Arg Gly Arg Asp Pro Glu Met
                245                 250                 255

Gly Gly Lys Pro Arg Arg Lys Asn Pro Gln Glu Gly Leu Tyr Asn Glu
            260                 265                 270

Leu Gln Lys Asp Lys Met Ala Glu Ala Tyr Ser Glu Ile Gly Met Lys
        275                 280                 285

Gly Glu Arg Arg Arg Gly Lys Gly His Asp Gly Leu Tyr Gln Gly Leu
    290                 295                 300

Ser Thr Ala Thr Lys Asp Thr Tyr Asp Ala Leu His Met Gln Ala Leu
305                 310                 315                 320

Pro Pro Arg Gly
```

<210> SEQ ID NO 16
<211> LENGTH: 1032
<212> TYPE: RNA
<213> ORGANISM: Artificial Sequence
<220> FEATURE:
<223> OTHER INFORMATION: SS-DmrC-TM-41BB-CD3z mRNA

<400> SEQUENCE: 16

```
auggcucugc cugugacagc ucugcugcug ccucuggccc ugcugcucca ugccgccaga    60
cccggaucca uccucuggca ugagaugugg caugaaggcc uggaagaggc aucucguuug   120
uacuuugggg aaaggaacgu gaaaggcaug uuugaggugc uggagcccuu gcaugcuaug   180
auggaacggg gccccagac ucugaaggaa acauccuuua aucaggccua ggucgagau    240 uuaauggagg cccaagagug gugcaggaag uacaugaaau cagggaaugu caaggaccuc   300
cuccaagccu gggaccucua uuaucaugug uuccgacgaa ucucaaaggc uagcgccaag   360
ccuaccacca ccccugcccc uagaccucca acaccgccc caacaaucgc cagccagccu    420
cugucucuga ggcccgaggc uuguagacca gcugcuggcg gagccgugca caccaggaga   480
cuggauuucg ccugcgacau cuacaucugg gccccucugg ccggcacaug uggcgugcug   540
cugcugagcc ucgugaucac caugcauaaa cggggcagaa agaaacuccu guauauauuc   600
aaacaaccau uuaugagacc aguacaaacu acucaagagg aagauggcug uagcugccga   660
uuuccagaag aagaagaagg aggaugugaa cugcggguga aguucagcag aagcgccgac   720
gccccugccu accagcaggg ccagaaucag cuguacaacg agcugaaccu gggcagaagg   780
gaagaguacg acguccugga uaagcggaga ggccgggacc cugagauggg cggcaagccu   840
cggcggaaga accccccagga aggccuguau aacgaacugc agaaagacaa gauggccgag   900
gccuacagcg agaucggcau gaagggcgag cggaggcggg gcaagggcca cgacggccug   960
uaucagggcc uguccaccgc caccaaggau accuacgacg cccugcacau gcaggcccug  1020
cccccaaggg gc                                                     1032

<210> SEQ ID NO 17
<211> LENGTH: 1032
<212> TYPE: DNA
<213> ORGANISM: Artificial Sequence
<220> FEATURE:
<223> OTHER INFORMATION: SS-DmrC-TM-41BB-CD3z DNA

<400> SEQUENCE: 17
atggctctgc ctgtgacagc tctgctgctg cctctggccc tgctgctcca tgccgccaga    60
cccggatcca tcctctggca tgagatgtgg catgaaggcc tggaagaggc atctcgtttg   120
tactttgggg aaaggaacgt gaaaggcatg tttgaggtgc tggagccctt gcatgctatg   180
atggaacggg gccccagac tctgaaggaa acatccttta atcaggccta ggtcgagat    240 ttaatggagg cccaagagtg gtgcaggaag tacatgaaat cagggaatgt caaggacctc   300
ctccaagcct gggacctcta ttatcatgtg ttccgacgaa tctcaaaggc tagcgccaag   360
cctaccacca ccctgcccc tagacctcca cacccgccc caacaatcgc cagccagcct    420
ctgtctctga ggcccgaggc ttgtagacca gctgctggcg gagccgtgca caccaggaga   480
ctggatttcg cctgcgacat ctacatctgg gcccctctgg ccggcacatg tggcgtgctg   540
ctgctgagcc tcgtgatcac catgcataaa cggggcagaa agaaactcct gtatatattc   600
aaacaaccat ttatgagacc agtacaaact actcaagagg aagatggctg tagctgccga   660
tttccagaag aagaagaagg aggatgtgaa ctgcgggtga agttcagcag aagcgccgac   720
gcccctgcct accagcaggg ccagaatcag ctgtacaacg agctgaacct gggcagaagg   780
gaagagtacg acgtcctgga taagcggaga ggccgggacc ctgagatggg cggcaagcct   840
cggcggaaga accccccagga aggcctgtat aacgaactgc agaaagacaa gatggccgag   900
gcctacagcg agatcggcat gaagggcgag cggaggcggg gcaagggcca cgacggcctg   960
```

| tatcagggcc tgtccaccgc caccaaggat acctacgacg ccctgcacat gcaggccctg | 1020 |
| cccccaaggg gc | 1032 |

<210> SEQ ID NO 18
<211> LENGTH: 1512
<212> TYPE: DNA
<213> ORGANISM: Artificial Sequence
<220> FEATURE:
<223> OTHER INFORMATION: SS-DmrC-spacer-TM-41BB-CD3z DNA

<400> SEQUENCE: 18

| atggctctgc ctgtgacagc tctgctgctg cctctggccc tgctgctcca tgccgccaga | 60 |
| cccggatcca tcctctggca tgagatgtgg catgaaggcc tggaagaggc atctcgtttg | 120 |
| tactttgggg aaaggaacgt gaaaggcatg tttgaggtgc tggagccctt gcatgctatg | 180 |
| atggaacggg cccccagac tctgaaggaa acatccttta atcaggccta tggtcgagat | 240 |
| ttaatggagg cccaagagtg gtgcaggaag tacatgaaat cagggaatgt caaggacctc | 300 |
| ctccaagcct gggacctcta ttatcatgtg ttccgacgaa tctcaaaggc tagcgagagc | 360 |
| aagtacggac cgccctgccc accttgccct gccccgagt tcctgggcgg acccagcgtg | 420 |
| ttcctgttcc cacccaagcc caaggacacc ctgatgatca gccggacccc cgaggtgacc | 480 |
| tgcgtggtgg tggacgtgag ccaggaagat cccgaggtcc agttcaattg gtacgtggac | 540 |
| ggcgtggaag tgcacaacgc caagaccaag cccagagagg aacagttcaa cagcacctac | 600 |
| cgggtggtgt ctgtgctgac cgtgctgcac caggactggc tgaacggcaa agaatacaag | 660 |
| tgcaaggtgt ccaacaaggg cctgcccagc agcatcgaaa agaccatcag caaggccaag | 720 |
| ggccagcctc gcgagcccca ggtgtacacc ctgcctccct cccaggaaga gatgaccaag | 780 |
| aaccaggtgt ccctgacctg cctggtgaag ggcttctacc ccagcgacat cgccgtggag | 840 |
| tgggagagca cggccagcc tgagaacaac tacaagacca cccctcccgt gctggacagc | 900 |
| gacggcagct cttcctgta cagccggctg accgtggaca gagccggtg gcaggaaggc | 960 |
| aacgtctttt actgcagcgt gatgcacgag gccctgcaca accactacac ccagaagagc | 1020 |
| ctgagcctgt ccctgggcaa gatgcataaa cggggcagaa agaaactcct gtatatattc | 1080 |
| aaacaaccat ttatgagacc agtacaaact actcaagagg aagatggctg tagctgccga | 1140 |
| tttccagaag aagaagaagg aggatgtgaa ctgcgggtga agttcagcag aagcgccgac | 1200 |
| gcccctgcct accagcaggg ccagaatcag ctgtacaacg agctgaacct gggcagaagg | 1260 |
| gaagagtacg acgtcctgga taagcggaga ggccgggacc ctgagatggg cggcaagcct | 1320 |
| cggcggaaga ccccccagga aggcctgtat aacgaactgc agaaagacaa gatggccgag | 1380 |
| gcctacagcg agatcggcat gaagggcgag cggaggcggg gcaagggcca cgacggcctg | 1440 |
| tatcagggcc tgtccaccgc caccaaggat acctacgacg ccctgcacat gcaggccctg | 1500 |
| cccccaaggg gc | 1512 |

<210> SEQ ID NO 19
<211> LENGTH: 338
<212> TYPE: PRT
<213> ORGANISM: Artificial Sequence
<220> FEATURE:
<223> OTHER INFORMATION: DmrB-TM-41BB-CD3z protein

<400> SEQUENCE: 19

Met Gly Ser Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
 50                  55                  60

Gly Val Ala Gln Met Ser Val Gly Gln Arg Ala Lys Leu Thr Ile Ser
 65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ala Ser
            100                 105                 110

Ala Lys Pro Thr Thr Thr Pro Ala Pro Arg Pro Pro Thr Pro Ala Pro
        115                 120                 125

Thr Ile Ala Ser Gln Pro Leu Ser Leu Arg Pro Glu Ala Cys Arg Pro
130                 135                 140

Ala Ala Gly Gly Ala Val His Thr Arg Gly Leu Asp Phe Ala Cys Asp
145                 150                 155                 160

Ile Tyr Ile Trp Ala Pro Leu Ala Gly Thr Cys Gly Val Leu Leu Leu
                165                 170                 175

Ser Leu Val Ile Thr Met His Lys Arg Gly Arg Lys Lys Leu Leu Tyr
            180                 185                 190

Ile Phe Lys Gln Pro Phe Met Arg Pro Val Gln Thr Thr Gln Glu Glu
        195                 200                 205

Asp Gly Cys Ser Cys Arg Phe Pro Glu Glu Glu Glu Gly Gly Cys Glu
210                 215                 220

Leu Arg Val Lys Phe Ser Arg Ser Ala Asp Ala Pro Ala Tyr Gln Gln
225                 230                 235                 240

Gly Gln Asn Gln Leu Tyr Asn Glu Leu Asn Leu Gly Arg Arg Glu Glu
                245                 250                 255

Tyr Asp Val Leu Asp Lys Arg Arg Gly Arg Asp Pro Glu Met Gly Gly
            260                 265                 270

Lys Pro Arg Arg Lys Asn Pro Gln Glu Gly Leu Tyr Asn Glu Leu Gln
        275                 280                 285

Lys Asp Lys Met Ala Glu Ala Tyr Ser Glu Ile Gly Met Lys Gly Glu
290                 295                 300

Arg Arg Arg Gly Lys Gly His Asp Gly Leu Tyr Gln Gly Leu Ser Thr
305                 310                 315                 320

Ala Thr Lys Asp Thr Tyr Asp Ala Leu His Met Gln Ala Leu Pro Pro
                325                 330                 335

Arg Gly

<210> SEQ ID NO 20
<211> LENGTH: 1074
<212> TYPE: RNA
<213> ORGANISM: Artificial Sequence
<220> FEATURE:
<223> OTHER INFORMATION: SS-DmrB-TM-41BB-CD3z mRNA

<400> SEQUENCE: 20
auggcucugc cugugacagc ucugcugcug ccucuggccc ugcugcucca ugccgccaga    60
cccggauccg agugcaggu ggaaaccauc uccccaggag acgggcgcac cuuccccaag   120
cgcggccaga ccugcguggu gcacuacacc gggaugcuug aagauggaaa gaaaguugau   180
uccucccggg acagaaacaa gccccuuaag uuuaugcuag gcaagcagga ggugauccga   240

```
ggcugggaag aagggguugc ccagaugagu gugggucaga gagccaaacu gacuauaucu      300
ccagauuaug ccuaugguge cacugggcac ccaggcauca ucccaccaca ugccacucuc      360
gucuucgaug uggagcuucu aaaacuggaa gcuagcgcca agccuaccac cacccougcc      420 ccuagaccuc caacacccgc cccaacaauc gccagcagc cucugucucu gaggcccgag       480
gcuuguagac cagcugcugg cggagccgug cacaccagag acuggauuu cgccugcgac       540 aucuacaucu gggcccucu ggccggcaca uguggcguge ugcugcugag ccucgugauc       600
accaugcaua acggggcag aagaaacuc cuguauauau ucaaacaacc auuuaugaga        660
ccaguacaaa cuacucaaga ggaagauggc uguagcugcc gauuccaga agaagaagaa       720 ggaggaugug aacugcgggu gaaguucagc agaagcgccg acgcccugc cuaccagcag       780 ggccagaauc agcuguacaa cgagcugaac cugggcagaa gggaagagua cgacguccug     840
gauaagcgga gaggccggga cccugagaug gcggcaagc cucggcggaa gaaccccag       900 gaaggccugu auaacgaacu gcagaaagac aagauggccg aggccuacag cgagaucggc     960
augaagggcg agcggaggcg gggcaagggc cacgacggcc uguaucaggg ccuguccacc    1020
gccaccaagg auaccuacga cgcccugcac augcaggccc ugcccccaag gggc          1074

<210> SEQ ID NO 21
<211> LENGTH: 1074
<212> TYPE: DNA
<213> ORGANISM: Artificial Sequence
<220> FEATURE:
<223> OTHER INFORMATION: SS-DmrB-TM-41BB-CD3z DNA

<400> SEQUENCE: 21
atggctctgc ctgtgacagc tctgctgctg cctctggccc tgctgctcca tgccgccaga     60
cccggatccg gagtgcaggt ggaaaccatc tccccaggag acgggcgcac cttccccaag    120
cgcggccaga cctgcgtggt gcactacacc gggatgcttg aagatggaaa gaaagttgat    180
tcctcccggg acagaaacaa gccctttaag tttatgctag gcaagcagga ggtgatccga    240
ggctgggaag aaggggttgc ccagatgagt gtgggtcaga gagccaaact gactatatct    300
ccagattatg cctatggtgc cactgggcac ccaggcatca tcccaccaca tgccactctc    360
gtcttcgatg tggagcttct aaaactggaa gctagcgcca agcctaccac caccccctgcc   420 cctagacctc caacacccgc cccaacaatc gccagcagc ctctgtctct gaggcccgag    480
gcttgtagac cagctgctgg cggagccgtg cacaccagag actggatttt cgcctgcgac    540
atctacatct gggccctct ggccggcaca tgtggcgtgc tgctgctgag cctcgtgatc    600
accatgcata acggggcag aagaaactc ctgtatatat tcaaacaacc atttatgaga     660
ccagtacaaa ctactcaaga ggaagatggc tgtagctgcc gatttccaga agaagaagaa     720
ggaggatgtg aactgcgggt gaagttcagc agaagcgccg acgcccctgc ctaccagcag     780
ggccagaatc agctgtacaa cgagctgaac ctgggcagaa gggaagagta cgacgtcctg     840
gataagcgga gaggccggga ccctgagatg gcggcaagc ctcggcggaa gaaccccag     900 gaaggcctgt ataacgaact gcagaaagac aagatggccg aggcctacag cgagatcggc     960
atgaagggcg agcggaggcg gggcaagggc cacgacggcc tgtatcaggg cctgtccacc    1020
gccaccaagg atacctacga cgccctgcac atgcaggccc tgcccccaag gggc          1074

<210> SEQ ID NO 22
<211> LENGTH: 1554
<212> TYPE: DNA
```

<213> ORGANISM: Artificial Sequence
<220> FEATURE:
<223> OTHER INFORMATION: SS-DmrB-spacer-TM-41BB-CD3z DNA

<400> SEQUENCE: 22

| | | |
|---|---|---|
| atggctctgc ctgtgacagc tctgctgctg cctctggccc tgctgctcca tgccgccaga | 60 |
| cccggatccg gagtgcaggt ggaaaccatc tccccaggag acgggcgcac cttccccaag | 120 |
| cgcggccaga cctgcgtggt gcactacacc gggatgcttg aagatggaaa gaaagttgat | 180 |
| tcctcccggg acagaaacaa gccctttaag tttatgctag caagcagga ggtgatccga | 240 |
| ggctgggaag aaggggttgc ccagatgagt gtgggtcaga gagccaaact gactatatct | 300 |
| ccagattatg cctatggtgc cactgggcac ccaggcatca tcccaccaca tgccactctc | 360 |
| gtcttcgatg tggagcttct aaaactggaa gctagcgaga gcaagtacgg accgccctgc | 420 |
| ccaccttgcc ctgccccga gttcctgggc ggacccagcg tgttcctgtt cccacccaag | 480 |
| cccaaggaca ccctgatgat cagccggacc cccgaggtga cctgcgtggt ggtggacgtg | 540 |
| agccaggaag atcccgaggt ccagttcaat tggtacgtgg acggcgtgga agtgcacaac | 600 |
| gccaagacca gcccagaga ggaacagttc aacagcacct accgggtggt gtctgtgctg | 660 |
| accgtgctgc accaggactg gctgaacggc aagaatataa agtgcaaggt gtccaacaag | 720 |
| ggcctgccca gcagcatcga aaagaccatc agcaaggcca agggccagcc tcgcgagccc | 780 |
| caggtgtaca ccctgcctcc ctcccaggaa gagatgacca gaaccaggt gtccctgacc | 840 |
| tgcctggtga agggcttcta ccccagcgac atcgccgtgg agtgggagag caacggccag | 900 |
| cctgagaaca actacaagac cacccctccc gtgctggaca cgacggcag cttcttcctg | 960 |
| tacagccggc tgaccgtgga caagagccgg tggcaggaag caacgtctt tagctgcagc | 1020 |
| gtgatgcacg aggccctgca caaccactac acccagaaga gcctgagcct gtccctgggc | 1080 |
| aagatgcata acggggcag aaagaaactc ctgtatatat tcaaacaacc atttatgaga | 1140 |
| ccagtacaaa ctactcaaga ggaagatggc tgtagctgcc gatttccaga agaagaagaa | 1200 |
| ggaggatgtg aactgcgggt gaagttcagc agaagcgccg acgccctgc ctaccagcag | 1260 |
| ggccagaatc agctgtacaa cgagctgaac ctgggcagaa gggaagagta cgacgtcctg | 1320 |
| gataagcgga gaggccggga ccctgagatg ggcggcaagc ctcggcggaa gaaccccag | 1380 |
| gaaggcctgt ataacgaact gcagaaagac aagatggccg aggcctacag cgagatcggc | 1440 |
| atgaagggcg agcggaggcg gggcaagggc cacgacggcc tgtatcaggg cctgtccacc | 1500 |
| gccaccaagg atacctacga cgccctgcac atgcaggccc tgccccaag gggc | 1554 |

<210> SEQ ID NO 23
<211> LENGTH: 338
<212> TYPE: PRT
<213> ORGANISM: Artificial Sequence
<220> FEATURE:
<223> OTHER INFORMATION: DmrA-TM-41BB-CD3z protein

<400> SEQUENCE: 23

Met Gly Ser Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Phe Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
            85                  90                  95

His Ala Thr Leu Val Phe Asp Val Glu Leu Leu Lys Leu Glu Ala Ser
        100                 105                 110

Ala Lys Pro Thr Thr Thr Pro Ala Pro Arg Pro Pro Thr Pro Ala Pro
            115                 120                 125

Thr Ile Ala Ser Gln Pro Leu Ser Leu Arg Pro Glu Ala Cys Arg Pro
130                 135                 140

Ala Ala Gly Gly Ala Val His Thr Arg Gly Leu Asp Phe Ala Cys Asp
145                 150                 155                 160

Ile Tyr Ile Trp Ala Pro Leu Ala Gly Thr Cys Gly Val Leu Leu Leu
                165                 170                 175

Ser Leu Val Ile Thr Met His Lys Arg Gly Arg Lys Lys Leu Leu Tyr
            180                 185                 190

Ile Phe Lys Gln Pro Phe Met Arg Pro Val Gln Thr Thr Gln Glu Glu
        195                 200                 205

Asp Gly Cys Ser Cys Arg Phe Pro Glu Glu Glu Glu Gly Gly Cys Glu
210                 215                 220

Leu Arg Val Lys Phe Ser Arg Ser Ala Asp Ala Pro Ala Tyr Gln Gln
225                 230                 235                 240

Gly Gln Asn Gln Leu Tyr Asn Glu Leu Asn Leu Gly Arg Arg Glu Glu
                245                 250                 255

Tyr Asp Val Leu Asp Lys Arg Arg Gly Arg Asp Pro Glu Met Gly Gly
            260                 265                 270

Lys Pro Arg Arg Lys Asn Pro Gln Glu Gly Leu Tyr Asn Glu Leu Gln
        275                 280                 285

Lys Asp Lys Met Ala Glu Ala Tyr Ser Glu Ile Gly Met Lys Gly Glu
290                 295                 300

Arg Arg Arg Gly Lys Gly His Asp Gly Leu Tyr Gln Gly Leu Ser Thr
305                 310                 315                 320

Ala Thr Lys Asp Thr Tyr Asp Ala Leu His Met Gln Ala Leu Pro Pro
                325                 330                 335

Arg Gly

<210> SEQ ID NO 24
<211> LENGTH: 1074
<212> TYPE: RNA
<213> ORGANISM: Artificial Sequence
<220> FEATURE:
<223> OTHER INFORMATION: DmrA-TM-41BB-CD3z mRNA

<400> SEQUENCE: 24
auggcucugc cugugacagc ucugcugcug ccucuggccc ugcugcucca ugccgccaga     60
cccggauccg gagugcaggu ggaaaccauc uccccaggag acgggcgcac cuuccccaag    120
cgcggccaga ccugcguggu gcacuacacc gggaugcuug aagauggaaa gaaauuugau    180
uccucccggg acagaaacaa gcccuuuaag uuuaugcuag gcaagcagga ggugauccga    240
ggcugggaag aagggguugc ccagaugagu gugggucaga gagccaaacu gacuauaucu    300
ccagauuaug ccuauggugc cacugggcac ccaggcauca ucccaccaca ugccacucuc    360
gucuucgaug uggagcuucu aaaacuggaa gcuagcgcca agccuaccac caccccugcc    420
ccuagaccuc caacacccgc cccaacaauc gccagccagc cucugucucu gaggcccgag    480

| | |
|---|---|
| gcuuguagac cagcugcugg cggagccgug cacaccagag gacuggauuu cgccugcgac | 540 |
| aucuacaucu gggccccucu ggccggcaca uguggcgugc ugcugcugag ccucgugauc | 600 |
| accaugcaua acggggcag aaagaaacuc cuguauauau ucaaacaacc auuuaugaga | 660 |
| ccaguacaaa cuacucaaga ggaagauggc uguagcugcc gauuuccaga agaagaagaa | 720 |
| ggaggaugug aacugcgggu gaaguucagc agaagcgccg acgcccugc cuaccagcag | 780 |
| ggccagaauc agcuguacaa cgagcugaac cugggcagaa gggaagagua cgacguccug | 840 |
| gauaagcgga gaggccggga cccugagaug ggcggcaagc cucggcggaa gaaccccag | 900 |
| gaaggccugu auaacgaacu gcagaaagac aagauggccg aggccuacag cgagaucggc | 960 |
| augaagggcg agcggaggcg gggcaagggc cacgacggcc uguaucaggg ccuguccacc | 1020 |
| gccaccaagg auaccuacga cgcccugcac augcaggccc ugccccaag gggc | 1074 |

<210> SEQ ID NO 25
<211> LENGTH: 1074
<212> TYPE: DNA
<213> ORGANISM: Artificial Sequence
<220> FEATURE:
<223> OTHER INFORMATION: DmrA-TM-41BB-CD3z DNA

<400> SEQUENCE: 25

| | |
|---|---|
| atggctctgc ctgtgacagc tctgctgctg cctctggccc tgctgctcca tgccgccaga | 60 |
| cccggatccg gagtgcaggt ggaaaccatc tccccaggag acgggcgcac cttccccaag | 120 |
| cgcggccaga cctgcgtggt gcactacacc gggatgcttg aagatggaaa gaaatttgat | 180 |
| tcctcccggg acagaaacaa gcccttaag tttatgctag gcaagcagga ggtgatccga | 240 |
| ggctgggaag aagggggttgc ccagatgagt gtgggtcaga gagccaaact gactatatct | 300 |
| ccagattatg cctatggtgc cactgggcac ccaggcatca tcccaccaca tgccactctc | 360 |
| gtcttcgatg tggagcttct aaaactggaa gctagcgcca agcctaccac caccctgcc | 420 |
| cctagacctc caacacccgc cccaacaatc gccagccagc tctgtctct gaggcccgag | 480 |
| gcttgtagac cagctgctgg cggagccgtg cacaccagag gactggattt cgcctgcgac | 540 |
| atctacatct gggcccctct ggccggcaca tgtggcgtgc tgctgctgag cctcgtgatc | 600 |
| accatgcata acggggcag aaagaaactc ctgtatatat tcaaacaacc atttatgaga | 660 |
| ccagtacaaa ctactcaaga ggaagatggc tgtagctgcc gatttccaga agaagaagaa | 720 |
| ggaggatgtg aactgcgggt gaagttcagc agaagcgccg acgccctgc ctaccagcag | 780 |
| ggccagaatc agctgtacaa cgagctgaac ctgggcagaa gggaagagta cgacgtcctg | 840 |
| gataagcgga gaggccggga ccctgagatg ggcggcaagc ctcggcggaa gaaccccag | 900 |
| gaaggcctgt ataacgaact gcagaaagac aagatggccg aggcctacag cgagatcggc | 960 |
| atgaagggcg agcggaggcg gggcaagggc cacgacggcc tgtatcaggg cctgtccacc | 1020 |
| gccaccaagg atacctacga cgccctgcac atgcaggccc tgccccaag gggc | 1074 |

<210> SEQ ID NO 26
<211> LENGTH: 1554
<212> TYPE: DNA
<213> ORGANISM: Artificial Sequence
<220> FEATURE:
<223> OTHER INFORMATION: DmrA-spacer-TM-41BB-CD3z DNA

<400> SEQUENCE: 26

| | |
|---|---|
| atggctctgc ctgtgacagc tctgctgctg cctctggccc tgctgctcca tgccgccaga | 60 |

| | |
|---|---:|
| cccggatccg gagtgcaggt ggaaaccatc tccccaggag acgggcgcac cttccccaag | 120 |
| cgcggccaga cctgcgtggt gcactacacc gggatgcttg aagatggaaa gaaatttgat | 180 |
| tcctcccggg acagaaacaa gcccttta ag tttatgctag gcaagcagga ggtgatccga | 240 |
| ggctgggaag aaggggttgc ccagatgagt gtgggtcaga gagccaaact gactatatct | 300 |
| ccagattatg cctatggtgc cactgggcac ccaggcatca tccca ccaca tgccactctc | 360 |
| gtcttcgatg tggagcttct aaaactggaa gctagcgaga gcaagtacgg accgccctgc | 420 |
| ccaccttgcc ctgcccccga gttcctgggc ggacccagcg tgttcctgtt cccacccaag | 480 |
| cccaaggaca ccctgatgat cagccggacc cccgaggtga cctgcgtggt ggtggacgtg | 540 |
| agccaggaag atcccgaggt ccagttcaat tggtacgtgg acggcgtgga agtgcacaac | 600 |
| gccaagacca gcccagaga ggaacagttc aacagcacct accgggtggt gtctgtgctg | 660 |
| accgtgctgc accaggactg gctgaacggc aaagaataca agtgcaaggt gtccaacaag | 720 |
| ggcctgccca gcagcatcga aaagaccatc agcaaggcca agggccagcc tcgcgagccc | 780 |
| caggtgtaca ccctgcctcc ctcccaggaa gagatgacca gaaccaggt gtccctgacc | 840 |
| tgcctggtga agggcttcta ccccagcgac atcgccgtgg agtgggagag caacggccag | 900 |
| cctgagaaca actacaagac caccccctccc gtgctggaca cgacggcag cttcttcctg | 960 |
| tacagccggc tgaccgtgga caagagccgg tggcaggaag caacgtcttt agctgcagc | 1020 |
| gtgatgcacg aggccctgca caaccactac acccagaaga cctgagcct gtccctgggc | 1080 |
| aagatgcata acggggcag aaagaaactc ctgtatatat tcaaacaacc atttatgaga | 1140 |
| ccagtacaaa ctactcaaga ggaagatggc tgtagctgcc gatttccaga agaagaagaa | 1200 |
| ggaggatgtg aactgcgggt gaagttcagc agaagcgccg acgccctgc ctaccagcag | 1260 |
| ggccagaatc agctgtacaa cgagctgaac ctgggcagaa gggaagagta cgacgtcctg | 1320 |
| gataagcgga gaggccggga ccctgagatg ggcggcaagc ctcggcggaa gaaccccag | 1380 |
| gaaggcctgt ataacgaact gcagaaagac aagatggccg aggcctacag cgagatcggc | 1440 |
| atgaagggcg agcggaggcg gggcaagggc cacgacggcc tgtatcaggg cctgtccacc | 1500 |
| gccaccaagg atacctacga cgccctgcac atgcaggccc tgccccaag gggc | 1554 |

<210> SEQ ID NO 27
<211> LENGTH: 7141
<212> TYPE: DNA
<213> ORGANISM: Artificial Sequence
<220> FEATURE:
<223> OTHER INFORMATION: pCVL_T7_DmrC-TM-41BB-CD3z lentiviral vector

<400> SEQUENCE: 27

| | |
|---|---:|
| aaaaataaac aaatagggt tccgcgcaca tttccccgaa aagtgccacc tgacgtcaat | 60 |
| gtagtcttat gcaatactct tgtagtcttg caacatggta acgatgagtt agcaacatgc | 120 |
| cttacaagga gagaaaaagc accgtgcatg ccgattggtg aagtaaggt ggtacgatcg | 180 |
| tgccttatta ggaaggcaac agacgggtct gacatggatt ggacgaacca ctgaattgcc | 240 |
| gcattgcaga gatattgtat ttaagtgcct agctcgatac ataaacgggt ctctctggtt | 300 |
| agaccagatc tgagcctggg agctctctgg ctaactaggg aacccactgc ttaagcctca | 360 |
| ataaagcttg ccttgagtgc ttcaagtagt gtgtgcccgt ctgttgtgtg actctggtaa | 420 |
| ctagagatcc ctcagaccct tttagtcagt gtggaaaatc tctagcagtg gcgcccgaac | 480 |
| agggacttga aagcgaaagg gaaaccagag gagctctctc gacgcaggac tcggcttgct | 540 |
| gaagcgcgca cggcaagagg cgaggggcgg cgactggtga gtacgccaaa aattttgact | 600 |

```
agcggaggct agaaggagag agatgggtgc gagagcgtca gtattaagcg ggggagaatt    660
agatcgcgat gggaaaaaat tcggttaagg ccaggggga agaaaaaata taaattaaaa    720
catatagtat gggcaagcag ggagctagaa cgattcgcag ttaatcctgg cctgttagaa    780
acatcagaag gctgtagaca aatactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaagag cagtgggaat aggagctttg   1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag ataccctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aagggggat tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg ggaggggtc ggcaattgaa ccggtgccta gagaaggtgg cgcggggtaa   2100
actgggaaag tgatgtcgtg tactggctcc gccttttttcc cgagggtggg ggagaaccgt   2160
atataagtgc agtagtcgcc gtgaacgttc tttttcgcaa cgggtttgcc gccagaacac   2220
acctgcaggt aatacgactc actatagggt ccactgccgc caccatggct ctgcctgtga   2280
cagctctgct gctgcctctg gccctgctgc tccatgccgc cagacccgga tccatcctct   2340
ggcatgagat gtggcatgaa ggcctggaag aggcatctcg tttgtacttt ggggaaagga   2400
acgtgaaagg catgtttgag gtgctggagc ccttgcatgc tatgatggaa cggggccccc   2460
agactctgaa ggaaacatcc tttaatcagg cctatggtcg agatttaatg gaggcccaag   2520
agtggtgcag gaagtacatg aaatcaggga atgtcaagga cctcctccaa gcctgggacc   2580
tctattatca tgtgttccga cgaatctcaa aggctagcgc caagcctacc accacccctg   2640
cccctagacc tccaacaccc gccccaacaa tcgccagcca gcctctgtct ctgaggcccg   2700
aggcttgtag accagctgct ggcggagccg tgcacaccag aggactggat ttcgcctgcg   2760
acatctacat ctgggccct ctggccggca catgtggcgt gctgctgctg agcctcgtga   2820
tcaccatgca taaacggggc agaaagaaac tcctgtatat attcaaacaa ccatttatga   2880
gaccagtaca aactactcaa gaggaagatg gctgtagctg ccgatttcca gaagaagaag   2940
```

```
aaggaggatg tgaactgcgg gtgaagttca gcagaagcgc cgacgcccct gcctaccagc      3000
agggccagaa tcagctgtac aacgagctga acctgggcag aagggaagag tacgacgtcc      3060
tggataagcg gagaggccgg gaccctgaga tgggcggcaa gcctcggcgg aagaaccccc      3120
aggaaggcct gtataacgaa ctgcagaaag acaagatggc cgaggcctac agcgagatcg      3180
gcatgaaggg cgagcggagg cggggcaagg gccacgacgg cctgtatcag ggcctgtcca      3240
ccgccaccaa ggatacctac gacgccctgc acatgcaggc cctgccccca aggggcggcc      3300
gctccggtga gggcagagga agtcttctaa catgcggtga cgtggaggag aatccgggcc      3360
cctctagaag cgagctgatt aaggagaaca tgcacatgaa gctgtacatg gagggcaccg      3420
tggacaacca tcacttcaag tgcacatccg agggcgaagg caagccctac gagggcaccc      3480
agaccatgag aatcaaggtg tcgagggcg gccctctccc cttcgccttc gacatcctgg       3540
ctactagctt cctctacggc agcaagacct tcatcaacca cacccagggc atccccgact      3600
tcttcaagca gtccttccct gagggcttca catgggagag agtcaccaca tacgaagacg      3660
ggggcgtgct gaccgctacc caggacacca gcctccagga cggctgcctc atctacaacg      3720
tcaagatcag aggggtgaac ttcacatcca acggccctgt gatgcagaag aaaacactcg      3780
gctgggaggc cttcaccgag cgctgtaccc cgctgacgg cggcctggaa ggcagaaacg       3840
acatggccct gaagctcgtg ggcgggagcc atctgatcgc aaacatcaag accacatata      3900
gatccaagaa acccgctaag aacctcaaga tgcctggcgt ctactatgtg gactacagac      3960
tggaaagaat caaggaggcc aacaacgaga cctacgtcga gcagcacgag gtggcagtgg      4020
ccagatactg cgacctccct agcaaactgg ggcacaagct taattgagtc gaccgagcat      4080
cttaccgcca tttataccca tatttgttct gttttcttg atttgggtat acatttaaat       4140
gttaatagaa caaaatggtg gggcaatcat ttacattttt agggatatgt aattactagt      4200
tcaggtgtat tgccacaaga caaacatgtt aagaaacttt cccgttattt acgctctgtt      4260
cctgttaatc aacctctgga ttacaaaatt tgtgaaagat tgactgatat tcttaactat      4320
gttgctcctt ttacgctgtg tggatatgct gctttatagc ctctgtatct agctattgct      4380
tcccgtacgg ctttcgtttt ctcctccttg tataaatcct ggttgctgtc tcttttagag      4440
gagttgtggc ccgttgtccg tcaacgtggc gtggtgtgct ctgtgtttgc tgacgcaacc      4500
cccactggct ggggcattgc caccacctgt caactccttt ctgggacttt cgctttcccc      4560
ctcccgatcg ccacggcaga actcatcgcc gcctgccttg cccgctgctg acagggget       4620 aggttgctgg gcactgataa ttccgtggtg ttgtcatcga attcggtacc ttttaaaag      4680 aaaaggggg actggaaggg ctaattcact cccaacgaag acaagatatc ataacttcgt        4740
atagcataca ttatacgaag ttataattta tttgtgaaat tgtgatgct attgcttttat       4800 ttgtaaccat atgtttattt gtgaaatttg tgatgctatt gctttatttg taaccattgc      4860
tttttgcttg tactgggtct ctctggttag accagatctg agcctgggag ctctctggct      4920
aactagggaa cccactgctt aagcctcaat aaagcttgcc tcgaccagcc tcgactgtgc      4980
cttctagttg ccagccatct gttgtttgcc cctccccgt gccttccttg accctggaag       5040
gtgccactcc cactgtcctt tcctaataaa atgaggaaat tgcatcgcat tgtctgagta      5100
ggtgtcattc tattctgggg gtgggtgg ggcaggacag caaggggag gattgggaag         5160 acaatagcag gcatgctggg gatgcggtgg gctctatggc ctgcagctgc attaatgaat      5220
cggccaacgc gcggggagag gcggtttgcg tattgggcgc tcttccgctt cctcgctcac      5280
tgactcgctg cgctcggtcg ttcggctgcg gcgagcggta tcagctcact caaaggcggt      5340
```

```
aatacggtta tccacagaat caggggataa cgcaggaaag aacatgtgag caaaaggcca      5400
gcaaaaggcc aggaaccgta aaaaggccgc gttgctggcg ttttccata ggctccgccc       5460 ccctgacgag catcacaaaa atcgacgctc aagtcagagg tggcgaaacc cgacaggact     5520
ataaagatac caggcgtttc ccctggaag ctccctcgtg cgctctcctg ttccgaccct      5580
gccgcttacc ggatacctgt ccgcctttct cccttcggga agcgtggcgc tttctcatag     5640
ctcacgctgt aggtatctca gttcggtgta ggtcgttcgc tccaagctgg gctgtgtgca    5700 cgaaccccc gttcagcccg accgctgcgc cttatccggt aactatcgtc ttgagtccaa      5760
cccggtaaga cacgacttat cgccactggc agcagccact ggtaacagga ttagcagagc    5820
gaggtatgta ggcggtgcta cagagttctt gaagtggtgg cctaactacg gctacactag    5880
aaggacagta tttggtatct gcgctctgct gaagccagtt accttcggaa aaagagttgg    5940
tagctcttga tccggcaaac aaaccaccgc tggtagcggt ggtttttttg tttgcaagca    6000
gcagattacg cgcagaaaaa aaggatctca agaagatcct ttgatctttt ctacggggtc   6060
tgacgctcag tggaacgaaa actcacgtta agggattttg gtcatgagat tatcaaaaag   6120
gatcttcacc tagatccttt taaattaaaa atgaagtttt aaatcaatct aaagtatata   6180
tgagtaaact tggtctgaca gttaccaatg cttaatcagt gaggcaccta tctcagcgat    6240
ctgtctattt cgttcatcca tagttgcctg actccccgtc gtgtagataa ctacgatacg    6300
ggagggctta ccatctggcc ccagtgctgc aatgataccg cgagacccac gctcaccggc   6360
tccagattta tcagcaataa accagccagc cggaagggcc gagcgcagaa gtggtcctgc   6420
aactttatcc gcctccatcc agtctattaa ttgttgccgg gaagctagag taagtagttc    6480
gccagttaat agtttgcgca acgttgttgc cattgctaca ggcatcgtgg tgtcacgctc   6540
gtcgtttggt atggcttcat tcagctccgg ttcccaacga tcaaggcgag ttacatgatc   6600
ccccatgttg tgcaaaaaag cggttagctc cttcggtcct ccgatcgttg tcagaagtaa   6660
gttggccgca gtgttatcac tcatggttat ggcagcactg cataattctc ttactgtcat    6720
gccatccgta agatgctttt ctgtgactgg tgagtactca accaagtcat tctgagaata    6780
gtgtatgcgg cgaccgagtt gctcttgccc ggcgtcaata cgggataata ccgcgccaca    6840
tagcagaact ttaaaagtgc tcatcattgg aaaacgttct cggggcgaa aactctcaag    6900 gatcttaccg ctgttgagat ccagttcgat gtaacccact cgtgcaccca actgatcttc    6960
agcatctttt actttcacca gcgtttctgg gtgagcaaaa acaggaaggc aaaatgccgc    7020
aaaaaaggga ataagggcga cacggaaatg ttgaatactc atactcttcc tttttcaata    7080
ttattgaagc atttatcagg gttattgtct catgagcgga tacatatttg aatgtattta    7140
g                                                                    7141
```

<210> SEQ ID NO 28
<211> LENGTH: 7621
<212> TYPE: DNA
<213> ORGANISM: Artificial Sequence
<220> FEATURE:
<223> OTHER INFORMATION: pCVL_T7_DmrC-spacer-TM-41BB-CD3z lentiviral
      vector

<400> SEQUENCE: 28

```
aaaaataaac aaatagggt tccgcgcaca tttccccgaa agtgccacc tgacgtcaat       60 gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
```

```
tgccttatta ggaaggcaac agacgggtct gacatggatt ggacgaacca ctgaattgcc      240
gcattgcaga gatattgtat ttaagtgcct agctcgatac ataaacgggt ctctctggtt      300
agaccagatc tgagcctggg agctctctgg ctaactaggg aacccactgc ttaagcctca      360
ataaagcttg ccttgagtgc ttcaagtagt gtgtgcccgt ctgttgtgtg actctggtaa      420
ctagagatcc ctcagaccct tttagtcagt gtggaaaatc tctagcagtg gcgcccgaac      480
agggacttga aagcgaaagg gaaaccagag gagctctctc gacgcaggac tcggcttgct      540
gaagcgcgca cggcaagagg cgaggggcgg cgactggtga gtacgccaaa aattttgact      600
agcggaggct agaaggagag agatgggtgc gagagcgtca gtattaagcg gggagaatt      660 agatcgcgat gggaaaaaat tcggttaagg ccagggggaa agaaaaaata taaattaaaa      720
catatagtat gggcaagcag ggagctagaa cgattcgcag ttaatcctgg cctgttagaa      780
acatcagaag gctgtagaca atactgggca gctacaacc catcccttca gacaggatca      840
gaagaactta gatcattata taatacagta gcaaccctct attgtgtgca tcaaaggata      900
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaaattg aaccattagg agtagcaccc     1080
accaaggcaa agagaagagt ggtgcagaga gaaaaaagag cagtgggaat aggagctttg     1140
ttccttgggt tcttgggagc agcaggaagc actatgggcg cagcgtcaat gacgctgacg     1200
gtacaggcca caattatt gtctggtata gtgcagcagc agaacaattt gctgagggct     1260
attgaggcgc aacagcatct gttgcaactc acagtctggg gcatcaagca gctccaggca     1320
agaatcctgg ctgtggaaag atacctaaag gatcaacagc tcctggggat ttggggttgc     1380
tctggaaaac tcatttgcac cactgctgtg ccttggaatg ctagttggag taatgaatct     1440
ctggaacaga tttggaatca cacgacctgg atggagtggg acagagaaat taacaattac     1500
acaagcttaa tacactcctt aattgaagaa tcgcaaaacc agcaagaaaa gaatgaacaa     1560
gaattattgg aattagataa atgggcaagt ttgtggaatt ggtttaacat aacaaattgg     1620
ctgtggtata taaaattatt cataatgata gtaggaggct tggtaggttt aagaatagtt     1680
tttgctgtac tttctatagt gaatagagtt aggcagggat attcaccatt atcgtttcag     1740
acccacctcc caaccccgag gggacccgac aggcccgaag gaatagaaga agaaggtgga     1800
gagagagaca gagacagatc cattcgatta gtgaacggat ctcgacggta tcggttaact     1860
tttaaaagaa aaggggggat tggggggtac agtgcagggg aaagaatagt agacataata     1920
gcaacagaca tacaaactaa agaattacaa aaacaaatta caaaaattca aaattttatc     1980
gattacgcgt aggctccggt gcccgtcagt gggcagagcg cacatcgccc acagtccccg     2040
agaagttggg gggaggggtc ggcaattgaa ccggtgccta gagaaggtgg cgcggggtaa     2100
actgggaaag tgatgtcgtg tactggctcc gcctttttcc cgagggtggg ggagaaccgt     2160
atataagtgc agtagtcgcc gtgaacgttc tttttcgcaa cgggtttgcc gccagaacac     2220
acctgcaggt aatacgactc actatagggt ccactgccgc caccatggct ctgcctgtga     2280
cagctctgct gctgcctctg gccctgctgc tccatgccgc cagacccgga tccatcctct     2340
ggcatgagat gtggcatgaa ggcctggaag aggcatctcg tttgtacttt ggggaaagga     2400
acgtgaaagg catgtttgag gtgctggagc ccttgcatgc tatgatggaa cggggccccc     2460
agactctgaa ggaaacatcc tttaatcagg cctatggtcg agatttaatg gaggcccaag     2520
```

```
agtggtgcag gaagtacatg aaatcaggga atgtcaagga cctcctccaa gcctgggacc    2580
tctattatca tgtgttccga cgaatctcaa aggctagcga gagcaagtac ggaccgccct    2640
gcccaccttg ccctgccccc gagttcctgg gcggacccag cgtgttcctg ttcccaccca    2700
agcccaagga caccctgatg atcagccgga ccccgaggt gacctgcgtg gtggtggacg    2760
tgagccagga agatcccgag gtccagttca attggtacgt ggacggcgtg gaagtgcaca    2820
acgccaagac caagcccaga gaggaacagt tcaacagcac ctaccgggtg gtgtctgtgc    2880
tgaccgtgct gcaccaggac tggctgaacg gcaaagaata caagtgcaag gtgtccaaca    2940
agggcctgcc cagcagcatc gaaaagacca tcagcaaggc caagggccag cctcgcgagc    3000
cccaggtgta caccctgcct ccctcccagg aagagatgac caagaaccag gtgtccctga    3060
cctgcctggt gaagggcttc taccccagcg acatcgccgt ggagtgggag agcaacggcc    3120
agcctgagaa caactacaag accacccctc ccgtgctgga cagcgacggc agcttcttcc    3180
tgtacagccg gctgaccgtg gacaagagcc ggtggcagga aggcaacgtc tttagctgca    3240
gcgtgatgca cgaggccctg cacaaccact acacccagaa gagcctgagc ctgtccctgg    3300
gcaagatgca taaacggggc agaaagaaac tcctgtatat attcaaacaa ccatttatga    3360
gaccagtaca aactactcaa gaggaagatg gctgtagctg ccgatttcca gaagaagaag    3420
aaggaggatg tgaactgcgg gtgaagttca gcagaagcgc cgacgcccct gcctaccagc    3480
agggccagaa tcagctgtac aacgagctga acctgggcag aagggaagag tacgacgtcc    3540
tggataagcg gagaggccgg gaccctgaga tgggcggcaa gcctcggcgg aagaaccccc    3600
aggaaggcct gtataacgaa ctgcagaaag acaagatggc cgaggcctac agcgagatcg    3660
gcatgaaggg cgagcggagg cggggcaagg gccacgacgg cctgtatcag ggcctgtcca    3720
ccgccaccaa ggatacctac gacgccctgc acatgcaggc cctgccccca aggggcggcc    3780
gctccggtga gggcagagga agtcttctaa catgcggtga cgtggaggag aatccgggcc    3840
cctctagaag cgagctgatt aaggagaaca tgcacatgaa gctgtacatg gagggcaccg    3900
tggacaacca tcacttcaag tgcacatccg agggcgaagg caagccctac gagggcaccc    3960
agaccatgag aatcaaggtg gtcgagggcg gccctctccc cttcgccttc gacatcctgg    4020
ctactagctt cctctacggc agcaagacct tcatcaacca cacccagggc atccccgact    4080
tcttcaagca gtccttccct gagggcttca catgggagag agtcaccaca tacgaagacg    4140
ggggcgtgct gaccgctacc caggacacca gcctccagga cggctgcctc atctacaacg    4200
tcaagatcag aggggtgaac ttcacatcca acggccctgt gatgcagaag aaaacactcg    4260
gctgggaggc cttcaccgag acgctgtacc ccgctgacgg cggcctggaa ggcagaaacg    4320
acatggccct gaagctcgtg ggcgggagcc atctgatcgc aaacatcaag accacatata    4380
gatccaagaa acccgctaag aacctcaaga tgcctggcgt ctactatgtg gactacagac    4440
tggaaagaat caaggaggcc aacaacgaga cctacgtcga gcagcacgag gtggcagtgg    4500
ccagatactg cgacctccct agcaaactgg ggcacaagct taattgagtc gaccgagcat    4560
cttaccgcca tttataccca tatttgttct gttttttcttg atttgggtat acatttaaat    4620
gttaatagaa caaaatggtg gggcaatcat ttacatttttt agggatatgt aattactagt    4680
tcaggtgtat tgccacaaga caaacatgtt aagaaacttt cccgttattt acgctctgtt    4740
cctgttaatc aacctctgga ttacaaaatt tgtgaaagat tgactgatat tcttaactat    4800
gttgctcctt ttacgctgtg tggatatgct gctttatagc ctctgtatct agctattgct    4860
tcccgtacgg ctttcgtttt ctcctccttg tataaatcct ggttgctgtc tctttagag    4920
```

```
gagttgtggc cgttgtccg tcaacgtggc gtggtgtgct ctgtgtttgc tgacgcaacc    4980
cccactggct ggggcattgc caccacctgt caactccttt ctgggacttt cgctttcccc    5040
ctcccgatcg ccacggcaga actcatcgcc gcctgccttg cccgctgctg gacaggggct    5100
aggttgctgg gcactgataa ttccgtggtg ttgtcatcga attcggtacc tttttaaaag    5160
aaaaggggg actggaaggg ctaattcact cccaacgaag acaagatatc ataacttcgt     5220
atagcataca ttatacgaag ttataattta tttgtgaaat ttgtgatgct attgctttat    5280
ttgtaaccat atgtttattt gtgaaatttg tgatgctatt gctttatttg taaccattgc    5340
tttttgcttg tactgggtct ctctggttag accagatctg agcctgggag ctctctggct    5400
aactagggaa cccactgctt aagcctcaat aaagcttgcc tcgaccagcc tcgactgtgc    5460
cttctagttg ccagccatct gttgtttgcc cctcccccgt gccttccttg accctggaag    5520
gtgccactcc cactgtcctt tcctaataaa atgaggaaat tgcatcgcat tgtctgagta    5580
ggtgtcattc tattctgggg ggtgggggtgg ggcaggacag caaggggag gattgggaag    5640
acaatagcag gcatgctggg gatgcggtgg gctctatggc ctgcagctgc attaatgaat    5700
cggccaacgc gcggggagag gcggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat cagggggataa cgcaggaaag aacatgtgag caaaaggcca    5880
gcaaaaggcc aggaaccgta aaaaggccgc gttgctggcg ttttttccata ggctccgccc    5940
ccctgacgag catcacaaaa atcgacgctc aagtcagagg tggcgaaacc cgacaggact    6000
ataaagatac caggcgtttc cccctggaag ctccctcgtg cgctctcctg ttccgaccct    6060
gccgcttacc ggatacctgt ccgcctttct cccttcggga agcgtggcgc tttctcatag    6120
ctcacgctgt aggtatctca gttcggtgta ggtcgttcgc tccaagctgg gctgtgtgca    6180
cgaacccccc gttcagcccg accgctgcgc cttatccggt aactatcgtc ttgagtccaa    6240
cccggtaaga cacgacttat cgccactggc agcagccact ggtaacagga ttagcagagc    6300
gaggtatgta ggcggtgcta cagagttctt gaagtggtgg cctaactacg gctacactag    6360
aaggacagta tttggtatct gcgctctgct gaagccagtt accttcggaa aaagagttgg    6420
tagctcttga tccggcaaac aaaccaccgc tggtagcggt ggtttttttg tttgcaagca    6480
gcagattacg cgcagaaaaa aaggatctca agaagatcct ttgatctttt ctacggggtc    6540
tgacgctcag tggaacgaaa actcacgtta agggattttg gtcatgagat tatcaaaaag    6600
gatcttcacc tagatccttt taaattaaaa atgaagtttt aaatcaatct aaagtatata    6660
tgagtaaact tggtctgaca gttaccaatg cttaatcagt gaggcaccta tctcagcgat    6720
ctgtctattt cgttcatcca tagttgcctg actccccgtc gtgtagataa ctacgatacg    6780
ggagggctta ccatctggcc ccagtgctgc aatgataccg cgagacccac gctcaccggc    6840
tccagattta tcagcaataa accagccagc cggaagggcc gagcgcagaa gtggtcctgc    6900
aactttatcc gcctccatcc agtctattaa ttgttgccgg gaagctagag taagtagttc    6960
gccagttaat agtttgcgca acgttgttgc cattgctaca ggcatcgtgg tgtcacgctc    7020
gtcgtttggt atggcttcat tcagctccgg ttcccaacga tcaaggcgag ttacatgatc    7080
ccccatgttg tgcaaaaaag cggttagctc cttcggtcct ccgatcgttg tcagaagtaa    7140
gttggccgca gtgttatcac tcatggttat ggcagcactg cataattctc ttactgtcat    7200
gccatccgta agatgctttt ctgtgactgg tgagtactca accaagtcat tctgagaata    7260
```

| | |
|---|---|
| gtgtatgcgg cgaccgagtt gctcttgccc ggcgtcaata cgggataata ccgcgccaca | 7320 |
| tagcagaact ttaaaagtgc tcatcattgg aaaacgttct tcggggcgaa aactctcaag | 7380 |
| gatcttaccg ctgttgagat ccagttcgat gtaacccact cgtgcaccca actgatcttc | 7440 |
| agcatctttt actttcacca gcgtttctgg gtgagcaaaa acaggaaggc aaaatgccgc | 7500 |
| aaaaaaggga taagggcga cacggaaatg ttgaatactc atactcttcc ttttcaata | 7560 |
| ttattgaagc atttatcagg gttattgtct catgagcgga tacatatttg aatgtattta | 7620 |
| g | 7621 |

<210> SEQ ID NO 29
<211> LENGTH: 7183
<212> TYPE: DNA
<213> ORGANISM: Artificial Sequence
<220> FEATURE:
<223> OTHER INFORMATION: pCVL_T7_DmrB-TM-41BB-CD3z lentiviral vector

<400> SEQUENCE: 29

| | |
|---|---|
| aaaaataaac aaatagggt tccgcgcaca tttccccgaa aagtgccacc tgacgtcaat | 60 |
| gtagtcttat gcaatactct tgtagtcttg caacatggta acgatgagtt agcaacatgc | 120 |
| cttacaagga gagaaaaagc accgtgcatg ccgattggtg gaagtaaggt ggtacgatcg | 180 |
| tgccttatta ggaaggcaac agacgggtct gacatggatt ggacgaacca ctgaattgcc | 240 |
| gcattgcaga gatattgtat ttaagtgcct agctcgatac ataaacgggt ctctctggtt | 300 |
| agaccagatc tgagcctggg agctctctgg ctaactaggg aacccactgc ttaagcctca | 360 |
| ataagcttg ccttgagtgc ttcaagtagt gtgtgcccgt ctgttgtgtg actctggtaa | 420 |
| ctagagatcc ctcagaccct tttagtcagt gtggaaaatc tctagcagtg gcgcccgaac | 480 |
| agggacttga agcgaaagg gaaaccagag gagctctctc gacgcaggac tcggcttgct | 540 |
| gaagcgcgca cggcaagagg cgaggggcgg cgactggtga gtacgccaaa aattttgact | 600 |
| agcggaggct agaaggagag agatgggtgc gagagcgtca gtattaagcg gggagaatt | 660 |
| agatcgcgat gggaaaaaat tcggttaagg ccaggggaa agaaaaaata taaattaaaa | 720 |
| catatagtat gggcaagcag ggagctgaaa cgattcgcag ttaatcctgg cctgttagaa | 780 |
| acatcagaag gctgtagaca atactgggga cagctacaac catcccttca gacaggatca | 840 |
| gaagaactta gatcattata taatacagta gcaaccctct attgtgtgca tcaaaggata | 900 |
| gagataaaag acaccaagga agctttagac aagatagagg aagagcaaaa caaaagtaag | 960 |
| accaccgcac agcaagcggc cctgatcttc agacctggag gaggagatat gagggacaat | 1020 |
| tggagaagtg aattatataa atataaagta gtaaaaattg aaccattagg agtagcaccc | 1080 |
| accaaggcaa agaagaagt ggtgcagaga gaaaaagag cagtgggaat aggagctttg | 1140 |
| ttccttgggt tcttgggagc agcaggaagc actatgggcg cagcgtcaat gacgctgacg | 1200 |
| gtacaggcca gacaattatt gtctggtata gtgcagcagc agaacaattt gctgagggct | 1260 |
| attgaggcgc aacagcatct gttgcaactc acagtctggg gcatcaagca gctccaggca | 1320 |
| agaatcctgg ctgtggaaag atacctaaag gatcaacagc tcctggggat ttggggttgc | 1380 |
| tctggaaaac tcatttgcac cactgctgtg ccttggaatg ctagttggag taatgaatct | 1440 |
| ctggaacaga tttggaatca cacgacctgg atggagtggg acagagaaat taacaattac | 1500 |
| acaagcttaa tacactcctt aattgaagaa tcgcaaaacc agcaagaaaa gaatgaacaa | 1560 |
| gaattattgg aattagataa atgggcaagt ttgtggaatt ggtttaacat aacaaattgg | 1620 |
| ctgtggtata taaaattatt cataatgata gtaggaggct tggtaggttt aagaatagtt | 1680 |

```
tttgctgtac tttctatagt gaatagagtt aggcagggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aaggggggat tgggggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gccttttcc cgagggtggg ggagaaccgt     2160
atataagtgc agtagtcgcc gtgaacgttc tttttcgcaa cgggtttgcc gccagaacac    2220
acctgcaggt aatacgactc actatagggt ccactgccgc caccatggct ctgcctgtga    2280
cagctctgct gctgcctctg gccctgctgc tccatgccgc cagacccgga tccggagtgc    2340
aggtggaaac catctcccca ggagacgggc gcaccttccc caagcgcggc cagacctgcg    2400
tggtgcacta caccgggatg cttgaagatg aaagaaagt tgattcctcc cgggacagaa     2460
acaagccctt taagtttatg ctaggcaagc aggaggtgat ccgaggctgg gaagaagggg    2520
ttgcccagat gagtgtgggt cagagagcca aactgactat atctccagat tatgcctatg    2580
gtgccactgg gcacccaggc atcatcccac acatgccac tctcgtcttc gatgtggagc     2640
ttctaaaact ggaagctagc gccaagccta ccaccacccc tgcccctaga cctccaacac    2700 ccgcccaac aatcgccagc cagcctctgt ctctgaggcc cgaggcttgt agaccagctg     2760
ctggcggagc cgtgcacacc agaggactgg atttcgcctg cgacatctac atctgggccc    2820
ctctggccgg cacatgtggc gtgctgctgc tgagcctcgt gatcaccatg cataaacggg    2880
gcagaaagaa actcctgtat atattcaaac aaccatttat gagaccagta caaactactc    2940
aagaggaaga tggctgtagc tgccgatttc cagaagaaga agaaggagga tgtgaactgc    3000
gggtgaagtt cagcagaagc gccgacgccc ctgcctacca gcagggccag aatcagctgt    3060
acaacgagct gaacctgggc agaagggaag agtacgacgt cctggataag cggagaggcc    3120
gggaccctga gatgggcggc aagcctcggc ggaagaaccc ccaggaaggc ctgtataacg    3180
aactgcagaa agacaagatg gccgaggcct acagcgagat cggcatgaag ggcgagcgga    3240
ggcggggcaa gggccacgac ggcctgtatc agggcctgtc caccgccacc aaggatacct    3300
acgacgccct gcacatgcag gccctgcccc aaggggcgg ccgctccggt gagggcagag     3360
gaagtcttct aacatgcggt gacgtggagg agaatccggg cccctctaga agcgagctga    3420
ttaaggagaa catgcacatg aagctgtaca tggagggcac cgtggacaac catcacttca    3480
agtgcacatc cgagggcgaa ggcaagccct acgagggcac ccagaccatg agaatcaagg    3540
tggtcgaggg cggccctctc cccttcgcct tcgacatcct ggctactagc ttcctctacg    3600
gcagcaagac cttcatcaac cacacccagg gcatccccga cttcttcaag cagtccttcc    3660
ctgagggctt cacatgggag agagtcacca catacgaaga cggggggcgtg ctgaccgcta   3720 cccaggacac cagcctccag gacggctgcc tcatctacaa cgtcaagatc agaggggtga    3780
acttcacatc caacggccct gtgatgcaga agaaaacact cggctgggag gccttcaccg    3840
agacgctgta ccccgctgac ggcggcctgg aaggcagaaa cgacatggcc ctgaagctcg    3900
tgggcgggag ccatctgatc gcaaacatca agaccacata tagatccaag aaacccgcta    3960
agaacctcaa gatgcctggc gtctactatg tggactacag actggaaaga atcaaggagg    4020
```

```
ccaacaacga gacctacgtc gagcagcacg aggtggcagt ggccagatac tgcgacctcc    4080
ctagcaaact ggggcacaag cttaattgag tcgaccgagc atcttaccgc catttatacc    4140
catatttgtt ctgtttttct tgatttgggt atacatttaa atgttaatag aacaaaatgg    4200
tggggcaatc atttacattt ttagggatat gtaattacta gttcaggtgt attgccacaa    4260
gacaaacatg ttaagaaact ttcccgttat ttacgctctg ttcctgttaa tcaacctctg    4320
gattacaaaa tttgtgaaag attgactgat attcttaact atgttgctcc ttttacgctg    4380
tgtggatatg ctgctttata gcctctgtat ctagctattg cttcccgtac ggctttcgtt    4440
ttctcctcct tgtataaatc ctggttgctg tctcttttag aggagttgtg gcccgttgtc    4500
cgtcaacgtg gcgtggtgtg ctctgtgttt gctgacgcaa cccccactgg ctggggcatt    4560
gccaccacct gtcaactcct ttctgggact ttcgctttcc cctcccgat cgccacggca    4620 gaactcatcg ccgcctgcct tgcccgctgc tggacagggg ctaggttgct gggcactgat    4680
aattccgtgg tgttgtcatc gaattcggta ccttttttaaa agaaaagggg ggactggaag    4740
ggctaattca ctcccaacga agacaagata tcataacttc gtatagcata cattatacga    4800
agttataatt tatttgtgaa atttgtgatg ctattgcttt atttgtaacc atatgtttat    4860
ttgtgaaatt tgtgatgcta ttgctttatt tgtaaccatt gcttttgct tgtactgggt    4920 ctctctggtt agaccagatc tgagcctggg agctctctgg ctaactaggg aacccactgc    4980
ttaagcctca ataaagcttg cctcgaccag cctcgactgt gccttctagt tgccagccat    5040
ctgttgtttg cccctccccc gtgccttcct tgaccctgga aggtgccact cccactgtcc    5100
tttcctaata aaatgaggaa attgcatcgc attgtctgag taggtgtcat tctattctgg    5160
ggggtggggt ggggcaggac agcaaggggg aggattggga agacaatagc aggcatgctg    5220
gggatgcggt gggctctatg gcctgcagct gcattaatga atcggccaac gcgcggggag    5280
aggcggtttg cgtattgggc gctcttccgc ttcctcgctc actgactcgc tgcgctcggt    5340
cgttcggctg cggcgagcgg tatcagctca ctcaaaggcg gtaatacggt tatccacaga    5400
atcaggggat aacgcaggaa agaacatgtg agcaaaaggc cagcaaaagg ccaggaaccg    5460
taaaaaggcc gcgttgctgg cgttttttcca taggctccgc ccccctgacg agcatcacaa    5520
aaatcgacgc tcaagtcaga ggtggcgaaa cccgacagga ctataaagat accaggcgtt    5580
tccccctgga agctccctcg tgcgctctcc tgttccgacc ctgccgctta ccggatacct    5640
gtccgccttt ctcccttcgg gaagcgtggc gctttctcat agctcacgct gtaggtatct    5700
cagttcggtg taggtcgttc gctccaagct gggctgtgtg cacgaacccc ccgttcagcc    5760
cgaccgctgc gccttatccg gtaactatcg tcttgagtcc aacccggtaa gacacgactt    5820
atcgccactg gcagcagcca ctggtaacag gattagcaga gcgaggtatg taggcggtgc    5880
tacagagttc ttgaagtggt ggcctaacta cggctacact agaaggacag tatttggtat    5940
ctgcgctctg ctgaagccag ttaccttcgg aaaaagagtt ggtagctctt gatccggcaa    6000
acaaaccacc gctggtagcg gtggtttttt tgtttgcaag cagcagatta cgcgcagaaa    6060
aaaaggatct caagaagatc ctttgatctt ttctacgggg tctgacgctc agtggaacga    6120
aaactcacgt taagggattt tggtcatgag attatcaaaa aggatcttca cctagatcct    6180
tttaaattaa aaatgaagtt ttaaatcaat ctaaagtata tatgagtaaa cttggtctga    6240
cagttaccaa tgcttaatca gtgaggcacc tatctcagcg atctgtctat ttcgttcatc    6300
catagttgcc tgactccccg tcgtgtagat aactacgata cgggagggct taccatctgg    6360
ccccagtgct gcaatgatac cgcgagaccc acgctcaccg gctccagatt tatcagcaat    6420
```

```
aaaccagcca gccggaaggg ccgagcgcag aagtggtcct gcaactttat ccgcctccat    6480
ccagtctatt aattgttgcc gggaagctag agtaagtagt tcgccagtta atagtttgcg    6540
caacgttgtt gccattgcta caggcatcgt ggtgtcacgc tcgtcgtttg gtatggcttc    6600
attcagctcc ggttcccaac gatcaaggcg agttacatga tcccccatgt tgtgcaaaaa    6660
agcggttagc tccttcggtc ctccgatcgt tgtcagaagt aagttggccg cagtgttatc    6720
actcatggtt atggcagcac tgcataattc tcttactgtc atgccatccg taagatgctt    6780
ttctgtgact ggtgagtact caaccaagtc attctgagaa tagtgtatgc ggcgaccgag    6840
ttgctcttgc ccggcgtcaa tacgggataa taccgcgcca catagcagaa ctttaaaagt    6900
gctcatcatt ggaaaacgtt cttcggggcg aaaactctca aggatcttac cgctgttgag    6960
atccagttcg atgtaaccca ctcgtgcacc caactgatct tcagcatctt ttactttcac    7020
cagcgtttct gggtgagcaa aacaggaag gcaaaatgcc gcaaaaaagg gaataagggc     7080
gacacggaaa tgttgaatac tcatactctt cctttttcaa tattattgaa gcatttatca    7140
gggttattgt ctcatgagcg gatacatatt tgaatgtatt tag                      7183
```

<210> SEQ ID NO 30
<211> LENGTH: 7663
<212> TYPE: DNA
<213> ORGANISM: Artificial Sequence
<220> FEATURE:
<223> OTHER INFORMATION: pCVL_T7_DmrB-spacer-TM-41BB-CD3z lentiviral
      vector

<400> SEQUENCE: 30

```
aaaaataaac aaatagggt tccgcgcaca tttccccgaa aagtgccacc tgacgtcaat     60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga agcgaaagg gaaaccagag agctctctc gacgcaggac tcggcttgct    540
gaagcgcgca cggcaagagg cgaggggcgg cgactggtga gtacgccaaa aattttgact    600
agcggaggct agaaggagag agatgggtgc gagagcgtca gtattaagcg ggggagaatt    660
agatcgcgat gggaaaaaat tcggttaagg ccagggggaa agaaaaaata taaattaaaa    720
catatagtat gggcaagcag ggagctagaa cgattcgcag ttaatcctgg cctgttagaa    780
acatcagaag gctgtagaca aatactggga cagctacaac catcccttca gacaggatca    840
gaagaactta gatcattata taatacagta gcaacccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat    1020
tggagaagtg aattatataa atataaagta gtaaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca gacaattatt gtctggtata gtgcagcagc agaacaattt gctgagggct    1260
```

```
attgaggcgc aacagcatct gttgcaactc acagtctggg gcatcaagca gctccaggca    1320
agaatcctgg ctgtggaaag atacctaaag gatcaacagc tcctgggat ttggggttgc    1380
tctggaaaac tcatttgcac cactgctgtg ccttggaatg ctagttggag taatgaatct    1440
ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcagggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aagggggat tgggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gccttttttcc cgagggtggg ggagaaccgt    2160
atataagtgc agtagtcgcc gtgaacgttc tttttcgcaa cgggtttgcc gccagaacac    2220
acctgcaggt aatacgactc actatagggt ccactgccgc caccatggct ctgcctgtga    2280
cagctctgct gctgcctctg gccctgctgc tccatgccgc cagacccgga tccggagtgc    2340
aggtggaaac catctcccca ggagacgggc gcaccttccc caagcgcggc cagacctgcg    2400
tggtgcacta caccgggatg cttgaagatg gaaagaaagt tgattcctcc cgggacagaa    2460
acaagccctt taagtttatg ctaggcaagc aggaggtgat ccgaggctgg gaagaagggg    2520
ttgcccagat gagtgtgggt cagagagcca aactgactat atctccagat tatgcctatg    2580
gtgccactgg gcacccaggc atcatcccac cacatgccac tctcgtcttc gatgtggagc    2640
ttctaaaact ggaagctagc gagagcaagt acgaccgcc ctgcccacct tgccctgccc    2700
ccgagttcct gggcggaccc agcgtgttcc tgttcccacc caagcccaag gacaccctga    2760
tgatcagccg gaccccgag gtgacctgcg tggtggtgga cgtgagccag gaagatcccg    2820
aggtccagtt caattggtac gtggacggcg tggaagtgca caacgccaag accaagccca    2880
gagaggaaca gttcaacagc acctaccggg tggtgtctgt gctgaccgtg ctgcaccagg    2940
actggctgaa cggcaaagaa tacaagtgca aggtgtccaa caagggcctg cccagcagca    3000
tcgaaaagac catcagcaag gccaagggcc agcctcgcga gccccaggtg tacaccctgc    3060
ctccctccca ggaagagatg accaagaacc aggtgtccct gacctgctg gtgaagggct    3120
tctaccccag cgacatcgcc gtggagtggg agagcaacgg ccagcctgag aacaactaca    3180
agaccacccc tcccgtgctg gacagcgacg gcagcttctt cctgtacagc cggctgaccg    3240
tggacaagag ccggtggcag gaaggcaacg tctttagctg cagcgtgatg cacgaggccc    3300
tgcacaacca ctacacccag aagagcctga gcctgtccct gggcaagatg cataaacggg    3360
gcagaaagaa actcctgtat atattcaaac aaccatttat gagaccagta caaactactc    3420
aagaggaaga tggctgtagc tgccgatttc agaagaaga agaaggagga tgtgaactgc    3480
gggtgaagtt cagcagaagc gccgacgccc ctgcctacca gcaggccag aatcagctgt    3540
acaacgagct gaacctgggc agaagggaag agtacgacgt cctggataag cggagagcc    3600
```

```
gggaccctga gatgggcggc aagcctcggc ggaagaaccc ccaggaaggc ctgtataacg    3660
aactgcagaa agacaagatg gccgaggcct acagcgagat cggcatgaag ggcgagcgga    3720 ggcgggcaa gggccacgac ggcctgtatc agggcctgtc caccgccacc aaggatacct     3780
acgacgccct gcacatgcag gccctgcccc aaggggcgg ccgctccggt gagggcagag     3840
gaagtcttct aacatgcggt gacgtggagg agaatccggg cccctctaga agcgagctga    3900
ttaaggagaa catgcacatg aagctgtaca tggaggcac cgtggacaac catcacttca     3960
agtgcacatc cgagggcgaa ggcaagccct acgagggcac ccagaccatg agaatcaagg    4020
tggtcgaggg cggccctctc cccttcgcct tcgacatcct ggctactagc ttcctctacg    4080
gcagcaagac cttcatcaac cacacccagg gcatccccga cttcttcaag cagtccttcc    4140
ctgagggctt cacatgggag agagtcacca catacgaaga cggggggcgtg ctgaccgcta   4200 cccaggacac cagcctccag gacggctgcc tcatctacaa cgtcaagatc agaggggtga    4260
acttcacatc caacgcccct gtgatgcaga gaaaacact cggctgggag gccttcaccg     4320
agacgctgta ccccgctgac ggcggcctgg aaggcagaaa cgacatggcc ctgaagctcg    4380
tgggcgggag ccatctgatc gcaaacatca gaccacata tagatccaag aaacccgcta    4440
agaacctcaa gatgcctggc gtctactatg tggactacag actggaaaga atcaaggagg    4500
ccaacaacga gacctacgtc gagcagcacg aggtggcagt ggccagatac tgcgacctcc    4560 ctagcaaaact ggggcacaag cttaattgag tcgaccgagc atcttaccgc catttatacc    4620
catatttgtt ctgtttttct tgatttgggt atacatttaa atgttaatag aacaaaatgg    4680
tggggcaatc atttacattt ttagggatat gtaattacta gttcaggtgt attgccacaa    4740
gacaaacatg ttaagaaact ttcccgttat ttacgctctg ttcctgttaa tcaacctctg    4800
gattacaaaa tttgtgaaag attgactgat attcttaact atgttgctcc ttttacgctg    4860
tgtggatatg ctgctttata gcctctgtat ctagctattg cttcccgtac ggctttcgtt    4920
ttctcctcct tgtataaatc ctggttgctg tctcttttag aggagttgtg gcccgttgtc    4980
cgtcaacgtg gcgtggtgtg ctctgtgttt gctgacgcaa ccccccactgg ctggggcatt    5040 gccaccacct gtcaactcct ttctgggact ttcgctttcc cctcccgat cgccacggca    5100 gaactcatcg ccgcctgcct tgcccgctgc tggacagggg ctaggttgct gggcactgat    5160
aattccgtgg tgttgtcatc gaattcggta ccttttaaa agaaaagggg ggactggaag    5220
ggctaattca ctcccaacga agacaagata tcataacttc gtatagcata cattatacga    5280
agttataatt tatttgtgaa atttgtgatg ctattgcttt atttgtaacc atatgtttat    5340
ttgtgaaatt tgtgatgcta ttgctttatt tgtaaccatt gcttttgct tgtactgggt    5400 ctctctggtt agaccagatc tgagcctggg agctctctgg ctaactaggg aacccactgc    5460
ttaagcctca ataaagcttg cctcgaccag cctcgactgt gccttctagt tgccagccat    5520
ctgttgtttg cccctccccc gtgccttcct tgaccctgga aggtgccact cccactgtcc    5580
tttcctaata aaatgaggaa attgcatcgc attgtctgag taggtgtcat tctattctgg    5640
ggggtggggt ggggcaggac agcaagggg aggattggga agacaatagc aggcatgctg    5700
gggatgcggt gggctctatg gcctgcagct gcattaatga atcggccaac gcgcgggag    5760 aggcggtttg cgtattgggc gctcttccgc ttcctcgctc actgactcgc tgcgctcggt    5820
cgttcggctg cggcgagcgg tatcagctca ctcaaaggcg gtaatacggt tatccacaga    5880
atcaggggat aacgcaggaa agaacatgtg agcaaaaggc cagcaaaagg ccaggaaccg    5940
taaaaaggcc gcgttgctgg cgttttccca taggctccgc cccctgacg agcatcacaa    6000
```

```
aaatcgacgc tcaagtcaga ggtggcgaaa cccgacagga ctataaagat accaggcgtt      6060
tccccctgga agctccctcg tgcgctctcc tgttccgacc ctgccgctta ccggatacct      6120
gtccgccttt ctcccttcgg aagcgtggc gctttctcat agctcacgct gtaggtatct       6180
cagttcggtg taggtcgttc gctccaagct gggctgtgtg cacgaacccc cgttcagcc       6240 cgaccgctgc gccttatccg gtaactatcg tcttgagtcc aacccggtaa gacacgactt      6300
atcgccactg gcagcagcca ctggtaacag gattagcaga gcgaggtatg taggcggtgc      6360
tacagagttc ttgaagtggt ggcctaacta cggctacact agaaggacag tatttggtat      6420
ctgcgctctg ctgaagccag ttaccttcgg aaaaagagtt ggtagctctt gatccggcaa      6480
acaaaccacc gctggtagcg gtggtttttt tgtttgcaag cagcagatta cgcgcagaaa      6540
aaaaggatct caagaagatc ctttgatctt ttctacgggg tctgacgctc agtggaacga      6600
aaactcacgt taagggattt tggtcatgag attatcaaaa aggatcttca cctagatcct      6660
tttaaattaa aaatgaagtt ttaaatcaat ctaaagtata tatgagtaaa cttggtctga      6720
cagttaccaa tgcttaatca gtgaggcacc tatctcagcg atctgtctat ttcgttcatc      6780
catagttgcc tgactccccg tcgtgtagat aactacgata cgggagggct taccatctgg      6840
ccccagtgct gcaatgatac cgcgagaccc acgctcaccg gctccagatt tatcagcaat      6900
aaaccagcca gccggaaggg ccgagcgcag aagtggtcct gcaactttat ccgcctccat      6960
ccagtctatt aattgttgcc gggaagctag agtaagtagt tcgccagtta atagtttgcg      7020
caacgttgtt gccattgcta caggcatcgt ggtgtcacgc tcgtcgtttg gtatggcttc      7080
attcagctcc ggttcccaac gatcaaggcg agttacatga tcccccatgt tgtgcaaaaa      7140
agcggttagc tccttcggtc ctccgatcgt tgtcagaagt aagttggccg cagtgttatc      7200
actcatggtt atggcagcac tgcataattc tcttactgtc atgccatccg taagatgctt      7260
ttctgtgact ggtgagtact caaccaagtc attctgagaa tagtgtatgc ggcgaccgag      7320
ttgctcttgc ccggcgtcaa tacgggataa taccgcgcca catagcagaa ctttaaaagt      7380
gctcatcatt ggaaaacgtt cttcggggcg aaaactctca aggatcttac cgctgttgag      7440
atccagttcg atgtaaccca ctcgtgcacc caactgatct tcagcatctt ttactttcac      7500
cagcgtttct gggtgagcaa aaacaggaag gcaaaatgcc gcaaaaaagg gaataagggc      7560
gacacggaaa tgttgaatac tcatactctt ccttttcaa tattattgaa gcatttatca       7620
gggttattgt ctcatgagcg gatacatatt tgaatgtatt tag                        7663
```

<210> SEQ ID NO 31
<211> LENGTH: 7183
<212> TYPE: DNA
<213> ORGANISM: Artificial Sequence
<220> FEATURE:
<223> OTHER INFORMATION: pCVL_T7_DmrA-TM-41BB-CD3z lentiviral vector

<400> SEQUENCE: 31

```
aaaaataaac aaatagggggt tccgcgcaca tttccccgaa aagtgccacc tgacgtcaat      60
gtagtcttat gcaatactct tgtagtcttg caacatggta acgatgagtt agcaacatgc       120
cttacaagga gagaaaaagc accgtgcatg ccgattggtg gaagtaaggt ggtacgatcg       180
tgccttatta ggaaggcaac agacgggtct gacatggatt ggacgaacca ctgaattgcc      240
gcattgcaga gatattgtat ttaagtgcct agctcgatac ataaacgggt ctctctggtt       300
agaccagatc tgagcctggg agctctctgg ctaactaggg aacccactgc ttaagcctca      360
```

```
ataaagcttg ccttgagtgc ttcaagtagt gtgtgcccgt ctgttgtgtg actctggtaa      420
ctagagatcc ctcagaccct tttagtcagt gtggaaaatc tctagcagtg gcgcccgaac      480
agggacttga aagcgaaagg gaaaccagag gagctctctc gacgcaggac tcggcttgct      540
gaagcgcgca cggcaagagg cgaggggcgg cgactggtga gtacgccaaa aattttgact      600
agcggaggct agaaggagag agatgggtgc gagagcgtca gtattaagcg ggggagaatt      660
agatcgcgat gggaaaaaat tcggttaagg ccagggggaa agaaaaaata taaattaaaa      720
catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaaccctct attgtgtgca tcaaaggata      900
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaaattg aaccattagg agtagcaccc     1080
accaaggcaa agagaagagt ggtgcagaga gaaaaaagag cagtgggaat aggagctttg     1140
ttccttgggt tcttgggagc agcaggaagc actatgggcg cagcgtcaat gacgctgacg     1200
gtacaggcca gacaattatt gtctggtata gtgcagcagc agaacaattt gctgagggct     1260
attgaggcgc aacagcatct gttgcaactc acagtctggg gcatcaagca gctccaggca     1320
agaatcctgg ctgtggaaag atacctaaag gatcaacagc tcctggggat ttggggttgc     1380
tctggaaaac tcatttgcac cactgctgtg ccttggaatg ctagttggag taatgaatct     1440
ctggaacaga tttggaatca cacgacctgg atggagtggg acagagaaat taacaattac     1500
acaagcttaa tacactcctt aattgaagaa tcgcaaaacc agcaagaaaa gaatgaacaa     1560
gaattattgg aattagataa atgggcaagt ttgtggaatt ggtttaacat aacaaattgg     1620
ctgtggtata taaaattatt cataatgata gtaggaggct tggtaggttt aagaatagtt     1680
tttgctgtac tttctatagt gaatagagtt aggcagggat attcaccatt atcgtttcag     1740
acccacctcc caaccccgag gggacccgac aggcccgaag gaatagaaga agaaggtgga     1800
gagagagaca gagacagatc cattcgatta gtgaacggat ctcgacggta tcggttaact     1860
tttaaaagaa aagggggat tgggggtac agtgcagggg aaagaatagt agacataata     1920
gcaacagaca tacaaactaa agaattacaa aaacaaatta caaaaattca aaattttatc     1980
gattacgcgt aggctccggt gcccgtcagt gggcagagcg cacatcgccc acagtccccg     2040
agaagttggg gggaggggtc ggcaattgaa ccggtgccta gagaaggtgg cgcggggtaa     2100
actgggaaag tgatgtcgtg tactggctcc gcctttttcc cgagggtggg ggagaaccgt     2160
atataagtgc agtagtcgcc gtgaacgttc ttttctcgcaa cgggtttgcc gccagaacac     2220
acctgcaggt aatacgactc actatagggt ccactgccgc caccatggct ctgcctgtga     2280
cagctctgct gctgcctctg gccctgctgc tccatgccgc cagacccgga tccgagtgc      2340
aggtggaaac catctcccca ggagacgggc gcaccttccc caagcgcggc cagacctgcg     2400
tggtgcacta caccgggatg cttgaagatg gaagaaatt tgattcctcc cgggacagaa     2460
acaagccctt taagttatg ctaggcaagc aggaggtgat ccgaggctgg gaagaagggg     2520
ttgcccagat gagtgtgggt cagagagcca aactgactat atctccagat tatgcctatg     2580
gtgccactgg gcacccaggc atcatcccac acatgccac tctcgtcttc gatgtggagc     2640
ttctaaaact ggaagctagc gccaagccta ccaccacccc tgcccctaga cctccaacac     2700
ccgccccaac aatcgccagc cagcctctgt ctctgaggcc cgaggcttgt agaccagctg     2760
```

| | |
|---|---|
| ctggcggagc cgtgcacacc agaggactgg atttcgcctg cgacatctac atctgggccc | 2820 |
| ctctggccgg cacatgtggc gtgctgctgc tgagcctcgt gatcaccatg cataaacggg | 2880 |
| gcagaaagaa actcctgtat atattcaaac aaccatttat gagaccagta caaactactc | 2940 |
| aagaggaaga tggctgtagc tgccgatttc cagaagaaga agaaggagga tgtgaactgc | 3000 |
| gggtgaagtt cagcagaagc gccgacgccc tgcctacca gcagggccag aatcagctgt | 3060 |
| acaacgagct gaacctgggc agaagggaag agtacgacgt cctggataag cggagagggcc | 3120 |
| gggaccctga gatgggcggc aagcctcggc ggaagaaccc ccaggaaggc ctgtataacg | 3180 |
| aactgcagaa agacaagatg gccgaggcct acagcgagat cggcatgaag ggcgagcgga | 3240 |
| ggcggggcaa gggccacgac ggcctgtatc agggcctgtc caccgccacc aaggatacct | 3300 |
| acgacgccct gcacatgcag gccctgcccc aaggggcgg ccgctccggt gagggcagag | 3360 |
| gaagtcttct aacatgcggt gacgtggagg agaatccggg cccctctaga agcgagctga | 3420 |
| ttaaggagaa catgcacatg aagctgtaca tggaggcac cgtggacaac catcacttca | 3480 |
| agtgcacatc cgagggcgaa ggcaagccct acgagggcac ccagaccatg agaatcaagg | 3540 |
| tggtcgaggg cggcccctct cccttcgcct tcgacatcct ggctactagc ttcctctacg | 3600 |
| gcagcaagac cttcatcaac cacacccagg gcatccccga cttcttcaag cagtccttcc | 3660 |
| ctgagggctt cacatgggag agagtcacca catacgaaga cggggggcgtg ctgaccgcta | 3720 |
| cccaggacac cagcctccag gacggctgcc tcatctacaa cgtcaagatc agaggggtga | 3780 |
| acttcacatc caacgcccct gtgatgcaga gaaaaacact cggctgggag gccttcaccg | 3840 |
| agacgctgta ccccgctgac ggcggcctgg aaggcagaaa cgacatggcc ctgaagctcg | 3900 |
| tgggcgggag ccatctgatc gcaaacatca gaccacata tagatccaag aaacccgcta | 3960 |
| agaacctcaa gatgcctggc gtctactatg tggactacag actggaaaga atcaaggagg | 4020 |
| ccaacaacga gacctacgtc gagcagcacg aggtggcagt ggccagatac tgcgacctcc | 4080 |
| ctagcaaact ggggcacaag cttaattgag tcgaccgagc atcttaccgc catttatacc | 4140 |
| catatttgtt ctgttttct tgatttgggt atacatttaa atgttaatag aacaaaatgg | 4200 |
| tggggcaatc atttacattt ttagggatat gtaattacta gttcaggtgt attgccacaa | 4260 |
| gacaaacatg ttaagaaact ttcccgttat ttacgctctg ttcctgttaa tcaacctctg | 4320 |
| gattacaaaa tttgtgaaag attgactgat attcttaact atgttgctcc ttttacgctg | 4380 |
| tgtggatatg ctgctttata gcctctgtat ctagctattg cttcccgtac ggctttcgtt | 4440 |
| ttctcctcct tgtataaatc ctggttgctg tctcttttag aggagttgtg gcccgttgtc | 4500 |
| cgtcaacgtg gcgtggtgtg ctctgtgttt gctgacgcaa cccccactgg ctggggcatt | 4560 |
| gccaccacct gtcaactcct ttctgggact ttcgctttcc cctcccgat cgccacggca | 4620 |
| gaactcatcg ccgcctgcct tgcccgctgc tggacagggg ctaggttgct gggcactgat | 4680 |
| aattccgtgt gttgtcatc gaattcggta ccttttaaa agaaaagggg ggactggaag | 4740 |
| ggctaattca ctcccaacga agacaagata tcataacttc gtatagcata cattatacga | 4800 |
| agttataatt tatttgtgaa atttgtgatg ctattgcttt atttgtaacc atatgtttat | 4860 |
| ttgtgaaatt tgtgatgcta ttgctttatt tgtaaccatt gcttttttgct tgtactgggt | 4920 |
| ctctctggtt agaccagatc tgagcctggg agctctctgg ctaactaggg aacccactgc | 4980 |
| ttaagcctca ataaagcttg cctcgaccag cctcgactgt gccttctagt tgccagccat | 5040 |
| ctgttgtttg ccctccccc gtgccttcct tgaccctgga aggtgccact cccactgtcc | 5100 |

```
tttcctaata aaatgaggaa attgcatcgc attgtctgag taggtgtcat tctattctgg    5160
ggggtggggt gggcaggac agcaaggggg aggattggga agacaatagc aggcatgctg     5220
gggatgcggt gggctctatg gcctgcagct gcattaatga atcggccaac gcgcggggag    5280
aggcggtttg cgtattgggc gctcttccgc ttcctcgctc actgactcgc tgcgctcggt    5340
cgttcggctg cggcgagcgg tatcagctca ctcaaaggcg gtaatacggt tatccacaga    5400
atcaggggat aacgcaggaa agaacatgtg agcaaaaggc cagcaaaagg ccaggaaccg    5460
taaaaaggcc gcgttgctgg cgttttccca taggctccgc cccctgacg agcatcacaa     5520
aaatcgacgc tcaagtcaga ggtggcgaaa cccgacagga ctataaagat accaggcgtt    5580
tccccctgga agctccctcg tgcgctctcc tgttccgacc ctgccgctta ccggatacct    5640
gtccgccttt ctcccttcgg gaagcgtggc gctttctcat agctcacgct gtaggtatct    5700
cagttcggtg taggtcgttc gctccaagct gggctgtgtg cacgaacccc ccgttcagcc    5760
cgaccgctgc gccttatccg gtaactatcg tcttgagtcc aacccggtaa gacacgactt    5820
atcgccactg gcagcagcca ctggtaacag gattagcaga gcgaggtatg taggcggtgc    5880
tacagagttc ttgaagtggt ggcctaacta cggctacact agaaggacag tatttggtat    5940
ctgcgctctg ctgaagccag ttaccttcgg aaaaagagtt ggtagctctt gatccggcaa    6000
acaaaccacc gctggtagcg gtggtttttt tgtttgcaag cagcagatta cgcgcagaaa    6060
aaaaggatct caagaagatc ctttgatctt ttctacgggg tctgacgctc agtggaacga    6120
aaactcacgt taagggattt tggtcatgag attatcaaaa aggatcttca cctagatcct    6180
tttaaattaa aaatgaagtt ttaaatcaat ctaaagtata tatgagtaaa cttggtctga    6240
cagttaccaa tgcttaatca gtgaggcacc tatctcagcg atctgtctat ttcgttcatc    6300
catagttgcc tgactccccg tcgtgtagat aactacgata cgggagggct taccatctgg    6360
ccccagtgct gcaatgatac cgcgagaccc acgctcaccg gctccagatt tatcagcaat    6420
aaaccagcca gccggaaggg ccgagcgcag aagtggtcct gcaactttat ccgcctccat    6480
ccagtctatt aattgttgcc gggaagctag agtaagtagt tcgccagtta atagtttgcg    6540
caacgttgtt gccattgcta caggcatcgt ggtgtcacgc tcgtcgtttg gtatggcttc    6600
attcagctcc ggttcccaac gatcaaggcg agttacatga tcccccatgt tgtgcaaaaa    6660
agcggttagc tccttcggtc ctccgatcgt tgtcagaagt aagttggccg cagtgttatc    6720
actcatggtt atggcagcac tgcataattc tcttactgtc atgccatccg taagatgctt    6780
ttctgtgact ggtgagtact caaccaagtc attctgagaa tagtgtatgc ggcgaccgag    6840
ttgctcttgc ccggcgtcaa tacgggataa taccgcgcca catagcagaa ctttaaaagt    6900
gctcatcatt ggaaaacgtt cttcggggcg aaaactctca aggatcttac cgctgttgag    6960
atccagttcg atgtaaccca ctcgtgcacc caactgatct tcagcatctt ttactttcac    7020
cagcgtttct gggtgagcaa aaacaggaag gcaaaatgcc gcaaaaaagg gaataagggc    7080
gacacggaaa tgttgaatac tcatactctt ccttttcaa tattattgaa gcatttatca     7140
gggttattgt ctcatgagcg gatacatatt tgaatgtatt tag                       7183
```

<210> SEQ ID NO 32
<211> LENGTH: 7663
<212> TYPE: DNA
<213> ORGANISM: Artificial Sequence
<220> FEATURE:
<223> OTHER INFORMATION: pCVL_T7_DmrA-spacer-TM-41BB-CD3z lentiviral
      vector

```
<400> SEQUENCE: 32
aaaaataaac aaatagggt tccgcgcaca tttccccgaa aagtgccacc tgacgtcaat        60
gtagtcttat gcaatactct tgtagtcttg caacatggta acgatgagtt agcaacatgc       120
cttacaagga gagaaaaagc accgtgcatg ccgattggtg gaagtaaggt ggtacgatcg       180
tgccttatta ggaaggcaac agacgggtct gacatggatt ggacgaacca ctgaattgcc      240
gcattgcaga gatattgtat ttaagtgcct agctcgatac ataaacgggt ctctctggtt      300
agaccagatc tgagcctggg agctctctgg ctaactaggg aacccactgc ttaagcctca      360
ataaagcttg ccttgagtgc ttcaagtagt gtgtgcccgt ctgttgtgtg actctggtaa      420
ctagagatcc ctcagaccct tttagtcagt gtggaaaatc tctagcagtg gcgcccgaac      480
agggacttga agcgaaagg gaaaccagag gagctctctc gacgcaggac tcggcttgct      540
gaagcgcgca cggcaagagg cgaggggcgg cgactggtga gtacgccaaa aattttgact      600
agcggaggct agaaggagag atgggtgc gagagcgtca gtattaagcg gggagaatt       660 agatcgcgat gggaaaaaat tcggttaagg ccaggggaa agaaaaaata taaattaaaa      720
catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaaccctct attgtgtgca tcaaaggata      900
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaattg aaccattagg agtagcaccc     1080
accaaggcaa agagaagagt ggtgcagaga gaaaaagag cagtgggaat aggagctttg     1140
ttccttgggt tcttgggagc agcaggaagc actatgggcg cagcgtcaat gacgctgacg     1200
gtacaggcca gacaattatt gtctggtata gtgcagcagc agaacaattt gctgagggct     1260
attgaggcgc aacagcatct gttgcaactc acagtctggg gcatcaagca gctccaggca     1320
agaatcctgg ctgtggaaag atacctaaag gatcaacagc tcctggggat ttggggttgc     1380
tctggaaaac tcatttgcac cactgctgtg ccttggaatg ctagttggag taatgaatct     1440
ctggaacaga tttggaatca cacgacctgg atggagtggg acagagaaat taacaattac     1500
acaagcttaa tacactcctt aattgaagaa tcgcaaaacc agcaagaaaa gaatgaacaa     1560
gaattattgg aattagataa atgggcaagt ttgtggaatt ggtttaacat aacaaattgg     1620
ctgtggtata taaaattatt cataatgata gtaggaggct tggtaggttt aagaatagtt     1680
tttgctgtac tttctatagt gaatagagtt aggcagggat attcaccatt atcgtttcag     1740
acccacctcc caaccccgag gggacccgac aggcccgaag gaatagaaga agaaggtgga     1800
gagagagaca gagacagatc cattcgatta gtgaacggat ctcgacggta tcggttaact     1860
tttaaaagaa aaggggggat tggggggtac agtgcagggg aaagaatagt agacataata     1920
gcaacagaca tacaaactaa agaattacaa aaacaaatta caaaaattca aaattttatc     1980
gattacgcgt aggctccggt gcccgtcagt gggcagagcg cacatcgccc acagtccccg     2040
agaagtgggg gagggtc ggcaattgaa ccggtgccta gagaaggtgg cgcggggtaa     2100
actgggaaag tgatgtcgtg tactggctcc gcctttttcc cgagggtggg ggagaaccgt     2160
atataagtgc agtagtcgcc gtgaacgttc ttttcgcaa cgggtttgcc gccagaacac     2220
acctgcaggt aatacgactc actatagggt ccactgccgc caccatggct ctgcctgtga     2280
cagctctgct gctgcctctg gccctgctgc tccatgccgc cagacccgga tccggagtgc     2340
```

```
aggtggaaac catctcccca ggagacgggc gcaccttccc caagcgcggc cagacctgcg   2400
tggtgcacta caccgggatg cttgaagatg gaaagaaatt tgattcctcc cgggacagaa   2460
acaagccctt taagtttatg ctaggcaagc aggaggtgat ccgaggctgg gaagaagggg   2520
ttgcccagat gagtgtgggt cagagagcca aactgactat atctccagat tatgcctatg   2580
gtgccactgg gcacccaggc atcatcccac cacatgccac tctcgtcttc gatgtggagc   2640
ttctaaaact ggaagctagc gagagcaagt acggaccgcc ctgcccacct tgccctgccc   2700
ccgagttcct gggcggaccc agcgtgttcc tgttcccacc caagcccaag gacaccctga   2760
tgatcagccg gacccccgag gtgacctgcg tggtggtgga cgtgagccag gaagatcccg   2820
aggtccagtt caattggtac gtggacggcg tggaagtgca aacgccaag accaagccca   2880 gagaggaaca gttcaacagc acctaccggg tggtgtctgt gctgaccgtg ctgcaccagg   2940
actggctgaa cggcaaagaa tacaagtgca aggtgtccaa caagggcctg cccagcagca   3000
tcgaaaagac catcagcaag gccaaggccc agcctcgcga gccccaggtg tacaccctgc   3060
ctccctccca ggaagagatg accaagaacc aggtgtccct gacctgcctg gtgaagggct   3120
tctaccccag cgacatcgcc gtggagtggg agagcaacgg ccagcctgag aacaactaca   3180
agaccacccc tcccgtgctg gacagcgacg gcagcttctt cctgtacagc cggctgaccg   3240
tggacaagag ccgtggcag gaaggcaacg tctttagctg cagcgtgatg cacgaggccc   3300
tgcacaacca ctacacccag aagagcctga gcctgtccct gggcaagatg cataaacggg   3360
gcagaaagaa actcctgtat atattcaaac aaccatttat gagaccagta caaactactc   3420
aagaggaaga tggctgtagc tgccgatttc agaagaagaa agaaggagga tgtgaactgc   3480
gggtgaagtt cagcagaagc gccgacgccc tgcctacca gcagggccag aatcagctgt   3540
acaacgagct gaacctgggc agaagggaag agtacgacgt cctggataag cggagaggcc   3600
gggaccctga gatgggcggc aagcctcggc ggaagaaccc ccaggaaggc ctgtataacg   3660
aactgcagaa agacaagatg gccgaggcct acagcgagat cggcatgaag ggcgagcgga   3720
ggcggggcaa gggccacgac ggcctgtatc agggcctgtc caccgccacc aaggatacct   3780
acgacgccct gcacatgcag gccctgcccc caaggggcgg ccgctccggt gagggcagag   3840
gaagtcttct aacatgcggt gacgtggagg agaatccggg ccctctaga agcgagctga   3900 ttaaggagaa catgcacatg aagctgtaca tggagggcac cgtggacaac catcacttca   3960
agtgcacatc cgagggcgaa ggcaagccct acgagggcac ccagaccatg agaatcaagg   4020
tggtcgaggg cggccctctc cccttcgcct tcgacatcct ggctactagc ttcctctacg   4080
gcagcaagac cttcatcaac cacacccagg gcatccccga cttcttcaag cagtccttcc   4140
ctgagggctt cacatgggag agagtcacca catacgaaga cggggcgtg ctgaccgcta   4200 cccaggacac cagcctccag gacggctgcc tcatctacaa cgtcaagatc agagggtga   4260 acttcacatc caacggccct gtgatgcaga gaaaaacact cggctgggag ccttcaccg   4320 agacgctgta ccccgctgac ggcggcctgg aaggcagaaa cgacatggcc ctgaagctcg   4380
tgggcgggag ccatctgatc gcaaacatca gaccacata tagatccaag aaacccgcta   4440
agaacctcaa gatgcctggc gtctactatg tggactacac actggaaaga atcaaggagg   4500
ccaacaacga gacctacgtc gagcagcacg aggtggcagt ggccagatac tgcgacctcc   4560
ctagcaaact ggggcacaag cttaattgag tcgaccgagc atcttaccgc catttatacc   4620
catatttgtt ctgttttttct tgatttgggt atacatttaa atgttaatag aacaaaatgg   4680
```

| | |
|---|---|
| tggggcaatc atttacattt ttagggatat gtaattacta gttcaggtgt attgccacaa | 4740 |
| gacaaacatg ttaagaaact ttcccgttat ttacgctctg ttcctgttaa tcaacctctg | 4800 |
| gattacaaaa tttgtgaaag attgactgat attcttaact atgttgctcc ttttacgctg | 4860 |
| tgtggatatg ctgctttata gcctctgtat ctagctattg cttcccgtac ggctttcgtt | 4920 |
| ttctcctcct tgtataaatc ctggttgctg tctcttttag aggagttgtg gcccgttgtc | 4980 |
| cgtcaacgtg gcgtggtgtg ctctgtgttt gctgacgcaa cccccactgg ctggggcatt | 5040 |
| gccaccacct gtcaactcct ttctgggact ttcgctttcc ccctcccgat cgccacggca | 5100 |
| gaactcatcg ccgcctgcct tgcccgctgc tggacagggg ctaggttgct gggcactgat | 5160 |
| aattccgtgg tgttgtcatc gaattcggta ccttttttaaa agaaaagggg ggactggaag | 5220 |
| ggctaattca ctcccaacga agacaagata tcataacttc gtatagcata cattatacga | 5280 |
| agttataatt tatttgtgaa atttgtgatg ctattgcttt atttgtaacc atatgtttat | 5340 |
| ttgtgaaatt tgtgatgcta ttgctttatt tgtaaccatt gcttttttgct tgtactgggt | 5400 |
| ctctctggtt agaccagatc tgagcctggg agctctctgg ctaactaggg aacccactgc | 5460 |
| ttaagcctca ataaagcttg cctcgaccag cctcgactgt gccttctagt tgccagccat | 5520 |
| ctgttgtttg cccctccccc gtgccttcct tgacccctgga aggtgccact cccactgtcc | 5580 |
| tttcctaata aaatgaggaa attgcatcgc attgtctgag taggtgtcat tctattctgg | 5640 |
| ggggtggggt ggggcaggac agcaagggg g aggattggga agacaatagc aggcatgctg | 5700 |
| gggatgcggt gggctctatg gcctgcagct gcattaatga atcggccaac gcgcggggag | 5760 |
| aggcggtttg cgtattgggc gctcttccgc ttcctcgctc actgactcgc tgcgctcggt | 5820 |
| cgttcggctg cggcgagcgg tatcagctca ctcaaaggcg gtaatacggt tatccacaga | 5880 |
| atcaggggat aacgcaggaa agaacatgtg agcaaaaggc cagcaaaagg ccaggaaccg | 5940 |
| taaaaaggcc gcgttgctgg cgtttttcca taggctccgc cccctgacg agcatcacaa | 6000 |
| aaatcgacgc tcaagtcaga ggtggcgaaa cccgacagga ctataaagat accaggcgtt | 6060 |
| tccccctgga agctccctcg tgcgctctcc tgttccgacc ctgccgctta ccggatacct | 6120 |
| gtccgccttt ctcccttcgg gaagcgtggc gctttctcat agctcacgct gtaggtatct | 6180 |
| cagttcggtg taggtcgttc gctccaagct gggctgtgtg cacgaacccc ccgttcagcc | 6240 |
| cgaccgctgc gccttatccg gtaactatcg tcttgagtcc aacccggtaa gacacgactt | 6300 |
| atcgccactg gcagcagcca ctggtaacag gattagcaga gcgaggtatg taggcggtgc | 6360 |
| tacagagttc ttgaagtggt ggcctaacta cggctacact agaaggacag tatttggtat | 6420 |
| ctgcgctctg ctgaagccag ttaccttcgg aaaaagagtt ggtagctctt gatccggcaa | 6480 |
| acaaaccacc gctggtagcg tggtttttt tgtttgcaag cagcagatta cgcgcagaaa | 6540 |
| aaaaggatct caagaagatc ctttgatctt ttctacgggg tctgacgctc agtggaacga | 6600 |
| aaactcacgt taagggattt tggtcatgag attatcaaaa aggatcttca cctagatcct | 6660 |
| tttaaattaa aaatgaagtt ttaaatcaat ctaaagtata tatgagtaaa cttggtctga | 6720 |
| cagttaccaa tgcttaatca gtgaggcacc tatctcagcg atctgtctat ttcgttcatc | 6780 |
| catagttgcc tgactcccg tcgtgtagat aactacgata cgggagggct taccatctgg | 6840 |
| ccccagtgct gcaatgatac cgcgagaccc acgctcaccg gctccagatt tatcagcaat | 6900 |
| aaaccagcca gccggaaggg ccgagcgcag aagtggtcct gcaactttat ccgcctccat | 6960 |
| ccagtctatt aattgttgcc gggaagctag agtaagtagt tcgccagtta atagtttgcg | 7020 |
| caacgttgtt gccattgcta caggcatcgt ggtgtcacgc tcgtcgtttg gtatggcttc | 7080 |

```
attcagctcc ggttcccaac gatcaaggcg agttacatga tcccccatgt tgtgcaaaaa    7140
agcggttagc tccttcggtc ctccgatcgt tgtcagaagt aagttggccg cagtgttatc    7200
actcatggtt atggcagcac tgcataattc tcttactgtc atgccatccg taagatgctt    7260
ttctgtgact ggtgagtact caaccaagtc attctgagaa tagtgtatgc ggcgaccgag    7320
ttgctcttgc ccggcgtcaa tacgggataa taccgcgcca catagcagaa ctttaaaagt    7380
gctcatcatt ggaaaacgtt cttcggggcg aaaactctca aggatcttac cgctgttgag    7440
atccagttcg atgtaaccca ctcgtgcacc caactgatct tcagcatctt ttactttcac    7500
cagcgtttct gggtgagcaa aaacaggaag gcaaaatgcc gcaaaaaagg gaataagggc    7560
gacacggaaa tgttgaatac tcatactctt ccttttttcaa tattattgaa gcatttatca    7620
gggttattgt ctcatgagcg gatacatatt tgaatgtatt tag                     7663
```

<210> SEQ ID NO 33
<211> LENGTH: 7477
<212> TYPE: DNA
<213> ORGANISM: Artificial Sequence
<220> FEATURE:
<223> OTHER INFORMATION: pCVL_T7_DmrB-DmrC-TM-41BB-CD3z lentiviral vector

<400> SEQUENCE: 33

```
aaaaataaac aaatagggt tccgcgcaca tttccccgaa aagtgccacc tgacgtcaat      60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg gcgcccgaac     480
agggacttga aagcgaaagg gaaaccagag gagctctctc gacgcaggac tcggcttgct     540
gaagcgcgca cggcaagagg cgaggggcgg cgactggtga gtacgccaaa aattttgact     600
agcggaggct agaaggagag agatgggtgc gagagcgtca gtattaagcg gggagaatt     660 agatcgcgat gggaaaaaat tcggttaagg ccaggggaa agaaaaaata taaattaaaa     720
catatagtat gggcaagcag ggagctagaa cgattcgcag ttaatcctgg cctgttagaa     780
acatcagaag gctgtagaca aatactggga cagctacaac catcccttca gacaggatca     840
gaagaactta gatcattata taatacagta gcaaccctct attgtgtgca tcaaaggata     900
gagataaaag acaccaagga agctttagac aagatagagg aagagcaaaa caaaagtaag     960
accaccgcac agcaagcggc cctgatcttc agacctggag gaggagatat gagggacaat    1020
tggagaagtg aattatataa atataaagta gtaaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca gacaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taatgaatct    1440
```

```
ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcagggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aaggggggat tggggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gcctttttcc cgagggtggg ggagaaccgt    2160
atataagtgc agtagtcgcc gtgaacgttc tttttcgcaa cgggtttgcc gccagaacac    2220
acctgcaggt aatacgactc actataggg ccactgccgc caccatggct ctgcctgtga    2280
cagctctgct gctgcctctg gccctgctgc tccatgccgc cagacccgga tccggagtgc    2340
aggtggaaac catctcccca ggagacgggc gcaccttccc caagcgcggc cagacctgcg    2400
tggtgcacta caccgggatg cttgaagatg gaaagaaagt tgattcctcc cgggacagaa    2460
acaagccctt taagtttatg ctaggcaagc aggaggtgat ccgaggctgg gaagaagggg    2520
ttgcccagat gagtgtgggt cagagagcca aactgactat atctccagat tatgcctatg    2580
gtgccactgg gcacccaggc atcatcccac cacatgccac tctcgtcttc gatgtggagc    2640
ttctaaaact ggaaggcgga ggtgggagca tcctctggca tgagatgtgg catgaaggcc    2700
tggaagaggc atctcgtttg tactttgggg aaaggaacgt gaaaggcatg tttgaggtgc    2760
tggagcccct gcatgctatg atggaacggg cccccagac tctgaaggaa acatccttta    2820
atcaggccta tggtcgagat ttaatggagg cccaagagtg gtgcaggaag tacatgaaat    2880
cagggaatgt caaggacctc ctccaagcct gggacctcta ttatcatgtg ttccgacgaa    2940
tctcaaaggc tagcgccaag cctaccacca ccctgccccc tagacctcca acacccgccc    3000
caacaatcgc cagccagcct ctgtctctga ggcccgagcc ttgtagacca gctgctggcg    3060
gagccgtgca caccagagga ctggatttcg cctgcgacat ctacatctgg gcccctctgg    3120
ccggcacatg tggcgtgctg ctgctgagcc tcgtgatcac catgcataaa cggggcagaa    3180
agaaactcct gtatatattc aaacaaccat ttatgagacc agtacaaact actcaagagg    3240
aagatggctg tagctgccga tttccagaag aagaagaagg aggatgtgaa ctgcgggtga    3300
agttcagcag aagcgccgac gcccctgcct accagcaggg ccagaatcag ctgtacaacg    3360
agctgaacct gggcagaagg gaagagtacg acgtcctgga taagcggaga ggccgggacc    3420
ctgagatggg cggcaagcct cggcggaaga accccagga aggcctgtat aacgaactgc    3480
agaaagacaa gatggccgag gcctacagcg agatcggcat gaagggcgag cggaggcggg    3540
gcaagggcca cgacggcctg tatcagggcc tgtccaccgc caccaaggat acctacgacg    3600
ccctgcacat gcaggccctg ccccaaggg gcggccgctc cggtgagggc agaggaagtc    3660
ttctaacatg cggtgacgtg gaggagaatc cgggccctc tagaagcgag ctgattaagg    3720
agaacatgca catgaagctg tacatggagg gcaccgtgga caaccatcac ttcaagtgca    3780
```

```
catccgaggg cgaaggcaag ccctacgagg gcacccagac catgagaatc aaggtggtcg    3840
agggcggccc tctcccctcc gccttcgaca tcctggctac tagcttcctc tacggcagca    3900
agaccttcat caaccacacc cagggcatcc ccgacttctt caagcagtcc ttccctgagg    3960
gcttcacatg ggagagagtc accacatacg aagacgggggg cgtgctgacc gctacccagg   4020
acaccagcct ccaggacggc tgcctcatct acaacgtcaa gatcagaggg gtgaacttca    4080
catccaacgg ccctgtgatg cagaagaaaa cactcggctg ggaggccttc accgagacgc    4140
tgtaccccgc tgacggcggc ctggaaggca gaaacgacat ggccctgaag ctcgtgggcg    4200
ggagccatct gatcgcaaac atcaagacca catatagatc caagaaaccc gctaagaacc    4260
tcaagatgcc tggcgtctac tatgtggact acagactgga aagaatcaag gaggccaaca    4320
acgagaccta cgtcgagcag cacgaggtgg cagtggccag atactgcgac ctccctagca    4380
aactggggca caagcttaat tgagtcgacc gagcatctta ccgccattta tacccatatt    4440
tgttctgttt ttcttgattt gggtatacat ttaaatgtta atagaacaaa atggtggggc    4500
aatcatttac attttagggg atatgtaatt actagttcag gtgtattgcc acaagacaaa    4560
catgttaaga aacttcccg ttatttacgc tctgttcctg ttaatcaacc tctggattac    4620
aaaatttgtg aaagattgac tgatattctt aactatgttg ctccttttac gctgtgtgga    4680
tatgctgctt tatagcctct gtatctagct attgcttccc gtacggcttt cgttttctcc    4740
tccttgtata aatcctggtt gctgtctctt ttagaggagt gtggcccgt tgtccgtcaa    4800
cgtggcgtgg tgtgctctgt gtttgctgac gcaaccccca ctggctgggg cattgccacc    4860
acctgtcaac tcctttctgg gactttcgct ttccccctcc cgatcgccac ggcagaactc    4920
atcgccgcct gccttgcccg ctgctggaca ggggctaggt tgctgggcac tgataattcc    4980
gtggtgttgt catcgaattc ggtaccttt taaaagaaaa gggggggactg aagggctaa    5040
ttcactccca acgaagacaa gatatcataa cttcgtatag catacattat acgaagttat    5100
aatttatttg tgaaatttgt gatgctattg ctttatttgt aaccatatgt ttatttgtga    5160
aatttgtgat gctattgctt tatttgtaac cattgctttt tgcttgtact gggtctctct    5220
ggttagacca gatctgagcc tgggagctct ctggctaact agggaaccca ctgcttaagc    5280
ctcaataaag cttgcctcga ccagcctcga ctgtgccttc tagttgccag ccatctgttg    5340
tttgcccctc ccccgtgcct tccttgaccc tggaaggtgc cactcccact gtcctttcct    5400
aataaaatga ggaaattgca tcgcattgtc tgagtaggtg tcattctatt ctggggggtg    5460
gggtggggca ggacagcaag ggggaggatt gggaagacaa tagcaggcat gctgggatg     5520
cggtgggctc tatggcctgc agctgcatta atgaatcggc caacgcgcgg ggagaggcgg    5580
tttgcgtatt gggcgctctt ccgcttcctc gctcactgac tcgctgcgct cggtcgttcg    5640
gctgcggcga gcggtatcag ctcactcaaa ggcggtaata cggttatcca cagaatcagg    5700
ggataacgca ggaaagaaca tgtgagcaaa aggccagcaa aaggccagga accgtaaaaa    5760
ggccgcgttg ctggcgtttt tccataggct ccgcccccct gacgagcatc acaaaaatcg    5820
acgctcaagt cagaggtggc gaaacccgac aggactataa agataccagg cgtttccccc    5880
tggaagctcc ctcgtgcgct ctcctgttcc gaccctgccg cttaccggat acctgtccgc    5940
cttctccct tcgggaagcg tggcgctttc tcatagctca cgctgtaggt atctcagttc    6000
ggtgtaggtc gttcgctcca agctgggctg tgtgcacgaa ccccccgttc agcccgaccg    6060
ctgcgcctta tccggtaact atcgtcttga gtccaacccg gtaagacacg acttatcgcc    6120
actggcagca gccactggta acaggattag cagagcgagg tatgtaggcg gtgctacaga    6180
```

```
gttcttgaag tggtggccta actacggcta cactagaagg acagtatttg gtatctgcgc   6240
tctgctgaag ccagttacct tcggaaaaag agttggtagc tcttgatccg gcaaacaaac   6300
caccgctggt agcggtggtt ttttttgtttg caagcagcag attacgcgca gaaaaaaagg   6360
atctcaagaa gatcctttga tcttttctac ggggtctgac gctcagtgga acgaaaactc   6420
acgttaaggg attttggtca tgagattatc aaaaaggatc ttcacctaga tccttttaaa   6480
ttaaaaatga agttttaaat caatctaaag tatatatgag taaacttggt ctgacagtta   6540
ccaatgctta atcagtgagg cacctatctc agcgatctgt ctatttcgtt catccatagt   6600
tgcctgactc cccgtcgtgt agataactac gatacgggag ggcttaccat ctggccccag   6660
tgctgcaatg ataccgcgag acccacgctc accggctcca gatttatcag caataaacca   6720
gccagccgga agggccgagc gcagaagtgg tcctgcaact ttatccgcct ccatccagtc   6780
tattaattgt tgccgggaag ctagagtaag tagttcgcca gttaatagtt tgcgcaacgt   6840
tgttgccatt gctacaggca tcgtggtgtc acgctcgtcg tttggtatgg cttcattcag   6900
ctccggttcc caacgatcaa ggcgagttac atgatccccc atgttgtgca aaaaagcggt   6960
tagctccttc ggtcctccga tcgttgtcag aagtaagttg gccgcagtgt tatcactcat   7020
ggttatggca gcactgcata attctcttac tgtcatgcca tccgtaagat gcttttctgt   7080
gactggtgag tactcaacca agtcattctg agaatagtgt atgcggcgac cgagttgctc   7140
ttgcccggcg tcaatacggg ataataccgc gccacatagc agaactttaa aagtgctcat   7200
cattggaaaa cgttcttcgg ggcgaaaact ctcaaggatc ttaccgctgt tgagatccag   7260
ttcgatgtaa cccactcgtg cacccaactg atcttcagca tcttttactt tcaccagcgt   7320
ttctgggtga gcaaaaacag gaaggcaaaa tgccgcaaaa aagggaataa gggcgacacg   7380
gaaatgttga atactcatac tcttcctttt tcaatattat tgaagcattt atcagggtta   7440
ttgtctcatg agcggataca tatttgaatg tatttag   7477
```

<210> SEQ ID NO 34
<211> LENGTH: 7519
<212> TYPE: DNA
<213> ORGANISM: Artificial Sequence
<220> FEATURE:
<223> OTHER INFORMATION: pCVL_T7_DmrB-DmrA-TM-41BB-CD3z lentiviral
      vector

<400> SEQUENCE: 34

```
aaaaataaac aaatagggt tccgcgcaca tttccccgaa aagtgccacc tgacgtcaat     60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga aagcgaaagg gaaaccagag gagctctctc gacgcaggac tcggcttgct    540
gaagcgcgca cggcaagagg cgaggggcgg cgactggtga gtacgccaaa aattttgact    600
agcggaggct agaaggagag agatgggtgc gagagcgtca gtattaagcg ggggagaatt    660
agatcgcgat gggaaaaaat tcggttaagg ccagggggaa agaaaaaata taaattaaaa    720
```

```
catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaaccctct attgtgtgca tcaaaggata      900
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaaattg aaccattagg agtagcaccc     1080
accaaggcaa agagaagagt ggtgcagaga gaaaaaagag cagtgggaat aggagctttg     1140
ttccttgggt tcttgggagc agcaggaagc actatgggcg cagcgtcaat gacgctgacg     1200
gtacaggcca gacaattatt gtctggtata gtgcagcagc agaacaattt gctgagggct     1260
attgaggcgc aacagcatct gttgcaactc acagtctggg gcatcaagca gctccaggca     1320
agaatcctgg ctgtggaaag atacctaaag gatcaacagc tcctggggat ttggggttgc     1380
tctggaaaac tcatttgcac cactgctgtg ccttggaatg ctagttggag taatgaatct     1440
ctggaacaga tttggaatca cacgacctgg atggagtggg acagagaaat taacaattac     1500
acaagcttaa tacactcctt aattgaagaa tcgcaaaacc agcaagaaaa gaatgaacaa     1560
gaattattgg aattagataa atgggcaagt ttgtggaatt ggtttaacat aacaaattgg     1620
ctgtggtata taaaattatt cataatgata gtaggaggct tggtaggttt aagaatagtt     1680
tttgctgtac tttctatagt gaatagagtt aggcagggat attcaccatt atcgtttcag     1740
acccacctcc caaccccgag gggacccgac aggcccgaag gaatagaaga agaaggtgga     1800
gagagagaca gagacagatc cattcgatta gtgaacggat ctcgacggta tcggttaact     1860
tttaaaagaa aagggggggat tggggggtac agtgcagggg aaagaatagt agacataata     1920
gcaacagaca tacaaactaa agaattacaa aaacaaatta caaaaattca aaattttatc     1980
gattacgcgt aggctccggt gcccgtcagt gggcagagcg cacatcgccc acagtccccg     2040
agaagttggg gggaggggtc ggcaattgaa ccggtgccta gagaaggtgg cgcggggtaa     2100
actgggaaag tgatgtcgtg tactggctcc gcctttttcc cgagggtggg ggagaaccgt     2160
atataagtgc agtagtcgcc gtgaacgttc tttttcgcaa cgggtttgcc gccagaacac     2220
acctgcaggt aatacgactc actatagggt ccactgccgc caccatggct ctgcctgtga     2280
cagctctgct gctgcctctg gccctgctgc tccatgccgc cagacccgga tccggagtgc     2340
aggtggaaac catctcccca ggagacgggc gcaccttccc caagcgcggc cagacctgcg     2400
tggtgcacta caccgggatg cttgaagatg gaaagaaagt tgattcctcc cgggacagaa     2460
acaagccctt taagtttatg ctaggcaagc aggaggtgat ccgaggctgg gaagaagggg     2520
ttgcccagat gagtgtgggt cagagagcca aactgactat atctccagat tatgcctatg     2580
gtgccactgg gcacccaggc atcatcccac acatgccac tctcgtcttc gatgtggagc     2640
ttctaaaact ggaaggcgga ggtggagcg gagtgcaggt ggaaaccatc tccccaggag     2700
acgggcgcac cttccccaag cgcggccaga cctgcgtggt gcactacacc gggatgcttg     2760
aagatggaaa gaaatttgat tcctcccggg acagaaacaa gccctttaag tttatgctag     2820
gcaagcagga ggtgatccga ggctgggaag aaggggttgc ccagatgagt gtgggtcaga     2880
gagccaaact gactatatct ccagattatg cctatggtgc cactgggcac ccaggcatca     2940
tcccaccaca tgccactctc gtcttcgatg tggagcttct aaaactggaa gctagcgcca     3000
agcctaccac cacccctgcc cctagacctc aacacccgc cccaacaatc gccagccagc     3060
```

-continued

```
ctctgtctct gaggcccgag gcttgtagac cagctgctgg cggagccgtg cacaccagag    3120
gactggattt cgcctgcgac atctacatct gggcccctct ggccggcaca tgtggcgtgc    3180
tgctgctgag cctcgtgatc accatgcata acggggcag aaagaaactc ctgtatatat     3240
tcaaacaacc atttatgaga ccagtacaaa ctactcaaga ggaagatggc tgtagctgcc    3300
gatttccaga agaagaagaa ggaggatgtg aactgcgggt gaagttcagc agaagcgccg    3360
acgcccctgc ctaccagcag ggccagaatc agctgtacaa cgagctgaac ctgggcagaa    3420
gggaagagta cgacgtcctg ataagcgga gaggccggga ccctgagatg gcggcaagc     3480
ctcggcggaa gaaccccag gaaggcctgt ataacgaact gcagaaagac aagatggccg    3540
aggcctacag cgagatcggc atgaagggcg agcggaggcg gggcaagggc cacgacggcc    3600
tgtatcaggg cctgtccacc gccaccaagg atacctacga cgccctgcac atgcaggccc    3660
tgcccccaag gggcggccgc tccggtgagg gcagaggaag tcttctaaca tgcggtgacg    3720
tggaggagaa tccgggcccc tctagaagcg agctgattaa ggagaacatg cacatgaagc    3780
tgtacatgga gggcaccgtg gacaaccatc acttcaagtg cacatccgag ggcgaaggca    3840
agccctacga gggcacccag accatgagaa tcaaggtggt cgagggcggc cctctcccct    3900
tcgccttcga catcctggct actagcttcc tctacgcag caagaccttc atcaaccaca    3960
cccagggcat ccccgacttc ttcaagcagt ccttccctga gggcttcaca tgggagagag    4020
tcaccacata cgaagacggg ggcgtgctga ccgctaccca ggacaccagc tccaggacg    4080
gctgcctcat ctacaacgtc aagatcagag gggtgaactt cacatccaac ggccctgtga    4140
tgcagaagaa aacactcggc tgggaggcct tcaccgagac gctgtacccc gctgacggcg    4200
gcctggaagg cagaaacgac atggccctga agctcgtggg cgggagccat ctgatcgcaa    4260
acatcaagac cacatataga tccaagaaac ccgctaagaa cctcaagatg cctggcgtct    4320
actatgtgga ctacagactg gaaagaatca aggaggccaa caacgagacc tacgtcgagc    4380
agcacgaggt ggcagtggcc agatactgcg acctccctag caaactgggg cacaagctta    4440
attgagtcga ccgagcatct taccgccatt tatacccata tttgttctgt ttttcttgat    4500
ttgggtatac atttaaatgt taatagaaca aaatggtggg gcaatcattt acatttttag    4560
ggatatgtaa ttactagttc aggtgtattg ccacaagaca aacatgttaa gaaactttcc    4620
cgttatttac gctctgttcc tgttaatcaa cctctggatt acaaaatttg tgaaagattg    4680
actgatattc ttaactatgt tgctcctttt acgctgtgtg gatatgctgc tttatagcct    4740
ctgtatctag ctattgcttc ccgtacggct ttcgttttct cctccttgta taaatcctgg    4800
ttgctgtctc tttttagagga gttgtggccc gttgtccgtc aacgtggcgt ggtgtgctct    4860
gtgtttgctg acgcaacccc cactggctgg ggcattgcca ccacctgtca actccttttct   4920
gggactttcg ctttcccct cccgatcgcc acggcagaac tcatcgccgc ctgccttgcc    4980
cgctgctgga caggggctag gttgctgggc actgataatt ccgtggtgtt gtcatcgaat    5040
tcggtacctt tttaaaagaa aaggggggac tggaagggct aattcactcc caacgaagac    5100
aagatatcat aacttcgtat agcatacatt atacgaagtt ataatttatt tgtgaaattt    5160
gtgatgctat tgctttattt gtaaccatat gtttatttgt gaaatttgtg atgctattgc    5220
tttatttgta accattgctt tttgcttgta ctgggtctct ctggttagac cagatctgag    5280
cctgggagct ctctggctaa ctagggaacc cactgcttaa gcctcaataa agcttgcctc    5340
gaccagcctc gactgtgcct tctagttgcc agccatctgt tgtttgcccc tccccgtgc     5400
cttccttgac cctggaaggt gccactccca ctgtcctttc ctaataaaat gaggaaattg    5460
```

```
catcgcattg tctgagtagg tgtcattcta ttctgggggg tggggtgggg caggacagca    5520
aggggaggga ttgggaagac aatagcaggc atgctgggga tgcggtgggc tctatggcct    5580
gcagctgcat taatgaatcg gccaacgcgc ggggagaggc ggtttgcgta ttgggcgctc    5640
ttccgcttcc tcgctcactg actcgctgcg ctcggtcgtt cggctgcggc gagcggtatc    5700
agctcactca aaggcggtaa tacggttatc cacagaatca ggggataacg caggaaagaa    5760
catgtgagca aaaggccagc aaaaggccag gaaccgtaaa aaggccgcgt tgctggcgtt    5820
tttccatagg ctccgccccc ctgacgagca tcacaaaaat cgacgctcaa gtcagaggtg    5880
gcgaaacccg acaggactat aaagatacca ggcgtttccc cctggaagct ccctcgtgcg    5940
ctctcctgtt ccgaccctgc cgcttaccgg atacctgtcc gcctttctcc cttcgggaag    6000
cgtggcgctt tctcatagct cacgctgtag gtatctcagt tcggtgtagg tcgttcgctc    6060
caagctgggc tgtgtgcacg aaccccccgt tcagcccgac cgctgcgcct tatccggtaa    6120
ctatcgtctt gagtccaacc cggtaagaca cgacttatcg ccactggcag cagccactgg    6180
taacaggatt agcagagcga ggtatgtagg cggtgctaca gagttcttga agtggtggcc    6240
taactacggc tacactagaa ggacagtatt tggtatctgc gctctgctga gccagttac    6300 cttcggaaaa agagttggta gctcttgatc cggcaaacaa accaccgctg gtagcggtgg    6360
tttttttgtt tgcaagcagc agattacgcg cagaaaaaaa ggatctcaag aagatccttt    6420
gatcttttct acggggtctg acgctcagtg gaacgaaaac tcacgttaag ggattttggt    6480
catgagatta tcaaaaagga tcttcaccta gatccttta aattaaaaat gaagttttaa    6540
atcaatctaa agtatatatg agtaaacttg gtctgacagt taccaatgct taatcagtga    6600
ggcacctatc tcagcgatct gtctatttcg ttcatccata gttgcctgac tccccgtcgt    6660
gtagataact acgatacggg agggcttacc atctggcccc agtgctgcaa tgataccgcg    6720
agacccacgc tcaccggctc cagatttatc agcaataaac cagccagccg gaagggccga    6780
gcgcagaagt ggtcctgcaa ctttatccgc ctccatccag tctattaatt gttgccggga    6840
agctagagta gtagttcgc cagttaatag tttgcgcaac gttgttgcca ttgctacagg    6900
catcgtggtg tcacgctcgt cgtttggtat ggcttcattc agctccggtt cccaacgatc    6960
aaggcgagtt acatgatccc ccatgttgtg caaaaaagcg gttagctcct tcggtcctcc    7020
gatcgttgtc agaagtaagt tggccgcagt gttatcactc atggttatgg cagcactgca    7080
taattctctt actgtcatgc catccgtaag atgcttttct gtgactggtg agtactcaac    7140
caagtcattc tgagaatagt gtatgcggcg accgagttgc tcttgcccgg cgtcaatacg    7200
ggataatacc gcgccacata gcagaacttt aaaagtgctc atcattggaa aacgttcttc    7260
ggggcgaaaa ctctcaagga tcttaccgct gttgagatcc agttcgatgt aacccactcg    7320
tgcacccaac tgatcttcag catcttttac tttcaccagc gtttctgggt gagcaaaaac    7380
aggaaggcaa aatgccgcaa aaaagggaat aagggcgaca cggaaatgtt gaatactcat    7440
actcttcctt tttcaatatt attgaagcat ttatcagggt tattgtctca tgagcggata    7500
catatttgaa tgtatttag                                                 7519

<210> SEQ ID NO 35
<211> LENGTH: 7672
<212> TYPE: DNA
<213> ORGANISM: Artificial Sequence
<220> FEATURE:
<223> OTHER INFORMATION: pCVL_sEF1a_CD19-Puro lentiviral vector
```

<400> SEQUENCE: 35

```
aaaaataaac aaatagggt tccgcgcaca tttccccgaa aagtgccacc tgacgtcaat      60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg gcgcccgaac     480
agggacttga aagcgaaagg gaaccagag gagctctctc gacgcaggac tcggcttgct     540
gaagcgcgca cggcaagagg cgaggggcgg cgactggtga gtacgccaaa aattttgact     600
agcggaggct agaaggagag atgggtgc gagagcgtca gtattaagcg gggagaatt       660
agatcgcgat gggaaaaaat tcggttaagg ccaggggaa agaaaaata taattaaaa        720
catatagtat gggcaagcag ggagctagaa cgattcgcag ttaatcctgg cctgttagaa     780
acatcagaag gctgtagaca aatactggga cagctacaac catcccttca gacaggatca     840
gaagaactta gatcattata taatacagta gcaaccctct attgtgtgca tcaaaggata     900
gagataaaag acaccaagga agctttagac aagatagagg aagagcaaaa caaaagtaag     960
accaccgcac agcaagcggc cctgatcttc agacctggag gaggagatat gagggacaat    1020
tggagaagtg aattatataa atataaagta gtaaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca gacaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taatgaatct    1440
ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcagggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaagaa aagggggat tgggggtac agtgcagggg aaagaatagt agacataata     1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcgggtaa     2100
actgggaaag tgatgtcgtg tactggctcc gcctttttcc cgagggtggg ggagaaccgt    2160
atataagtgc agtagtcgcc gtgaacgttc ttttcgcaa cgggtttgcc gccagaacac    2220
acctgcaggg ccgccaccat gccacctcct cgcctcctct tcttcctcct cttcctcacc    2280
cccatggaag tcaggcccga ggaacctcta gtggtgaagg tggaagaggg agataacgct    2340
```

```
gtgctgcagt gcctcaaggg gacctcagat ggccccactc agcagctgac ctggtctcgg    2400
gagtccccgc ttaaaccctt cttaaaactc agcctgggat tacctgggtt aggcatccac    2460
atgaggcccc tggccatctg gcttttcatc ttcaacgtct ctcaacagat gggaggcttc    2520
tacctgtgcc agccgggcc tccctctgag aaggcctggc agcctggctg acagtcaat     2580 gtggagggca gcggggagct gttccggtgg aatgtttcgg acctaggtgg cctgggctgt    2640
ggcctgaaga acaggtcctc agagggcccc agctcccctt ccgggaagct catgagcccc    2700
aagctgtatg tgtgggccaa agaccgccct gagatctggg agggagagcc tccgtgtctc    2760
ccaccgaggg acagcctgaa ccagagcctc agccaggacc tcaccatggc ccctggctcc    2820
acactctggc tgtcctgtgg ggtaccccct gactctgtgt ccaggggccc cctctcctgg    2880
acccatgtgc accccaaggg gcctaagtca ttgctgagcc tagagctgaa ggacgatcgc    2940
ccggccagag atatgtgggt aatggagacg ggtctgttgt tgccccgggc cacagctcaa    3000
gacgctggaa agtattattg tcaccgtggc aacctgacca tgtcattcca cctggagatc    3060
actgctcggc cagtactatg gcactggctg ctgaggactg gtggctggaa ggtctcagct    3120
gtgactttgg cttatctgat cttctgcctg tgttcccttg tgggcattct tcatcttcaa    3180
agagccctgg tcctgaggag gaagaggaag cgtatgactg accccaccag gagattttc    3240 aaagtgacgc ctcccccagg aagcgggccc cagaaccagt acgggaacgt gctgtctctc    3300
cccacaccca cctcaggcct cggacgcgcc cagcgttggg ccgcaggcct gggaggcact    3360
gccccgtctt atggaaaccc gagcagcgac gtccaggcgg atggagcctt ggggtcccgg    3420
agcccgccgg gagtgggccc agaagaagag gaaggggagg gctacgagga acctgacagt    3480
gaggaggact ccgagttcta tgagaacgac tccaaccttg gcaggacca gctctcccag     3540 gatggcagcg gctacgagaa ccctgaggat gagccctgg gtcctgagga cgaggactcc    3600
ttctccaacg ctgagagcta tgaaaatgaa gatgaggagc tcacacaacc cgtcgccagg    3660
acaatggact tcctgagccc tcatgggtca gcatgggatc cgagccggga agcaacctcc    3720
ctggcagggt cccagtccta tgaggatatg agaggaatcc tgtatgcagc ccctcagctc    3780
cgctccattc ggggccagcc tggacccaat catgaggaag atgcagactc ttatgagaac    3840
atggataatc ccgatgggcc agacccagcc tggggaggag ggggccgcat gggcacctgg    3900
agcactcgcg gcgccgcctc cggtgagggc agaggaagtc ttctaacatg cggtgacgtg    3960
gaggagaatc cgggcccctc tagaaccgag tacaagccca cggtgcgcct cgccacccgc    4020
gacgacgtcc ccggggccgt acgcaccctc gccgccgcgt tcgccgacta ccccgccacg    4080
cgccacaccg tcgatcccga ccgccacatc gagcgggtca ccgagctgca agaactcttc    4140
ctcacgcgcg tcgggctcga catcggcaag gtgtgggtcg gcgacgacgg cgccgcggtg    4200
gcggtctgga ccacgccgga gagcgtcgaa gcggggcgg tgttcgccga tcggcccg     4260 cgcatggccg agttgagcgg ttcccggctg gccgcgcagc aacagatgga aggcctcctg    4320
gcgccgcacc ggcccaagga gccgcgtgg ttcctggcca ccgtcggcgt ctcgcccgac    4380
caccagggca agggtctggg cagcgccgtc gtgctcccg gagtggaggc ggccgagcgc    4440
gccggggtgc ccgccttcct ggagacctcc gcgcccgca acctccccct ctacgagcgg    4500
ctcggcttca ccgtcaccgc cgacgtcgag gtgcccgaag accgcgcac ctggtgcatg    4560 acccgcaagc ccggtgccct cgagtgatga gagtcatcgt cgaccgagca tcttaccgcc    4620
atttataccc atatttgttc tgttttcctt gatttgggta tacatttaaa tgttaataga    4680
```

```
acaaaatggt ggggcaatca tttacatttt tagggatatg taattactag ttcaggtgta    4740
ttgccacaag acaaacatgt taagaaactt tcccgttatt tacgctctgt tcctgttaat    4800
caacctctgg attacaaaat ttgtgaaaga ttgactgata ttcttaacta tgttgctcct    4860
tttacgctgt gtggatatgc tgctttatag cctctgtatc tagctattgc ttcccgtacg    4920
gctttcgttt tctcctcctt gtataaatcc tggttgctgt ctcttttaga ggagttgtgg    4980
cccgttgtcc gtcaacgtgg cgtggtgtgc tctgtgtttg ctgacgcaac ccccactggc    5040
tggggcattg ccaccacctg tcaactcctt tctgggactt tcgctttccc cctcccgatc    5100
gccacggcag aactcatcgc cgcctgcctt gcccgctgct ggacagggc taggttgctg    5160 ggcactgata attccgtggt gttgtcatcg aattcggtac cttttaaaa gaaaaggggg    5220 gactggaagg gctaattcac tcccaacgaa gacaagatat cataacttcg tatagcatac    5280
attatacgaa gttataattt atttgtgaaa tttgtgatgc tattgcttta tttgtaacca    5340 tatgttatt tgtgaaattt gtgatgctat tgctttattt gtaaccattg ctttttgctt    5400
gtactgggtc tctctggtta gaccagatct gagcctggga gctctctggc taactaggga    5460
acccactgct taagcctcaa taaagcttgc ctcgaccagc ctcgactgtg ccttctagtt    5520
gccagccatc tgttgtttgc ccctcccccg tgccttcctt gaccctggaa ggtgccactc    5580
ccactgtcct ttcctaataa aatgaggaaa ttgcatcgca ttgtctgagt aggtgtcatt    5640
ctattctggg gggtggggtg gggcaggaca gcaaggggga ggattgggaa gacaatagca    5700
ggcatgctgg ggatgcggtg ggctctatgg cctgcagctg cattaatgaa tcggccaacg    5760
cgcggggaga ggcggtttgc gtattgggcg ctcttccgct tcctcgctca ctgactcgct    5820
gcgctcggtc gttcggctgc ggcgagcggt atcagctcac tcaaaggcgg taatacggtt    5880
atccacagaa tcaggggata acgcaggaaa gaacatgtga gcaaaaggcc agcaaaaggc    5940
caggaaccgt aaaaaggccg cgttgctggc gtttttccat aggctccgcc ccctgacga    6000 gcatcacaaa aatcgacgct caagtcagag gtggcgaaac ccgacaggac tataaagata    6060
ccaggcgttt ccccctggaa gctccctcgt gcgctctcct gttccgaccc tgccgcttac    6120
cggatacctg tccgcctttc tcccttcggg aagcgtggcg ctttctcata gctcacgctg    6180
taggtatctc agttcggtgt aggtcgttcg ctccaagctg ggctgtgtgc acgaaccccc    6240
cgttcagccc gaccgctgcg ccttatccgg taactatcgt cttgagtcca acccggtaag    6300
acacgactta tcgccactgg cagcagccac tggtaacagg attagcagag cgaggtatgt    6360
aggcggtgct acagagttct tgaagtggtg gcctaactac ggctacacta aggacagt    6420 atttggtatc tgcgctctgc tgaagccagt taccttcgga aaaagagttg gtagctcttg    6480
atccggcaaa caaaccaccg ctggtagcgg tggttttttt gtttgcaagc agcagattac    6540
gcgcagaaaa aaaggatctc aagaagatcc tttgatcttt tctacggggt ctgacgctca    6600
gtggaacgaa aactcacgtt aagggatttt ggtcatgaga ttatcaaaaa ggatcttcac    6660
ctagatcctt ttaaattaaa aatgaagttt taaatcaatc taaagtatat atgagtaaac    6720
ttggtctgac agttaccaat gcttaatcag tgaggcacct atctcagcga tctgtctatt    6780
tcgttcatcc atagttgcct gactccccgt cgtgtagata actacgatac gggagggctt    6840
accatctggc cccagtgctg caatgatacc gcgagaccca cgctcaccgg ctccagattt    6900
atcagcaata aaccagccag ccggaagggc cgagcgcaga agtggtcctg caactttatc    6960
cgcctccatc cagtctatta attgttgccg ggaagctaga gtaagtagtt cgccagttaa    7020
tagtttgcgc aacgttgttg ccattgctac aggcatcgtg gtgtcacgct cgtcgtttgg    7080
```

```
tatggcttca ttcagctccg gttcccaacg atcaaggcga gttacatgat cccccatgtt    7140
gtgcaaaaaa gcggttagct ccttcggtcc tccgatcgtt gtcagaagta agttggccgc    7200
agtgttatca ctcatggtta tggcagcact gcataattct cttactgtca tgccatccgt    7260
aagatgcttt tctgtgactg gtgagtactc aaccaagtca ttctgagaat agtgtatgcg    7320
gcgaccgagt tgctcttgcc cggcgtcaat acgggataat accgcgccac atagcagaac    7380
tttaaaagtg ctcatcattg gaaaacgttc ttcgggggcga aaactctcaa ggatcttacc    7440
gctgttgaga tccagttcga tgtaacccac tcgtgcaccc aactgatctt cagcatcttt    7500
tactttcacc agcgtttctg ggtgagcaaa acaggaagg caaaatgccg caaaaaaggg    7560
aataagggcg acacggaaat gttgaatact catactcttc ctttttcaat attattgaag    7620
catttatcag ggttattgtc tcatgagcgg atacatattt gaatgtattt ag            7672
```

<210> SEQ ID NO 36
<211> LENGTH: 6892
<212> TYPE: DNA
<213> ORGANISM: Artificial Sequence
<220> FEATURE:
<223> OTHER INFORMATION: pCVL_sEF1a_CD20-Puro lentiviral vector

<400> SEQUENCE: 36

```
aaaaataaac aaatagggt tccgcgcaca tttccccgaa aagtgccacc tgacgtcaat      60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga agcgaaagg gaaaccagag gagctctctc gacgcaggac tcggcttgct    540
gaagcgcgca cggcaagagg cgaggggcgg cgactggtga gtacgccaaa aattttgact    600
agcggaggct agaaggagag agatgggtgc gagagcgtca gtattaagcg ggggagaatt    660
agatcgcgat gggaaaaaat tcggttaagg ccagggggaa agaaaaaata taaattaaaa    720
catatagtat gggcaagcag ggagctagaa cgattcgcag ttaatcctgg cctgttagaa    780
acatcagaag gctgtagaca atactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat    1020
tggagaagtg aattatataa atataaagta gtaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca acaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taatgaatct    1440
```

```
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aaggggggat tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggaggggtc ggcaattgaa ccggtgccta gagaaggtgg cgcggggtaa   2100
actgggaaag tgatgtcgtg tactggctcc gccttttttcc cgagggtggg ggagaaccgt   2160
atataagtgc agtagtcgcc gtgaacgttc ttttttcgcaa cgggtttgcc gccagaacac   2220
acctgcaggg ccgccaccat gacaacaccc agaaattcag taaatgggac tttcccggca   2280
gagccaatga aaggccctat tgctatgcaa tctggtccaa aaccactctt caggaggatg   2340
tcttcactgg tgggccccac gcaaagcttc ttcatgaggg aatctaagac tttgggggct   2400
gtccagatta tgaatgggct cttccacatt gccctgggag gtcttctgat gatcccagca   2460
gggatctatg cacccatctg tgtgactgtg tggtaccctc tctggggagg cattatgtat   2520
attatttccg gatcactcct ggcagcaacg gagaaaaact ccaggaagtg tttggtcaaa   2580
ggaaaaatga taatgaattc attgagcctc tttgctgcca tttctggaat gattcttttca   2640 atcatggaca tacttaatat taaaatttcc cattttttaa aaatgagag tctgaatttt   2700 attagagctc acacaccata tattaacata taaactgtg aaccagctaa tccctctgag   2760
aaaaactccc catctaccca atactgttac agcatacaat ctctgttctt gggcattttg   2820
tcagtgatgc tgatctttgc cttcttccag gaacttgtaa tagctggcat cgttgagaat   2880
gaatggaaaa gaacgtgctc cagacccaaa tctaacatag ttctcctgtc agcagaagaa   2940
aaaaaagaac agactattga aataaaagaa gaagtggttg ggctaactga aacatcttcc   3000
caaccaaaga atgaagaaga cattgaaatt attccaatcc aagaagagga agaagaagaa   3060
acagagacga acttttccaga acctccccaa gatcaggaat cctcaccaat agaaaatgac   3120
agctctcctg gcgccgcgctc cggtgagggc agaggaagtc ttctaacatg cggtgacgtg   3180
gaggagaatc cgggcccctc tagaaccgag tacaagccca cggtgcgcct cgccacccgc   3240
gacgacgtcc cccgggccgt acgcaccctc gccgccgcgt tcgccgacta ccccgccacg   3300
cgccacaccg tcgatcccga ccgccacatc gagcgggtca ccgagctgca agaactcttc   3360
ctcacgcgcg tcgggctcga catcggcaag gtgtgggtcg cggacgacgg cgccgcggtg   3420
gcggtctgga ccacgccgga gagcgtcgaa gcggggcgg tgttcgccga tcggcccg   3480 cgcatggccg agttgagcgg ttccggctg gccgcgcagc aacagatgga aggcctcctg   3540
gcgccgcacc ggcccaagga gcccgcgtgg ttcctggcca ccgtcggcgt ctcgcccgac   3600
caccagggca agggtctggg cagcgccgtc gtgctccccg agtggaggc ggccgagcgc   3660 gccgggtgc ccgccttcct ggagacctcc gcgcccgcca acctcccctt ctacgagcgg   3720
ctcggcttca ccgtcaccgc cgacgtcgag gtgcccgaag accgcgcac ctggtgcatg   3780 acccgcaagc ccggtgccct cgagtgatga gagtcatcgt cgaccgagca tcttaccgcc   3840
```

```
atttataccc atatttgttc tgtttttctt gatttgggta tacatttaaa tgttaataga    3900
acaaaatggt ggggcaatca tttacatttt tagggatatg taattactag ttcaggtgta    3960
ttgccacaag acaaacatgt taagaaactt tcccgttatt tacgctctgt tcctgttaat    4020
caacctctgg attacaaaat tgtgaaaga ttgactgata ttcttaacta tgttgctcct    4080
tttacgctgt gtggatatgc tgctttatag cctctgtatc tagctattgc ttcccgtacg    4140
gctttcgttt tctcctcctt gtataaatcc tggttgctgt ctcttttaga ggagttgtgg    4200
cccgttgtcc gtcaacgtgg cgtggtgtgc tctgtgtttg ctgacgcaac ccccactggc    4260
tggggcattg ccaccacctg tcaactcctt tctgggactt tcgctttccc cctcccgatc    4320
gccacggcag aactcatcgc cgcctgcctt gcccgctgct ggacaggggc taggttgctg    4380
ggcactgata attccgtggt gttgtcatcg aattcggtac cttttaaaa gaaaagggggg    4440
gactggaagg gctaattcac tcccaacgaa gacaagatat cataacttcg tatagcatac    4500
attatacgaa gttataattt atttgtgaaa tttgtgatgc tattgcttta tttgtaacca    4560
tatgtttatt tgtgaaattt gtgatgctat tgctttattt gtaaccattg cttttttgctt    4620
gtactgggtc tctctggtta gaccagatct gagcctggga gctctctggc taactaggga    4680
acccactgct taagcctcaa taaagcttgc ctcgaccagc ctcgactgtg ccttctagtt    4740
gccagccatc tgttgtttgc ccctccccg tgccttcctt gaccctggaa ggtgccactc    4800
ccactgtcct ttcctaataa aatgaggaaa ttgcatcgca ttgtctgagt aggtgtcatt    4860
ctattctggg gggtggggtg gggcaggaca gcaaggggga ggattgggaa gacaatagca    4920
ggcatgctgg ggatgcggtg ggctctatgg cctgcagctg cattaatgaa tcggccaacg    4980
cgcggggaga ggcggtttgc gtattgggcg ctcttccgct tcctcgctca ctgactcgct    5040
gcgctcggtc gttcggctgc ggcgagcggt atcagctcac tcaaaggcgg taatacggtt    5100
atccacagaa tcaggggata acgcaggaaa gaacatgtga gcaaaaggcc agcaaaaggc    5160
caggaaccgt aaaaaggccg cgttgctggc gtttttccat aggctccgcc cccctgacga    5220
gcatcacaaa aatcgacgct caagtcagag gtggcgaaac ccgacaggac tataaagata    5280
ccaggcgttt ccccctggaa gctccctcgt gcgctctcct gttccgaccc tgccgcttac    5340
cggatacctg tccgcctttc tcccttcggg aagcgtggcg ctttctcata gctcacgctg    5400
taggtatctc agttcggtgt aggtcgttcg ctccaagctg ggctgtgtgc acgaaccccc    5460
cgttcagccc gaccgctgcg ccttatccgg taactatcgt cttgagtcca acccggtaag    5520
acacgactta tcgccactgg cagcagccac tggtaacagg attagcagag cgaggtatgt    5580
aggcggtgct acagagttct tgaagtggtg gcctaactac ggctacacta aaggacagt     5640
atttggtatc tgcgctctgc tgaagccagt taccttcgga aaaagagttg gtagctcttg    5700
atccggcaaa caaaccaccg ctggtagcgg tggtttttt gtttgcaagc agcagattac    5760
gcgcagaaaa aaggatctc aagaagatcc tttgatcttt tctacggggt ctgacgctca    5820
gtggaacgaa aactcacgtt aagggatttt ggtcatgaga ttatcaaaaa ggatcttcac    5880
ctagatcctt ttaaattaaa aatgaagttt taaatcaatc taagtatat atgagtaaac     5940
ttggtctgac agttaccaat gcttaatcag tgaggcacct atctcagcga tctgtctatt    6000
tcgttcatcc atagttgcct gactccccgt cgtgtagata actacgatac gggagggctt    6060
accatctggc cccagtgctg caatgatacc gcgagaccca cgctcaccgg ctccagattt    6120
atcagcaata aaccagccag ccggaagggc cgagcgcaga agtggtcctg caactttatc    6180
```

-continued

```
cgcctccatc cagtctatta attgttgccg ggaagctaga gtaagtagtt cgccagttaa    6240
tagtttgcgc aacgttgttg ccattgctac aggcatcgtg gtgtcacgct cgtcgtttgg    6300
tatggcttca ttcagctccg gttcccaacg atcaaggcga gttacatgat cccccatgtt    6360
gtgcaaaaaa gcggttagct ccttcggtcc tccgatcgtt gtcagaagta agttggccgc    6420
agtgttatca ctcatggtta tggcagcact gcataattct cttactgtca tgccatccgt    6480
aagatgcttt tctgtgactg gtgagtactc aaccaagtca ttctgagaat agtgtatgcg    6540
gcgaccgagt tgctcttgcc cggcgtcaat acgggataat accgcgccac atagcagaac    6600
tttaaaagtg ctcatcattg gaaaacgttc ttcggggcga aaactctcaa ggatcttacc    6660
gctgttgaga tccagttcga tgtaacccac tcgtgcaccc aactgatctt cagcatcttt    6720
tactttcacc agcgtttctg ggtgagcaaa aacaggaagg caaaatgccg caaaaaaggg    6780
aataagggcg acacggaaat gttgaatact catactcttc cttttcaat attattgaag     6840 catttatcag ggttattgtc tcatgagcgg atacatattt gaatgtattt ag            6892
```

<210> SEQ ID NO 37
<211> LENGTH: 570
<212> TYPE: PRT
<213> ORGANISM: Artificial Sequence
<220> FEATURE:
<223> OTHER INFORMATION: SS-2xDmrB-DmrC-TM-41BB-CD3z protein

<400> SEQUENCE: 37

```
Met Ala Leu Pro Val Thr Ala Leu Leu Leu Pro Leu Ala Leu Leu Leu
1               5                   10                  15

His Ala Ala Arg Pro Gly Ser Gly Gly Val Gln Val Glu Thr Ile Ser
                20                  25                  30

Pro Gly Asp Gly Arg Thr Phe Pro Lys Arg Gly Gln Thr Cys Val Val
            35                  40                  45

His Tyr Thr Gly Met Leu Glu Asp Gly Lys Lys Val Asp Ser Ser Arg
        50                  55                  60

Asp Arg Asn Lys Pro Phe Lys Phe Met Leu Gly Lys Gln Glu Val Ile
65                  70                  75                  80

Arg Gly Trp Glu Glu Gly Val Ala Gln Met Ser Val Gly Gln Arg Ala
                85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Phe Leu
        115                 120                 125

Lys Leu Glu Ser Gly Thr Ser Gly Thr Ser Gly Val Gln Val Glu Thr
    130                 135                 140

Ile Ser Pro Gly Asp Gly Arg Thr Phe Pro Lys Arg Gly Gln Thr Cys
145                 150                 155                 160

Val Val His Tyr Thr Gly Met Leu Glu Asp Gly Lys Lys Val Asp Ser
                165                 170                 175

Ser Arg Asp Arg Asn Lys Pro Phe Lys Phe Met Leu Gly Lys Gln Glu
            180                 185                 190

Val Ile Arg Gly Trp Glu Glu Gly Val Ala Gln Met Ser Val Gly Gln
        195                 200                 205

Arg Ala Lys Leu Thr Ile Ser Pro Asp Tyr Ala Tyr Gly Ala Thr Gly
    210                 215                 220

His Pro Gly Ile Ile Pro Pro His Ala Thr Leu Val Phe Asp Val Glu
225                 230                 235                 240
```

Leu Leu Lys Leu Glu Gly Ser Arg Ser Ile Leu Trp His Glu Met Trp
            245                 250                 255
His Glu Gly Leu Glu Glu Ala Ser Arg Leu Tyr Phe Gly Glu Arg Asn
        260                 265                 270
Val Lys Gly Met Phe Glu Val Leu Glu Pro Leu His Ala Met Met Glu
    275                 280                 285
Arg Gly Pro Gln Thr Leu Lys Glu Thr Ser Phe Asn Gln Ala Tyr Gly
290                 295                 300
Arg Asp Leu Met Glu Ala Gln Glu Trp Cys Arg Lys Tyr Met Lys Ser
305                 310                 315                 320
Gly Asn Val Lys Asp Leu Leu Gln Ala Trp Asp Leu Tyr Tyr His Val
                325                 330                 335
Phe Arg Arg Ile Ser Lys Ala Ser Ala Lys Pro Thr Thr Thr Pro Ala
                340                 345                 350
Pro Arg Pro Pro Thr Pro Ala Pro Thr Ile Ala Ser Gln Pro Leu Ser
            355                 360                 365
Leu Arg Pro Glu Ala Cys Arg Pro Ala Ala Gly Gly Ala Val His Thr
        370                 375                 380
Arg Gly Leu Asp Phe Ala Cys Asp Ile Tyr Ile Trp Ala Pro Leu Ala
385                 390                 395                 400
Gly Thr Cys Gly Val Leu Leu Leu Ser Leu Val Ile Thr Met His Lys
                405                 410                 415
Arg Gly Arg Lys Lys Leu Leu Tyr Ile Phe Lys Gln Pro Phe Met Arg
                420                 425                 430
Pro Val Gln Thr Thr Gln Glu Glu Asp Gly Cys Ser Cys Arg Phe Pro
            435                 440                 445
Glu Glu Glu Glu Gly Gly Cys Glu Leu Arg Val Lys Phe Ser Arg Ser
        450                 455                 460
Ala Asp Ala Pro Ala Tyr Gln Gln Gly Gln Asn Gln Leu Tyr Asn Glu
465                 470                 475                 480
Leu Asn Leu Gly Arg Arg Glu Glu Tyr Asp Val Leu Asp Lys Arg Arg
                485                 490                 495
Gly Arg Asp Pro Glu Met Gly Gly Lys Pro Arg Arg Lys Asn Pro Gln
            500                 505                 510
Glu Gly Leu Tyr Asn Glu Leu Gln Lys Asp Lys Met Ala Glu Ala Tyr
        515                 520                 525
Ser Glu Ile Gly Met Lys Gly Glu Arg Arg Arg Gly Lys Gly His Asp
530                 535                 540
Gly Leu Tyr Gln Gly Leu Ser Thr Ala Thr Lys Asp Thr Tyr Asp Ala
545                 550                 555                 560
Leu His Met Gln Ala Leu Pro Pro Arg Gly
                565                 570

<210> SEQ ID NO 38
<211> LENGTH: 1710
<212> TYPE: RNA
<213> ORGANISM: Artificial Sequence
<220> FEATURE:
<223> OTHER INFORMATION: SS-2xDmrB-DmrC-TM-41BB-CD3z mRNA

<400> SEQUENCE: 38
auggcucugc cugugacagc ucugcugcug ccucuggccc ugcugcucca ugccgccaga      60
cccggauccg gcggugucca agucgaaacu auaucgccug gcgauggcag aacguuuccc     120
aaacguggcc agaccugugu cguacacuau accggcaugc uagaggaugg gaaaaagguu     180

| | |
|---|---|
| gauuccaguc gcgaucggaa caaaccguuu aaauucaugu ggggaagca agagguuauc | 240 |
| aggggaugggg aagagggugu cgcgcaaaug ucgguugggc aacgugcgaa acucacaauu | 300 |
| uccccggauu acgcauacgg agcuaccgga cacccuggga uuaucccacc gcaugcgacg | 360 |
| cuaguguuug acguagaguu cuugaagcuc gaaucaggua caagcggcac uucuggcgua | 420 |
| cagguugaga caauuagucc cggagacgga cguacauucc caaagagagg gcaaacuugc | 480 |
| guaguccauu acacuggaau guuggaagac ggcaagaaag uggacaguuc aagagaccgc | 540 |
| aauaagccuu ucaaguuuau gcucggaaaa caggaaguca uacgcgguug ggaggaaggc | 600 |
| guggcucaga ugagcgucgg acagagggca aaguugacca ucaguccccga cuaugcguau | 660 |
| ggcgcgacag gccaucccgg aaucauaccu ccccacgcaa ccuugguauu cgaugucgaa | 720 |
| cugcucaaau uagagggguag uagauccauc cucuggcaug agauguggca ugaaggccug | 780 |
| gaagaggcau cucguuugua cuuugggaa aggaacguga aaggcauguu ugaggugcug | 840 |
| gagcccuugc augcuaugau ggaacggggc ccccagacuc ugaaggaaac auccuuuaau | 900 |
| caggccuaug gucgagauuu aauggaggcc caagaguggu gcaggaagua caugaaauca | 960 |
| gggaauguca aggaccuccu ccaagccugg gaccucuauu aucaugaguu ccgacgaauc | 1020 |
| ucaaaggcua gcgccaagcc uaccaccacc ccugcccccua gaccuccaac acccgccccca | 1080 |
| acaaucgcca gccagccucu gucucugagg cccgaggcuu guagaccagc ugcuggcgga | 1140 |
| gccguacaca ccagaggacu ggauuucgcc ugcgacaucu acaucugggc cccucuggcc | 1200 |
| ggcacaugug gcgugcugcu gcugagccuc gugaucacca ugcauaaacg gggcagaaag | 1260 |
| aaacuccugu auauauucaa acaaccauuu augagaccag acaaacuac ucaagaggaa | 1320 |
| gauggcugua gcugccgauu uccagaagaa gaagaaggag gaugugaacu gcggguugaag | 1380 |
| uucagcagaa gcgccgacgc cccugccuac cagcagggcc agaaucagcu guacaacgag | 1440 |
| cugaaccugg gcagaaggga gaguacgac gucccuggaua agcggagagg ccgggacccu | 1500 |
| gagaugggcg gcaagcccg gcggaagaac ccccaggaag ccuguauaa cgaacugcag | 1560 |
| aaagacaaga uggccgaggc cuacagcgag aucggcauga gggcgagcg gaggcggggc | 1620 |
| aagggccacg acggcugua ucagggccug uccaccgcca ccaaggauac cuacgacgcc | 1680 |
| cugcacaugc aggcccugcc cccaagggggc | 1710 |

<210> SEQ ID NO 39
<211> LENGTH: 1710
<212> TYPE: DNA
<213> ORGANISM: Artificial Sequence
<220> FEATURE:
<223> OTHER INFORMATION: SS-2xDmrB-DmrC-TM-41BB-CD3z DNA

<400> SEQUENCE: 39

| | |
|---|---|
| atggctctgc ctgtgacagc tctgctgctg cctctggccc tgctgctcca tgccgccaga | 60 |
| cccggatccg gcggtgtcca agtcgaaact atatcgcctg cgatggcag aacgtttccc | 120 |
| aaacgtggcc agacctgtgt cgtacactat accggcatgc tagaggatgg gaaaaaggtt | 180 |
| gattccagtc gcgatcggaa caaaccgttt aaattcatgt ggggaagca gaggttatc | 240 |
| aggggatggg aagagggtgt cgcgcaaatg tcggttgggc aacgtgcgaa actcacaatt | 300 |
| tccccggatt acgcatacgg agctaccgga caccctggga ttatcccacc gcatgcgacg | 360 |
| ctagtgtttg acgtagagtt cttgaagctc gaatcaggta caagcggcac ttctggcgta | 420 |
| caggttgaga caattagtcc cggagacgga cgtacattcc caaagagagg gcaaacttgc | 480 |
| gtagtccatt acactggaat gttggaagac ggcaagaaag tggacagttc aagagaccgc | 540 |

```
aataagcctt tcaagtttat gctcggaaaa caggaagtca tacgcggttg ggaggaaggc      600
gtggctcaga tgagcgtcgg acagagggca aagttgacca tcagtcccga ctatgcgtat      660
ggcgcgacag gccatcccgg aatcatacct ccccacgcaa ccttggtatt cgatgtcgaa      720
ctgctcaaat tagagggtag tagatccatc tctctggcatg agatgtggca tgaaggcctg     780
gaagaggcat ctcgtttgta ctttggggaa aggaacgtga aaggcatgtt gaggtgctg       840 gagcccttgc atgctatgat ggaacggggc ccccagactc tgaaggaaac atcctttaat     900
caggcctatg gtcgagattt aatggaggcc aagagtggt gcaggaagta catgaaatca      960
gggaatgtca aggacctcct ccaagcctgg gacctctatt atcatgtgtt ccgacgaatc    1020
tcaaaggcta gcgccaagcc taccaccacc cctgcccta gacctccaac acccgcccca     1080
acaatcgcca gccagcctct gtctctgagg cccgaggctt gtagaccagc tgctggcgga   1140
gccgtacaca ccagaggact ggatttcgcc tgcgacatct acatctgggc ccctctggcc     1200
ggcacatgtg gcgtgctgct gctgagcctc gtgatcacca tgcataaacg ggcagaaag    1260 aaactcctgt atatattcaa acaaccattt atgagaccag tacaaactac tcaagaggaa    1320
gatggctgta gctgccgatt tccagaagaa gaagaaggag gatgtgaact gcgggtgaag    1380
ttcagcagaa gcgccgacgc ccctgcctac cagcagggcc agaatcagct gtacaacgag     1440
ctgaacctgg gcagaaggga gagtacgac gtcctggata gcggagagg ccggacccct       1500 gagatgggcg gcaagcctcg gcggaagaac ccccaggaag gcctgtataa cgaactgcag    1560
aaagacaaga tggccgaggc ctacagcgag atcggcatga agggcgagcg gaggcggggc    1620
aagggccacg acggcctgta tcagggcctg tccaccgcca ccaaggatac ctacgacgcc    1680
ctgcacatgc aggccctgcc cccaaggggc                                      1710

<210> SEQ ID NO 40
<211> LENGTH: 7819
<212> TYPE: DNA
<213> ORGANISM: Artificial Sequence
<220> FEATURE:
<223> OTHER INFORMATION: pCVL_sEF1a_T7_2xDmrB-DmrC-TM-41BB-CD3z
      lentiviral vector

<400> SEQUENCE: 40
aaaaataaac aaatagggt tccgcgcaca tttccccgaa aagtgccacc tgacgtcaat        60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg cgcccgaac     480 agggacttga aagcgaaagg gaaaccagag gagctctctc gacgcaggac tcggcttgct    540
gaagcgcgca cggcaagagg cgaggggcgg cgactggtga gtacgccaaa aattttgact    600
agcggaggct agaaggagag gatgggtgc gagagcgtca gtattaagcg ggggagaatt    660
agatcgcgat gggaaaaaat tcggttaagg ccagggggaa agaaaaaata taaattaaaa    720
catatagtat gggcaagcag ggagctgaa cgattcgcag ttaatcctgg cctgttagaa    780
acatcagaag gctgtagaca atactggga cagctacaac catcccttca gacaggatca    840
```

```
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaagag cagtgggaat aggagctttg    1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag atacctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aaggggggat tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggaggggtc ggcaattgaa ccggtgccta gagaaggtgg cgcggggtaa   2100
actgggaaag tgatgtcgtg tactggctcc gccttttcc cgagggtggg ggagaaccgt    2160
atataagtgc agtagtcgcc gtgaacgttc tttttcgcaa cgggtttgcc gccagaacac   2220
acctgcaggt aatacgactc actataggg ccactgccgc caccatggct ctgcctgtga    2280
cagctctgct gctgcctctg gccctgctgc tccatgccgc cagacccgga tccggcggtg   2340
tccaagtcga aactatatcg cctggcgatg gcagaacgtt tcccaaacgt ggccagacct   2400
gtgtcgtaca ctataccggc atgctagagg atgggaaaaa ggttgattcc agtcgcgatc   2460
ggaacaaacc gtttaaattc atgttgggga agcaagaggt tatcagggga tgggaagagg   2520
gtgtcgcgca aatgtcggtt gggcaacgtg cgaaactcac aatttccccg gattacgcat   2580
acggagctac cggacaccct gggattatcc caccgcatgc gacgctagtg tttgacgtag   2640
agttcttgaa gctcgaatca ggtacaagcg gcacttctgg cgtacaggtt gagacaatta   2700
gtcccggaga cggacgtaca ttcccaaaga gagggcaaac ttgcgtagtc cattacactg   2760
gaatgttgga agacggcaag aaagtggaca gttcaagaga ccgcaataag cctttcaagt   2820
ttatgctcgg aaaacaggaa gtcatacgcg gttgggagga aggcgtggct cagatgagcg   2880
tcggacagag ggcaaagttg accatcagtc ccgactatgc gtatggcgcg acaggccatc   2940
ccggaatcat acctcccac gcaaccttgg tattcgatgt cgaactgctc aaattagagg     3000
gtagtagatc catcctctgg catgagatgt ggcatgaagg cctggaagag gcatctcgtt   3060
tgtactttgg ggaaaggaac gtgaaaggca tgtttgaggt gctggagccc ttgcatgcta   3120
tgatggaacg ggcccccag actctgaagg aaacatcctt taatcaggcc tatggtcgag    3180
```

```
atttaatgga ggcccaagag tggtgcagga agtacatgaa atcagggaat gtcaaggacc   3240
tcctccaagc ctgggacctc tattatcatg tgttccgacg aatctcaaag gctagcgcca   3300
agcctaccac cacccctgcc cctagacctc aacacccgc cccaacaatc gccagccagc    3360
ctctgtctct gaggcccgag gcttgtagac cagctgctgg cggagccgta cacaccagag   3420
gactggattt cgcctgcgac atctacatct gggcccctct ggccggcaca tgtggcgtgc   3480
tgctgctgag cctcgtgatc accatgcata acgggcag aaagaaactc ctgtatatat     3540
tcaaacaacc atttatgaga ccagtacaaa ctactcaaga ggaagatggc tgtagctgcc   3600
gatttccaga agaagaagaa ggaggatgtg aactgcgggt gaagttcagc agaagcgccg   3660
acgcccctgc ctaccagcag ggccagaatc agctgtacaa cgagctgaac ctgggcagaa   3720
gggaagagta cgacgtcctg ataagcggaa gaggccggga ccctgagatg ggcggcaagc   3780
ctcggcggaa gaacccccag gaaggcctgt ataacgaact gcagaaagac aagatggccg   3840
aggcctacag cgagatcggc atgaaggcg agcggaggcg gggcaagggc cacgacggcc    3900
tgtatcaggg cctgtccacc gccaccaagg atacctacga cgccctgcac atgcaggccc   3960 tgccccaag gggcggccgc tccggtgagg gcagaggaag tcttctaaca tgcggtgacg    4020
tggaggagaa tccgggcccc tctagaagcg agctgattaa ggagaacatg cacatgaagc   4080
tgtacatgga gggcaccgtg gacaaccatc acttcaagtg cacatccgag ggcgaaggca   4140
agccctacga gggcacccag accatgagaa tcaaggtggt cgagggcggc cctctcccct   4200
tcgccttcga catcctggct actagcttcc tctacggcag caagaccttc atcaaccaca   4260
cccagggcat ccccgacttc ttcaagcagt ccttccctga gggcttcaca tgggagagag   4320
tcaccacata cgaagacggg ggcgtgctga ccgctaccca ggacaccagc ctccaggacg   4380
gctgcctcat ctacaacgtc aagatcgag gggtgaactt cacatccaac ggccctgtga   4440
tgcagaagaa aacactcggc tgggaggcct tcaccgagac gctgtacccc gctgacggcg   4500
gcctggaagg cagaaacgac atgggccctga agctcgtggg cggagccat ctgatcgcaa    4560 acatcaagac cacatataga tccaagaaac ccgctaagaa cctcaagatg cctggcgtct   4620
actatgtgga ctacagactg gaaagaatca aggaggccaa caacgagacc tacgtcgagc   4680
agcacgaggt ggcagtggcc agatactgcg acctccctag caaactgggg cacaagctta   4740
attgagtcga ccgagcatct taccgccatt tatacccata tttgttctgt ttttcttgat   4800
ttgggtatac atttaaatgt taatagaaca aaatggtggg gcaatcattt acattttag    4860 ggatatgtaa ttactagttc aggtgtattg ccacaagaca aacatgttaa gaaactttcc   4920
cgttatttac gctctgttcc tgttaatcaa cctctggatt acaaaatttg tgaaagattg   4980
actgatattc ttaactatgt tgctcctttt acgctgtgtg gatatgctgc tttatagcct   5040
ctgtatctag ctattgcttc ccgtacggct ttcgttttct cctccttgta taaatcctgg   5100
ttgctgtctc ttttagagga gttgtggccc gttgtccgtc aacgtggcgt ggtgtgctct   5160
gtgtttgctg acgcaacccc cactggctgg ggcattgcca ccacctgtca actcctttct   5220
gggactttcg cttcccccct cccgatcgcc acggcagaac tcatcgccgc ctgccttgcc   5280
cgctgctgga caggggctag gttgctgggc actgataatt ccgtggtgtt gtcatcgaat   5340
tcggtacctt tttaaaagaa aagggggggac tggaagggct aattcactcc caacgaagac   5400
aagatatcat aacttcgtat agcatacatt atacgaagtt ataatttatt tgtgaaattt   5460
gtgatgctat tgctttattt gtaaccatat gtttatttgt gaaatttgtg atgctattgc   5520
tttatttgta accattgctt tttgcttgta ctgggtctct ctggttagac cagatctgag   5580
```

```
cctgggagct ctctggctaa ctagggaacc cactgcttaa gcctcaataa agcttgcctc    5640
gaccagcctc gactgtgcct tctagttgcc agccatctgt tgtttgcccc tccccgtgc     5700 cttccttgac cctggaaggt gccactccca ctgtcctttc ctaataaaat gaggaaattg    5760
catcgcattg tctgagtagg tgtcattcta ttctgggggg tggggtgggg caggacagca    5820 aggggagga ttgggaagac aatagcaggc atgctggga tgcggtgggc tctatggcct      5880
gcagctgcat taatgaatcg gccaacgcgc ggggagaggc ggtttgcgta ttgggcgctc    5940
ttccgcttcc tcgctcactg actcgctgcg ctcggtcgtt cggctgcggc gagcggtatc    6000
agctcactca aaggcggtaa tacggttatc cacagaatca ggggataacg caggaaagaa    6060
catgtgagca aaaggccagc aaaaggccag gaaccgtaaa aaggccgcgt tgctggcgtt    6120
tttccatagg ctccgccccc ctgacgagca tcacaaaaat cgacgctcaa gtcagaggtg    6180
gcgaaacccg acaggactat aaagatacca ggcgtttccc cctggaagct ccctcgtgcg    6240
ctctcctgtt ccgaccctgc cgcttaccgg atacctgtcc gcctttctcc cttcgggaag    6300
cgtggcgctt tctcatagct cacgctgtag gtatctcagt tcggtgtagg tcgttcgctc    6360
caagctgggc tgtgtgcacg aaccccccgt tcagcccgac cgctgcgcct tatccggtaa    6420
ctatcgtctt gagtccaacc cggtaagaca cgacttatcg ccactggcag cagccactgg    6480
taacaggatt agcagagcga ggtatgtagg cggtgctaca gagttcttga agtggtggcc    6540
taactacggc tacactagaa ggacagtatt tggtatctgc gctctgctga gccagttac     6600 cttcggaaaa agagttggta gctcttgatc cggcaaacaa accaccgctg gtagcggtgg    6660
tttttttgtt tgcaagcagc agattacgcg cagaaaaaaa ggatctcaag aagatccttt    6720
gatcttttct acggggtctg acgctcagtg gaacgaaaac tcacgttaag ggattttggt    6780
catgagatta tcaaaaagga tcttcaccta gatccttta aattaaaaat gaagttttaa     6840
atcaatctaa agtatatatg agtaaacttg gtctgacagt taccaatgct taatcagtga    6900
ggcacctatc tcagcgatct gtctatttcg ttcatccata gttgcctgac tccccgtcgt    6960
gtagataact acgatacggg agggcttacc atctggcccc agtgctgcaa tgataccgcg    7020
agacccacgc tcaccggctc cagatttatc agcaataaac cagccagccg gaagggccga    7080
gcgcagaagt ggtcctgcaa ctttatccgc ctccatccag tctattaatt gttgccggga    7140
agctagagta agtagttcgc cagttaatag tttgcgcaac gttgttgcca ttgctacagg    7200
catcgtggtg tcacgctcgt cgtttggtat ggcttcattc agctccggtt cccaacgatc    7260
aaggcgagtt acatgatccc ccatgttgtg caaaaaagcg gttagctcct tcggtcctcc    7320
gatcgttgtc agaagtaagt tggccgcagt gttatcactc atggttatgg cagcactgca    7380
taattctctt actgtcatgc catccgtaag atgcttttct gtgactggtg agtactcaac    7440
caagtcattc tgagaatagt gtatgcggcg accgagttgc tcttgcccgg cgtcaatacg    7500
ggataatacc gcgccacata gcagaacttt aaaagtgctc atcattggaa aacgttcttc    7560
ggggcgaaaa ctctcaagga tcttaccgct gttgagatcc agttcgatgt aacccactcg    7620
tgcacccaac tgatcttcag catctttta tttcaccagc gtttctgggt gagcaaaaac    7680
aggaaggcaa aatgccgcaa aaaagggaat aagggcgaca cggaaatgtt gaatactcat    7740
actcttcctt tttcaatatt attgaagcat ttatcagggt tattgtctca tgagcggata    7800
catatttgaa tgtatttag                                                 7819
```

<210> SEQ ID NO 41

<211> LENGTH: 741
<212> TYPE: PRT
<213> ORGANISM: Artificial Sequence
<220> FEATURE:
<223> OTHER INFORMATION: SS-scFvCD19-DmrA-fuP2A-DmrC-TM-41BB-CD3z
    protein

<400> SEQUENCE: 41

```
Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser Asp Ile Gln Met Thr
            20                  25                  30

Gln Thr Thr Ser Ser Leu Ser Ala Ser Leu Gly Asp Arg Val Thr Ile
        35                  40                  45

Ser Cys Arg Ala Ser Gln Asp Ile Ser Lys Tyr Leu Asn Trp Tyr Gln
    50                  55                  60

Gln Lys Pro Asp Gly Thr Val Lys Leu Leu Ile Tyr His Thr Ser Arg
65                  70                  75                  80

Leu His Ser Gly Val Pro Ser Arg Phe Ser Gly Ser Gly Ser Gly Thr
                85                  90                  95

Asp Tyr Ser Leu Thr Ile Ser Asn Leu Glu Gln Glu Asp Ile Ala Thr
            100                 105                 110

Tyr Phe Cys Gln Gln Gly Asn Thr Leu Pro Tyr Thr Phe Gly Gly Gly
        115                 120                 125

Thr Lys Leu Glu Ile Thr Gly Ser Thr Ser Gly Ser Gly Lys Pro Gly
    130                 135                 140

Ser Gly Glu Gly Ser Thr Lys Gly Glu Val Lys Leu Gln Glu Ser Gly
145                 150                 155                 160

Pro Gly Leu Val Ala Pro Ser Gln Ser Leu Ser Val Thr Cys Thr Val
                165                 170                 175

Ser Gly Val Ser Leu Pro Asp Tyr Gly Val Ser Trp Ile Arg Gln Pro
            180                 185                 190

Pro Arg Lys Gly Leu Glu Trp Leu Gly Val Ile Trp Gly Ser Glu Thr
        195                 200                 205

Thr Tyr Tyr Asn Ser Ala Leu Lys Ser Arg Leu Thr Ile Ile Lys Asp
    210                 215                 220

Asn Ser Lys Ser Gln Val Phe Leu Lys Met Asn Ser Leu Gln Thr Asp
225                 230                 235                 240

Asp Thr Ala Ile Tyr Tyr Cys Ala Lys His Tyr Tyr Tyr Gly Gly Ser
                245                 250                 255

Tyr Ala Met Asp Tyr Trp Gly Gln Gly Thr Ser Val Thr Val Ser Ser
            260                 265                 270

Ala Ser Gly Ser Gly Gly Val Gln Val Glu Thr Ile Ser Pro Gly Asp
        275                 280                 285

Gly Arg Thr Phe Pro Lys Arg Gly Gln Thr Cys Val Val His Tyr Thr
    290                 295                 300

Gly Met Leu Glu Asp Gly Lys Lys Phe Asp Ser Ser Arg Asp Arg Asn
305                 310                 315                 320

Lys Pro Phe Lys Phe Met Leu Gly Lys Gln Glu Val Ile Arg Gly Trp
                325                 330                 335

Glu Glu Gly Val Ala Gln Met Ser Val Gly Gln Arg Ala Lys Leu Thr
            340                 345                 350

Ile Ser Pro Asp Tyr Ala Tyr Gly Ala Thr Gly His Pro Gly Ile Ile
        355                 360                 365

Pro Pro His Ala Thr Leu Val Phe Asp Val Glu Leu Leu Lys Leu Glu
```

370             375             380
Gly Gly Arg Ala Arg Tyr Lys Arg Ser Val Ser Gly Ser Gly Ala Thr
385                 390                 395                 400

Asn Phe Ser Leu Leu Lys Gln Ala Gly Asp Val Glu Asn Pro Gly
                405                 410                 415

Pro Ser Arg Ser Ile Leu Trp His Glu Met Trp His Glu Gly Leu Glu
                420                 425                 430

Glu Ala Ser Arg Leu Tyr Phe Gly Glu Arg Asn Val Lys Gly Met Phe
            435                 440                 445

Glu Val Leu Glu Pro Leu His Ala Met Met Glu Arg Gly Pro Gln Thr
450                 455                 460

Leu Lys Glu Thr Ser Phe Asn Gln Ala Tyr Gly Arg Asp Leu Met Glu
465                 470                 475                 480

Ala Gln Glu Trp Cys Arg Lys Tyr Met Lys Ser Gly Asn Val Lys Asp
                485                 490                 495

Leu Leu Gln Ala Trp Asp Leu Tyr Tyr His Val Phe Arg Arg Ile Ser
                500                 505                 510

Lys Ala Ser Ala Lys Pro Thr Thr Thr Pro Ala Pro Arg Pro Pro Thr
515                 520                 525

Pro Ala Pro Thr Ile Ala Ser Gln Pro Leu Ser Leu Arg Pro Glu Ala
530                 535                 540

Cys Arg Pro Ala Ala Gly Gly Ala Val His Thr Arg Gly Leu Asp Phe
545                 550                 555                 560

Ala Cys Asp Ile Tyr Ile Trp Ala Pro Leu Ala Gly Thr Cys Gly Val
                565                 570                 575

Leu Leu Leu Ser Leu Val Ile Thr Met His Lys Arg Gly Arg Lys Lys
                580                 585                 590

Leu Leu Tyr Ile Phe Lys Gln Pro Phe Met Arg Pro Val Gln Thr Thr
                595                 600                 605

Gln Glu Glu Asp Gly Cys Ser Cys Arg Phe Pro Glu Glu Glu Glu Gly
610                 615                 620

Gly Cys Glu Leu Arg Val Lys Phe Ser Arg Ser Ala Asp Ala Pro Ala
625                 630                 635                 640

Tyr Gln Gln Gly Gln Asn Gln Leu Tyr Asn Glu Leu Asn Leu Gly Arg
                645                 650                 655

Arg Glu Glu Tyr Asp Val Leu Asp Lys Arg Arg Gly Arg Asp Pro Glu
                660                 665                 670

Met Gly Gly Lys Pro Arg Arg Lys Asn Pro Gln Glu Gly Leu Tyr Asn
            675                 680                 685

Glu Leu Gln Lys Asp Lys Met Ala Glu Ala Tyr Ser Glu Ile Gly Met
690                 695                 700

Lys Gly Glu Arg Arg Arg Gly Lys Gly His Asp Gly Leu Tyr Gln Gly
705                 710                 715                 720

Leu Ser Thr Ala Thr Lys Asp Thr Tyr Asp Ala Leu His Met Gln Ala
                725                 730                 735

Leu Pro Pro Arg Gly
            740

<210> SEQ ID NO 42
<211> LENGTH: 2223
<212> TYPE: DNA
<213> ORGANISM: Artificial Sequence
<220> FEATURE:
<223> OTHER INFORMATION: SS-scFvCD19-DmrA-fuP2A-DmrC-TM-41BB-CD3z DNA

```
<400> SEQUENCE: 42
atggagacag acacactcct gctatgggta ctgctgctct gggttccagg ttccactggt      60
gactacaagg acgagggatc cgatatccag atgacccaga ccaccagcag cctgagcgcc     120
agcctgggcg atagagtgac catcagctgc agagccagcc aggacatcag caagtacctg     180
aactggtatc agcagaaacc cgacggcacc gtgaagctgc tgatctacca caccagcaga     240
ctgcacagcg gcgtgcccag cagatttttc ggcagcggct ccggcaccga ctacagcctg     300
accatctcca acctggaaca ggaagatatc gctacctact ctgtcagca aggcaacacc     360
ctgcccctaca ccttcggcgg aggcaccaag ctggaaatca ccggcagcac aagcggcagc     420
ggcaagcctg gatctggcga gggaagcacc aagggcgaag tgaaactgca ggaaagcggc     480
cctggactgg tggccccaag ccagtctctg agcgtgacct gtaccgtgtc cggcgtgtcc     540
ctgcctgact atggcgtgtc ctggatcaga cagccaccca gaaagggcct ggaatggctg     600
ggagtgatct gggcagcga gacaacctac tacaacagcg ccctgaagtc ccggctgacc     660
atcatcaagg acaactccaa gagccaggtg ttcctgaaga tgaacagcct gcagaccgac     720
gacaccgcca tctactactg cgccaagcac tactactacg gcggcagcta cgccatggac     780
tactggggcc agggcacaag cgtgaccgtg tccagcgcta cggctcagg aggagtgcag     840
gttgaaacca tctccccagg agacgggcgc accttcccga agcgcggaca gacatgcgtg     900
gtgcactaca ccgggatgct gaagatggag aagaaattcg attcatcgcg ggacagaaac     960
aagcccttta agtttatgct gggcaagcag gaggtcatcc gaggctggga agaagggggtt    1020
gcccagatga gtgtcggcca gagagccaaa ctgactatat acctgactac cgcctatggg    1080
gccactgggc accctggcat aattccgcca cacgccactc tcgtcttcga tgtggagctt    1140
ctaaaactgg aaggcggccg cgctcgttac aagcgaagtg tctcaggatc tggcgccacg    1200
aacttctctc tgttaaagca agcaggagat gttgaagaaa accccgggcc ttcaagatcc    1260
atcctctggc atgagatgtg gcatgaaggc ctggaagagg catctcgttt gtactttggg    1320
gaaaggaacg tgaaaggcat gtttgaggtg ctggagccct tgcatgctat gatggaacgg    1380
ggccccagga ctctgaagga acatcctttt aatcaggcct atggtcgaga tttaatggag    1440
gcccaagagt ggtgcaggaa gtacatgaaa tcagggaatg tcaaggacct cctccaagcc    1500
tgggacctct attatcatgt gttccgacga atctcaaagg ctagcgccaa gcctaccacc    1560
accccctgccc ctagacctcc aacacccgcc ccaacaatcg ccagccagcc tctgtctctg    1620
aggcccgagg cttgtagacc agctgctggc ggagccgtac acaccagagg actggatttc    1680
gcctgcgaca tctacatctg gcccctctg gccggcacat gtggcgtgct gctgctgagc    1740
ctcgtgatca ccatgcataa acggggcaga aagaaactcc tgtatatatt caaacaacca    1800
tttatgagac cagtacaaac tactcaagag gaagatggct gtagctgccg atttccagaa    1860
gaagaagaag aggatgtgaa actgcgggtg aagttcagca agagcgccga cgcccctgcc    1920
taccagcagg gccagaatca gctgtacaac gagctgaacc tgggcagaag ggaagagtac    1980
gacgtcctgg ataagcggag aggccgggac cctgagatgg gcggcaagcc tcggcggaag    2040
aacccccagg aaggcctgta taacgaactg cagaaagaca gatggccga ggcctacagc    2100
gagatcggca tgaagggcga gcggaggcgg ggcaagggcc acgacggcct gtatcagggc    2160
ctgtccaccg ccaccaagga tacctacgac gccctgcaca tgcaggccct gccccaagg    2220
ggc                                                                  2223
```

```
<210> SEQ ID NO 43
<211> LENGTH: 8306
<212> TYPE: DNA
<213> ORGANISM: Artificial Sequence
<220> FEATURE:
<223> OTHER INFORMATION: SS-scFvCD19-DmrA-fuP2A-DmrC-TM-41BB-CD3z
      lentiviral vector

<400> SEQUENCE: 43
aaaaataaac aaatagggdt tccgcgcaca tttccccgaa aagtgccacc tgacgtcaat      60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg gcgcccgaac     480
agggacttga agcgaaagg gaaaccagag agctctctc gacgcaggac tcggcttgct     540
gaagcgcgca cggcaagagg cgaggggcgg cgactggtga gtacgccaaa aattttgact     600
agcggaggct agaaggagag agatgggtgc gagagcgtca gtattaagcg gggagaatt     660 agatcgcgat gggaaaaaat tcggttaagg ccagggggga gaaaaaata taaattaaaa     720 catatagtat gggcaagcag ggagctagaa cgattcgcag ttaatcctgg cctgttagaa     780
acatcagaag gctgtagaca atactggga cagctacaac catcccttca gacaggatca     840
gaagaactta gatcattata taatacagta gcaaccctct attgtgtgca tcaaaggata     900
gagataaaag acaccaagga agctttagac aagatagagg aagagcaaaa caaaagtaag     960
accaccgcac agcaagcggc cctgatcttc agacctggag gaggagatat gagggacaat    1020
tggagaagtg aattatataa atataaagta gtaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca gacaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taataatct    1440 ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcaggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aagggggat tgggggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
```

```
actgggaaag tgatgtcgtg tactggctcc gccttttcc cgagggtggg ggagaaccgt    2160
atataagtgc agtagtcgcc gtgaacgttc tttttcgcaa cgggtttgcc gccagaacac    2220
acctgcaggg ccgccaccat ggagacagac acactcctgc tatgggtact gctgctctgg    2280
gttccaggtt ccactggtga ctacaaggac gagggatccg atatccagat gacccagacc    2340
accagcagcc tgagcgccag cctgggcgat agagtgacca tcagctgcag agccagccag    2400
gacatcagca gtacctgaa ctggtatcag cagaaaccg acggcaccgt gaagctgctg    2460
atctaccaca ccagcagact gcacagcggc gtgcccagca gattttctgg cagcggctcc    2520
ggcaccgact acagcctgac catctccaac ctggaacagg aagatatcgc tacctacttc    2580
tgtcagcaag caacaccct gccctacacc ttcggcggag gcaccaagct ggaaatcacc    2640
ggcagcacaa gcggcagcgg caagcctgga tctggcgagg gaagcaccaa gggcgaagtg    2700
aaactgcagg aaagcggccc tggactggtg gccccaagcc agtctctgag cgtgacctgt    2760
accgtgtccg gcgtgtccct gcctgactat ggcgtgtcct ggatcagaca gccacccaga    2820
aagggcctgg aatggctggg agtgatctgg ggcagcgaga aacctactaa caacagcgcc    2880
ctgaagtccc ggctgaccat catcaaggac aactccaaga gccaggtgtt cctgaagatg    2940
aacagcctgc agaccgacga caccgccatc tactactgcg ccaagcacta ctactacggc    3000
ggcagctacg ccatggacta ctggggccag ggcacaagcg tgaccgtgtc cagcgctagc    3060
ggctcaggag gagtgcaggt tgaaaccatc tccccaggag acgggcgcac cttcccgaag    3120
cgcggacaga catgcgtggt gcactacacc gggatgcttg aagatggaaa gaaattcgat    3180
tcatcgcggg acagaaacaa gcccttaag tttatgctgg gcaagcagga ggtcatccga    3240
ggctgggaag aaggggttgc ccagatgagt gtcggccaga gagccaaact gactatatca    3300
cctgactacg cctatggggc cactgggcac cctggcataa ttccgccaca cgccactctc    3360
gtcttcgatg tggagcttct aaaactggaa ggcggccgcg ctcgttacaa gcgaagtgtc    3420
tcaggatctg gcgccacgaa cttctctctg ttaaagcaag caggagatgt tgaagaaaac    3480
cccgggcctt caagatccat cctctggcat gagatgtggc atgaaggcct ggaagaggca    3540
tctcgtttgt actttgggga aaggaacgtg aaaggcatgt ttgaggtgct ggagcccttg    3600
catgctatga tggaacgggg ccccagact ctgaaggaaa catcctttaa tcaggcctat    3660
ggtcgagatt aatggaggc caagagtgg tgcaggaagt acatgaaatc agggaatgtc    3720
aaggacctcc tccaagcctg ggacctctat tatcatgtgt tccgacgaat ctcaaaggct    3780
agcgccaagc ctaccaccac ccctgcccct agacctccaa cacccgcccc aacaatcgcc    3840
agccagcctc tgtctctgag gcccgaggct tgtagaccag ctgctggcgg agccgtacac    3900
accagaggac tggatttcgc ctgcgacatc tacatctggg cccctctggc cggcacatgt    3960
ggcgtgctgc tgctgagcct cgtgatcacc atgcataaac ggggcagaaa gaaactcctg    4020
tatatattca acaaccatt tatgagacca gtacaaacta ctcaagagga gatggctgt    4080
agctgccgat ttccagaaga agaagaagga ggatgtgaac tgcgggtgaa gttcagcaga    4140
agcgccgacg cccctgccta ccagcagggc cagaatcagc tgtacaacga gctgaacctg    4200
ggcagaaggg aagagtacga cgtcctggat aagcggagag ccggggaccc tgagatgggc    4260
ggcaagcctc ggcggaagaa ccccaggaa ggcctgtata cgaactgca gaaagacaag    4320
atggccgagg cctacagcga gatcggcatg aagggcgagc ggaggcgggg caagggccac    4380
gacggcctgt atcagggcct gtccaccgcc accaaggata cctacgacgc cctgcacatg    4440
```

```
caggccctgc ccccaagggg cggccgctcc ggtgagggca gaggaagtct tctaacatgc    4500
ggtgacgtgg aggagaatcc gggcccctct agaagcgagc tgattaagga gaacatgcac    4560
atgaagctgt acatggaggg caccgtggac aaccatcact tcaagtgcac atccgagggc    4620
gaaggcaagc cctacgaggg cacccagacc atgagaatca aggtggtcga gggcggccct    4680
ctccccttcg ccttcgacat cctggctact agcttcctct acggcagcaa gaccttcatc    4740
aaccacaccc agggcatccc cgacttcttc aagcagtcct ccctgaggg cttcacatgg    4800 gagagagtca ccacatacga agacgggggc gtgctgaccg ctacccagga caccagcctc    4860
caggacggct gcctcatcta caacgtcaag atcagagggg tgaacttcac atccaacggc    4920
cctgtgatgc agaagaaaac actcggctgg gaggccttca ccgagacgct gtaccccgct    4980
gacggcggcc tggaaggcag aaacgacatg gccctgaagc tcgtgggcgg gagccatctg    5040
atcgcaaaca tcaagaccac atatagatcc aagaaacccg ctaagaacct caagatgcct    5100
ggcgtctact atgtggacta cagactggaa agaatcaagg aggccaacaa cgagacctac    5160
gtcgagcagc acgaggtggc agtggccaga tactgcgacc tccctagcaa actggggcac    5220
aagcttaatt gagtcgaccg agcatcttac cgccatttat acccatattt gttctgtttt    5280
tcttgatttg ggtatacatt taaatgttaa tagaacaaaa tggtggggca atcatttaca    5340
tttttaggga tatgtaatta ctagttcagg tgtattgcca caagacaaac atgttaagaa    5400
actttcccgt tatttacgct ctgttcctgt taatcaacct ctggattaca aaatttgtga    5460
aagattgact gatattctta actatgttgc tccttttacg ctgtgtggat atgctgcttt    5520
atagcctctg tatctagcta ttgcttcccg tacggctttc gttttctcct ccttgtataa    5580
atcctggttg ctgtctcttt tagaggagtt gtggcccgtt gtccgtcaac gtggcgtggt    5640
gtgctctgtg tttgctgacg caaccccccac tggctgggc attgccacca cctgtcaact    5700
cctttctggg actttcgctt tcccctccc gatcgccacg gcagaactca tcgccgcctg    5760
ccttgcccgc tgctggacag gggctaggtt gctgggcact gataattccg tggtgttgtc    5820
atcgaattcg gtaccttttt aaaagaaaag gggggactgg aagggctaat tcactcccaa    5880
cgaagacaag atatcataac ttcgtatagc atacattata cgaagttata atttatttgt    5940
gaaatttgtg atgctattgc tttatttgta accatatgtt tatttgtgaa atttgtgatg    6000
ctattgcttt atttgtaacc attgcttttt gcttgtactg ggtctctctg ttagaccag    6060 atctgagcct gggagctctc tggctaacta gggaacccac tgcttaagcc tcaataaagc    6120
ttgcctcgac cagcctcgac tgtgccttct agttgccagc catctgttgt ttgcccctcc    6180
cccgtgcctt ccttgaccct ggaaggtgcc actcccactg tcctttccta taaaatgag    6240 gaaattgcat cgcattgtct gagtaggtgt cattctattc tggggggtgg ggtggggcag    6300
gacagcaagg gggaggattg ggaagacaat agcaggcatg ctggggatgc ggtgggctct    6360
atggcctgca gctgcattaa tgaatcggcc aacgcgcggg gagaggcggt ttgcgtattg    6420
ggcgctcttc cgcttcctcg ctcactgact cgctgcgctc ggtcgttcgg ctgcggcgag    6480
cggtatcagc tcactcaaag gcggtaatac ggttatccac agaatcaggg gataacgcag    6540
gaaagaacat gtgagcaaaa ggccagcaaa aggccaggaa ccgtaaaaag gccgcgttgc    6600
tggcgttttt ccataggctc cgcccccctg acgagcatca caaaaatcga cgctcaagtc    6660
agaggtggcg aaacccgaca ggactataaa gataccaggc gtttccccct ggaagctccc    6720
tcgtgcgctc tcctgttccg accctgccgc ttaccggata cctgtccgcc tttctccctt    6780
cgggaagcgt ggcgctttct catagctcac gctgtaggta tctcagttcg gtgtaggtcg    6840
```

-continued

```
ttcgctccaa gctgggctgt gtgcacgaac ccccgttca gcccgaccgc tgcgccttat      6900
ccggtaacta tcgtcttgag tccaacccgg taagacacga cttatcgcca ctggcagcag      6960
ccactggtaa caggattagc agagcgaggt atgtaggcgg tgctacagag ttcttgaagt      7020
ggtggcctaa ctacgctac actagaagga cagtatttgg tatctgcgct ctgctgaagc      7080
cagttacctt cggaaaaaga gttggtagct cttgatccgg caaacaaacc accgctggta      7140
gcggtggttt ttttgtttgc aagcagcaga ttacgcgcag aaaaaaagga tctcaagaag      7200
atcctttgat cttttctacg gggtctgacg ctcagtggaa cgaaaactca cgttaaggga      7260
ttttggtcat gagattatca aaaggatct tcacctagat ccttttaaat taaaaatgaa       7320
gttttaaatc aatctaaagt atatatgagt aaacttggtc tgacagttac caatgcttaa      7380
tcagtgaggc acctatctca gcgatctgtc tatttcgttc atccatagtt gcctgactcc      7440
ccgtcgtgta gataactacg atacgggagg gcttaccatc tggccccagt gctgcaatga      7500
taccgcgaga cccacgctca ccggctccag atttatcagc aataaaccag ccagccggaa      7560
gggccgagcg cagaagtggt cctgcaactt tatccgcctc catccagtct attaattgtt      7620
gccgggaagc tagagtaagt agttcgccag ttaatagttt gcgcaacgtt gttgccattg      7680
ctacaggcat cgtggtgtca cgctcgtcgt ttggtatggc ttcattcagc tccggttccc      7740
aacgatcaag gcgagttaca tgatcccca tgttgtgcaa aaaagcggtt agctccttcg       7800
gtcctccgat cgttgtcaga agtaagttgg ccgcagtgtt atcactcatg gttatggcag      7860
cactgcataa ttctcttact gtcatgccat ccgtaagatg cttttctgtg actggtgagt      7920
actcaaccaa gtcattctga gaatagtgta tgcggcgacc gagttgctct tgcccggcgt      7980
caatacggga taataccgcg ccacatagca gaactttaaa agtgctcatc attggaaaac      8040
gttcttcggg gcgaaaactc tcaaggatct taccgctgtt gagatccagt tcgatgtaac      8100
ccactcgtgc acccaactga tcttcagcat cttttacttt caccagcgtt tctgggtgag      8160
caaaaacagg aaggcaaaat gccgcaaaaa agggaataag ggcgacacgg aaatgttgaa      8220
tactcatact cttccttttt caatattatt gaagcattta tcagggttat tgtctcatga      8280
gcggatacat atttgaatgt atttag                                            8306
```

<210> SEQ ID NO 44
<211> LENGTH: 741
<212> TYPE: PRT
<213> ORGANISM: Artificial Sequence
<220> FEATURE:
<223> OTHER INFORMATION: SS-scFvCD19-DmrA-fuP2A-FRB-TM-41BB-CD3z protein

<400> SEQUENCE: 44

```
Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser Asp Ile Gln Met Thr
            20                  25                  30

Gln Thr Thr Ser Ser Leu Ser Ala Ser Leu Gly Asp Arg Val Thr Ile
        35                  40                  45

Ser Cys Arg Ala Ser Gln Asp Ile Ser Lys Tyr Leu Asn Trp Tyr Gln
    50                  55                  60

Gln Lys Pro Asp Gly Thr Val Lys Leu Leu Ile Tyr His Thr Ser Arg
65                  70                  75                  80

Leu His Ser Gly Val Pro Ser Arg Phe Ser Gly Ser Gly Ser Gly Thr
                85                  90                  95
```

Asp Tyr Ser Leu Thr Ile Ser Asn Leu Glu Gln Glu Asp Ile Ala Thr
            100                 105                 110

Tyr Phe Cys Gln Gln Gly Asn Thr Leu Pro Tyr Thr Phe Gly Gly Gly
        115                 120                 125

Thr Lys Leu Glu Ile Thr Gly Ser Thr Ser Gly Ser Gly Lys Pro Gly
    130                 135                 140

Ser Gly Glu Gly Ser Thr Lys Gly Glu Val Lys Leu Gln Glu Ser Gly
145                 150                 155                 160

Pro Gly Leu Val Ala Pro Ser Gln Ser Leu Ser Val Thr Cys Thr Val
                165                 170                 175

Ser Gly Val Ser Leu Pro Asp Tyr Gly Val Ser Trp Ile Arg Gln Pro
            180                 185                 190

Pro Arg Lys Gly Leu Glu Trp Leu Gly Val Ile Trp Gly Ser Glu Thr
        195                 200                 205

Thr Tyr Tyr Asn Ser Ala Leu Lys Ser Arg Leu Thr Ile Ile Lys Asp
    210                 215                 220

Asn Ser Lys Ser Gln Val Phe Leu Lys Met Asn Ser Leu Gln Thr Asp
225                 230                 235                 240

Asp Thr Ala Ile Tyr Tyr Cys Ala Lys His Tyr Tyr Gly Gly Ser
                245                 250                 255

Tyr Ala Met Asp Tyr Trp Gly Gln Gly Thr Ser Val Thr Val Ser Ser
            260                 265                 270

Ala Ser Gly Ser Gly Gly Val Gln Val Glu Thr Ile Ser Pro Gly Asp
        275                 280                 285

Gly Arg Thr Phe Pro Lys Arg Gly Gln Thr Cys Val Val His Tyr Thr
290                 295                 300

Gly Met Leu Glu Asp Gly Lys Lys Phe Asp Ser Ser Arg Asp Arg Asn
305                 310                 315                 320

Lys Pro Phe Lys Phe Met Leu Gly Lys Gln Glu Val Ile Arg Gly Trp
                325                 330                 335

Glu Glu Gly Val Ala Gln Met Ser Val Gly Gln Arg Ala Lys Leu Thr
            340                 345                 350

Ile Ser Pro Asp Tyr Ala Tyr Gly Ala Thr Gly His Pro Gly Ile Ile
        355                 360                 365

Pro Pro His Ala Thr Leu Val Phe Asp Val Glu Leu Leu Lys Leu Glu
    370                 375                 380

Gly Gly Arg Ala Arg Tyr Lys Arg Ser Val Ser Gly Ser Gly Ala Thr
385                 390                 395                 400

Asn Phe Ser Leu Leu Lys Gln Ala Gly Asp Val Glu Glu Asn Pro Gly
                405                 410                 415

Pro Ser Arg Ser Ile Leu Trp His Glu Met Trp His Glu Gly Leu Glu
            420                 425                 430

Glu Ala Ser Arg Leu Tyr Phe Gly Glu Arg Asn Val Lys Gly Met Phe
        435                 440                 445

Glu Val Leu Glu Pro Leu His Ala Met Met Glu Arg Gly Pro Gln Thr
    450                 455                 460

Leu Lys Glu Thr Ser Phe Asn Gln Ala Tyr Gly Arg Asp Leu Met Glu
465                 470                 475                 480

Ala Gln Glu Trp Cys Arg Lys Tyr Met Lys Ser Gly Asn Val Lys Asp
                485                 490                 495

Leu Thr Gln Ala Trp Asp Leu Tyr Tyr His Val Phe Arg Arg Ile Ser
            500                 505                 510

Lys Ala Ser Ala Lys Pro Thr Thr Thr Pro Ala Pro Arg Pro Pro Thr

```
               515                 520                 525
        Pro Ala Pro Thr Ile Ala Ser Gln Pro Leu Ser Leu Arg Pro Glu Ala
            530                 535                 540
        Cys Arg Pro Ala Ala Gly Gly Ala Val His Thr Arg Gly Leu Asp Phe
        545                 550                 555                 560
        Ala Cys Asp Ile Tyr Ile Trp Ala Pro Leu Ala Gly Thr Cys Gly Val
                        565                 570                 575
        Leu Leu Leu Ser Leu Val Ile Thr Met His Lys Arg Gly Arg Lys Lys
                    580                 585                 590
        Leu Leu Tyr Ile Phe Lys Gln Pro Phe Met Arg Pro Val Gln Thr Thr
                595                 600                 605
        Gln Glu Glu Asp Gly Cys Ser Cys Arg Phe Pro Glu Glu Glu Glu Gly
            610                 615                 620
        Gly Cys Glu Leu Arg Val Lys Phe Ser Arg Ser Ala Asp Ala Pro Ala
        625                 630                 635                 640
        Tyr Gln Gln Gly Gln Asn Gln Leu Tyr Asn Glu Leu Asn Leu Gly Arg
                        645                 650                 655
        Arg Glu Glu Tyr Asp Val Leu Asp Lys Arg Arg Gly Arg Asp Pro Glu
                    660                 665                 670
        Met Gly Gly Lys Pro Arg Arg Lys Asn Pro Gln Glu Gly Leu Tyr Asn
                675                 680                 685
        Glu Leu Gln Lys Asp Lys Met Ala Glu Ala Tyr Ser Glu Ile Gly Met
            690                 695                 700
        Lys Gly Glu Arg Arg Gly Lys Gly His Asp Gly Leu Tyr Gln Gly
        705                 710                 715                 720
        Leu Ser Thr Ala Thr Lys Asp Thr Tyr Asp Ala Leu His Met Gln Ala
                        725                 730                 735
        Leu Pro Pro Arg Gly
                    740

<210> SEQ ID NO 45
<211> LENGTH: 2223
<212> TYPE: DNA
<213> ORGANISM: Artificial Sequence
<220> FEATURE:
<223> OTHER INFORMATION: SS-scFvCD19-DmrA-fuP2A-FRB-TM-41BB-CD3z DNA

<400> SEQUENCE: 45
atggagacag acacactcct gctatgggta ctgctgctct gggttccagg ttccactggt     60
gactacaagg acgagggatc cgatatccag atgacccaga ccaccagcag cctgagcgcc    120
agcctgggcg atagagtgac catcagctgc agagccagcc aggacatcag caagtacctg    180
aactggtatc agcagaaacc cgacggcacc gtgaagctgc tgatctacca caccagcaga    240
ctgcacagcg gcgtgcccag cagattttct ggcagcggct ccggcaccga ctacagcctg    300
accatctcca acctggaaca ggaagatatc gctacctact ctgtcagca aggcaacacc    360 ctgcccctaca ccttcggcgg aggcaccaag ctggaaatca ccggcagcac aagcggcagc    420
ggcaagcctg gatctggcga gggaagcacc aagggcgaag tgaaactgca ggaaagcggc    480
cctggactgg tggccccaag ccagtctctg agcgtgacct gtaccgtgtc cggcgtgtcc    540
ctgcctgact atggcgtgtc ctggatcaga cagccaccca gaaagggcct ggaatggctg    600
ggagtgatct ggggcagcga gacaacctac tacaacagcg ccctgaagtc ccggctgacc    660
atcatcaagg acaactccaa gagccaggtg ttcctgaaga tgaacagcct gcagaccgac    720
gacaccgcca tctactactg cgccaagcac tactactacg gcggcagcta cgccatggac    780
```

```
tactggggcc agggcacaag cgtgaccgtg tccagcgcta gcggctcagg aggagtgcag    840
gttgaaacca tctccccagg agacgggcgc accttcccga agcgcggaca gacatgcgtg    900
gtgcactaca ccgggatgct tgaagatgga aagaaattcg attcatcgcg ggacagaaac    960 aagccctta agtttatgct gggcaagcag gaggtcatcc gaggctggga agaaggggtt     1020
gcccagatga gtgtcggcca gagagccaaa ctgactatat cacctgacta cgcctatggg   1080
gccactgggc accctggcat aattccgcca cacgccactc tcgtcttcga tgtggagctt    1140
ctaaaactgg aaggcggccg cgctcgttac aagcgaagtg tctcaggatc tggcgccacg    1200
aacttctctc tgttaaagca agcaggagat gttgaagaaa accccgggcc ttcaagatcc    1260
atcctctggc atgagatgtg gcatgaaggc ctggaagagg catctcgttt gtactttggg    1320
gaaaggaacg tgaaaggcat gtttgaggtg ctggagccct gcatgctat gatgaacgg     1380 ggcccccaga ctctgaagga acatcctt aatcaggcct atggtcgaga tttaatggag     1440
gcccaagagt ggtgcaggaa gtacatgaaa tcagggaatg tcaaggacct cacccaagcc    1500
tgggacctct attatcatgt gttccgacga atctcaaagg ctagcgccaa gcctaccacc    1560 accctgccc ctagacctcc aacacccgcc ccaacaatcg ccagccagcc tctgtctctg    1620
aggcccgagg cttgtagacc agctgctggc ggagccgtac acaccagagg actggatttc    1680
gcctgcgaca tctacatctg gccccctctg gccggcacat gtggcgtgct gctgctgagc    1740
ctcgtgatca ccatgcataa acgggcaga aagaaactcc tgtatatatt caaacaacca    1800
tttatgagac cagtacaaac tactcaagag gaagatgcct gtagctgccg atttccagaa    1860
gaagaagaag gaggatgtga actgcgggtg aagttcagca agcgccga cgcccctgcc     1920 taccagcagg gccagaatca gctgtacaac gagctgaacc tgggcagaag gaagagtac    1980 gacgtcctgg ataagcggag aggccgggac cctgagatgg gcggcaagcc tcggcggaag    2040 aaccccagg aaggcctgta taacgaactg cagaaagaca gatggccga ggcctacagc    2100 gagatcggca tgaagggcga gcggaggcgg ggcaagggcc acgacggcct gtatcagggc    2160
ctgtccaccg ccaccaagga tacctacgac gccctgcaca tgcaggccct gccccaagg    2220 ggc                                                                 2223
```

<210> SEQ ID NO 46
<211> LENGTH: 8306
<212> TYPE: DNA
<213> ORGANISM: Artificial Sequence
<220> FEATURE:
<223> OTHER INFORMATION: SS-scFvCD19-DmrA-fuP2A-FRB-TM-41BB-CD3z
    lentiviral vector

<400> SEQUENCE: 46

```
aaaaataaac aaatagggt tccgcgcaca tttccccgaa aagtgccacc tgacgtcaat    60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg cgcccgaac    480 agggacttga agcgaaagg gaaaccagag gagctctctc gacgcaggac tcggcttgct    540
```

```
gaagcgcgca cggcaagagg cgaggggcgg cgactggtga gtacgccaaa aattttgact    600
agcggaggct agaaggagag agatgggtgc gagagcgtca gtattaagcg ggggagaatt    660
agatcgcgat gggaaaaaat tcggttaagg ccagggggaa agaaaaaata taaattaaaa    720
catatagtat gggcaagcag ggagctagaa cgattcgcag ttaatcctgg cctgttagaa    780
acatcagaag gctgtagaca aatactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaaagag cagtgggaat aggagctttg   1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag atacctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aagggggggat tgggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggagggggtc ggcaattgaa ccggtgccta gagaaggtgg cgcggggtaa   2100
actgggaaag tgatgtcgtg tactggctcc gccttttttcc cgagggtggg ggagaaccgt   2160
atataagtgc agtagtcgcc gtgaacgttc ttttttcgcaa cgggtttgcc gccagaacac   2220
acctgcaggg ccgccaccat ggagacagac acactcctgc tatgggtact gctgctctgg   2280
gttccaggtt ccactggtga ctacaaggac gagggatccg atatccagat gacccagacc   2340
accagcagcc tgagcgccag cctgggcgat agagtgacca tcagctgcag agccagccag   2400
gacatcagca gtacctgaa ctggtatcag cagaaacccg acggcaccgt gaagctgctg   2460
atctaccaca ccagcagact gcacagcggc gtgcccagca gatttctgg cagcggctcc   2520 ggcaccgact acagcctgac catctccaac ctggaacagg aagatatcgc tacctacttc   2580
tgtcagcaag caacaccct gccctacacc ttcggcggag gcaccaagct ggaaatcacc   2640
ggcagcacaa gcggcagcgg caagcctgga tctggcgagg gaagcaccaa gggcgaagtg   2700
aaactgcagg aaagcggccc tggactggtg gccccaagcc agtctctgag cgtgacctgt   2760
accgtgtccg gcgtgtccct gcctgactat ggcgtgtcct ggatcagaca gccacccaga   2820
aagggcctgg aatggctggg agtgatctgg ggcagcgaga caacctacta caacagcgcc   2880
```

```
ctgaagtccc ggctgaccat catcaaggac aactccaaga gccaggtgtt cctgaagatg    2940
aacagcctgc agaccgacga caccgccatc tactactgcg ccaagcacta ctactacggc    3000
ggcagctacg ccatggacta ctggggccag ggcacaagcg tgaccgtgtc cagcgctagc    3060
ggctcaggag gagtgcaggt tgaaaccatc tccccaggag acgggcgcac cttcccgaag    3120
cgcggacaga catgcgtggt gcactacacc gggatgcttg aagatggaaa gaaattcgat    3180
tcatcgcggg acagaaacaa gcccttttaag tttatgctgg gcaagcagga ggtcatccga    3240
ggctgggaag aaggggttgc ccagatgagt gtcggccaga gagccaaact gactatatca    3300
cctgactacg cctatggggc cactgggcac cctggcataa ttccgccaca cgccactctc    3360
gtcttcgatg tggagcttct aaaactggaa ggcggccgcg ctcgttacaa gcgaagtgtc    3420
tcaggatctg gcgccacgaa cttctctctg ttaaagcaag caggagatgt tgaagaaaac    3480
cccgggcctt caagatccat cctctggcat gagatgtggc atgaaggcct ggaagaggca    3540
tctcgtttgt actttgggga aaggaacgtg aaaggcatgt tgaggtgct ggagcccttg    3600 catgctatga tggaacgggg cccccagact ctgaaggaaa catcctttaa tcaggcctat    3660
ggtcgagatt taatggaggc caagagtgg tgcaggaagt acatgaaatc agggaatgtc    3720
aaggacctca cccaagcctg ggacctctat tatcatgtgt tccgacgaat ctcaaaggct    3780
agcgccaagc ctaccaccac ccctgcccct agacctccaa cacccgcccc aacaatcgcc    3840
agccagcctc tgtctctgag gcccgaggct tgtagaccag ctgctggcgg agccgtacac    3900
accagaggac tggatttcgc ctgcgacatc tacatctggg ccctctggc cggcacatgt    3960 ggcgtgctgc tgctgagcct cgtgatcacc atgcataaac ggggcagaaa gaaactcctg    4020
tatatattca acaaccatt tatgagacca gtacaaacta ctcaagagga gatggctgt    4080 agctgccgat ttccagaaga agaaggaaa gggatgtgaac tgcgggtgaa gttcagcaga    4140
agcgccgacg cccctgccta ccagcagggc cagaatcagc tgtacaacga gctgaacctg    4200
ggcagaaggg aagagtacga cgtcctggat aagcggagag ccgggaccc tgagatgggc    4260 ggcaagcctc ggcggaagaa ccccaggaa ggcctgtata cgaactgca gaaagacaag    4320 atggccgagc cctacagcga gatcggcatg aagggcgagc ggaggcgggg caagggccac    4380
gacggcctgt atcagggcct gtccaccgcc accaaggata cctacgacgc cctgcacatg    4440
caggccctgc ccccaagggg cggccgctcc ggtgagggca gaggaagtct tctaacatgc    4500
ggtgacgtgg aggagaatcc gggccctct agaagcgagc tgattaagga gaacatgcac    4560
atgaagctgt acatggaggg caccgtggac aaccatcact tcaagtgcac atccgagggc    4620
gaaggcaagc cctacgaggg cacccagacc atgagaatca aggtggtcga gggcggccct    4680
ctccccttcg ccttcgacat cctggctact agcttcctct acggcagcaa gaccttcatc    4740
aaccacaccc agggcatccc cgacttcttc aagcagtcct ccctgagggg cttcacatgg    4800
gagagagtca ccacatacga agacgggggc gtgctgaccg ctacccagga caccagcctc    4860
caggacggct gcctcatcta caacgtcaag atcagagggg tgaacttcac atccaacggc    4920
cctgtgatgc agaagaaaac actcggctgg gaggccttca ccgagacgct gtaccccgct    4980
gacggcggcc tggaaggcag aaacgacatg gccctgaagc tcgtgggcgg gagccatctg    5040
atcgcaaaca tcaagaccac atatagatcc aagaaacccg ctaagaacct caagatgcct    5100
ggcgtctact atgtggacta cagactggaa agaatcaagg aggccaacaa cgagacctac    5160
gtcgagcagc acgaggtggc agtggccaga tactgcgacc tccctagcaa actggggcac    5220
aagcttaatt gagtcgaccg agcatcttac cgccatttat acccatattt gttctgtttt    5280
```

```
tcttgatttg ggtatacatt taaatgttaa tagaacaaaa tggtggggca atcatttaca    5340
tttttaggga tatgtaatta ctagttcagg tgtattgcca caagacaaac atgttaagaa    5400
actttcccgt tatttacgct ctgttcctgt taatcaacct ctggattaca aaatttgtga    5460
aagattgact gatattctta actatgttgc tccttttacg ctgtgtggat atgctgcttt    5520
atagcctctg tatctagcta ttgcttcccg tacggctttc gttttctcct ccttgtataa    5580
atcctggttg ctgtctcttt tagaggagtt gtggcccgtt gtccgtcaac gtggcgtggt    5640
gtgctctgtg tttgctgacg caaccccccac tggctggggc attgccacca cctgtcaact    5700
cctttctggg actttcgctt tcccctccc gatcgccacg gcagaactca tcgccgcctg    5760
ccttgcccgc tgctggacag gggctaggtt gctgggcact gataattccg tggtgttgtc    5820
atcgaattcg gtacctttt aaaagaaaag gggggactgg aagggctaat tcactcccaa    5880
cgaagacaag atatcataac ttcgtatagc atacattata cgaagttata atttatttgt    5940
gaaatttgtg atgctattgc tttatttgta accatatgtt tatttgtgaa atttgtgatg    6000
ctattgcttt atttgtaacc attgcttttt gcttgtactg ggtctctctg gttagaccag    6060
atctgagcct gggagctctc tggctaacta gggaacccac tgcttaagcc tcaataaagc    6120
ttgcctcgac cagcctcgac tgtgccttct agttgccagc catctgttgt ttgcccctcc    6180
cccgtgcctt ccttgaccct ggaaggtgcc actcccactg tccttcccta taaaatgag    6240
gaaattgcat cgcattgtct gagtaggtgt cattctattc tgggggtgg ggtggggcag    6300
gacagcaagg gggaggattg ggaagacaat agcaggcatg ctgggatgc ggtgggctct    6360
atggcctgca gctgcattaa tgaatcggcc aacgcgcggg gagaggcggt ttgcgtattg    6420
ggcgctcttc cgcttcctcg ctcactgact cgctgcgctc ggtcgttcgg ctgcggcgag    6480
cggtatcagc tcactcaaag gcggtaatac ggttatccac agaatcaggg gataacgcag    6540
gaaagaacat gtgagcaaaa ggccagcaaa aggccaggaa ccgtaaaaag gccgcgttgc    6600
tggcgttttt ccataggctc cgcccccctg acgagcatca aaaaatcga cgctcaagtc    6660
agaggtggcg aaacccgaca ggactataaa gataccaggc gtttccccct ggaagctccc    6720
tcgtgcgctc tcctgttccg accctgccgc ttaccggata cctgtccgcc tttctccctt    6780
cgggaagcgt ggcgctttct catagctcac gctgtaggta tctcagttcg gtgtaggtcg    6840
ttcgctccaa gctgggctgt gtgcacgaac cccccgttca gcccgaccgc tgcgccttat    6900
ccggtaacta tcgtcttgag tccaacccgg taagacacga cttatcgcca ctggcagcag    6960
ccactggtaa caggattagc agagcgaggt atgtaggcgg tgctacagag ttcttgaagt    7020
ggtggcctaa ctacggctac actagaagga cagtatttgg tatctgcgct ctgctgaagc    7080
cagttacctt cggaaaaaga gttggtagct cttgatccgg caaacaaacc accgctggta    7140
gcggtggttt ttttgtttgc aagcagcaga ttacgcgcag aaaaaaagga tctcaagaag    7200
atcctttgat cttttctacg gggtctgacg ctcagtggaa cgaaaactca cgttaaggga    7260
ttttggtcat gagattatca aaaaggatct tcacctagat ccttttaaat taaaaatgaa    7320
gttttaaatc aatctaaagt atatatgagt aaacttggtc tgacagttac caatgcttaa    7380
tcagtgaggc acctatctca gcgatctgtc tatttcgttc atccatagtt gcctgactcc    7440
ccgtcgtgta gataactacg atacgggagg gcttaccatc tggccccagt gctgcaatga    7500
taccgcgaga cccacgctca ccggctccag atttatcagc aataaaccag ccagccgaa    7560
gggccgagcg cagaagtggt cctgcaactt tatccgcctc catccagtct attaattgtt    7620
```

-continued

```
gccgggaagc tagagtaagt agttcgccag ttaatagttt gcgcaacgtt gttgccattg   7680
ctacaggcat cgtggtgtca cgctcgtcgt ttggtatggc ttcattcagc tccggttccc   7740
aacgatcaag gcgagttaca tgatccccca tgttgtgcaa aaaagcggtt agctccttcg   7800
gtcctccgat cgttgtcaga agtaagttgg ccgcagtgtt atcactcatg gttatggcag   7860
cactgcataa ttctcttact gtcatgccat ccgtaagatg cttttctgtg actggtgagt   7920
actcaaccaa gtcattctga gaatagtgta tgcggcgacc gagttgctct tgcccggcgt   7980
caatacggga taataccgcg ccacatagca gaactttaaa agtgctcatc attggaaaac   8040
gttcttcggg gcgaaaactc tcaaggatct taccgctgtt gagatccagt tcgatgtaac   8100
ccactcgtgc acccaactga tcttcagcat cttttacttt caccagcgtt tctgggtgag   8160
caaaaacagg aaggcaaaat gccgcaaaaa agggaataag ggcgacacgg aaatgttgaa   8220
tactcatact cttccttttt caatattatt gaagcattta tcagggttat tgtctcatga   8280
gcggatacat atttgaatgt atttag                                        8306
```

<210> SEQ ID NO 47
<211> LENGTH: 967
<212> TYPE: PRT
<213> ORGANISM: Artificial Sequence
<220> FEATURE:
<223> OTHER INFORMATION: SS-scFvCD19-DmrA-fuP2A-2xDmrB-DmrC-TM-41BB-CD3z
       protein <400> SEQUENCE: 47

```
Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser Asp Ile Gln Met Thr
            20                  25                  30

Gln Thr Thr Ser Ser Leu Ser Ala Ser Leu Gly Asp Arg Val Thr Ile
        35                  40                  45

Ser Cys Arg Ala Ser Gln Asp Ile Ser Lys Tyr Leu Asn Trp Tyr Gln
    50                  55                  60

Gln Lys Pro Asp Gly Thr Val Lys Leu Leu Ile Tyr His Thr Ser Arg
65                  70                  75                  80

Leu His Ser Gly Val Pro Ser Arg Phe Ser Gly Ser Gly Ser Gly Thr
                85                  90                  95

Asp Tyr Ser Leu Thr Ile Ser Asn Leu Glu Gln Glu Asp Ile Ala Thr
            100                 105                 110

Tyr Phe Cys Gln Gln Gly Asn Thr Leu Pro Tyr Thr Phe Gly Gly Gly
        115                 120                 125

Thr Lys Leu Glu Ile Thr Gly Ser Thr Ser Gly Ser Gly Lys Pro Gly
    130                 135                 140

Ser Gly Glu Gly Ser Thr Lys Gly Glu Val Lys Leu Gln Glu Ser Gly
145                 150                 155                 160

Pro Gly Leu Val Ala Pro Ser Gln Ser Leu Ser Val Thr Cys Thr Val
                165                 170                 175

Ser Gly Val Ser Leu Pro Asp Tyr Gly Val Ser Trp Ile Arg Gln Pro
            180                 185                 190

Pro Arg Lys Gly Leu Glu Trp Leu Gly Val Ile Trp Gly Ser Glu Thr
        195                 200                 205

Thr Tyr Tyr Asn Ser Ala Leu Lys Ser Arg Leu Thr Ile Ile Lys Asp
    210                 215                 220

Asn Ser Lys Ser Gln Val Phe Leu Lys Met Asn Ser Leu Gln Thr Asp
225                 230                 235                 240
```

-continued

```
Asp Thr Ala Ile Tyr Tyr Cys Ala Lys His Tyr Tyr Gly Gly Ser
                245                 250                 255

Tyr Ala Met Asp Tyr Trp Gly Gln Gly Thr Ser Val Thr Val Ser Ser
            260                 265                 270

Ala Ser Gly Ser Gly Gly Val Gln Val Glu Thr Ile Ser Pro Gly Asp
        275                 280                 285

Gly Arg Thr Phe Pro Lys Arg Gly Gln Thr Cys Val Val His Tyr Thr
    290                 295                 300

Gly Met Leu Glu Asp Gly Lys Lys Phe Asp Ser Ser Arg Asp Arg Asn
305                 310                 315                 320

Lys Pro Phe Lys Phe Met Leu Gly Lys Gln Glu Val Ile Arg Gly Trp
                325                 330                 335

Glu Glu Gly Val Ala Gln Met Ser Val Gly Gln Arg Ala Lys Leu Thr
            340                 345                 350

Ile Ser Pro Asp Tyr Ala Tyr Gly Ala Thr Gly His Pro Gly Ile Ile
        355                 360                 365

Pro Pro His Ala Thr Leu Val Phe Asp Val Glu Leu Leu Lys Leu Glu
    370                 375                 380

Gly Gly Arg Ala Arg Tyr Lys Arg Ser Val Ser Gly Ser Gly Ala Thr
385                 390                 395                 400

Asn Phe Ser Leu Leu Lys Gln Ala Gly Asp Val Glu Glu Asn Pro Gly
                405                 410                 415

Pro Ser Arg Ser Gly Gly Val Gln Val Glu Thr Ile Ser Pro Gly Asp
            420                 425                 430

Gly Arg Thr Phe Pro Lys Arg Gly Gln Thr Cys Val Val His Tyr Thr
        435                 440                 445

Gly Met Leu Glu Asp Gly Lys Lys Val Asp Ser Ser Arg Asp Arg Asn
    450                 455                 460

Lys Pro Phe Lys Phe Met Leu Gly Lys Gln Glu Val Ile Arg Gly Trp
465                 470                 475                 480

Glu Glu Gly Val Ala Gln Met Ser Val Gly Gln Arg Ala Lys Leu Thr
                485                 490                 495

Ile Ser Pro Asp Tyr Ala Tyr Gly Ala Thr Gly His Pro Gly Ile Ile
            500                 505                 510

Pro Pro His Ala Thr Leu Val Phe Asp Val Glu Phe Leu Lys Leu Glu
        515                 520                 525

Ser Gly Thr Ser Gly Thr Ser Gly Val Gln Val Glu Thr Ile Ser Pro
    530                 535                 540

Gly Asp Gly Arg Thr Phe Pro Lys Arg Gly Gln Thr Cys Val Val His
545                 550                 555                 560

Tyr Thr Gly Met Leu Glu Asp Gly Lys Lys Val Asp Ser Ser Arg Asp
                565                 570                 575

Arg Asn Lys Pro Phe Lys Phe Met Leu Gly Lys Gln Glu Val Ile Arg
            580                 585                 590

Gly Trp Glu Glu Gly Val Ala Gln Met Ser Val Gly Gln Arg Ala Lys
        595                 600                 605

Leu Thr Ile Ser Pro Asp Tyr Ala Tyr Gly Ala Thr Gly His Pro Gly
    610                 615                 620

Ile Ile Pro Pro His Ala Thr Leu Val Phe Asp Val Glu Leu Leu Lys
625                 630                 635                 640

Leu Glu Gly Ser Arg Ser Ile Leu Trp His Glu Met Trp His Glu Gly
                645                 650                 655
```

```
Leu Glu Glu Ala Ser Arg Leu Tyr Phe Gly Arg Asn Val Lys Gly
            660                 665                 670

Met Phe Glu Val Leu Glu Pro Leu His Ala Met Met Glu Arg Gly Pro
675                 680                 685

Gln Thr Leu Lys Glu Thr Ser Phe Asn Gln Ala Tyr Gly Arg Asp Leu
            690                 695                 700

Met Glu Ala Gln Glu Trp Cys Arg Lys Tyr Met Lys Ser Gly Asn Val
705                 710                 715                 720

Lys Asp Leu Leu Gln Ala Trp Asp Leu Tyr Tyr His Val Phe Arg Arg
                725                 730                 735

Ile Ser Lys Ala Ser Ala Lys Pro Thr Thr Thr Pro Ala Pro Arg Pro
            740                 745                 750

Pro Thr Pro Ala Pro Thr Ile Ala Ser Gln Pro Leu Ser Leu Arg Pro
        755                 760                 765

Glu Ala Cys Arg Pro Ala Ala Gly Gly Ala Val His Thr Arg Gly Leu
770                 775                 780

Asp Phe Ala Cys Asp Ile Tyr Ile Trp Ala Pro Leu Ala Gly Thr Cys
785                 790                 795                 800

Gly Val Leu Leu Leu Ser Leu Val Ile Thr Met His Lys Arg Gly Arg
                805                 810                 815

Lys Lys Leu Leu Tyr Ile Phe Lys Gln Pro Phe Met Arg Pro Val Gln
            820                 825                 830

Thr Thr Gln Glu Glu Asp Gly Cys Ser Cys Arg Phe Pro Glu Glu Glu
        835                 840                 845

Glu Gly Gly Cys Glu Leu Arg Val Lys Phe Ser Arg Ser Ala Asp Ala
850                 855                 860

Pro Ala Tyr Gln Gln Gly Gln Asn Gln Leu Tyr Asn Glu Leu Asn Leu
865                 870                 875                 880

Gly Arg Arg Glu Glu Tyr Asp Val Leu Asp Lys Arg Arg Gly Arg Asp
                885                 890                 895

Pro Glu Met Gly Gly Lys Pro Arg Arg Lys Asn Pro Gln Glu Gly Leu
            900                 905                 910

Tyr Asn Glu Leu Gln Lys Asp Lys Met Ala Glu Ala Tyr Ser Glu Ile
        915                 920                 925

Gly Met Lys Gly Glu Arg Arg Arg Gly Lys Gly His Asp Gly Leu Tyr
930                 935                 940

Gln Gly Leu Ser Thr Ala Thr Lys Asp Thr Tyr Asp Ala Leu His Met
945                 950                 955                 960

Gln Ala Leu Pro Pro Arg Gly
                965
```

<210> SEQ ID NO 48
<211> LENGTH: 2901
<212> TYPE: DNA
<213> ORGANISM: Artificial Sequence
<220> FEATURE:
<223> OTHER INFORMATION: SS-scFvCD19-DmrA-fuP2A-2xDmrB-DmrC-TM-41BB-CD3z
    DNA

<400> SEQUENCE: 48
atggagacag acacactcct gctatgggta ctgctgctct gggttccagg ttccactggt    60
gactacaagg acgagggatc cgatatccag atgacccaga ccaccagcag cctgagcgcc   120
agcctgggcg atagagtgac catcagctgc agagccagcc aggacatcag caagtacctg   180
aactggtatc agcagaaacc cgacggcacc gtgaagctgc tgatctacca caccagcaga   240

```
ctgcacagcg gcgtgcccag cagattttct ggcagcggct ccggcaccga ctacagcctg    300
accatctcca acctggaaca ggaagatatc gctacctact tctgtcagca aggcaacacc    360 ctgcccctaca ccttcggcgg aggcaccaag ctggaaatca ccggcagcac aagcggcagc   420
ggcaagcctg gatctggcga gggaagcacc aagggcgaag tgaaactgca ggaaagcggc    480
cctggactgg tggccccaag ccagtctctg agcgtgacct gtaccgtgtc cggcgtgtcc    540
ctgcctgact atggcgtgtc ctggatcaga cagccaccca gaaagggcct ggaatggctg    600
ggagtgatct ggggcagcga gacaacctac tacaacagcg ccctgaagtc ccggctgacc    660
atcatcaagg acaactccaa gagccaggtg ttcctgaaga tgaacagcct gcagaccgac    720
gacaccgcca tctactactg cgccaagcac tactactacg gcggcagcta cgccatggac    780
tactggggcc agggcacaag cgtgaccgtg tccagcgcta gcggctcagg aggagtgcag    840
gttgaaacca tctccccagg agacgggcgc accttcccga agcgcggaca gacatgcgtg    900
gtgcactaca ccgggatgct tgaagatgga aagaaattcg attcatcgcg ggacagaaac    960
aagcccttta agtttatgct gggcaagcag gaggtcatcc gaggctggga agaaggggtt   1020
gcccagatga gtgtcggcca gagagccaaa ctgactatat cacctgacta cgcctatggg   1080
gccactgggc accctggcat aattccgcca cacgccactc tcgtcttcga tgtggagctt   1140
ctaaaactgg aaggcggccg cgctcgttac aagcgaagtg tctcaggatc tggcgccacg   1200
aacttctctc tgttaaagca agcaggagat gttgaagaaa accccgggcc ttcaagatcc   1260
ggcggtgtcc aagtcgaaac tatatcgcct ggcgatggca gaacgtttcc caaacgtggc   1320
cagacctgtg tcgtacacta taccggcatg ctagaggatg gaaaaaaggt tgattccagt   1380
cgcgatcgga acaaaccgtt taaattcatg ttggggaagc aagaggttat caggggatgg   1440
gaagagggtg tcgcgcaaat gtcggttggg caacgtgcga aactcacaat ttccccggat   1500
tacgcatacg gagctaccgg acaccctggg attatcccac cgcatgcgac gctagtgttt   1560
gacgtagagt tcttgaagct cgaatcaggt acaagcggca cttctggcgt acaggttgag   1620
acaattagtc ccggagacgg acgtacattc ccaaagagag gcaaacttg cgtagtccat   1680 tacactggaa tgttggaaga cggcaagaaa gtggacagtt caagaccga caataagcct   1740 ttcaagttta tgctcggaaa acaggaagtc atacgcggtt gggaggaagg cgtggctcag   1800
atgagcgtcg gacagagggc aaagttgacc atcagtcccg actatgcgta tggcgcgaca   1860
ggccatcccg gaatcatacc tccccacgca accttggtat tcgatgtcga actgctcaaa   1920
ttagagggta gtagatccat cctctggcat gagatgtggc atgaaggcct ggaagaggca   1980
tctcgtttgt actttgggga aaggaacgtg aaaggcatgt tgaggtgct ggagcccttg    2040 catgctatga tggaacgggg ccccccagact ctgaaggaaa catcctttaa tcaggcctat   2100
ggtcgagatt taatggaggc caagagtgg tgcaggaagt acatgaaatc agggaatgtc    2160
aaggacctcc tccaagcctg ggacctctat tatcatgtgt tccgacgaat ctcaaaggct   2220
agcgccaagc ctaccaccac ccctgcccct agacctccaa cacccgcccc aacaatcgcc   2280
agccagcctc tgtctctgag gcccgaggct tgtagaccag ctgctggcgg agccgtacac   2340
accagaggac tggatttcgc ctgcgacatc tacatctggg cccctctggc cggcacatgt   2400
ggcgtgctgc tgctgagcct cgtgatcacc atgcataaac ggggcagaaa gaaactcctg   2460
tatatattca acaaccatt tatgagacca gtacaaacta ctcaagagga agatggctgt    2520
agctgccgat ttccagaaga agaagaagga ggatgtgaac tgcgggtgaa gttcagcaga   2580
agcgccgacg cccctgccta ccagcagggc cagaatcagc tgtacaacga gctgaacctg   2640
```

-continued

```
ggcagaaggg aagagtacga cgtcctggat aagcggagag gccgggaccc tgagatgggc    2700
ggcaagcctc ggcggaagaa ccccccaggaa ggcctgtata cgaactgca gaaagacaag    2760 atggccgagg cctacagcga gatcggcatg aagggcgagc ggaggcgggg caagggccac    2820
gacggcctgt atcagggcct gtccaccgcc accaaggata cctacgacgc cctgcacatg    2880
caggccctgc ccccaagggg c                                              2901
```

<210> SEQ ID NO 49
<211> LENGTH: 8984
<212> TYPE: DNA
<213> ORGANISM: Artificial Sequence
<220> FEATURE:
<223> OTHER INFORMATION: SS-scFvCD19-DmrA-fuP2A-2xDmrB-DmrC-TM-41BB-CD3z
      lentiviral vector

<400> SEQUENCE: 49

```
aaaaataaac aaatagggt  tccgcgcaca tttccccgaa aagtgccacc tgacgtcaat     60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga agcgaaagg  gaaaccagag gagctctctc gacgcaggac tcggcttgct    540
gaagcgcgca cggcaagagg cgaggggcgg cgactggtga gtacgccaaa aattttgact    600
agcggaggct agaaggagag agatgggtgc gagagcgtca gtattaagcg gggagaatt    660 agatcgcgat gggaaaaaat tcggttaagg ccagggggaa agaaaaaata taaattaaaa    720
catatagtat gggcaagcag ggagctagaa cgattcgcag ttaatcctgg cctgttagaa    780
acatcagaag gctgtagaca atactgggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agagaagagt ggtgcagaga gaaaaaagag cagtgggaat aggagctttg   1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag atacctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
```

```
acccacctcc caaccccgag gggacccgac aggcccgaag gaatagaaga agaaggtgga   1800
gagagagaca gagacagatc cattcgatta gtgaacggat ctcgacggta tcggttaact   1860
tttaaaagaa aaggggggat tgggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggaggggtc ggcaattgaa ccggtgccta gagaaggtgg cgcggggtaa   2100
actgggaaag tgatgtcgtg tactggctcc gccttttcc cgagggtggg ggagaaccgt   2160
atataagtgc agtagtcgcc gtgaacgttc tttttcgcaa cgggtttgcc gccagaacac   2220
acctgcaggg ccgccaccat ggagacagac acactcctgc tatgggtact gctgctctgg   2280
gttccaggtt ccactggtga ctacaaggac gagggatccg atatccagat gacccagacc   2340
accagcagcc tgagcgccag cctgggcgat agagtgacca tcagctgcag agccagccag   2400
gacatcagca agtacctgaa ctggtatcag cagaaacccg acggcaccgt gaagctgctg   2460
atctaccaca ccagcagact gcacagcggc gtgcccagca gattttctgg cagcggctcc   2520
ggcaccgact acagcctgac catctccaac ctggaacagg aagatatcgc tacctacttc   2580
tgtcagcaag caacacccct gccctacacc ttcggcggag gcaccaagct ggaaatcacc   2640
ggcagcacaa gcggcagcgg caagcctgga tctggcgagg aagcaccaa gggcgaagtg   2700 aaactgcagg aaagcggccc tggactggtg gccccaagcc agtctctgag cgtgacctgt   2760
accgtgtccg gcgtgtccct gcctgactat ggcgtgtcct ggatcagaca gccacccaga   2820
aagggcctgg aatggctggg agtgatctgg ggcagcgaga caacctacta caacagcgcc   2880
ctgaagtccc ggctgaccat catcaaggac aactccaaga gccaggtgtt cctgaagatg   2940
aacagcctgc agaccgacga caccgccatc tactactgcg ccaagcacta ctactacggc   3000
ggcagctacg ccatggacta ctggggccag ggcacaagcg tgaccgtgtc cagcgctagc   3060
ggctcaggag gagtgcaggt tgaaaccatc tccccaggag acggcgcac cttcccgaag   3120 cgcggacaga catgcgtggt gcactacacc gggatgcttg aagatggaaa gaaattcgat   3180
tcatcgcggg acagaaacaa gcccttaag tttatgctgg gcaagcagga ggtcatccga   3240
ggctgggaag aaggggttgc ccagatgagt gtcggccaga gagccaaact gactatatca   3300
cctgactacg cctatggggc cactgggcac cctggcataa ttccgccaca cgccactctc   3360
gtcttcgatg tggagcttct aaaactggaa ggcggccgcg ctcgttacaa gcgaagtgtc   3420
tcaggatctg gcgccacgaa cttctctctg ttaaagcaag caggagatgt tgaagaaaac   3480
cccgggcctt caagatccgg cggtgtccaa gtcgaaacta tatcgcctgg cgatggcaga   3540
acgtttccca acgtggcca gacctgtgtc gtacactata ccggcatgct agaggatggg   3600
aaaaaggttg attccagtcg cgatcggaac aaaccgttta aattcatgtt ggggaagcaa   3660
gaggttatca ggggatggga agagggtgtc gcgcaaatgt cggttgggca acgtgcgaaa   3720
ctcacaattt ccccggatta cgcatacgga gctaccggac accctgggat tatcccaccg   3780
catgcgacgc tagtgtttga cgtagagttc ttgaagctcg aatcaggtac aagcggcact   3840
tctggcgtac aggttgagac aattagtccc ggagacggac gtacattccc aaagagaggg   3900
caaacttgcg tagtccatta cactggaatg ttggaagacg gcaagaaagt ggacagttca   3960
agagaccgca ataagccttt caagtttatc ctcggaaaac aggaagtcat acgcggttgg   4020
gaggaaggcg tggctcagat gagcgtcgga cagagggcaa agttgaccat cagtcccgac   4080
```

```
tatgcgtatg gcgcgacagg ccatcccgga atcatacctc cccacgcaac cttggtattc    4140
gatgtcgaac tgctcaaatt agagggtagt agatccatcc tctggcatga gatgtggcat    4200
gaaggcctgg aagaggcatc tcgtttgtac tttggggaaa ggaacgtgaa aggcatgttt    4260
gaggtgctgg agcccttgca tgctatgatg gaacggggcc cccagactct gaaggaaaca    4320
tcctttaatc aggcctatgg tcgagattta atggaggccc aagagtggtg caggaagtac    4380
atgaaatcag ggaatgtcaa ggacctcctc caagcctggg acctctatta tcatgtgttc    4440
cgacgaatct caaaggctag cgccaagcct accaccaccc ctgcccctag acctccaaca    4500
cccgccccaa caatcgccag ccagcctctg tctctgaggc ccgaggcttg tagaccagct    4560
gctggcggag ccgtacacac cagaggactg gatttcgcct gcgacatcta catctgggcc    4620
cctctggccg gcacatgtgg cgtgctgctg ctgagcctcg tgatcaccat gcataaacgg    4680
ggcagaaaga aactcctgta tatattcaaa caaccattta tgagaccagt acaaactact    4740
caagaggaag atggctgtag ctgccgattt ccagaagaag aagaaggagg atgtgaactg    4800
cgggtgaagt tcagcagaag cgccgacgcc cctgcctacc agcagggcca gaatcagctg    4860
tacaacgagc tgaacctggg cagaagggaa gagtacgacg tcctggataa gcggagaggc    4920
cgggaccctg agatgggcgg caagcctcgg cggaagaacc cccaggaagg cctgtataac    4980
gaactgcaga aagacaagat ggccgaggcc tacagcgaga tcggcatgaa gggcgagcgg    5040
aggcggggca agggccacga cggcctgtat cagggcctgt ccaccgccac caaggatacc    5100
tacgacgccc tgcacatgca ggccctgccc ccaaggggcg gccgctccgg tgagggcaga    5160
ggaagtcttc taacatgcgg tgacgtggag gagaatccgg gccctctag aagcgagctg    5220 attaaggaga acatgcacat gaagctgtac atggagggca ccgtggacaa ccatcacttc    5280
aagtgcacat ccgagggcga aggcaagccc tacgagggca cccagaccat gagaatcaag    5340
gtggtcgagg gcggccctct ccccttcgcc ttcgacatcc tggctactag cttcctctac    5400
ggcagcaaga ccttcatcaa ccacacccag ggcatccccg acttcttcaa gcagtccttc    5460
cctgagggct tcacatggga gagagtcacc acatacgaag acgggggcgt gctgaccgct    5520
acccaggaca ccagcctcca ggacggctgc ctcatctaca acgtcaagat cagaggggtg    5580
aacttcacat ccaacggccc tgtgatgcag aagaaaacac tcggctggga ggccttcacc    5640
gagacgctgt accccgctga cggcggcctg gaaggcagaa acgacatggc cctgaagctc    5700
gtgggcggga gccatctgat cgcaaacatc aagaccacat atagatccaa gaaacccgct    5760
aagaacctca gatgcctggt cgtctactat gtggactaca actgtgaaag aatcaaggag    5820
gccaacaacg agacctacgt cgagcagcac gaggtggcag tggccagata ctgcgacctc    5880
cctagcaaac tggggcacaa gcttaattga gtcgaccgag catcttaccg ccatttatac    5940
ccatatttgt tctgttttc ttgatttggg tatacattta aatgttaata gaacaaaatg    6000
gtggggcaat catttacatt tttagggata tgtaattact agttcaggtg tattgccaca    6060
agacaaacat gttaagaaac tttcccgtta tttacgctct gttcctgtta atcaacctct    6120
ggattacaaa atttgtgaaa gattgactga tattcttaac tatgttgctc cttttacgct    6180
gtgtggatat gctgctttat agcctctgta tctagctatt gcttcccgta cggctttcgt    6240
tttctcctcc ttgtataaat cctggttgct gtctctttta gaggagttgt ggcccgttgt    6300
ccgtcaacgt ggcgtggtgt gctctgtgtt tgctgacgca accccactg gctggggcat    6360 tgccaccacc tgtcaactcc tttctgggac tttcgctttc ccctcccga tcgccacggc    6420 agaactcatc gccgcctgcc ttgcccgctg ctggacaggg gctaggttgc tgggcactga    6480
```

```
taattccgtg gtgttgtcat cgaattcggt acctttttaa aagaaaaggg gggactggaa    6540
gggctaattc actcccaacg aagacaagat atcataactt cgtatagcat acattatacg    6600
aagttataat ttatttgtga aatttgtgat gctattgctt tatttgtaac catatgttta    6660
tttgtgaaat ttgtgatgct attgctttat ttgtaaccat tgcttttgc ttgtactggg     6720 tctctctggt tagaccagat ctgagcctgg gagctctctg gctaactagg gaacccactg    6780
cttaagcctc aataaagctt gccttcgacca gcctcgactg tgccttctag ttgccagcca    6840
tctgttgttt gcccctcccc cgtgccttcc ttgaccctgg aaggtgccac tcccactgtc    6900
ctttcctaat aaaatgagga aattgcatcg cattgtctga gtaggtgtca ttctattctg    6960 ggggtgggg tggggcagga cagcaagggg gaggattggg aagacaatag caggcatgct    7020
ggggatgcgg tgggctctat ggcctgcagc tgcattaatg aatcggccaa cgcgcgggga    7080
gaggcggttt gcgtattggg cgctcttccg cttcctcgct cactgactcg ctgcgctcgg    7140
tcgttcggct gcggcgagcg gtatcagctc actcaaaggc ggtaatacgg ttatccacag    7200
aatcagggga taacgcagga aagaacatgt gagcaaaagg ccagcaaaag gccaggaacc    7260
gtaaaaaggc cgcgttgctg gcgttttttcc ataggctccg ccccctgac gagcatcaca    7320 aaaatcgacg ctcaagtcag aggtggcgaa acccgacagg actataaaga taccaggcgt    7380
ttccccctgg aagctccctc gtgcgctctc ctgttccgac cctgccgctt accggatacc    7440
tgtccgcctt tctcccttcg ggaagcgtgg cgctttctca tagctcacgc tgtaggtatc    7500
tcagttcggt gtaggtcgtt cgctccaagc tgggctgtgt gcacgaaccc cccgttcagc    7560
ccgaccgctg cgccttatcc ggtaactatc gtcttgagtc caacccggta agacacgact    7620
tatcgccact ggcagcagcc actggtaaca ggattagcag agcgaggtat gtaggcggtg    7680
ctacagagtt cttgaagtgg tggcctaact acggctacac tagaaggaca gtatttggta    7740
tctgcgctct gctgaagcca gttaccttcg gaaaaagagt tggtagctct tgatccggca    7800
aacaaaccac cgctggtagc ggtggttttt tgtttgcaa gcagcagatt acgcgcagaa    7860
aaaaaggatc tcaagaagat cctttgatct tttctacggg gtctgacgct cagtggaacg    7920
aaaactcacg ttaagggatt ttggtcatga gattatcaaa aaggatcttc acctagatcc    7980
ttttaaatta aaaatgaagt tttaaatcaa tctaaagtat atatgagtaa acttggtctg    8040
acagttacca atgcttaatc agtgaggcac ctatctcagc gatctgtcta tttcgttcat    8100
ccatagttgc ctgactcccc gtcgtgtaga taactacgat acgggagggc ttaccatctg    8160
gccccagtgc tgcaatgata ccgcgagacc cacgctcacc ggctccagat ttatcagcaa    8220
taaaccagcc agccggaagg gccgagcgca gaagtggtcc tgcaacttta tccgcctcca    8280
tccagtctat taattgttgc cgggaagcta gagtaagtag ttcgccagtt aatagtttgc    8340
gcaacgttgt tgccattgct acaggcatcg tggtgtcacg ctcgtcgttt ggtatggctt    8400
cattcagctc cggttcccaa cgatcaaggc gagttacatg atcccccatg ttgtgcaaaa    8460
aagcggttag ctccttcggt cctccgatcg ttgtcagaag taagttggcc gcagtgttat    8520
cactcatggt tatggcagca ctgcataatt ctcttactgt catgccatcc gtaagatgct    8580
tttctgtgac tggtgagtac tcaaccaagt cattctgaga atagtgtatg cggcgaccga    8640
gttgctcttg cccggcgtca atacgggata ataccgcgcc acatagcaga actttaaaag    8700
tgctcatcat tggaaaacgt tcttcggggc gaaaactctc aaggatctta ccgctgttga    8760
gatccagttc gatgtaaccc actcgtgcac ccaactgatc ttcagcatct tttactttca    8820
```

```
ccagcgtttc tgggtgagca aaaacaggaa ggcaaaatgc cgcaaaaaag ggaataaggg    8880
cgacacggaa atgttgaata ctcatactct tccttttca atattattga agcatttatc    8940
agggttattg tctcatgagc ggatacatat ttgaatgtat ttag                    8984
```

<210> SEQ ID NO 50
<211> LENGTH: 406
<212> TYPE: PRT
<213> ORGANISM: Artificial Sequence
<220> FEATURE:
<223> OTHER INFORMATION: SS-CD19scFv-DmrA-CD4TM protein

<400> SEQUENCE: 50

```
Met Pro Leu Gly Leu Leu Trp Leu Gly Leu Ala Leu Leu Gly Ala Leu
1               5                  10                  15

His Ala Gln Ala Gly Ser Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ser Gly Gly Gly
            260                 265                 270

Gly Ser Gly Val Gln Val Glu Thr Ile Ser Pro Gly Asp Gly Arg Thr
        275                 280                 285

Phe Pro Lys Arg Gly Gln Thr Cys Val Val His Tyr Thr Gly Met Leu
    290                 295                 300

Glu Asp Gly Lys Lys Phe Asp Ser Ser Arg Asp Arg Asn Lys Pro Phe
305                 310                 315                 320

Lys Phe Met Leu Gly Lys Gln Glu Val Ile Arg Gly Trp Glu Glu Gly
                325                 330                 335
```

```
Val Ala Gln Met Ser Val Gly Gln Arg Ala Lys Leu Thr Ile Ser Pro
            340                 345                 350

Asp Tyr Ala Tyr Gly Ala Thr Gly His Pro Gly Ile Ile Pro Pro His
        355                 360                 365

Ala Thr Leu Val Phe Asp Val Glu Leu Leu Lys Leu Glu Gly Gly Arg
    370                 375                 380

Met Ala Leu Ile Val Leu Gly Val Ala Gly Leu Leu Leu Phe Ile
385                 390                 395                 400

Gly Leu Gly Ile Phe Phe
            405

<210> SEQ ID NO 51
<211> LENGTH: 1218
<212> TYPE: DNA
<213> ORGANISM: Artificial Sequence
<220> FEATURE:
<223> OTHER INFORMATION: SS-CD19scFv-DmrA-CD4TM DNA

<400> SEQUENCE: 51
atgcccctgg gcctgctgtg gctgggcctg gccctgctgg gcgccctgca cgcccaggcc      60
ggatccgata tccagatgac ccagaccacc agcagcctga cgccagcct gggcgataga     120 gtgaccatca gctgcagagc cagccaggac atcagcaagt acctgaactg gtatcagcag     180
aaacccgacg gcaccgtgaa gctgctgatc taccacacca gcagactgca cagcggcgtg     240
cccagcagat tttctggcag cggctccggc accgactaca gcctgaccat ctccaacctg     300
gaacaggaag atatcgctac ctacttctgt cagcaaggca cacccctgcc ctacaccttc     360
ggcggaggca ccaagctgga aatcaccggc agcacaagcg gcagcggcaa gcctggatct     420
ggcgagggaa gcaccaaggg cgaagtgaaa ctgcaggaaa gcggccctgg actggtggcc     480
ccaagccagt ctctgagcgt gacctgtacc gtgtccggcg tgtccctgcc tgactatggc     540
gtgtcctgga tcagacagcc acccagaaag ggcctggaat ggctgggagt gatctggggc     600
agcgagacaa cctactacaa cagcgccctg aagtcccggc tgaccatcat caaggacaac     660
tccaagagcc aggtgttcct gaagatgaac agcctgcaga ccgacgacac cgccatctac     720
tactgcgcca agcactacta ctacggcggc agctacgcca tggactactg gggccagggc     780
acaagcgtga ccgtgtccag cgctagcggc ggaggtggga gcggagtgca ggtggaaacc     840
atctccccag agacgggcg caccttcccc agcgcggcc agacctgcgt ggtgcactac     900
accgggatgc ttgaagatgg aaagaaattt gattcctccc gggacagaaa caagcccttt     960
aagtttatgc taggcaagca ggaggtgatc cgaggctggg aagaagggt gcccagatg    1020 agtgtgggtc agagagccaa actgactata tctccagatt atgcctatgg tgccactggg    1080
cacccaggca tcatcccacc acatgccact ctcgtcttcg atgtggagct tctaaaactg    1140
gaaggcggcc gcatggccct gattgtgctg ggggcgtcg ccggcctcct gcttttcatt    1200
gggctaggca tcttcttc                                                   1218

<210> SEQ ID NO 52
<211> LENGTH: 7336
<212> TYPE: DNA
<213> ORGANISM: Artificial Sequence
<220> FEATURE:
<223> OTHER INFORMATION: pCVL_sEF1a-T7-hScnSS-CD19scFv-DmrA-CD4TM
      lentiviral vector

<400> SEQUENCE: 52
aaaaataaac aaatagggg t tccgcgcaca tttccccgaa aagtgccacc tgacgtcaat      60
```

```
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga aagcgaaagg gaaaccagag gagctctctc gacgcaggac tcggcttgct    540
gaagcgcgca cggcaagagg cgaggggcgg cgactggtga gtacgccaaa aattttgact    600
agcggaggct agaaggagag agatgggtgc gagagcgtca gtattaagcg gggagaatt    660 agatcgcgat gggaaaaaat tcggttaagg ccaggggg aa agaaaaaata taaattaaaa    720
catatagtat gggcaagcag ggagctagaa cgattcgcag ttaatcctgg cctgttagaa    780
acatcagaag gctgtagaca atactgggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat   1020
tggagaagtg aattatataa atataaagta gtaaaaattg aaccattagg agtagcaccc   1080
accaaggcaa agaagaagt ggtgcagaga gaaaaaagag cagtgggaat aggagctttg   1140
ttccttgggt tcttgggagc agcaggaagc actatgggcg cagcgtcaat gacgctgacg   1200
gtacaggcca gacaattatt gtctggtata gtgcagcagc agaacaattt gctgagggct   1260
attgaggcgc aacagcatct gttgcaactc acagtctggg gcatcaagca gctccaggca   1320
agaatcctgg ctgtggaaag ataccctaaag gatcaacagc tcctggggat ttggggttgc   1380
tctggaaaac tcatttgcac cactgctgtg ccttggaatg ctagttggag taatgaatct   1440
ctggaacaga tttggaatca cacgacctgg atggagtggg acagagaaat taacaattac   1500
acaagcttaa tacactcctt aattgaagaa tcgcaaaacc agcaagaaaa gaatgaacaa   1560
gaattattgg aattagataa atgggcaagt ttgtggaatt ggtttaacat aacaaattgg   1620
ctgtggtata taaaattatt cataatgata gtaggaggct tggtaggttt aagaatagtt   1680
tttgctgtac tttctatagt gaatagagtt aggcagggat attcaccatt atcgtttcag   1740
acccacctcc caaccccgag gggacccgac aggcccgaag gaatagaaga gaaggtggag  1800
gagagagaca gagacagatc cattcgatta gtgaacggat ctcgacggta tcggttaact   1860
tttaaaagaa aagggggggat tggggggtac agtgcagggg aaagaatagt agacataata   1920
gcaacagaca tacaaactaa agaattacaa aaacaaatta caaaaattca aaattttatc   1980
gattacgcgt aggctccggt gcccgtcagt gggcagagcg cacatcgccc acagtccccg   2040
agaagttggg gggaggggtc ggcaattgaa ccggtgccta gagaaggtgg cgcggggtaa   2100
actgggaaag tgatgtcgtg tactggctcc gccttttttcc cgagggtggg ggagaaccgt   2160
atataagtgc agtagtcgcc gtgaacgttc tttttcgcaa cgggtttgcc gccagaacac   2220
acctgcaggt aatacgactc actatagggt ccactgccgc caccatgccc ctgggcctgc   2280
tgtggctggg cctggccctg ctgggcgccc tgcacgccca ggccggatcc gatatccaga   2340
tgacccagac caccagcagc ctgagcgcca gcctgggcga tagagtgacc atcagctgca   2400
```

```
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag aagatatcg    2580
ctacctactt ctgtcagcaa ggcaacaccc tgccctacac cttcggcgga ggcaccaagc    2640
tggaaatcac cggcagcaca agcggcagcg gcaagcctgg atctggcgag ggaagcacca    2700
agggcgaagt gaaactgcag gaaagcggcc ctggactggt ggcccaagc cagtctctga    2760
gcgtgacctg taccgtgtcc ggcgtgtccc tgcctgacta tggcgtgtcc tggatcagac    2820
agccacccag aaagggcctg gaatggctgg gagtgatctg gggcagcgag acaacctact    2880
acaacagcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt ggagcgag tgcaggtgga aaccatctcc ccaggagacg    3120
gccgcaccttt ccccaagcgc ggccagacct gcgtggtgca ctacaccggg atgcttgaag    3180
atggaaagaa atttgattcc tcccgggaca gaaacaagcc cttttaagttt atgctaggca    3240
agcaggaggt gatccgaggc tgggaagaag gggttgccca tgagtgtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgcatgg    3420
ccctgattgt gctggggggc gtcgccggcc tcctgctttt cattgggcta ggcatcttct    3480
tcatgcattc cggtgagggc agaggaagtc ttctaacatg cggtgacgtg gaggagaatc    3540
cgggccccctc tagagtgagc aagggcgagg aggataacat ggccatcatc aaggagttca    3600
tgcgcttcaa ggtgcacatg gagggctccg tgaacggcca cgagttcgag atcgagggcg    3660
agggcgaggg ccgcccctac gagggcaccc agaccgccaa gctgaaggtg accaagggtg    3720
gccccctgcc cttcgcctgg gacatcctgt cccctcagtt catgtacggc tccaaggcct    3780
acgtgaagca ccccgccgac atccccgact acttgaagct gtccttcccc gagggcttca    3840
agtgggagcg cgtgatgaac ttcgaggacg gcggcgtggt gaccgtgacc caggactcct    3900
ctctgcagga cggcgagttc atctacaagg tgaagctgcg cggcaccaac ttcccctccg    3960
acggccccgt aatgcagaag aagactatgg gctgggaggc ctcctccgag cggatgtacc    4020
ccgaggacgg cgccctgaag ggcgagatca agcagaggct gaagctgaag gacggcggcc    4080
actacgacgc tgaggtcaag accacctaca aggccaagaa gcccgtgcag ctgcccggcg    4140
cctacaacgt caacatcaag ttggacatca cctcccacaa cgaggactac accatcgtgg    4200
aacagtacga acgcgccgag ggccgccact ccaccggcgg catggacgag ctgtacaagt    4260
aagtcgaccg agcatcttac cgccatttat acccatattt gttctgtttt tcttgatttg    4320
ggtatacatt taaatgttaa tagaacaaaa tggtggggca atcatttaca ttttagggga    4380
tatgtaatta ctagttcagg tgtattgcca caagacaaac atgttaagaa actttcccgt    4440
tatttacgct ctgttcctgt taatcaacct ctggattaca aaatttgtga agattgact    4500
gatattctta actatgttgc tcctttacg ctgtgtggat atgctgcttt atagcctctg    4560
tatctagcta ttgcttcccg tacggctttc gttttctcct ccttgtataa atcctggttg    4620
ctgtctcttt tagaggagtt gtggcccgtt gtccgtcaac gtggcgtggt gtgctctgtg    4680
tttgctgacg caacccccac tggctggggc attgccacca cctgtcaact cctttctggg    4740
actttcgctt tcccccctccc gatcgccacg gcagaactca tcgccgcctg ccttgcccgc    4800
```

-continued

```
tgctggacag gggctaggtt gctgggcact gataattccg tggtgttgtc atcgaattcg    4860 gtacctttt  aaaagaaaag gggggactgg aagggctaat tcactcccaa cgaagacaag    4920
atatcataac ttcgtatagc atacattata cgaagttata atttatttgt gaaatttgtg    4980
atgctattgc tttatttgta accatatgtt tatttgtgaa atttgtgatg ctattgcttt    5040
atttgtaacc attgcttttt gcttgtactg ggtctctctg gttagaccag atctgagcct    5100
gggagctctc tggctaacta gggaacccac tgcttaagcc tcaataaagc ttgcctcgac    5160
cagcctcgac tgtgccttct agttgccagc catctgttgt ttgcccctcc ccgtgcctt     5220 ccttgaccct ggaaggtgcc actcccactg tcctttccta ataaaatgag gaaattgcat    5280
cgcattgtct gagtaggtgt cattctattc tggggggtgg ggtggggcag gacagcaagg    5340
gggaggattg ggaagacaat agcaggcatg ctggggatgc ggtgggctct atggcctgca    5400
gctgcattaa tgaatcggcc aacgcgcggg gagaggcggt ttgcgtattg ggcgctcttc    5460
cgcttcctcg ctcactgact cgctgcgctc ggtcgttcgg ctgcggcgag cggtatcagc    5520
tcactcaaag gcggtaatac ggttatccac agaatcaggg gataacgcag gaaagaacat    5580
gtgagcaaaa ggccagcaaa aggccaggaa ccgtaaaaag gccgcgttgc tggcgttttt    5640
ccataggctc cgcccccctg acgagcatca caaaaatcga cgctcaagtc agaggtggcg    5700
aaacccgaca ggactataaa gataccaggc gtttccccct ggaagctccc tcgtgcgctc    5760
tcctgttccg accctgccgc ttaccggata cctgtccgcc tttctccctt cgggaagcgt    5820
ggcgctttct catagctcac gctgtaggta tctcagttcg gtgtaggtcg ttcgctccaa    5880
gctgggctgt gtgcacgaac ccccgttca  gcccgaccgc tgcgccttat ccggtaacta    5940
tcgtcttgag tccaacccgg taagacacga cttatcgcca ctggcagcag ccactggtaa    6000
caggattagc agagcgaggt atgtaggcgg tgctacagag ttcttgaagt ggtggcctaa    6060
ctacggctac actagaagga cagtatttgg tatctgcgct ctgctgaagc cagttacctt    6120
cggaaaaaga gttggtagct cttgatccgg caaacaaacc accgctggta gcggtggttt    6180
ttttgtttgc aagcagcaga ttacgcgcag aaaaaaagga tctcaagaag atcctttgat    6240
cttttctacg gggtctgacg ctcagtggaa cgaaaactca cgttaaggga ttttggtcat    6300
gagattatca aaaaggatct tcacctagat ccttttaaat taaaaatgaa gttttaaatc    6360
aatctaaagt atatatgagt aaacttggtc tgacagttac caatgcttaa tcagtgaggc    6420
acctatctca gcgatctgtc tatttcgttc atccatagtt gcctgactcc ccgtcgtgta    6480
gataactacg atacgggagg gcttaccatc tggccccagt gctgcaatga taccgcgaga    6540
cccacgctca ccggctccag atttatcagc aataaaccag ccagccggaa gggccgagcg    6600
cagaagtggt cctgcaactt tatccgcctc catccagtct attaattgtt gccgggaagc    6660
tagagtaagt agttcgccag ttaatagttt gcgcaacgtt gttgccattg ctacaggcat    6720
cgtggtgtca cgctcgtcgt ttggtatggc ttcattcagc tccggttccc aacgatcaag    6780
gcgagttaca tgatccccca tgttgtgcaa aaaagcggtt agctccttcg gtcctccgat    6840
cgttgtcaga agtaagttgg ccgcagtgtt atcactcatg gttatggcag cactgcataa    6900
ttctcttact gtcatgccat ccgtaagatg cttttctgtg actggtgagt actcaaccaa    6960
gtcattctga gaatagtgta tgcggcgacc gagttgctct tgcccggcgt caatacggga    7020
taataccgcg ccacatagca gaactttaaa agtgctcatc attggaaaac gttcttcggg    7080
gcgaaaactc tcaaggatct taccgctgtt gagatccagt tcgatgtaac ccactcgtgc    7140
```

```
acccaactga tcttcagcat cttttacttt caccagcgtt tctgggtgag caaaaacagg    7200
aaggcaaaat gccgcaaaaa agggaataag ggcgacacgg aaatgttgaa tactcatact    7260 cttcctttt  caatattatt gaagcattta tcagggttat tgtctcatga gcggatacat    7320
atttgaatgt atttag                                                     7336
```

<210> SEQ ID NO 53
<211> LENGTH: 453
<212> TYPE: PRT
<213> ORGANISM: Artificial Sequence
<220> FEATURE:
<223> OTHER INFORMATION: SS-CD19scFv-DmrA-CD8hingeTM protein

<400> SEQUENCE: 53

```
Met Pro Leu Gly Leu Leu Trp Leu Gly Leu Ala Leu Leu Gly Ala Leu
1               5                   10                  15

His Ala Gln Ala Gly Ser Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ser Gly Gly Gly
            260                 265                 270

Gly Ser Gly Val Gln Val Glu Thr Ile Ser Pro Gly Asp Gly Arg Thr
        275                 280                 285

Phe Pro Lys Arg Gly Gln Thr Cys Val Val His Tyr Thr Gly Met Leu
    290                 295                 300

Glu Asp Gly Lys Lys Phe Asp Ser Ser Arg Asp Arg Asn Lys Pro Phe
305                 310                 315                 320

Lys Phe Met Leu Gly Lys Gln Glu Val Ile Arg Gly Trp Glu Glu Gly
```

```
            325                 330                 335
Val Ala Gln Met Ser Val Gly Gln Arg Ala Lys Leu Thr Ile Ser Pro
            340                 345                 350

Asp Tyr Ala Tyr Gly Ala Thr Gly His Pro Gly Ile Ile Pro Pro His
        355                 360                 365

Ala Thr Leu Val Phe Asp Val Glu Leu Leu Lys Leu Glu Gly Gly Arg
        370                 375                 380

Ala Lys Pro Thr Thr Thr Pro Ala Pro Arg Pro Pro Thr Pro Ala Pro
385                 390                 395                 400

Thr Ile Ala Ser Gln Pro Leu Ser Leu Arg Pro Glu Ala Cys Arg Pro
                405                 410                 415

Ala Ala Gly Gly Ala Val His Thr Arg Gly Leu Asp Phe Ala Cys Asp
                420                 425                 430

Ile Tyr Ile Trp Ala Pro Leu Ala Gly Thr Cys Gly Val Leu Leu Leu
                435                 440                 445

Ser Leu Val Ile Thr
        450

<210> SEQ ID NO 54
<211> LENGTH: 1359
<212> TYPE: DNA
<213> ORGANISM: Artificial Sequence
<220> FEATURE:
<223> OTHER INFORMATION: SS-CD19scFv-DmrA-CD8hingeTM DNA

<400> SEQUENCE: 54
atgcccctgg gcctgctgtg gctgggcctg gccctgctgg gcgccctgca cgcccaggcc      60
ggatccgata tccagatgac ccagaccacc agcagcctga gcgccagcct gggcgatcga     120
gtgaccatca gctgcagagc cagccaggac atcagcaagt acctgaactg gtatcagcag     180
aaacccgacg gcaccgtgaa gctgctgatc taccacacca gcagactgca cagcggcgtg     240
cccagcagat ttctggcag cggctccggc accgactaca gcctgaccat ctccaacctg      300
gaacaggaag atatcgctac ctacttctgt cagcaaggca cacccctgcc ctacaccttc     360
ggcggaggca ccaagctgga aatcaccggc agcacaagcg gcagcggcaa gcctggatct     420
ggcgagggaa gcaccaaggg cgaagtgaaa ctgcaggaaa gcggccctgg actggtggcc     480
ccaagccagt ctctgagcgt gacctgtacc gtgtccggcg tgtccctgcc tgactatggc     540
gtgtcctgga tcagacagcc acccagaaag ggcctggaat ggctgggagt gatctggggc     600
agcgagacaa cctactacaa cagcgccctg aagtcccggc tgaccatcat caaggacaac     660
tccaagagcc aggtgttcct gaagatgaac agcctgcaga ccgacgacac cgccatctac     720
tactgcgcca gcactacta ctacggcggc agctacgcca tggactactg gggccagggc      780
acaagcgtga ccgtgtccag cgctagcggc ggaggtggga gcggagtgca ggtggaaacc     840
atctccccag agacgggcg caccttcccc aagcgcggcc agacctgcgt ggtgcactac      900
accgggatgc ttgaagatgg aaagaaattt gattcctccc gggacagaaa caagcccttt     960
aagtttatgc taggcaagca ggaggtgatc cgaggctggg aagaagggt tgcccagatg     1020 agtgtgggtc agagagccaa actgactata tctccagatt atgcctatgg tgccactggg    1080
cacccaggca tcatcccacc acatgccact ctcgtcttcg atgtggagct tctaaaactg    1140
gaaggcggcc gcgccaagcc taccaccacc cctgccccta gacctccaac cccgcccca    1200 acaatcgcca gccagcctct gtctctgagg cccgaggctt gtagaccagc tgctggcgga    1260
gccgtgcaca ccagaggact ggatttcgcc tgcgacatct acatctgggc ccctctggcc    1320
```

```
ggcacatgtg gcgtgctgct gctgagcctc gtgatcacc                          1359
```

<210> SEQ ID NO 55
<211> LENGTH: 7477
<212> TYPE: DNA
<213> ORGANISM: Artificial Sequence
<220> FEATURE:
<223> OTHER INFORMATION: pCVL_sEF1a-T7-hScnSS-CD19scFv-DmrA-CD8hingeTM
      lentiviral vector

<400> SEQUENCE: 55

```
aaaaataaac aaatagggt tccgcgcaca tttccccgaa aagtgccacc tgacgtcaat     60
gtagtcttat gcaatactct tgtagtcttg caacatggta acgatgagtt agcaacatgc   120
cttacaagga gagaaaaagc accgtgcatg ccgattggtg aagtaaggt ggtacgatcg    180
tgccttatta ggaaggcaac agacgggtct gacatggatt ggacgaacca ctgaattgcc   240
gcattgcaga gatattgtat ttaagtgcct agctcgatac ataaacgggt ctctctggtt   300
agaccagatc tgagcctggg agctctctgg ctaactaggg aacccactgc ttaagcctca   360
ataaagcttg ccttgagtgc ttcaagtagt gtgtgcccgt ctgttgtgtg actctggtaa   420
ctagagatcc ctcagaccct tttagtcagt gtggaaaatc tctagcagtg gcgcccgaac   480
agggacttga agcgaaagg gaaaccagag agctctctc gacgcaggac tcggcttgct    540
gaagcgcgca cggcaagagg cgaggggcgg cgactggtga gtacgccaaa attttgact    600
agcggaggct agaaggagag atgggtgc gagagcgtca gtattaagcg ggggagaatt     660
agatcgcgat gggaaaaaat tcggttaagg ccagggggga agaaaaata taaattaaaa   720
catatagtat gggcaagcag ggagctagaa cgattcgcag ttaatcctgg cctgttagaa   780
acatcagaag gctgtagaca atactgggga cagctacaac catcccttca gacaggatca   840
gaagaactta gatcattata ataacagta gcaaccctct attgtgtgca tcaaaggata    900
gagataaaag acaccaagga agctttagac aagatagagg aagagcaaaa caaaagtaag   960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcaggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aagggggat tggggggtac agtgcagggg aaagaatagt agacataata  1920
gcaacagaca tacaaactaa agaattacaa aaacaaatta caaaaattca aaattttatc  1980
```

```
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gccttttcc cgagggtggg ggagaaccgt    2160
atataagtgc agtagtcgcc gtgaacgttc ttttcgcaa cgggtttgcc gccagaacac    2220
acctgcaggt aatacgactc actatagggt ccactgccgc caccatgccc ctgggcctgc    2280
tgtggctggg cctggccctg ctgggcgccc tgcacgccca ggccggatcc gatatccaga    2340
tgacccagac caccagcagc ctgagcgcca gcctgggcga tagagtgacc atcagctgca    2400
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag gaagatatcg    2580
ctacctactt ctgtcagcaa ggcaacaccc tgccctacac cttcggcgga ggcaccaagc    2640
tggaaatcac cggcagcaca agcggcagcg gcaagcctgg atctggcgag gaagcacca    2700 agggcgaagt gaaactgcag gaaagcggcc ctggactggt ggccccaagc cagtctctga    2760
gcgtgacctg taccgtgtcc ggcgtgtccc tgcctgacta tggcgtgtcc tggatcagac    2820
agccacccag aaagggcctg aatggctgg gagtgatctg gggcagcgag acaacctact    2880
acaacagcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt gggagcggag tgcaggtgga aaccatctcc ccaggagacg    3120 gcgcacctt ccccaagcgc ggccagacct gcgtggtgca ctacaccggg atgcttgaag    3180
atggaaagaa atttgattcc tcccgggaca gaaacaagcc ctttaagttt atgctaggca    3240
agcaggaggt gatccgaggc tgggaagaag gggttgccca gatgagtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgcgcca    3420
agcctaccac caccctgcc cctagacctc aacacccgc cccaacaatc gccagccagc    3480
ctctgtctct gaggcccgag gcttgtagac agctgctgg cggagccgtg cacaccagag    3540
gactggattt cgcctgcgac atctacatct gggcccctct ggccggcaca tgtggcgtgc    3600
tgctgctgag cctcgtgatc accatgcatt ccggtgaggg cagaggaagt cttctaacat    3660
gcggtgacgt ggaggagaat ccgggcccct ctagagtgag caagggcgag gaggataaca    3720
tggccatcat caaggagttc atgcgcttca aggtgcacat ggagggctcc gtgaacggcc    3780
acgagttcga gatcgagggc gagggcgagg ccgcccta cgagggcacc cagaccgcca    3840
agctgaaggt gaccaagggt ggccccctgc ccttcgcctg gacatcctg tccctcagt    3900 tcatgtacgg ctccaaggcc tacgtgaagc acccccgcga catccccgac tacttgaagc    3960
tgtccttccc cgagggcttc aagtgggagc gcgtgatgaa cttcgaggac ggcggcgtgg    4020
tgaccgtgac ccaggactcc tctctgcagg acggcgagtt catctacaag gtgaagctgc    4080
gcggcaccaa cttcccctcc gacggccccg taatgcagaa gaagactatg ggctgggagg    4140
cctcctccga gcggatgtac cccgaggacg gcgccctgaa gggcgagatc aagcagaggc    4200
tgaagctgaa ggacggcggc cactacgacg ctgaggtcaa gaccacctac aaggccaaga    4260
agcccgtgca gctgcccggc gcctacaacg tcaacatcaa gttggacatc acctcccaca    4320
```

```
acgaggacta caccatcgtg gaacagtacg aacgcgccga gggccgccac tccaccggcg    4380
gcatggacga gctgtacaag taagtcgacc gagcatctta ccgccattta tacccatatt    4440
tgttctgttt ttcttgattt gggtatacat ttaaatgtta atagaacaaa atggtggggc    4500
aatcatttac atttttaggg atatgtaatt actagttcag gtgtattgcc acaagacaaa    4560
catgttaaga aactttcccg ttatttacgc tctgttcctg ttaatcaacc tctggattac    4620
aaaatttgtg aaagattgac tgatattctt aactatgttg ctccttttac gctgtgtgga    4680
tatgctgctt tatagcctct gtatctagct attgcttccc gtacggcttt cgttttctcc    4740
tccttgtata aatcctggtt gctgtctctt ttagaggagt tgtggcccgt tgtccgtcaa    4800
cgtggcgtgg tgtgctctgt gtttgctgac gcaaccccca ctggctgggg cattgccacc    4860
acctgtcaac tccttctgg actttcgct ttccccctcc cgatcgccac ggcagaactc    4920
atcgccgcct gccttgcccg ctgctggaca ggggctaggt tgctgggcac tgataattcc    4980
gtggtgttgt catcgaattc ggtacctttt taaaagaaaa ggggggactg aagggctaa    5040 ttcactccca acgaagacaa gatatcataa cttcgtatag catacattat acgaagttat    5100
aatttatttg tgaaatttgt gatgctattg ctttatttgt aaccatatgt ttatttgtga    5160
aatttgtgat gctattgctt tatttgtaac cattgctttt tgcttgtact gggtctctct    5220
ggttagacca gatctgagcc tgggagctct ctggctaact agggaaccca ctgcttaagc    5280
ctcaataaag cttgcctcga ccagcctcga ctgtgccttc tagttgccag ccatctgttg    5340 tttgccccte cccegtgcct ccttgaccc tggaaggtgc cactcccact gtcctttcct    5400
aataaaatga ggaaattgca tcgcattgtc tgagtaggtg tcattctatt ctgggggtg    5460 gggtggggca ggacagcaag ggggaggatt gggaagacaa tagcaggcat gctggggatg    5520
cggtgggctc tatggcctgc agctgcatta atgaatcggc caacgcgcgg ggagaggcgg    5580
tttgcgtatt gggcgctctt ccgcttcctc gctcactgac tcgctgcgct cggtcgttcg    5640
gctgcggcga gcggtatcag ctcactcaaa ggcggtaata cggttatcca cagaatcagg    5700
ggataacgca ggaaagaaca tgtgagcaaa aggccagcaa aaggccagga accgtaaaaa    5760
ggccgcgttg ctggcgtttt tccataggct ccgcccccct gacgagcatc acaaaaatcg    5820
acgctcaagt cagaggtggc gaaacccgac aggactataa agataccagg cgtttccccc    5880
tggaagctcc ctcgtgcgct ctcctgttcc gaccctgccg cttaccggat acctgtccgc    5940 cttctccct tcgggaagcg tggcgctttc tcatagctca cgctgtaggt atctcagttc    6000
ggtgtaggtc gttcgctcca agctgggctg tgtgcacgaa ccccccgttc agcccgaccg    6060
ctgcgcctta tccggtaact atcgtcttga gtccaacccg gtaagacacg acttatcgcc    6120
actggcagca gccactggta acaggattag cagagcgagg tatgtaggcg gtgctacaga    6180
gttcttgaag tggtggccta actacggcta cactagaagg acagtatttg gtatctgcgc    6240
tctgctgaag ccagttacct tcggaaaaag agttggtagc tcttgatccg gcaaacaaac    6300
caccgctggt agcggtggtt ttttgtttg caagcagcag attacgcgca gaaaaaaagg    6360
atctcaagaa gatcctttga tcttttctac ggggtctgac gctcagtgga acgaaaactc    6420
acgttaaggg attttggtca tgagattatc aaaaaggatc ttcacctaga tccttttaaa    6480
ttaaaaatga agttttaaat caatctaaag tatatatgag taaacttggt ctgacagtta    6540
ccaatgctta atcagtgagg cacctatctc agcgatctgt ctatttcgtt catccatagt    6600
tgcctgactc cccgtcgtgt agataactac gatacgggag ggcttaccat ctggccccag    6660
tgctgcaatg ataccgcgag acccacgctc accggctcca gatttatcag caataaacca    6720
```

```
gccagccgga agggccgagc gcagaagtgg tcctgcaact ttatccgcct ccatccagtc    6780
tattaattgt tgccgggaag ctagagtaag tagttcgcca gttaatagtt tgcgcaacgt    6840
tgttgccatt gctacaggca tcgtggtgtc acgctcgtcg tttggtatgg cttcattcag    6900
ctccggttcc caacgatcaa ggcgagttac atgatccccc atgttgtgca aaaaagcggt    6960
tagctccttc ggtcctccga tcgttgtcag aagtaagttg gccgcagtgt tatcactcat    7020
ggttatggca gcactgcata attctcttac tgtcatgcca tccgtaagat gcttttctgt    7080
gactggtgag tactcaacca agtcattctg agaatagtgt atgcggcgac cgagttgctc    7140
ttgcccggcg tcaatacggg ataataccgc gccacatagc agaactttaa aagtgctcat    7200
cattggaaaa cgttcttcgg ggcgaaaact ctcaaggatc ttaccgctgt tgagatccag    7260
ttcgatgtaa cccactcgtg cacccaactg atcttcagca tcttttactt tcaccagcgt    7320
ttctgggtga gcaaaaacag gaaggcaaaa tgccgcaaaa aagggaataa gggcgacacg    7380
gaaatgttga atactcatac tcttcctttt tcaatattat tgaagcattt atcagggtta    7440
ttgtctcatg agcggataca tatttgaatg tatttag                             7477
```

<210> SEQ ID NO 56
<211> LENGTH: 635
<212> TYPE: PRT
<213> ORGANISM: Artificial Sequence
<220> FEATURE:
<223> OTHER INFORMATION: SS-CD19scFv-DmrA-Spacer-CD4TM protein

<400> SEQUENCE: 56

```
Met Pro Leu Gly Leu Leu Trp Leu Gly Leu Ala Leu Leu Gly Ala Leu
1               5                   10                  15

His Ala Gln Ala Gly Ser Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220
```

-continued

```
Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ser Gly Gly Gly
                260                 265                 270

Gly Ser Gly Val Gln Val Glu Thr Ile Ser Pro Gly Asp Gly Arg Thr
            275                 280                 285

Phe Pro Lys Arg Gly Gln Thr Cys Val Val His Tyr Thr Gly Met Leu
        290                 295                 300

Glu Asp Gly Lys Lys Phe Asp Ser Ser Arg Asp Arg Asn Lys Pro Phe
305                 310                 315                 320

Lys Phe Met Leu Gly Lys Gln Glu Val Ile Arg Gly Trp Glu Glu Gly
                325                 330                 335

Val Ala Gln Met Ser Val Gly Gln Arg Ala Lys Leu Thr Ile Ser Pro
                340                 345                 350

Asp Tyr Ala Tyr Gly Ala Thr Gly His Pro Gly Ile Ile Pro Pro His
            355                 360                 365

Ala Thr Leu Val Phe Asp Val Glu Leu Leu Lys Leu Glu Gly Gly Arg
370                 375                 380

Glu Ser Lys Tyr Gly Pro Pro Cys Pro Pro Cys Pro Ala Pro Glu Phe
385                 390                 395                 400

Leu Gly Gly Pro Ser Val Phe Leu Phe Pro Pro Lys Pro Lys Asp Thr
                405                 410                 415

Leu Met Ile Ser Arg Thr Pro Glu Val Thr Cys Val Val Val Asp Val
                420                 425                 430

Ser Gln Glu Asp Pro Glu Val Gln Phe Asn Trp Tyr Val Asp Gly Val
            435                 440                 445

Glu Val His Asn Ala Lys Thr Lys Pro Arg Glu Gln Phe Asn Ser
            450                 455                 460

Thr Tyr Arg Val Val Ser Val Leu Thr Val Leu His Gln Asp Trp Leu
465                 470                 475                 480

Asn Gly Lys Glu Tyr Lys Cys Lys Val Ser Asn Lys Gly Leu Pro Ser
                485                 490                 495

Ser Ile Glu Lys Thr Ile Ser Lys Ala Lys Gly Gln Pro Arg Glu Pro
            500                 505                 510

Gln Val Tyr Thr Leu Pro Pro Ser Gln Glu Glu Met Thr Lys Asn Gln
        515                 520                 525

Val Ser Leu Thr Cys Leu Val Lys Gly Phe Tyr Pro Ser Asp Ile Ala
530                 535                 540

Val Glu Trp Glu Ser Asn Gly Gln Pro Glu Asn Asn Tyr Lys Thr Thr
545                 550                 555                 560

Pro Pro Val Leu Asp Ser Asp Gly Ser Phe Phe Leu Tyr Ser Arg Leu
                565                 570                 575

Thr Val Asp Lys Ser Arg Trp Gln Glu Gly Asn Val Phe Ser Cys Ser
            580                 585                 590

Val Met His Glu Ala Leu His Asn His Tyr Thr Gln Lys Ser Leu Ser
        595                 600                 605

Leu Ser Leu Gly Lys Met Ala Leu Ile Val Leu Gly Gly Val Ala Gly
        610                 615                 620

Leu Leu Leu Phe Ile Gly Leu Gly Ile Phe Phe
625                 630                 635
```

<210> SEQ ID NO 57
<211> LENGTH: 1905
<212> TYPE: DNA
<213> ORGANISM: Artificial Sequence
<220> FEATURE:
<223> OTHER INFORMATION: SS-CD19scFv-DmrA-Spacer-CD4TM DNA

<400> SEQUENCE: 57

```
atgcccctgg gcctgctgtg gctgggcctg gccctgctgg gcgccctgca cgcccaggcc      60
ggatccgata tccagatgac ccagaccacc agcagcctga cgccagcct gggcgataga      120
gtgaccatca gctgcagagc cagccaggac atcagcaagt acctgaactg gtatcagcag     180
aaacccgacg gcaccgtgaa gctgctgatc taccacacca gcagactgca cagcggcgtg     240
cccagcagat ttctggcag cggctccggc accgactaca gcctgaccat ctccaacctg      300
gaacaggaag atatcgctac ctacttctgt cagcaaggca cacccctgcc ctacaccttc     360
ggcggaggca ccaagctgga aatcaccggc agcacaagcg gcagcggcaa gcctggatct     420
ggcgagggaa gcaccaaggg cgaagtgaaa ctgcaggaaa gcggccctgg actggtggcc     480
ccaagccagt ctctgagcgt gacctgtacc gtgtccggcg tgtccctgcc tgactatggc     540
gtgtcctgga tcagacagcc acccagaaag ggcctggaat ggctgggagt gatctggggc     600
agcgagacaa cctactacaa cagcgccctg aagtcccggc tgaccatcat caaggacaac     660
tccaagagcc aggtgttcct gaagatgaac agcctgcaga ccgacgacac cgccatctac     720
tactgcgcca gcactacta ctcggcggc agctacgcca tggactactg gggccagggc      780
acaagcgtga ccgtgtccag cgctagcggc ggaggtggga gcggagtgca ggtgaaaacc     840
atctccccag agacgggcg caccttcccc aagcgcggcc agacctgcgt ggtgcactac     900
accgggatgc ttgaagatgg aaagaaattt gattcctccc gggacagaaa caagcccttt     960
aagtttatgc taggcaagca ggaggtgatc cgaggctggg aagaagggt tgcccagatg     1020
agtgtgggtc agagagccaa actgactata tctccagatt atgcctatgg tgccactggg     1080
cacccaggca tcatcccacc acatgccact ctcgtcttcg atgtggagct tctaaaactg     1140
gaaggcggcc gcgagagcaa gtacggaccg ccctgcccac cttgccctgc ccccgagttc     1200
ctgggcggac ccagcgtgtt cctgttccca cccaagccca aggacaccct gatgatcagc     1260
cggaccccg aggtgacctg cgtggtggtg gacgtgagcc aggaagatcc cgaggtccag     1320
ttcaattggt acgtggacgg cgtggaagtg cacaacgcca agaccaagcc cagagaggaa     1380
cagttcaaca gcacctaccg ggtggtgtct gtgctgaccg tgctgcacca ggactggctg     1440
aacggcaaag aatacaagtg caaggtgtcc aacaagggcc tgcccagcag catcgaaaag     1500
accatcagca aggccaaggg ccagcctcgc gagcccaggg tgtacaccct gcctccctcc     1560
caggaagaga tgaccaagaa ccaggtgtcc ctgacctgcc tggtgaaggg cttctacccc     1620
agcgacatcg ccgtggagtg ggagagcaac ggccagcctg agaacaacta caagaccacc     1680
cctcccgtgc tggacagcga cggcagcttc ttcctgtaca gcggctgac cgtggacaag     1740
agccggtggc aggaaggcaa cgtctttagc tgcagcgtga tgcacgaggc cctgcacaac     1800
cactacaccc agaagagcct gagcctgtcc ctgggcaaga tggccctgat tgtgctgggg     1860
ggcgtcgccg gcctcctgct tttcattggg ctaggcatct tcttc                     1905
```

<210> SEQ ID NO 58
<211> LENGTH: 8023
<212> TYPE: DNA
<213> ORGANISM: Artificial Sequence
<220> FEATURE:

<223> OTHER INFORMATION: pCVL_sEF1a-T7-hScnSS-CD19scFv-DmrA-Spacer-CD4TM lentiviral vector

<400> SEQUENCE: 58

```
aaaaataaac aaatagggt tccgcgcaca tttccccgaa aagtgccacc tgacgtcaat      60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg gcgcccgaac     480
agggacttga aagcgaaagg gaaaccagag gagctctctc gacgcaggac tcggcttgct     540
gaagcgcgca cggcaagagg cgaggggcgg cgactggtga gtacgccaaa aattttgact     600
agcggaggct agaaggagag gatgggtgc gagagcgtca gtattaagcg gggagaatt     660
agatcgcgat gggaaaaaat tcggttaagg ccagggggga agaaaaaata taaattaaaa     720
catatagtat gggcaagcag ggagctagaa cgattcgcag ttaatcctgg cctgttagaa     780
acatcagaag gctgtagaca aatactggga cagctacaac catcccttca gacaggatca     840
gaagaactta gatcattata taatacagta gcaaccctct attgtgtgca tcaaaggata     900
gagataaaag acaccaagga agctttagac aagatagagg aagagcaaaa caaaagtaag     960
accaccgcac agcaagcggc cctgatcttc agacctggag gaggagatat gagggacaat    1020
tggagaagtg aattatataa atataaagta gtaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca gacaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taatgaatct    1440
ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcaggat attcaccatt atcgtttcag    1740
acccacctcc caaccccgag gggacccgac aggcccgaag gaatagaaga gaaggtgga    1800
gagagagaca gagacagatc cattcgatta gtgaacggat ctcgacggta tcggttaact    1860
tttaaaagaa aagggggat tggggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggaggggtc ggcaattgaa ccggtgccta gagaaggtgg cgcggggtaa    2100
actgggaaag tgatgtcgtg tactggctcc gccttttttcc cgagggtggg ggagaaccgt    2160
atataagtgc agtagtcgcc gtgaacgttc ttttccgcaa cgggtttgcc gccagaacac    2220
```

```
acctgcaggt aatacgactc actatagggt ccactgccgc caccatgccc ctgggcctgc    2280
tgtggctggg cctggccctg ctgggcgccc tgcacgccca ggccggatcc gatatccaga    2340
tgacccagac caccagcagc ctgagcgcca gcctgggcga tagagtgacc atcagctgca    2400
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag gaagatatcg    2580
ctacctactt ctgtcagcaa ggcaacaccc tgccctacac cttcggcgga ggcaccaagc    2640
tggaaatcac cggcagcaca gcggcagcg gcaagcctgg atctggcgag gaagcacca    2700
agggcgaagt gaaactgcag gaaagcggcc ctggactggt ggccccaagc cagtctctga    2760
gcgtgacctg taccgtgtcc ggcgtgtccc tgcctgacta tggcgtgtcc tggatcagac    2820
agccacccag aaagggcctg aatggctgg gagtgatctg gggcagcgag acaacctact    2880
acaacgcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt gggagcggag tgcaggtgga aaccatctcc caggagacg    3120
ggcgcacctt ccccaagcgc ggccagacct gcgtggtgca ctacaccggg atgcttgaag    3180
atggaaagaa atttgattcc tcccgggaca gaaacaagcc cttaagttt atgctaggca    3240
agcaggaggt gatccgaggc tgggaagaag gggttgccca gatgagtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgcgaga    3420
gcaagtacgg accgccctgc ccaccttgcc ctgccccga gttcctgggc gacccagcg    3480
tgttcctgtt cccacccaag cccaaggaca ccctgatgat cagccggacc cccgaggtga    3540
cctgcgtggt ggtggacgtg agccaggaag atcccgaggt ccagttcaat tggtacgtgg    3600
acggcgtgga agtgcacaac gccaagacca gcccagaga ggaacagttc aacagcacct    3660
accgggtggt gtctgtgctg accgtgctgc accaggactg gctgaacggc aaagaataca    3720
agtgcaaggt gtccaacaag ggcctgccca gcagcatcga aaagaccatc agcaaggcca    3780
agggccagcc tcgcgagccc caggtgtaca ccctgcctcc ctcccaggaa gatgacca    3840
agaaccaggt gtccctgacc tgcctggtga agggcttcta cccagcgac atcgccgtgg    3900
agtgggagag caacggccag cctgagaaca actacaagac caccctccc gtgctggaca    3960
gcgacggcag cttcttcctg tacagccggc tgaccgtgga caagagccgg tggcaggaag    4020
gcaacgtctt tagctgcagc gtgatgcacg aggccctgca caaccactac acccagaaga    4080
gcctgagcct gtccctgggc aagatggccc tgattgtgct ggggggcgtc gccggcctcc    4140
tgcttttcat tgggctaggc atcttcttca tgcattccgg tgagggcaga ggaagtcttc    4200
taacatgcgg tgacgtggag gagaatccgg cccctctag agtgagcaag ggcgaggagg    4260
ataacatggc catcatcaag gagttcatgc gcttcaaggt gcacatggag ggctccgtga    4320
acggccacga gttcgagatc gagggcgagg gcgaggccg cccctacgag ggcacccaga    4380
ccgccaagct gaaggtgacc aagggtggcc ccctgccctt cgcctgggac atcctgtccc    4440
ctcagttcat gtacggctcc aaggcctacg tgaagcaccc cgccgacatc cccgactact    4500
tgaagctgtc cttccccgag ggcttcaagt gggagcgcgt gatgaacttc gaggacggcg    4560
gcgtggtgac cgtgacccag gactcctctc tgcaggacgg cgagttcatc tacaaggtga    4620
```

```
agctgcgcgg caccaacttc ccctccgacg gccccgtaat gcagaagaag actatgggct    4680
gggaggcctc ctccgagcgg atgtacccccg aggacggcgc cctgaagggc gagatcaagc   4740
agaggctgaa gctgaaggac ggcggccact acgacgctga ggtcaagacc acctacaagg    4800
ccaagaagcc cgtgcagctg cccggcgcct acaacgtcaa catcaagttg gacatcacct    4860
cccacaacga ggactacacc atcgtggaac agtacgaacg cgccgagggc cgccactcca    4920
ccggcggcat ggacgagctg tacaagtaag tcgaccgagc atcttaccgc catttatacc    4980
catatttgtt ctgttttttct tgatttgggt atacatttaa atgttaatag aacaaaatgg   5040
tggggcaatc atttacattt ttagggatat gtaattacta gttcaggtgt attgccacaa    5100
gacaaacatg ttaagaaact ttcccgttat ttacgctctg ttcctgttaa tcaacctctg    5160
gattacaaaa tttgtgaaag attgactgat attcttaact atgttgctcc ttttacgctg    5220
tgtggatatg ctgctttata gcctctgtat ctagctattg cttcccgtac ggctttcgtt    5280
ttctcctcct tgtataaatc ctggttgctg tctcttttag aggagttgtg gcccgttgtc    5340
cgtcaacgtg gcgtggtgtg ctctgtgttt gctgacgcaa cccccactgg ctggggcatt    5400
gccaccacct gtcaactcct ttctgggact ttcgctttcc cctcccgat cgccacggca     5460
gaactcatcg ccgcctgcct tgcccgctgc tggacagggg ctaggttgct gggcactgat    5520
aattccgtgg tgttgtcatc gaattcggta cctttttaaa agaaaagggg ggactggaag    5580
ggctaattca ctcccaacga agacaagata tcataacttc gtatagcata cattatacga    5640
agttataatt tatttgtgaa atttgtgatg ctattgcttt atttgtaacc atatgtttat    5700
ttgtgaaatt tgtgatgcta ttgctttatt tgtaaccatt gcttttgct tgtactgggt     5760
ctctctggtt agaccagatc tgagcctggg agctctctgg ctaactaggg aacccactgc    5820
ttaagcctca ataaagcttg cctcgaccag cctcgactgt gccttctagt tgccagccat    5880
ctgttgtttg cccctccccc gtgccttcct tgacctgga aggtgccact cccactgtcc     5940
tttcctaata aaatgaggaa attgcatcgc attgtctgag taggtgtcat tctattctgg    6000
ggggtgggt ggggcaggac agcaaggggg aggattggga agacaatagc aggcatgctg     6060
gggatgcggt gggctctatg gcctgcagct gcattaatga atcggccaac gcgcggggag    6120
aggcggtttg cgtattgggc gctcttccgc ttcctcgctc actgactcgc tgcgctcggt    6180
cgttcggctg cggcgagcgg tatcagctca ctcaaaggcg gtaatacggt tatccacaga    6240
atcaggggat aacgcaggaa agaacatgtg agcaaaaggc cagcaaaagg ccaggaaccg    6300
taaaaaggcc gcgttgctgg cgttttccca taggctccgc cccctgacg agcatcacaa     6360
aaatcgacgc tcaagtcaga ggtggcgaaa cccgacagga ctataaagat accaggcgtt    6420
tccccctgga agctccctcg tgcgctctcc tgttccgacc ctgccgctta ccggatacct    6480
gtccgccttt ctcccttcgg gaagcgtggc gctttctcat agctcacgct gtaggtatct    6540
cagttcggtg taggtcgttc gctccaagct gggctgtgtg cacgaacccc ccgttcagcc    6600
cgaccgctgc gccttatccg gtaactatcg tcttgagtcc aacccggtaa gacacgactt    6660
atcgccactg gcagcagcca ctggtaacag gattagcaga gcgaggtatg taggcggtgc    6720
tacagagttc ttgaagtggt ggcctaacta cggctacact agaaggacag tatttggtat    6780
ctgcgctctg ctgaagccag ttaccttcgg aaaaagagtt ggtagctctt gatccggcaa    6840
acaaaccacc gctggtagcg gtggtttttt tgtttgcaag cagcagatta cgcgcagaaa    6900
aaaaggatct caagaagatc ctttgatctt ttctacgggg tctgacgctc agtggaacga    6960
```

```
aaactcacgt taagggattt tggtcatgag attatcaaaa aggatcttca cctagatcct    7020
tttaaattaa aaatgaagtt ttaaatcaat ctaaagtata tatgagtaaa cttggtctga    7080
cagttaccaa tgcttaatca gtgaggcacc tatctcagcg atctgtctat ttcgttcatc    7140
catagttgcc tgactcccg tcgtgtagat aactacgata cgggagggct taccatctgg     7200
ccccagtgct gcaatgatac cgcgagaccc acgctcaccg gctccagatt tatcagcaat    7260
aaaccagcca gccggaaggg ccgagcgcag aagtggtcct gcaactttat ccgcctccat    7320
ccagtctatt aattgttgcc gggaagctag agtaagtagt tcgccagtta atagtttgcg    7380
caacgttgtt gccattgcta caggcatcgt ggtgtcacgc tcgtcgtttg gtatggcttc    7440
attcagctcc ggttcccaac gatcaaggcg agttacatga tcccccatgt tgtgcaaaaa    7500
agcggttagc tccttcggtc ctccgatcgt tgtcagaagt aagttggccg cagtgttatc    7560
actcatggtt atggcagcac tgcataattc tcttactgtc atgccatccg taagatgctt    7620
ttctgtgact ggtgagtact caaccaagtc attctgagaa tagtgtatgc ggcgaccgag    7680
ttgctcttgc ccggcgtcaa tacgggataa taccgcgcca catagcagaa ctttaaaagt    7740
gctcatcatt ggaaaacgtt cttcggggcg aaaactctca aggatcttac cgctgttgag    7800
atccagttcg atgtaaccca ctcgtgcacc caactgatct tcagcatctt ttactttcac    7860
cagcgtttct gggtgagcaa aacaggaag gcaaaatgcc gcaaaaaagg gaataagggc     7920
gacacggaaa tgttgaatac tcatactctt ccttttcaa tattattgaa gcatttatca     7980
gggttattgt ctcatgagcg gatacatatt tgaatgtatt tag                     8023
```

<210> SEQ ID NO 59
<211> LENGTH: 417
<212> TYPE: PRT
<213> ORGANISM: Artificial Sequence
<220> FEATURE:
<223> OTHER INFORMATION: SS-CD19scFv-DmrA-CD52 GPI anchor protein

<400> SEQUENCE: 59

```
Met Pro Leu Gly Leu Leu Trp Leu Gly Leu Ala Leu Leu Gly Ala Leu
1               5                   10                  15

His Ala Gln Ala Gly Ser Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175
```

```
Pro Asp Tyr Gly Val Ser Trp Ile Arg Gln Pro Pro Arg Lys Gly Leu
            180                 185                 190
Glu Trp Leu Gly Val Ile Trp Gly Ser Glu Thr Thr Tyr Tyr Asn Ser
        195                 200                 205
Ala Leu Lys Ser Arg Leu Thr Ile Ile Lys Asp Asn Ser Lys Ser Gln
    210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Gly Gly Ser Tyr Ala Met Asp Tyr
                245                 250                 255
Trp Gly Gln Gly Thr Ser Val Thr Val Ser Ser Ala Ser Gly Gly Gly
            260                 265                 270
Gly Ser Gly Val Gln Val Glu Thr Ile Ser Pro Gly Asp Gly Arg Thr
        275                 280                 285
Phe Pro Lys Arg Gly Gln Thr Cys Val Val His Tyr Thr Gly Met Leu
    290                 295                 300
Glu Asp Gly Lys Lys Phe Asp Ser Ser Arg Asp Arg Asn Lys Pro Phe
305                 310                 315                 320
Lys Phe Met Leu Gly Lys Gln Glu Val Ile Arg Gly Trp Glu Glu Gly
                325                 330                 335
Val Ala Gln Met Ser Val Gly Gln Arg Ala Lys Leu Thr Ile Ser Pro
            340                 345                 350
Asp Tyr Ala Tyr Gly Ala Thr Gly His Pro Gly Ile Ile Pro Pro His
        355                 360                 365
Ala Thr Leu Val Phe Asp Val Glu Leu Leu Lys Leu Glu Gly Gly Arg
    370                 375                 380
Thr Ser Gln Thr Ser Ser Pro Ser Ala Ser Ser Asn Ile Ser Gly Gly
385                 390                 395                 400
Ile Phe Leu Phe Phe Val Ala Asn Ala Ile Ile His Leu Phe Cys Phe
                405                 410                 415
Ser

<210> SEQ ID NO 60
<211> LENGTH: 1251
<212> TYPE: DNA
<213> ORGANISM: Artificial Sequence
<220> FEATURE:
<223> OTHER INFORMATION: SS-CD19scFv-DmrA-CD52 GPI anchor DNA

<400> SEQUENCE: 60
atgcccctgg gcctgctgtg gctgggcctg gccctgctgg gcgccctgca cgcccaggcc      60
ggatccgata tccagatgac ccagaccacc agcagcctga gcgccagcct gggcgataga     120
gtgaccatca gctgcagagc cagccaggac atcagcaagt acctgaactg gtatcagcag     180
aaacccgacg gcaccgtgaa gctgctgatc taccacacca gcagactgca cagcggcgtg     240
cccagcagat ttctggcag cggctccggc accgactaca gcctgaccat ctccaacctg     300
gaacaggaag atatcgctac ctacttctgt cagcaaggca cacccctgcc ctacaccttc     360
ggcggaggca ccaagctgga aatcaccggc agcacaagcg gcagcggcaa gcctggatct     420
ggcgagggaa gcaccaaggg cgaagtgaaa ctgcaggaaa gcggccctgg actggtggcc     480
ccaagccagt ctctgagcgt gacctgtacc gtgtccggcg tgtccctgcc tgactatggc     540
gtgtcctgga tcagacagcc acccagaaag ggcctggaat ggctgggagt gatctggggc     600
agcgagacaa cctactacaa cagcgccctg aagtcccggc tgaccatcat caaggacaac     660
```

```
tccaagagcc aggtgttcct gaagatgaac agcctgcaga ccgacgacac cgccatctac     720
tactgcgcca agcactacta ctacggcggc agctacgcca tggactactg gggccagggc     780
acaagcgtga ccgtgtccag cgctagcggc ggaggtggga gcggagtgca ggtggaaacc     840
atctccccag gagacgggcg caccttcccc aagcgcggcc agacctgcgt ggtgcactac     900
accgggatgc ttgaagatgg aaagaaattt gattcctccc gggacagaaa caagcccttt     960
aagtttatgc taggcaagca ggaggtgatc cgaggctggg aagaagggg tgcccagatg    1020 agtgtgggtc agagagccaa actgactata tctccagatt atgcctatgg tgccactggg    1080
cacccaggca tcatcccacc acatgccact ctcgtcttcg atgtggagct tctaaaactg    1140
gaaggcggcc gcaccagcca accagcagc cctcagcat ccagcaacat aagcggaggc    1200
attttccttt tcttcgtggc caatgccata atccacctct tctgcttcag t             1251

<210> SEQ ID NO 61
<211> LENGTH: 7369
<212> TYPE: DNA
<213> ORGANISM: Artificial Sequence
<220> FEATURE:
<223> OTHER INFORMATION: pCVL_sEF1a-T7-hScnSS-CD19scFv-DmrA-CD52 GPI
      anchor lentiviral vector

<400> SEQUENCE: 61
aaaaataaac aaatagggt tccgcgcaca tttccccgaa aagtgccacc tgacgtcaat     60
gtagtcttat gcaatactct tgtagtcttg caacatggta acgatgagtt agcaacatgc    120
cttacaagga gagaaaaagc accgtgcatg ccgattggtg gaagtaaggt ggtacgatcg    180
tgccttatta ggaaggcaac agacgggtct gacatggatt ggacgaacca ctgaattgcc    240
gcattgcaga gatattgtat ttaagtgcct agctcgatac ataaacgggt ctctctggtt    300
agaccagatc tgagcctggg agctctctgg ctaactaggg aacccactgc ttaagcctca    360
ataaagcttg ccttgagtgc ttcaagtagt gtgtgcccgt ctgttgtgtg actctggtaa    420
ctagagatcc ctcagaccct tttagtcagt gtggaaaatc tctagcagtg gcgcccgaac    480
agggacttga agcgaaaagg gaaccagag gagctctctc gacgcaggac tcggcttgct    540
gaagcgcgca cggcaagagg cgaggggcgg cgactggtga gtacgccaaa aattttgact    600
agcggaggct agaaggagag atgggtgcg agagcgtca gtattaagcg gggagaatt    660 agatcgcgat gggaaaaaat tcggttaagg ccagggggaa agaaaaaata taaattaaaa    720
catatagtat gggcaagcag ggagctagaa cgattcgcag ttaatcctgg cctgttagaa    780
acatcagaag gctgtagaca aatactggga cagctacaac catcccttca gacaggatca    840
gaagaactta gatcattata taatacagta gcaaccctct attgtgtgca tcaaaggata    900
gagataaaag acaccaagga agctttagac aagatagagg aagagcaaaa caaaagtaag    960
accaccgcac agcaagcggc cctgatcttc agacctggag gaggagatat gagggacaat    1020
tggagaagtg aattatataa atataaagta gtaaaattg aaccattagg agtagcaccc    1080
accaaggcaa agagaagagt ggtgcagaga gaaaaaagag cagtgggaat aggagctttg    1140
ttccttgggt tcttgggagc agcaggaagc actatgggcg cagcgtcaat gacgctgacg    1200
gtacaggcca caaattatt gtctggtata gtgcagcagc agaacaattt gctgagggct    1260
attgaggcgc aacagcatct gttgcaactc acagtctggg gcatcaagca gctccaggca    1320
agaatcctgg ctgtggaaag atacctaaag gatcaacagc tcctggggat ttggggttgc    1380
tctggaaaac tcatttgcac cactgctgtg ccttggaatg ctagttggag taatgaatct    1440
```

```
ctggaacaga tttggaatca cacgacctgg atggagtggg acagagaaat taacaattac    1500
acaagcttaa tacactcctt aattgaagaa tcgcaaaacc agcaagaaaa gaatgaacaa    1560
gaattattgg aattagataa atgggcaagt ttgtggaatt ggtttaacat aacaaattgg    1620
ctgtggtata taaaattatt cataatgata gtaggaggct tggtaggttt aagaatagtt    1680
tttgctgtac tttctatagt gaatagagtt aggcagggat attcaccatt atcgtttcag    1740
acccacctcc caaccccgag gggacccgac aggcccgaag gaatagaaga agaaggtgga    1800
gagagagaca gagacagatc cattcgatta gtgaacggat ctcgacggta tcggttaact    1860
tttaaaagaa aagggggat tgggggtac agtgcagggg aaagaatagt agacataata    1920
gcaacagaca tacaaactaa agaattacaa aaacaaatta caaaaattca aaattttatc    1980
gattacgcgt aggctccggt gcccgtcagt gggcagagcg cacatcgccc acagtccccg    2040
agaagttggg gggagggtc ggcaattgaa ccggtgccta gagaaggtgg cgcggggtaa    2100
actgggaaag tgatgtcgtg tactggctcc gccttttttcc cgagggtggg ggagaaccgt   2160
atataagtgc agtagtcgcc gtgaacgttc ttttcgcaa cgggtttgcc gccagaacac    2220
acctgcaggt aatacgactc actatagggt ccactgccgc caccatgccc ctgggcctgc    2280
tgtggctggg cctggccctg ctgggcgccc tgcacgccca ggccggatcc gatatccaga    2340
tgacccagac caccagcagc ctgagcgcca gcctgggcga tagagtgacc atcagctgca    2400
gagccagcca ggacatcagc aagtacctga actggtatca gcagaaaccc gacggcaccg    2460
tgaagctgct gatctaccac accagcagac tgcacagcgg cgtgcccagc agattttctg    2520
gcagcggctc cggcaccgac tacagcctga ccatctccaa cctggaacag gaagatatcg    2580
ctacctactt ctgtcagcaa ggcaacaccc tgccctacac cttcggcgga ggcaccaagc    2640
tggaaatcac cggcagcaca agcggcagcg gcaagcctgg atctggcgag gaagcacca    2700
agggcgaagt gaaactgcag gaaagcggcc ctggactggt ggccccaagc cagtctctga    2760
gcgtgacctg taccgtgtcc ggcgtgtccc tgcctgacta tggcgtgtcc tggatcagac    2820
agccacccag aaagggcctg aatggctgg gagtgatctg gggcagcgag acaacctact    2880
acaacagcgc cctgaagtcc cggctgacca tcatcaagga caactccaag agccaggtgt    2940
tcctgaagat gaacagcctg cagaccgacg acaccgccat ctactactgc gccaagcact    3000
actactacgg cggcagctac gccatggact actggggcca gggcacaagc gtgaccgtgt    3060
ccagcgctag cggcggaggt gggagcggag tgcaggtgga aaccatctcc ccaggagacg    3120
ggcgcacctt ccccaagcgc ggccagacct gcgtggtgca ctacaccggg atgcttgaag    3180
atggaaagaa atttgattcc tcccgggaca gaaacaagcc ctttaagttt atgctaggca    3240
agcaggaggt gatccgaggc tgggaagaag gggttgccca gatgagtgtg ggtcagagag    3300
ccaaactgac tatatctcca gattatgcct atggtgccac tgggcaccca ggcatcatcc    3360
caccacatgc cactctcgtc ttcgatgtgg agcttctaaa actggaaggc ggccgcacca    3420
gccaaaccag cagcccctca gcatccagca acataagcgg aggcattttc cttttcttcg    3480
tggccaatgc cataatccac ctcttctgct tcagtatgca ttccggtgag ggcagaggaa    3540
gtcttctaac atgcggtgac gtggaggaga tccggccc ctctagagtg agcaagggcg    3600
aggaggataa catggccatc atcaaggagt tcatgcgctt caaggtgcac atggagggct    3660
ccgtgaacgg ccacgagttc gagatcgagg gcgagggcga gggccgcccc tacgagggca    3720
cccagaccgc caagctgaag gtgaccaagg gtggcccct gcccttcgcc tgggacatcc    3780
tgtcccctca gttcatgtac ggctccaagg cctacgtgaa gcaccccgcc gacatccccg    3840
```

```
actacttgaa gctgtccttc cccgagggct tcaagtggga gcgcgtgatg aacttcgagg    3900
acggcggcgt ggtgaccgtg acccaggact cctctctgca ggacggcgag ttcatctaca    3960
aggtgaagct gcgcggcacc aacttcccct ccgacggccc cgtaatgcag aagaagacta    4020
tgggctggga ggcctcctcc gagcggatgt accccgagga cggcgccctg aagggcgaga    4080
tcaagcagag gctgaagctg aaggacggcg ccactacga cgctgaggtc aagaccacct    4140
acaaggccaa gaagcccgtg cagctgcccg gcgcctacaa cgtcaacatc aagttggaca    4200
tcacctccca caacgaggac tacaccatcg tggaacagta cgaacgcgcc gagggccgcc    4260
actccaccgg cggcatggac gagctgtaca agtaagtcga ccgagcatct taccgccatt    4320
tatacccata tttgttctgt ttttcttgat ttgggtatac atttaaatgt taatagaaca    4380
aaatggtggg gcaatcattt acatttttag ggatatgtaa ttactagttc aggtgtattg    4440
ccacaagaca aacatgttaa gaaactttcc cgttatttac gctctgttcc tgttaatcaa    4500
cctctggatt acaaaatttg tgaaagattg actgatattc ttaactatgt tgctccttt    4560 acgctgtgtg gatatgctgc tttatagcct ctgtatctag ctattgcttc ccgtacggct    4620 ttcgtttttct cctccttgta taaatcctgg ttgctgtctc ttttagagga gttgtggccc    4680
gttgtccgtc aacgtggcgt ggtgtgctct gtgtttgctg acgcaacccc cactggctgg    4740
ggcattgcca ccacctgtca actccttct gggactttcg cttccccct ccgatcgcc      4800 acggcagaac tcatcgccgc ctgccttgcc cgctgctgga caggggctag gttgctgggc    4860
actgataatt ccgtggtgtt gtcatcgaat tcggtaccct tttaaaagaa aagggggac     4920 tggaagggct aattcactcc caacgaagac aagatatcat aacttcgtat agcatacatt    4980
atacgaagtt ataatttatt tgtgaaattt gtgatgctat tgctttattt gtaaccatat    5040
gtttatttgt gaaatttgtg atgctattgc tttatttgta accattgctt tttgcttgta    5100
ctgggtctct ctggttagac cagatctgag cctgggagct ctctggctaa ctagggaacc    5160
cactgcttaa gcctcaataa agcttgcctc gaccagcctc gactgtgcct tctagttgcc    5220
agccatctgt tgtttgcccc tcccccgtgc cttccttgac cctggaaggt gccactccca    5280
ctgtcctttc ctaataaaat gaggaaattg catcgcattg tctgagtagg tgtcattcta    5340
ttctgggggg tggggtgggg caggacagca aggggagga ttgggaagac aatagcaggc     5400
atgctgggga tgcggtgggc tctatggcct gcagctgcat taatgaatcg ccaacgcgc     5460 ggggagaggc ggtttgcgta ttgggcgctc ttccgcttcc tcgctcactg actcgctgcg    5520
ctcggtcgtt cggctgcggc gagcggtatc agctcactca aaggcggtaa tacgttatc     5580 cacagaatca ggggataacg caggaaagaa catgtgagca aaaggccagc aaaaggccag    5640
gaaccgtaaa aaggccgcgt tgctggcgtt tttccatagg ctccgcccc ctgacgagca     5700 tcacaaaaat cgacgctcaa gtcagaggtg gcgaaacccg acaggactat aaagatacca    5760
ggcgtttccc cctggaagct ccctcgtgcg ctctcctgtt ccgaccctgc cgcttaccgg    5820
atacctgtcc gcctttctcc cttcgggaag cgtggcgctt tctcatagct cacgctgtag    5880
gtatctcagt tcggtgtagg tcgttcgctc caagctgggc tgtgtgcacg aaccccccgt    5940
tcagcccgac cgctgcgcct tatccggtaa ctatcgtctt gagtccaacc cggtaagaca    6000
cgacttatcg ccactggcag cagccactgg taacaggatt agcagagcga ggtatgtagg    6060
cggtgctaca gagttcttga agtggtggcc taactacggc tacactagaa ggacagtatt    6120
tggtatctgc gctctgctga agccagttac cttcggaaaa agagttggta gctcttgatc    6180
```

```
cggcaaacaa accaccgctg gtagcggtgg ttttttttgtt tgcaagcagc agattacgcg      6240
cagaaaaaaa ggatctcaag aagatccttt gatcttttct acggggtctg acgctcagtg      6300
gaacgaaaac tcacgttaag ggattttggt catgagatta tcaaaaagga tcttcaccta      6360
gatcctttta aattaaaaat gaagttttaa atcaatctaa agtatatatg agtaaacttg      6420
gtctgacagt taccaatgct taatcagtga ggcacctatc tcagcgatct gtctatttcg      6480
ttcatccata gttgcctgac tccccgtcgt gtagataact acgatacggg agggcttacc      6540
atctggcccc agtgctgcaa tgataccgcg agacccacgc tcaccggctc cagatttatc      6600
agcaataaac cagccagccg aagggccgag cgcagaagt ggtcctgcaa ctttatccgc      6660
ctccatccag tctattaatt gttgccggga agctagagta agtagttcgc cagttaatag      6720
tttgcgcaac gttgttgcca ttgctacagg catcgtggtg tcacgctcgt cgtttggtat      6780
ggcttcattc agctccggtt cccaacgatc aaggcgagtt acatgatccc ccatgttgtg      6840
caaaaaagcg gttagctcct tcggtcctcc gatcgttgtc agaagtaagt tggccgcagt      6900
gttatcactc atggttatgg cagcactgca taattctctt actgtcatgc catccgtaag      6960
atgcttttct gtgactggtg agtactcaac caagtcattc tgagaatagt gtatgcggcg      7020
accgagttgc tcttgcccgg cgtcaatacg ggataatacc gcgccacata gcagaacttt      7080
aaaagtgctc atcattggaa aacgttcttc ggggcgaaaa ctctcaagga tcttaccgct      7140
gttgagatcc agttcgatgt aacccactcg tgcacccaac tgatcttcag catcttttac      7200
tttcaccagc gtttctgggt gagcaaaaac aggaaggcaa aatgccgcaa aaaagggaat      7260
aagggcgaca cggaaatgtt gaatactcat actcttcctt tttcaatatt attgaagcat      7320
ttatcagggt tattgtctca tgagcggata catatttgaa tgtatttag                   7369
```

<210> SEQ ID NO 62
<211> LENGTH: 7141
<212> TYPE: DNA
<213> ORGANISM: Artificial Sequence
<220> FEATURE:
<223> OTHER INFORMATION: pCVL_T7_FRB-TM-41BB-CD3z lentiviral vector

<400> SEQUENCE: 62

```
aaaaataaac aaatagggt tccgcgcaca tttccccgaa aagtgccacc tgacgtcaat       60
gtagtcttat gcaatactct tgtagtcttg caacatggta acgatgagtt agcaacatgc      120
cttacaagga gagaaaaagc accgtgcatg ccgattggtg gaagtaaggt ggtacgatcg      180
tgccttatta ggaaggcaac agacgggtct gacatggatt ggacgaacca ctgaattgcc      240
gcattgcaga gatattgtat ttaagtgcct agctcgatac ataaacgggt ctctctggtt      300
agaccagatc tgagcctggg agctctctgg ctaactaggg aacccactgc ttaagcctca      360
ataaagcttg ccttgagtgc ttcaagtagt gtgtgcccgt ctgttgtgtg actctggtaa      420
ctagagatcc ctcagaccct tttagtcagt gtggaaaatc tctagcagtg gcgcccgaac      480
agggacttga aagcgaaagg gaaaccagag gagctctctc gacgcaggac tcggcttgct      540
gaagcgcgca cggcaagagg cgaggggcgg cgactggtga gtacgccaaa aattttgact      600
agcggaggct agaaggagag agatgggtgc gagagcgtca gtattaagcg gggagaatt      660 agatcgcgat gggaaaaaat tcggttaagg ccaggggaa agaaaaata taaattaaaa      720 catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaacccctct attgtgtgca tcaaaggata      900
```

```
gagataaaag acaccaagga agctttagac aagatagagg aagagcaaaa caaaagtaag      960
accaccgcac agcaagcggc cctgatcttc agacctggag gaggagatat gagggacaat     1020
tggagaagtg aattatataa atataaagta gtaaaaattg aaccattagg agtagcaccc     1080
accaaggcaa agagaagagt ggtgcagaga gaaaaaagag cagtgggaat aggagctttg     1140
ttccttgggt tcttgggagc agcaggaagc actatgggcg cagcgtcaat gacgctgacg     1200
gtacaggcca gacaattatt gtctggtata gtgcagcagc agaacaattt gctgagggct     1260
attgaggcgc aacagcatct gttgcaactc acagtctggg gcatcaagca gctccaggca     1320
agaatcctgg ctgtggaaag atacctaaag gatcaacagc tcctggggat ttggggttgc     1380
tctggaaaac tcatttgcac cactgctgtg ccttggaatg ctagttggag taatgaatct     1440
ctggaacaga tttggaatca cacgacctgg atggagtggg acagagaaat taacaattac     1500
acaagcttaa tacactcctt aattgaagaa tcgcaaaacc agcaagaaaa gaatgaacaa     1560
gaattattgg aattagataa atgggcaagt ttgtggaatt ggtttaacat aacaaattgg     1620
ctgtggtata taaaattatt cataatgata gtaggaggct tggtaggttt aagaatagtt     1680
tttgctgtac tttctatagt gaatagagtt aggcagggat attcaccatt atcgtttcag     1740
acccacctcc caaccccgag gggacccgac aggcccgaag gaatagaaga agaaggtgga     1800
gagagagaca gagacagatc cattcgatta gtgaacggat ctcgacggta tcggttaact     1860
tttaaaagaa aaggggggat tggggggtac agtgcagggg aaagaatagt agacataata     1920
gcaacagaca tacaaactaa agaattacaa aaacaaatta caaaaattca aaattttatc     1980
gattacgcgt aggctccggt gcccgtcagt gggcagagcg cacatcgccc acagtccccg     2040
agaagttggg gggaggggtc ggcaattgaa ccggtgccta gagaaggtgg cgcggggtaa     2100
actgggaaag tgatgtcgtg tactggctcc gcctttttcc cgagggtggg ggagaaccgt     2160
atataagtgc agtagtcgcc gtgaacgttc tttttcgcaa cgggtttgcc gccagaacac     2220
acctgcaggt aatacgactc actataggct ccactgccgc caccatggct ctgcctgtga     2280
cagctctgct gctgcctctg gcctgctgc tccatgccgc cagacccgga tccatcctct     2340
ggcatgagat gtggcatgaa ggcctggaag aggcatctcg tttgtacttt ggggaaagga     2400
acgtgaaagg catgtttgag gtgctggagc ccttgcatgc tatgatggaa cggggcccc     2460
agactctgaa ggaaacatcc tttaatcagg cctatggtcg agatttaatg gaggcccaag     2520
agtggtgcag gaagtacatg aaatcaggga atgtcaagga cctcacccaa gcctgggacc     2580
tctattatca tgtgttccga cgaatctcaa aggctagcgc caagcctacc accacccctg     2640
ccctagacc tccaacaccc gccccaacaa tcgccagcca gcctctgtct ctgaggcccg     2700
aggcttgtag accagctgct ggcggagccg tgcacaccag aggactggat ttcgcctgcg     2760
acatctacat ctgggcccct ctggccggca catgtggcgt gctgctgctg agcctcgtga     2820
tcaccatgca taaacgggc agaaagaaac tcctgtatat attcaaacaa ccatttatga     2880
gaccagtaca aactactcaa gaggaagatg gctgtagctg ccgatttcca gaagaagaag     2940
aaggaggatg tgaactgcgg gtgaagttca gcagaagcgc cgacgcccct gcctaccagc     3000
agggccagaa tcagctgtac aacgagctga acctgggcag aagggaagag tacgacgtcc     3060
tggataagcg gagaggccgg gaccctgaga tgggcggcaa gcctcggcgg aagaaccccc     3120
aggaaggcct gtataacgaa ctgcagaaag acaagatggc cgaggcctac agcgagatcg     3180
gcatgaaggg cgagcggagg cggggcaagg gccacgacgg cctgtatcag ggcctgtcca     3240
```

```
ccgccaccaa ggatacctac gacgccctgc acatgcaggc cctgccccca aggggcggcc      3300
gctccggtga gggcagagga agtcttctaa catgcggtga cgtggaggag aatccgggcc      3360
cctctagaag cgagctgatt aaggagaaca tgcacatgaa gctgtacatg gagggcaccg      3420
tggacaacca tcacttcaag tgcacatccg agggcgaagg caagccctac gagggcaccc      3480
agaccatgag aatcaaggtg gtcgagggcg ccctctccc cttcgccttc gacatcctgg       3540
ctactagctt cctctacggc agcaagacct tcatcaacca cacccagggc atccccgact      3600
tcttcaagca gtccttccct gagggcttca catgggagag agtcaccaca tacgaagacg      3660
ggggcgtgct gaccgctacc caggacacca gcctccagga cggctgcctc atctacaacg      3720
tcaagatcag aggggtgaac ttcacatcca acggccctgt gatgcagaag aaaacactcg      3780
gctgggaggc cttcaccgag acgctgtacc ccgctgacgg cggcctggaa ggcagaaacg      3840
acatggccct gaagctcgtg ggcgggagcc atctgatcgc aaacatcaag accacatata      3900
gatccaagaa acccgctaag aacctcaaga tgcctggcgt ctactatgtg gactacagac      3960
tggaaagaat caaggaggcc aacaacgaga cctacgtcga gcagcacgag gtggcagtgg      4020
ccagatactg cgacctccct agcaaactgg ggcacaagct taattgagtc gaccgagcat      4080
cttaccgcca tttataccca tatttgttct gttttcttg atttgggtat acatttaaat       4140
gttaatagaa caaatggtg gggcaatcat ttacatttt agggatatgt aattactagt        4200
tcaggtgtat tgccacaaga caaacatgtt aagaaacttt cccgttattt acgctctgtt      4260
cctgttaatc aacctctgga ttacaaaatt tgtgaaagat tgactgatat tcttaactat      4320
gttgctcctt ttacgctgtg tggatatgct gctttatagc ctctgtatct agctattgct      4380
tcccgtacgg ctttcgtttt ctcctccttg tataaatcct ggttgctgtc tcttttagag      4440
gagttgtggc ccgttgtccg tcaacgtggc gtggtgtgct ctgtgtttgc tgacgcaacc      4500
cccactggct ggggcattgc caccacctgt caactccttt ctgggactt cgctttcccc       4560 ctcccgatcg ccacggcaga actcatcgcc gcctgcttg cccgctgctg acaggggct       4620 aggttgctgg gcactgataa ttccgtggtg ttgtcatcga attcggtacc ttttaaaag      4680 aaaagggggg actggaaggg ctaattcact cccaacgaag acaagatatc ataacttcgt      4740
atagcataca ttatacgaag ttataattta tttgtgaaat ttgtgatgct attgctttat      4800
ttgtaaccat atgtttattt gtgaaatttg tgatgctatt gctttatttg taaccattgc      4860
tttttgcttg tactgggtct ctctggttag accagatctg agcctgggag ctctctggct      4920
aactagggaa cccactgctt aagcctcaat aaagcttgcc tcgaccagcc tcgactgtgc      4980
cttctagttg ccagccatct gttgtttgcc ctcccccgt gccttccttg accctggaag       5040
gtgccactcc cactgtcctt tcctaataaa atgaggaaat tgcatcgcat tgtctgagta      5100
ggtgtcattc tattctgggg gtgggtgg ggcaggacag caaggggag gattgggaag         5160 acaatagcag gcatgctggg gatgcggtgg gctctatggc ctgcagctgc attaatgaat      5220
cggccaacgc gcgggagag gcggtttgcg tattgggcgc tcttccgctt cctcgctcac      5280
tgactcgctg cgctcggtcg ttcggctgcg gcgagcggta tcagctcact caaaggcggt      5340
aatacggtta tccacagaat cagggataa cgcaggaaag aacatgtgag caaaaggcca      5400
gcaaaaggcc aggaaccgta aaaaggccgc gttgctggcg ttttccata ggctccgccc       5460 ccctgacgag catcacaaaa atcgacgctc aagtcagagg tggcgaaacc cgacaggact      5520
ataaagatac caggcgtttc ccctggaag ctccctcgtg cgctctcctg ttccgaccct       5580
gccgcttacc ggatacctgt ccgcctttct cccttcggga agcgtggcgc tttctcatag      5640
```

```
ctcacgctgt aggtatctca gttcggtgta ggtcgttcgc tccaagctgg gctgtgtgca    5700
cgaacccccc gttcagcccg accgctgcgc cttatccggt aactatcgtc ttgagtccaa    5760
cccggtaaga cacgacttat cgccactggc agcagccact ggtaacagga ttagcagagc    5820
gaggtatgta ggcggtgcta cagagttctt gaagtggtgg cctaactacg gctacactag    5880
aaggacagta tttggtatct gcgctctgct gaagccagtt accttcggaa aaagagttgg    5940
tagctcttga tccggcaaac aaaccaccgc tggtagcggt ggtttttttg tttgcaagca    6000
gcagattacg cgcagaaaaa aaggatctca agaagatcct ttgatctttt ctacggggtc    6060
tgacgctcag tggaacgaaa actcacgtta agggattttg gtcatgagat tatcaaaaag    6120
gatcttcacc tagatccttt taaattaaaa atgaagtttt aaatcaatct aaagtatata    6180
tgagtaaact tggtctgaca gttaccaatg cttaatcagt gaggcaccta tctcagcgat    6240
ctgtctattt cgttcatcca tagttgcctg actccccgtc gtgtagataa ctacgatacg    6300
ggagggctta ccatctggcc ccagtgctgc aatgataccg cgagacccac gctcaccggc    6360
tccagattta tcagcaataa accagccagc cggaagggcc gagcgcagaa gtggtcctgc    6420
aactttatcc gcctccatcc agtctattaa ttgttgccgg gaagctagag taagtagttc    6480
gccagttaat agtttgcgca acgttgttgc cattgctaca ggcatcgtgg tgtcacgctc    6540
gtcgtttggt atggcttcat tcagctccgg ttcccaacga tcaaggcgag ttacatgatc    6600
ccccatgttg tgcaaaaaag cggttagctc cttcggtcct ccgatcgttg tcagaagtaa    6660
gttggccgca gtgttatcac tcatggttat ggcagcactg cataattctc ttactgtcat    6720
gccatccgta agatgctttt ctgtgactgg tgagtactca accaagtcat tctgagaata    6780
gtgtatgcgg cgaccgagtt gctcttgccc ggcgtcaata cgggataata ccgcgccaca    6840
tagcagaact ttaaaagtgc tcatcattgg aaaacgttct cggggcgaaa actctcaag    6900
gatcttaccg ctgttgagat ccagttcgat gtaaccccact cgtgcaccca actgatcttc    6960
agcatctttt actttcacca gcgtttctgg gtgagcaaaa acaggaaggc aaaatgccgc    7020
aaaaaaggga ataagggcga cacggaaatg ttgaatactc atactcttcc ttttttcaata    7080
ttattgaagc atttatcagg gttattgtct catgagcgga tacatatttg aatgtattta    7140
g                                                                   7141
```

<210> SEQ ID NO 63
<211> LENGTH: 7264
<212> TYPE: DNA
<213> ORGANISM: Artificial Sequence
<220> FEATURE:
<223> OTHER INFORMATION: pCVL_T7_scFvCD19-DmrA-mCherry lentiviral vector

<400> SEQUENCE: 63

```
aaaaataaac aaatagggt tccgcgcaca tttccccgaa aagtgccacc tgacgtcaat      60
gtagtcttat gcaatactct tgtagtcttg caacatggta acgatgagtt agcaacatgc     120
cttacaagga gagaaaaagc accgtgcatg ccgattggtg gaagtaaggt ggtacgatcg     180
tgccttatta ggaaggcaac agacgggtct gacatggatt ggacgaacca ctgaattgcc     240
gcattgcaga gatattgtat ttaagtgcct agctcgatac ataaacgggt ctctctggtt     300
agaccagatc tgagcctggg agctctctgg ctaactaggg aacccactgc ttaagcctca     360
ataaagcttg ccttgagtgc ttcaagtagt gtgtgcccgt ctgttgtgtg actctggtaa     420
ctagagatcc ctcagaccct tttagtcagt gtggaaaatc tctagcagtg gcgcccgaac     480
```

```
agggacttga aagcgaaagg gaaaccagag gagctctctc gacgcaggac tcggcttgct   540
gaagcgcgca cggcaagagg cgaggggcgg cgactggtga gtacgccaaa aattttgact   600
agcggaggct agaaggagag agatgggtgc gagagcgtca gtattaagcg ggggagaatt   660
agatcgcgat gggaaaaaat tcggttaagg ccagggggaa agaaaaaata taaattaaaa   720
catatagtat gggcaagcag ggagctagaa cgattcgcag ttaatcctgg cctgttagaa   780
acatcagaag gctgtagaca aatactggga cagctacaac catcccttca gacaggatca   840
gaagaactta gatcattata taatacagta gcaaccctct attgtgtgca tcaaaggata   900
gagataaaag acaccaagga agctttagac aagatagagg aagagcaaaa caaaagtaag   960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcaggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc ttttctcgcaa cgggtttgcc gccagaacac  2220
acctgcaggt aatacgactc actataggct ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggcccaagcc agtctctga   2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
```

-continued

```
acaacagcgc cctgaagtcc cggctgacca tcatcaagga caactccaag agccaggtgt   2940
tcctgaagat gaacagcctg cagaccgacg acaccgccat ctactactgc gccaagcact   3000
actactacgg cggcagctac gccatggact actggggcca gggcacaagc gtgaccgtgt   3060
ccagcgctag cggcgaggt gggagcgag tgcaggtgga aaccatctcc ccaggagacg   3120
ggcgcacctt ccccaagcgc ggccagacct gcgtggtgca ctacaccggg atgcttgaag   3180
atggaaagaa atttgattcc tcccgggaca gaaacaagcc ctttaagttt atgctaggca   3240
agcaggaggt gatccgaggc tgggaagaag gggttgccca gatgagtgtg ggtcagagag   3300
ccaaactgac tatatctcca gattatgcct atggtgccac tgggcaccca ggcatcatcc   3360
caccacatgc cactctcgtc ttcgatgtgg agcttctaaa actggaaggc ggccgctccg   3420
gtgagggcag aggaagtctt ctaacatgcg gtgacgtgga ggagaatccg ggcccctcta   3480
gagtgagcaa gggcgaggag ataacatgg ccatcatcaa ggagttcatg cgcttcaagg   3540
tgcacatgga gggctccgtg aacggccacg agttcgagat cgagggcgag ggcgagggcc   3600 gccctacga gggcacccag accgccaagc tgaaggtgac caagggtggc cccctgccct   3660 cgcctggga catcctgtcc cctcagttca tgtacggctc caaggcctac gtgaagcacc   3720
ccgccgacat cccccgactac ttgaagctgt ccttccccga gggcttcaag tgggagcgcg   3780
tgatgaactt cgaggacggc ggcgtggtga ccgtgaccca ggactcctct ctgcaggacg   3840
gcgagttcat ctacaaggtg aagctgcgcg gcaccaactt cccctccgac ggccccgtaa   3900
tgcagaagaa gactatgggc tgggaggcct cctccgagcg gatgtacccc gaggacggcg   3960
ccctgaaggg cgagatcaag cagaggctga agctgaagga cggcggccac tacgacgctg   4020
aggtcaagac cacctacaag gccaagaagc ccgtgcagct gccccggcgcc tacaacgtca   4080 acatcaagtt ggacatcacc tcccacaacg aggactacac catcgtggaa cagtacgaac   4140
gcgccgaggg ccgccactcc accggcggca tggacgagct gtacaagtaa gtcgaccgag   4200
catcttaccg ccatttatac ccatatttgt tctgtttttc ttgatttggg tatacattta   4260
aatgttaata gaacaaaatg gtggggcaat catttacatt tttagggata tgtaattact   4320
agttcaggtg tattgccaca agacaaacat gttaagaaac tttcccgtta tttacgctct   4380
gttcctgtta atcaacctct ggattacaaa atttgtgaaa gattgactga tattcttaac   4440
tatgttgctc cttttacgct gtgtggatat gctgctttat agcctctgta tctagctatt   4500
gcttcccgta cggctttcgt tttctcctcc ttgtataaat cctggttgct gtctctttta   4560
gaggagttgt ggcccgttgt ccgtcaacgt ggcgtggtgt gctctgtgtt tgctgacgca   4620 accccactg gctggggcat tgccaccacc tgtcaactcc tttctgggac tttcgctttc   4680
cccctcccga tcgccacggc agaactcatc gccgcctgcc ttgcccgctg ctggacaggg   4740
gctaggttgc tgggcactga taattccgtg gtgttgtcat cgaattcggt accttttaa   4800 aagaaaaggg gggactggaa gggctaattc actcccaacg aagacaagat atcataactt   4860
cgtatagcat acattatacg aagttataat ttatttgtga aatttgtgat gctattgctt   4920
tatttgtaac catatgttta tttgtgaaat ttgtgatgct attgctttat ttgtaaccat   4980 tgcttttttgc ttgtactggg tctctctggt tagaccagat ctgagcctgg gagctctctg   5040
gctaactagg gaacccactg cttaagcctc aataaagctt gcctcgacca gcctcgactg   5100
tgccttctag ttgccagcca tctgttgttt gcccctcccc cgtgccttcc ttgaccctgg   5160
aaggtgccac tcccactgtc ctttcctaat aaaatgagga aattgcatcg cattgtctga   5220
```

| | |
|---|---|
| gtaggtgtca ttctattctg gggggtgggg tggggcagga cagcaagggg gaggattggg | 5280 |
| aagacaatag caggcatgct ggggatgcgg tgggctctat ggcctgcagc tgcattaatg | 5340 |
| aatcggccaa cgcgcgggga gaggcggttt gcgtattggg cgctcttccg cttcctcgct | 5400 |
| cactgactcg ctgcgctcgg tcgttcggct gcggcgagcg tatcagctc actcaaaggc | 5460 |
| ggtaatacgg ttatccacag aatcagggga taacgcagga agaacatgt gagcaaaagg | 5520 |
| ccagcaaaag gccaggaacc gtaaaaaggc cgcgttgctg gcgtttttcc ataggctccg | 5580 |
| ccccccctgac gagcatcaca aaaatcgacg ctcaagtcag aggtggcgaa acccgacagg | 5640 |
| actataaaga taccaggcgt ttccccctgg aagctccctc gtgcgctctc ctgttccgac | 5700 |
| cctgccgctt accggatacc tgtccgcctt tctcccttcg ggaagcgtgg cgctttctca | 5760 |
| tagctcacgc tgtaggtatc tcagttcggt gtaggtcgtt cgctccaagc tgggctgtgt | 5820 |
| gcacgaaccc cccgttcagc ccgaccgctg cgccttatcc ggtaactatc gtcttgagtc | 5880 |
| caacccggta agacacgact tatcgccact ggcagcagcc actggtaaca ggattagcag | 5940 |
| agcgaggtat gtaggcggtg ctacagagtt cttgaagtgg tggcctaact acggctacac | 6000 |
| tagaaggaca gtatttggta tctgcgctct gctgaagcca gttaccttcg gaaaaagagt | 6060 |
| tggtagctct tgatccggca aacaaaccac cgctggtagc ggtggttttt tgtttgcaa | 6120 |
| gcagcagatt acgcgcagaa aaaaaggatc tcaagaagat cctttgatct tttctacggg | 6180 |
| gtctgacgct cagtggaacg aaaactcacg ttaagggatt ttggtcatga gattatcaaa | 6240 |
| aaggatcttc acctagatcc ttttaaatta aaatgaagt tttaaatcaa tctaaagtat | 6300 |
| atatgagtaa acttggtctg acagttacca atgcttaatc agtgaggcac ctatctcagc | 6360 |
| gatctgtcta tttcgttcat ccatagttgc ctgactcccc gtcgtgtaga taactacgat | 6420 |
| acgggagggc ttaccatctg gccccagtgc tgcaatgata ccgcgagacc cacgctcacc | 6480 |
| ggctccagat ttatcagcaa taaaccagcc agccggaagg gccgagcgca gaagtggtcc | 6540 |
| tgcaacttta tccgcctcca tccagtctat taattgttgc cgggaagcta gagtaagtag | 6600 |
| ttcgccagtt aatagtttgc gcaacgttgt tgccattgct acaggcatcg tggtgtcacg | 6660 |
| ctcgtcgttt ggtatggctt cattcagctc cggttcccaa cgatcaaggc gagttacatg | 6720 |
| atcccccatg ttgtgcaaaa aagcggttag ctccttcggt cctccgatcg ttgtcagaag | 6780 |
| taagttggcc gcagtgttat cactcatggt tatggcagca ctgcataatt ctcttactgt | 6840 |
| catgccatcc gtaagatgct tttctgtgac tggtgagtac tcaaccaagt cattctgaga | 6900 |
| atagtgtatg cggcgaccga gttgctcttg cccggcgtca atacgggata ataccgcgcc | 6960 |
| acatagcaga actttaaaag tgctcatcat tggaaaacgt tcttcggggc gaaaactctc | 7020 |
| aaggatctta ccgctgttga gatccagttc gatgtaaccc actcgtgcac ccaactgatc | 7080 |
| ttcagcatct tttactttca ccagcgtttc tgggtgagca aaaacaggaa ggcaaaatgc | 7140 |
| cgcaaaaaag ggaataaggg cgacacggaa atgttgaata ctcatactct tccttttca | 7200 |
| atattattga agcatttatc agggttattg tctcatgagc ggatacatat ttgaatgtat | 7260 |
| ttag | 7264 |

<210> SEQ ID NO 64
<211> LENGTH: 740
<212> TYPE: PRT
<213> ORGANISM: Artificial Sequence
<220> FEATURE:
<223> OTHER INFORMATION: CD8ss-DmrC-CD8TM-41BB-CD3z-P2A-IgKss-CD19scFv-
    DmrA-CD4TM protein

<400> SEQUENCE: 64

```
Met Ala Leu Pro Val Thr Ala Leu Leu Leu Pro Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Ser Asp Ile Gln Met Thr Gln
            340                 345                 350

Thr Thr Ser Ser Leu Ser Ala Ser Leu Gly Asp Arg Val Thr Ile Ser
        355                 360                 365

Cys Arg Ala Ser Gln Asp Ile Ser Lys Tyr Leu Asn Trp Tyr Gln Gln
    370                 375                 380

Lys Pro Asp Gly Thr Val Lys Leu Leu Ile Tyr His Thr Ser Arg Leu
385                 390                 395                 400

His Ser Gly Val Pro Ser Arg Phe Ser Gly Ser Gly Ser Gly Thr Asp
                405                 410                 415
```

Tyr Ser Leu Thr Ile Ser Asn Leu Glu Gln Glu Asp Ile Ala Thr Tyr
            420                 425                 430

Phe Cys Gln Gln Gly Asn Thr Leu Pro Tyr Thr Phe Gly Gly Gly Thr
            435                 440                 445

Lys Leu Glu Ile Thr Gly Ser Thr Ser Gly Ser Gly Lys Pro Gly Ser
450                 455                 460

Gly Glu Gly Ser Thr Lys Gly Glu Val Lys Leu Gln Glu Ser Gly Pro
465                 470                 475                 480

Gly Leu Val Ala Pro Ser Gln Ser Leu Ser Val Thr Cys Thr Val Ser
            485                 490                 495

Gly Val Ser Leu Pro Asp Tyr Gly Val Ser Trp Ile Arg Gln Pro Pro
            500                 505                 510

Arg Lys Gly Leu Glu Trp Leu Gly Val Ile Trp Gly Ser Glu Thr Thr
            515                 520                 525

Tyr Tyr Asn Ser Ala Leu Lys Ser Arg Leu Thr Ile Ile Lys Asp Asn
            530                 535                 540

Ser Lys Ser Gln Val Phe Leu Lys Met Asn Ser Leu Gln Thr Asp Asp
545                 550                 555                 560

Thr Ala Ile Tyr Tyr Cys Ala Lys His Tyr Tyr Gly Gly Ser Tyr
            565                 570                 575

Ala Met Asp Tyr Trp Gly Gln Gly Thr Ser Val Thr Val Ser Ser Ala
            580                 585                 590

Ser Gly Gly Gly Gly Ser Gly Val Gln Val Glu Thr Ile Ser Pro Gly
            595                 600                 605

Asp Gly Arg Thr Phe Pro Lys Arg Gly Gln Thr Cys Val Val His Tyr
            610                 615                 620

Thr Gly Met Leu Glu Asp Gly Lys Lys Phe Asp Ser Ser Arg Asp Arg
625                 630                 635                 640

Asn Lys Pro Phe Lys Phe Met Leu Gly Lys Gln Glu Val Ile Arg Gly
            645                 650                 655

Trp Glu Glu Gly Val Ala Gln Met Ser Val Gly Gln Arg Ala Lys Leu
            660                 665                 670

Thr Ile Ser Pro Asp Tyr Ala Tyr Gly Ala Thr Gly His Pro Gly Ile
            675                 680                 685

Ile Pro Pro His Ala Thr Leu Val Phe Asp Val Glu Leu Leu Lys Leu
            690                 695                 700

Glu Gly Gly Arg Met Ala Leu Ile Val Leu Gly Gly Val Ala Gly Leu
705                 710                 715                 720

Leu Leu Phe Ile Gly Leu Gly Ile Phe Phe Cys Val Arg Cys Arg His
            725                 730                 735

Arg Arg Arg Gln
            740

<210> SEQ ID NO 65
<211> LENGTH: 2223
<212> TYPE: DNA
<213> ORGANISM: Artificial Sequence
<220> FEATURE:
<223> OTHER INFORMATION: CD8ss-DmrC-CD8TM-41BB-CD3z-P2A-IgKss-CD19scFv-
      DmrA-CD4TM DNA

<400> SEQUENCE: 65
atggctctgc ctgtgacagc tctgctgctg cctctggccc tgctgctcca tgccgccaga       60
cccggatcca tcctctggca tgagatgtgg catgaaggcc tggaagaggc atctcgtttg      120

```
tactttgggg aaaggaacgt gaaaggcatg tttgaggtgc tggagccctt gcatgctatg    180
atggaacggg ccccccagac tctgaaggaa acatccttta atcaggccta tggtcgagat    240
ttaatggagg cccaagagtg gtgcaggaag tacatgaaat cagggaatgt caaggacctc    300
ctccaagcct gggacctcta ttatcatgtg ttccgacgaa tctcaaaggc tagcgccggc    360
actggttccg acatctacat ctgggcccct ctggccggca catgtggcgt gctgctgctg    420
agcctcgtga tcaccatgca taaacggggc agaaagaaac tcctgtatat attcaaacaa    480
ccatttatga gaccagtaca aactactcaa gaggaagatg gctgtagctg ccgatttcca    540
gaagaagaag aaggaggatg tgaactgcgg gtgaagttca gcagaagcgc cgacgcccct    600
gcctaccagc agggccagaa tcagctgtac aacgagctga acctgggcag aagggaagag    660
tacgacgtcc tggataagcg gagaggccgg gaccctgaga tgggcggcaa gcctcggcgg    720
aagaaccccc aggaaggcct gtataacgaa ctgcagaaag acaagatggc cgaggcctac    780
agcgagatcg gcatgaaggg cgagcggagg cggggcaagg gccacgacgg cctgtatcag    840
ggcctgtcca ccgccaccaa ggatacctac gacgccctgc acatgcaggc cctgcccca    900
aggtcaggat ctggcgccac gaacttctct ctgttaaagc aagcaggaga tgttgaagaa    960
aaccccgggc cttcaatgga gacagacaca ctcctgctat gggtactgct gctctgggtt   1020
ccaggttcca ctggttccga tatccagatg acccagacca ccagcagcct gagcgccagc   1080
ctgggcgata gagtgaccat cagctgcaga gccagccagg acatcagcaa gtacctgaac   1140
tggtatcagc agaaacccga cggcaccgtg aagctgctga tctaccacac cagcagactg   1200
cacagcggcg tgcccagcag attttctggc agcggctccg gcaccgacta cagcctgacc   1260
atctccaacc tggaacagga agatatcgct acctacttct gtcagcaagg caacaccctg   1320
ccctacacct tcggcggagg caccaagctg gaaatcaccg gcagcacaag cggcagcggc   1380
aagcctggat ctggcgaggg aagcaccaag ggcgaagtga aactgcagga aagcggccct   1440
ggactggtgg ccccaagcca gtctctgagc gtgacctgta ccgtgtccgg cgtgtccctg   1500
cctgactatg gcgtgtcctg gatcagacag ccacccagaa agggcctgga atggctggga   1560
gtgatctggg gcagcgagac aacctactac aacagcgccc tgaagtcccg gctgaccatc   1620
atcaaggaca actccaagag ccaggtgttc ctgaagatga acagcctgca gaccgacgac   1680
accgccatct actactgcgc caagcactac tactacggcg gcagctacgc catggactac   1740
tggggccagg gcacaagcgt gaccgtgtcc agcgctagcg gcggaggtgg gagcggagtg   1800
caggtggaaa ccatctcccc aggagacggg cgcaccttcc ccaagcgcgg ccagacctgc   1860
gtggtgcact acaccgggat gcttgaagat ggaaagaaat ttgattcctc ccgggacaga   1920
aacaagccct ttaagtttat gctaggcaag caggaggtga tccgaggctg ggaagaaggg   1980
gttgcccaga tgagtgtggg tcagagagcc aaactgacta tatctccaga ttatgcctat   2040
ggtgccactg gcacccaggc atcatcccca ccacatgcca ctctcgtctt cgatgtggag   2100
cttctaaaac tggaaggcgg ccgcatggcc ctgattgtgc tgggggcgt cgccggcctc   2160
ctgcttttca ttgggctagg catcttcttc tgtgtcaggt gccggcaccg aagcgccaa   2220
taa                                                                 2223
```

<210> SEQ ID NO 66
<211> LENGTH: 7651
<212> TYPE: DNA
<213> ORGANISM: Artificial Sequence
<220> FEATURE:
<223> OTHER INFORMATION: pCVL_MND-CD8ss-DmrC-CD8TM-41BB-CD3z-P2A-IgKss- CD19scFv-DmrA-CD4TM lentiviral vector

<400> SEQUENCE: 66

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga    600
attagatcgc gatgggaaaa aattcggtta aggccagggg gaagaaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccctgatc ttcagacctg gaggaggaga tatgagggac    960
aattggagaa gtgaattata taaatataaa gtagtaaaaa ttgaaccatt aggagtagca   1020
cccaccaagg caaagagaag agtggtgcag agagaaaaaa gagcagtggg aataggagct   1080
ttgttccttg ggttcttggg agcagcagga agcactatgg gcgcagcgtc aatgacgctg   1140
acggtacagg ccagacaatt attgtctggt atagtgcagc agcagaacaa tttgctgagg   1200
gctattgagg cgcaacagca tctgttgcaa ctcacagtct ggggcatcaa gcagctccag   1260
gcaagaatcc tggctgtgga agataccta aaggatcaac agctcctggg gatttggggt   1320
tgctctggaa aactcatttg caccactgct gtgccttgga atgctagttg gagtaatgaa   1380
tctctggaac agatttggaa tcacacgacc tggatggagt gggacagaga aattaacaat   1440
tacacaagct taatacactc cttaattgaa gaatcgcaaa accagcaaga aaagaatgaa   1500
caagaattat tggaattaga taaatgggca gtttgtggaa ttggttttaa cataacaaat   1560
tggctgtggt atataaaatt attcataatg atagtaggag gcttggtagg tttaagaata   1620
gtttttgctg tactttctat agtgaataga gttaggcagg gatattcacc attatcgttt   1680
cagacccacc tcccaacccc gaggggaccc gacaggcccg aaggaataga agaagaaggt   1740
ggagagagag acagagacag atccattcga ttagtgaacg gatctcgacg gtatcggtta   1800
acttttaaaa gaaagggggg gattggggggg tacagtgcag gggaaagaat agtagacata   1860
atagcaacag acatacaaac taaagaatta caaaaacaaa ttacaaaaat tcaaaatttt   1920
atcgattacg cgtgtacaga gagacagcag aatatgggcc aaacaggata tctgtggtaa   1980
gcagttcctg ccccggctca gggccaagaa cagttggaac agcagaatat gggccaaaca   2040
ggatatctgt ggtaagcagt tcctgccccg gctcagggcc aagaacagat ggtccccaga   2100
tgcggtcccg ccctcagcag tttctagaga accatcagat gtttccaggg tgccccaagg   2160
acctgaaatg accctgtgcc ttatttgaac taaccaatca gttcgcttct cgcttctgtt   2220
cgcgcgcttc tgctccccga gctctatata agcagagctc gtttagtgaa ccgtcagatc   2280
```

```
cctgcagggc cgccaccatg gctctgcctg tgacagctct gctgctgcct ctggccctgc   2340
tgctccatgc cgccagaccc ggatccatcc tctggcatga gatgtggcat gaaggcctgg   2400
aagaggcatc tcgtttgtac tttggggaaa ggaacgtgaa aggcatgttt gaggtgctgg   2460
agcccttgca tgctatgatg gaacgggcc cccagactct gaaggaaaca tcctttaatc   2520
aggcctatgg tcgagattta atggaggccc aagagtggtg caggaagtac atgaaatcag   2580
ggaatgtcaa ggacctcctc caagcctggg acctctatta tcatgtgttc cgacgaatct   2640
caaaggctag cgccggcact ggttccgaca tctacatctg ggcccctctg ccggcacat    2700
gtggcgtgct gctgctgagc ctcgtgatca ccatgcataa acggggcaga aagaaactcc   2760
tgtatatatt caaacaacca tttatgagac cagtacaaac tactcaagag gaagatggct   2820
gtagctgccg atttccagaa gaagaagaag gaggatgtga actgcgggtg aagttcagca   2880
gaagcgccga cgcccctgcc taccagcagg ccagaatca gctgtacaac gagctgaacc    2940
tgggcagaag ggaagagtac gacgtcctgg ataagcggag aggccgggac ctgagatgg    3000
gcggcaagcc tcggcggaag aaccccccagg aaggcctgta acgaactg cagaaagaca    3060
agatggccga ggcctacagc gagatcggca tgaaggcga gcggaggcgg ggcaagggcc   3120
acgacggcct gtatcagggc ctgtccaccg ccaccaagga tacctacgac gccctgcaca   3180
tgcaggcct gccccaagg tcaggatctg gcgccacgaa cttctctctg ttaaagcaag    3240
caggagatgt tgaagaaaac cccgggcctt caatggagac agacacactc ctgctatggg   3300
tactgctgct ctgggttcca ggttccactg gttccgatat ccagatgacc cagaccacca   3360
gcagcctgag cgccagcctg ggcgatagag tgaccatcag ctgcagagcc agccaggaca   3420
tcagcaagta cctgaactgg tatcagcaga acccgacgg caccgtgaag ctgctgatct    3480
accacaccag cagactgcac agcggcgtgc ccagcagatt ttctggcagc ggctccggca   3540
ccgactacag cctgaccatc tccaacctgg aacaggaaga tatcgctacc tacttctgtc   3600
agcaaggcaa caccctgccc tacaccttcg gcggaggcac caagctggaa atcaccggca   3660
gcacaagcgg cagcggcaag cctggatctg gcgaggaag caccaagggc gaagtgaaac   3720
tgcaggaaag cggccctgga ctggtggccc caagccagtc tctgagcgtg acctgtaccg   3780
tgtccggcgt gtccctgcct gactatggcg tgtcctggat cagacagcca cccagaaagg   3840
gcctggaatg gctgggagtg atctgggca gcgagacaac ctactacaac agcgccctga   3900
agtcccggct gaccatcatc aaggacaact ccaagagcca ggtgttcctg aagatgaaca   3960
gcctgcagac cgacgacacc gccatctact actgcgccaa gcactactac tacggcggca   4020
gctacgccat ggactactgg ggccagggca aagcgtgac cgtgtccagc gctagcggcg   4080
gaggtgggag cggagtgcag gtggaaacca tctccccagg agacggcgc accttcccca   4140
agcgcggcca gacctgcgtg gtgcactaca ccgggatgct tgaagatgga agaaatttg   4200
attcctcccg ggacagaaac aagccctta agtttatgct aggcaagcag gaggtgatcc   4260
gaggctggga agaagggtt gcccagatga gtgtgggtca gagagccaaa ctgactatat   4320
ctccagatta tgcctatggt gccactgggc acccaggcat catccccacca catgccactc   4380
tcgtcttcga tgtggagctt ctaaaactgg aaggcggccg catggccctg attgtgctgg   4440
ggggcgtcgc cggcctcctg cttttcattg ggctaggcat cttcttctgt gtcaggtgcc   4500
ggcaccgaag cgccaataa gtcgaccgag catcttaccg ccatttatac ccatatttgt   4560
tctgttttc ttgatttggg tatacattta aatgttaata gaacaaaatg gtggggcaat   4620
```

```
catttacatt tttagggata tgtaattact agttcaggtg tattgccaca agacaaacat    4680
gttaagaaac tttcccgtta tttacgctct gttcctgtta atcaacctct ggattacaaa    4740
atttgtgaaa gattgactga tattcttaac tatgttgctc cttttacgct gtgtggatat    4800
gctgctttat agcctctgta tctagctatt gcttcccgta cggctttcgt tttctcctcc    4860
ttgtataaat cctggttgct gtctctttta gaggagttgt ggcccgttgt ccgtcaacgt    4920
ggcgtggtgt gctctgtgtt tgctgacgca acccccactg gctggggcat tgccaccacc    4980
tgtcaactcc tttctgggac tttcgctttc ccctcccga tcgccacggc agaactcatc    5040
gccgcctgcc ttgcccgctg ctggacaggg gctaggttgc tgggcactga taattccgtg    5100
gtgttgtcat cgaattcggt accttttttaa agaaaaggg gggactggaa gggctaattc    5160
actcccaacg aagacaagat atcataactt cgtatagcat acattatacg aagttataat    5220
ttatttgtga aatttgtgat gctattgctt tatttgtaac catatgttta tttgtgaaat    5280
ttgtgatgct attgctttat ttgtaaccat tgcttttttgc ttgtactggg tctctctggt    5340
tagaccagat ctgagcctgg gagctctctg gctaactagg gaacccactg cttaagcctc    5400
aataaagctt gcctcgacca gcctcgactg tgccttctag ttgccagcca tctgttgttt    5460
gccctccccc cgtgccttcc ttgaccctgg aaggtgccac tcccactgtc ctttcctaat    5520
aaaatgagga aattgcatcg cattgtctga gtaggtgtca ttctattctg ggggtgggg    5580
tggggcagga cagcaagggg gaggattggg aagacaatag caggcatgct ggggatgcgg    5640
tgggctctat ggcctgcagc tgcattaatg aatcggccaa cgcgcgggga gaggcggttt    5700
gcgtattggg cgctcttccg cttcctcgct cactgactcg ctgcgctcgg tcgttcggct    5760
gcggcgagcg gtatcagctc actcaaaggc ggtaatacgg ttatccacag aatcagggga    5820
taacgcagga aagaacatgt gagcaaaagg ccagcaaaag gccaggaacc gtaaaaaggc    5880
cgcgttgctg gcgtttttcc ataggctccg ccccctgac gagcatcaca aaaatcgacg    5940
ctcaagtcag aggtggcgaa acccgacagg actataaaga taccaggcgt ttccccctgg    6000
aagctccctc gtgcgctctc ctgttccgac cctgccgctt accggatacc tgtccgcctt    6060
tctcccttcg ggaagcgtgg cgcttttctca tagctcacgc tgtaggtatc tcagttcggt    6120
gtaggtcgtt cgctccaagc tgggctgtgt gcacgaaccc cccgttcagc ccgaccgctg    6180
cgccttatcc ggtaactatc gtcttgagtc caacccggta agacacgact tatcgccact    6240
ggcagcagcc actggtaaca ggattagcag agcgaggtat gtaggcggtg ctacagagtt    6300
cttgaagtgg tggcctaact acggctacac tagaaggaca gtatttggta tctgcgctct    6360
gctgaagcca gttaccttcg aaaaagagt tggtagctct tgatccggca aacaaaccac    6420
cgctggtagc ggtggttttt tgtttgcaa gcagcagatt acgcgcagaa aaaaaggatc    6480
tcaagaagat cctttgatct tttctacggg gtctgacgct cagtggaacg aaaactcacg    6540
ttaagggatt ttggtcatga gattatcaaa aaggatcttc acctagatcc ttttaaatta    6600
aaaatgaagt tttaaatcaa tctaaagtat atatgagtaa acttggtctg acagttacca    6660
atgcttaatc agtgaggcac ctatctcagc gatctgtcta tttcgttcat ccatagttgc    6720
ctgactcccc gtcgtgtaga taactacgat acgggagggc ttaccatctg gccccagtgc    6780
tgcaatgata ccgcgagacc cacgctcacc ggctccagat ttatcagcaa taaaccagcc    6840
agccggaagg gccgagcgca gaagtggtcc tgcaacttta tccgcctcca tccagtctat    6900
taattgttgc cgggaagcta gagtaagtag ttcgccagtt aatagtttgc gcaacgttgt    6960
tgccattgct acaggcatcg tggtgtcacg ctcgtcgttt ggtatggctt cattcagctc    7020
```

```
cggttcccaa cgatcaaggc gagttacatg atcccccatg ttgtgcaaaa aagcggttag    7080
ctccttcggt cctccgatcg ttgtcagaag taagttggcc gcagtgttat cactcatggt    7140
tatggcagca ctgcataatt ctcttactgt catgccatcc gtaagatgct tttctgtgac    7200
tggtgagtac tcaaccaagt cattctgaga atagtgtatg cggcgaccga gttgctcttg    7260
cccggcgtca atacgggata ataccgcgcc acatagcaga actttaaaag tgctcatcat    7320
tggaaaacgt tcttcggggc gaaaactctc aaggatctta ccgctgttga gatccagttc    7380
gatgtaaccc actcgtgcac ccaactgatc ttcagcatct tttactttca ccagcgtttc    7440
tgggtgagca aaaacaggaa ggcaaaatgc cgcaaaaaag ggaataaggg cgacacggaa    7500
atgttgaata ctcatactct tccttttttca atattattga agcatttatc agggttattg    7560
tctcatgagc ggatacatat ttgaatgtat ttagaaaaat aaacaaatag gggttccgcg    7620
cacatttccc cgaaaagtgc cacctgacgt c                                    7651
```

<210> SEQ ID NO 67
<211> LENGTH: 739
<212> TYPE: PRT
<213> ORGANISM: Artificial Sequence
<220> FEATURE:
<223> OTHER INFORMATION: CD8ss-DmrC-CD8TM-41BB-CD3z-P2A-IgKss-CD19scFv-
      DmrA-CD4TM codon optimized protein

<400> SEQUENCE: 67

```
Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240
```

```
Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Asp Ile Gln Met Thr Gln Thr
            340                 345                 350

Thr Ser Ser Leu Ser Ala Ser Leu Gly Asp Arg Val Thr Ile Ser Cys
        355                 360                 365

Arg Ala Ser Gln Asp Ile Ser Lys Tyr Leu Asn Trp Tyr Gln Gln Lys
    370                 375                 380

Pro Asp Gly Thr Val Lys Leu Leu Ile Tyr His Thr Ser Arg Leu His
385                 390                 395                 400

Ser Gly Val Pro Ser Arg Phe Ser Gly Ser Gly Ser Gly Thr Asp Tyr
                405                 410                 415

Ser Leu Thr Ile Ser Asn Leu Glu Gln Glu Asp Ile Ala Thr Tyr Phe
            420                 425                 430

Cys Gln Gln Gly Asn Thr Leu Pro Tyr Thr Phe Gly Gly Gly Thr Lys
        435                 440                 445

Leu Glu Ile Thr Gly Ser Thr Ser Gly Ser Gly Lys Pro Gly Ser Gly
    450                 455                 460

Glu Gly Ser Thr Lys Gly Glu Val Lys Leu Gln Glu Ser Gly Pro Gly
465                 470                 475                 480

Leu Val Ala Pro Ser Gln Ser Leu Ser Val Thr Cys Thr Val Ser Gly
                485                 490                 495

Val Ser Leu Pro Asp Tyr Gly Val Ser Trp Ile Arg Gln Pro Pro Arg
            500                 505                 510

Lys Gly Leu Glu Trp Leu Gly Val Ile Trp Gly Ser Glu Thr Thr Tyr
        515                 520                 525

Tyr Asn Ser Ala Leu Lys Ser Arg Leu Thr Ile Ile Lys Asp Asn Ser
    530                 535                 540

Lys Ser Gln Val Phe Leu Lys Met Asn Ser Leu Gln Thr Asp Asp Thr
545                 550                 555                 560

Ala Ile Tyr Tyr Cys Ala Lys His Tyr Tyr Gly Gly Ser Tyr Ala
                565                 570                 575

Met Asp Tyr Trp Gly Gln Gly Thr Ser Val Thr Val Ser Ser Pro Arg
            580                 585                 590

Gly Gly Gly Gly Ser Gly Val Gln Val Glu Thr Ile Ser Pro Gly Asp
        595                 600                 605

Gly Arg Thr Phe Pro Lys Arg Gly Gln Thr Cys Val Val His Tyr Thr
    610                 615                 620

Gly Met Leu Glu Asp Gly Lys Lys Phe Asp Ser Ser Arg Asp Arg Asn
625                 630                 635                 640

Lys Pro Phe Lys Phe Met Leu Gly Lys Gln Glu Val Ile Arg Gly Trp
                645                 650                 655

Glu Glu Gly Val Ala Gln Met Ser Val Gly Gln Arg Ala Lys Leu Thr
```

```
                 660                 665                 670
Ile Ser Pro Asp Tyr Ala Tyr Gly Ala Thr Gly His Pro Gly Ile Ile
            675                 680                 685

Pro Pro His Ala Thr Leu Val Phe Asp Val Glu Leu Leu Lys Leu Glu
        690                 695                 700

Gly Gly Arg Met Ala Leu Ile Val Leu Gly Gly Val Ala Gly Leu Leu
705                 710                 715                 720

Leu Phe Ile Gly Leu Gly Ile Phe Phe Cys Val Arg Cys Arg His Arg
                725                 730                 735

Arg Arg Gln

<210> SEQ ID NO 68
<211> LENGTH: 2220
<212> TYPE: DNA
<213> ORGANISM: Artificial Sequence
<220> FEATURE:
<223> OTHER INFORMATION: CD8ss-DmrC-CD8TM-41BB-CD3z-P2A-IgKss-CD19scFv-
      DmrA-CD4TM codon optimized DNA

<400> SEQUENCE: 68
atggccctcc ctgtgaccgc cctgctgctc cccctcgccc tgttgctcca tgctgcccga      60
cctggatcca tcctttggca cgagatgtgg cacgagggac tcgaagaagc gtcccggctg     120
tacttcggag agcggaacgt gaaggggatg ttcgaagtgc tggaacccct gcacgccatg     180
atggagcggg gtcctcagac ccttaaagaa acaagcttca accaggcgta cgggcgcgac     240
ctgatggaag cccaggagtg gtgccgcaag tacatgaagt ccggaaacgt gaaggatctg     300
ctgcaagcct gggatctgta ctaccacgtg ttcagaagga tctcaaaggc tagcgccggc     360
actggttcgg atatctacat ttgggcaccg ctcgccggca cttgtggagt gctgttgctg     420
tccctcgtga tcaccatgca taagagggga cggaagaagc tgctgtacat tttcaagcag     480
ccattcatgc ggcctgtgca aaccacccag gaggaggacg gtgcagctg ccggttccct      540 gaggaagagg agggcggatg cgaactgcgc gtgaagttca gccggagcgc agatgctccc     600
gcataccaac aggacagaa ccagctgtat aacgagctga acctgggcag aagggaagag      660
tacgacgtcc tcgacaagcg gcggggacgc gacccagaaa tgggaggaaa gccccgccgg     720
aagaacccgc aggaaggcct gtacaacgag ttgcagaaag acaagatggc tgaagcttac     780
tcggagattg gcatgaaggg ggagagaaga gagggaaggg ccacgacgg cctttaccaa     840 ggactgagca ctgccaccaa ggacacctac gatgcgctgc acatgcaggc cctgccccg     900 cggtccggtt cggcgcgcac taacttcagc ctgctgaagc aggccggaga tgtggaggaa     960
aaccctggac cgtccatgga gactgatacc ctgcttctgt gggtcctgct cctctgggtg    1020
ccgggctcca ccggtgacat ccagatgacc cagaccacct catccctgag cgcctctctg    1080
ggtgatcgcg tgactatctc ctgccgggcg tcgcaggata tctccaagta cctgaactgg    1140
taccagcaaa aaccggacgg gaccgtgaaa ctgctgatct accatacttc ccgccttcat    1200
tccggagtgc cctccggtt ttccggctcg ggttcaggga ctgattattc gctgaccatt     1260
tccaacctgg agcaggagga cattgcgacc tacttctgcc aacaaggaaa caccctgccc    1320
tacactttcg gtgtggaac caagctcgag atcaccggta acctcggg cagcgggaag       1380 cgggcagcg gagagggatc gacgaaagga gaagtcaagc tgcaggaatc cggcccggga    1440
ctggtgcccc cgagccagtc gctctccgtc acttgcaccg tgtcgggagt gtccttgccc    1500
gactacggag tgtcatggat tcggcagcca cctcgcaagg gcctggaatg gctcggcgtg    1560
```

```
atttggggct cagaaaccac atactacaac agcgccctga agtctcggct caccatcatc    1620
aaggacaatt ccaagtccca agtgttcctg aagatgaata gcttgcagac tgacgacacc    1680
gcgatctact actgtgccaa gcactactac tacggcggtt cctacgccat ggactactgg    1740
ggacaaggaa cttccgtgac tgtctcctcc cctagggggg gtggtggttc gggggtccag    1800
gtggaaacca tttcccccgg cgacgggcgc accttcccga agcgcggaca gacctgtgtg    1860
gtgcactata ccggaatgct cgaagatgga aagaagtttg acagctccag ggaccgcaac    1920 aagccttca gtttatgct tggaaagcag gaagtcatcc ggggctggga agagggagtc    1980
gcccagatga gcgtcggcca gcgggccaag ctgacgatct cccctgacta tgcctacggc    2040
gctaccggcc atcccggaat cattccgccg cacgcaaccc tcgtgttcga cgtggaattg    2100
ctcaagctgg aaggcggccg catggcgctg atagtgctcg gcggagtggc cggactgctg    2160
ctgttcatcg gcctgggcat cttcttctgc gtgagatgcc gccatagaag gcggcaatga    2220

<210> SEQ ID NO 69
<211> LENGTH: 7648
<212> TYPE: DNA
<213> ORGANISM: Artificial Sequence
<220> FEATURE:
<223> OTHER INFORMATION: pCVL-MND-CD8ss-DmrC-CD8TM-41BB-Zeta-P2A-IgKss-
      CD19scFv-DmrA-CD4TM codon optimized lentiviral vector

<400> SEQUENCE: 69
taacttttaa aagaaaaggg gggattgggg ggtacagtgc aggggaaaga atagtagaca      60
taatagcaac agacatacaa actaaagaat tacaaaaaca aattacaaaa attcaaaatt     120
ttatcgatta cgcgtgtaca gagagacagc agaatatggg ccaaacagga tatctgtggt    180
aagcagttcc tgccccggct cagggccaag aacagttgga acagcagaat atgggccaaa    240
caggatatct gtggtaagca gttcctgccc cggctcaggg ccaagaacag atggtcccca    300
gatgcggtcc cgccctcagc agtttctaga gaaccatcag atgtttccag gtgccccaa    360 ggacctgaaa tgaccctgtg ccttatttga actaaccaat cagttcgctt ctcgcttctg    420
ttcgcgcgct tctgctcccc gagctctata taagcagagc tcgtttagtg aaccgtcaga    480
tccctgcagg gccgccacca tggccctccc tgtgaccgcc ctgctgctcc cctcgccct    540 gttgctccat gctgcccgac ctggatccat cctttggcac gagatgtggc acgagggact    600
cgaagaagcg tccggctgt acttcggaga gcggaacgtg aaggggatgt cgaagtgct    660 ggaacccctg cacgccatga tggagcgggg tcctcagacc cttaaagaaa caagcttcaa    720
ccaggcgtac gggcgcgacc tgatggaagc ccaggagtgg tgccgcaagt acatgaagtc    780
cggaaacgtg aaggatctgc tgcaagcctg ggatctgtac taccacgtgt tcagaaggat    840
ctcaaaggct agcgccggca ctggttcgga tatctacatt tgggcaccgc tcgccggcac    900
ttgtggagtg ctgttgctgt ccctcgtgat caccatgcat aagagggac ggaagaagct    960 gctgtacatt ttcaagcagc cattcatgcg gcctgtgcaa accacccagg aggaggacgg    1020
gtgcagctgc cggttccctg aggaagagga gggcggatgc gaactgcgcg tgaagttcag    1080
ccggagcgca gatgctcccg cataccaaca gggacagaac cagctgtata acgagctgaa    1140
cctgggcaga agggaagagt acgacgtcct cgacaagcgg cggggacgcg acccagaaat    1200
gggaggaaag ccccgccgga gaaccccgca ggaaggcctg tacaacgagt gcagaaagga    1260
caagatggct gaagcttact cggagattgg catgaagggg gagagaagaa gagggaaggg    1320
ccacgacggc ctttaccaag gactgagcac tgccaccaag gacacctacg atgcgctgca    1380
```

```
catgcaggcc ctgcccccgc ggtccggttc gggcgcgact aacttcagcc tgctgaagca    1440
ggccggagat gtggaggaaa accctggacc gtccatggag actgataccc tgcttctgtg    1500
ggtcctgctc ctctgggtgc cgggctccac cggtgacatc cagatgaccc agaccacctc    1560
atccctgagc gcctctctgg gtgatcgcgt gactatctcc tgccgggcgt cgcaggatat    1620
ctccaagtac ctgaactggt accagcaaaa accggacggg accgtgaaac tgctgatcta    1680
ccatacttcc cgccttcatt ccggagtgcc ctcccggttt tccggctcgg gttcagggac    1740
tgattattcg ctgaccattt ccaacctgga gcaggaggac attgcgacct acttctgcca    1800
acaaggaaac accctgccct cactttcgg tggtggaacc aagctcgaga tcaccggatc    1860
aacctcgggc agcgggaagc cgggcagcgg agagggatcg acgaaaggag aagtcaagct    1920
gcaggaatcc ggcccgggac tggtggcccc gagccagtcg ctctccgtca cttgcaccgt    1980
gtcgggagtg tccttgcccg actacggagt gtcatggatt cggcagccac ctcgcaaggg    2040
cctggaatgg ctcggcgtga tttgggctc agaaaccaca tactacaaca gcgccctgaa    2100
gtctcggctc accatcatca aggacaattc caagtcccaa gtgttcctga agatgaatag    2160
cttgcagact gacgacaccg cgatctacta ctgtgccaag cactactact acggcggttc    2220
ctacgccatg gactactggg gacaaggaac ttccgtgact gtctcctccc ctaggggggg    2280
tggtggttcg ggggtccagg tggaaaccat tccccccggc gacgggcgca ccttcccgaa    2340
gcgcggacag acctgtgtgg tgcactatac cggaatgctc gaagatggaa agaagtttga    2400
cagctccagg gaccgcaaca agcctttcaa gtttatgctt ggaaagcagg aagtcatccg    2460
gggctgggaa gagggagtcg cccagatgag cgtcggccag cgggccaagc tgacgatctc    2520
ccctgactat gcctacggcg ctaccggcca tcccggaatc attccgccgc acgcaaccct    2580
cgtgttcgac gtgaattgc tcaagctgga aggcggccgc atggcgctga tagtgctcgg    2640
cggagtggcc ggactgctgc tgttcatcgg cctgggcatc ttcttctgcg tgagatgccg    2700
ccatagaagg cggcaatgag tcgaccgagc atcttaccgc catttatacc catatttgtt    2760
ctgttttct tgatttgggt atacatttaa atgttaatag aacaaatgg tggggcaatc    2820
atttacattt ttagggatat gtaattacta gttcaggtgt attgccacaa gacaaacatg    2880
ttaagaaact ttcccgttat ttacgctctg ttcctgttaa tcaacctctg gattacaaaa    2940
tttgtgaaag attgactgat attcttaact atgttgctcc ttttacgctg tgtggatatg    3000
ctgctttata gcctctgtat ctagctattg cttcccgtac ggctttcgtt ttctcctcct    3060
tgtataaatc ctggttgctg tctcttttag aggagttgtg gcccgttgtc cgtcaacgtg    3120
gcgtggtgtg ctctgtgttt gctgacgcaa cccccactgg ctggggcatt gccaccacct    3180
gtcaactcct ttctgggact ttcgctttcc cctcccgat cgccacggca gaactcatcg    3240
ccgcctgcct tgcccgctgc tggacagggg ctaggttgct gggcactgat aattccgtgg    3300
tgttgtcatc gaattcggta ccttttaaa agaaaagggg ggactggaag gctaattca    3360
ctcccaacga agacaagata tcataacttc gtatagcata cattatacga agttataatt    3420
tatttgtgaa atttgtgatg ctattgcttt atttgtaacc atatgtttat ttgtgaaatt    3480
tgtgatgcta ttgctttatt tgtaaccatt gcttttgct tgtactgggt ctctctggtt    3540
agaccagatc tgagcctggg agctctctgg ctaactaggg aacccactgc ttaagcctca    3600
ataaagcttg cctcgaccag cctcgactgt gccttctagt tgccagccat ctgttgtttg    3660
cccctccccc gtgccttcct tgaccctgga aggtgccact cccactgtcc tttcctaata    3720
aaatgaggaa attgcatcgc attgtctgag taggtgtcat tctattctgg ggggtggggt    3780
```

```
ggggcaggac agcaaggggg aggattggga agacaatagc aggcatgctg gggatgcggt   3840
gggctctatg gcctgcagct gcattaatga atcggccaac gcgcggggag aggcggtttg   3900
cgtattgggc gctcttccgc ttcctcgctc actgactcgc tgcgctcggt cgttcggctg   3960
cggcgagcgg tatcagctca ctcaaaggcg gtaatacggt tatccacaga atcagggga t  4020 aacgcaggaa agaacatgtg agcaaaaggc cagcaaaagg ccaggaaccg taaaaaggcc   4080
gcgttgctgg cgttttttcca taggctccgc cccctgacg agcatcacaa aaatcgacgc   4140
tcaagtcaga ggtggcgaaa cccgacagga ctataaagat accaggcgtt tccccctgga   4200
agctccctcg tgcgctctcc tgttccgacc ctgccgctta ccggatacct gtccgccttt   4260
ctcccttcgg aagcgtggc gctttctcat agctcacgct gtaggtatct cagttcggtg   4320
taggtcgttc gctccaagct gggctgtgtg cacgaaccc ccgttcagcc cgaccgctgc    4380
gccttatccg gtaactatcg tcttgagtcc aacccggtaa gacacgactt atcgccactg   4440
gcagcagcca ctggtaacag gattagcaga gcgaggtatg taggcggtgc tacagagttc   4500
ttgaagtggt ggcctaacta cggctacact agaaggacag tatttggtat ctgcgctctg   4560
ctgaagccag ttaccttcgg aaaaagagtt ggtagctctt gatccggcaa acaaaccacc   4620
gctggtagcg gtggtttttt tgtttgcaag cagcagatta cgcgcagaaa aaaggatct    4680 caagaagatc ctttgatctt ttctacgggg tctgacgctc agtggaacga aaactcacgt   4740 taagggatt tggtcatgag attatcaaaa aggatcttca cctagatcct tttaaattaa    4800
aaatgaagtt ttaaatcaat ctaaagtata tatgagtaaa cttggtctga cagttaccaa   4860
tgcttaatca gtgaggcacc tatctcagcg atctgtctat ttcgttcatc catagttgcc   4920 tgactcccg tcgtgtagat aactacgata cgggagggct taccatctgg ccccagtgct    4980
gcaatgatac cgcgagaccc acgctcaccg gctccagatt tatcagcaat aaaccagcca   5040
gccggaaggg ccgagcgcag aagtggtcct gcaactttat ccgcctccat ccagtctatt   5100
aattgttgcc gggaagctag agtaagtagt tcgccagtta atagtttgcg caacgttgtt   5160
gccattgcta caggcatcgt ggtgtcacgc tcgtcgtttg gtatggcttc attcagctcc   5220
ggttcccaac gatcaaggcg agttacatga tcccccatgt tgtgcaaaaa agcggttagc   5280
tccttcggtc ctccgatcgt tgtcagaagt aagttggccg cagtgttatc actcatggtt   5340
atggcagcac tgcataattc tcttactgtc atgccatccg taagatgctt ttctgtgact   5400
ggtgagtact caaccaagtc attctgagaa tagtgtatgc ggcgaccgag ttgctcttgc   5460
ccggcgtcaa tacgggataa taccgcgcca catagcagaa ctttaaaagt gctcatcatt   5520
ggaaaacgtt cttcggggcg aaaactctca aggatcttac cgctgttgag atccagttcg   5580
atgtaaccca ctcgtgcacc caactgatct tcagcatctt ttactttcac cagcgtttct   5640
gggtgagcaa aaacaggaag gcaaaatgcc gcaaaaaagg gaataagggc gacacggaaa   5700
tgttgaatac tcatactctt cctttttcaa tattattgaa gcatttatca gggttattgt   5760
ctcatgagcg gatacatatt tgaatgtatt tagaaaaata aacaaatagg ggttccgcgc   5820
acatttcccc gaaaagtgcc acctgacgtc aatgtagtct tatgcaatac tcttgtagtc   5880
ttgcaacatg gtaacgatga gttagcaaca tgccttacaa ggagagaaaa agcaccgtgc   5940
atgccgattg gtggaagtaa ggtggtacga tcgtgcctta ttaggaaggc aacagacggg   6000
tctgacatgg attggacgaa ccactgaatt gccgcattgc agagatattg tatttaagtg   6060
cctagctcga tacataaacg ggtctctctg gttagaccag atctgagcct gggagctctc   6120
```

```
tggctaacta gggaacccac tgcttaagcc tcaataaagc ttgccttgag tgcttcaagt    6180
agtgtgtgcc cgtctgttgt gtgactctgg taactagaga tccctcagac ccttttagtc    6240
agtgtggaaa atctctagca gtggcgcccg aacagggact tgaaagcgaa agggaaacca    6300
gaggagctct ctcgacgcag gactcggctt gctgaagcgc gcacggcaag aggcgagggg    6360
cggcgactgg tgagtacgcc aaaaattttg actagcggag gctagaagga gagagatggg    6420
tgcgagagcg tcagtattaa gcgggggaga attagatcgc gatgggaaaa aattcggtta    6480
aggccagggg gaagaaaaaa atataaatta aaacatatag tatgggcaag cagggagcta    6540
gaacgattcg cagttaatcc tggcctgtta gaaacatcag aaggctgtag acaaatactg    6600
ggacagctac aaccatccct tcagacagga tcagaagaac ttagatcatt atataataca    6660
gtagcaaccc tctattgtgt gcatcaaagg atagagataa aagacaccaa ggaagcttta    6720
gacaagatag aggaagagca aaacaaaagt aagaccaccg cacagcaagc ggccctgatc    6780
ttcagacctg gaggaggaga tatgagggac aattggagaa gtgaattata taaatataaa    6840
gtagtaaaaa ttgaaccatt aggagtagca cccaccaagg caaagagaag agtggtgcag    6900
agagaaaaaa gagcagtggg aataggagct ttgttccttg ggttcttggg agcagcagga    6960
agcactatgg gcgcagcgtc aatgacgctg acggtacagg ccagacaatt attgtctggt    7020
atagtgcagc agcagaacaa tttgctgagg gctattgagg cgcaacagca tctgttgcaa    7080
ctcacagtct ggggcatcaa gcagctccag gcaagaatcc tggctgtgga agataccta    7140 aaggatcaac agctcctggg gatttggggt tgctctggaa aactcatttg caccactgct    7200
gtgccttgga atgctagttg gagtaatgaa tctctggaac agatttggaa tcacacgacc    7260
tggatggagt gggacagaga aattaacaat tacacaagct taatacactc cttaattgaa    7320
gaatcgcaaa accagcaaga aaagaatgaa caagaattat tggaattaga taatgggca    7380 agtttgtgga attggtttaa cataacaaat tggctgtggt atataaaatt attcataatg    7440
atagtaggag gcttggtagg tttaagaata gttttgctg tactttctat agtgaataga    7500
gttaggcagg gatattcacc attatcgttt cagacccacc tcccaacccc gaggggaccc    7560
gacaggcccg aaggaataga agaagaaggt ggagagagag acagagacag atccattcga    7620
ttagtgaacg gatctcgacg gtatcggt                                       7648
```

<210> SEQ ID NO 70
<211> LENGTH: 762
<212> TYPE: PRT
<213> ORGANISM: Artificial Sequence
<220> FEATURE:
<223> OTHER INFORMATION: SS-DmrC-CD8TM-41BB-CD3z-P2A-SS-CD123scFv-DmrA-CD4TM protein

<400> SEQUENCE: 70

```
Met Arg Pro Thr Trp Ala Trp Trp Leu Phe Leu Val Leu Leu Leu Ala
1               5                   10                  15

Leu Trp Ala Pro Ala Arg Gly Gly Ser Ile Leu Trp His Glu Met Trp
            20                  25                  30

His Glu Gly Leu Glu Glu Ala Ser Arg Leu Tyr Phe Gly Glu Arg Asn
        35                  40                  45

Val Lys Gly Met Phe Glu Val Leu Glu Pro Leu His Ala Met Met Glu
    50                  55                  60

Arg Gly Pro Gln Thr Leu Lys Glu Thr Ser Phe Asn Gln Ala Tyr Gly
65                  70                  75                  80

Arg Asp Leu Met Glu Ala Gln Glu Trp Cys Arg Lys Tyr Met Lys Ser
```

```
                    85                  90                  95
Gly Asn Val Lys Asp Leu Leu Gln Ala Trp Asp Leu Tyr Tyr His Val
                100                 105                 110
Phe Arg Arg Ile Ser Lys Ala Ser Ala Gly Thr Gly Ser Asp Ile Tyr
                115                 120                 125
Ile Trp Ala Pro Leu Ala Gly Thr Cys Gly Val Leu Leu Leu Ser Leu
            130                 135                 140
Val Ile Thr Met His Lys Arg Gly Arg Lys Lys Leu Leu Tyr Ile Phe
145                 150                 155                 160
Lys Gln Pro Phe Met Arg Pro Val Gln Thr Thr Gln Glu Glu Asp Gly
                165                 170                 175
Cys Ser Cys Arg Phe Pro Glu Glu Glu Glu Gly Gly Cys Glu Leu Arg
                180                 185                 190
Val Lys Phe Ser Arg Ser Ala Asp Ala Pro Ala Tyr Gln Gln Gly Gln
                195                 200                 205
Asn Gln Leu Tyr Asn Glu Leu Asn Leu Gly Arg Arg Glu Glu Tyr Asp
                210                 215                 220
Val Leu Asp Lys Arg Arg Gly Arg Asp Pro Glu Met Gly Gly Lys Pro
225                 230                 235                 240
Arg Arg Lys Asn Pro Gln Glu Gly Leu Tyr Asn Glu Leu Gln Lys Asp
                245                 250                 255
Lys Met Ala Glu Ala Tyr Ser Glu Ile Gly Met Lys Gly Glu Arg Arg
                260                 265                 270
Arg Gly Lys Gly His Asp Gly Leu Tyr Gln Gly Leu Ser Thr Ala Thr
                275                 280                 285
Lys Asp Thr Tyr Asp Ala Leu His Met Gln Ala Leu Pro Pro Arg Gly
                290                 295                 300
Gly Arg Ser Gly Ser Gly Ala Thr Asn Phe Ser Leu Leu Lys Gln Ala
305                 310                 315                 320
Gly Asp Val Glu Glu Asn Pro Gly Pro Ser Leu Trp Trp Arg Leu Trp
                325                 330                 335
Trp Leu Leu Leu Leu Leu Leu Leu Trp Pro Met Val Trp Ala Pro
                340                 345                 350
Arg Ala Asp Tyr Lys Asp Ile Val Met Thr Gln Ser His Lys Phe Met
                355                 360                 365
Ser Thr Ser Val Gly Asp Arg Val Asn Ile Thr Cys Lys Ala Ser Gln
            370                 375                 380
Asn Val Asp Ser Ala Val Ala Trp Tyr Gln Gln Lys Pro Gly Gln Ser
385                 390                 395                 400
Pro Lys Ala Leu Ile Tyr Ser Ala Ser Tyr Arg Tyr Ser Gly Val Pro
                405                 410                 415
Asp Arg Phe Thr Gly Arg Gly Ser Gly Thr Asp Phe Thr Leu Thr Ile
                420                 425                 430
Ser Ser Val Gln Ala Glu Asp Leu Ala Val Tyr Tyr Cys Gln Gln Tyr
                435                 440                 445
Tyr Ser Thr Pro Trp Thr Phe Gly Gly Gly Thr Lys Leu Glu Ile Lys
                450                 455                 460
Arg Gly Gly Gly Gly Ser Gly Gly Gly Ser Gly Gly Gly Gly Ser
465                 470                 475                 480
Gly Gly Gly Gly Ser Glu Val Lys Leu Val Glu Ser Gly Gly Gly Leu
                485                 490                 495
Val Gln Pro Gly Gly Ser Leu Ser Leu Ser Cys Ala Ala Ser Gly Phe
                500                 505                 510
```

```
Thr Phe Thr Asp Tyr Tyr Met Ser Trp Val Arg Gln Pro Pro Gly Lys
            515                 520                 525

Ala Leu Glu Trp Leu Ala Leu Ile Arg Ser Lys Ala Asp Gly Tyr Thr
        530                 535                 540

Thr Glu Tyr Ser Ala Ser Val Lys Gly Arg Phe Thr Leu Ser Arg Asp
545                 550                 555                 560

Asp Ser Gln Ser Ile Leu Tyr Leu Gln Met Asn Ala Leu Arg Pro Glu
                565                 570                 575

Asp Ser Ala Thr Tyr Tyr Cys Ala Arg Asp Ala Ala Tyr Tyr Ser Tyr
            580                 585                 590

Tyr Ser Pro Glu Gly Ala Met Asp Tyr Trp Gly Gln Gly Thr Ser Val
        595                 600                 605

Thr Val Ser Ser Ala Ser Gly Gly Gly Gly Ser Gly Val Gln Val
610                 615                 620

Glu Thr Ile Ser Pro Gly Asp Gly Arg Thr Phe Pro Lys Arg Gly Gln
625                 630                 635                 640

Thr Cys Val Val His Tyr Thr Gly Met Leu Glu Asp Gly Lys Lys Phe
                645                 650                 655

Asp Ser Ser Arg Asp Arg Asn Lys Pro Phe Lys Phe Met Leu Gly Lys
            660                 665                 670

Gln Glu Val Ile Arg Gly Trp Glu Glu Gly Val Ala Gln Met Ser Val
        675                 680                 685

Gly Gln Arg Ala Lys Leu Thr Ile Ser Pro Asp Tyr Ala Tyr Gly Ala
        690                 695                 700

Thr Gly His Pro Gly Ile Ile Pro Pro His Ala Thr Leu Val Phe Asp
705                 710                 715                 720

Val Glu Leu Leu Lys Leu Glu Gly Gly Arg Met Ala Leu Ile Val Leu
                725                 730                 735

Gly Gly Val Ala Gly Leu Leu Leu Phe Ile Gly Leu Gly Ile Phe Phe
            740                 745                 750

Cys Val Arg Cys Arg His Arg Arg Gln
            755                 760

<210> SEQ ID NO 71
<211> LENGTH: 2289
<212> TYPE: DNA
<213> ORGANISM: Artificial Sequence
<220> FEATURE:
<223> OTHER INFORMATION: SS-DmrC-CD8TM-41BB-CD3z-P2A-SS-CD123scFv-DmrA-
      CD4TM DNA

<400> SEQUENCE: 71
atgcgcccca cctgggcctg gtggctgttc ctggtgctgc tgctggccct gtgggcaccc      60
gctcgcggcg gatccatcct ctggcatgag atgtggcatg aaggcctgga agaggcatct     120
cgtttgtact ttggggaaag gaacgtgaaa ggcatgtttg aggtgctgga gcccttgcat     180
gctatgatgg aacggggccc ccagactctg aaggaaacat cctttaatca ggcctatggt     240
cgagatttaa tggaggccca gagtggtgca ggaagtacat gaaatcagg gaatgtcaag      300 gacctcctcc aagcctggga cctctattat catgtgttcc gacgaatctc aaaggctagc     360
gccggcactg gttccgacat ctacatctgg gcccctctgg ccggcacatg tggcgtgctg     420
ctgctgagcc tcgtgatcac catgcataaa cggggcagaa agaaactcct gtatatattc     480
aaacaaccat ttatgagacc agtacaaact actcaagagg aagatggctg tagctgccga     540
tttccagaag aagaagaagg aggatgtgaa ctgcgggtga agttcagcag aagcgccgac     600
```

```
gcccctgcct accagcaggg ccagaatcag ctgtacaacg agctgaacct gggcagaagg      660
gaagagtacg acgtcctgga taagcggaga ggccgggacc ctgagatggg cggcaagcct      720
cggcggaaga accccagga aggcctgtat aacgaactgc agaaagacaa gatggccgag      780
gcctacagcg agatcggcat gaagggcgag cggaggcggg caagggcca cgacggcctg      840 tatcagggcc tgtccaccgc caccaaggat acctacgacg ccctgcacat gcaggccctg      900
cccccaaggg gcggccgctc aggatctggc gccacgaact tctctctgtt aaagcaagca      960
ggagatgttg aagaaaaccc cgggccttca ctgtggtggc cctgtggtg ctgctcctg      1020 cttctgttgc tcctgtggcc catggtgtgg cccctaggg cggactacaa agatattgtg      1080
atgacccagt ctcacaaatt catgtccaca tcagtaggag acagggtcaa catcacctgc      1140
aaggccagtc agaatgtgga tagtgctgta gcctggtatc aacagaaacc agggcaatct      1200
cctaaagcac tgatttactc ggcatcctac cggtacagtg gagtccctga tcgcttcaca      1260 ggcagggat ctgggacaga tttcactctc accatcagca gtgtgcaggc tgaagacctg      1320
gcagtttatt actgtcagca atattatagc actccgtgga cgttcggtgg aggcaccaag      1380
ctggaaatca aacgtggtgg tggtggttct ggtggtggtg gttctggcgg cggcggctcc      1440
ggtggtggtg gatccgaggt gaagctggtg gagtctggag gaggcttggt acagcctggg      1500
ggttctctga gtctctcctg tgcagcttct ggattcacct tcactgatta ctacatgagc      1560
tgggtccgcc agcctccagg gaaggcactt gagtggttgg ctttgattag aagcaaagct      1620
gatggttaca acagaaata cagtgcatct gtgaagggtc ggttcaccct ctccagagat      1680
gattcccaaa gcatcctcta tcttcaaatg aatgccctga cctgaagaa cagtgccact      1740 tattactgtg caagagatgc ggcctactat agttactata gtcccgaggg ggctatggac      1800
tactggggtc aaggaacctc agtcaccgtc tcctcgagcg ctagcggcgg aggtgggagc      1860
ggagtgcagg tggaaaccat ctccccagga gacgggcgca ccttcccaa gcgcggccag      1920 acctgcgtgg tgcactacac cgggatgctt gaagatggaa agaaatttga ttcctcccgg      1980
gacagaaaca gcccttaa gtttatgcta ggcaagcagg aggtgatccg aggctgggaa      2040
gaaggggttg cccagatgag tgtgggtcag agagccaaac tgactatatc tccagattat      2100
gcctatggtg ccactgggca cccaggcatc atcccaccac atgccactct cgtcttcgat      2160
gtggagcttc taaaactgga aggcggccgc atggccctga ttgtgctggg gggcgtcgcc      2220
ggcctcctgc ttttcattgg gctaggcatc ttcttctgtg tcaggtgccg gcaccgaagg      2280
cgccaataa                                                             2289
```

<210> SEQ ID NO 72
<211> LENGTH: 7717
<212> TYPE: DNA
<213> ORGANISM: Artificial Sequence
<220> FEATURE:
<223> OTHER INFORMATION: pCVL_MND-SS34-DmrC-CD8TM-41BB-CD3z-P2A-SS38-
      CD123scFv-DmrA-CD4TM lentiviral vector

<400> SEQUENCE: 72

```
gtacagagag acagcagaat atgggccaaa caggatatct gtggtaagca gttcctgccc       60
cggctcaggg ccaagaacag ttggaacagc agaatatggg ccaaacagga tatctgtggt      120
aagcagttcc tgccccggct cagggccaag aacagatggt ccccagatgc ggtcccgccc      180
tcagcagttt ctagagaacc atcagatgtt tccagggtgc cccaaggacc tgaaatgacc      240
ctgtgcctta tttgaactaa ccaatcagtt cgcttctcgc ttctgttcgc gcgcttctgc      300
```

-continued

```
tccccgagct ctatataagc agagctcgtt tagtgaaccg tcagatccct gcagggccgc      360
caccatgcgc cccacctggg cctggtggct gttcctggtg ctgctgctgg ccctgtgggc      420
acccgctcgc ggcggatcca tcctctggca tgagatgtgg catgaaggcc tggaagaggc      480
atctcgtttg tactttgggg aaaggaacgt gaaaggcatg tttgaggtgc tggagcccctt     540 gcatgctatg atggaacggg gcccccagac tctgaaggaa acatccttta atcaggccta      600
tggtcgagat ttaatggagg cccaagagtg gtgcaggaag tacatgaaat cagggaatgt      660
caaggacctc ctccaagcct gggacctcta ttatcatgtg ttccgacgaa tctcaaaggc      720
tagcgccggc actggttccg acatctacat ctgggcccct ctggccggca catgtggcgt      780
gctgctgctg agcctcgtga tcaccatgca taaacggggc agaaagaaac tcctgtatat      840
attcaaacaa ccatttatga gaccagtaca aactactcaa gaggaagatg ctgtagctg       900 ccgatttcca gaagaagaag aaggaggatg tgaactgcgg gtgaagttca gcagaagcgc      960
cgacgcccct gcctaccagc agggccagaa tcagctgtac aacgagctga acctgggcag     1020
aagggaagag tacgacgtcc tggataagcg gagaggccgg gaccctgaga tgggcggcaa     1080
gcctcggcgc aagaacccc aggaaggcct gtataacgaa ctgcagaaag acaagatggc      1140
cgaggcctac agcgagatcg gcatgaaggg cgagcggagg cggggcaagg ccacgacgg      1200 cctgtatcag gcctgtcca ccgccaccaa ggatacctac gacgccctgc acatgcaggc      1260 cctgcccca aggggcggcc gctcaggatc tggcgccacg aacttctctc tgttaaagca     1320
agcaggagat gttgaagaaa accccgggcc ttcactgtgg tggcgcctgt ggtggctgct     1380
cctgcttctg ttgctcctgt ggcccatggt gtgggcccct agggcggact acaaagatat     1440
tgtgatgacc cagtctcaca aattcatgtc cacatcagta ggagacaggg tcaacatcac     1500
ctgcaaggcc agtcagaatg tggatagtgc tgtagcctgg tatcaacaga aaccagggca     1560
atctcctaaa gcactgattt actcggcatc ctaccggtac agtggagtcc ctgatcgctt     1620
cacaggcagg ggatctggga cagatttcac tctcaccatc agcagtgtgc aggctgaaga     1680
cctggcagtt tattactgtc agcaatatta tagcactccg tggacgttcg gtggaggcac     1740
caagctggaa atcaaacgtg gtggtggtgg ttctggtggt ggtggttctg gcggcggcgg     1800
ctccggtggt ggtggatccg aggtgaagct ggtggagtct ggaggaggct tggtacagcc     1860
tgggggttct ctgagtctct cctgtgcagc ttctggattc accttcactg attactacat     1920
gagctgggtc cgccagcctc cagggaaggc acttgagtgg ttggctttga ttagaagcaa     1980
agctgatggt tacacaacag aatacagtgc atctgtgaag ggtcggttca ccctctccag     2040
agatgattcc caaagcatcc tctatcttca aatgaatgcc ctgagacctg aagacagtgc     2100
cacttattac tgtgcaagag atgcggccta ctatagttac tatagtcccg aggggctat      2160 ggactactgg ggtcaaggaa cctcagtcac cgtctcctcg agcgctagcg cggaggtgg      2220 gagcggagtg caggtggaaa ccatctcccc aggagacggg cgcaccttcc caagcgcgg     2280 ccagacctgc gtggtgcact acaccgggat gcttgaagat ggaaagaaat tgattcctc      2340 ccgggacaga aacaagccct ttaagtttat gctaggcaag caggaggtga tccgaggctg     2400
ggaagaaggg gttgcccaga tgagtgtggg tcagagagcc aaactgacta tatctccaga     2460
ttatgcctat ggtgccactg ggcacccagg catcatccca ccacatgcca ctctcgtctt     2520
cgatgtggag cttctaaaac tggaaggcgg ccgcatggcc ctgattgtgc tggggggcgt     2580
cgccggcctc ctgcttttca ttgggctagg catcttcttc tgtgtcaggt gccggcaccg     2640
```

```
aaggcgccaa taagtcgacc gagcatctta ccgccattta tacccatatt tgttctgttt    2700
ttcttgattt gggtatacat ttaaatgtta atagaacaaa atggtggggc aatcatttac    2760 attttttaggg atatgtaatt actagttcag gtgtattgcc acaagacaaa catgttaaga   2820
aactttcccg ttatttacgc tctgttcctg ttaatcaacc tctggattac aaaatttgtg    2880
aaagattgac tgatattctt aactatgttg ctccttttac gctgtgtgga tatgctgctt    2940
tatagcctct gtatctagct attgcttccc gtacggcttt cgttttctcc tccttgtata    3000
aatcctggtt gctgtctctt ttagaggagt tgtggcccgt tgtccgtcaa cgtggcgtgg    3060
tgtgctctgt gtttgctgac gcaaccccca ctggctgggg cattgccacc acctgtcaac    3120
tcctttctgg gactttcgct ttcccccctcc cgatcgccac ggcagaactc atcgccgcct   3180
gccttgcccg ctgctggaca ggggctaggt tgctgggcac tgataattcc gtggtgttgt    3240
catcgaattc ggtacctttt taaaagaaaa gggggggactg aagggctaa ttcactccca    3300 acgaagacaa gatatcataa cttcgtatag catacattat acgaagttat aatttatttg    3360
tgaaatttgt gatgctattg ctttatttgt aaccatatgt ttatttgtga aatttgtgat    3420
gctattgctt tatttgtaac cattgctttt tgcttgtact gggtctctct ggttagacca    3480
gatctgagcc tgggagctct ctggctaact agggaaccca ctgcttaagc ctcaataaag    3540 cttgccctcga ccagcctcga ctgtgccttc tagttgccag ccatctgttg tttgcccctc    3600
ccccgtgcct tccttgaccc tggaaggtgc cactcccact gtccttctcct aataaaatga   3660 ggaaattgca tcgcattgtc tgagtaggtg tcattctatt ctgggggggtg gggtggggca   3720 ggacagcaag ggggaggatt gggaagacaa tagcaggcat gctggggatg cggtgggctc    3780
tatggcctgc agctgcatta atgaatcggc caacgcgcgg ggagaggcgg tttgcgtatt    3840
gggcgctctt ccgcttcctc gctcactgac tcgctgcgct cggtcgttcg gctgcggcga    3900
gcggtatcag ctcactcaaa ggcggtaata cggttatcca cagaatcagg ggataacgca    3960
ggaaagaaca tgtgagcaaa aggccagcaa aaggccagga accgtaaaaa ggccgcgttg    4020
ctggcgtttt tccataggct ccgcccccct gacgagcatc acaaaaatcg acgctcaagt    4080
cagaggtggc gaaacccgac aggactataa agataccagg cgtttccccc tggaagctcc    4140
ctcgtgcgct ctcctgttcc gaccctgccg cttaccggat acctgtccgc ctttctccct    4200
tcgggaagcg tggcgctttc tcatagctca cgctgtaggt atctcagttc ggtgtaggtc    4260
gttcgctcca agctgggctg tgtgcacgaa ccccccgttc agcccgaccg ctgcgcctta    4320
tccggtaact atcgtcttga gtccaacccg gtaagacacg acttatcgcc actggcagca    4380
gccactggta acaggattag cagagcgagg tatgtaggcg gtgctacaga gttcttgaag    4440
tggtggccta actacggcta cactagaagg acagtatttg gtatctgcgc tctgctgaag    4500
ccagttacct tcggaaaaag agttggtagc tcttgatccg gcaaacaaac caccgctggt    4560
agcggtggtt ttttttgtttg caagcagcag attacgcgca gaaaaaaagg atctcaagaa    4620
gatcctttga tcttttctac ggggtctgac gctcagtgga acgaaaactc acgttaaggg   4680
attttggtca tgagattatc aaaaaggatc ttcacctaga tccttttaaa ttaaaaatga    4740
agttttaaat caatctaaag tatatatgag taaacttggt ctgacagtta ccaatgctta    4800
atcagtgagg cacctatctc agcgatctgt ctatttcgtt catccatagt tgcctgactc    4860
cccgtcgtgt agataactac gatacgggag ggcttaccat ctggccccag tgctgcaatg    4920
ataccgcgag acccacgctc accggctcca gatttatcag caataaacca gccagccgga    4980
agggccgagc gcagaagtgg tcctgcaact ttatccgcct ccatccagtc tattaattgt    5040
```

-continued

```
tgccgggaag ctagagtaag tagttcgcca gttaatagtt tgcgcaacgt tgttgccatt      5100
gctacaggca tcgtggtgtc acgctcgtcg tttggtatgg cttcattcag ctccggttcc      5160
caacgatcaa ggcgagttac atgatccccc atgttgtgca aaaaagcggt tagctccttc      5220
ggtcctccga tcgttgtcag aagtaagttg gccgcagtgt tatcactcat ggttatggca      5280
gcactgcata attctcttac tgtcatgcca tccgtaagat gcttttctgt gactggtgag      5340
tactcaacca agtcattctg agaatagtgt atgcggcgac cgagttgctc ttgcccggcg      5400
tcaatacggg ataataccgc gccacatagc agaactttaa aagtgctcat cattggaaaa      5460
cgttcttcgg ggcgaaaact ctcaaggatc ttaccgctgt tgagatccag ttcgatgtaa      5520
cccactcgtg cacccaactg atcttcagca tcttttactt tcaccagcgt ttctgggtga      5580
gcaaaaacag gaaggcaaaa tgccgcaaaa aagggaataa gggcgacacg gaaatgttga      5640
atactcatac tcttcctttt tcaatattat tgaagcattt atcagggtta ttgtctcatg      5700
agcggataca tatttgaatg tatttagaaa aataaacaaa tagggggttcc gcgcacattt      5760
ccccgaaaag tgccacctga cgtcaatgta gtcttatgca atactcttgt agtcttgcaa      5820
catggtaacg atgagttagc aacatgcctt acaaggagag aaaaagcacc gtgcatgccg      5880
attggtggaa gtaaggtggt acgatcgtgc cttattagga aggcaacaga cgggtctgac      5940
atggattgga cgaaccactg aattgccgca ttgcagagat attgtattta agtgcctagc      6000
tcgatacata aacgggtctc tctggttaga ccagatctga gcctgggagc tctctggcta      6060
actagggaac ccactgctta agcctcaata agcttgcct tgagtgcttc aagtagtgtg      6120
tgcccgtctg ttgtgtgact ctggtaacta gagatccctc agaccctttt agtcagtgtg      6180
gaaaatctct agcagtggcg cccgaacagg gacttgaaag cgaaagggaa accagaggag      6240
ctctctcgac gcaggactcg gcttgctgaa gcgcgcacgg caagaggcga ggggcggcga      6300
ctggtgagta cgccaaaaat tttgactagc ggaggctaga aggagagaga tgggtgcgag      6360
agcgtcagta ttaagcgggg gagaattaga tcgcgatggg aaaaaattcg gttaaggcca      6420
gggggaaaga aaaatataa attaaaacat atagtatggg caagcaggga gctagaacga      6480
ttcgcagtta atcctggcct gttagaaaca tcagaaggct gtagacaaat actgggacag      6540
ctacaaccat cccttcagac aggatcagaa gaacttagat cattatataa tacagtagca      6600
accctctatt gtgtgcatca aaggatagag ataaaagaca ccaaggaagc tttagacaag      6660
atagaggaag agcaaaacaa aagtaagacc accgcacagc aagcggccct gatcttcaga      6720
cctggaggag gagatatgag ggacaattgg agaagtgaat tatataaata taagtagta      6780
aaaattgaac cattaggagt agcacccacc aaggcaaaga gaagagtggt gcagagagaa      6840
aaaagagcag tgggaatagg agctttgttc cttgggttct tgggagcagc aggaagcact      6900
atgggcgcag cgtcaatgac gctgacggta caggccagac aattattgtc tggtatagtg      6960
cagcagcaga acaatttgct gagggctatt gaggcgcaac agcatctgtt gcaactcaca      7020
gtctggggca tcaagcagct ccaggcaaga atcctggctg tggaaagata cctaaaggat      7080
caacagctcc tggggatttg gggttgctct ggaaaactca tttgcaccac tgctgtgcct      7140
tggaatgcta gttggagtaa tgaatctctg aacagattt ggaatcacac gacctggatg      7200
gagtgggaca gagaaattaa caattacaca agcttaatac actccttaat tgaagaatcg      7260
caaaaccagc aagaaaagaa tgaacaagaa ttattggaat tagataaatg gcaagtttg      7320
tggaattggt ttaacataac aaattggctg tggtatataa aattattcat aatgatagta      7380
```

```
ggaggcttgg taggtttaag aatagttttt gctgtacttt ctatagtgaa tagagttagg      7440
cagggatatt caccattatc gtttcagacc cacctcccaa ccccgagggg acccgacagg      7500
cccgaaggaa tagaagaaga aggtggagag agagacagag acagatccat tcgattagtg      7560
aacggatctc gacggtatcg gttaactttt aaaagaaaag gggggattgg ggggtacagt      7620 gcagggggaaa gaatagtaga cataatagca acagacatac aaactaaaga attacaaaaa     7680
caaattacaa aaattcaaaa ttttatcgat tacgcgt                               7717

<210> SEQ ID NO 73
<211> LENGTH: 8230
<212> TYPE: DNA
<213> ORGANISM: Artificial Sequence
<220> FEATURE:
<223> OTHER INFORMATION: pBB_REV-CMV-IgKss-CD19scFv-DmrA-CD4TM_FOR-MND-
      CD8ss-DmrC-CD8TM-41BB-CD3z lentiviral vector

<400> SEQUENCE: 73
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accatcatat gccagcctat ggtgacattg attattgact agttattaat agtaatcaat       240 tacgggtca ttagttcata gcccatatat ggagttccgc gttacataac ttacggtaaa       300
tggcccgcct ggctgaccgc ccaacgaccc ccgcccattg acgtcaataa tgacgtatgt       360
tcccatagta acgccaatag ggactttcca ttgacgtcaa tgggtggagt atttacggta       420
aactgcccac ttggcagtac atcaagtgta tcatatgcca gtacgcccc ctattgacgt       480 caatgacggt aaatggcccg cctggcatta tgcccagtac atgaccttat ggactttcc       540 tacttggcag tacatctacg tattagtcat cgctattacc atggtgatgc ggttttggca      600
gtacatcaat gggcgtggat agcggtttga ctcacgggga tttccaagtc tccaccccat       660
tgacgtcaat gggagtttgt tttggcacca aaatcaacgg gactttccaa aatgtcgtaa      720
caactccgcc ccattgacgc aaatgggcgg taggcgtgta cggtgggagg tctatataag     780
cagagctcgt ttagtgaacc gggtctctct ggttagacca gatctgagcc tgggagctct      840
ctggctaact agggaaccca ctgcttaagc ctcaataaag cttgccttga gtgctcaaag      900
tagtgtgtgc ccgtctgttg tgtgactctg gtaactagag atccctcaga cccttttagt      960
cagtgtggaa aatctctagc agtggcgccc gaacagggac ttgaaagcga aagtaaagcc     1020
agaggagatc tctcgacgca ggactcggct tgctgaagcg cgcacggcaa gaggcgaggg     1080
gcggcgactg gtgagtacgc caaaattttt gactagcgga ggctagaagg agagagtagg     1140
gtgcgagagc gtcggtatta agcggggag aattagataa atgggaaaaa attcggttaa     1200
ggccaggggg aaagaaacaa tataaactaa acatatagt tagggcaagc agggagctag      1260
aacgattcgc agttaatcct ggccttttag acatcaga aggctgtaga caaatactgg      1320
gacagctaca accatcccctt cagacaggat cagaagaact tagatcatta tataatacaa     1380
tagcagtcct ctattgtgtg catcaaagga tagatgtaaa agacaccaag gaagccttag     1440
ataagataga ggaagagcaa aacaaaagta agaaaaaggc acagcaagca gcagctgaca     1500
caggaaacaa cagccaggtc agccaaaatt accctatagt gcagaacctc caggggcaaa     1560
tggtacatca ggccatatca cctagaactt taaattaaga cagcagtaca aatggcagta     1620
ttcatccaca attttaaaag aaaaggggggg attggggggt acagtgcagg ggaaagaata     1680
```

```
gtagacataa tagcaacaga catacaaact aaagaattac aaaaacaaat tacaaaaatt    1740 caaaatttc gggtttatta cagggacagc agagatccag tttggaaagg accagcaaag     1800
ctcctctgga aaggtgaagg ggcagtagta atacaagata atagtgacat aaaagtagtg    1860
ccaagaagaa aagcaaagat catcagggat tatggaaaac agatggcagg tgatgattgt    1920
gtggcaagta gacaggatga ggattaacac atggaaaga ttagtaaaac accatagctc     1980
tagagcgatc ccgatcttca gacctggagg aggagatatg agggacaatt ggagaagtga    2040
attatataaa tataaagtag taaaaattga accattagga gtagcaccca ccaaggcaaa    2100
gagaagagtg gtgcagagag aaaaagagc agtgggaata ggagctttgt tccttgggtt     2160
cttgggagca gcaggaagca ctatgggcgc agcgtcaatg acgctgacgg tacaggccag    2220
acaattattg tctggtatag tgcagcagca gaacaatttg ctgagggcta ttgaggcgca    2280
acagcatctg ttgcaactca cagtctgggg catcaagcag ctccaggcaa gaatcctggc    2340
tgtggaaaga tacctaaagg atcaacagct cctggggatt tggggttgct ctggaaaact    2400
catttgcacc actgctgtgc cttggaatgc tagttggagt aataaatctc tggaacagat    2460
ttggaatcac acgacctgga tggagtggga cagagaaatt aacaattaca caagcttggt    2520
aggtttaaga atagttttg ctgtactttc tatagtgaat agagttaggc agggatattc     2580
accattatcg tttcagaccc acctcccaac cccgagggga cccgacaggc ccgaaggaat    2640
agaagaagaa ggtggagaga gagacagaga cagatccatt cgattagtga acggatcctc    2700
acacaaaaaa ccaacacaca gatgtctagt agctctgatc ttttattcta gcggccgcgt    2760
accgaagcta tcattgccgc cttctatggc ggcatctcac gcagaagaag atgcccaggc    2820
cgatgaacag cagcagtccg gccactccgc cgagcactat cagcgccatg cggccgcctt    2880
ccagcttgag caattccacg tcgaacacga gggttgcgtg cggcggaatg attccgggat    2940
ggccggtagc gccgtaggca tagtcagggg agatcgtcag cttggcccgc tggccgacgc    3000
tcatctgggc gactccctct tcccagcccc ggatgacttc ctgctttcca agcataaact    3060
tgaaaggctt gttgcggtcc ctggagctgt caaacttctt tccatcttcg agcattccgg    3120
tatagtgcac cacacaggtc tgtccgcgct tcgggaaggt gcgcccgtcg ccggggggaaa   3180 tggtttccac ctggaccccc gaaccaccac ccccctagg ggaggagaca gtcacggaag     3240
ttccttgtcc ccagtagtcc atggcgtagg aaccgccgta gtagtagtgc ttggcacagt    3300
agtagatcgc ggtgtcgtca gtctgcaagc tattcatctt caggaacact gggacttgg     3360 aattgtcctt gatgatggtg agccgagact tcagggcgct gttgtagtat gtggtttctg    3420
agccccaaat cacgccgagc cattccaggc ccttgcgagg tggctgccga atccatgaca    3480
ctccgtagtc gggcaaggac actcccgaca cggtgcaagt gacggagagc gactggctcg    3540
gggccaccag tcccgggccg gattcctgca gcttgacttc tcctttcgtc gatccctctc    3600
cgctgcccgg cttcccgctg cccgaggttg atccggtgat ctcgagcttg gttccaccac    3660
cgaaagtgta gggcagggtg tttccttgtt ggcagaagta ggtcgcaatg tcctcctgct    3720
ccaggttgga aatggtcagc gaataatcag tccctgaacc cgagccggaa aaccgggagg    3780
gcactccgga atgaaggcgg gaagtatggt agatcagcag tttcacggtc ccgtccggtt    3840
tttgctggta ccagttcagg tacttggaga tatcctgcga cgcccggcag gagatagtca    3900
cgcgatcacc cagagaggcg ctcagggatg aggtggtctg ggtcatctgg atgtcaccgg    3960
tggagcccgg cacccagagg agcaggaccc acagaagcag ggtatcagtc tccatggtgg    4020
cacgcgcctt gctagctaga caaaagtgtt gtggaattgc tccaggcgat ctgacggttc    4080
```

```
actaaacgag ctctgctttt ataggcgccc accgtacacg cctaagcgtc gacggaatga   4140
aagaccccac ctgtaggttt ggcaagctag gatcaaggtt aggaacagag agacagcaga   4200
atatgggcca aacaggatat ctgtggtaag cagttcctgc cccggctcag ggccaagaac   4260
agttggaaca gcagaatatg ggccaaacag gatatctgtg gtaagcagtt cctgccccgg   4320
ctcagggcca agaacagatg gtccccagat gcggtcccgc cctcagcagt ttctagagaa   4380
ccatcagatg tttccagggt gccccaagga cctgaaatga ccctgtgcct tatttgaact   4440
aaccaatcag ttcgcttctc gcttctgttc gcgcgcttct gctccccgag ctcaataaaa   4500
gagcccacaa cccctcactc ggcgcgattc acctgacgcg taccatggcc ctccctgtga   4560
ccgccctgct gctcccccctc gccctgttgc tccatgctgc ccgacctgga tccatccttt   4620
ggcacgagat gtggcacgag ggactcgaag aagcgtcccg gctgtacttc ggagagcgga   4680
acgtgaaggg gatgttcgaa gtgctggaac ccctgcacgc catgatggag cggggtcctc   4740
agacccttaa agaaacaagc ttcaaccagg cgtacgggcg cgacctgatg gaagcccagg   4800
agtggtgccg caagtacatg aagtccggaa acgtgaagga tctgctgcaa gcctgggatc   4860
tgtactacca cgtgttcaga aggatctcaa aggctagcgc cggcactggt tcggatatct   4920
acatttgggc accgctcgcc ggcacttgtg gagtgctgtt gctgtccctc gtgatcacca   4980
tgcataagag gggacggaag aagctgctgt acatttttcaa gcagccattc atgcggcctg   5040
tgcaaaccac ccaggaggag gacgggtgca gctgccggtt ccctgaggaa gaggagggcg   5100
gatgcgaact gcgcgtgaag ttcagccgga gcgcagatgc tcccgcatac caacagggac   5160
agaaccagct gtataacgag ctgaacctgg gcagaaggga gagtacgac gtcctcgaca   5220 agcggcgggg acgcgaccca gaaatgggag gaaagccccg ccggaagaac cgcaggaag   5280 gcctgtacaa cgagttgcag aaagacaaga tggctgaagc ttactcggag attggcatga   5340
agggggagag aagaagaggg aagggccacg acggcccttta ccaaggactg agcactgcca   5400
ccaaggacac ctacgatgcg ctgcacatgc aggccctgcc ccgcggtga gcggccaac   5460 tcgacgttat tcccttcgaa ggaaacctgc aggtaccttt aagaccaatg acttacaagg   5520
cagctgtaga tcttagccac ttttaaaag aaaagggggg actggaaggg ctaattcact   5580
cccaaagaag acaagatctg cttttttgcct gtactgggtc tctctggtta gaccagatct   5640
gagcctggga gctctctggc taactaggga acccactgct taagcctcaa taaagcttgc   5700
cttgagtgct tcaatgtgtg tgttggtttt ttgtgtgtcg aaattctagc gattctagct   5760
tggcgtaatc atggtcatag ctgtttcctg tgtgaaattg ttatccgctc acaattccac   5820
acaacatacg agccggaagc ataaagtgta aagcctgggg tgcctaatga gtgagctaac   5880
tcacattaat tgcgttgcgc tcactgcccg ctttccagtc gggaaacctg tcgtgccagc   5940
tgcattaatg aatcggccaa cgcgcgggga gaggcggttt gcgtattggg cgctcttccg   6000
cttcctcgct cactgactcg ctgcgctcgg tcgttcggct gcggcgagcg gtatcagctc   6060
actcaaaggc ggtaatacgg ttatccacag aatcaggggga taacgcagga agaacatgt   6120 gagcaaaagg ccagcaaaag gccaggaacc gtaaaaaggc cgcgttgctg gcgttttttcc   6180 ataggctccg ccccctgac gagcatcaca aaaatcgacg ctcaagtcag aggtggcgaa   6240
acccgacagg actataaaga taccaggcgt ttccccctgg aagctccctc gtgcgctctc   6300
ctgttccgac cctgccgctt accggatacc tgtccgcctt tctcccttcg ggaagcgtgg   6360
cgctttctca tagctcacgc tgtaggtatc tcagttcggt gtaggtcgtt cgctccaagc   6420
```

| | |
|---|---|
| tgggctgtgt gcacgaaccc cccgttcagc ccgaccgctg cgccttatcc ggtaactatc | 6480 |
| gtcttgagtc caacccggta agacacgact tatcgccact ggcagcagcc actggtaaca | 6540 |
| ggattagcag agcgaggtat gtaggcggtg ctacagagtt cttgaagtgg tggcctaact | 6600 |
| acggctacac tagaagaaca gtatttggta tctgcgctct gctgaagcca gttaccttcg | 6660 |
| gaaaaagagt tggtagctct tgatccggca aacaaaccac cgctggtagc ggtggttttt | 6720 |
| ttgtttgcaa gcagcagatt acgcgcagaa aaaaaggatc tcaagaagat cctttgatct | 6780 |
| tttctacggg gtctgacgct cagtggaacg aaaactcacg ttaagggatt ttggtcatga | 6840 |
| gattatcaaa aaggatcttc acctagatcc ttttaaatta aaaatgaagt tttaaatcaa | 6900 |
| tctaaagtat atatgagtaa acttggtctg acagttacca atgcttaatc agtgaggcac | 6960 |
| ctatctcagc gatctgtcta tttcgttcat ccatagttgc ctgactcccc gtcgtgtaga | 7020 |
| taactacgat acgggagggc ttaccatctg gccccagtgc tgcaatgata ccgcgagacc | 7080 |
| cacgctcacc ggctccagat ttatcagcaa taaaccagcc agccggaagg gccgagcgca | 7140 |
| gaagtggtcc tgcaacttta tccgcctcca tccagtctat taattgttgc cgggaagcta | 7200 |
| gagtaagtag ttcgccagtt aatagtttgc gcaacgttgt tgccattgct acaggcatcg | 7260 |
| tggtgtcacg ctcgtcgttt ggtatggctt cattcagctc cggttcccaa cgatcaaggc | 7320 |
| gagttacatg atcccccatg ttgtgcaaaa aagcggttag ctccttcggt cctccgatcg | 7380 |
| ttgtcagaag taagttggcc gcagtgttat cactcatggt tatggcagca ctgcataatt | 7440 |
| ctcttactgt catgccatcc gtaagatgct tttctgtgac tggtgagtac tcaaccaagt | 7500 |
| cattctgaga atagtgtatg cggcgaccga gttgctcttg cccggcgtca atacgggata | 7560 |
| ataccgcgcc acatagcaga actttaaaag tgctcatcat tggaaaacgt tcttcggggc | 7620 |
| gaaaactctc aaggatctta ccgctgttga gatccagttc gatgtaaccc actcgtgcac | 7680 |
| ccaactgatc ttcagcatct tttactttca ccagcgtttc tgggtgagca aaaacaggaa | 7740 |
| ggcaaaatgc cgcaaaaaag ggaataaggg cgacacggaa atgttgaata ctcatactct | 7800 |
| tcctttttca atattattga agcatttatc agggttattg tctcatgagc ggatacatat | 7860 |
| ttgaatgtat ttagaaaaat aaacaaatag gggttccgcg cacatttccc cgaaaagtgc | 7920 |
| cacctgggac tagcttttg caaaagccta ggcctccaaa aaagcctcct cactacttct | 7980 |
| ggaatagctc agaggccgag gcggcctcgg cctctgcata ataaaaaaaa attagtcagc | 8040 |
| catgggcgg agaatgggcg gaactgggcg gagttagggg cgggatgggc ggagttaggg | 8100 |
| gcgggactat ggttgctgac taattgagat gagcttgcat gccgacattg attattgact | 8160 |
| agtccctaag aaaccattct tatcatgaca ttaacctata aaaataggcg tatcacgagg | 8220 |
| ccctttcgtc | 8230 |

<210> SEQ ID NO 74
<211> LENGTH: 7135
<212> TYPE: DNA
<213> ORGANISM: Artificial Sequence
<220> FEATURE:
<223> OTHER INFORMATION: pCVL_sEF1a-CD123target-T2A-Puro lentiviral
    vector

<400> SEQUENCE: 74

| | |
|---|---|
| aggctccggt gcccgtcagt gggcagagcg cacatcgccc acagtccccg agaagttggg | 60 |
| gggaggggtc ggcaattgaa ccggtgccta gagaaggtgg cgcggggtaa actgggaaag | 120 |
| tgatgtcgtg tactggctcc gcctttttcc cgagggtggg ggagaaccgt atataagtgc | 180 |

-continued

| | |
|---|---|
| agtagtcgcc gtgaacgttc tttttcgcaa cgggtttgcc gccagaacac acctgcaggg | 240 |
| ccgccaccat ggtcctcctt tggctcacgc tgctcctgat cgccctgccc tgtctcctgc | 300 |
| aaacgaagga agatccaaac ccaccaatca cgaacctaag gatgaaagca aaggctcagc | 360 |
| agttgacctg ggaccttaac agaaatgtga ccgatatcga gtgtgttaaa gacgccgact | 420 |
| attctatgcc ggcagtgaac aatagctatt gccagtttgg agcaatttcc ttatgtgaag | 480 |
| tgaccaacta caccgtccga gtggccaacc caccattctc cacgtggatc ctcttccctg | 540 |
| agaacagtgg gaagccttgg gcaggtgcgg agaatctgac ctgctggatt catgacgtgg | 600 |
| atttcttgag ctgcagctgg gcggtaggcc cgggggcccc cgcggacgtc cagtacgacc | 660 |
| tgtacttgaa cgttgccaac aggcgtcaac agtacgagtg tcttcactac aaaacggatg | 720 |
| ctcagggaac acgtatcggg tgtcgtttcg atgacatctc tcgactctcc agcggttctc | 780 |
| aaagttccca catcctggtg cggggcagga gcgcagcctt cggtatcccc tgcacagata | 840 |
| agtttgtcgt cttttcacag attgagatat taactccacc caacatgact gcaaagtgta | 900 |
| ataagacaca ttcctttatg cactggaaaa tgagaagtca tttcaatcgc aaatttcgct | 960 |
| atgagcttca gatacaaaag agaatgcagc ctgtaatcac agaacaggtc agagacagaa | 1020 |
| cctccttcca gctactcaat cctggaacgt acacagtaca aataagagcc cgggaaagag | 1080 |
| tgtatgaatt cttgagcgcc tggagcaccc cccagcgctt cgagtgcgac caggaggagg | 1140 |
| gcgcaaacac acgtgcctgg cggacgtcgc tgctgatcgc gctggggacg ctgctggccc | 1200 |
| tggtctgtgt cttcgtgatc tgcagaaggt atctggtgat gcagagactc tttccccgca | 1260 |
| tccctcacat gaaagacccc atcggtgaca gcttccaaaa cgacaagctg gtggtctggg | 1320 |
| aggcgggcaa agccggcctg gaggagtgtc tggtgactga agtacaggtc gtgcagaaaa | 1380 |
| ctggcggccg ctccggtgag ggcagaggaa gtcttctaac atgcggtgac gtggaggaga | 1440 |
| atccgggccc ctctagaacc gagtacaagc ccacggtgcg cctcgccacc cgcgacgacg | 1500 |
| tcccccgggc cgtacgcacc ctcgccgccg cgttcgccga ctaccccgcc acgcgccaca | 1560 |
| ccgtcgatcc ggaccgccac atcgagcggg tcaccgagct gcaagaactc ttcctcacgc | 1620 |
| gcgtcgggct cgacatcggc aaggtgtggg tcgcggacga cggcgccgcg gtggcggtct | 1680 |
| ggaccacgcc ggagagcgtc gaagcggggg cggtgttcgc cgagatcggc ccgcgcatgg | 1740 |
| ccgagttgag cggttcccgg ctggccgcgc agcaacagat ggaaggcctc ctggcgccgc | 1800 |
| accggcccaa ggagcccgcg tggttcctgg ccaccgtcgg cgtctcgccc gaccaccagg | 1860 |
| gcaagggtct gggcagcgcc gtcgtgctcc ccggagtgga ggcggccgag cgcgccgggg | 1920 |
| tgcccgcctt cctggagacc tccgcgcccc gcaacctccc cttctacgag cggctcggct | 1980 |
| tcaccgtcac cgccgacgtc gaggtgcccg aaggaccgcg cacctggtgc atgacccgca | 2040 |
| agcccggtgc cctcgagtga tgagagtcat cgtcgaccga gcatcttacc gccatttata | 2100 |
| cccatatttg ttctgttttt cttgatttgg gtatacattt aaatgttaat agaacaaaat | 2160 |
| ggtgggcaa tcatttacat ttttagggat atgtaattac tagttcaggt gtattgccac | 2220 |
| aagacaaaca tgttaagaaa ctttcccgtt atttacgctc tgttcctgtt aatcaacctc | 2280 |
| tggattacaa aatttgtgaa agattgactg atattcttaa ctatgttgct ccttttacgc | 2340 |
| tgtgtggata tgctgcttta tagcctctgt atctagctat tgcttcccgt acggctttcg | 2400 |
| ttttctcctc cttgtataaa tcctggttgc tgtctctttt agaggagttg tggcccgttg | 2460 |
| tccgtcaacg tggcgtggtg tgctctgtgt ttgctgacgc aacccccact ggctgggca | 2520 |
| ttgccaccac ctgtcaactc ctttctggga ctttcgcttt cccccctcccg atcgccacgg | 2580 |

```
cagaactcat cgccgcctgc cttgcccgct gctggacagg ggctaggttg ctgggcactg   2640
ataattccgt ggtgttgtca tcgaattcgg tacctttta aaagaaaagg ggggactgga    2700
agggctaatt cactcccaac gaagacaaga tatcataact tcgtatagca tacattatac   2760
gaagttataa tttatttgtg aaatttgtga tgctattgct ttatttgtaa ccatatgttt   2820
atttgtgaaa tttgtgatgc tattgcttta tttgtaacca ttgcttttg cttgtactgg    2880 gtctctctgg ttagaccaga tctgagcctg ggagctctct ggctaactag ggaacccact   2940
gcttaagcct caataaagct tgcctcgacc agcctcgact gtgccttcta gttgccagcc   3000
atctgttgtt tgcccctccc ccgtgccttc cttgaccctg gaaggtgcca ctcccactgt   3060
cctttcctaa taaaatgagg aaattgcatc gcattgtctg agtaggtgtc attctattct   3120
ggggggtggg gtggggcagg acagcaaggg ggaggattgg gaagacaata gcaggcatgc   3180
tggggatgcg gtgggctcta tggcctgcag ctgcattaat gaatcggcca acgcgcgggg   3240
agaggcggtt tgcgtattgg gcgctcttcc gcttcctcgc tcactgactc gctgcgctcg   3300
gtcgttcggc tgcggcgagc ggtatcagct cactcaaagg cggtaatacg ttatccaca    3360 gaatcagggg ataacgcagg aaagaacatg tgagcaaaag gccagcaaaa ggccaggaac   3420
cgtaaaaagg ccgcgttgct ggcgtttttc cataggctcc gcccccctga cgagcatcac   3480
aaaaatcgac gctcaagtca gaggtggcga acccgacag gactataaag ataccaggcg    3540
tttccccctg gaagctccct cgtgcgctct cctgttccga ccctgccgct taccggatac   3600
ctgtccgcct ttctcccttc gggaagcgtg gcgctttctc atagctcacg ctgtaggtat   3660
ctcagttcgg tgtaggtcgt tcgctccaag ctgggctgtg tgcacgaacc ccccgttcag   3720
cccgaccgct gcgccttatc cggtaactat cgtcttgagt ccaacccggt aagacacgac   3780
ttatcgccac tggcagcagc cactggtaac aggattagca gagcgaggta tgtaggcggt   3840
gctacagagt tcttgaagtg gtggcctaac tacggctaca ctagaaggac agtatttggt   3900
atctgcgctc tgctgaagcc agttaccttc ggaaaaagag ttggtagctc ttgatccggc   3960
aaacaaacca ccgctggtag cggtggtttt tttgtttgca agcagcagat tacgcgcaga   4020
aaaaaaggat ctcaagaaga tcctttgatc ttttctacgg ggtctgacgc tcagtggaac   4080
gaaaactcac gttaagggat tttggtcatg agattatcaa aaaggatctt cacctagatc   4140 ctttttaaatt aaaaatgaag ttttaaatca atctaaagta tatatgagta aacttggtct   4200
gacagttacc aatgcttaat cagtgaggca cctatctcag cgatctgtct atttcgttca   4260
tccatagttg cctgactccc cgtcgtgtag ataactacga tacgggaggg cttaccatct   4320
ggccccagtg ctgcaatgat accgcgagac ccacgctcac cggctccaga tttatcagca   4380 ataaccagc cagccggaag ggccgagcgc agaagtggtc ctgcaacttt atccgcctcc    4440
atccagtcta ttaattgttg ccgggaagct agagtaagta gttcgccagt taatagtttg   4500
cgcaacgttg ttgccattgc tacaggcatc gtggtgtcac gctcgtcgtt tggtatggct   4560
tcattcagct ccggttccca acgatcaagg cgagttacat gatccccat gttgtgcaaa    4620 aaagcggtta gctccttcgg tcctccgatc gttgtcagaa gtaagttggc cgcagtgtta   4680
tcactcatgg ttatggcagc actgcataat tctcttactg tcatgccatc cgtaagatgc   4740
ttttctgtga ctggtgagta ctcaaccaag tcattctgag aatagtgtat gcggcgaccg   4800
agttgctctt gcccggcgtc aatacgggat aataccgcgc cacatagcag aactttaaaa   4860
gtgctcatca ttggaaaacg ttcttcgggg cgaaaactct caaggatctt accgctgttg   4920
```

| | |
|---|---|
| agatccagtt cgatgtaacc cactcgtgca cccaactgat cttcagcatc ttttactttc | 4980 |
| accagcgttt ctgggtgagc aaaaacagga aggcaaaatg ccgcaaaaaa gggaataagg | 5040 |
| gcgacacgga aatgttgaat actcatactc ttcctttttc aatattattg aagcatttat | 5100 |
| cagggttatt gtctcatgag cggatacata tttgaatgta tttagaaaaa taaacaaata | 5160 |
| ggggttccgc gcacatttcc ccgaaaagtg ccacctgacg tcaatgtagt cttatgcaat | 5220 |
| actcttgtag tcttgcaaca tggtaacgat gagttagcaa catgccttac aaggagagaa | 5280 |
| aaagcaccgt gcatgccgat tggtggaagt aaggtggtac gatcgtgcct tattaggaag | 5340 |
| gcaacgacg ggtctgacat ggattggacg aaccactgaa ttgccgcatt gcagagatat | 5400 |
| tgtatttaag tgcctagctc gatacataaa cgggtctctc tggttagacc agatctgagc | 5460 |
| ctgggagctc tctggctaac tagggaaccc actgcttaag cctcaataaa gcttgccttg | 5520 |
| agtgcttcaa gtagtgtgtg cccgtctgtt gtgtgactct ggtaactaga gatccctcag | 5580 |
| acccttttag tcagtgtgga aaatctctag cagtggcgcc cgaacaggga cttgaaagcg | 5640 |
| aaagggaaac cagaggagct ctctcgacgc aggactcggc ttgctgaagc gcgcacggca | 5700 |
| agaggcgagg ggcggcgact ggtgagtacg ccaaaaattt tgactagcgg aggctagaag | 5760 |
| gagagagatg ggtgcgagag cgtcagtatt aagcggggga gaattagatc gcgatgggaa | 5820 |
| aaaattcggt taaggccagg gggaaagaaa aaatataaat taaaacatat agtatgggca | 5880 |
| agcagggagc tagaacgatt cgcagttaat cctggcctgt tagaaacatc agaaggctgt | 5940 |
| agacaaatac tgggacagct acaaccatcc cttcagacag gatcagaaga acttagatca | 6000 |
| ttatataata cagtagcaac cctctattgt gtgcatcaaa ggatagagat aaaagacacc | 6060 |
| aaggaagctt tagacaagat agaggaagag caaaacaaaa gtaagaccac cgcacagcaa | 6120 |
| gcggccctga tcttcagacc tggaggagga gatatgaggg acaattggag aagtgaatta | 6180 |
| tataaatata agtagtaaa aattgaacca ttaggagtag cacccaccaa ggcaaagaga | 6240 |
| agagtggtgc agagagaaaa aagagcagtg ggaataggag ctttgttcct tgggttcttg | 6300 |
| ggagcagcag gaagcactat gggcgcagcg tcaatgacgc tgacggtaca ggccagacaa | 6360 |
| ttattgtctg gtatagtgca gcagcagaac aatttgctga gggctattga ggcgcaacag | 6420 |
| catctgttgc aactcacagt ctggggcatc aagcagctcc aggcaagaat cctggctgtg | 6480 |
| gaaagatacc taaaggatca acagctcctg gggatttggg gttgctctgg aaaactcatt | 6540 |
| tgcaccactg ctgtgccttg gaatgctagt tggagtaatg aatctctgga acagatttgg | 6600 |
| aatcacacga cctggatgga gtgggacaga gaaattaaca attacacaag cttaatacac | 6660 |
| tccttaattg aagaatcgca aaaccagcaa gaaaagaatg aacaagaatt attggaatta | 6720 |
| gataaatggg caagtttgtg gaattggttt aacataacaa attggctgtg gtatataaaa | 6780 |
| ttattcataa tgatagtagg aggcttggta ggtttaagaa tagttttgc tgtactttct | 6840 |
| atagtgaata gagttaggca gggatattca ccattatcgt ttcagaccca cctcccaacc | 6900 |
| ccgagggac ccgacaggcc cgaaggaata gaagaagaag tggagagag agacagagac | 6960 |
| agatccattc gattagtgaa cggatctcga cggtatcggt taacttttaa aagaaagggg | 7020 |
| gggattgggg ggtacagtgc aggggaaaga atagtagaca taatagcaac agacatacaa | 7080 |
| actaaagaat tacaaaaaca aattacaaaa attcaaaatt ttatcgatta cgcgt | 7135 |

<210> SEQ ID NO 75
<211> LENGTH: 7735
<212> TYPE: DNA
<213> ORGANISM: Artificial Sequence
<220> FEATURE:
<223> OTHER INFORMATION: pCVL_MND-CD8ss-DmrC-CD3scFv-P2A-IgKss-CD19scFv-DmrA lentiviral vector

<400> SEQUENCE: 75

```
taacttttaa aagaaaaggg gggattgggg ggtacagtgc aggggaaaga atagtagaca    60
taatagcaac agacatacaa actaaagaat tacaaaaaca aattacaaaa attcaaaatt   120
ttatcgatta cgcgtgtaca gagagacagc agaatatggg ccaaacagga tatctgtggt   180
aagcagttcc tgccccggct cagggccaag aacagttgga acagcagaat atgggccaaa   240
caggatatct gtggtaagca gttcctgccc cggctcaggg ccaagaacag atggtcccca   300
gatgcggtcc cgccctcagc agtttctaga gaaccatcag atgtttccag ggtgccccaa   360
ggacctgaaa tgaccctgtg ccttatttga actaaccaat cagttcgctt ctcgcttctg   420
ttcgcgcgct tctgctcccc gagctctata aagcagagc tcgtttagtg aaccgtcaga   480
tccctgcagg gccgccacca tggcctcccc tgtgaccgcc ctgctgctcc ccctcgccct   540
gttgctccat gctgcccgac ctggatccat cctttggcac gagatgtggc acgagggact   600
cgaagaagcg tcccggctgt acttcggaga gcggaacgtg aaggggatgt tcgaagtgct   660
ggaacccctg cacgccatga tggagcgggg tcctcagacc cttaaagaaa caagcttcaa   720
ccaggcgtac gggcgcgacc tgatggaagc ccaggagtgg tgccgcaagt acatgaagtc   780
cggaaacgtg aaggatctgc tgcaagcctg ggatctgtac taccacgtgt tcagaaggat   840
ctcaaaggct agccaggtgc aactggtgca gagcggcggt ggcgttgtgc agccgggccg   900
cagcctgcgc ctgtcttgca aagcgagcgg ctataccttt acgcgctata ccatgcactg   960
ggtgcgccag gcgccgggca aaggtctgga atggattggc tatattaacc cgtctcgcgg  1020
ctataccaac tataatcaga aagtgaaaga tcgctttacc attagccgcg ataactctaa  1080
aaacaccgcg tttctgcaga tggatagcct gcgcccggaa gataccggcg tgtattttg  1140
cgcgcgctac tatgatgacc attatagcct ggattattgg ggccagggca ccccggtgac  1200
cgttagctcg ggcagcacaa gcggcagcgg caagcctgga tctggcgagg gaagcaccaa  1260
gggcgatatc cagatgaccc agagcccgag ctctctgagc gcgagcgtgg gcgatcgcgt  1320
gaccattacg tgcagcgcgt ctagctctgt gagctatatg aactggtacc agcaaacccc  1380
aggcaaagcg ccgaaacgct ggatttatga taccagcaaa ctggcgagcg gcgtgccgag  1440
ccgctttagc ggctctggta gcggcaccga ttatacgttt accattagct ctctgcagcc  1500
ggaagatatt gcgacctatt actgccagca atggagctct aacccgttta cctttggcca  1560
gggtaccaaa ctgcagatta cccgctccgg ttcgggcgcg actaacttca gcctgctgaa  1620
gcaggccgga gatgtggagg aaaaccctgg accgtccatg gagactgata ccctgcttct  1680
gtgggtcctg ctcctctggg tgccgggctc caccggtgac atccagatga cccagaccac  1740
ctcatccctg agcgcctctc tgggtgatcg cgtgactatc tcctgccggg cgtcgcagga  1800
tatctccaag tacctgaact ggtaccagca aaaaccggac gggaccgtga aactgctgat  1860
ctaccatact tcccgccttc attccggagt gccctcccgg ttttccggct cgggttcagg  1920
gactgattat tcgctgacca tttccaacct ggagcaggag gacattgcga cctacttctg  1980
ccaacaagga aacaccctgc cctacacttt cggtggtgga accaagctcg agatcaccgg  2040
atcaacctcg ggcagcggga agccgggcag cggagaggga tcgacgaaag agaagtcaa  2100
gctgcaggaa tccggcccgg gactggtggc cccgagccag tcgctctccg tcacttgcac  2160
cgtgtcggga gtgtccttgc ccgactacgg agtgtcatgg attcggcagc cacctcgcaa  2220
```

```
gggcctggaa tggctcggcg tgatttgggg ctcagaaacc acatactaca acagcgccct    2280
gaagtctcgg ctcaccatca tcaaggacaa ttccaagtcc caagtgttcc tgaagatgaa    2340
tagcttgcag actgacgaca ccgcgatcta ctactgtgcc aagcactact actacggcgg    2400
ttcctacgcc atggactact ggggacaagg aacttccgtg actgtctcct cccctagggg    2460
gggtggtggt tcggggggtcc agtgggaaac catttccccc ggcgacgggc gcaccttccc    2520
gaagcgcgga cagacctgtg tggtgcacta taccggaatg ctcgaagatg aaagaagtt    2580
tgacagctcc agggaccgca acaagccttt caagtttatg cttggaaagc aggaagtcat    2640
ccggggctgg gaagagggag tcgcccagat gagcgtcggc cagcgggcca agctgacgat    2700
ctcccctgac tatgcctacg cgctaccgg ccatcccgga atcattccgc cgcacgcaac    2760
cctcgtgttc gacgtggaat tgctcaagct ggaatgaggc ggccgcgtcg accgagcatc    2820
ttaccgccat ttatacccat atttgttctg ttttcttga tttgggtata catttaaatg    2880
ttaatagaac aaaatggtgg ggcaatcatt tacatttta gggatatgta attactagtt    2940
caggtgtatt gccacaagac aaacatgtta agaaactttc ccgttattta cgctctgttc    3000
ctgttaatca acctctggat tacaaaattt gtgaaagatt gactgatatt cttaactatg    3060
ttgctccttt tacgctgtgt ggatatgctg ctttatagcc tctgtatcta gctattgctt    3120
cccgtacggc tttcgttttc tcctccttgt ataaatcctg gttgctgtct cttttagagg    3180
agttgtggcc cgttgtccgt caacgtggcg tggtgtgctc tgtgtttgct gacgcaaccc    3240
ccactgctg gggcattgcc accacctgtc aactcctttc tgggactttc gctttccccc    3300
tccgatcgc cacggcagaa ctcatcgccg cctgccttgc ccgctgctgg acaggggcta    3360
ggttgctggg cactgataat tccgtggtgt tgtcatcgaa ttcggtacct ttttaaaaga    3420
aaaggggga ctggaagggc taattcactc ccaacgaaga caagatatca taacttcgta    3480
tagcatacat tatacgaagt tataatttat ttgtgaaatt tgtgatgcta ttgctttatt    3540
tgtaaccata tgtttatttg tgaaatttgt gatgctattg ctttatttgt aaccattgct    3600
ttttgcttgt actgggtctc tctggttaga ccagatctga gcctgggagc tctctggcta    3660
actagggaac ccactgctta agcctcaata aagcttgcct cgaccagcct cgactgtgcc    3720
ttctagttgc cagccatctg ttgtttgccc ctcccccgtg ccttccttga ccctggaagg    3780
tgccactccc actgtccttt cctaataaaa tgaggaaatt gcatcgcatt gtctgagtag    3840
gtgtcattct attctggggg gtggggtggg gcaggacagc aagggggagg attgggaaga    3900
caatagcagg catgctgggg atgcggtggg ctctatggcc tgcagctgca ttaatgaatc    3960
ggccaacgcg cggggagagg cggtttgcgt attgggcgct cttccgcttc ctcgctcact    4020
gactcgctgc gctcggtcgt tcggctgcgg cgagcggtat cagctcactc aaaggcggta    4080
atacggttat ccacagaatc aggggataac gcaggaaaga acatgtgagc aaaaggccag    4140
caaaaggcca ggaaccgtaa aaaggccgcg ttgctggcgt ttttccatag gctccgcccc    4200
cctgacgagc atcacaaaaa tcgacgctca agtcagaggt ggcgaaaccc gacaggacta    4260
taaagatacc aggcgtttcc ccctggaagc tccctcgtgc gctctcctgt tccgaccctg    4320
ccgcttaccg gatacctgtc cgcctttctc ccttcgggaa gcgtggcgct ttctcatagc    4380
tcacgctgta ggtatctcag ttcggtgtag tcgttcgct ccaagctggg ctgtgtgcac    4440
gaaccccccg ttcagcccga ccgctgcgcc ttatccggta actatcgtct tgagtccaac    4500
ccggtaagac acgacttatc gccactggca gcagccactg gtaacaggat tagcagagcg    4560
```

```
aggtatgtag gcggtgctac agagttcttg aagtggtggc ctaactacgg ctacactaga    4620
aggacagtat ttggtatctg cgctctgctg aagccagtta ccttcggaaa aagagttggt    4680
agctcttgat ccggcaaaca aaccaccgct ggtagcggtg gttttttttgt ttgcaagcag    4740 cagattacgc gcagaaaaaa aggatctcaa gaagatcctt tgatcttttc tacggggtct    4800
gacgctcagt ggaacgaaaa ctcacgttaa gggattttgg tcatgagatt atcaaaaagg    4860
atcttcacct agatcctttt aaattaaaaa tgaagtttta atcaatctaa agtatatat    4920 gagtaaactt ggtctgacag ttaccaatgc ttaatcagtg aggcacctat ctcagcgatc    4980
tgtctatttc gttcatccat agttgcctga ctccccgtcg tgtagataac tacgatacgg    5040
gagggcttac catctggccc cagtgctgca atgataccgc gagacccacg ctcaccggct    5100
ccagatttat cagcaataaa ccagccagcc ggaagggccg agcgcagaag tggtcctgca    5160
actttatccg cctccatcca gtctattaat tgttgccggg aagctagagt aagtagttcg    5220
ccagttaata gtttgcgcaa cgttgttgcc attgctacag gcatcgtggt gtcacgctcg    5280
tcgtttggta tggcttcatt cagctccggt tcccaacgat caaggcgagt tacatgatcc    5340
cccatgttgt gcaaaaaagc ggttagctcc ttcggtcctc cgatcgttgt cagaagtaag    5400
ttggccgcag tgttatcact catggttatg gcagcactgc ataattctct tactgtcatg    5460
ccatccgtaa gatgcttttc tgtgactggt gagtactcaa ccaagtcatt ctgagaatag    5520
tgtatgcggc gaccgagttg ctcttgcccg gcgtcaatac gggataatac cgcgccacat    5580
agcagaactt taaaagtgct catcattgga aaacgttctt cggggcgaaa actctcaagg    5640
atcttaccgc tgttgagatc cagttcgatg taacccactc gtgcacccaa ctgatcttca    5700
gcatctttta ctttcaccag cgtttctggg tgagcaaaaa caggaaggca aaatgccgca    5760
aaaaagggaa taagggcgac acggaaatgt tgaatactca tactcttcct ttttcaatat    5820
tattgaagca tttatcaggg ttattgtctc atgagcggat acatatttga atgtatttag    5880
aaaaataaac aaataggggt tccgcgcaca tttccccgaa aagtgccacc tgacgtcaat    5940
gtagtcttat gcaatactct tgtagtcttg caacatggta acgatgagtt agcaacatgc    6000
cttacaagga gagaaaaagc accgtgcatg ccgattggtg gaagtaaggt ggtacgatcg    6060
tgccttatta ggaaggcaac agacgggtct gacatggatt ggacgaacca ctgaattgcc    6120
gcattgcaga gatattgtat ttaagtgcct agctcgatac ataaacgggt ctctctggtt    6180
agaccagatc tgagcctggg agctctctgg ctaactaggg aacccactgc ttaagcctca    6240
ataaagcttg ccttgagtgc ttcaagtagt gtgtgcccgt ctgttgtgtg actctggtaa    6300
ctagagatcc ctcagaccct tttagtcagt gtggaaaatc tctagcagtg gcgcccgaac    6360
agggacttga aagcgaaagg gaaaccagag gagctctctc gacgcaggac tcggcttgct    6420
gaagcgcgca cggcaagagg cgaggggcgg cgactggtga gtacgccaaa aattttgact    6480
agcggaggct agaaggagag agatgggtgc gagagcgtca gtattaagcg gggagaatt    6540 agatcgcgat gggaaaaaat tcggttaagg ccaggggaa agaaaaaata taaattaaaa    6600
catatagtat gggcaagcag ggagctagaa cgattcgcag ttaatcctgg cctgttagaa    6660
acatcagaag gctgtagaca atactggga cagctacaac catcccttca gacaggatca    6720
gaagaactta gatcattata taatacagta gcaaccctct attgtgtgca tcaaaggata    6780
gagataaaag acaccaagga agctttagac aagatagagg aagagcaaaa caaaagtaag    6840
accaccgcac agcaagcggc cctgatcttc agacctggag gaggagatat gagggacaat    6900
tggagaagtg aattatataa atataaagta gtaaaaattg aaccattagg agtagcaccc    6960
```

```
accaaggcaa agagaagagt ggtgcagaga gaaaaaagag cagtgggaat aggagctttg    7020
ttccttgggt tcttgggagc agcaggaagc actatgggcg cagcgtcaat gacgctgacg    7080
gtacaggcca gacaattatt gtctggtata gtgcagcagc agaacaattt gctgagggct    7140
attgaggcgc aacagcatct gttgcaactc acagtctggg gcatcaagca gctccaggca    7200
agaatcctgg ctgtggaaag atacctaaag gatcaacagc tcctggggat ttggggttgc    7260
tctggaaaac tcatttgcac cactgctgtg ccttggaatg ctagttggag taatgaatct    7320
ctggaacaga tttggaatca cacgacctgg atggagtggg acagagaaat taacaattac    7380
acaagcttaa tacactcctt aattgaagaa tcgcaaaacc agcaagaaaa gaatgaacaa    7440
gaattattgg aattagataa atgggcaagt ttgtggaatt ggtttaacat aacaaattgg    7500
ctgtggtata taaaattatt cataatgata gtaggaggct tggtaggttt aagaatagtt    7560
tttgctgtac tttctatagt gaatagagtt aggcagggat attcaccatt atcgtttcag    7620
acccacctcc caaccccgag gggacccgac aggcccgaag gaatagaaga agaaggtgga    7680
gagagagaca gagacagatc cattcgatta gtgaacggat ctcgacggta tcggt         7735
```